US012779041B2

(12) United States Patent
Lei et al.

(10) Patent No.: US 12,779,041 B2
(45) Date of Patent: Nov. 3, 2026

(54) EGFR DEGRADERS AND METHODS OF USE

(71) Applicant: BeiGene Switzerland GmbH, Basel (CH)

(72) Inventors: Bailin Lei, Beijing (CN); Huaqing Liu, Beijing (CN); Songzhe Han, Beijing (CN); Zhiwei Wang, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 499 days.

(21) Appl. No.: 18/264,881

(22) PCT Filed: Feb. 9, 2022

(86) PCT No.: PCT/CN2022/075651
§ 371 (c)(1),
(2) Date: Aug. 9, 2023

(87) PCT Pub. No.: WO2022/171123
PCT Pub. Date: Aug. 18, 2022

(65) Prior Publication Data

US 2024/0165243 A1 May 23, 2024

(30) Foreign Application Priority Data

Feb. 10, 2021 (WO) ................ PCT/CN2021/076500

(51) Int. Cl.
*A61K 47/55* (2017.01)
*A61K 47/54* (2017.01)

(52) U.S. Cl.
CPC ............ *A61K 47/55* (2017.08); *A61K 47/545* (2017.08)

(58) Field of Classification Search
CPC .............................. A61K 47/55; A61K 47/545
USPC ............................................................ 514/81
See application file for complete search history.

(56) References Cited

U.S. PATENT DOCUMENTS

| | | | |
|---|---|---|---|
| 2013/0225527 | A1 | 8/2013 | Wang |
| 2014/0066406 | A1 | 3/2014 | Wang |
| 2016/0045607 | A1 | 2/2016 | Crew |
| 2017/0008904 | A1 | 1/2017 | Crew |
| 2018/0050021 | A1 | 2/2018 | Ciulli |
| 2018/0072711 | A1 | 3/2018 | Crew |
| 2019/0106417 | A1 | 4/2019 | Gray |

FOREIGN PATENT DOCUMENTS

| | | | |
|---|---|---|---|
| CA | 3141413 | A1 | 12/2020 |
| CN | 101374818 | A | 2/2009 |
| CN | 102105150 | A | 6/2011 |
| CN | 103153064 | A | 6/2013 |
| CN | 107257800 | A | 10/2017 |
| CN | 109422733 | A | 3/2019 |
| CN | 109912655 | A | 6/2019 |
| CN | 109928956 | A | 6/2019 |
| CN | 110357889 | A | 10/2019 |
| CN | 110684015 | A | 1/2020 |
| CN | 110753693 | A | 2/2020 |
| CN | 110818690 | A | 2/2020 |
| CN | 112079866 | A | 12/2020 |
| EP | 3 725 771 | A1 | 10/2020 |
| EP | 3 778 590 | A1 | 2/2021 |
| WO | 2002020740 | A2 | 3/2002 |
| WO | 2012051587 | A1 | 4/2012 |
| WO | 2014108452 | A1 | 7/2014 |
| WO | 2016105518 | A1 | 6/2016 |
| WO | 2016146985 | A1 | 9/2016 |
| WO | 2016149668 | A1 | 9/2016 |
| WO | 2016197032 | A1 | 12/2016 |
| WO | 2016197114 | A1 | 12/2016 |
| WO | 2017011590 | A1 | 1/2017 |
| WO | 2017030814 | A1 | 2/2017 |
| WO | 2017079267 | A1 | 5/2017 |
| WO | 2017182418 | A1 | 10/2017 |
| WO | 2017197036 | A1 | 11/2017 |
| WO | 2017197046 | A1 | 11/2017 |
| WO | 2017197051 | A1 | 11/2017 |
| WO | 2017197056 | A1 | 11/2017 |
| WO | 2017201449 | A1 | 11/2017 |
| WO | 2017204445 | A2 | 11/2017 |
| WO | 2018071606 | A1 | 4/2018 |
| WO | 2018119441 | A1 | 6/2018 |
| WO | 2019015655 | A1 | 1/2019 |
| WO | 2019040274 | A1 | 2/2019 |
| WO | 2019042444 | A1 | 3/2019 |
| WO | 2019060742 | A1 | 3/2019 |
| WO | 2019113071 | A1 | 6/2019 |
| WO | 2019114770 | A1 | 6/2019 |
| WO | 2019121562 | A1 | 6/2019 |
| WO | 2019133531 | A1 | 7/2019 |
| WO | 2019149922 | A1 | 8/2019 |
| WO | 2019183523 | A1 | 9/2019 |
| WO | 2019190259 | A1 | 10/2019 |
| WO | 2019196812 | A1 | 10/2019 |

(Continued)

OTHER PUBLICATIONS

International Search Report issued May 9, 2022 in PCT/CN2022/075651.
Written Opinion issued May 9, 2022 in PCT/CN2022/075651.
Extended European Search Report on Appl. No. EP 22752283.6 dated Apr. 3, 2025 (11 pages).
Sun et al., "PROTACs: great opportunities for academia and industry," Signal Transduction and Targeted Therapy, Dec. 2019, vol. 4 (pp. 1-33).
Ardley, H.C. et al., "E3 ubiquitin ligases," Essays Biochemistry, 41: 15-30, 2005.
Cermakova, K. et al., "Next-Generation Drugs and Probes for Chromatin Biology: From Targeted Protein Degradation to Phase Separation," Molecules, 23(1958):26 pages, 2018.
Chen, Y. et al., "The cullin 4A/B-DDB1-cereblon E3 ubiquitin ligase complex mediates the degradation of CLC-1 chloride channels," Scientific Reports, 5(10667):1-13, 2015.

(Continued)

*Primary Examiner* — Kristin A Vajda
(74) *Attorney, Agent, or Firm* — Foley & Lardner LLP

(57) ABSTRACT

Disclosed herein are novel bifunctional compounds formed by conjugating EGFR inhibitor moieties with E3 ligase Ligand moieties, which function to recruit targeted proteins to E3 ubiquitin ligase for degradation, and methods of preparation and uses thereof.

35 Claims, No Drawings

(56) References Cited

FOREIGN PATENT DOCUMENTS

| | | | |
|---|---|---|---|
| WO | 2020010210 | A1 | 1/2020 |
| WO | 2020113233 | A1 | 6/2020 |
| WO | 2020200291 | A1 | 10/2020 |
| WO | 2020216371 | A1 | 10/2020 |
| WO | 2020253862 | A1 | 12/2020 |
| WO | 2021011871 | A1 | 1/2021 |
| WO | 2021011913 | A1 | 1/2021 |
| WO | 2021023233 | A1 | 2/2021 |
| WO | 2021036922 | A1 | 3/2021 |
| WO | 2021057882 | A1 | 4/2021 |
| WO | 2021073498 | A1 | 4/2021 |
| WO | 2021123087 | A1 | 6/2021 |
| WO | 2021127190 | A1 | 6/2021 |
| WO | 2021127283 | A2 | 6/2021 |
| WO | 2021127561 | A1 | 6/2021 |
| WO | 2021133809 | A1 | 7/2021 |
| WO | 2021168074 | A1 | 8/2021 |
| WO | 2021173677 | A1 | 9/2021 |
| WO | 2021178920 | A1 | 9/2021 |
| WO | 2021208918 | A1 | 10/2021 |
| WO | 2021216440 | A1 | 10/2021 |
| WO | 2022012622 | A1 | 1/2022 |
| WO | 2022012623 | A1 | 1/2022 |
| WO | 2022063106 | A1 | 3/2022 |
| WO | 2022068849 | A1 | 4/2022 |
| WO | 2022171123 | A1 | 8/2022 |
| WO | 2022228556 | A1 | 11/2022 |

OTHER PUBLICATIONS

Chu, T. T. et al., "Specific knockdown of endogenous tau protein by peptide-directed ubiquitin-proteasome degradation", Cell Chemical Biology, 23(4):453-461, 2016.
Chung Hyo Kang et al., "Induced protein degradation of anaplastic lymphoma kinase (ALK) by proteolysis targeting chimera (PROTAC)", Biochemical and Biophysical Research Communications, 505(2):542-547, 2018, Abstract.
Crews, Craig M. et al., "Inducing Protein Degradation as a Therapeutic Strategy," J. Med. Chem., 61(2):403-404, 2018.
Extended European Search Report dated Feb. 3, 2025 issued for European Pat. App. No. 22795025 (8 pages).
Grice, G. L. et al., "The Proteasome Distinguishes between Heterotypic and Homotypic Lysine-11-Linked Polyubiquitin Chains," Cell Rep., 12(4):545-553, 2015.
He, Kailun, et al., "Discovery and biological evaluation of proteolysis targeting chimeras (PROTACs) as an EGFR degraders based on osimertinib and lenalidomide", Bioorganic & Medicinal Chemistry Letters, 30(12):127167, 2020.
International Search Report and Written Opinion for PCT/CN2021/121563 mailed on Dec. 30, 2021 (11 pages).
International Search Report and Written Opinion for PCT/CN2022/090342 issued on Jul. 27, 2022 (18 pages).
Komander, D. et al., "The Ubiquitin Code," Annu. Rev. Biochem., 81:203-229, 2012.
Konduri et al., "EGFR fusions as novel therapeutic targets in lung cancer", Cancer Discovery, 6(6):601-611, 2016.
Lebraud, H. et al., "Protein degradation by in-cell self-assembly of proteolysis targeting chimeras," ACS Central Science, 2(12):927-934, 2016.
Lebraud, H. et al., "Protein degradation: a validated therapeutic strategy with exciting prospects," Essays Biochem., 61(5):517-527, 2017.
Lim, K. M. H. et al., "Dynamic Kinetic Resolution in Rhodium-Catalyzed Asymmetric Arylation of Phospholene Oxides", Journal of the American Chemical Society, 139(24):8122-8125, 2017.
Liu, S. et al., "Targeted selective degradation of Bruton's tyrosine kinase by PROTACs", Medicinal Chemistry Research, 29:802-808, 2020.
Lochmuller, C. H. et al., "Chromatographic Resolution of Enantiomers," Journal of Chromatography, 113:283-302, 1975.
Lu, J. et al., "Hijacking the E3 Ubiquitin ligase cereblon to efficiently target BRD4," Chemistry and Biology, 22(6):755-763, 2015.
Lu, X. et al., "Targeting EGFRL858R/T790M and EGFRL858R/T790M/C797S resistance mutations in NSCLC: Current developments in medicinal chemistry," Medicinal Research Reviews, 38(5):1550-1581, 2018.
Maemondo, M. et al., "Gefitinib or chemotherapy for non-small-cell lung cancer with mutated EGFR," New England Journal of Medicine, 362(25):2380-2388, 2010.
Matyskiela, M. E. et al., "SALL4 mediates teratogenicity as a thalidomide-dependent cereblon substrate," Nature Chemical Biology, 14(10):981-987, 2018.
Neklesa, T. K. et al., "Targeted protein degradation by PROTACs," Pharmacology & Therapeutics, 174:138-144, 2017.
Ottis, P. et al., "Assessing Different E3 Ligases for Small Molecule Induced Protein Ubiquitination and Degradation," ACS Chem. Biol., 12(10):2570-2578, 2017.
Ottis, P. et al., "Proteolysis-Targeting Chimeras: Induced Protein Degradation as a Therapeutic Strategy," ACS Chem. Biol., 12(4):892-898, 2017.
Pav, O. et al., "Novel phosphanucleoside analogs of dideoxynucleosides", Tetrahedron, 73: 5220-5228, 2017.
Qin, C. et al., "Discovery of QCA570 as an exceptionally potent and efficacious proteolysis targeting chimera (PROTAC) degrader of the bromodomain and extra-terminal (BET) proteins capable of inducing complete and durable tumor regression", Journal of Medicinal Chemistry, 61(15):6685-6704, 2018.
Qu, X. et al., "Effective degradation of EGFRL858R+T790M mutant proteins by CRBN-based PROTACs through both proteosome and autophagy/lysosome degradation systems," European Journal of Medicinal Chemistry, 218 (113328):1-14, 2021.
Sainan, A. et al., "Small-molecule PROTACs: An emerging and promising approach for the development of targeted therapy drugs", EBioMedicine, 36:552-562, 2018.
Sakamoto, Kathleen M., "Chimeric molecules to target proteins for ubiquitination and degradation," Methods Enzymol., 399:833-847, 2005.
Sakamoto, Kathleen M., "Protacs: chimeric molecules that target proteins to the Skp1-Cullin-F box complex for ubiquitination and degradation," Proc Natl Acad Sci USA, 98(15):8554-8559, 2001.
Spradlin, J. N. et al., "Harnessing the anti-cancer natural product nimbolide for targeted protein degradation," Nat. Chem. Biol, 15(7):747-755, 2019.
Sun, N. et al., "Development of a Brigatinib degrader (SIAIS117) as a potential treatment for ALK positive cancer resistance", European Journal of Medicinal Chemistry, vol. 193, 7 pages, 2020.
Sun, Y. et al., "PROTAC-induced BTK degradation as a novel therapy for mutated Btk C481S induced ibrutinib-resistant B-cell malignancies", Cell Research, 28(7):779-781, 2018.
Sun, Y. et al., "Degradation of Bruton's tyrosine kinase mutants by PROTACs for potential treatment of ibrutinib-resistant non-Hodgkin lymphomas", Leukemia, 33:2105-2110, 2019.
Swatek, K. N. et al., "Ubiquitin modifications," Cell Research, 26(4):399-422, 2016.
Thress, K. S. et al., "Acquired EGFR C797S mutation mediates resistance to AZD9291 in non-small cell lung cancer harboring EGFR T790M," Nature Medicine, 21(6):560-562, 2015.
Tinworth, C. P. et al., "PROTAC-mediated degradation of Bruton's tyrosine kinase is inhibited by covalent binding", ACS Chemical Biology, 14(3):342-347, 2019.
Toure, M. et al., "Small-Molecule PROTACS: New Approaches to Protein Degradation," Angew. Chem. Int. Ed., 55 (6):1966-1973, 2016.
Winter, G. E. et al., "Phthalimide conjugation as a strategy for in vivo target protein degradation," Science, 348 (6241):1376-1381, 2015.
Xu, Y. et al., "Acquired resistance of lung adenocarcinoma to EGFR-tyrosine kinase inhibitors gefitinib and erlotinib," Cancer Biology & Therapy, 9(8):572-582, 2010.
Yarden, Y. et al., "Untangling the ErbB signalling network," Nature Reviews Molecular Cell Biology, 2(2):127-137, 2001.

(56) References Cited

OTHER PUBLICATIONS

Yewale, C. et al., "Epidermal growth factor receptor targeting in cancer: a review of trends and strategies", Biomaterials, 34(34):8690-8707, 2013.
Zhang, H. et al., "Design, synthesis and biological evaluation of novel EGFR PROTACs targeting Del19/T790M/C797S mutation," ACS Medicinal Chemistry Letters, 13:278-283, 2022.
Zhang, H. et al., "Discovery of potent epidermal growth factor receptor (EGFR) degraders by proteolysis targeting chimera (PROTAC)", European Journal of Medicinal Chemistry, 189, p. 112061, 2020.
Zhang, X. et al., "Design and synthesis of selective degraders of EGFRL858R/T790M mutant", European Journal of Medicinal Chemistry, 192, p. 112199, 2020.
Zhang, X. et al., "Electrophilic PROTACs that degrade nuclear proteins by engaging DCAF16", Nat. Chem. Biol., 15 (7):737-746, 2019.

EGFR DEGRADERS AND METHODS OF USE

FIELD OF THE INVENTION

Disclosed herein are novel bifunctional compounds formed by conjugating EGFR inhibitor moieties with E3 ligase Ligand moieties, which function to recruit targeted proteins to E3 ubiquitin ligase for degradation, and methods of preparation and uses thereof.

BACKGROUND OF THE INVENTION

Proteolysis targeting chimera (PROTAC) consists of two covalently linked protein-binding molecules: one capable of engaging an E3 ubiquitin ligase, and the other that binds to the protein of interest (POI) a target meant for degradation (Sakamoto K M et al., *Proc. Natl. Acad. Sci.* 2001, 98: 8554-9; Sakamoto K. M. et al., *Methods Enzymol.* 2005; 399:833-847). Rather than inhibiting the target protein's enzymatic activity, recruitment of the E3 ligase to the specific unwanted proteins results in ubiquitination and subsequent degradation of the target protein by the proteasome. The whole process of ubiquitination and proteasomal degradation is known as the ubiquitin-proteasome pathway (UPP) (Ardley H. et al., *Essays Biochem.* 2005, 41, 15-30; Komander D. et al., *Biochem.* 2012, 81, 203-229; Grice G. L. et al., *Cell Rep.* 2015, 12, 545-553; Swatek K. N. et al., *Cell Res.* 2016, 26, 399-422). Proteasomes are protein complexes which degrade unneeded, misfolded or abnormal proteins into small peptides to maintain health and productivity of the cells. Ubiquitin ligases, also called an E3 ubiquitin ligase, directly catalyze the transfer of ubiquitin from the E2 to the target protein for degradation. Although the human genome encodes over 600 putative E3 ligases, only a limited number of E3 ubiquitin ligases have been widely applied by small molecule PROTAC technology: cereblon (CRBN), Von Hippel-Lindau (VHL), mouse double minute 2 homologue (MDM2) and cellular inhibitor of apoptosis protein (cIAP) (Philipp O. et al., *Chem. Biol.* 2017, 12, 2570-2578), recombinant Human Ring Finger Protein 114 (RNF114) (Spradlin, J. N. et al. *Nat. Chem. Biol.* 2019, 15, 747-755) and DDB1 And CUL4 Associated Factor 16 (DCAF16) (Zhang, X. et al. *Nat. Chem. Biol.* 2019, 15, 737-746). For example, cereblon (CRBN) forms an E3 ubiquitin ligase complex with damaged DNA binding protein 1 (DDB1) and Cullin-4A (CUL4A) to ubiquitinate a number of other proteins followed by the degradation via proteasomes. (Yi-An Chen, et al., *Scientific Reports* 2015, 5, 1-13). Immunomodulatory drugs (IMiDs), including thalidomide, lenalidomide, and pomalidomide, function as monovalent promoters of PPIs by binding to the cereblon (CRBN) subunit of the CRL4A$^{CRBN}$ E3 ligase complex and recruiting neosubstrate proteins. (Matyskiela, M. E. et al., *Nat Chem Biol* 2018, 14, 981-987.) As a consequence, the ability of thalidomide, and its derivatives, to recruit CRBN has been widely applied in proteolysis-targeting chimeras (PROTACs) related studies (Christopher T. et al. *ACS Chem. Biol.* 2019, 14, 342-347; Honorine L. et al, *ACS Cent. Sci.* 2016, 2, 927-934). PROTACs have great potential to eliminate protein targets that are "undruggable" by traditional inhibitors or are non-enzymatic proteins. (Chu T T. et al., *Cell Chem Biol.* 2016; 23:453-461. Qin C. et al., *J Med Chem* 2018; 61: 6685-6704. Winter G E. et al., *Science* 2015; 348:1376-1381.) In the recent years, PROTACs as useful modulators promote the selective degradation of a wide range of target proteins have been reported in antitumor studies. (Lu J. et al., *Chem Biol.* 2015; 22(6):755-763; Ottis P. et al., *Chem Biol.* 2017; 12(4):892-898; Crews C. M. et al., *J Med Chem.* 2018; 61(2):403-404; Neklesa T. K. et al., *Pharmacol Ther.* 2017, 174:138-144; Cermakova K. et al., *Molecules,* 2018.23(8); An S. et al., *EBioMedicine,* 2018; Lebraud H. et al., *Essays Biochem.* 2017; 61(5): 517-527; Sun Y. H. et al., *Cell Res.* 2018; 28:779-81; Toure M. et al., *Angew Chem Int Ed Engl.* 2016; 55(6):1966-1973; Yonghui Sun et al., *Leukemia*, volume 33, pages 2105-2110 (2019); Shaodong Liu et al., *Medicinal Chemistry Research*, volume 29, pages 802-808(2020); and has been disclosed or discussed in patent publications, e.g., US20160045607, US20170008904, US20180050021, US20180072711, WO2002020740, WO2014108452, WO2016146985, WO2016149668, WO2016197032, WO2016197114, WO2017011590, WO2017030814, WO2017079267, WO2017182418, WO2017197036, WO2017197046, WO2017197051, WO2017197056, WO2017201449, and WO2018071606.

Epidermal growth factor receptor (EGFR) that belongs to the ErbB family is a transmembrane receptor tyrosine kinase (RTK), which plays a fundamentally key role in cell proliferation, differentiation, and motility (Y. Yarden, et al., *Nat. Rev. Mol. Cell Biol.* 2001; 2:127-137). Homo- or heterodimerization of EGFR and other ErbB family members activates cytoplasmic tyrosine kinase domains to initiate intracellular signaling. Overexpression or activating mutations of EGFR are associated with the development of many types of cancers, such as pancreatic cancer, breast cancer, glioblastoma multiforme, head and neck cancer, and non-small cell lung cancer (Yewale C., et al. *Biomaterials.* 2013, 34 (34): 8690-8707). The activating mutations in the EGFR tyrosine kinase domain (L858R mutation and exon-19 deletion) have been identified as oncogenic drivers for NSCLC (Konduri, K., et al. *Cancer Discovery* 2016, 6 (6), 601-611). The first-generation EGFR tyrosine kinase inhibitors (EGFR-TKIs) gefitinib and erlotinib have been approved for NSCLC patients with EGFR activation mutations (M. Maemondo, *N. Engl. J Med.* 362 (2010) 2380-2388). Although most patients with EGFR mutant NSCLC respond to these therapies, patients typically develop resistance after an average of one year on treatment. There are several mechanisms of acquired resistance to gefitinib and erlotinib, including a secondary threonine 790 to methionine 790 mutation (T790M), which is also called "gatekeeper" T790M mutation (Xu Y., et al. *Cancer Biol Ther.* 2010, 9 (8): 572-582). Therefore, the second-generation EGFR-TKIs afatinib and the third-generation EGFR-TKIs osimertinib (AZD9291) were developed as irreversible EGFR inhibitors that bind to Cys797 for the treatment of patients with T790M mutation. In particular, osimertinib that largely spares WT EGFR has achieved a greater clinical response rate in NSCLC patients with EGFR T790M. However, several recent studies have reported a tertiary Cys797 to Ser797 (C797S) point mutation with osimertinib clinical therapy (Thress K S, et al. *Nat. Med.* 2015, 21 (6): 560-562). There is a need for drugs which can overcome EGFR (C797S) resistance obstacle in non-small cell lung cancer (NSCLC). EGFR-Targeting PROTACs serve as a potential strategy to overcome drug resistance mediated by these mutants, which has been disclosed or discussed in patent publications, e.g. WO2018119441, WO2019149922, WO2019183523, WO2019121562 and US20190106417.

Although, a number of EGFR-targeting PROTACs which were designed to degrade EGFR mutant proteins have been published (Zhang H., et al. *ACS Med. Chem. Lett.* 2022, doi.org/10.1021/acsmedchemlett.1c00645; Qu X., et al. *Eur. J. Med. Chem.* 2021, 218, 113328; Zhang X., et al. *Eur. J.*

*Med. Chem.* 2020, 192, 112199; Zhang H, et al. *Eur. J. Med. Chem.* 2020, 189, 112061; Lu X, *Med. Res. Rev.* 2018, 38(5):1550-1581. He K., et al. *Bioorg. Med. Chem. Lett.* 2020, 15, 127167). Most of the published molecules are based on the first, second, and third generations of EGFR inhibitors. However, there were no data which showed those EGFR-Targeting PROTACs degrading all the main EGFR mutations, Such as Del19, L858R, Del19/T790M, L858R/T790M, Del19/T790M/C797S, L858R/T790M/C797S.

The present application provides novel bifunctional compounds and compositions for the treatment of serious diseases.

SUMMARY OF THE INVENTION

One objective of the present invention is to provide compounds and derivatives formed by conjugating EGFR inhibitor moieties with E3 ligase Ligand moieties, which function to recruit targeted proteins to E3 ubiquitin ligase for degradation, and methods of preparation and uses thereof.

The following aspects are for illustration only and should not be constructed as limiting the invention.

Aspect 1. A compound of Formula (X):

(X)

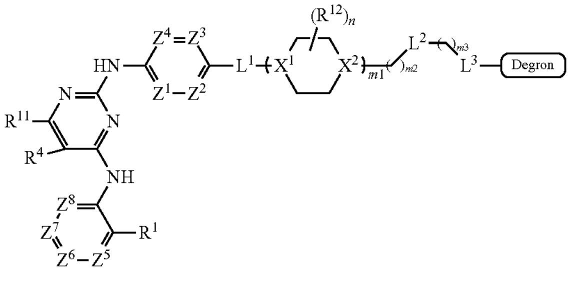

or a N-oxide thereof, or a pharmaceutically acceptable salt thereof, or a stereoisomer thereof, or a deuterated analog thereof, wherein:

- $R^1$ is selected from —$P(O)R^{1a}R^{1b}$, —$SO_2R^{1a}$, —$SO_2$—$NR^{1a}R^{1b}$ or —$N(R^{1a})$—$SO_2R^{1b}$, wherein $R^{1a}$ and $R^{1b}$ are each independently selected from hydrogen, —$C_{1-8}$ alkyl or $C_3$-$C_8$cycloalkyl, said —$C_{1-8}$alkyl or $C_3$-$C_8$cycloalkyl is optionally substituted with at least one halogen;
- $Z^5$ is selected from —$CR^2$, or N;
- $Z^6$ is selected from —$CR^3$, or N;
- $Z^7$ is selected from —$CR^9$, or N;
- $Z^8$ is selected from —$CR^{10}$, or N;
- at least one of $Z^5$, $Z^6$, $Z^7$ and $Z^8$ is N;
- $R^2$ and $R^3$ are each independently selected from hydrogen, halogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl, —CN, —$OR^{2a}$, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$, or —$NR^{2a}SO_2R^{2b}$, wherein each of —$C_8$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{2d}$; or
- $R^2$ and $R^3$ together with the carbon atoms to which they are attached, form a 5-6 membered saturated or partially or completely unsaturated (preferably completely unsaturated, i.e., aromatic) ring, said ring comprising 0-3 heteroatoms independently selected from nitrogen, oxygen or sulfur; said ring is optionally substituted with at least one substituent $R^{2e}$;
- $R^{2e}$, at each occurrence, is independently hydrogen, halogen, —$C_{1-8}$alkyl, —$C_{2-8}$alkenyl, —$C_{2-8}$alkynyl, —$C_{1-8}$ alkoxy, —$C_3$-$C_8$cycloalkyl, oxo, 3- to 8-membered heterocyclyl, $C_6$-$C_{12}$aryl, 5- to 12-membered heteroaryl, —CN, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$ or —$NR^{2a}SO_2R^{2b}$ wherein each of —$C_{1-8}$alkyl, —$C_{2-8}$alkenyl, —$C_{2-8}$ alkynyl, —$C_{1-8}$alkoxy, $C_3$-$C_8$cycloalkyl, 3- to 8-membered heterocyclyl, $C_6$-$C_{12}$aryl or 5- to 12-membered heteroaryl is optionally substituted with at least one substituent $R^{2d}$;
- $R^{2a}$ and $R^{2b}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl or 5- to 12-membered heteroaryl;
- $R^{2d}$, at each occurrence, is independently halogen, —OH, —$C_{1-8}$alkyl, —$C_{1-8}$alkoxy, $C_{1-8}$alkoxy-$C_{1-8}$alkyl-, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl;
- $R^4$ is selected from hydrogen, halogen, —$C_{1-8}$alkyl, —$C_{2-8}$alkenyl, —$C_{2-8}$alkynyl, —$C_{1-8}$alkoxy, —$C_3$-$C_8$cycloalkyl, 3- to 8-membered heterocyclyl, —$C_6$-$C_{12}$aryl, 5- to 12-membered heteroaryl, —CN, —$SO_2R^{4a}$, —$SO_2NR^{4a}R^{4b}$, —$COR^{4a}$, —$CO_2R^{4a}$, $CONR^{4a}R^{4b}$, —$NR^{4a}R^{4b}$, —$NR^{4a}COR^{4b}$, —$NR^{4a}CO_2R^{4b}$, or —$NR^{4a}SO_2R^{4b}$, wherein each of —$C_{1-8}$alkyl, —$C_{2-8}$alkenyl, —$C_{2-8}$alkynyl, —$C_{1-8}$ alkoxy, —$C_3$-$C_8$cycloalkyl, 3- to 8-membered heterocyclyl, —$C_6$-$C_{12}$aryl or 5- to 12-membered heteroaryl is optionally substituted with halogen, —$C_{1-8}$alkoxy, —$C_{1-8}$alkyl, —$C_{2-8}$alkenyl, —$C_{2-8}$alkynyl, —$C_3$-$C_8$cycloalkyl, 3- to 8-membered heterocyclyl, $C_6$-$C_{12}$aryl, 5- to 12-membered heteroaryl, oxo, —CN, —$OR^{4c}$, —$SO_2R^{4c}$, —$SO_2NR^{4c}R^{4d}$, —$COR^{4c}$, —$CO_2R^{4c}$, —$CONR^{4c}R^{4d}$, —$NR^{4c}R^{4d}$, —$NR^{4c}COR^{4d}$, —$NR^{4c}CO_2R^{4d}$, or —$NR^{4c}SO_2R^{4d}$;
- $R^{4a}$, $R^{4b}$, $R^{4c}$ and $R^{4d}$ are each independently hydrogen, —$C_{1-8}$alkyl, —$C_{2-8}$alkenyl, —$C_{2-8}$alkynyl, $C_3$-$C_8$cycloalkyl, 3- to 8-membered heterocyclyl, —$C_6$-$C_{12}$aryl, or 5- to 12-membered heteroaryl;
- $R^9$, $R^{10}$, $R^{11}$ and $R^{12}$ are each independently selected from hydrogen, halogen, —$C_{1-8}$alkyl, —$C_{2-8}$alkenyl, —$C_{2-8}$ alkynyl, —$NR^{9a}R^{9b}$, —$OR^{9a}$, oxo, —$C_3$-$C_8$cycloalkyl, 3- to 8-membered heterocyclyl, —$C_6$-$C_{12}$aryl, 5- to 12-membered heteroaryl, or —CN, wherein each of —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl is optionally substituted with at least one substituent $R^{9c}$; or
- two $R^{12}$ together with the carbon atoms to which they are attached, form a 3- to 12-membered ring, said ring comprising 0-3 heteroatoms independently selected from nitrogen, oxygen or sulfur; said ring is optionally substituted with at least one substituent $R^{9c}$;
- $R^{9a}$ and $R^{9b}$ are each independently selected from hydrogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{9d}$; or $R^{9c}$ and $R^{9d}$ are each independently halogen, hydroxy, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl, —CN or $NR^{9aa}R^{9bb}$, wherein each of said —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl is optionally substituted with at least one hydrogen, halogen, hydroxy, —$C_{1-8}$alkyl, —$C_{1-8}$alkoxy, —CN, —$NH_2$ or oxo, and $R^{9aa}$ and $R^{9bb}$ are each independently hydrogen or $C_{1-8}$alkyl;

$Z^1$, $Z^2$, $Z^3$ and $Z^4$ are each independently selected from —$CR^z$, or N;

$R^Z$, at each occurrence, is independently selected from hydrogen, halogen, —$C_{1-8}$alkyl, —$C_{2-8}$alkenyl, —$C_{2-8}$ alkynyl, —$NR^{Za}R^{Zb}$, —$OR^{Za}$, —$SR^{Za}$, $C_3$-$C_8$cycloalkyl, 3- to 8-membered heterocyclyl, $C_6$-$C_{12}$aryl, 5- to 12-membered heteroaryl, or CN, wherein each of —$C_{1-8}$alkyl, —$C_{2-8}$alkenyl, —$C_{2-8}$ alkynyl, $C_3$-$C_8$cycloalkyl, 3- to 8-membered heterocyclyl, $C_6$-$C_{12}$aryl, or 5- to 12-membered heteroaryl is optionally substituted with at least one $R^{Zc}$.

$R^{Za}$ and $R^{Zb}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl is optionally substituted with at least one substituent $R^{Zd}$;

$R^{Zc}$ and $R^{Zd}$ are each independently halogen, hydroxy, —$C_{1-8}$alkyl, —$C_{2-8}$alkenyl, —$C_{2-8}$alkynyl, —$C_{1-8}$ alkoxy, $C_{1-8}$alkoxy-$C_{1-8}$alkyl-, —$C_{2-8}$alkenyl, —$C_{2-8}$ alkynyl, $C_3$-$C_8$cycloalkyl, 3- to 8-membered heterocyclyl, $C_6$-$C_{12}$aryl, or 5- to 12-membered heteroaryl;

$L^1$ is selected from a single bond, —O—, —$SO_2$—, —C(O)—, —$NR^{L1a}$, —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—CO—$C_{1-8}$alkylene-$**^{L1}$, $*^{L1}$—$C_{1-8}$alkylene-CO—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L1}$, $*^{L1}$—$NR^{L1a}$C(O)—$**^{L1}$, $*^{L1}$—C(O)$NR^{L1a}$—$**^{L1}$, —$C_{1-8}$alkylene-, —$C_{2-8}$alkenylene-, —$C_{2-8}$alkynylene-. —$[O(CR^{L1a}R^{L1b})_{m4}]_{m5}$—,

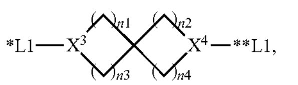

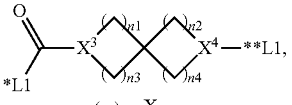

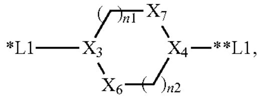

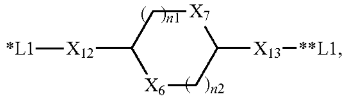

-continued

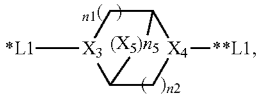

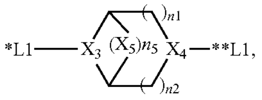

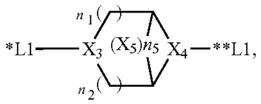

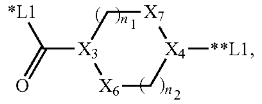

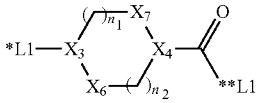

or

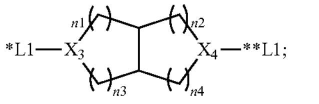

wherein each of said —$C_3$-$C_8$cycloalkylene-, $*^{L1}$—O—$C_{1-8}$alkylene-$**^{L1}$, $*^{L1}C_{1-8}$alkylene-O—$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—CO—$C_{1-8}$alkylene-$**^{L1}$, $*^{L1}$—$C_{1-8}$ alkylene-CO—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L1}$, —$C_{1-8}$alkylene-, —$C_{2-8}$alkenylene-, —$C_{2-8}$alkynylene-,

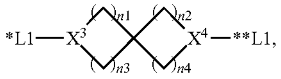

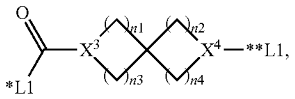

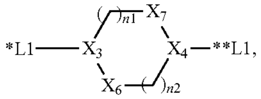

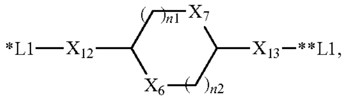

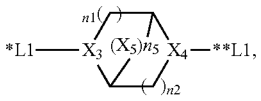

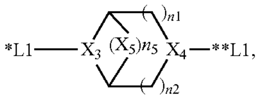

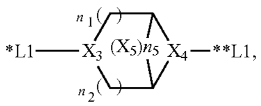

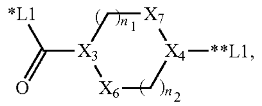

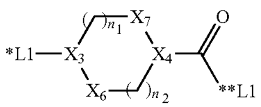

or

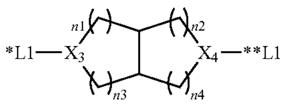

optionally substituted with at least one $R^{L1c}$;

wherein $*^{L1}$ refers to the position attached to

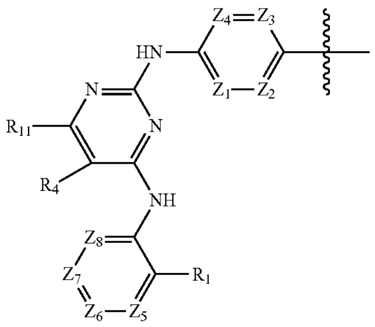

moiety, and $**^{L1}$ refers to the position attached to the

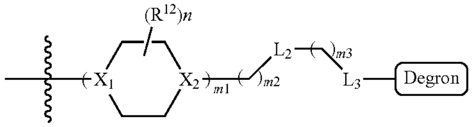

moiety;

$R^{L1a}$ and $R^{L1b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L1d}$;

each of said $R^{L1c}$ and $R^{L1d}$ are independently halogen, hydroxy, —$C_{1-8}$alkyl, —$C_{1-8}$alkoxy, $C_{1-8}$alkoxy-$C_{1-8}$ alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

$L^2$ is selected from a single bond, —O—, —$SO_2$—, —CO—, —$NR^{L2a}$—, —$C_3$-$C_8$cycloalkylene-, $*^{L2}$—O—$C_{1-8}$alkylene-$**^{L2}$, $*^{L2}$-$C_{1-8}$alkylene-O—$**^{L2}$, $*^{L2}$—$SO_2C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$ alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O)—$**^{L2}$, $*^{L2}$—C(O)$NR^{L2a}$, $**^{L2}$—$C_{1-8}$alkylene-, —$C_{2-8}$alkenylene-, —$C_{2-8}$alkynylene-, —[O$(CR^{L2a}R^{L2b})_{m4}]_{m5}$—,

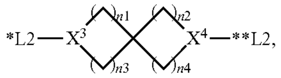

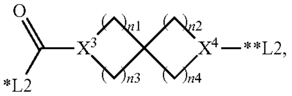

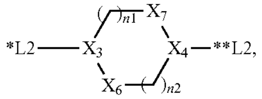

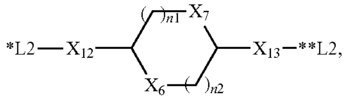

-continued

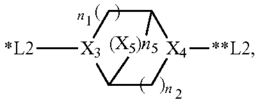

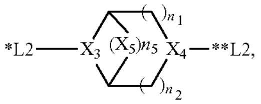

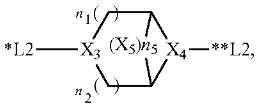

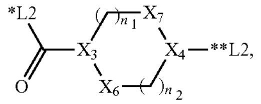

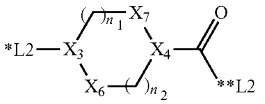

or

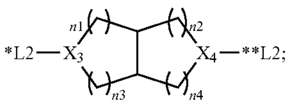

wherein each of said —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$ alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, —$C_{1-8}$alkylene-, —$C_{2-8}$alkenylene-, —$C_{2-8}$alkynylene-,

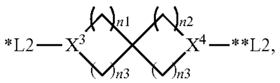

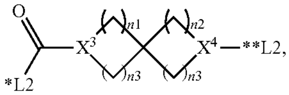

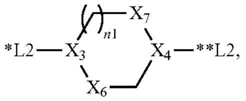

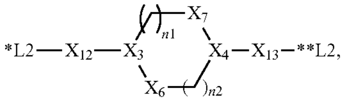

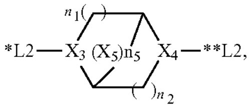

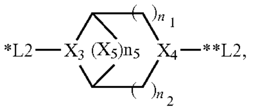

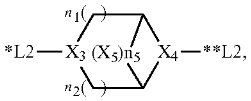

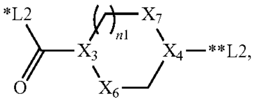

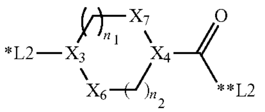

or

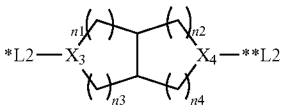

is optionally substituted with at least one substituent $R^{L2c}$;

wherein $*^{L2}$ refers to the position attached to

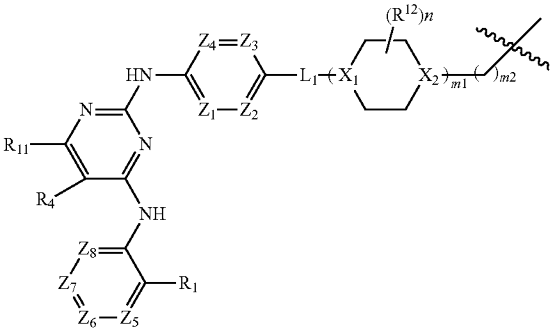

moiety, and $**^{L2}$ refers to the position attached to the

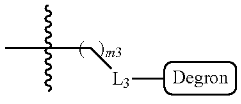

moiety;

$R^{L2a}$ and $R^{L2b}$ are each independently selected from hydrogen, $-C_{1-8}$alkyl, $-C_{2-8}$alkenyl, $-C_{2-8}$alkynyl, $C_3$-$C_8$cycloalkyl, 3- to 8-membered heterocyclyl, $C_6$-$C_{12}$aryl or 5- to 12-membered heteroaryl, wherein each of said $-C_{1-8}$alkyl, $-C_{2-8}$alkenyl, $-C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L2d}$;

each of said $R^{L2c}$ and $R^{L2d}$ are independently halogen, hydroxy, $-C_{1-8}$alkyl, $-C_{1-8}$alkoxy, $C_{1-8}$alkoxy-$C_{1-8}$ alkyl-, $-C_{2-8}$alkenyl, $-C_{2-8}$alkynyl, $C_3$-$C_8$cycloalkyl, 3- to 8-membered heterocyclyl, $C_6$-$C_{12}$aryl, 5- to 12-membered heteroaryl or oxo;

$L^3$ is selected from a single bond, —O—, $-SO_2-$, —CO—, $-NR^{L3a}-$, $C_3$-$C_8$cycloalkylene-, $*^{L3}$—O—$C_{1-8}$alkylene-$**^{L3}$, $*^{L3}$-$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$-$C_{1-8}$alkylene-CO—$**^{L3}$, $*^{L3}$—$NR^{L3a}$—$C_{1-8}$alkylene-$**^{L3}$, $*^{L3}$—$C_{1-8}$ alkylene-$NR^{L3a}$—$**^{L3}$, $*^{L3}$—$NR^{L3a}C(O)$—$**^{L3}$, $*^{L3}$-$C(O)NR^{L3a}$—$**^{L3}$, $-C_{1-8}$alkylene-, $-C_{2-8}$alkenylene-, $-C_{2-8}$alkynylene-, $-[O(CR^{L3a}R^{L3b})_{m4}]_{m5}-$,

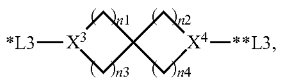

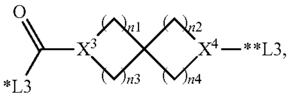

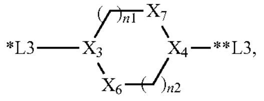

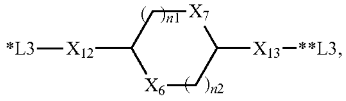

-continued

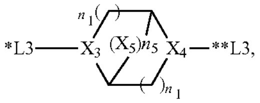

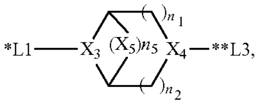

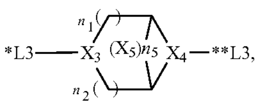

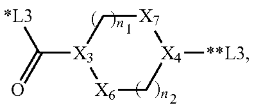

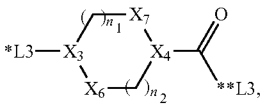

or

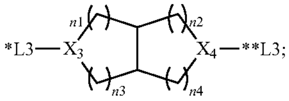

wherein each of said $-C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$ alkylene-CO—$**^{L3}$, $*^{L3}$-$NR^{L3a}$—$C_{1-8}$alkylene-$**^{L3}$, $*^{L3}$—$C_{1-8}$alkylene-$NR^{L3a}$, $**^{L3}$, $-C_{1-8}$alkylene-, $-C_{2-8}$alkenylene-, $-C_{2-8}$alkylene-,

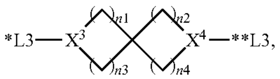

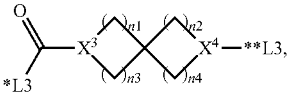

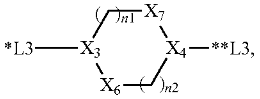

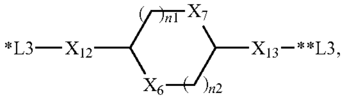

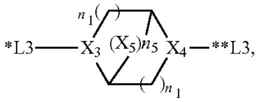

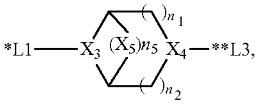

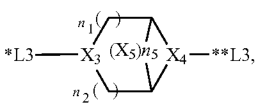

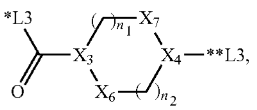

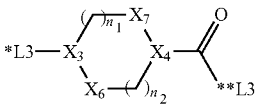

or

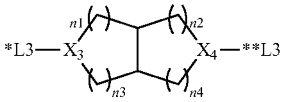

is optionally substituted with at least one substituent $R^{L3c}$;

wherein $*^{L3}$ refers to the position attached to

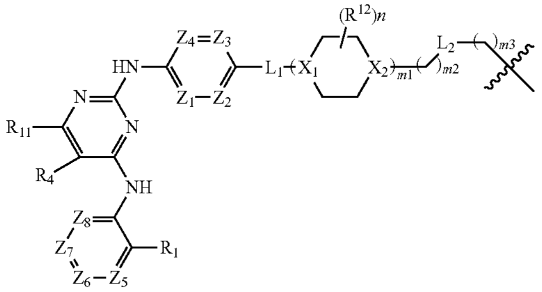

moiety, and $**^{L3}$ refers to the position attached to the

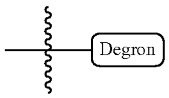

moiety;

$R^{L3a}$ and $R^{L3b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L3d}$;

each of said $R^{L3c}$ and $R^{L3d}$ are independently halogen, hydroxy, —$C_{1-8}$alkyl, —$C_{1-8}$alkoxy, $C_{1-8}$alkoxy-$C_{1-8}$ alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

Degron is selected from

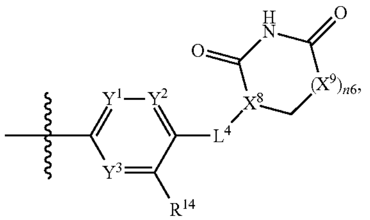

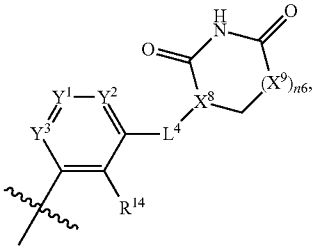

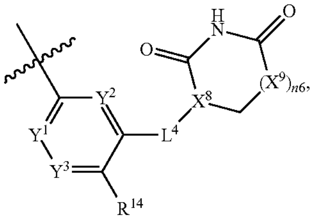

-continued

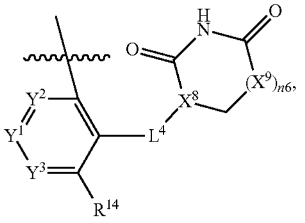

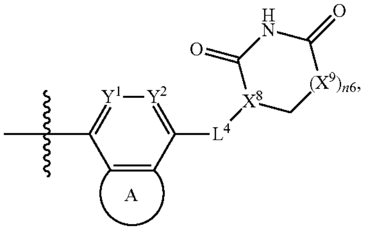

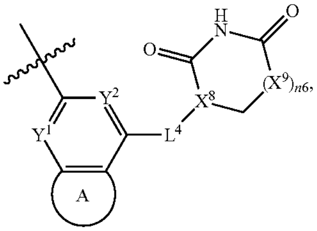

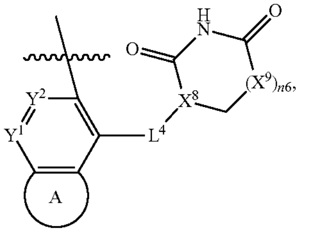

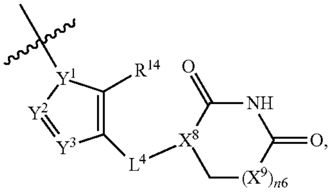

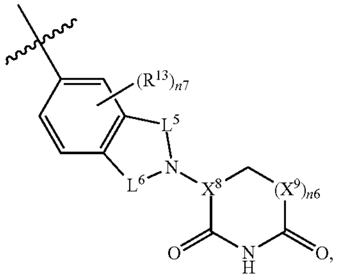

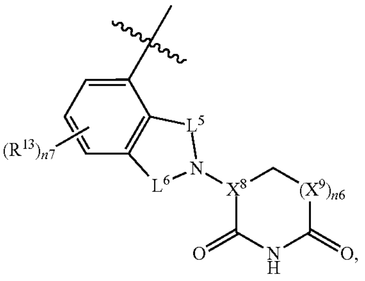

-continued
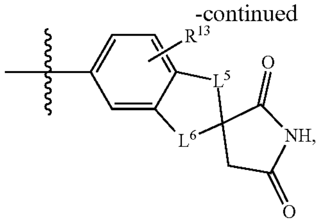
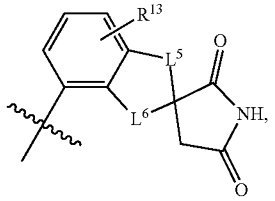
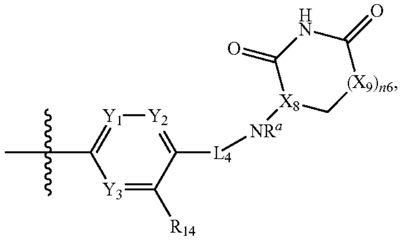
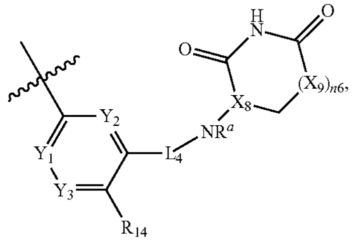
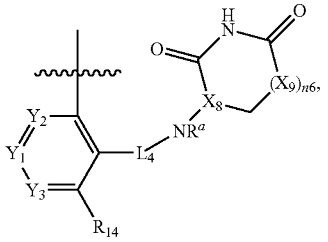
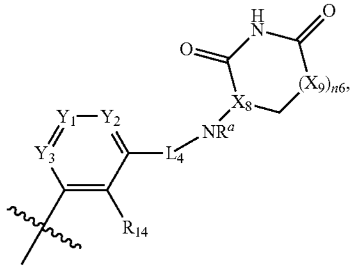
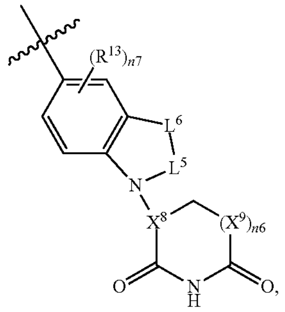
-continued
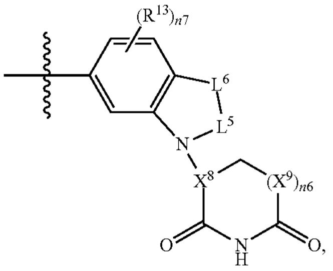
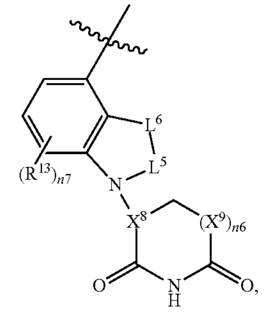
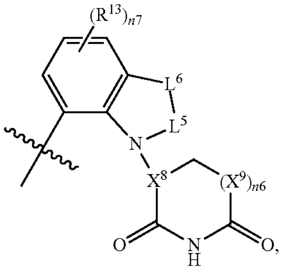
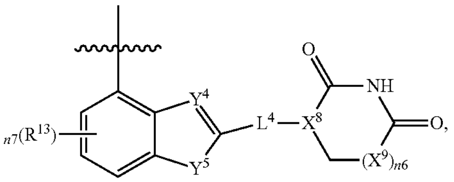
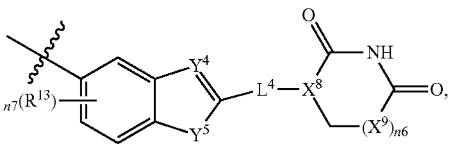
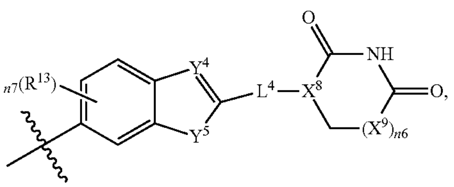
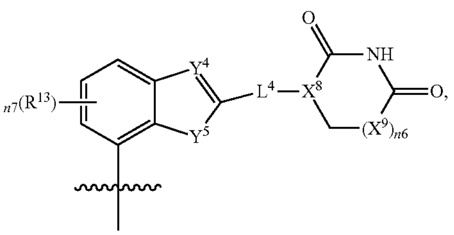

-continued

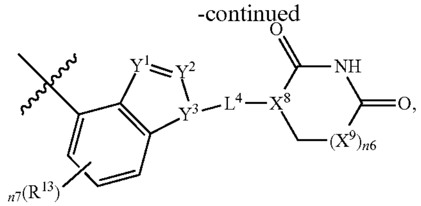

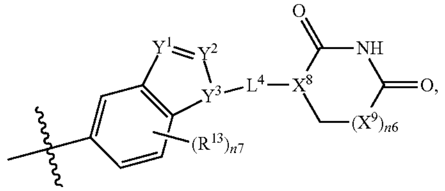

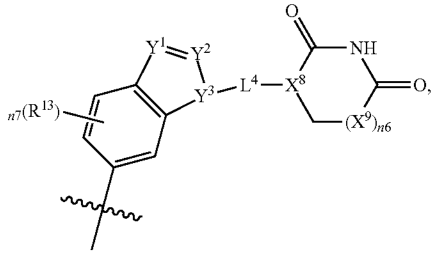

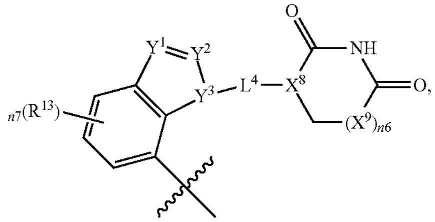

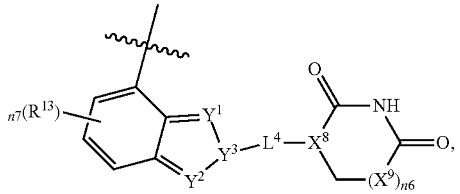

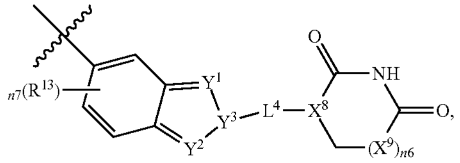

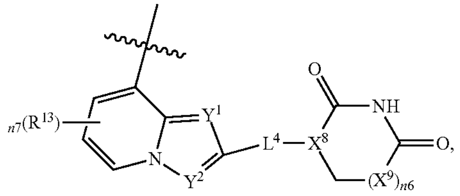

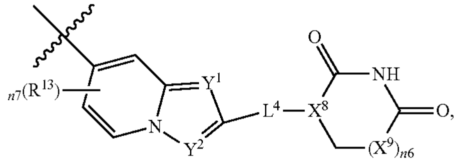

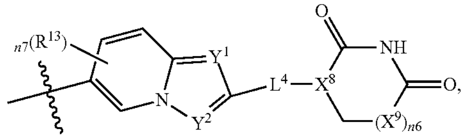

or

-continued

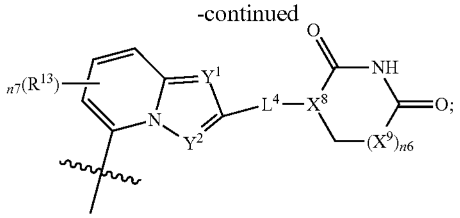

Ring A is selected from 3-12 membered cycloalkyl, 3-12 membered heterocyclyl, aryl, or heteroaryl;

$R^{13}$ and $R^{14}$ are independently selected from hydrogen, halogen, CN, —$C_{1-8}$alkyl, —$C_{2-8}$alkenyl, —$C_{2-8}$alkynyl, —$C_{1-8}$alkoxy, $C_3$-$C_8$cycloalkyl, 3- to 8-membered heterocyclyl, $C_6$-$C_{12}$aryl or 5- to 12-membered heteroaryl; said each —$C_{1-8}$alkyl, —$C_{2-8}$alkenyl, —$C_{2-8}$ alkynyl, —$C_{1-8}$alkoxy, $C_3$-$C_8$cycloalkyl, 3- to 8-membered heterocyclyl, $C_6$-$C_{12}$aryl or 5- to 12-membered heteroaryl is optionally substituted with at least one substituent halogen, —$C_{1-8}$alkyl, $C_{1-8}$alkoxy-$C_{1-8}$alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

$X^1$, $X^2$, $X^3$, $X^4$ and $X^8$ are each independently selected from —$CR^a$, or N;

$X^5$, $X^6$, $X^7$ and $X^9$ are each independently selected from —$NR^a$—, —O—, —S— and —$CR^aR^b$—;

$X^{12}$ and $X^{13}$ are each independently selected from —$NR^a$— and —O—;

$L^4$, $L^5$ and $L^6$ are each independently selected from a single bond, —O—, —$NR^a$—, —$(CR^aR^b)_{n8}$—, —$O(CR^aR^b)_{n8}$—, —$NR^a(CR^aR^b)_{n8}$— or —C(O)—;

$Y^1$, $Y^2$, $Y^3$ and $Y^4$ are each independently selected from $CR^a$ or N;

$Y^5$ is selected from $NR^a$, O or S;

$R^a$ and $R^b$ are each independently selected from hydrogen (H, D or T), halogen, CN, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl, wherein each of said —$C_{1-8}$ alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl is optionally substituted with at least one substituent halogen, hydroxy, halogen, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl; or $R^a$ and $R^b$ together with the carbon atoms to which they are attached, form a 3- to 12-membered ring, said ring comprising 0-3 heteroatoms independently selected from nitrogen, oxygen or sulfur; said ring is optionally substituted with at least one substituent halogen, hydroxy, —$C_{1-8}$alkyl, —$C_{2-8}$alkenyl, —$C_{2-8}$alkynyl, —$C_{1-8}$alkoxy, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

$m_1$ is 0 or 1;

$m_2$ and $m_3$ are each independently 0, 1, 2, 3, 4, 5, 6, 7 or 8;

$m_4$ and $m_5$ are each independently 0, 1, 2 or 3;

n, $n_1$, $n_2$, $n_3$, $n_4$ and $n_5$ are each independently 0, 1, 2 or 3; and $n_6$ is 0, 1, 2, 3 or 4

$n_7$ is 0, 1, 2 or 3;

$n_8$ is 0, 1, 2, 3, 4, 5, 6, 7 or 8.

Aspect 2. The compound of Aspect 1, wherein $R^1$ is selected from —$P(O)R^{1a}R^{1b}$ or —$N(R^{1a})$—$SO_2R^{1b}$, wherein $R^{1a}$ and $R^{1b}$ are each independently selected from hydrogen, —$C_{1-8}$alkyl (preferably —$CH_3$, —$C_2H_5$, —$C_3H_7$, —$C_4H_9$ or —$C_5H_{11}$; more preferably —$CH_3$, —$CH_2CH_3$, —$CH_2CH_2CH_3$, -iso-$C_3H_7$, —$CH_2CH_2CH_2CH_3$, -iso-$C_4H_9$, -sec-$C_4H_9$ or -tert-$C_4H_9$) or $C_3$-$C_8$cycloalkyl (preferably cyclopropyl, cyclobutyl or cyclopentyl).

Aspect 3. The compound of any one of Aspects 1-2, wherein $R^1$ is selected from —$P(O)(CH_3)_2$, —NH—$SO_2CH_3$ or —$N(CH_3)$—$SO_2CH_3$.

Aspect 4. The compound of any one of Aspects 1-3, wherein one of $Z^7$ and $Z^8$ is N.

Aspect 5. The compound of any one of Aspects 1-4, wherein $Z^7$ is N.

Aspect 6. The compound of any one of Aspects 1-5, wherein one of $Z^7$ and $Z^8$ is N, $Z^5$ is —$CR^2$, and $Z^6$ is —$CR^3$.

Aspect 7. The compound of any one of Aspects 1-6, wherein $R^2$ and $R^3$ are each independently selected from hydrogen, —F, —Cl, —Br, —I, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, $C_6$-$C_{12}$aryl, 5- to 12-membered heteroaryl, —CN, —$OR^{2a}$, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$, or —$NR^{2a}SO_2R^{2b}$, wherein each of methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, $C_6$-$C_{12}$aryl or 5- to 12-membered heteroaryl is optionally substituted with at least one substituent $R^{2d}$, $R^{2a}$ and $R^{2b}$ are each independently selected from hydrogen, methyl, ethyl, propyl, butyl, pentyl, hexyl, heptyl, octyl, methoxy, ethoxy, propoxy, butoxy, pentoxy, hexoxy, heptoxy, octoxy, $C_{1-8}$alkoxy-$C_{1-8}$alkyl-, cyclopropyl, cyclobutyl, cyclopentyl, cyclohexyl, cycloheptyl, cyclooctyl, 3- to 8-membered heterocyclyl, phenyl or 5- to 12-membered heteroaryl;

$R^{2d}$, at each occurrence, is independently halogen, —OH, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl.

Aspect 8. The compound of any one of Aspects 1-7, wherein $R^2$ and $R^3$ are each independently selected from hydrogen, halogen, methyl, ethyl, propyl, butyl, pentyl, hexyl, heptyl or octyl, preferably selected from —H, —F, —Cl, —Br, —I, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$.

Aspect 9. The compound of any one of Aspects 1-6, wherein when $Z^5$ is —$CR^2$ and $Z^6$ is —$CR^3$, wherein $R^2$ and $R^3$ together with the carbon atoms to which they are attached, form a 5 or 6 membered unsaturated (preferred aromatic) ring, said ring comprising 0, 1 or 2 heteroatoms independently selected from nitrogen, oxygen or sulfur; said ring is optionally substituted with at least one substituent $R^{2e}$;

$R^{2e}$, at each occurrence, is independently hydrogen, —F, —Cl, —Br, —I, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl or oxo, wherein each of methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl or cyclooctyl is optionally substituted with at least one substituent $R^{2d}$;

$R^{2d}$, at each occurrence, is independently —F, —Cl, —Br, —I, —OH, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl or phenyl.

Aspect 10. The compound of any one of Aspects 1-9, wherein the

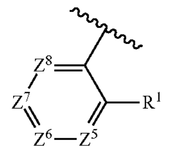

moiety is

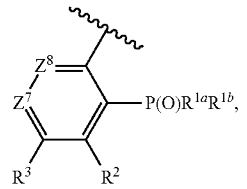

wherein $R^2$, $R^3$, $Z^7$, $Z^8$, $R^{1a}$ and $R^{1b}$ are defined as in Aspect 1.

Aspect 11. The compound of Aspect 10, wherein the

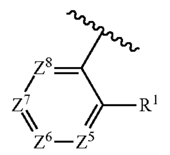

moiety is

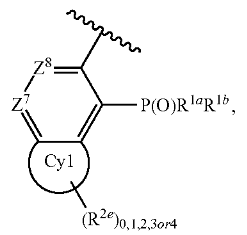

wherein Cy1 is a 5-6 membered unsaturated (preferred aromatic) or saturated ring, said ring comprising 0-3 heteroatoms independently selected from nitrogen, oxygen or sulfur;

preferable, the

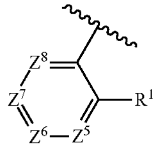

moiety is

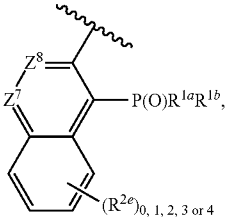 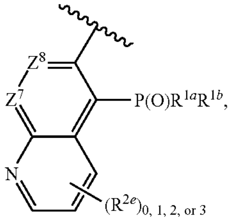

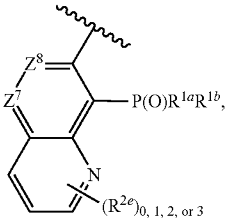 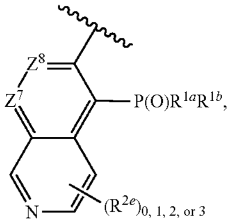

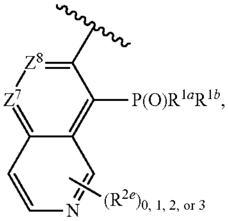 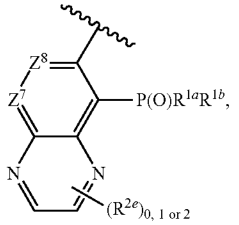

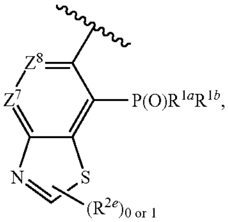 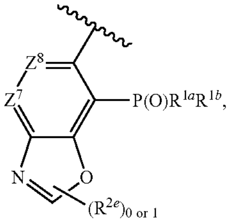

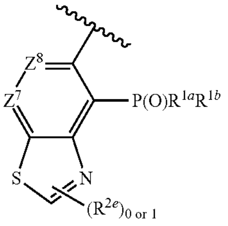 or 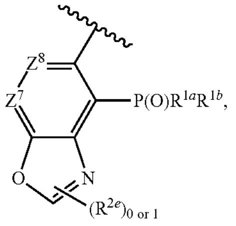

wherein $R^{2e}$, $Z^7$, $Z^8$, $R^{1a}$ and $R^{1b}$ are defined as in Aspect 1.

Aspect 12. The compound any of Aspects 1-11, wherein $R^{2e}$ at each occurrence, is independently hydrogen, —F, —Cl, —Br, —I, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl or oxo, wherein each of methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl or cyclooctyl is optionally substituted with at least one substituent $R^{2d}$.

$R^{2d}$, at each occurrence, is independently —F, —Cl, —Br, —I, —OH, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl or phenyl.

Aspect 13. The compound any one of Aspects 1-12, wherein $R^{2e}$ at each occurrence, is independently hydrogen, —F, —Cl, —Br, —I, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CF_3$,

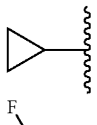, 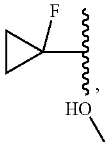, 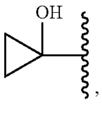,

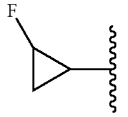 or 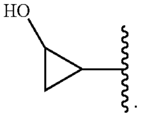.

Aspect 14. The compound of one of Aspects 1-13, wherein the

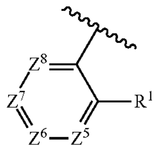

moiety is

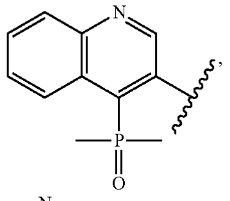, 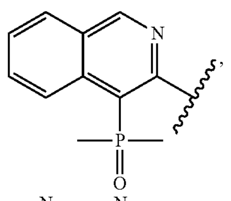,

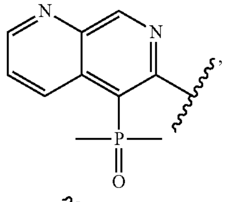, 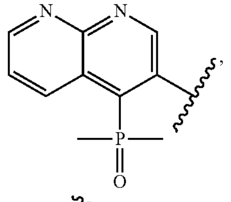,

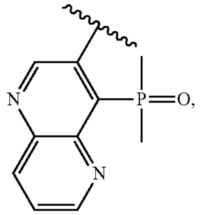 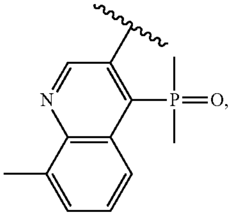

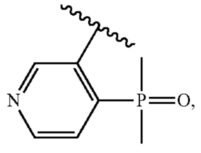 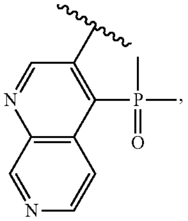

-continued

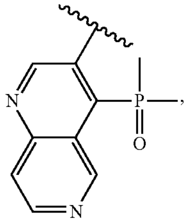
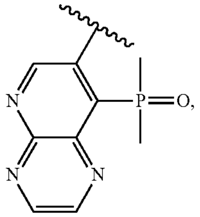

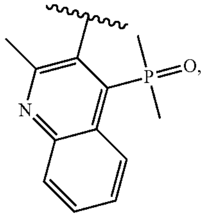
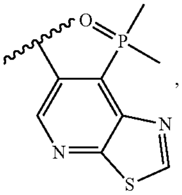

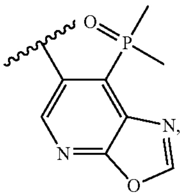
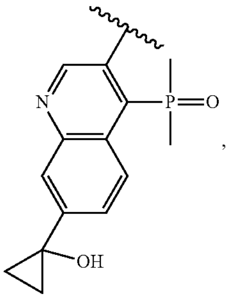

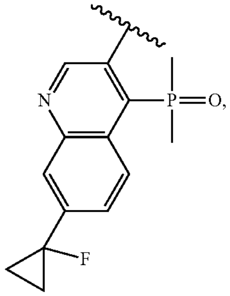
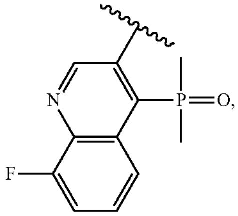

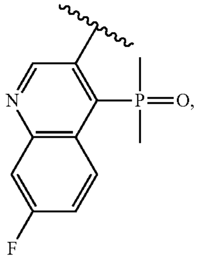
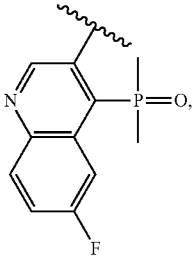

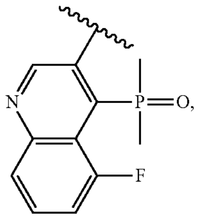
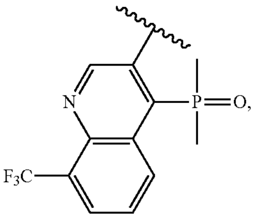

-continued

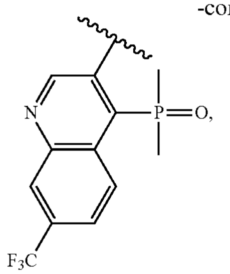
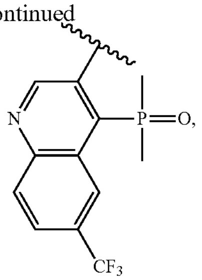

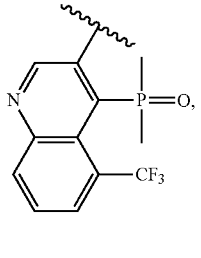
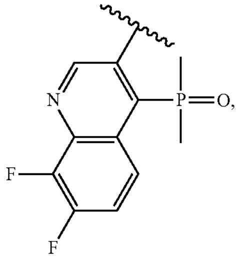

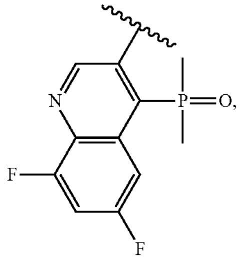
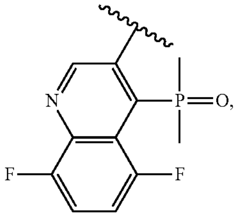

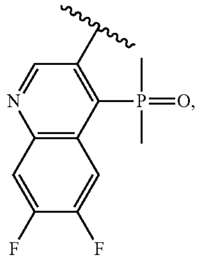
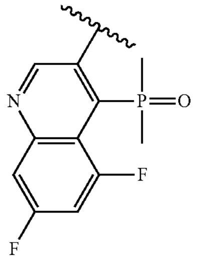
or

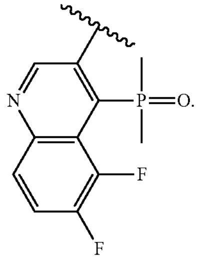

Aspect 15. The compound of any one of Aspects 1-14, wherein $R^9$, $R^{10}$, $R^{11}$ and $R^{12}$ are each independently selected from hydrogen, —F, —Cl, —Br, —I, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl, —$NH_2$ or oxo, wherein each of methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl is optionally substituted with at least one substituent $R^{9c}$; or two $R^{12}$ together with the carbon atoms to which they are attached, form a 3, 4, 5, 6, 7 or 8-membered ring, said ring comprising 0, 1, 2 or 3 heteroatoms independently selected from nitrogen, oxygen or sulfur; said ring is optionally substituted with at least one substituent $R^{9c}$;

$R^{9c}$ is independently —F, —Cl, —Br, —I, hydroxy, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl, —$C_{2-8}$ alkenyl, —$C_{2-8}$alkynyl, 3- to 8-membered heterocyclyl, phenyl, 5- to 12-membered heteroaryl, $NH_2$, or —$NHCH_3$.

Aspect 16. The compound of any one of Aspects 1-15, wherein $R^9$, $R^{10}$, $R^{11}$ and $R^{12}$ are each independently selected from hydrogen, F, Cl, Br, —$NH_2$, —$CH_3$, —$C_2H_5$, —$C_3H_7$, —$CH_2F$, —$CHF_2$, —$CF_3$, —$C_4H_9$, —$C_5H_{11}$, —$OCH_3$, —$OC_2H_5$, —$OC_3H_7$, —$OC_4H_9$, —$OC_5H_{11}$, —CN, cyclopropyl or oxo; or two $R^{12}$ together with the carbon atoms to which they are attached, form a 3, 4, 5, 6, 7 or 8-membered ring, said ring comprising 0, 1, 2 or 3 heteroatoms independently selected from nitrogen, oxygen or sulfur; said ring is optionally substituted with at least one substituent —H, —F, —Cl, —Br, —I, methyl, ethyl, propyl, butyl, —$NH_2$, —$NHCH_3$, —OH, —$OCH_3$, —$OC_2H_5$, cyclopropyl, cyclobutyl, cyclopentyl, or cyclohexyl.

Aspect 17. The compound of any one of Aspects 1-16, wherein $R^4$ is selected from —H, —F, —Cl, —Br, —I, —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, cyclopropyl, cyclobutyl, cyclopentyl, cyclohexyl, cycloheptyl, cyclooctyl, phenyl or —CN, wherein each of —$CH_3$, —$C_2H_5$, —$C_3H_7$, —$C_4H_9$, —$C_5H_{11}$, —$OCH_3$, —$OC_2H_5$, —$OC_3H_7$, —$OC_4H_9$, —$OC_5H_{11}$, cyclopropyl, cyclobutyl, cyclopentyl, cyclohexyl, cycloheptyl, cyclooctyl or phenyl is optionally substituted with —F, —Cl, —Br, —I, —$C_{1-8}$alkyl, —$C_{2-8}$ alkenyl, —$C_{2-8}$alkynyl, —$C_3$-$C_8$cycloalkyl, 3- to 8-membered heterocyclyl, $C_6$-$C_{12}$aryl, 5- to 12-membered heteroaryl, oxo, —CN, —$OR^{4c}$, —$SO_2R^{4c}$, —$SO_2NR^{4c}R^{4d}$, —$COR^{4c}$, —$CO_2R^{4c}$, —$CONR^{4c}R^{4d}$, —$NR^{4c}R^{4d}$, —$NR^{4c}COR^{4d}$, —$NR^{4c}CO_2R^{4d}$, or —$NR^{4c}SO_2R^{4d}$;

$R^{4c}$ and $R^{4d}$ are each independently hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl.

Aspect 18. The compound of any one of Aspects 1-17, wherein $R^4$ is selected from —F, —Cl, —Br, —I, —$CH_3$, —$CF_3$, —$CH_2F$, or —$CHF_2$.

Aspect 19. The compound of any one of Aspects 1-18, wherein U is selected from a single bond, —O—, —$SO_2$—, —C(O)—, —$NR^{L1a}$—, —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—$SO_2$—$C_{1-8}$alkylene-$**^{L1}$, $*^{L1}$—$C_{1-8}$alkylene-$SO_2$—$**^{L1}$, $*^{L1}$—CO—$C_{1-8}$alkylene-$**^{L1}$, $*^{L1}$—$C_{1-8}$alkylene-CO—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L1}$, $*^{L1}$—$NR^{L1a}C(O)$—$**^{L1}$, $*^{L1}$—$C(O)NR^{L1a}$—$**^{L1}$, —$C_{1-8}$alkylene-, —$C_{2-8}$alkenylene —$C_{2-8}$alkynylene-, —$[O(CR^{L1a}R^{L1b})_{m4}]_{m5}$—,

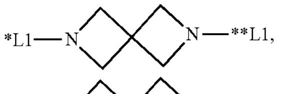

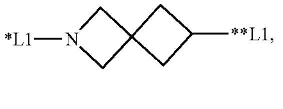

-continued

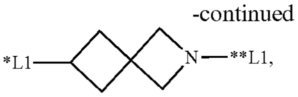

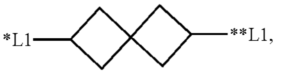

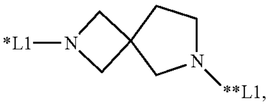

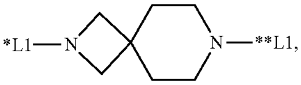

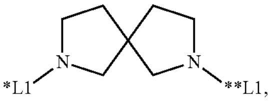

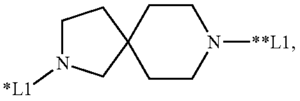

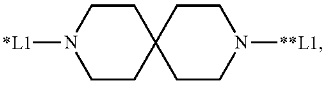

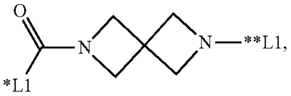

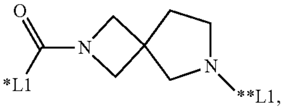

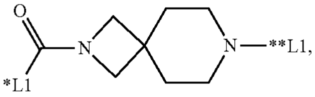

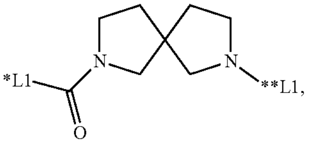

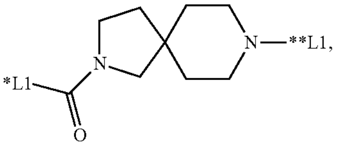

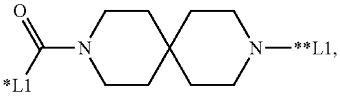

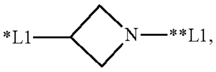 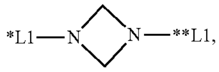

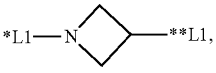 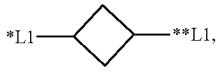

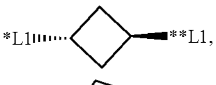 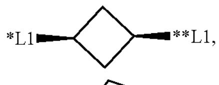

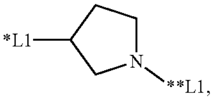 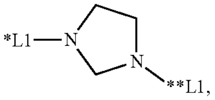

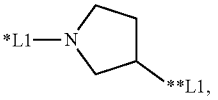 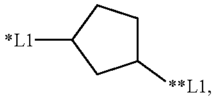

-continued
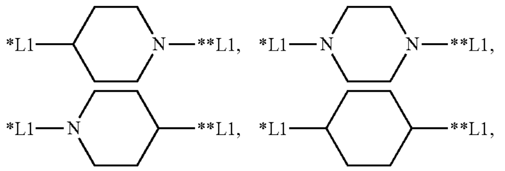
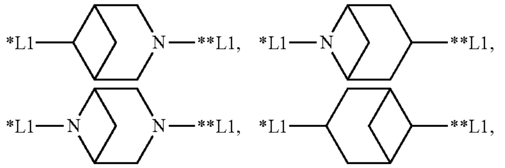
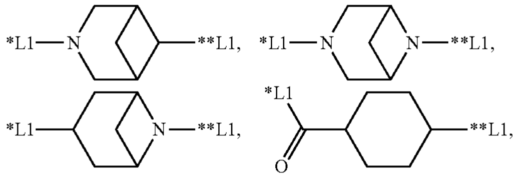
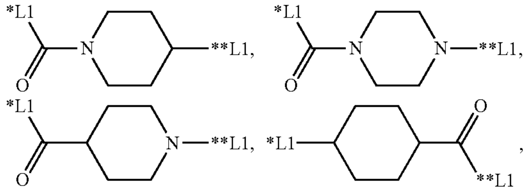
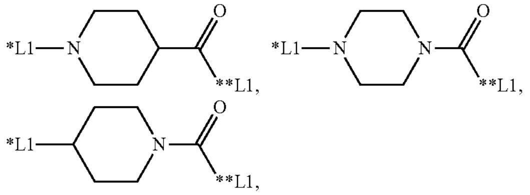
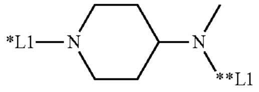
or
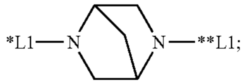
wherein each of said —$C_3$-$C_8$cycloalkylene-, $*^{L1}$—O—$C_{1-8}$alkylene-$**^{L1}$, $*^{L1}$—$C_{1-8}$alkylene-O—$**^{L1}$, $*^{L1}$—$SO_2$—$C_{1-8}$-alkylene-$**^{L1}$, $*^{L1}C_{1-8}$alkylene-$SO_2$—$**^{L1}$, $*^{L1}$—CO—$C_{1-8}$alkylene-$**^{L1}$, $*^{L1}$—$C_{1-8}$ alkylene-CO—$**^{L1}$, $*^{L1}$—$NR^{L1a}$—$C_{1-8}$alkylene-$**^{L1}$, $*^{L1}$—$C_{1-8}$alkylene-$NR^{L1a}$—$**^{L1}$, —$C_{1-8}$alkylene-, —$C_{2-8}$alkenylene-, —$C_{2-8}$alkynylene-,
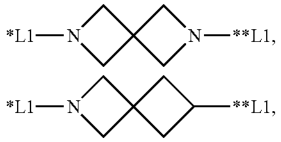
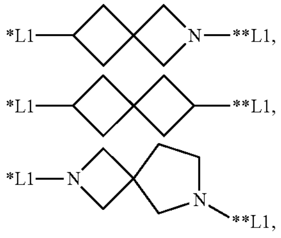
-continued
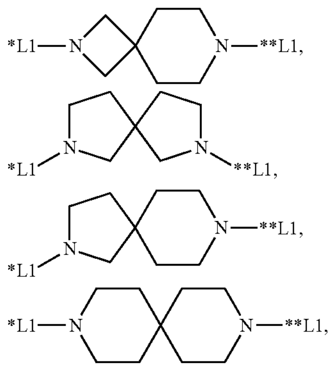
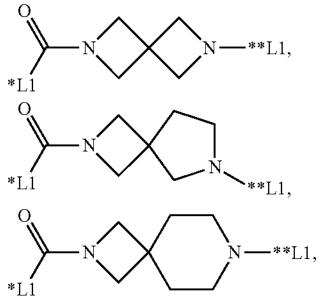
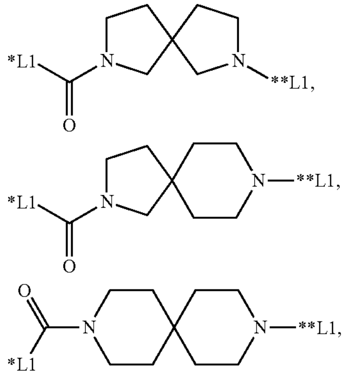
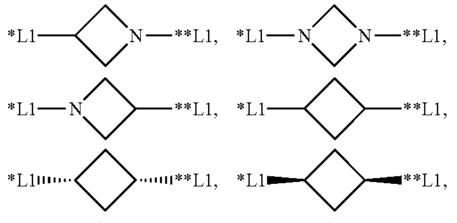
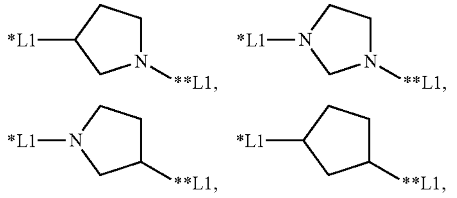
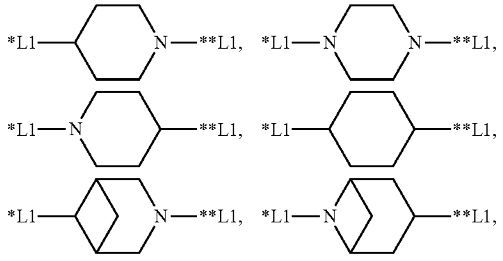

-continued

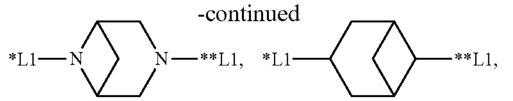
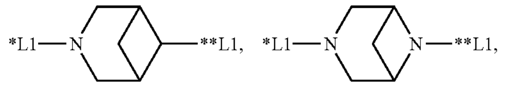
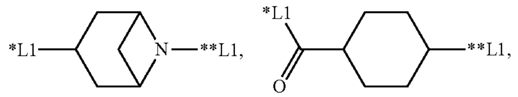
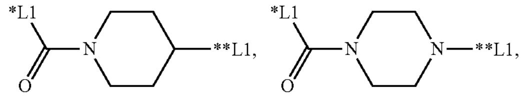
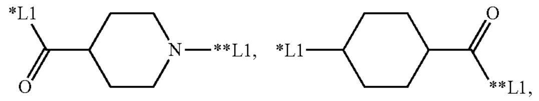
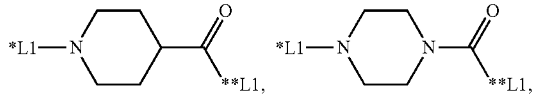
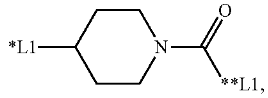
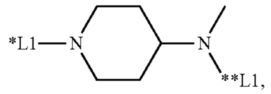

or

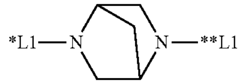

is substituted with at least one $R^{L1c}$;

$R^{L1a}$ and $R^{L1b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L1d}$;

each of said $R^{L1C}$ and $R^{L1d}$ are independently —F, —Cl, —Br, —I, —OH, methyl, ethyl, propyl, butyl, pentyl, hexyl, heptyl, octyl, vinyl, ethynyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo;

Aspect 20. The compound of any one of Aspects 1-19, wherein $L^1$ is selected from a single bond, —$C_{1-8}$alkylene- (preferably —$CH_2$—, —$C_2H_4$—, —$C_3H_6$—), —CO—, —O—, —$N(CH_3)$—, —NH—,

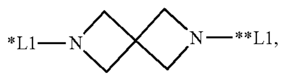
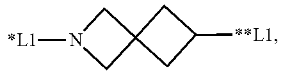
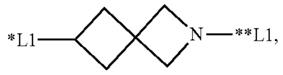
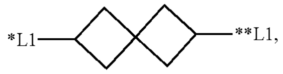
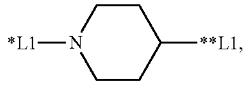
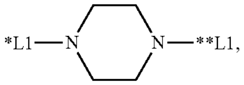
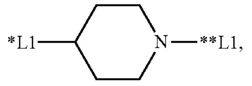
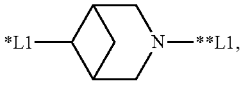
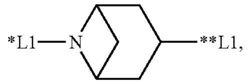
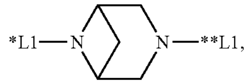
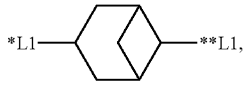
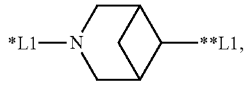
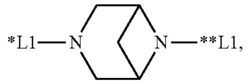
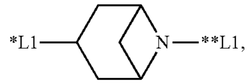
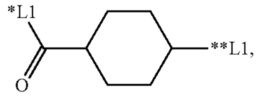
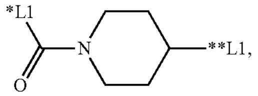
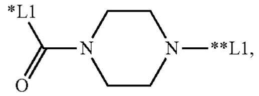
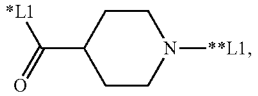
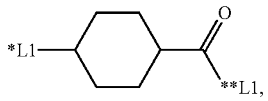
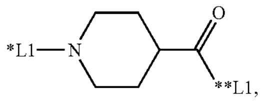
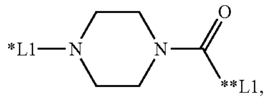
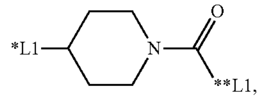
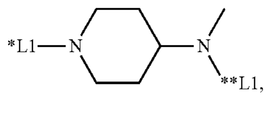
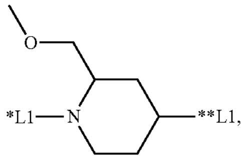
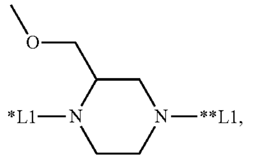
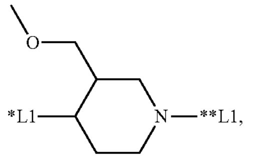
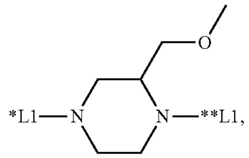

-continued

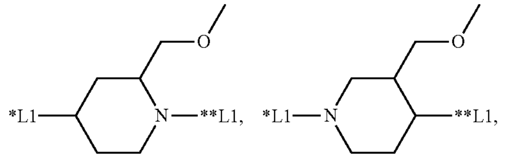
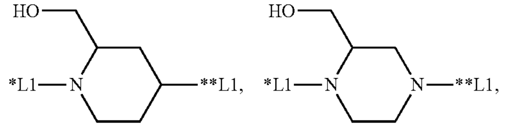
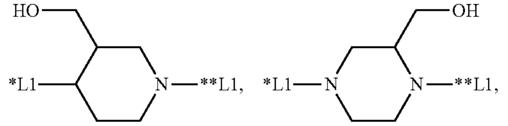
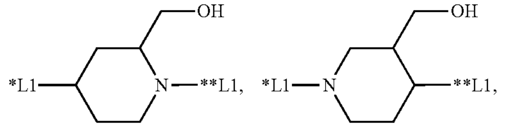
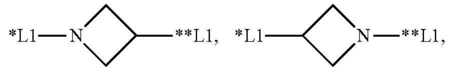
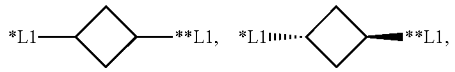
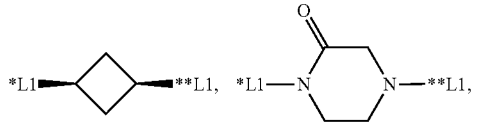
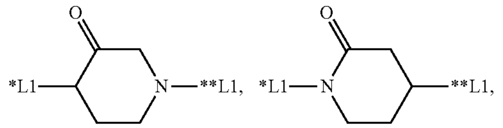
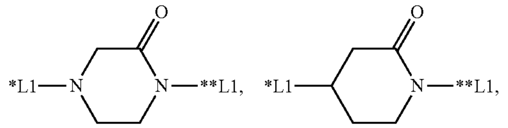
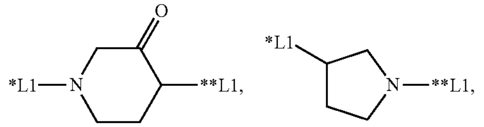
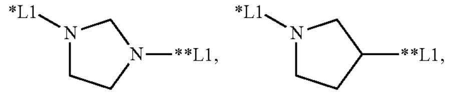
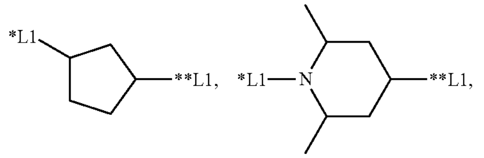
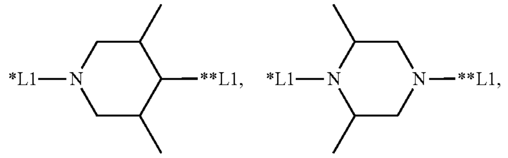

-continued

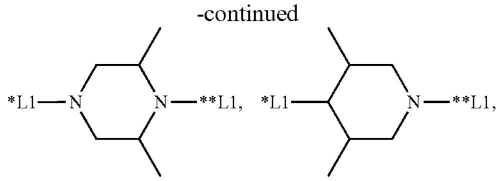
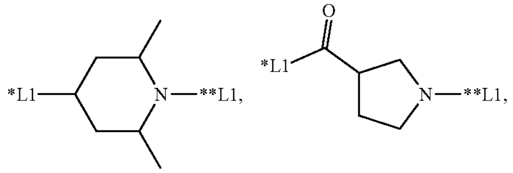
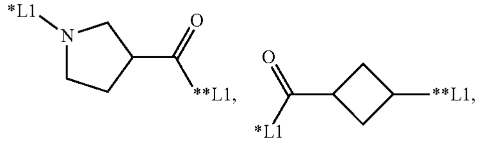
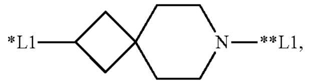
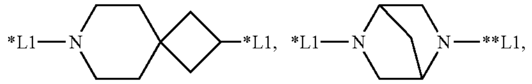
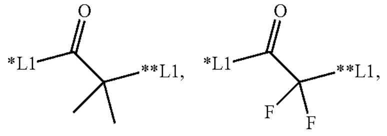
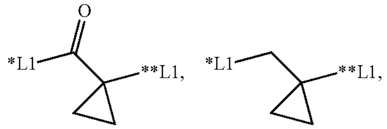
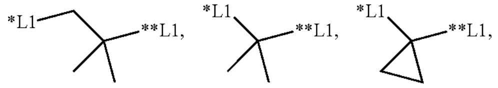
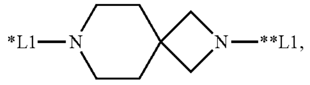
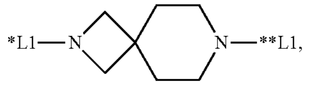
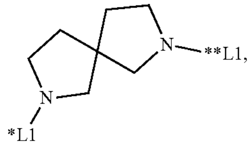
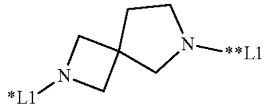

or

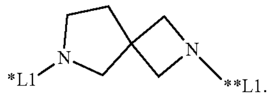

Aspect 21. The compound of any one of Aspects 1-20, wherein $X^1$ and $X^2$ are each independently selected from —$CR^a$ or N;

$R^a$ is selected from hydrogen, —F, —Cl, —Br, —I, CN, methyl, ethyl, methoxy, ethoxy, or cyclopropyl, wherein each of said methyl, ethyl, methoxy, ethoxy, or cyclopropyl is optionally substituted with at least one substituent —F, —Cl, —Br, —I, hydroxy, methyl, ethyl, (preferably, $X^1$ and $X^2$ are each independently selected from CH, C(F), $C(CH_3)$ or N);

m1=1 or 0;

$R^{12}$ is hydrogen, oxo, methoxymethyl, hydroxymethyl, —CN or —$CH_3$.

Aspect 22. The compound of any one of Aspects 1-21, wherein m1 is 1; preferably,

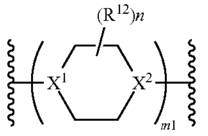

moiety is

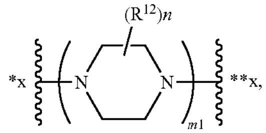

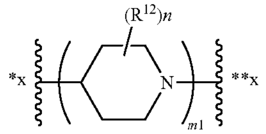

or

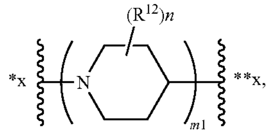

wherein $*^X$ refers to the position attached to

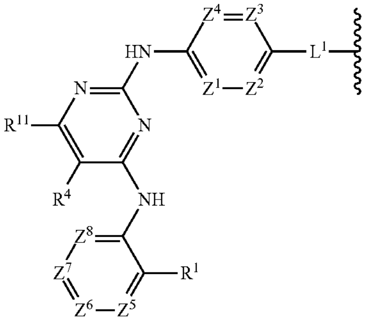

moiety, and $**^X$ refers to the position attached to the

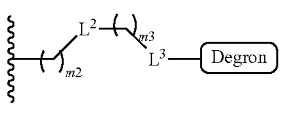

moiety.

Aspect 23. The compound of any one of Aspects 1-21, wherein m1 is 0.

Aspect 24. The compound of any one of Aspects 1-23, wherein

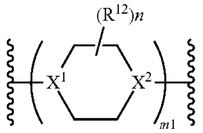

moiety is

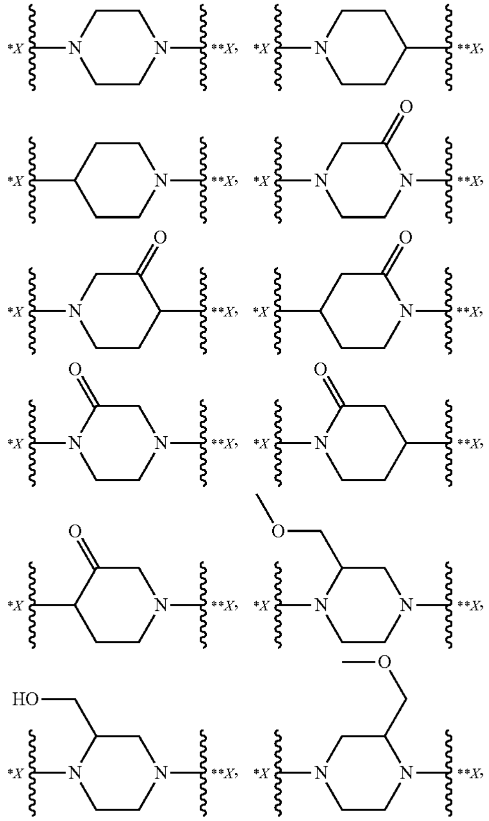

or

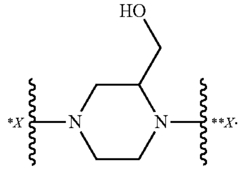

Aspect 25. The compound of any one of Aspects 1-24, wherein m2 is selected from 0, 1, 2, 3, 4 or 5.

Aspect 26. The compound of any one of Aspects 1-25, wherein $L^2$ is selected from a single bond, —O—, —$SO_2$—, —CO—, —$NR^{L2a}$—, —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}C_{1-8}$alkylene-$SO_2$—$**^{L2}$, $*^{L2}$—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}C(O)$—$**^{L2}$, $*^{L2}$—C(O)$NR^{L2a}$—$**^{L2}$, —$C_{1-8}$alkylene-, —$C_{2-8}$alkenylene-, —$C_{2-8}$alkynylene-, —$[O(CR^{L2a}R^{L2b})_{m4}]_{m5}$—,

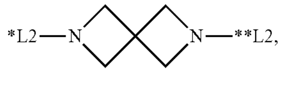

-continued
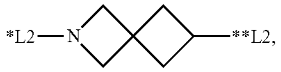
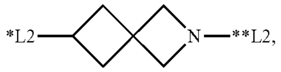
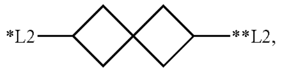
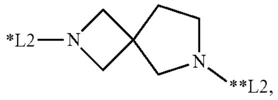
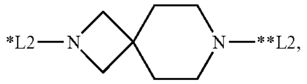
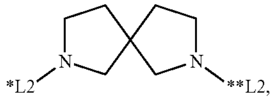
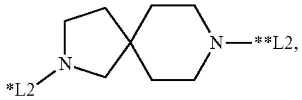
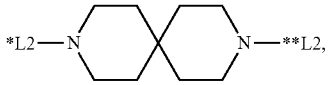
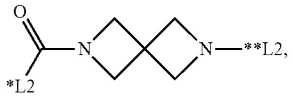
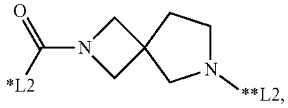
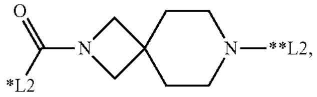
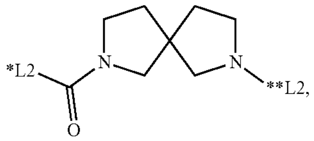
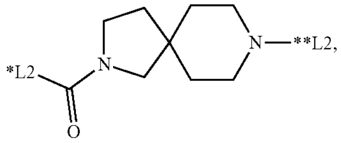
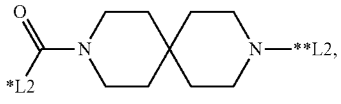
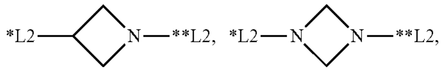
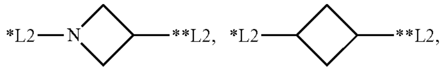
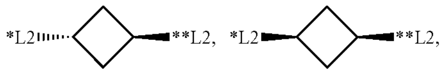
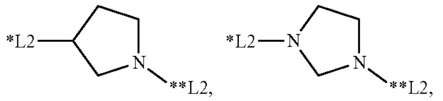
-continued
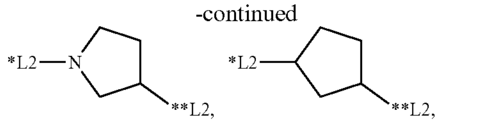
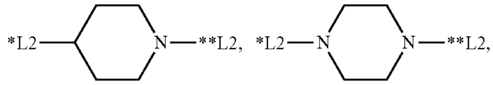
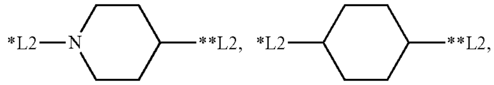
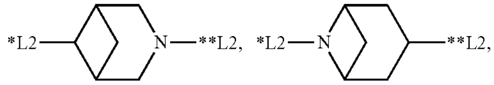
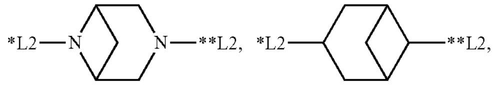
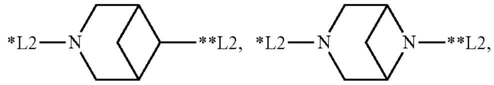
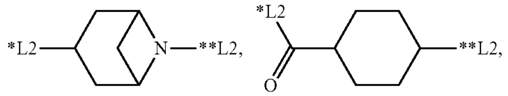
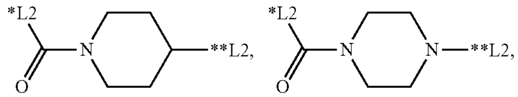
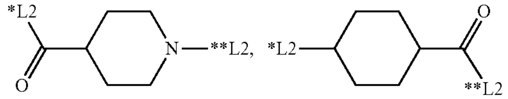
,
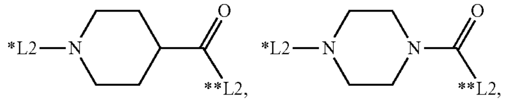
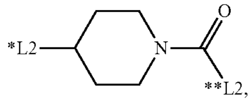
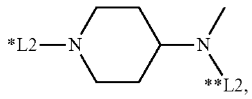
or
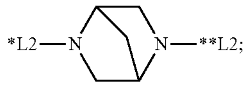
wherein each of said —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$S_2C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}C_{1-8}$alkylene-$**^{L2}$, $*^{L2}$—$C_{1-8}$alkylene-$NR^{L2a}$—$**^{L2}$, —$C_{1-8}$alkylene-, —$C_{2-8}$alkenylene-, —$C_{2-8}$alkynylene-,
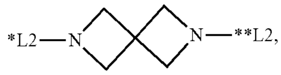
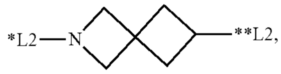
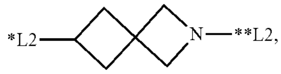

-continued

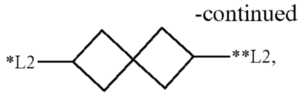
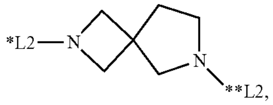
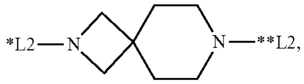
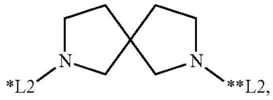
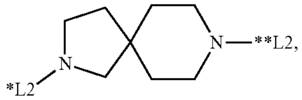
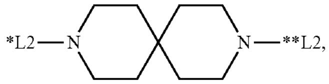
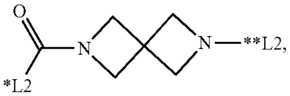
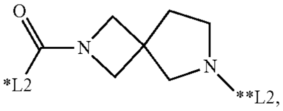
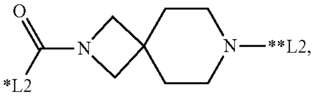
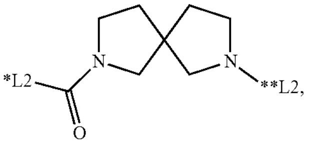
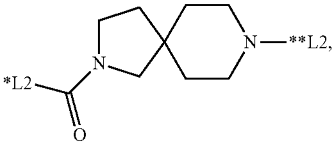
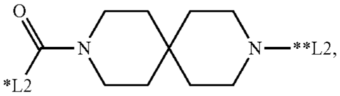
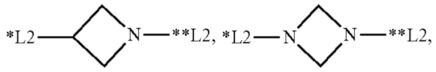
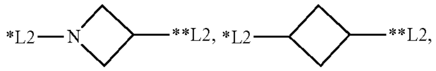
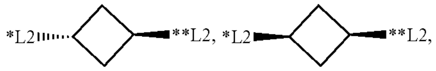
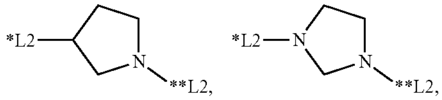
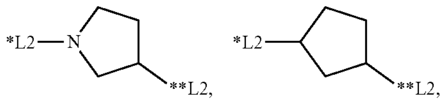
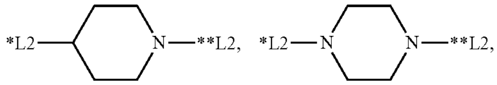

-continued

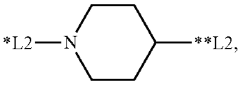
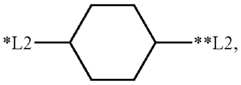
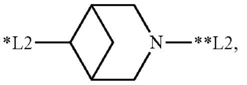
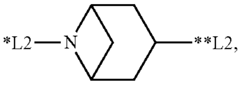
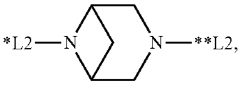
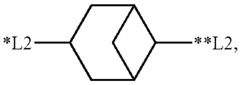
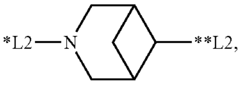
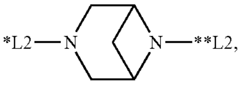
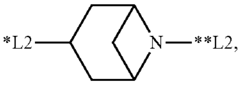
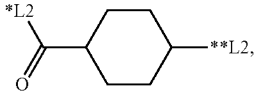
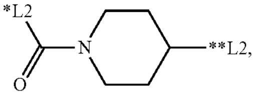
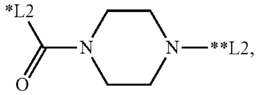
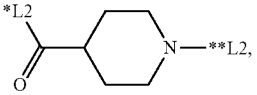
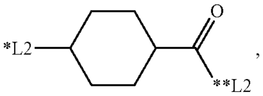
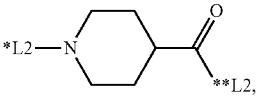
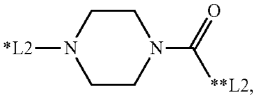
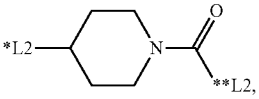
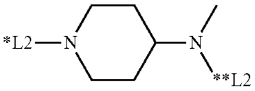
or
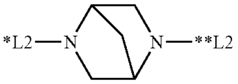

is optionally substituted with at least one substituent $R^{L2c}$;

$R^{L2a}$ and $R^{L2b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L2d}$;

each of said $R^{L2c}$ and $R^{L2d}$ are independently —F, —Cl, —Br, —I, —OH, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo; Aspect 27. The compound of any one of Aspects 1-26, wherein $L^2$ is selected from a single bond —$C_{1-8}$ alkylene-(preferably —$CH_2$—, —$C_2H_4$—, —$C_3H_6$—), —CO—, —O—, —$N(CH_3)$—, —NH—,

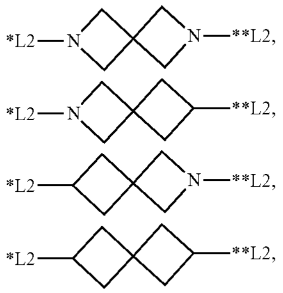
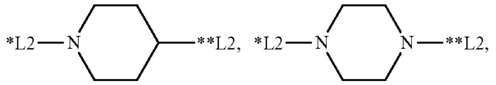
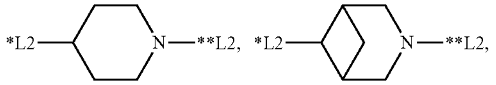
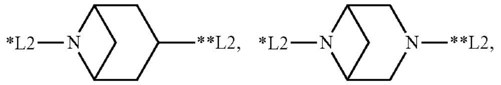
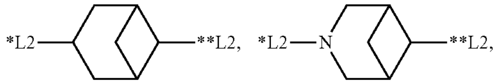
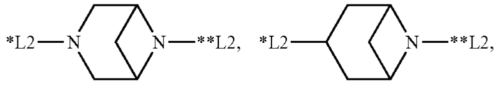
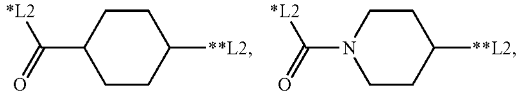
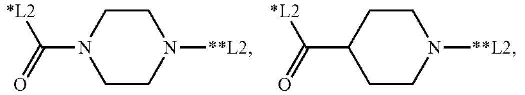
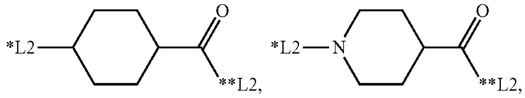
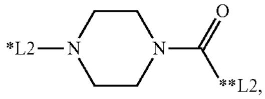
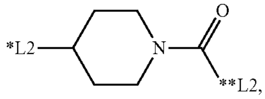
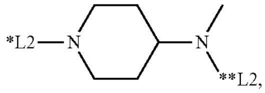
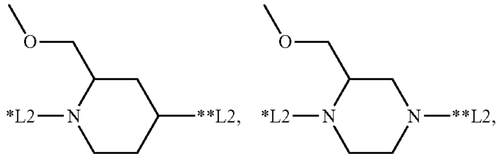

-continued

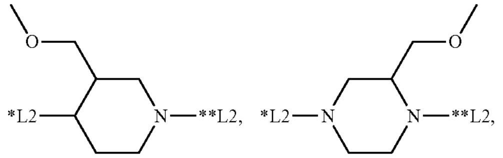
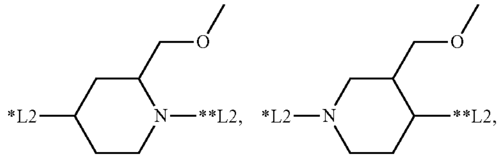
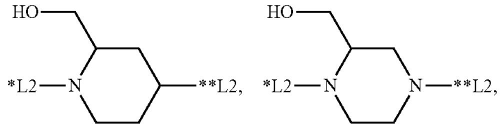
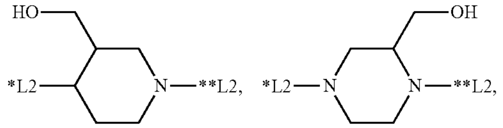
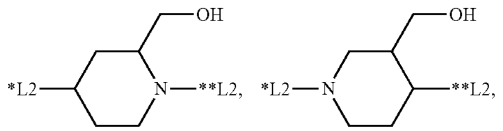
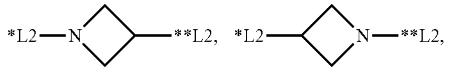
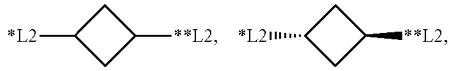
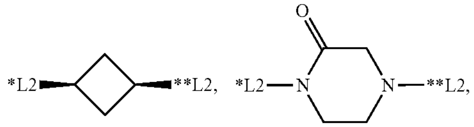
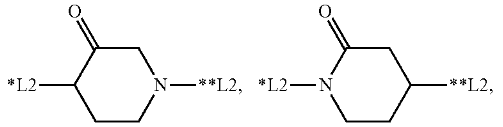
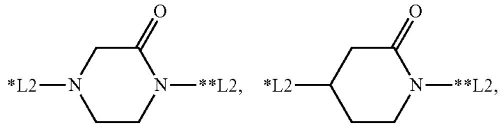
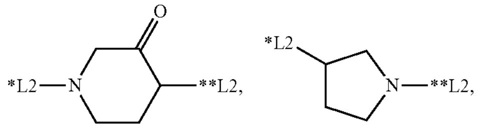
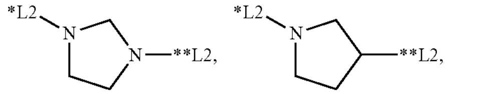
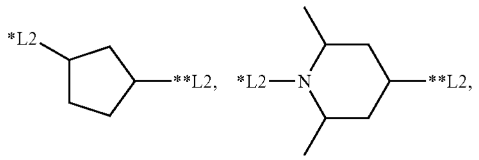

-continued

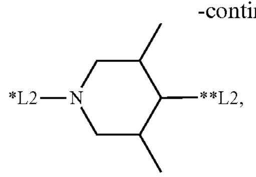
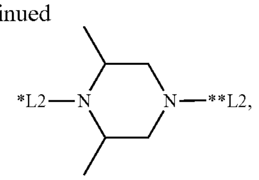
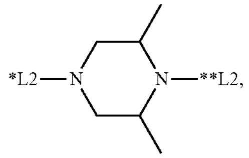
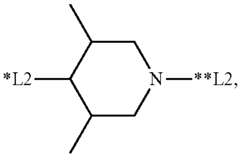
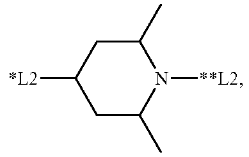
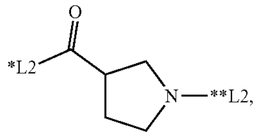
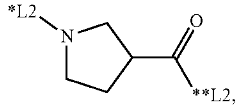
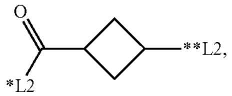
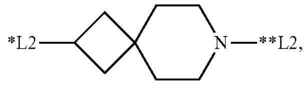
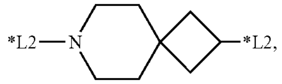
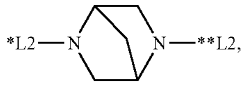
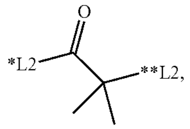
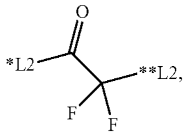
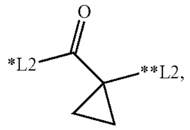
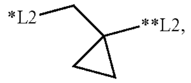
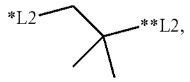
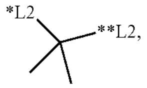
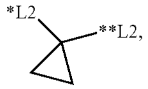
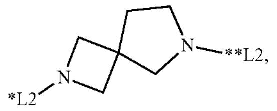
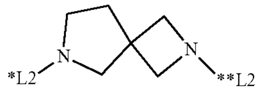
or
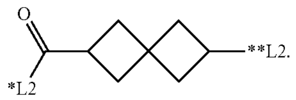

Aspect 28. The compound of any one of Aspects 1-27, wherein m3 is 0, 1, 2, 3, 4, 5 or 6.

Aspect 29. The compound of any one of Aspects 1-28, wherein $L^3$ is selected from a single bond, —O—, —$SO_2$—, —CO—, —$NR^{L3a}$—, —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$-$NR^{L3a}$—$C_{1-8}$alkylene-$**^{L3}$, $*^{L3}$—$C_{1-8}$alkylene-$NR^{L3a}**^{L3}$, $*^{L3}$—$NR^{L3a}$C(O)—$**^{L3}$, $*^{L3}$—C(O)$NR^{L3a}$—$*^{L3}$, —$C_{1-8}$alkylene-, —$C_{2-8}$alkenylene-, —$C_{2-8}$alkynylene-, —$[O(CR^{L3a}R^{L3b})_{m4}]_{m5}$—,

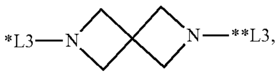
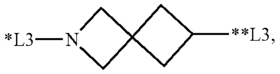
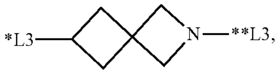
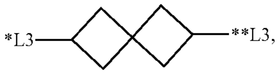
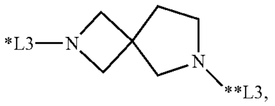
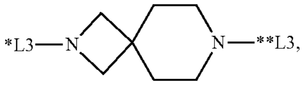
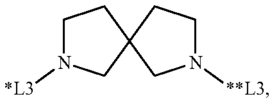
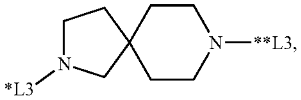
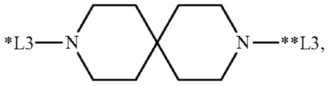
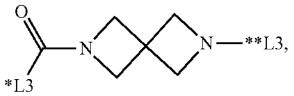
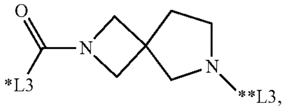
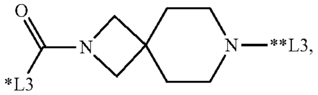
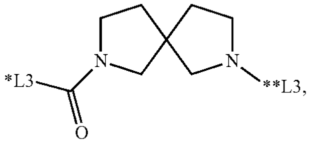
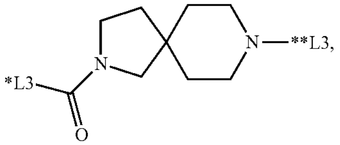
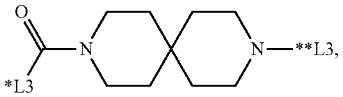
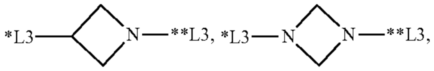
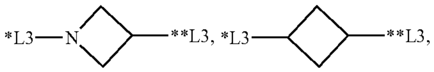
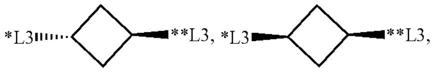

-continued
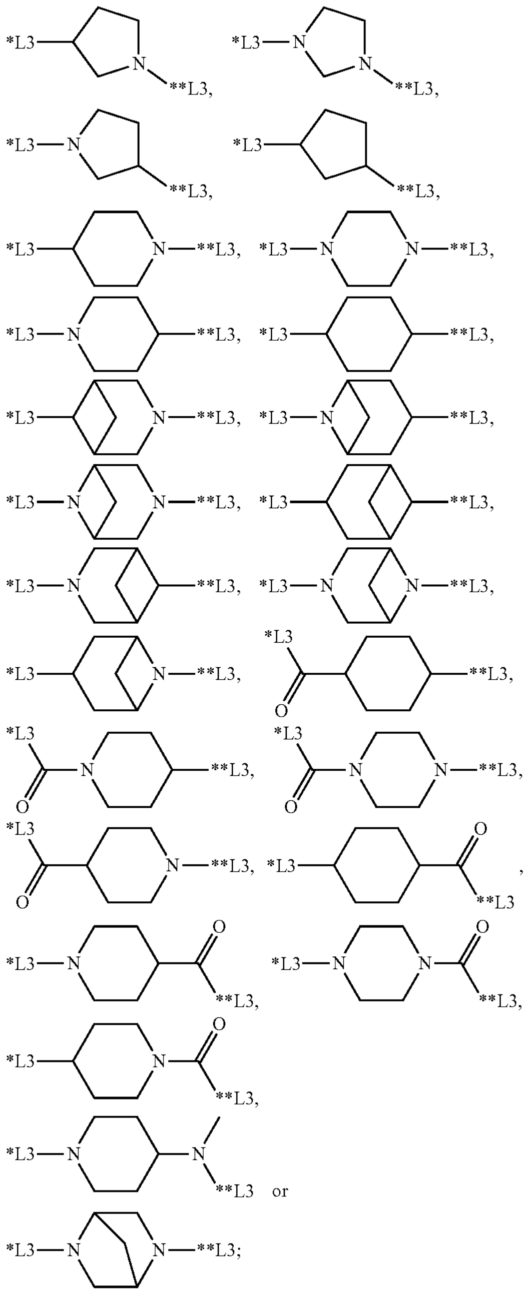
wherein each of said —$C_3$-$C_8$cycloalkylene-, $*^{L3}$—O—$C_{1-8}$alkylene-$**^{L3}$, $*^{L3}C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$-$NR^{L3a}$—$C_{1-8}$alkylene-$**^{L3}$, $*^{L3}$—$C_{1-8}$alkylene-$NR^{L3a}$—$**^{L3}$, —$C_{1-8}$alkylene-, —$C_{2-8}$alkenylene-, —$C_{2-8}$alkylene-,
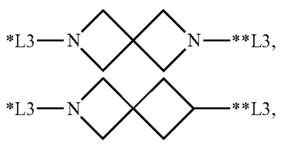
-continued
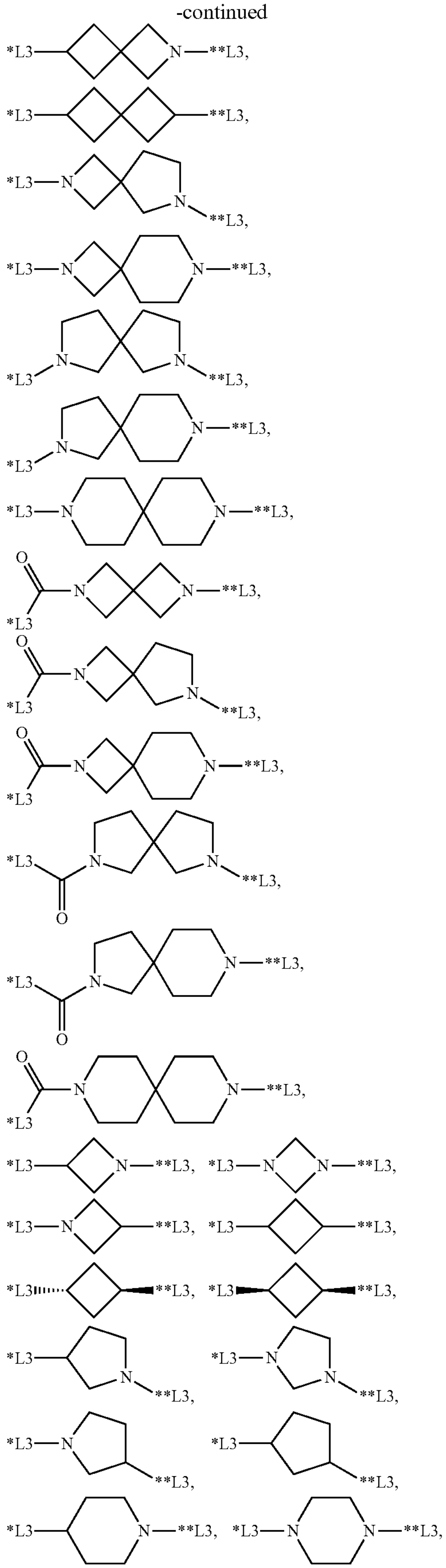

-continued

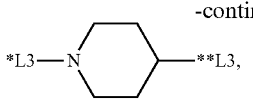 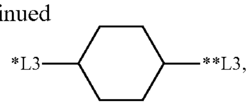

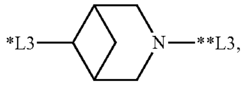 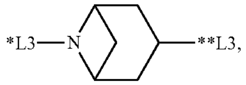

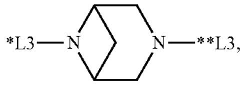 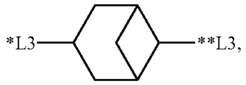

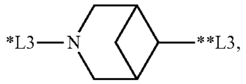 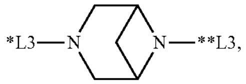

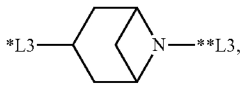 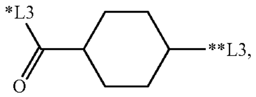

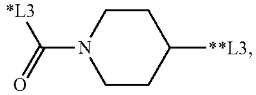 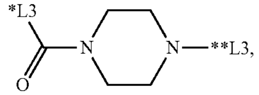

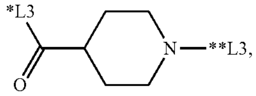 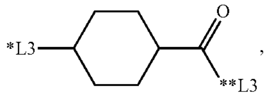 ,

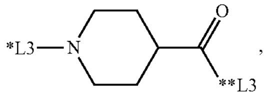 ,

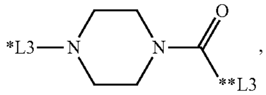 ,

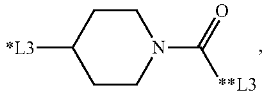 ,

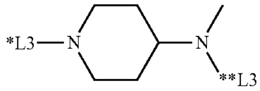 or

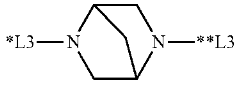

is optionally substituted with at least one substituent $R^{L3c}$.

$R^{L3a}$ and $R^{L3b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L3d}$;

each of said $R^{L3c}$ and $R^{L3d}$ are independently —F, —Cl, —Br, —I, —OH, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo.

Aspect 30. The compound of any one of Aspects 1-29, wherein $L^3$ is selected from single bond, —$C_{1-8}$alkylene- (preferably —$CH_2$—, —$C_2H_4$—, —$C_3H_6$—), —CO—, —O—, —$N(CH_3)$—, NH—,

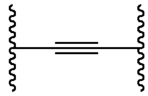 , 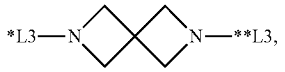

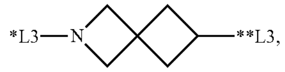

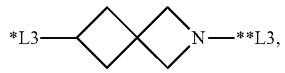

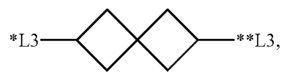 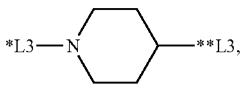

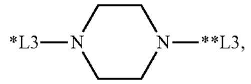 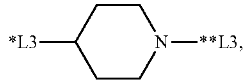

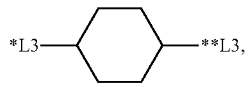 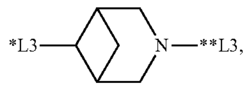

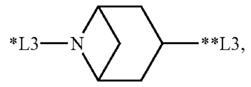 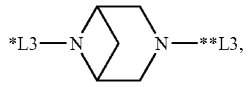

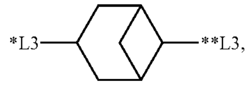 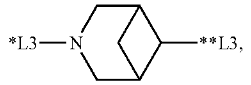

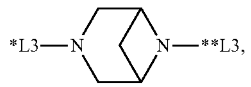 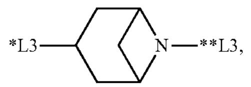

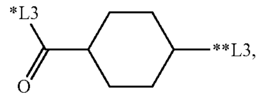 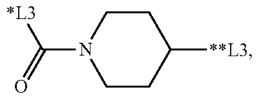

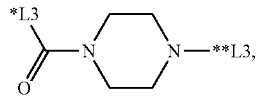 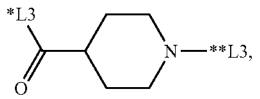

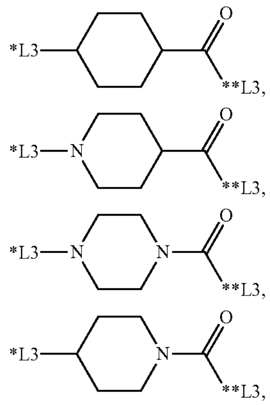

-continued
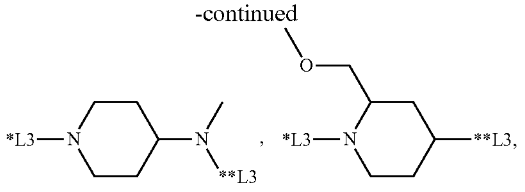
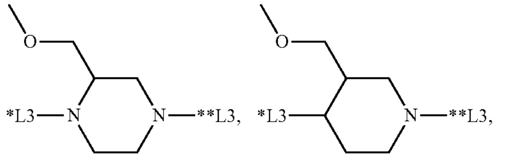
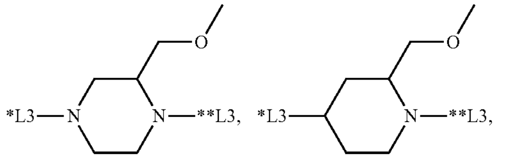
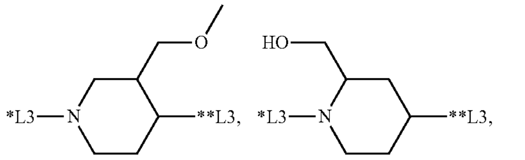
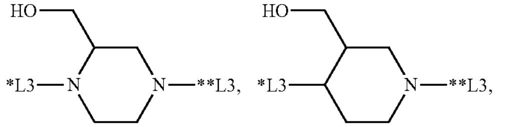
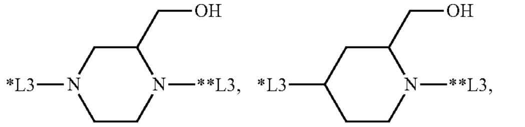
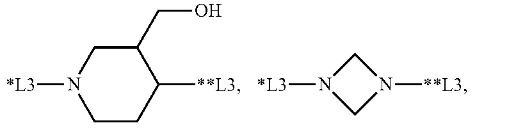
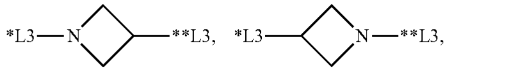
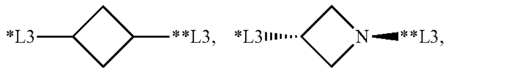
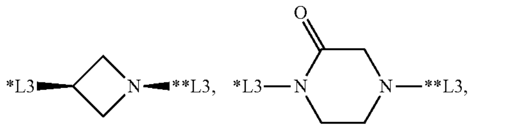
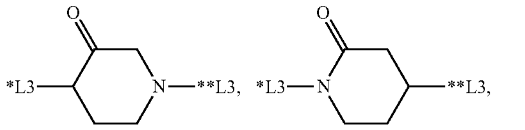
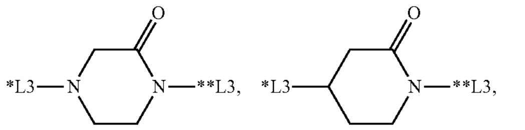
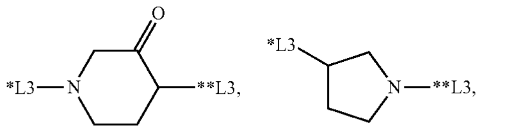
-continued
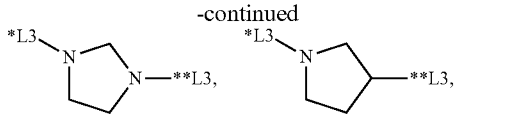
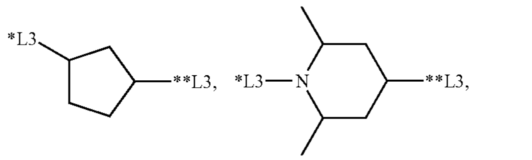
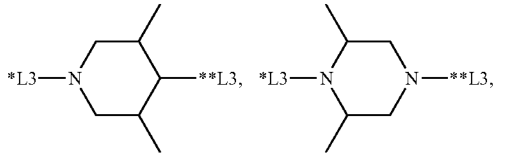
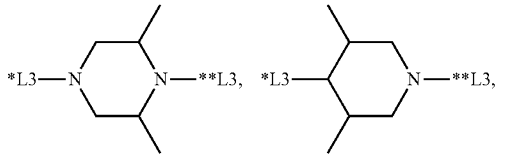
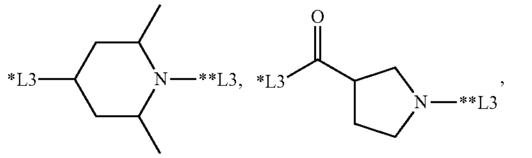
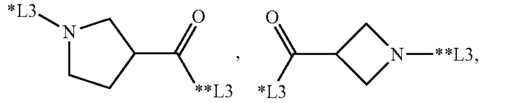
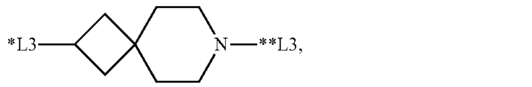
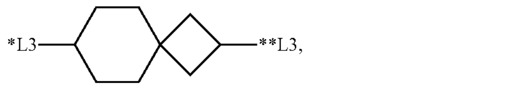
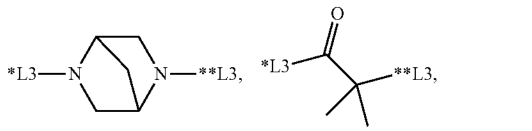
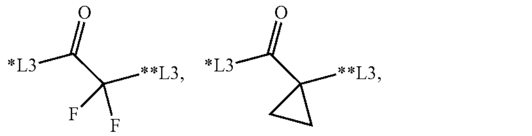
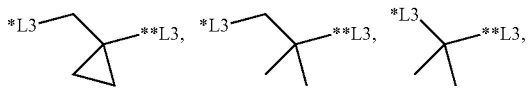
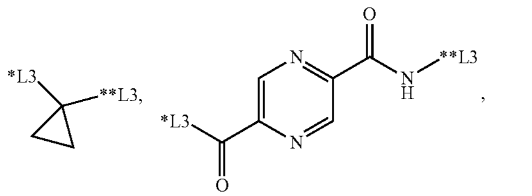
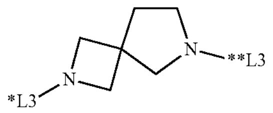 or -continued
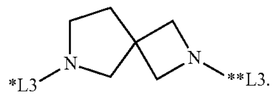
Aspect 31. The compound of any one of Aspects 1-30, wherein
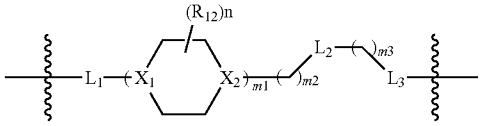
is selected from $-CH_2CH_2-$,
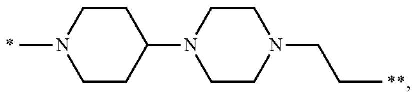
,
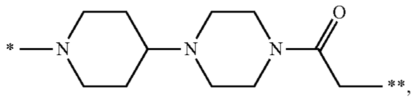
,
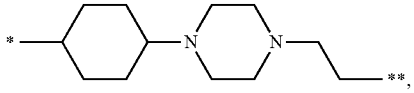
,
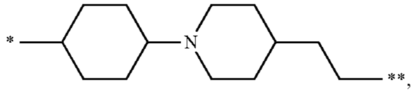
,
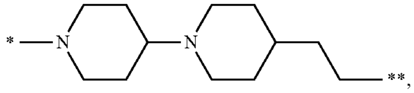
,
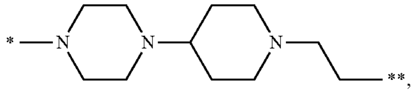
,
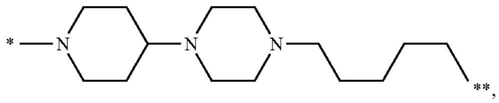
,
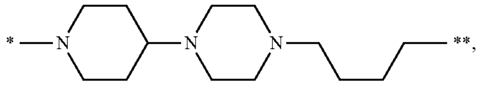
,
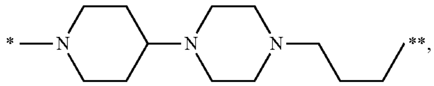
,
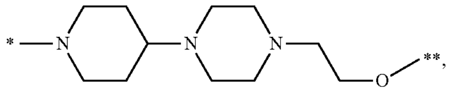
,
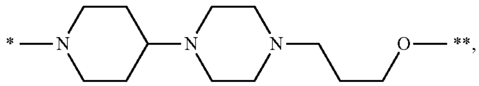
,
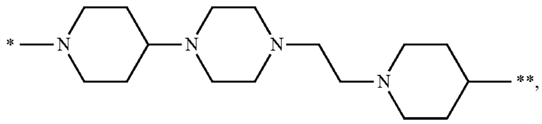
,
-continued
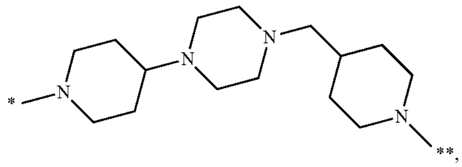
,
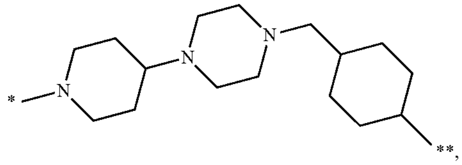
,
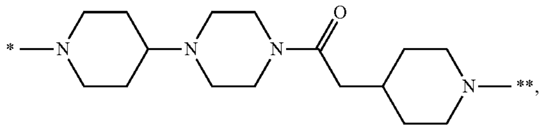
,
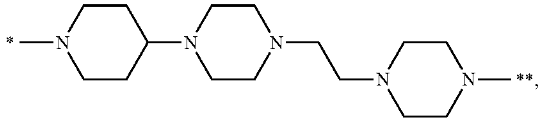
,
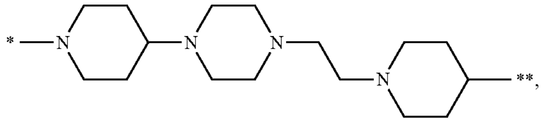
,
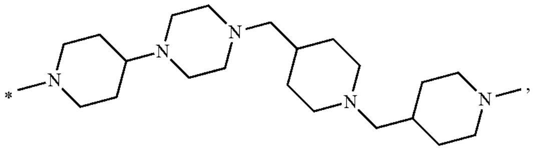
,
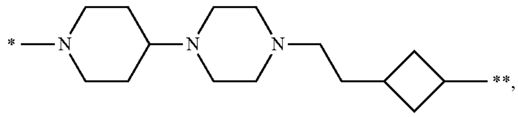
,
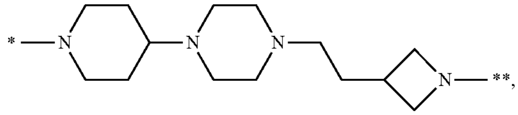
,
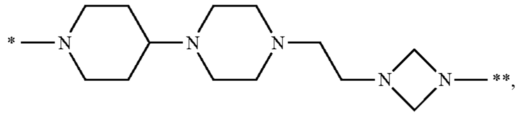
,
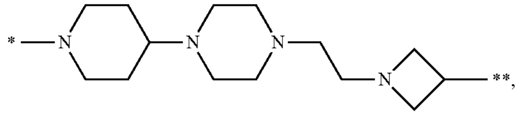
,
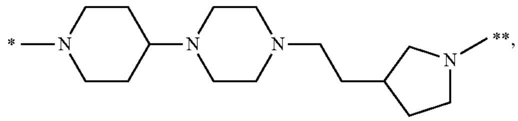
,
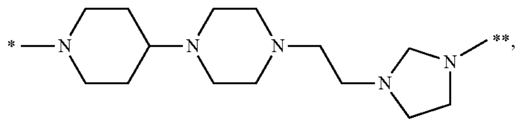
,
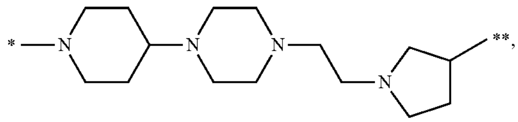
, -continued
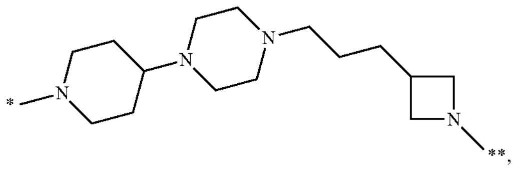
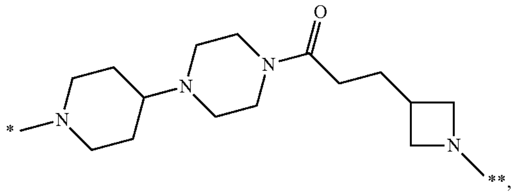
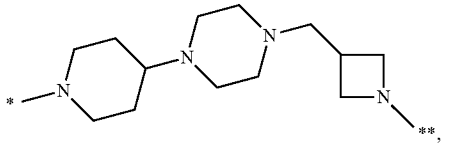
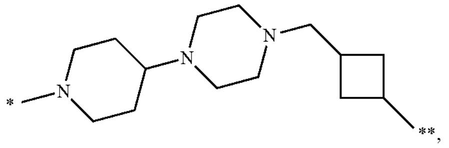
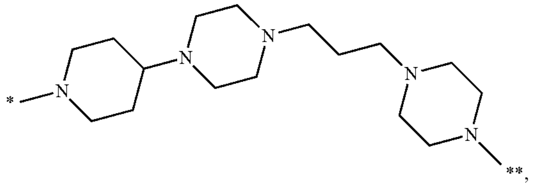
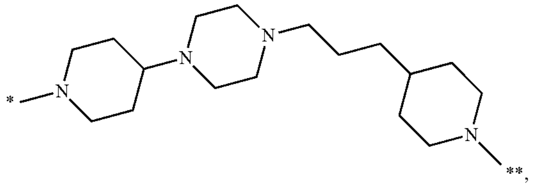
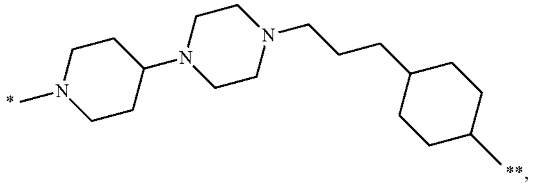
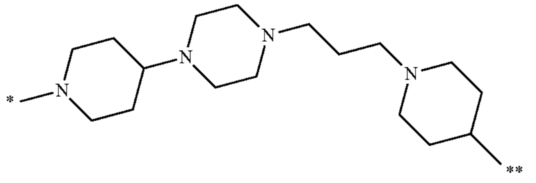
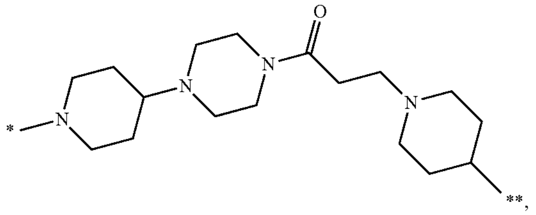
-continued
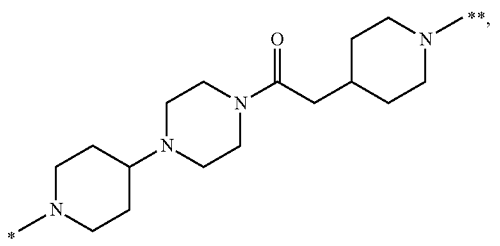
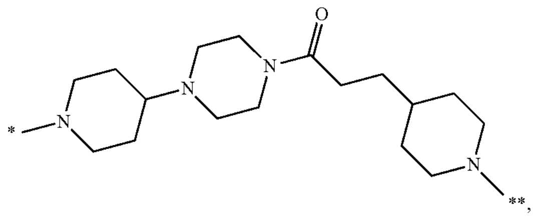
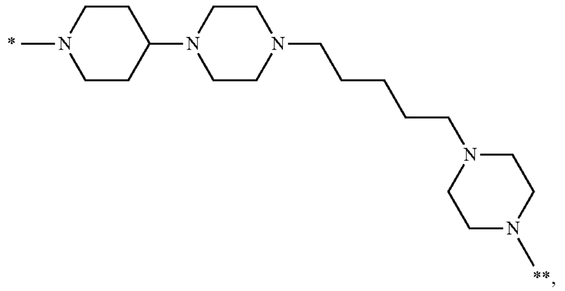
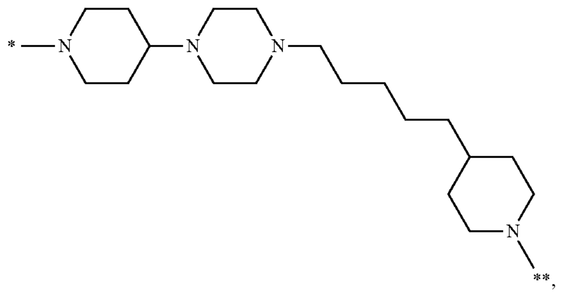
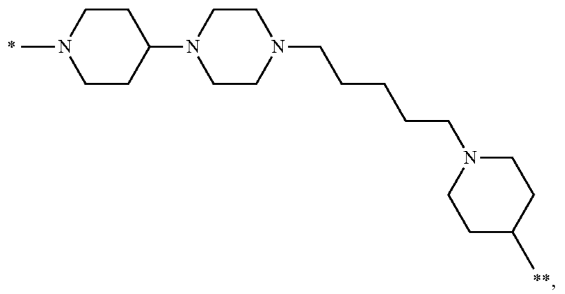
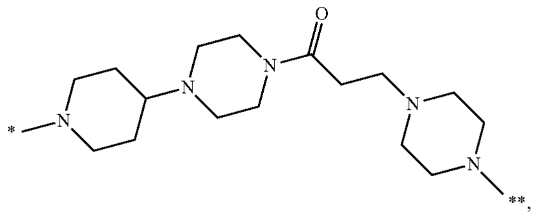

-continued
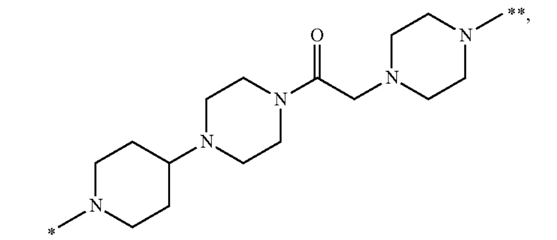
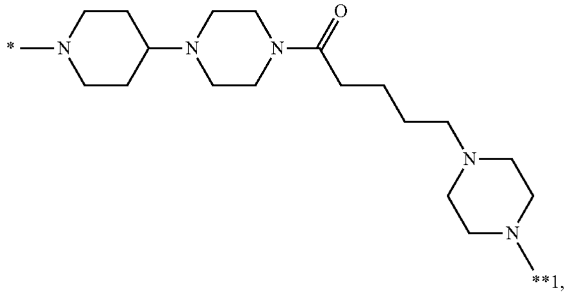
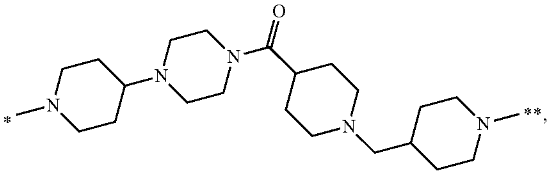
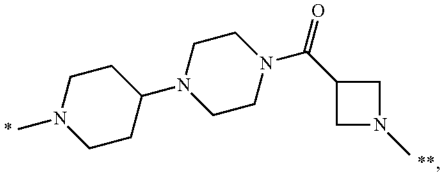
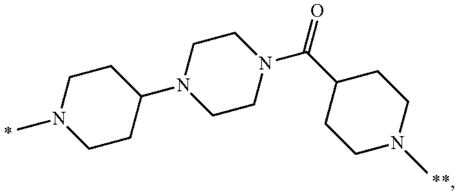
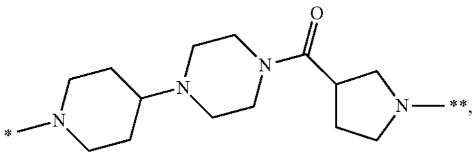
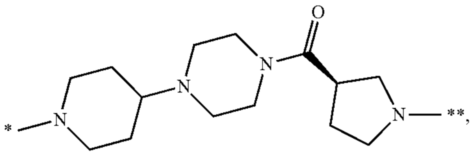
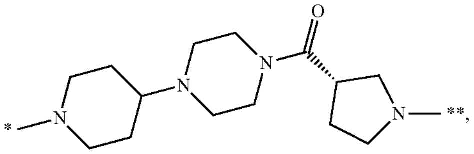
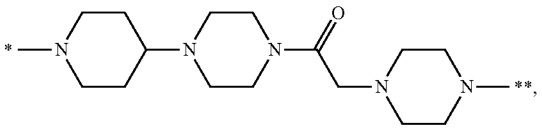
-continued
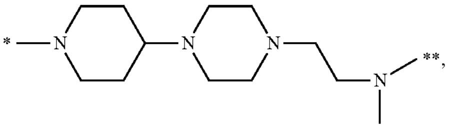
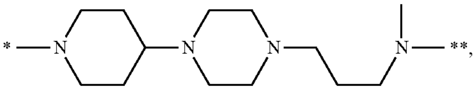
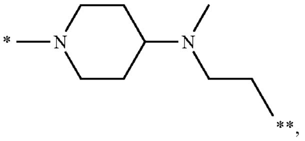
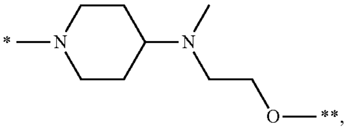
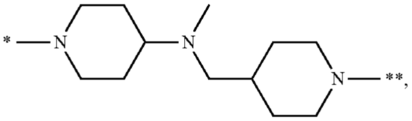
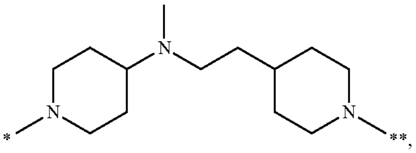
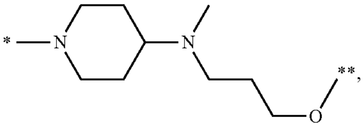
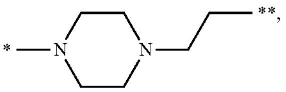
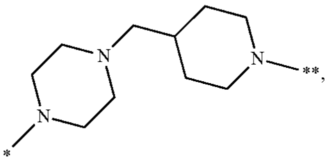
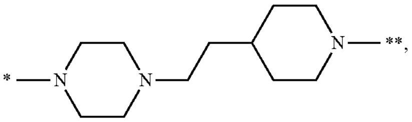
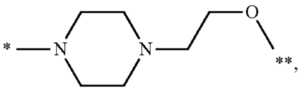
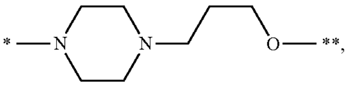
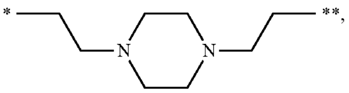
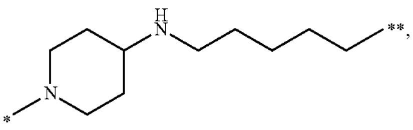

-continued
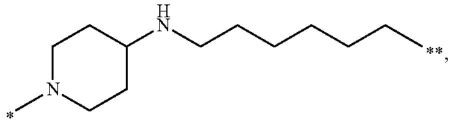
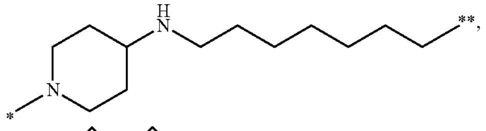
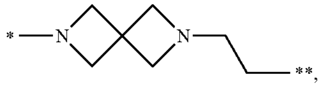
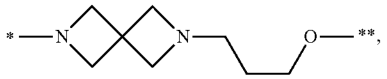
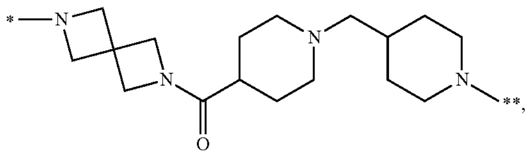
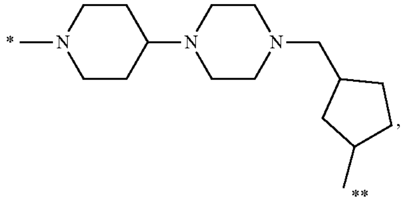
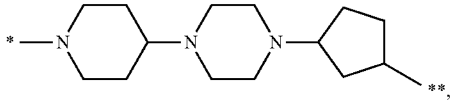
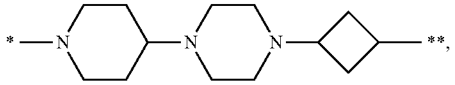
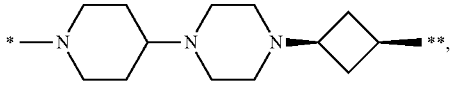
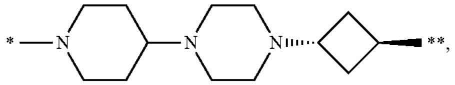
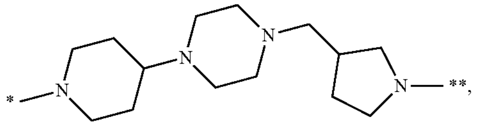
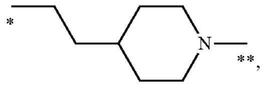
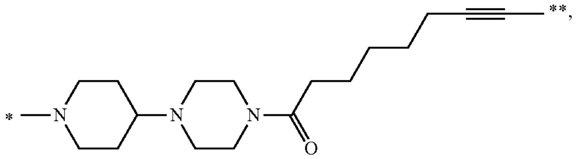
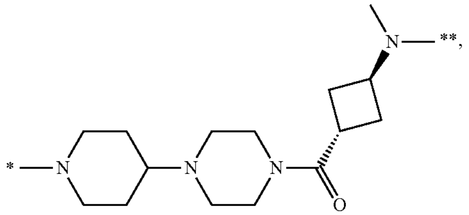
-continued
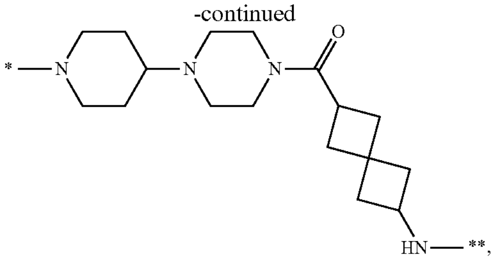
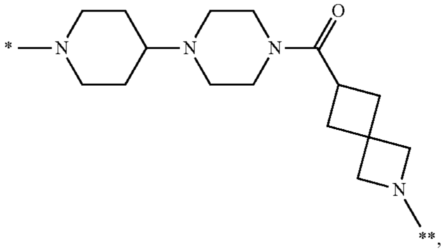
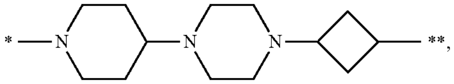
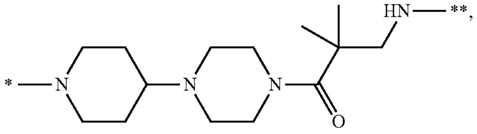
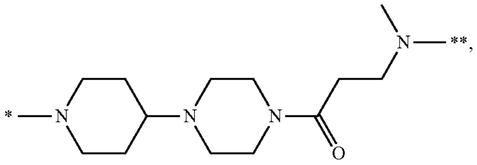
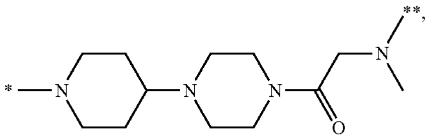
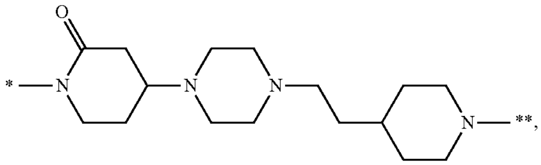
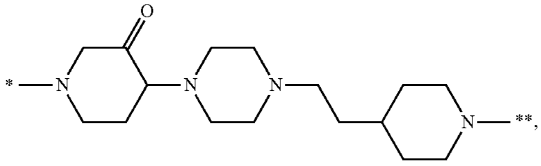
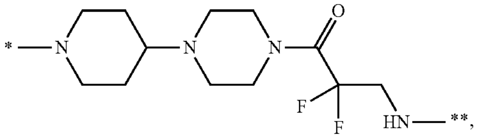
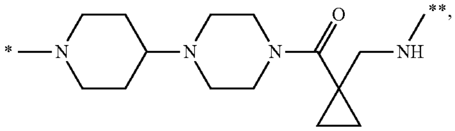
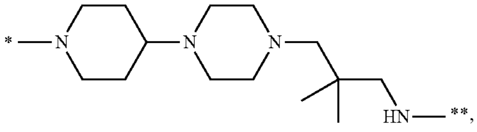

-continued
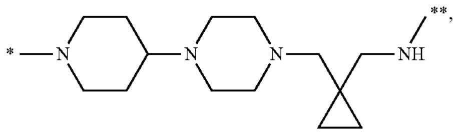
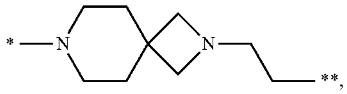
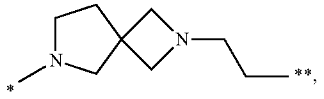
or
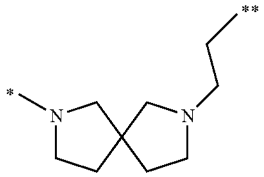
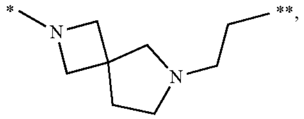
wherein * refers to the position attached to
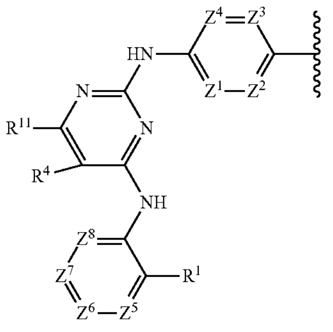
moiety, and ** refers to the position attached to the
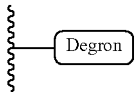
moiety.
Aspect 32. The compound of any one of Aspects 1-31, wherein 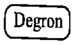 is selected from
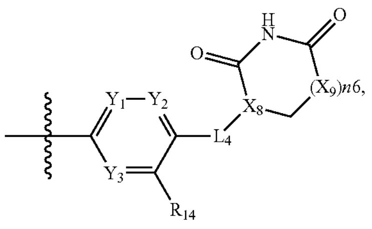
-continued
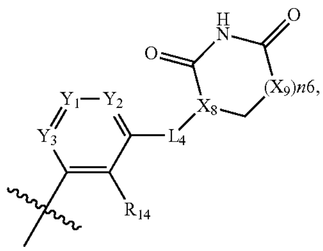
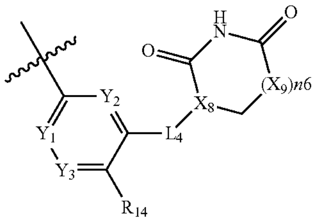
or
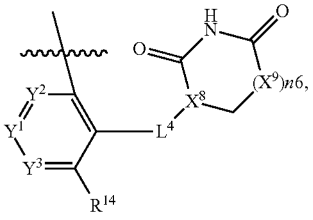
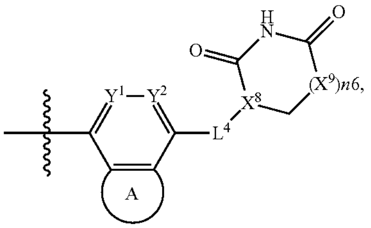
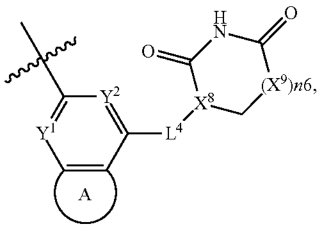
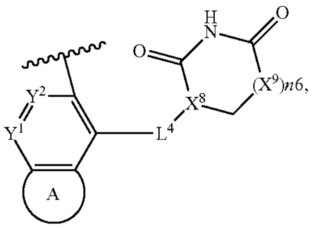
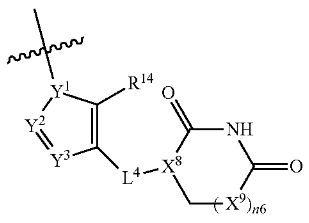
or -continued

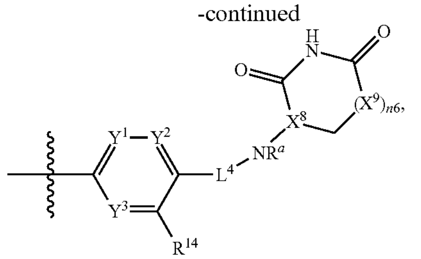

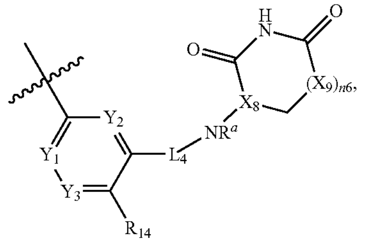

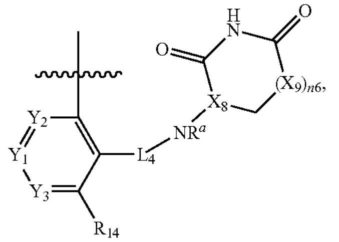

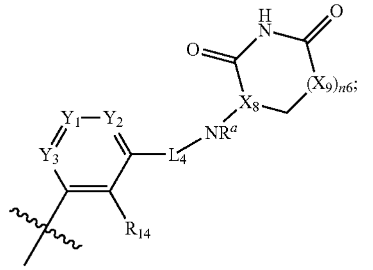

Ring A is selected from 5- to 7-membered cycloalkyl, 5- to 7-membered heterocyclyl, aryl, or heteroaryl;

$R^{14}$ is independently selected from hydrogen, halogen, $—C_{1-8}$alkyl, $—C_{1-8}$alkoxy, or CN; said each $—C_{1-8}$ alkyl, or $—C_{1-8}$alkoxy is optionally substituted by one or more halogen or $—C_{1-8}$alkyl; preferably $R^{14}$ is independently selected from H, F, Cl, Br, I, $CH_3$, $—OCH_3$, $CH_2F$, CN, $CHF_2$, or $CF_3$;

$X^8$ is independently selected from CH, CD, $C(CH_3)$, $C(C_2H_5)$, $C(C_3H_7)$, C(CN) or N;

$L^4$ is independently selected from a single bond,

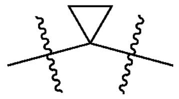,

—O—, —NH—, $—CH_2—$, —CHF—, or $—CF_2—$;

$Y^1$, $Y^2$, and $Y^3$ are each independently selected from $CR^a$ or N;

$X^9$ is $CH_2$;

$R^a$ is each independently selected from hydrogen, halogen, $—C_{1-8}$alkyl, or $—C_{1-8}$alkoxy, wherein each of said $—C_{1-8}$alkyl or $—C_{1-8}$alkoxy is optionally substituted with at least one or more halogen, hydroxy, halogen, $—C_{1-8}$alkyl, or $—C_{1-8}$alkoxy; and n6 is independently 0, 1 or 2.

Aspect 33. The compound of any one of Aspects 1-32, wherein Degron is

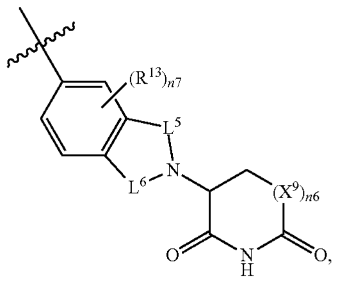

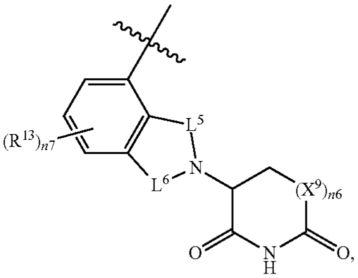

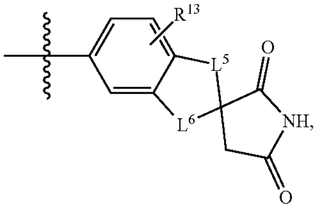

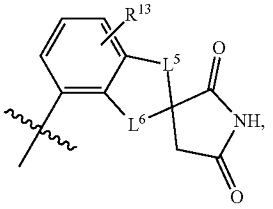

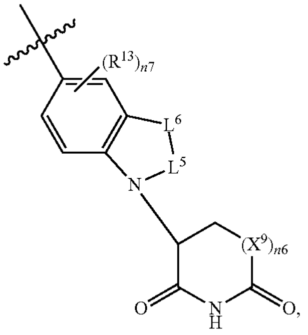

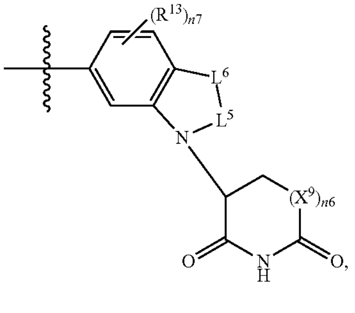

-continued

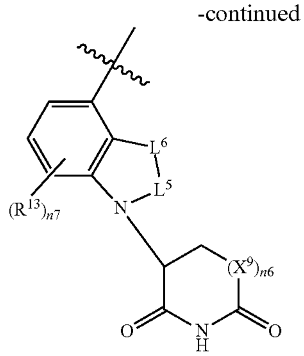

or

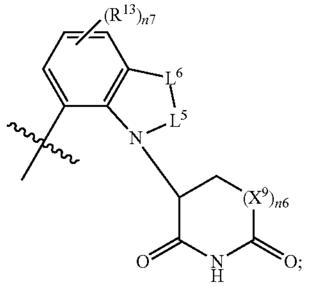

Wherein $L^5$ and $L^6$ is independently selected from a single bond,

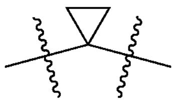

, $—O—$, $—NH—$, $—NMe$-, $—N(CH_2CH_3)—$, $—CH_2—$, $—CHF—$, $—CF_2—$, $—C(CH_3)_2—$ or $—CO—$ (preferably $L^5$ is $—CO—$ or $—CH_2—$, and $L^6$ is

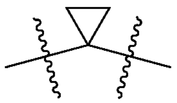

, $—O—$, $—NH—$, $—NMe$-, $—N(CH_2CH_3)—$, $—CH_2—$, $—CHF—$, $—CF_2—$, $—C(CH_3)_2—$ or $—CO—$);

$X^9$ is $CH_2$;

each $R^{13}$ is independently selected from hydrogen, —F, —Cl, —Br, —I, CN, $—C_{1-8}$alkyl, or $—C_{1-8}$alkoxy;

$n_6$ is 0 or 1; and $n_7$ is 0, 1 2.

Aspect 34. The compound of any one of Aspects 1-33, wherein (Degron) is

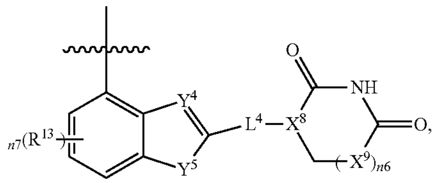

-continued

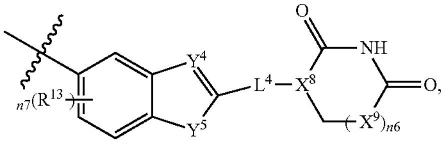

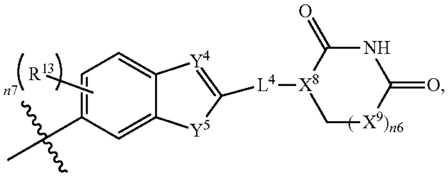

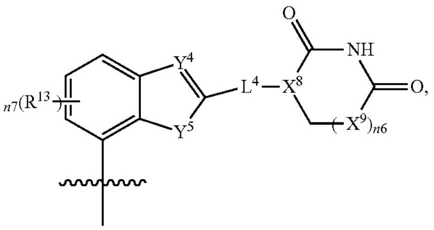

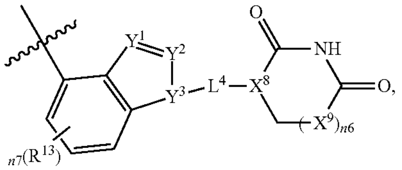

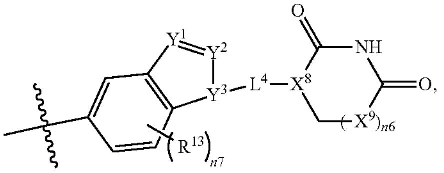

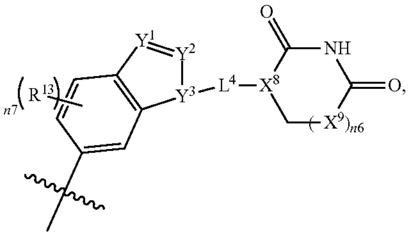

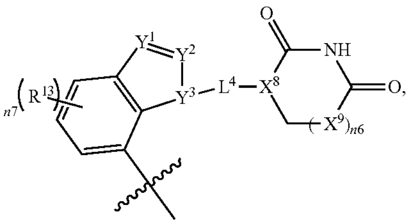

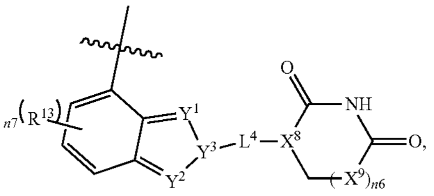

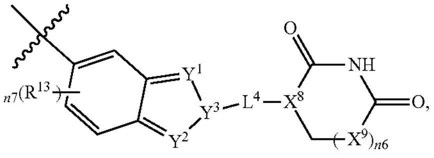

-continued

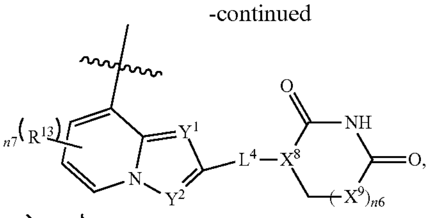

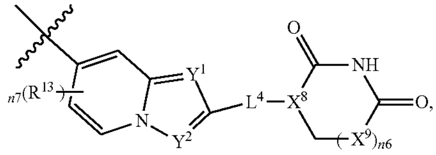

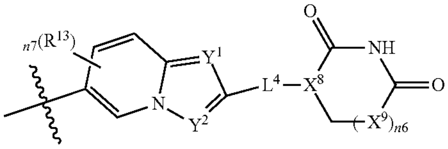

or

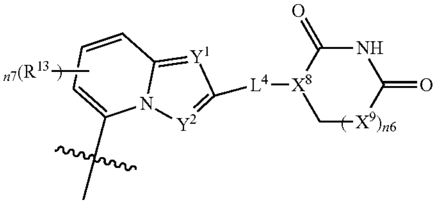

Wherein $L^4$ is independently selected from a single bond,

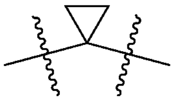

,

—O—, —NH—, —$CH_2$—, —CHF—, or —$CF_2$—;

$X^8$ is independently selected from CH, CD, $C(CH_3)$, $C(C_2H)$, $C(C_3H_7)$, C(F) or N;

$X^9$ is $CH_2$;

each $R^{13}$ is independently selected from hydrogen, —F, —Cl, —Br, —I, —CN, —$C_{1-8}$alkyl, or —$C_{1-8}$alkoxy;

$Y^1$, $Y^2$, $Y^3$ and $Y^4$ are each independently selected from CH, $C(CH_3)$, $C(CH_2CH_3)$, C(F), or N;

$Y^5$ is selected from NH, $N(CH_3)$, O or S;

$n_6$ is 0 or 1; and $n_7$ is 0, 1 or 2.

Aspect 35. The compound of any one of Aspects 1-34, wherein (Degron) is selected from

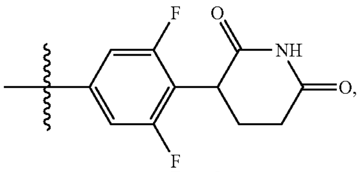

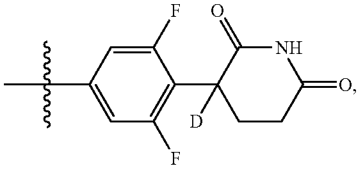

-continued

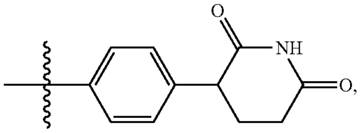

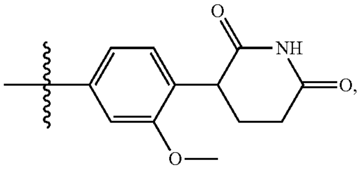

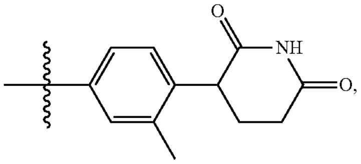

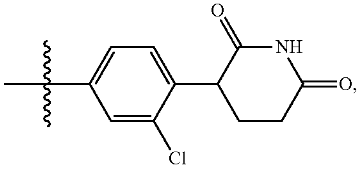

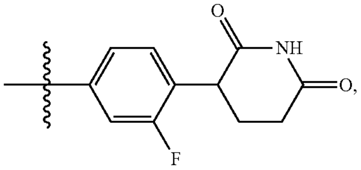

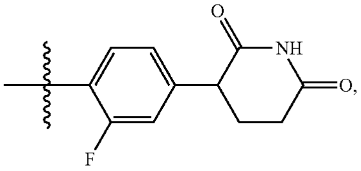

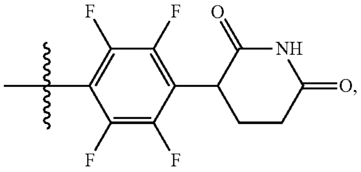

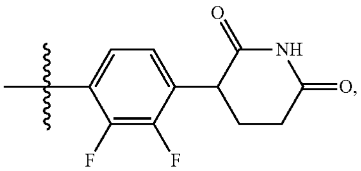

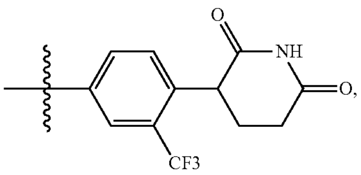

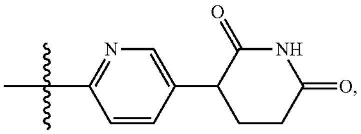

-continued
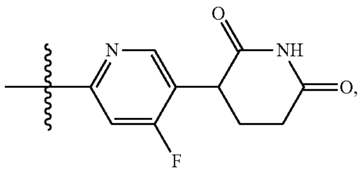
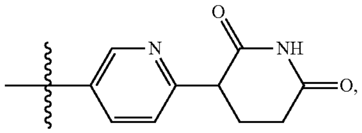
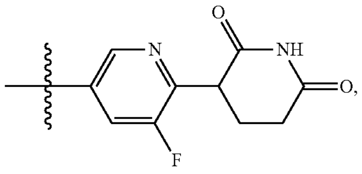
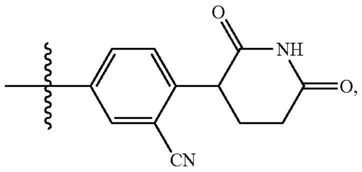
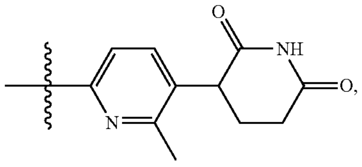
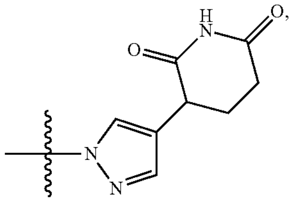
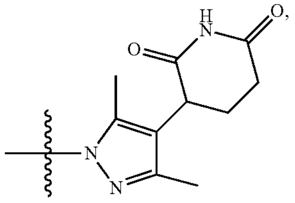
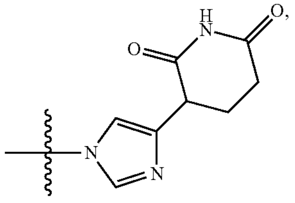
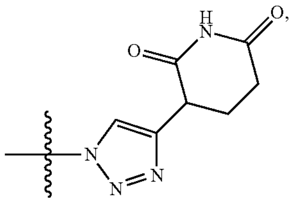
-continued
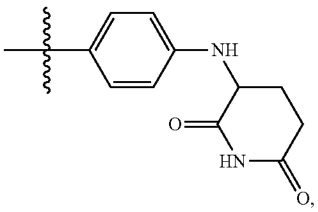
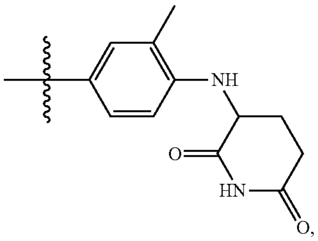
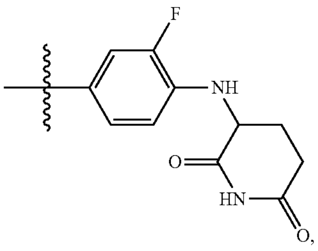
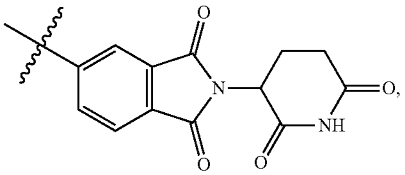
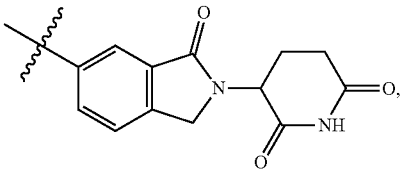
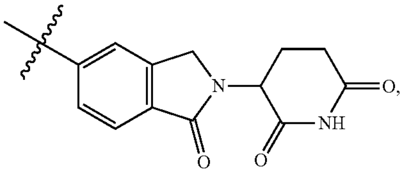
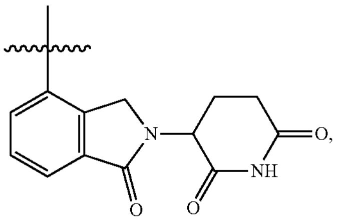
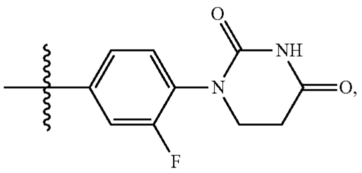

-continued
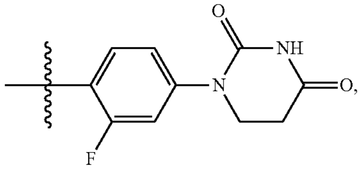
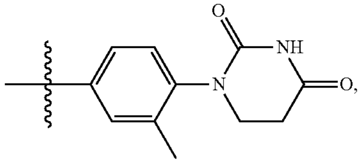
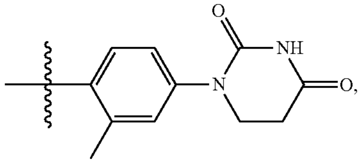
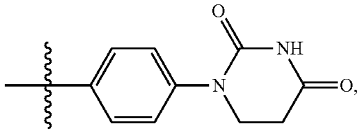
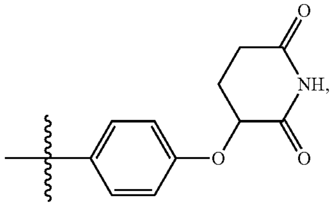
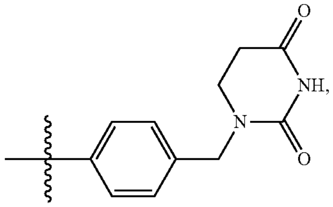
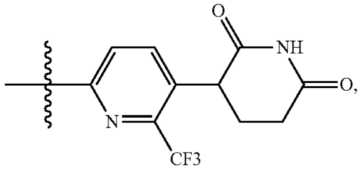
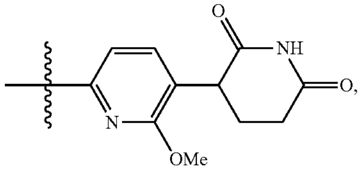
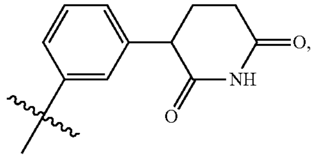
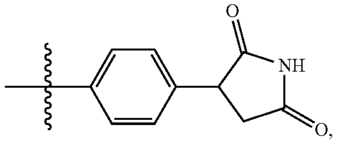
-continued
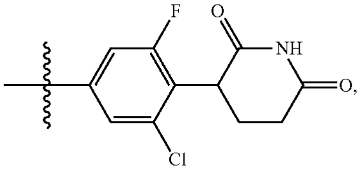
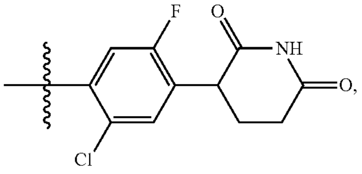
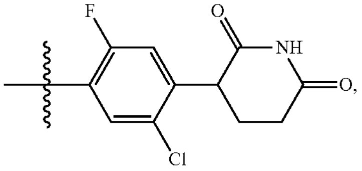
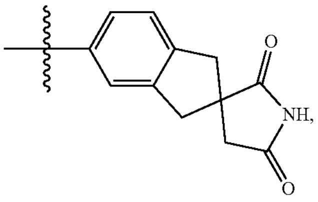
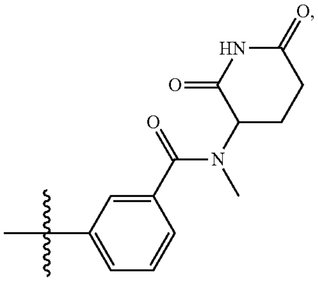
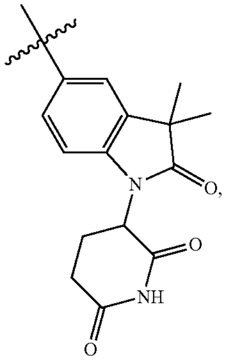
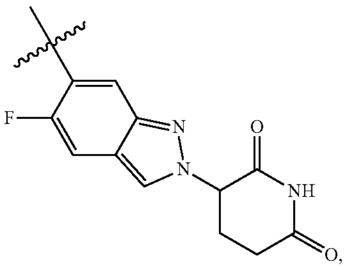

-continued
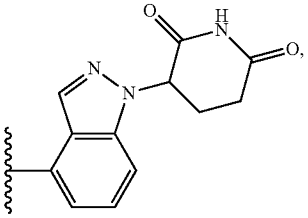
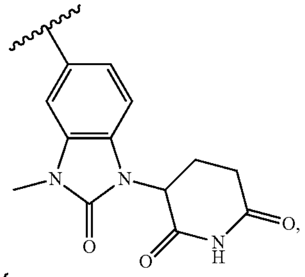
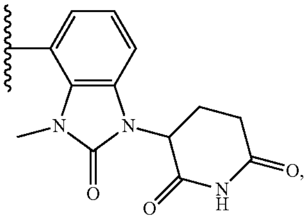
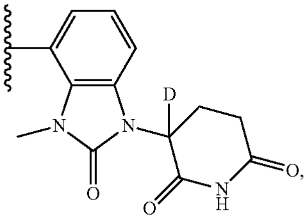
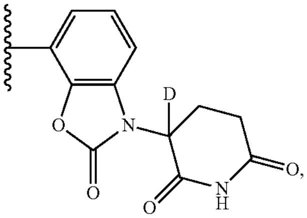
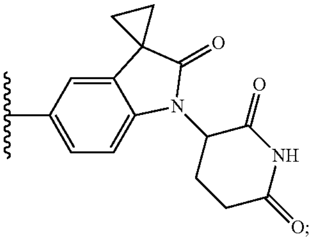
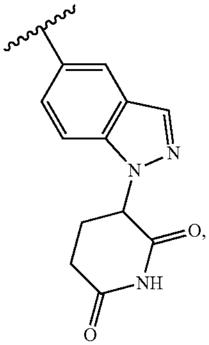
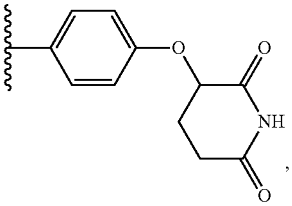
-continued
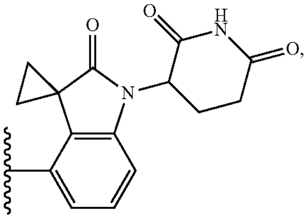
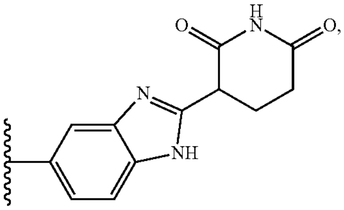
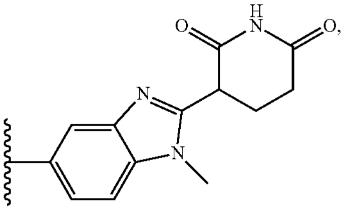
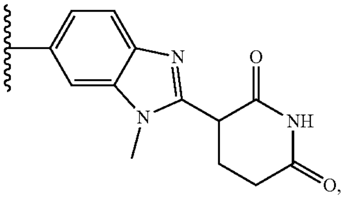
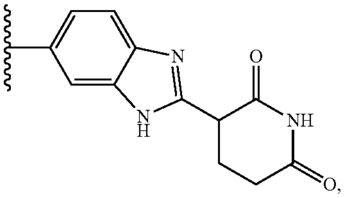
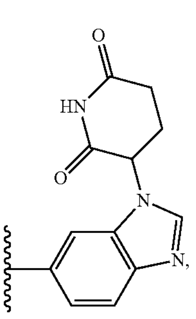
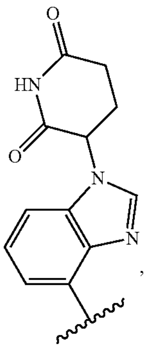
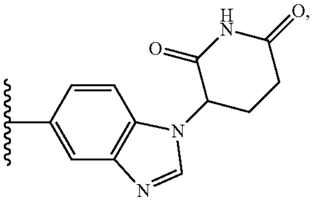

-continued
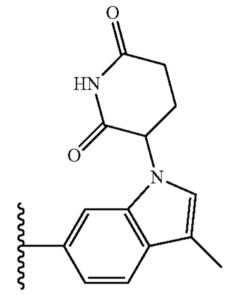
,
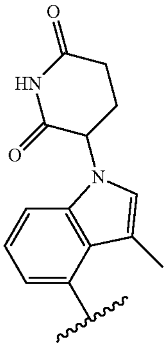
,
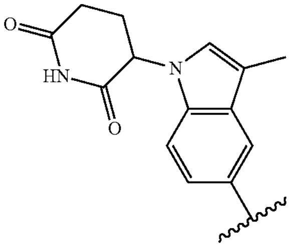
,
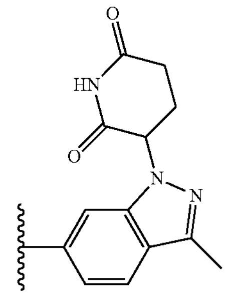
,
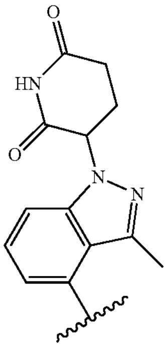
,
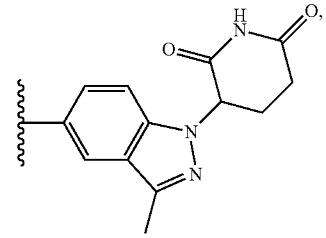
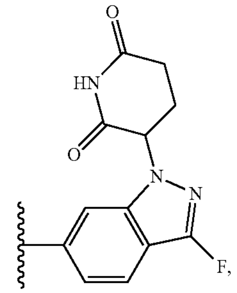
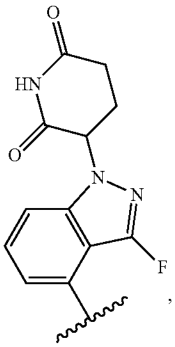
,
-continued
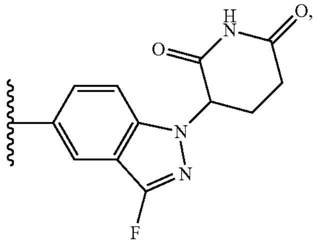
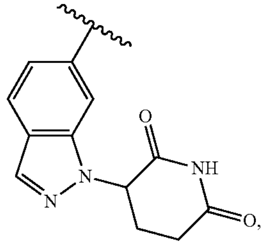
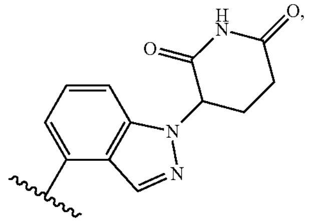
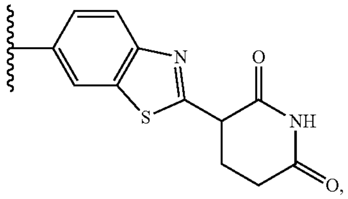
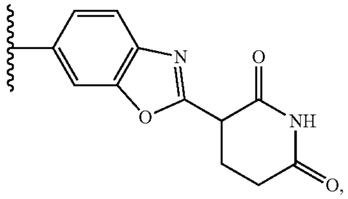
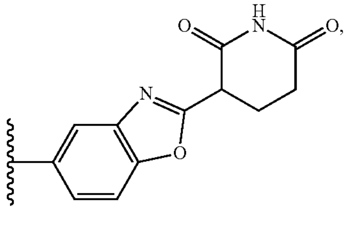
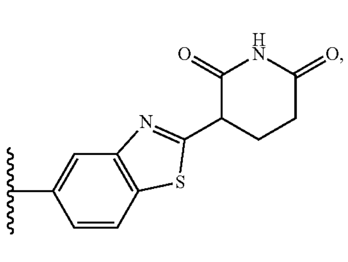
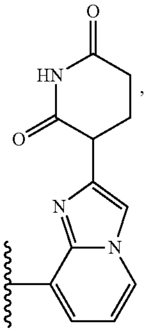
, -continued
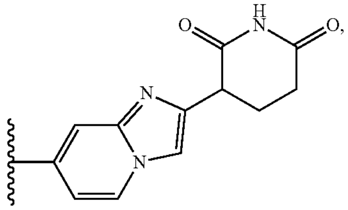
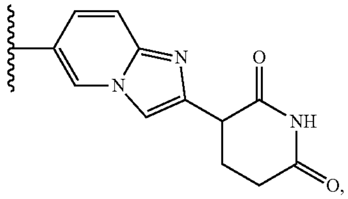
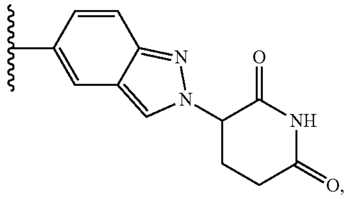
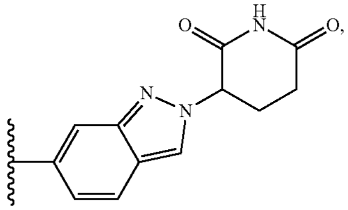
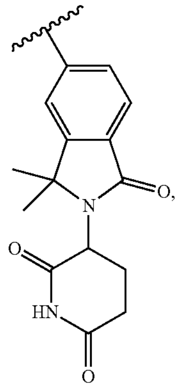
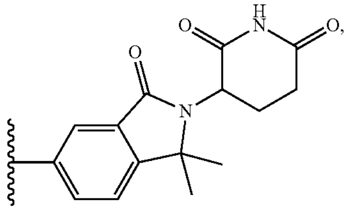
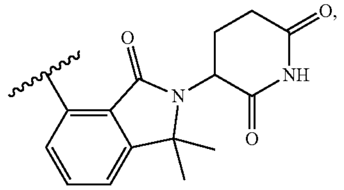
-continued
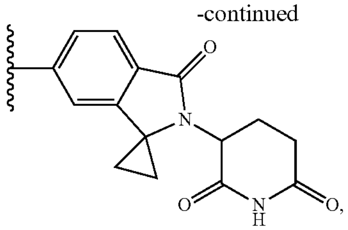
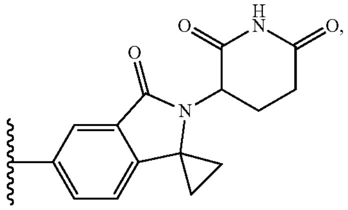
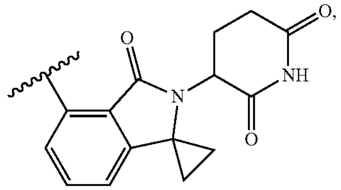
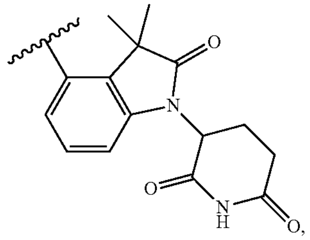
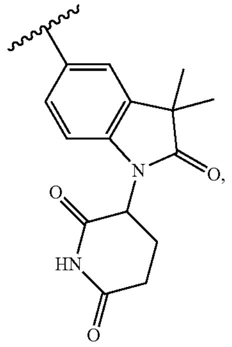
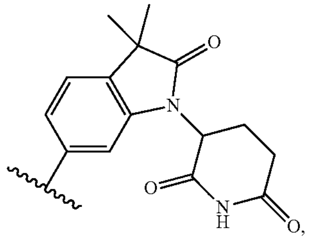
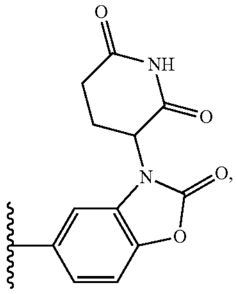

-continued
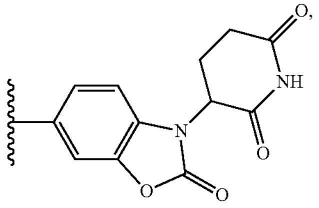
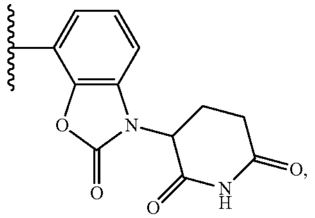
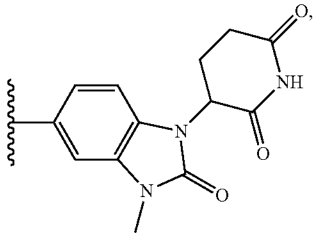
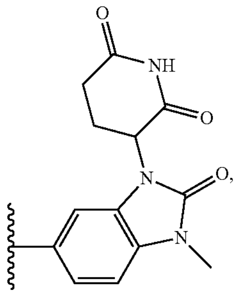
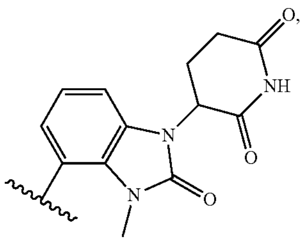
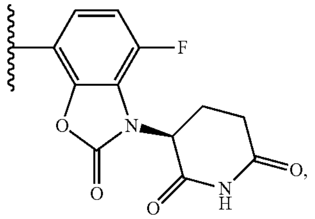
-continued
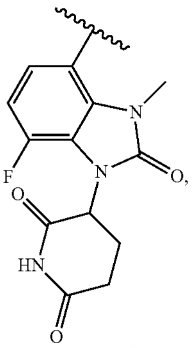
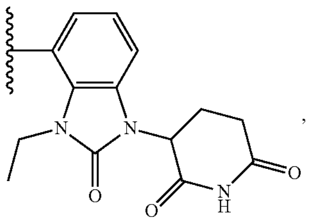
,
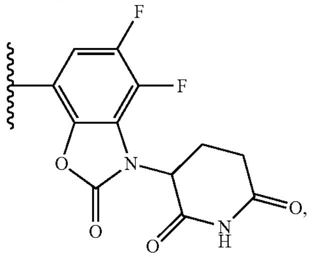
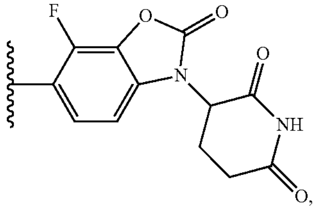
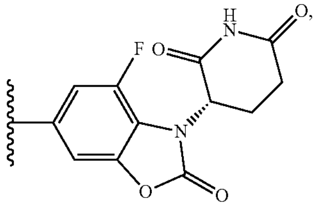
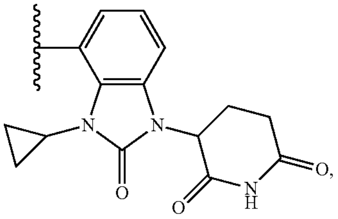
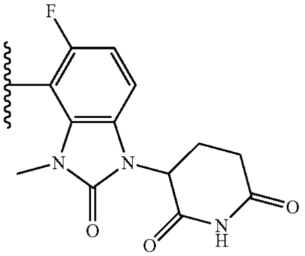
or
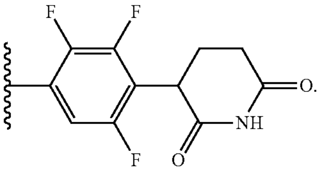
Aspect 36. The compound of any one of Aspects 1-35, wherein $Z^1$, $Z^2$, $Z^3$ and $Z^4$ are each independently —$CR^z$;

$R^Z$, at each occurrence, is independently selected from hydrogen, —F, —Cl, —Br, —I, methyl, ethyl, propyl, butyl, pentyl, hexyl, heptyl, octyl, $—NR^{Za}R^{Zb}$, $—OR^{Za}$, $—SR^{Za}$, cyclopropyl, cyclobutyl, cyclopentyl, cyclohexyl, cycloheptyl, cyclooctyl, 3- to 8-membered heterocyclyl, phenyl, 5- to 12-membered heteroaryl, or CN, wherein each of methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl is optionally substituted with at least one $R^{Zc}$;

$R^{Za}$ and $R^{Zb}$ are each independently selected from hydrogen, methyl, ethyl, propyl, butyl, pentyl, hexyl, heptyl, octyl, $—C_{2-8}$alkenyl, $—C_{2-8}$alkynyl, cyclopropyl, cyclobutyl, cyclopentyl, cyclohexyl, cycloheptyl, cyclooctyl, 3- to 8-membered heterocyclyl, phenyl or 5- to 12-membered heteroaryl, wherein each of said hydrogen, methyl, ethyl, propyl, butyl, pentyl, hexyl, heptyl, octyl, $—C_{2-8}$alkenyl, $—C_{2-8}$alkynyl, cyclopropyl, cyclobutyl, cyclopentyl, cyclohexyl, cycloheptyl, cyclooctyl, 3- to 8-membered heterocyclyl, phenyl or 5- to 12-membered heteroaryl is optionally substituted with at least one substituent $R^{Zd}$;

$R^{Zc}$ and $R^{Zd}$ are each independently —F, —Cl, —Br, —I, hydroxy, methyl, ethyl, propyl, butyl, pentyl, hexyl, heptyl, octyl, $—C_{1-8}$alkoxy, $—C_{2-8}$alkenyl, $—C_{2-8}$alkynyl, cyclopropyl, cyclobutyl, cyclopentyl, cyclohexyl, cycloheptyl, cyclooctyl, 3- to 8-membered heterocyclyl, phenyl, or 5- to 12-membered heteroaryl.

Aspect 37. The compound of any one of Aspects 1-36, wherein $R^z$ is independently selected from H, $—CH_3$, $—C_2H_5$, F, $—CH_2F$, $—CHF_2$, $—CF_3$, $—OCH_3$, $—OC_2H_5$, $—C_3H_7$, $—OCH_2F$, $—OCHF_2$, $—OCH_2CF_3$, $—OCF_3$, $—SCF_3$, $—CF_3$ or $—CH(OH)CH_3$.

Aspect 38. The compound of any one of Aspects 1-37, wherein the deuterium substitution is on the Degron moiety, preferable, deuterium substitution is on $X^8$.

Aspect 39. The compound of any one of Aspects 1-38, wherein the compound is selected from

1

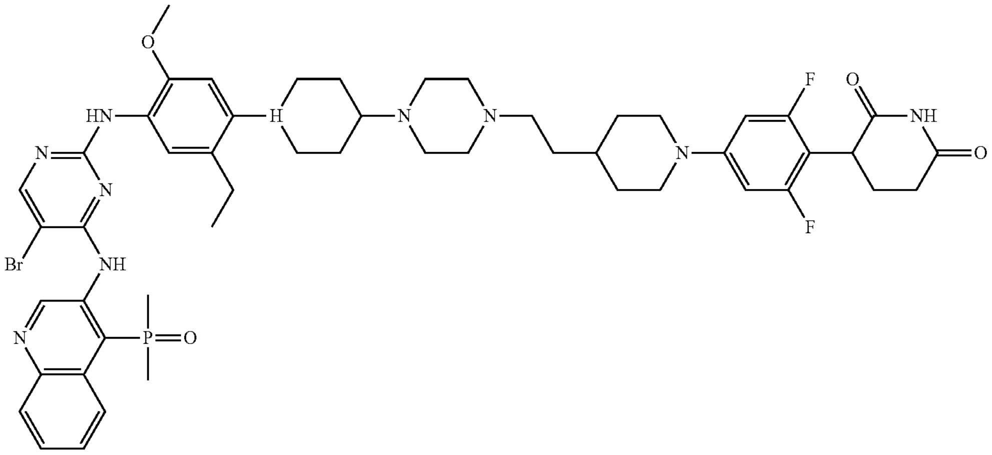

2

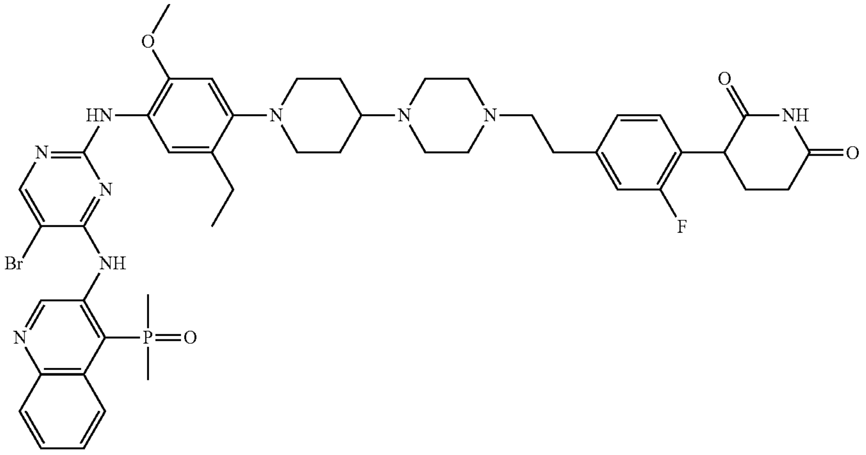

-continued
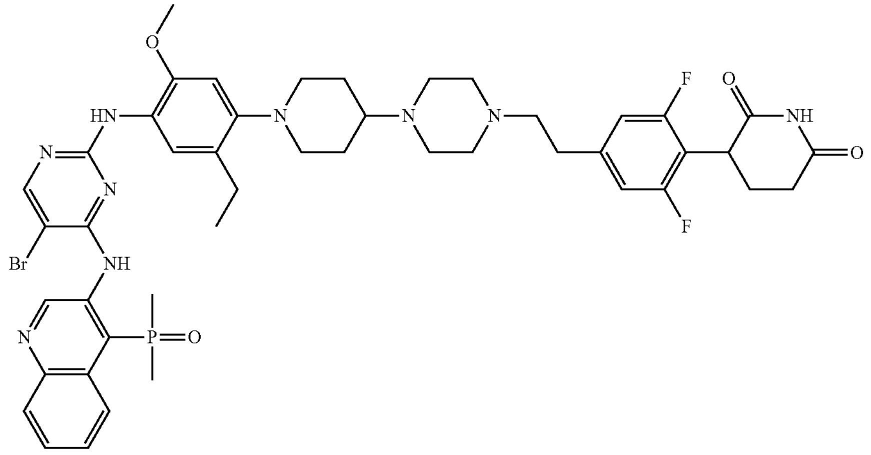
3
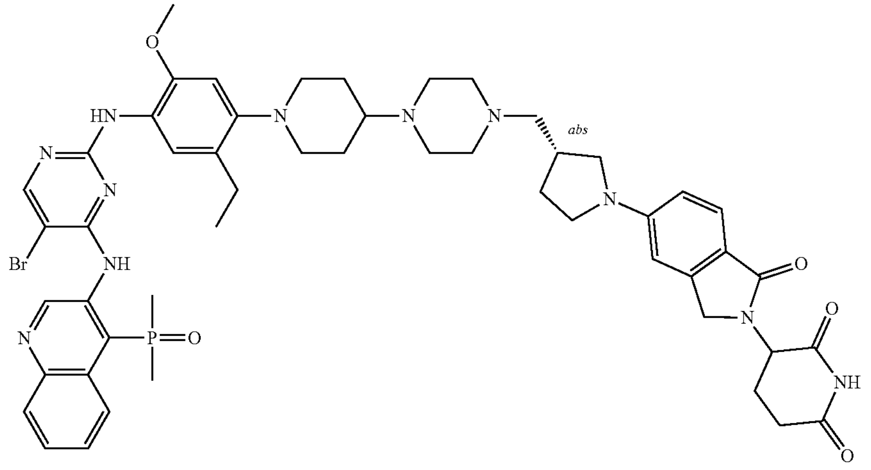
4
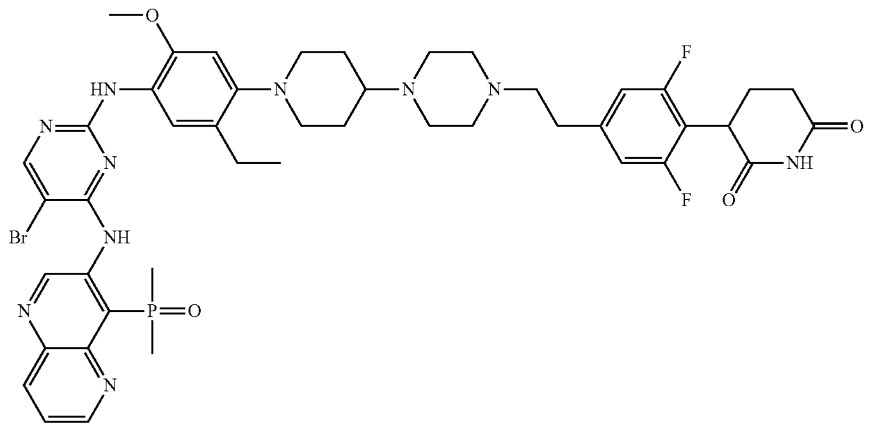
7

-continued
8
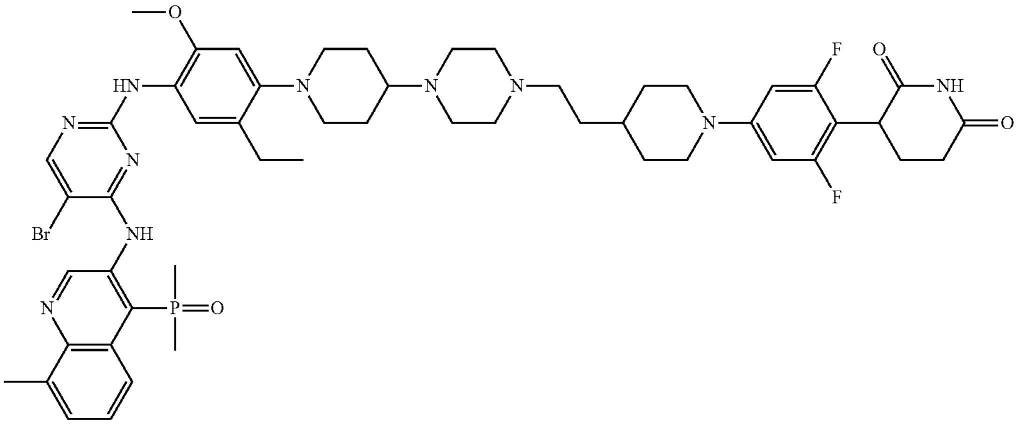
9
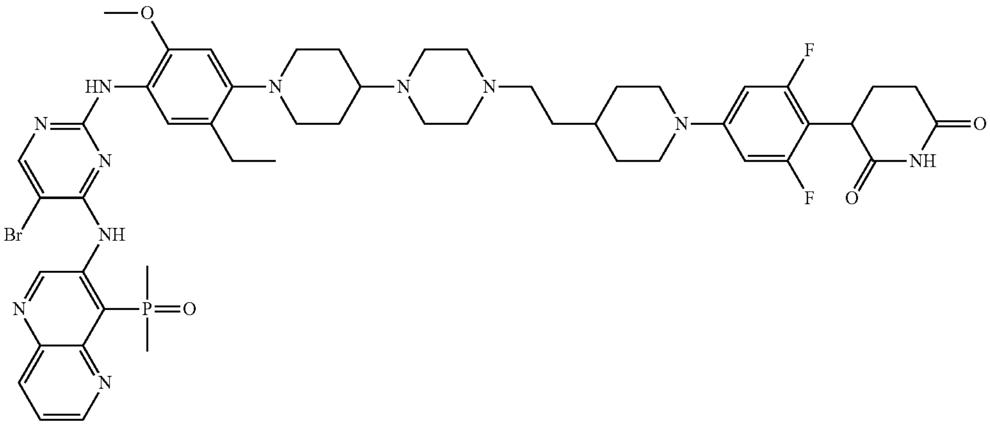
10
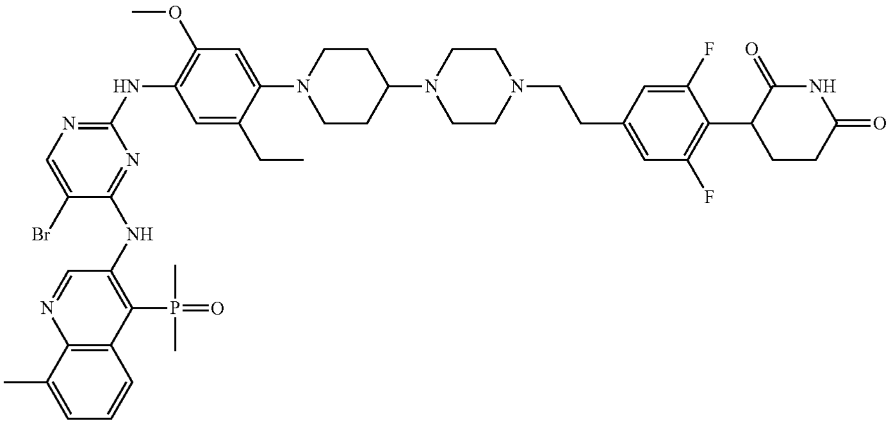

-continued
11
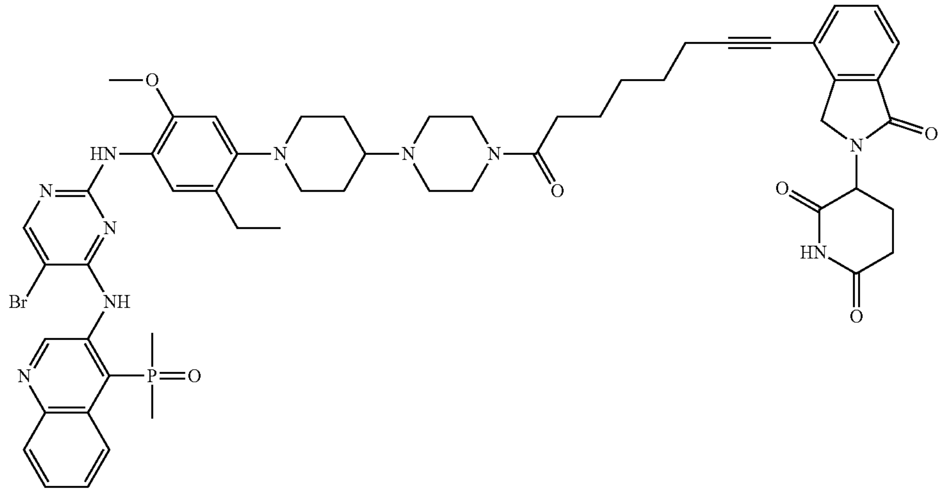
12
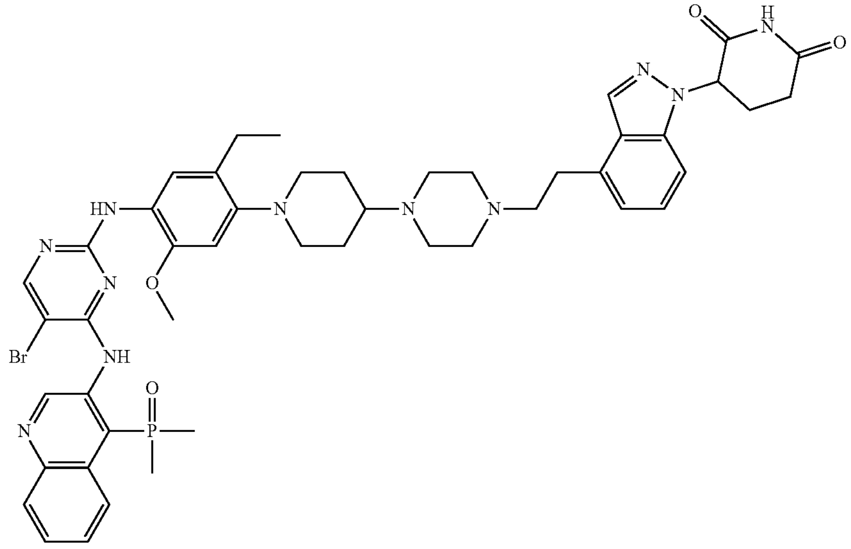
13
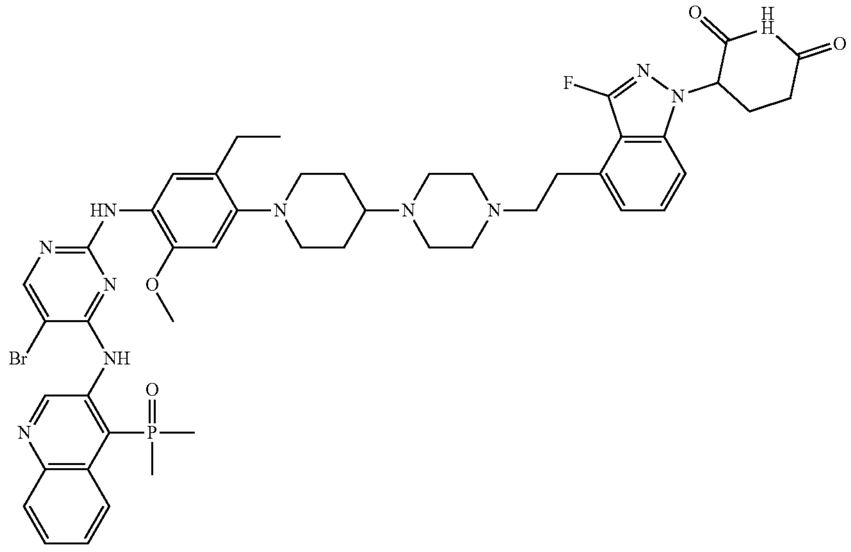

-continued
14
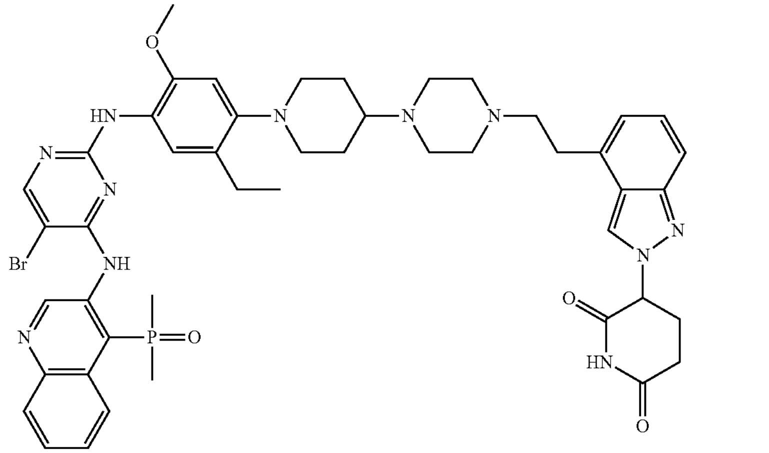
15
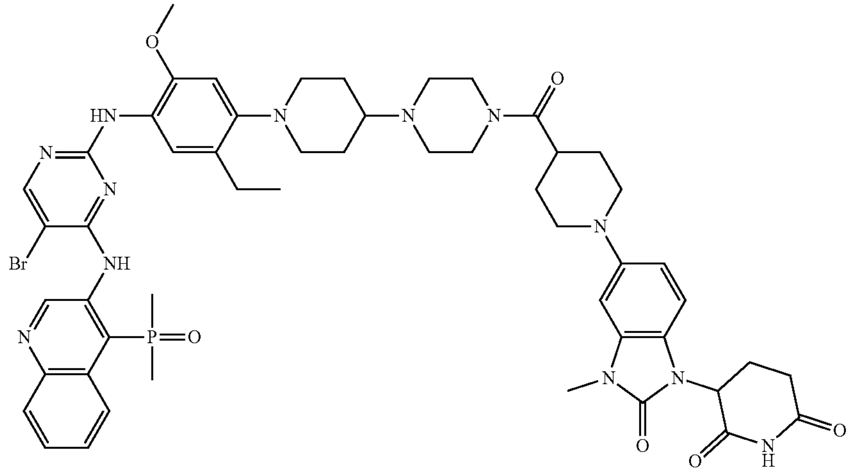
16
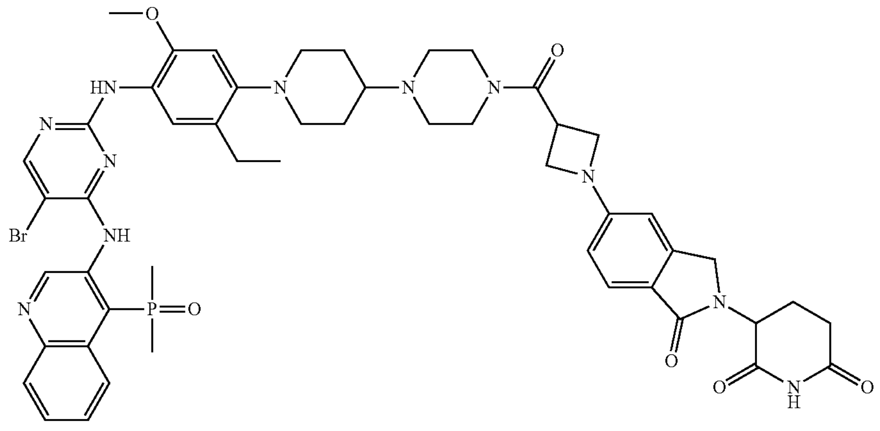

-continued
17
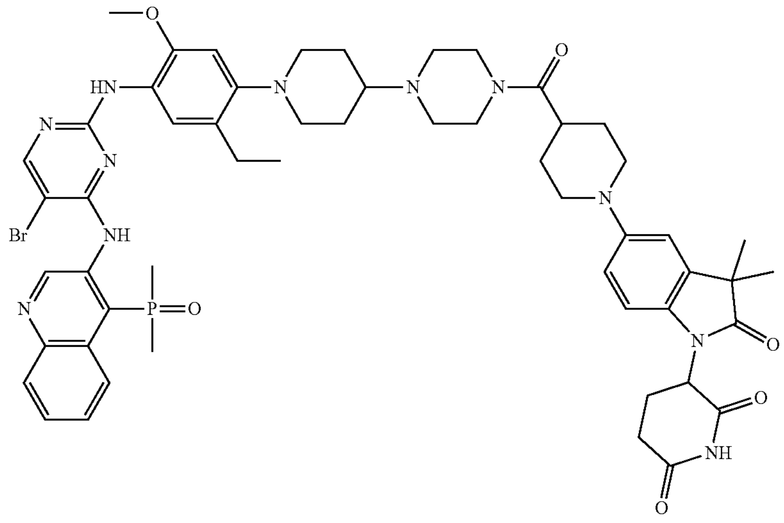
18
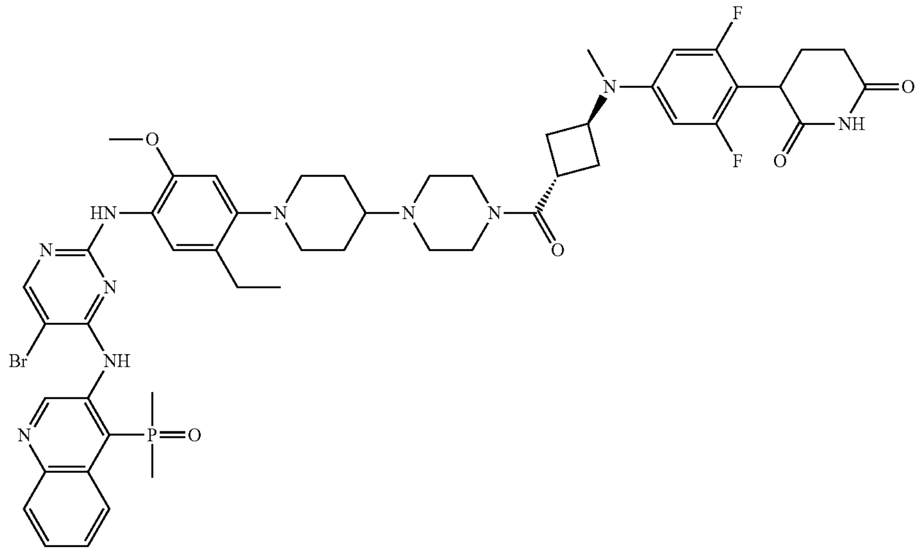
19
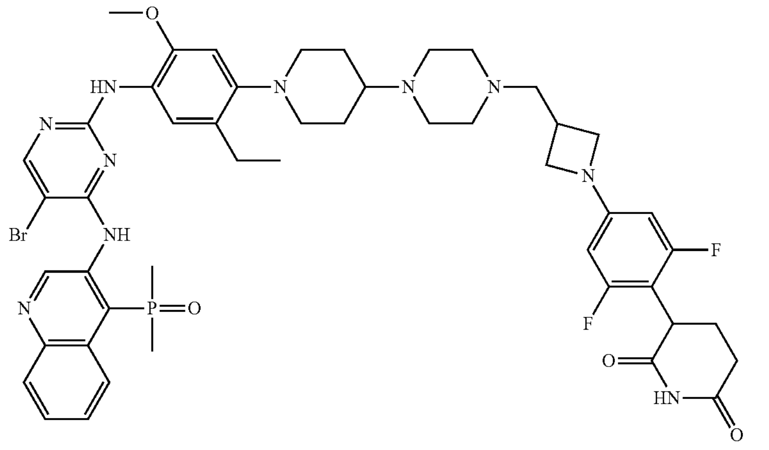

-continued
20
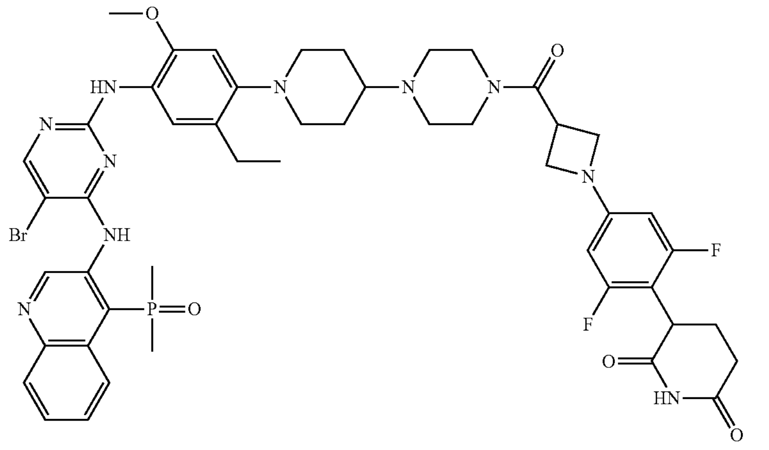
21
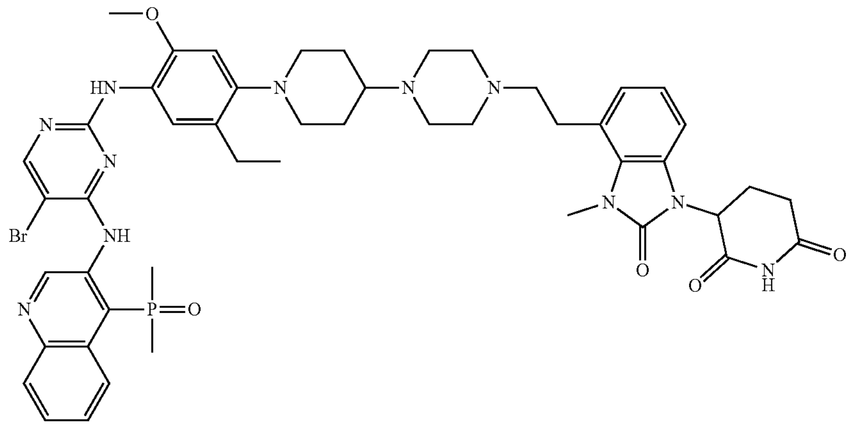
22
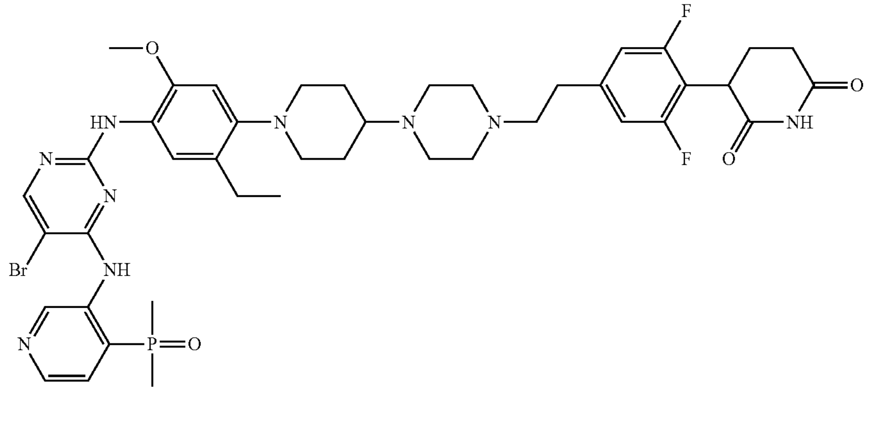

-continued
23
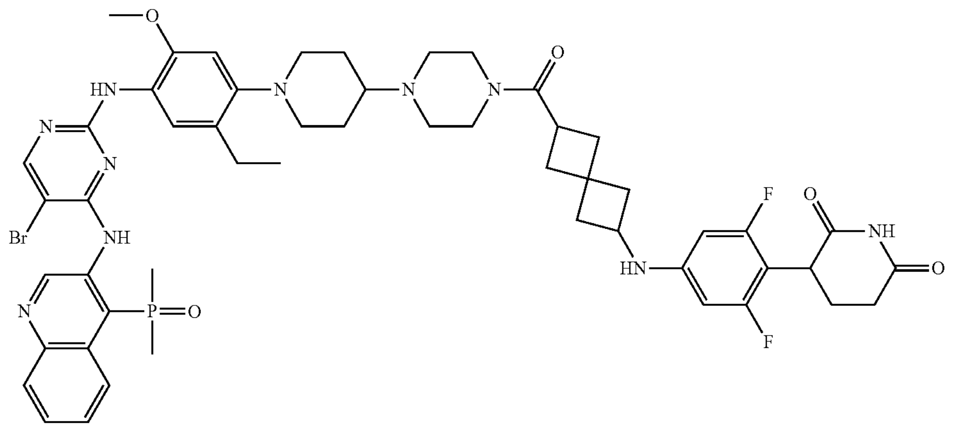
24
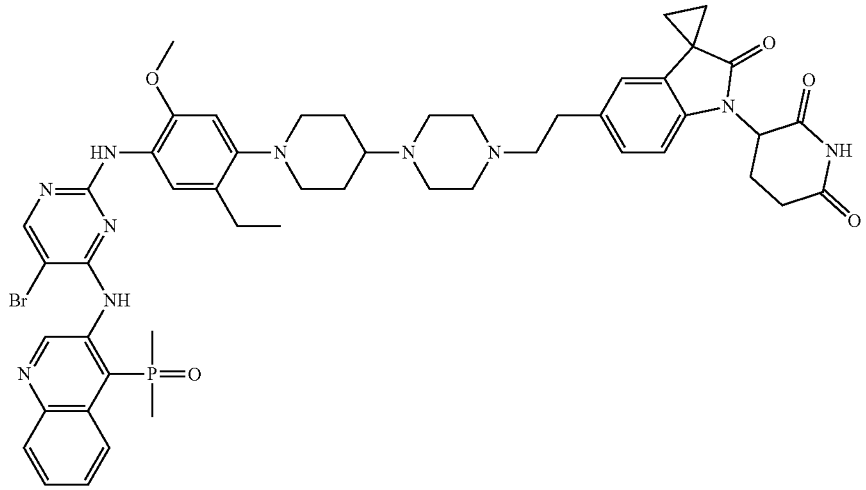
25
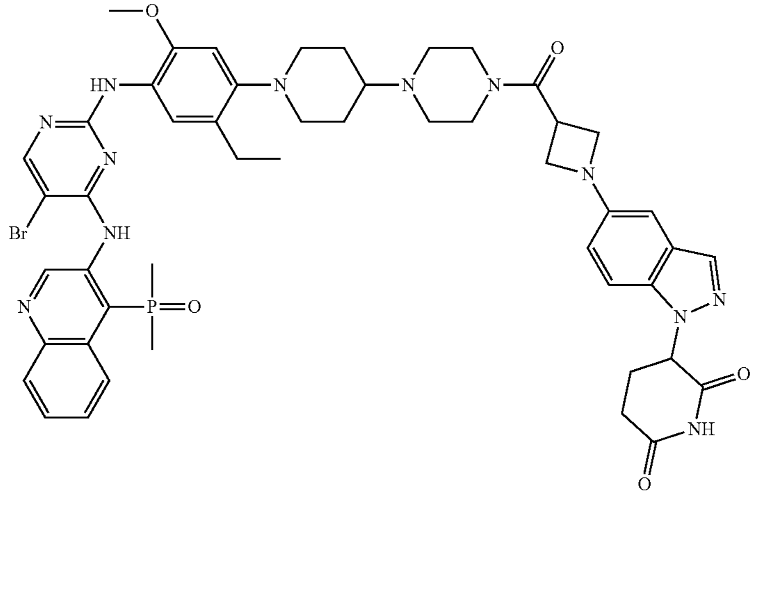

-continued
26
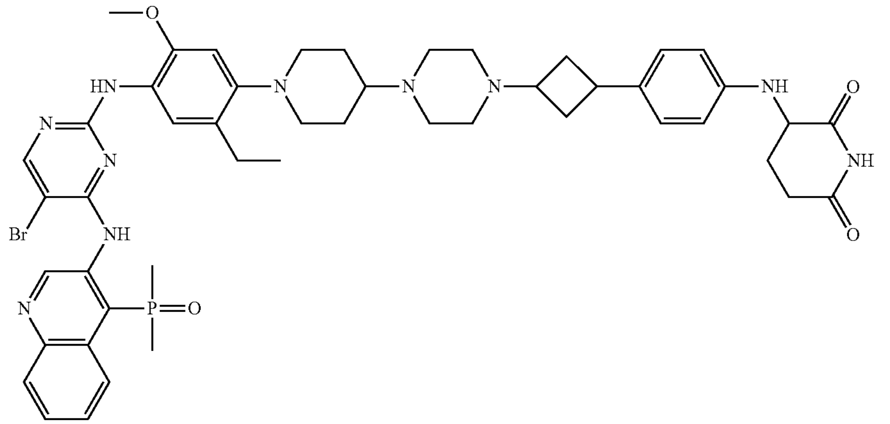
27
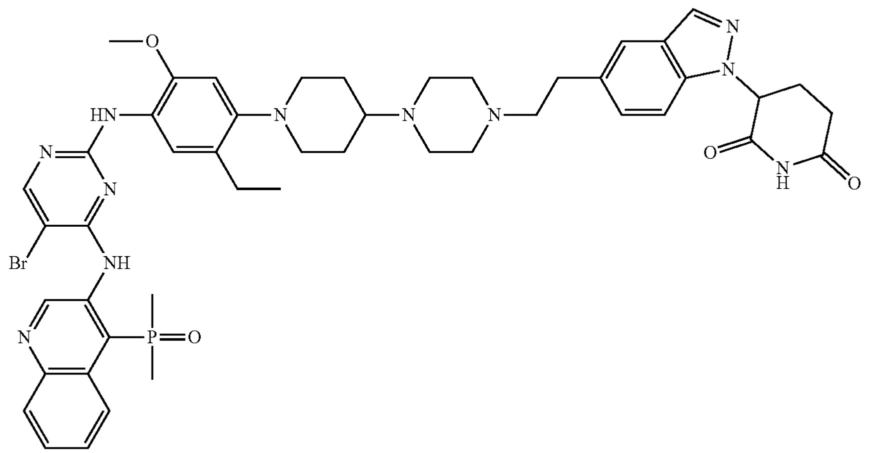
28
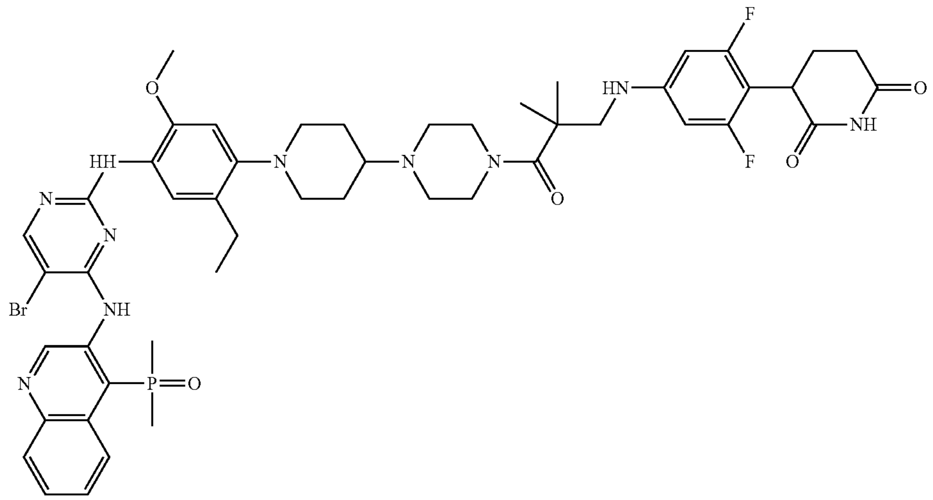

-continued
29
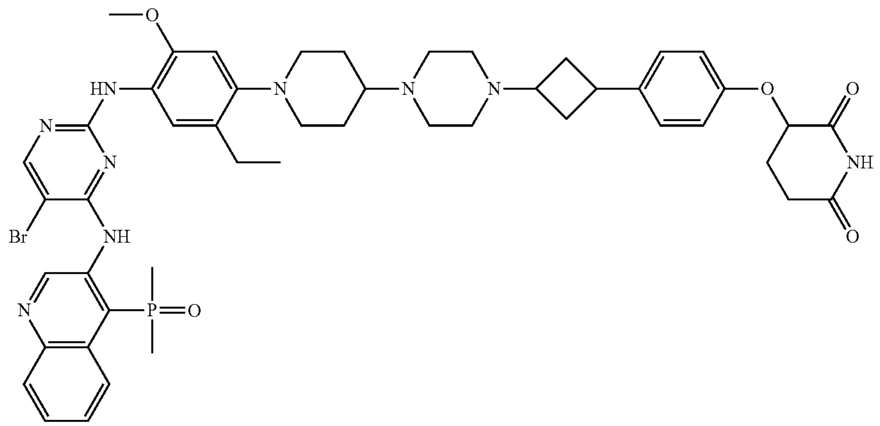
30
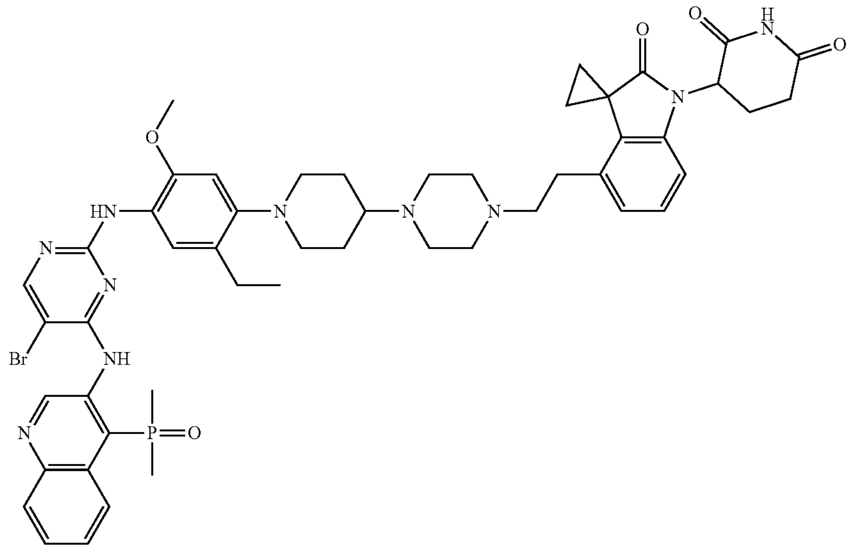
31
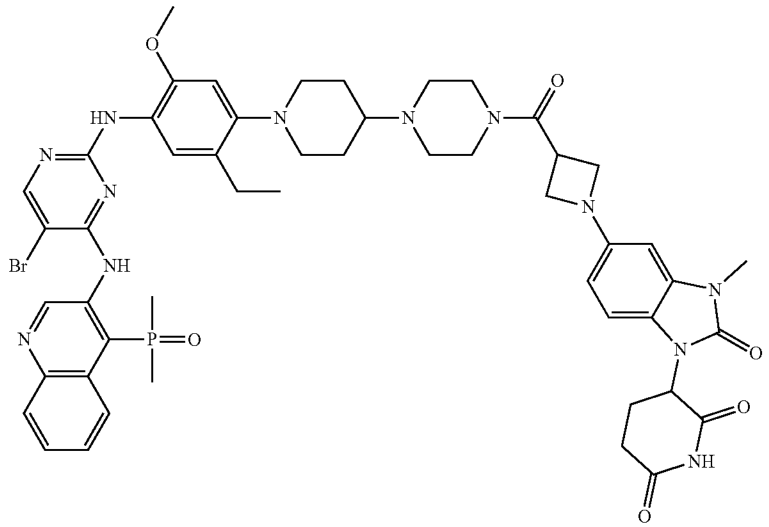

-continued
32
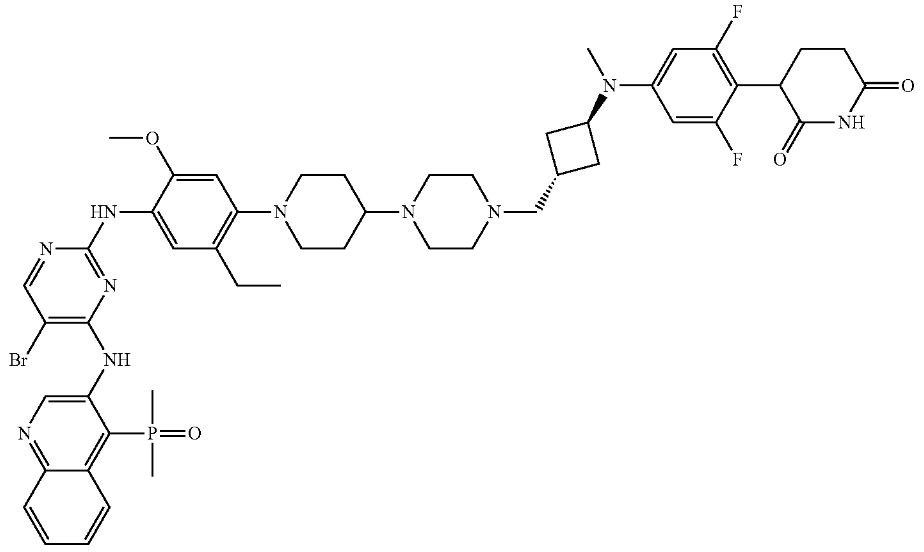
33
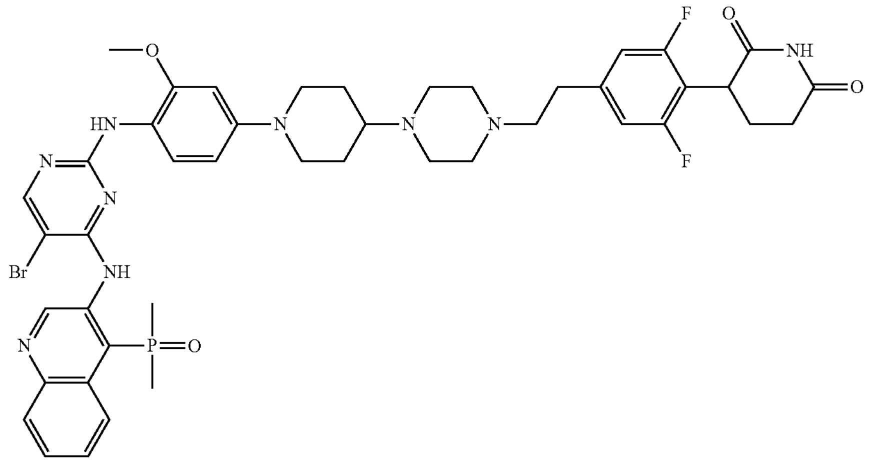
34
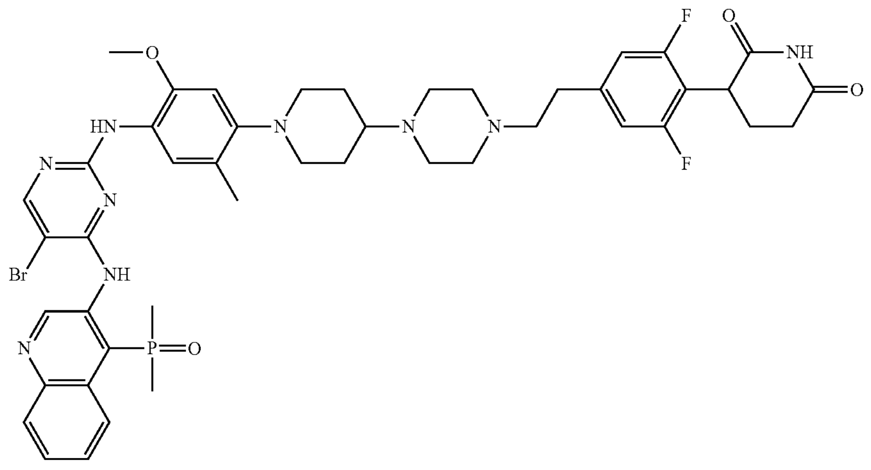

-continued
35
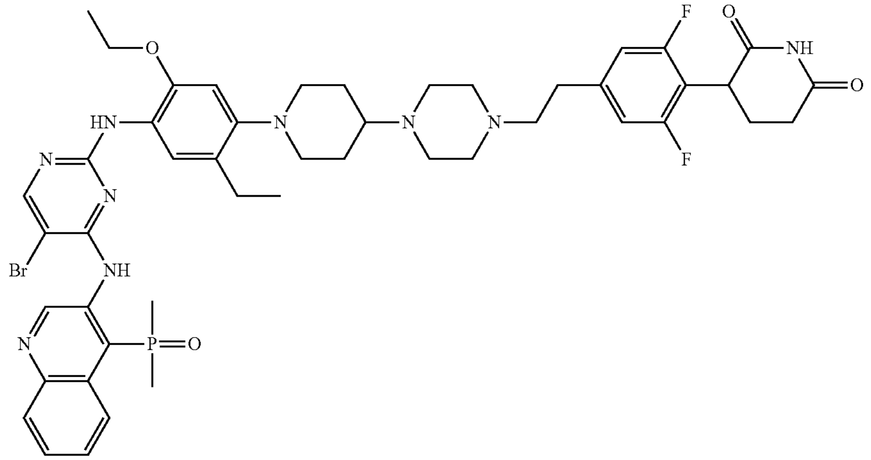
36
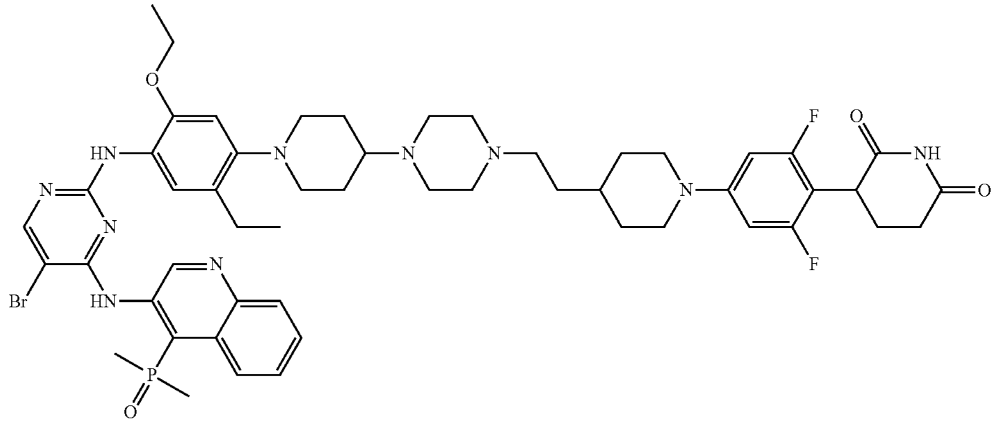
37
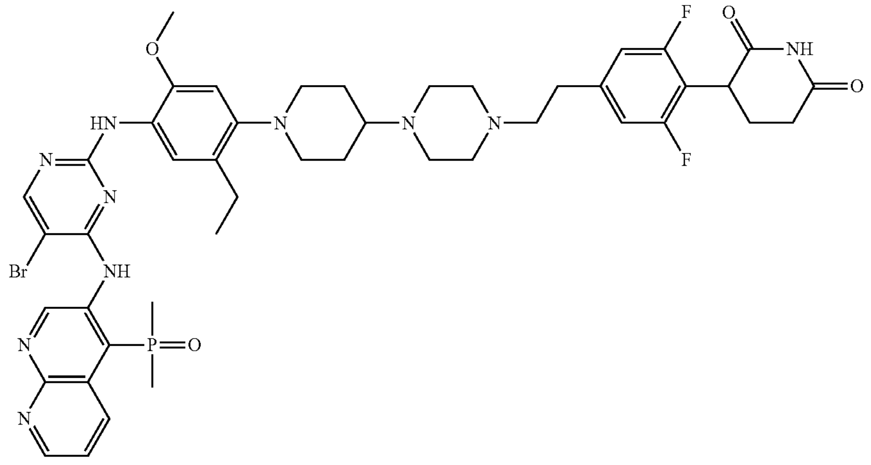

-continued
38
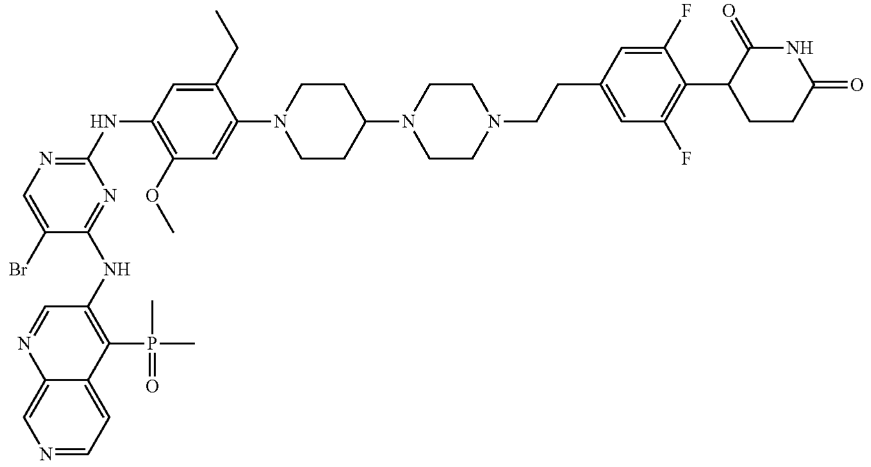
37
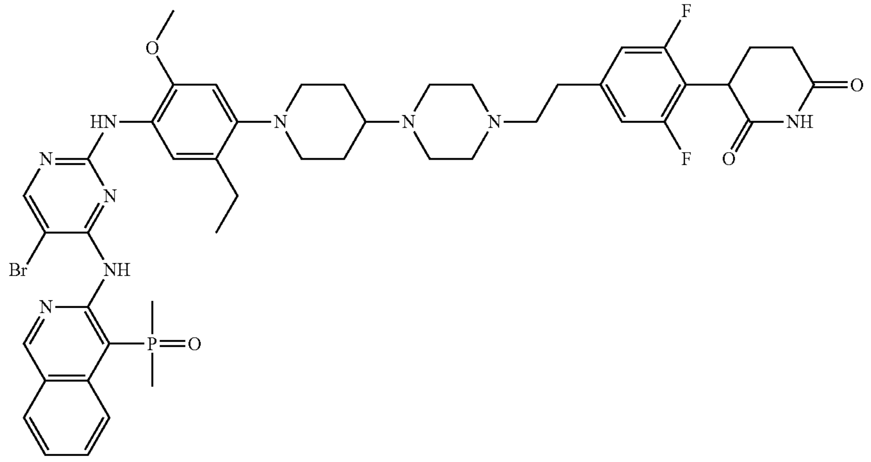
38
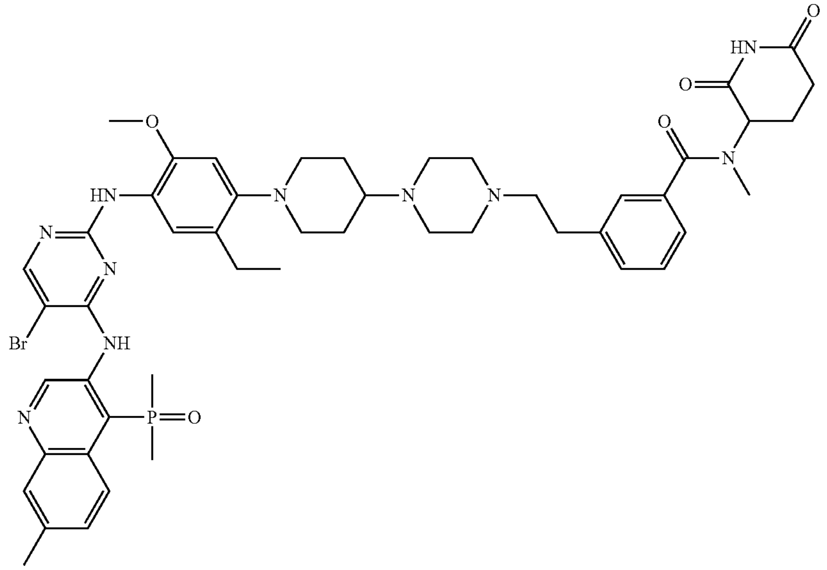

-continued
39
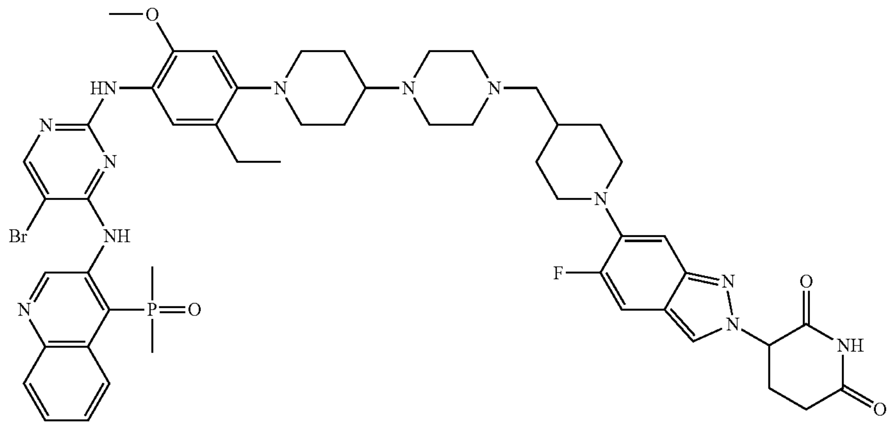
40
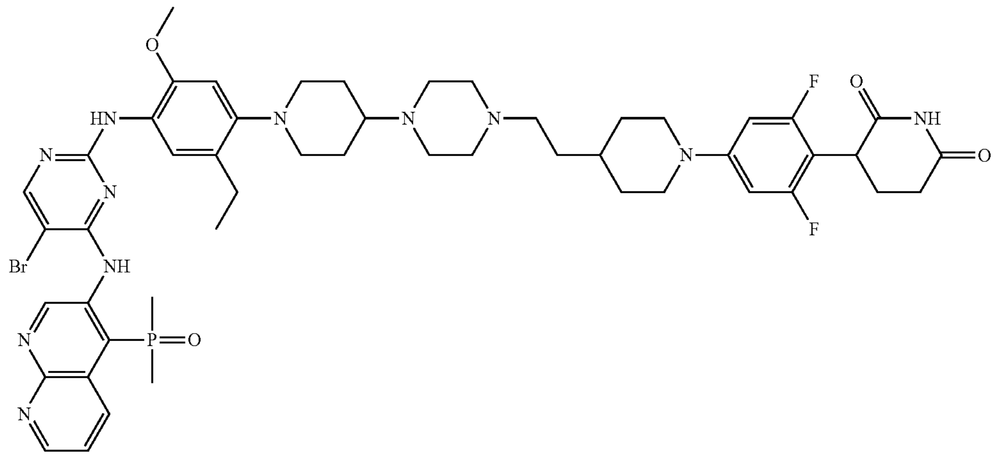
43
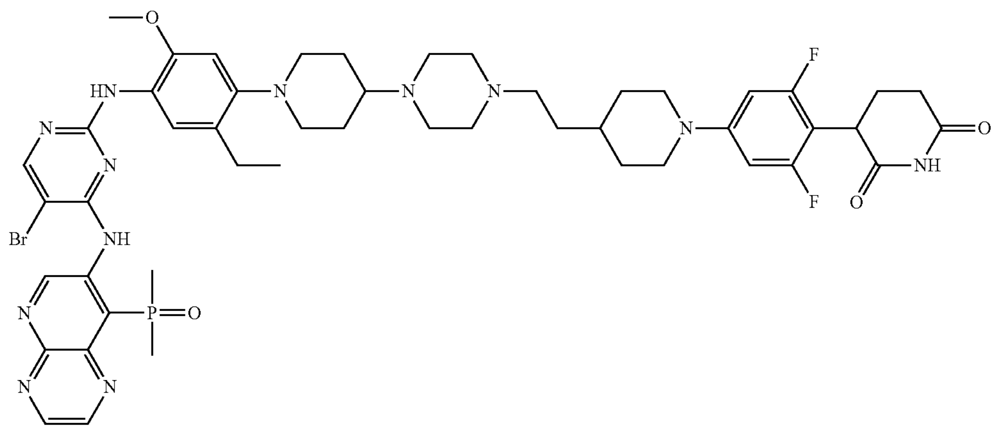

-continued
44
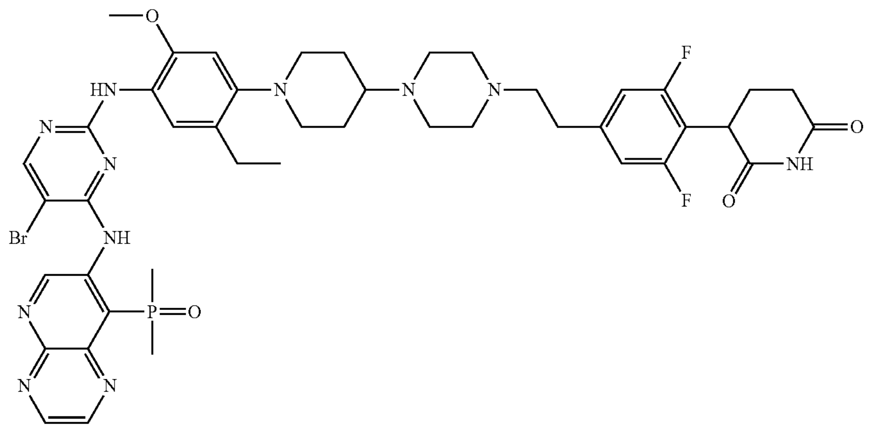
45
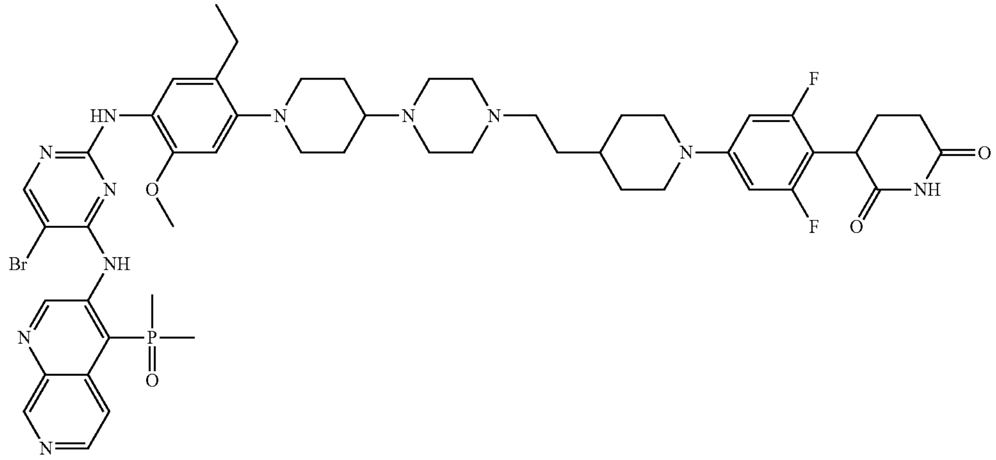
46
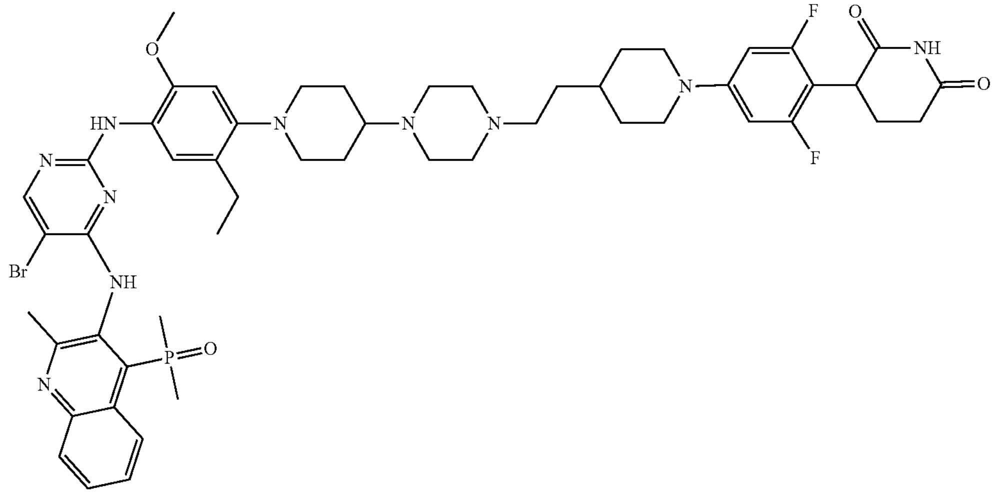

-continued
47
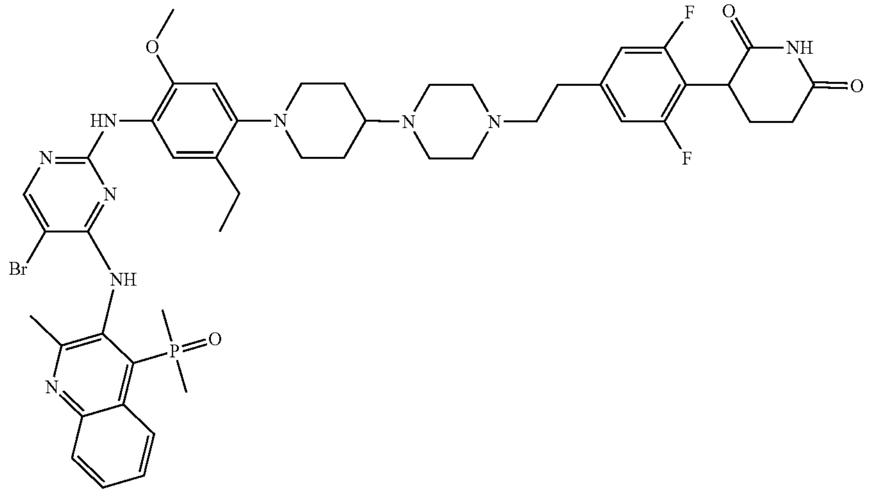
48
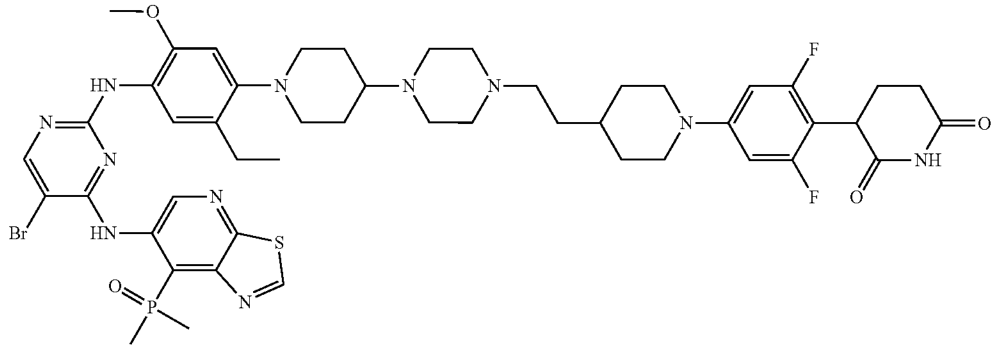
49
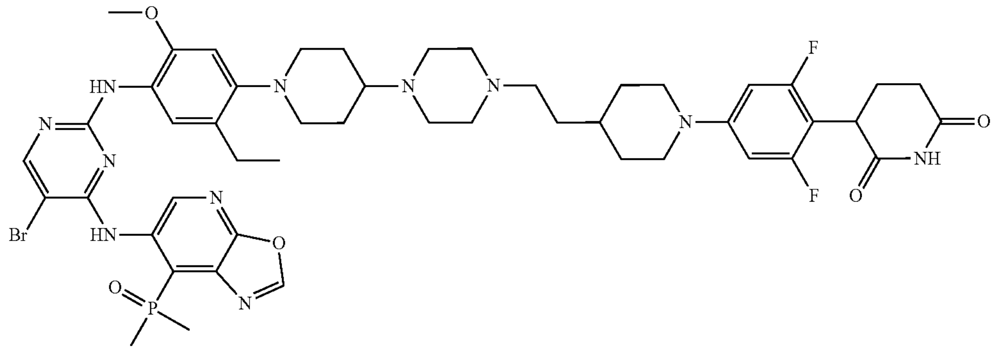
50
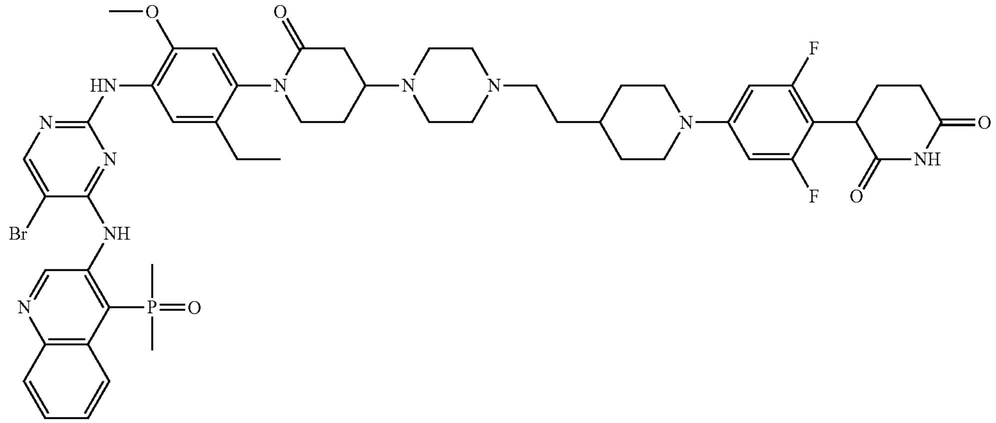

-continued
51
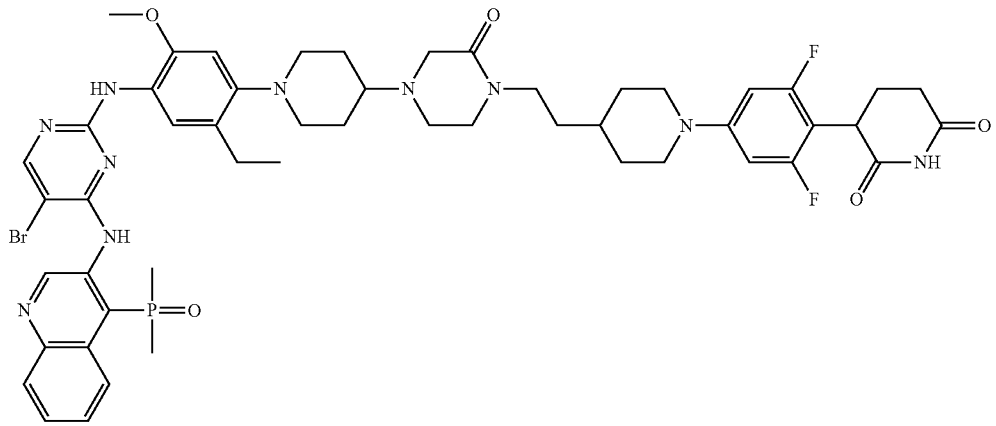
52
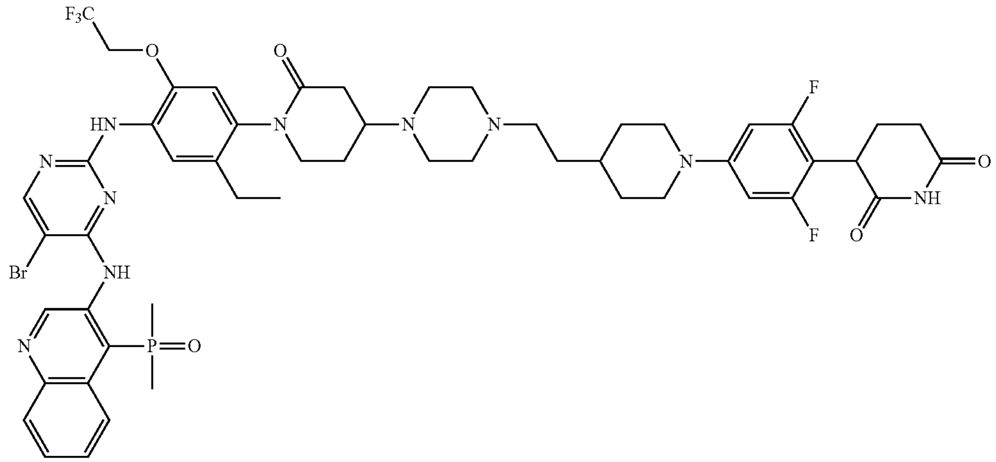
53
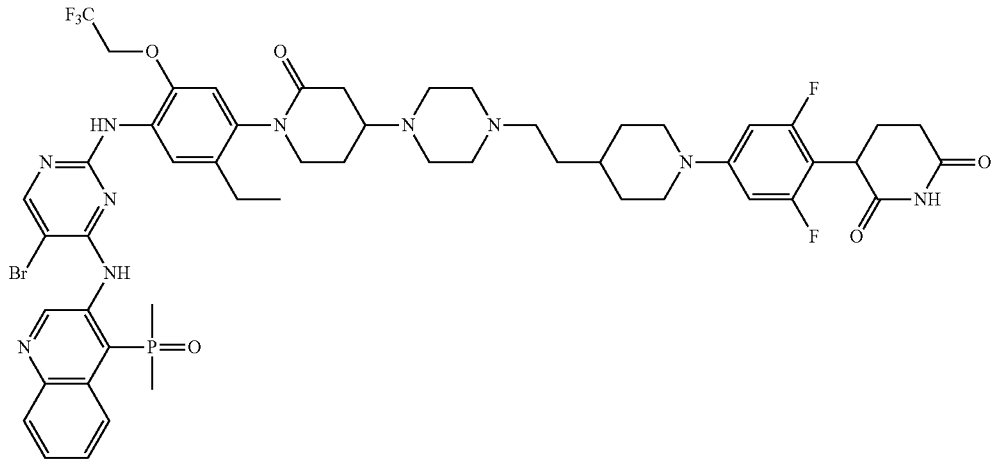

-continued
54
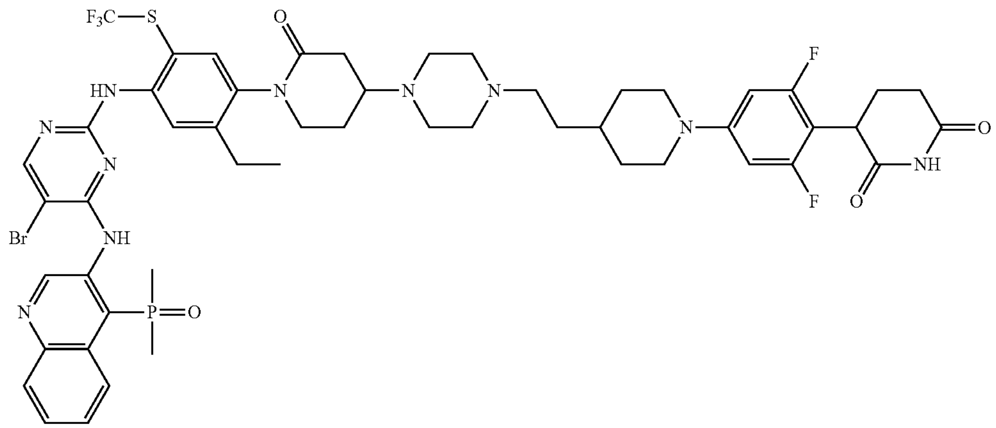
55
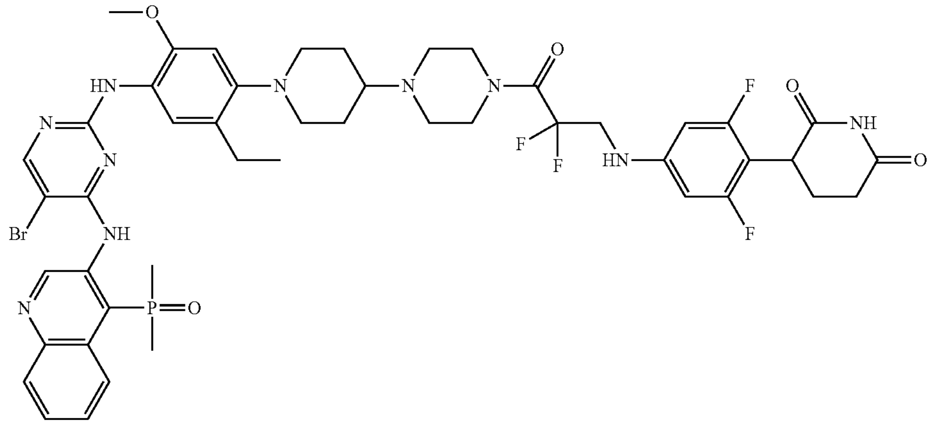
56
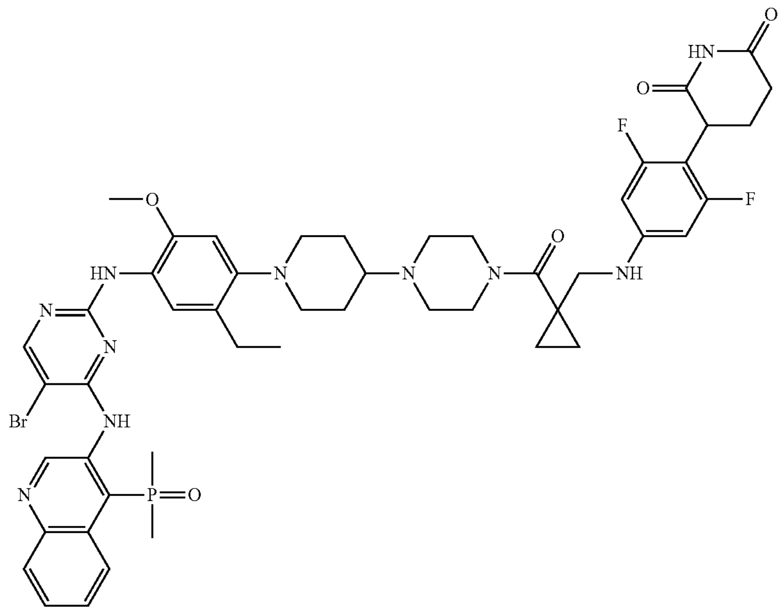

-continued
57
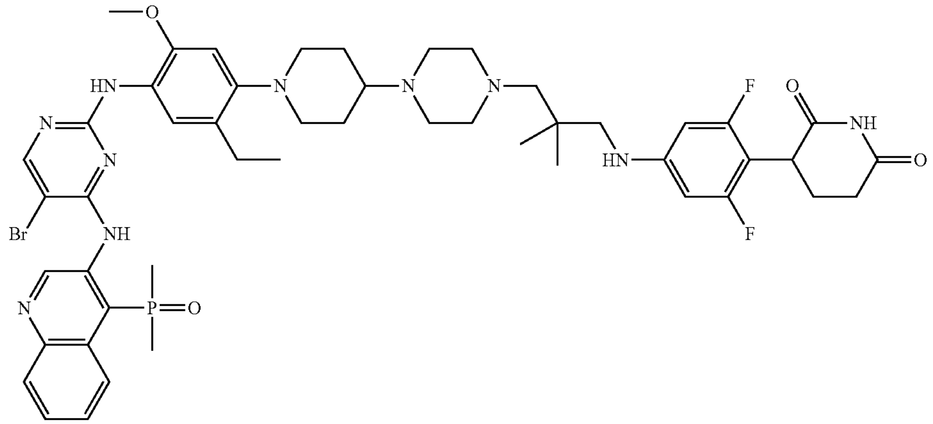
58
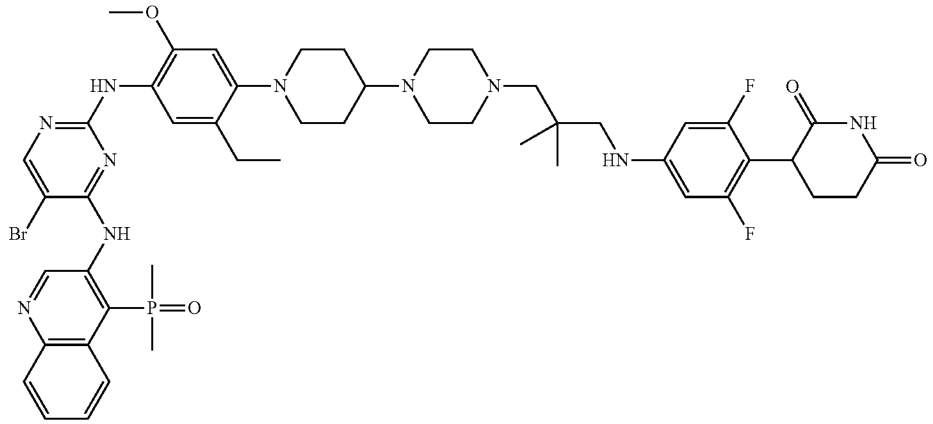
59
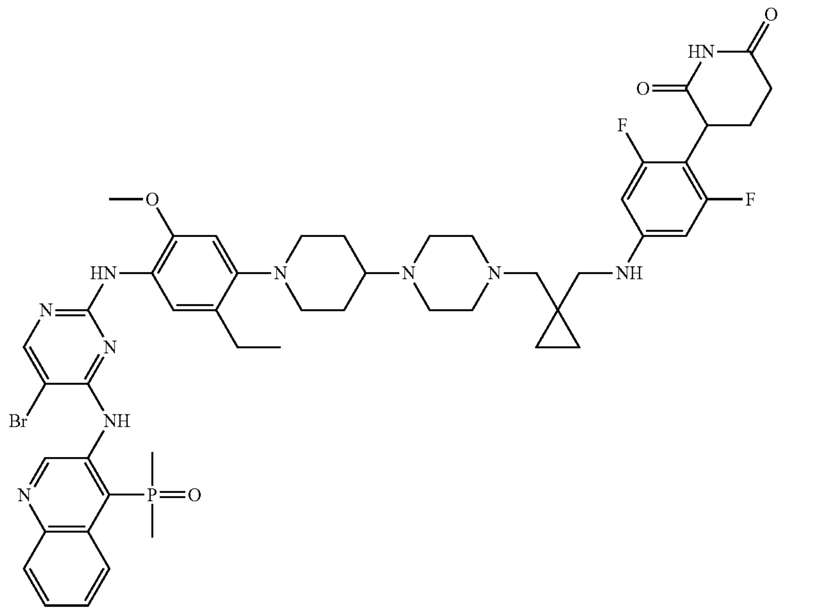

-continued
60
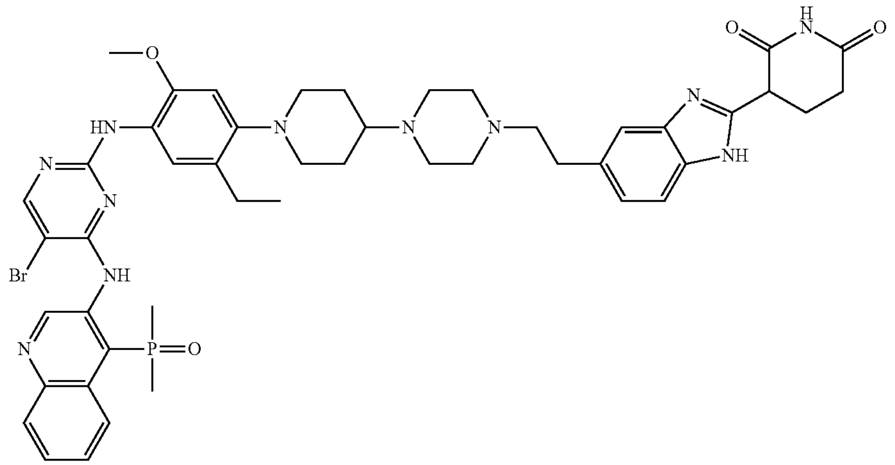
61
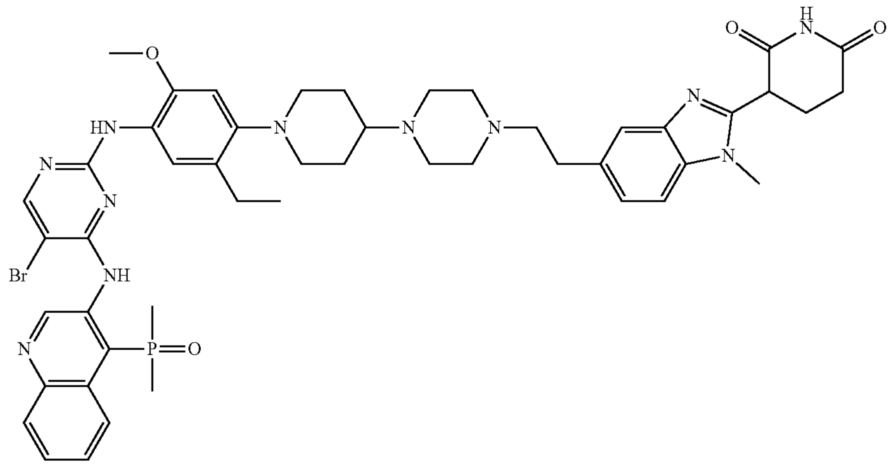
62
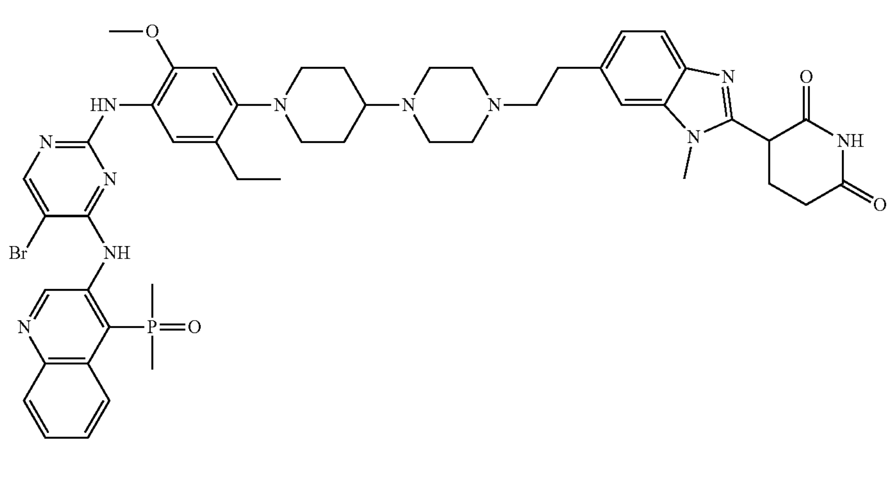

-continued
63
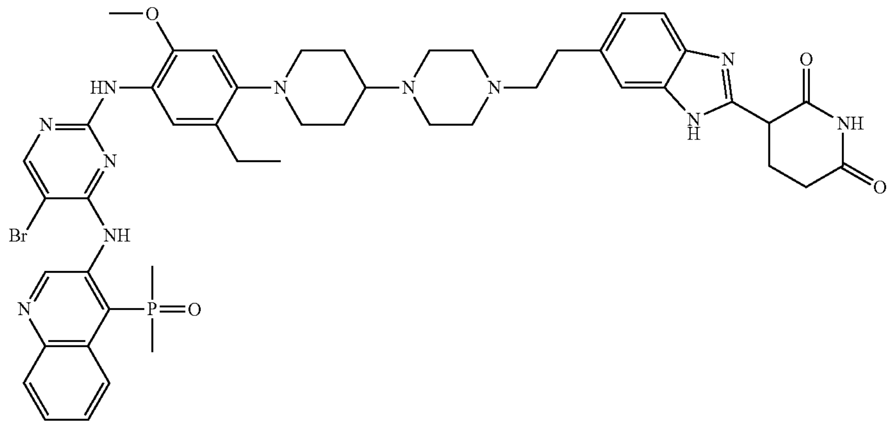
64
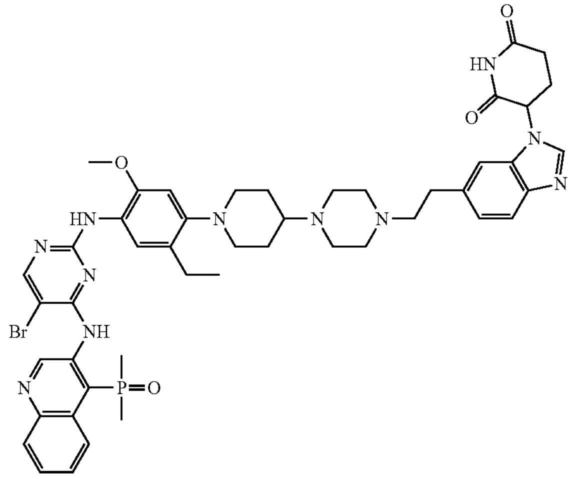
65
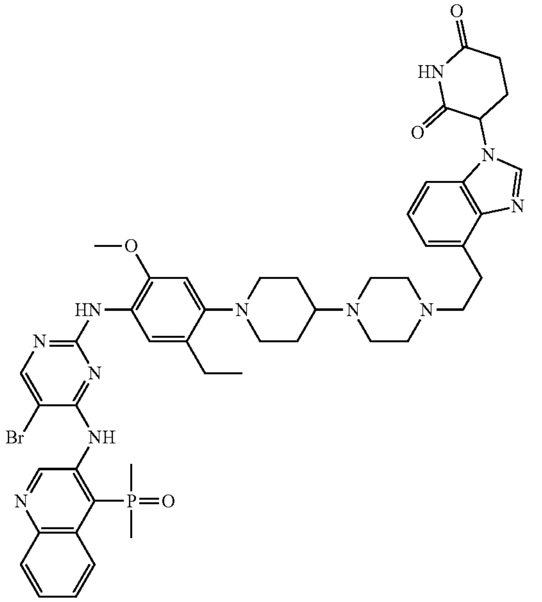
66
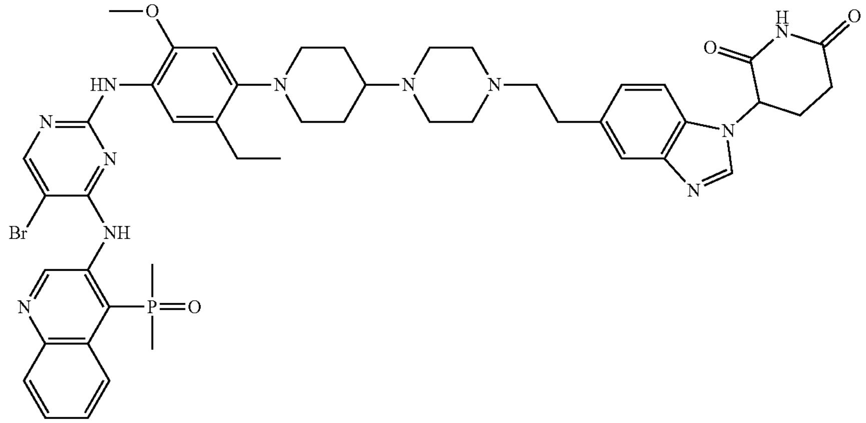

-continued
67
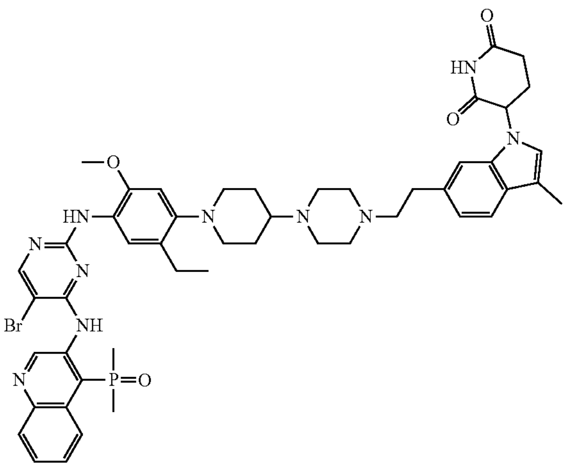
68
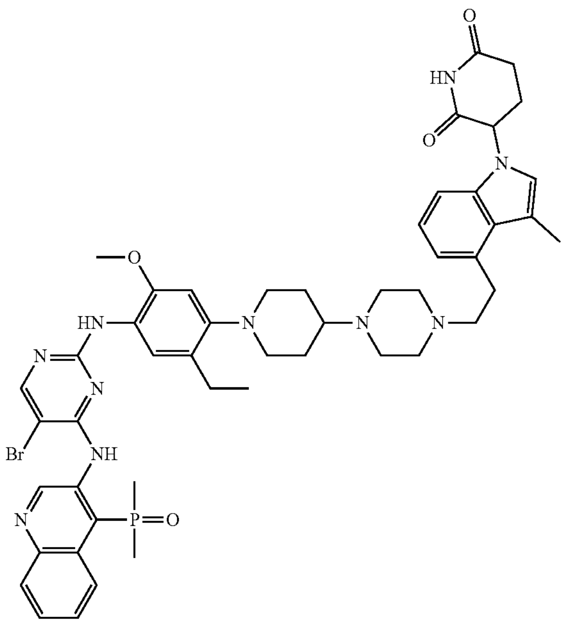
69
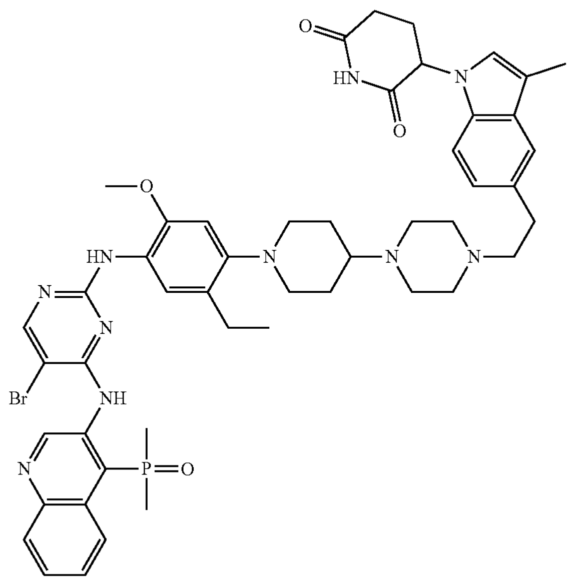
70
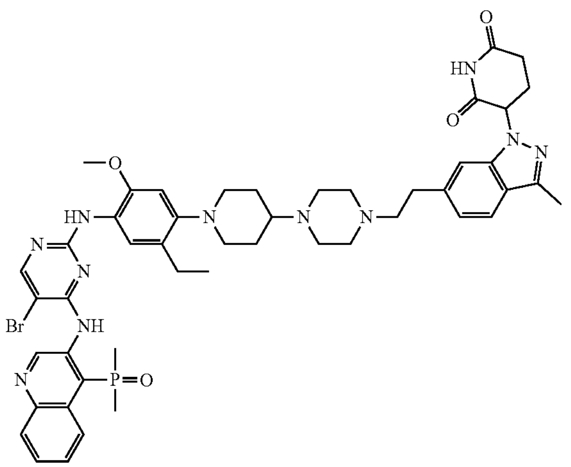

-continued
71
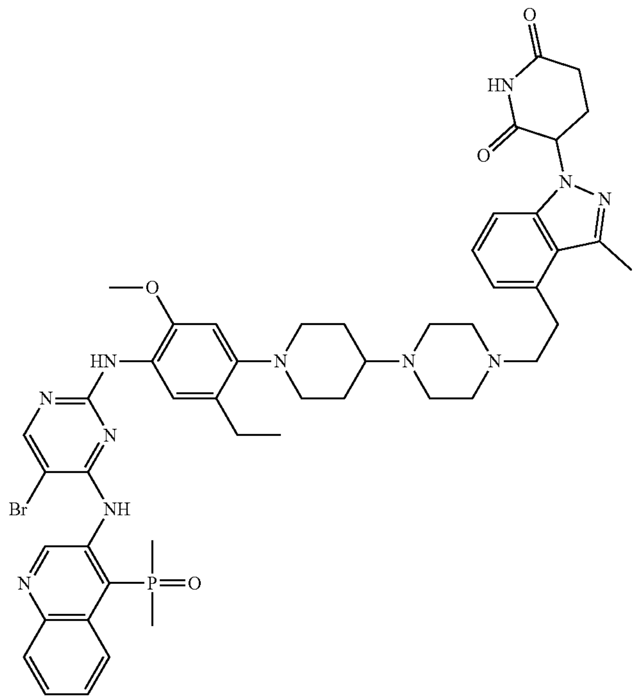
72
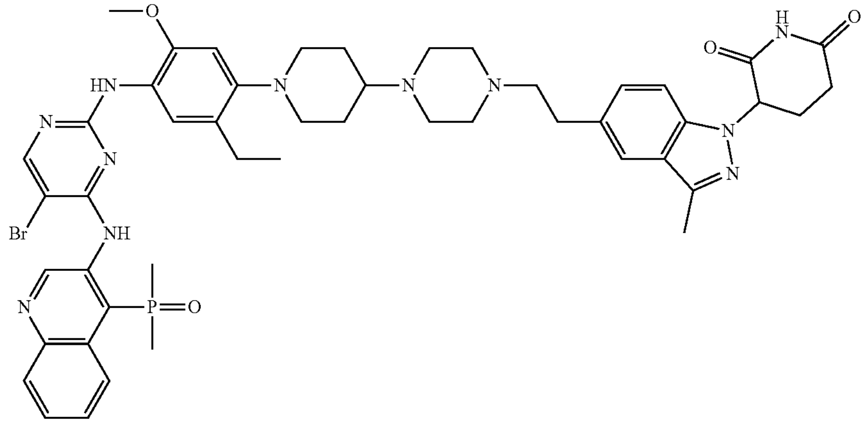

-continued
73
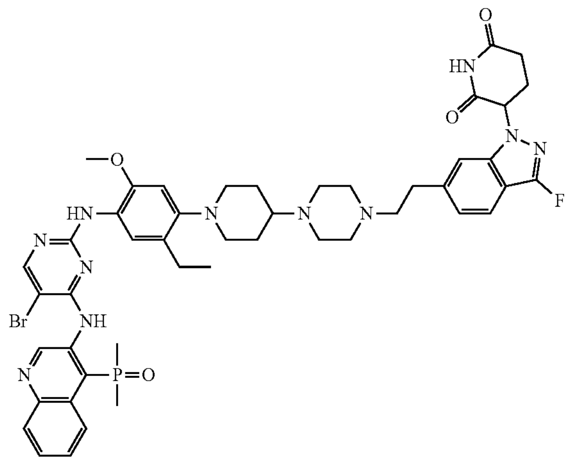
74
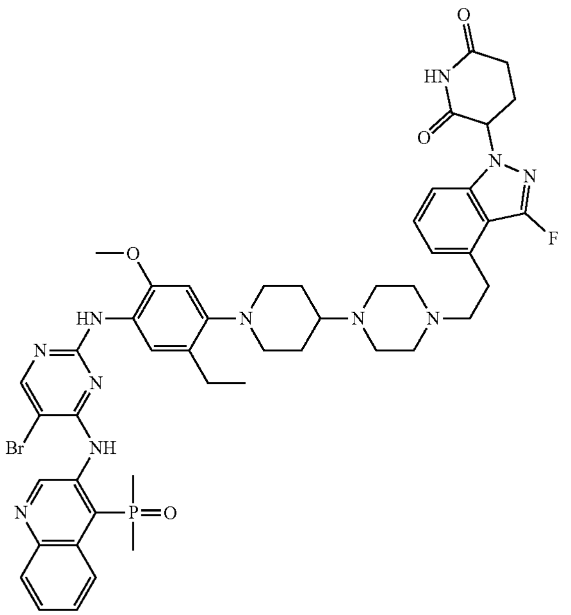
75
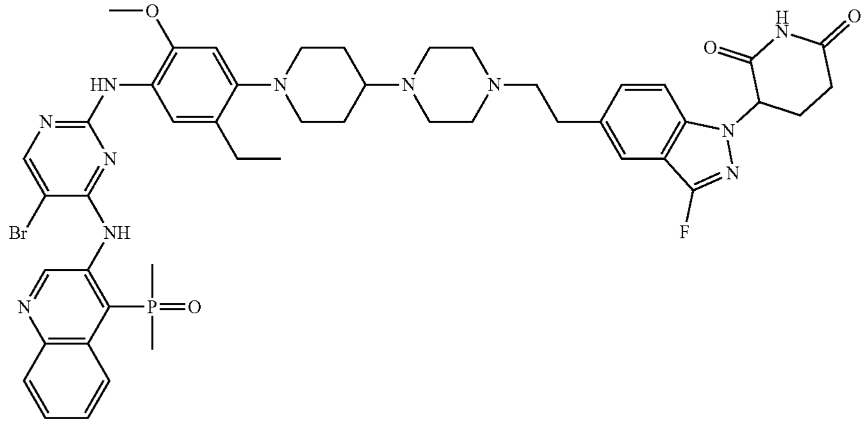
76
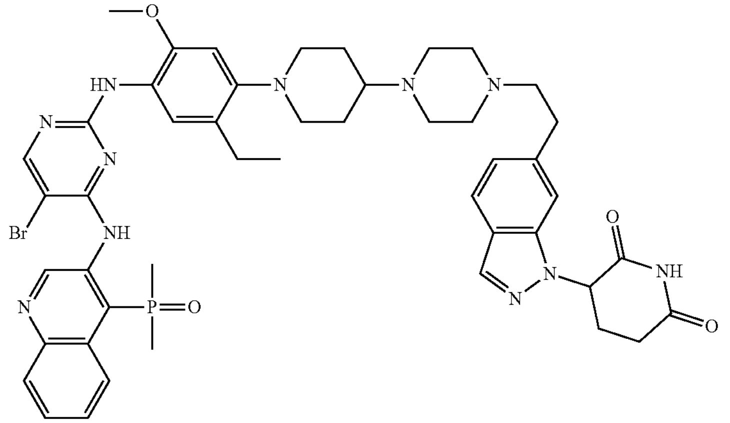

-continued
77
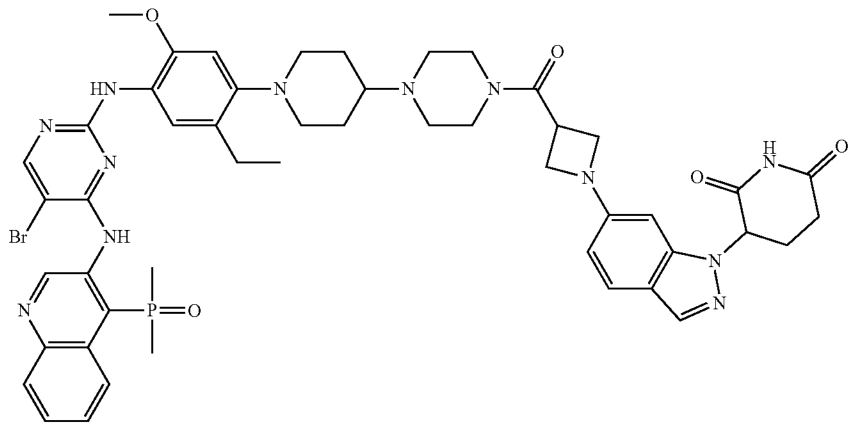
78
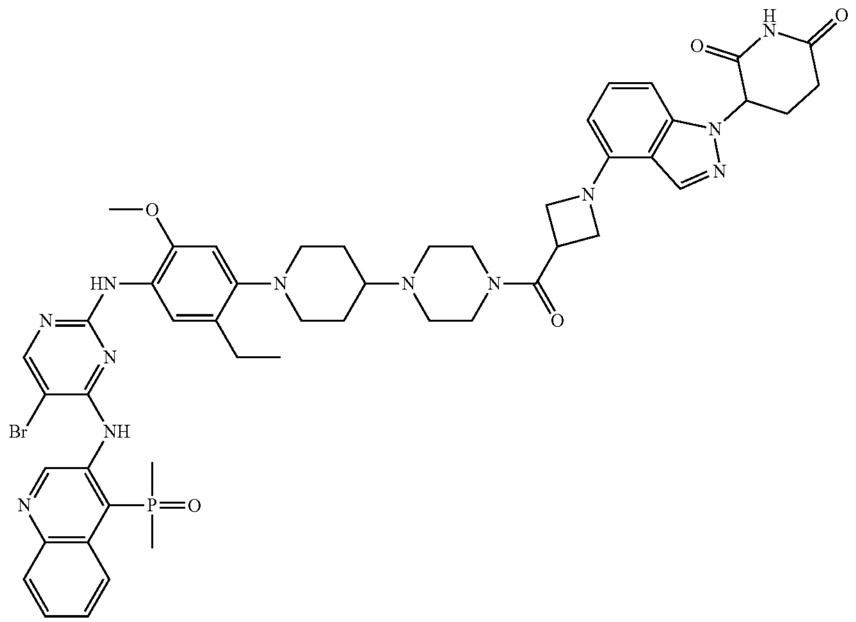
79
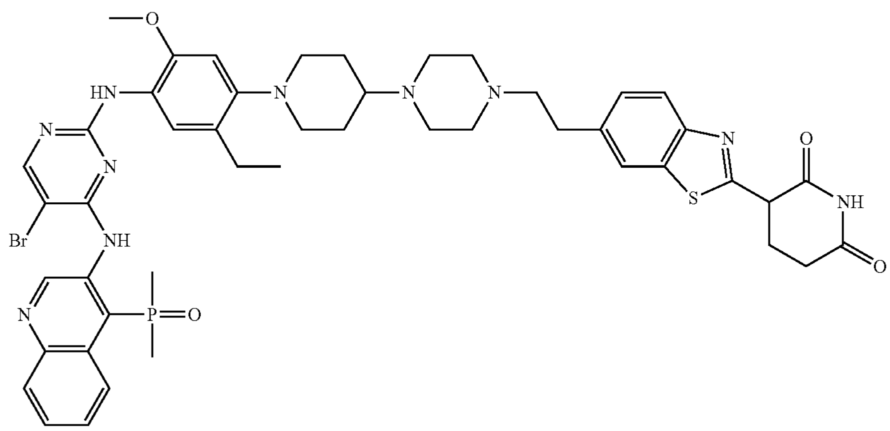

-continued
80
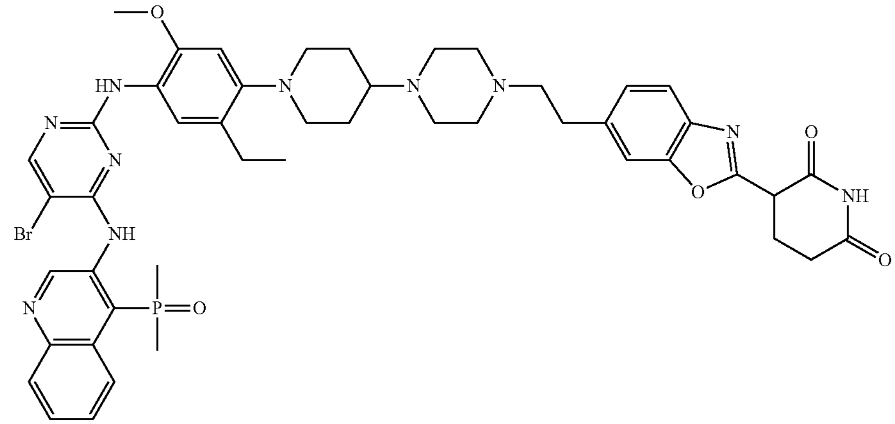
81
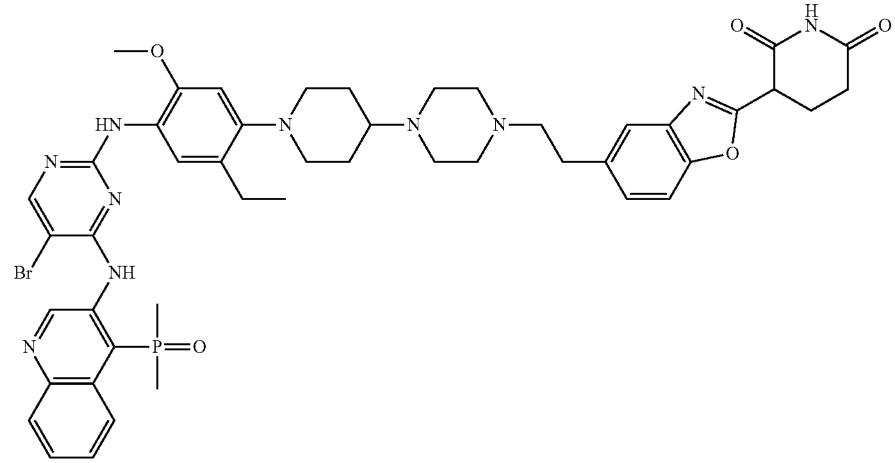
82
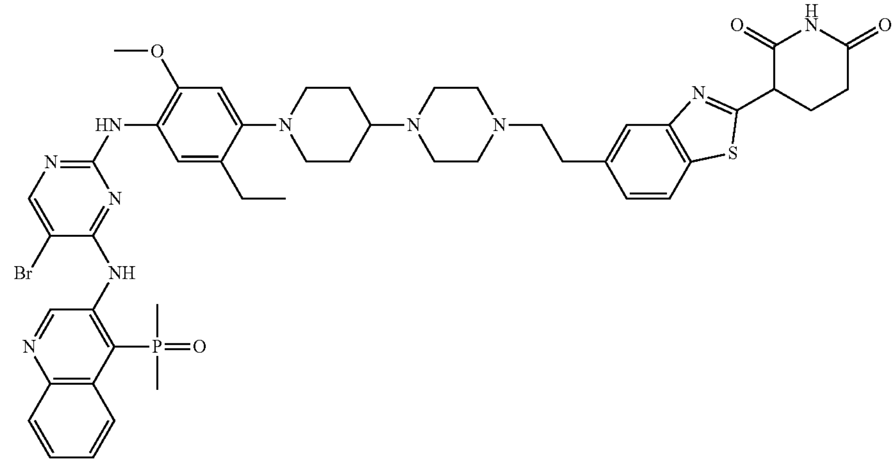

-continued
83
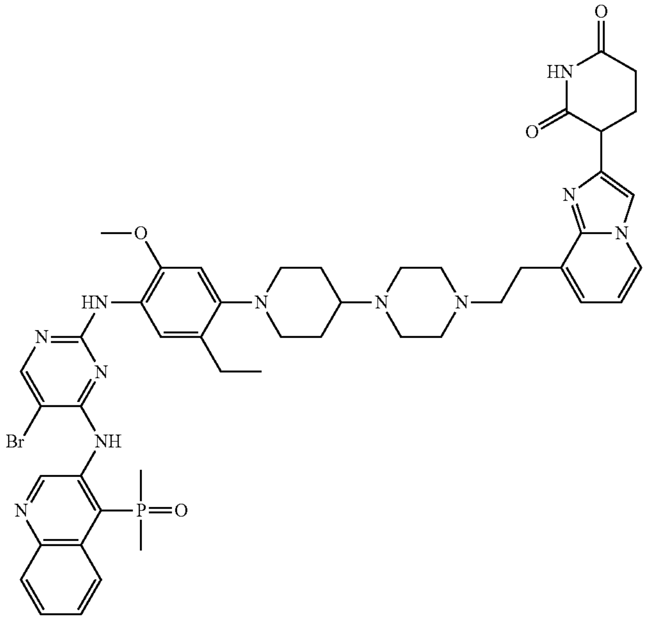
84
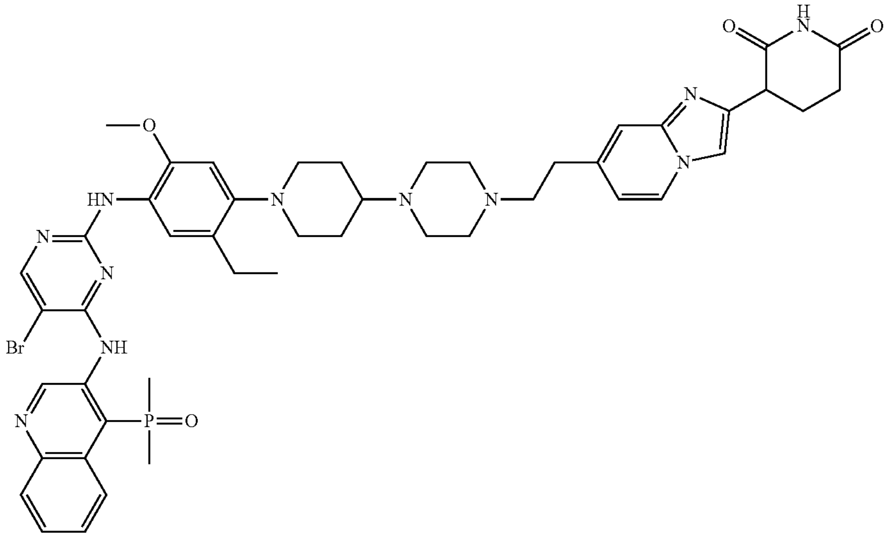

-continued
85
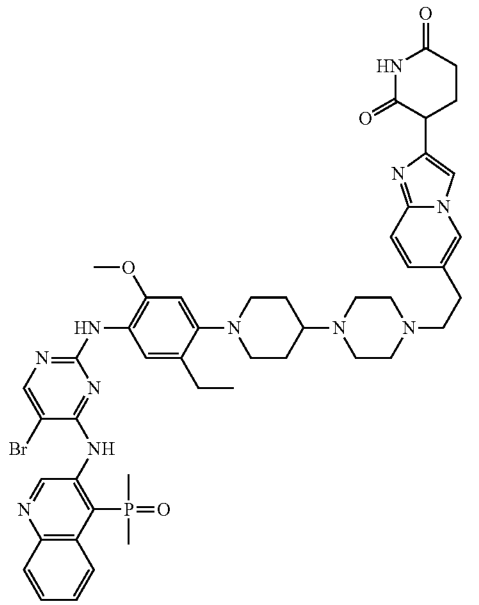
86
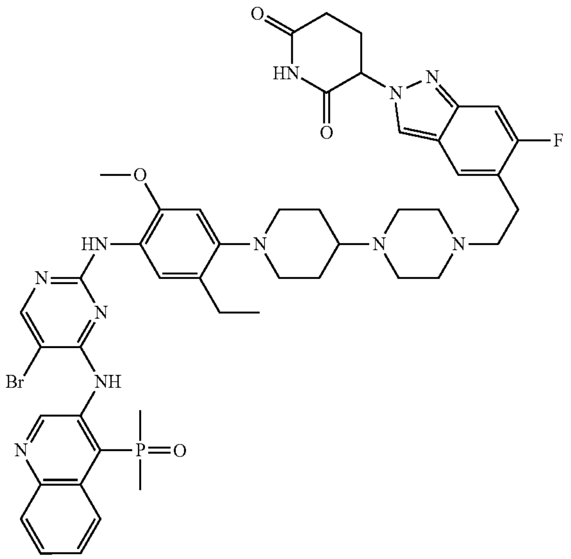
87
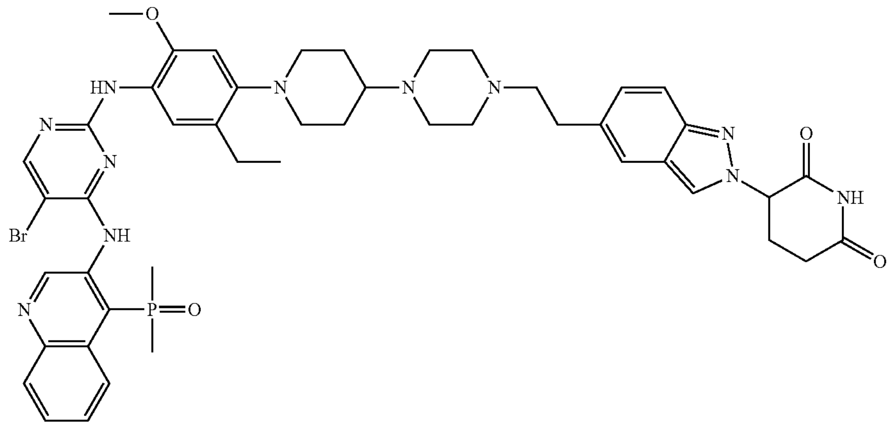
88
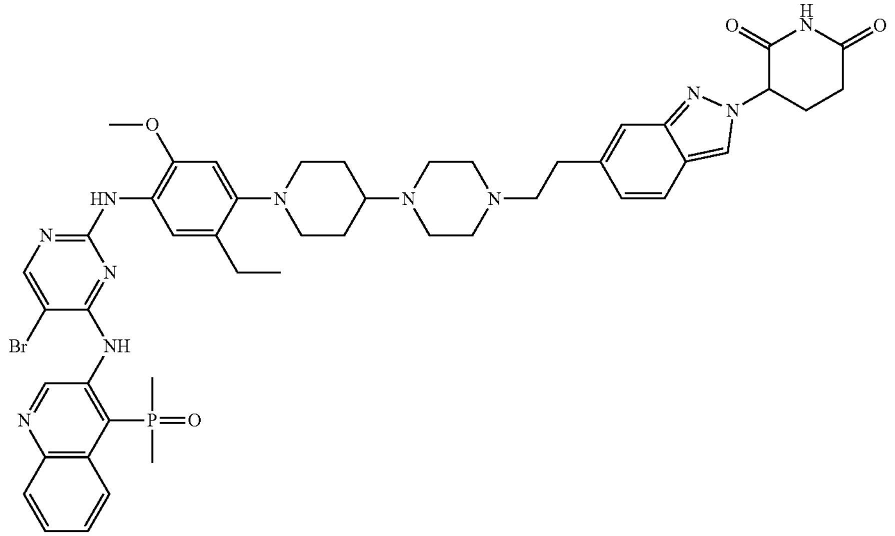

-continued
89
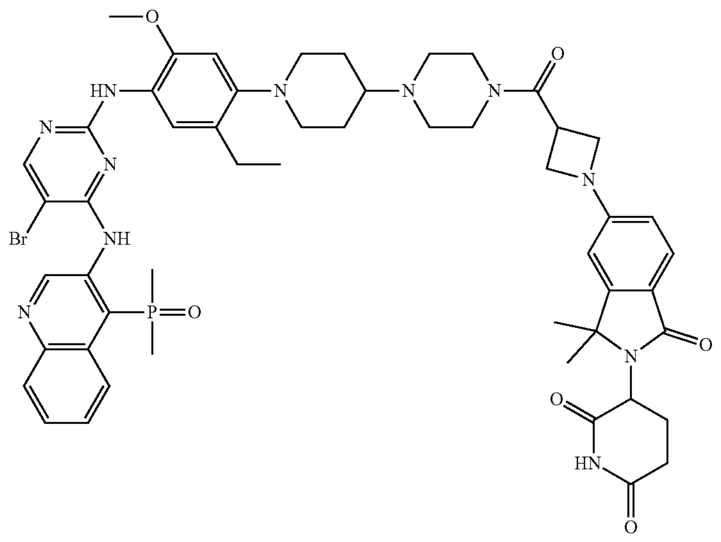
90
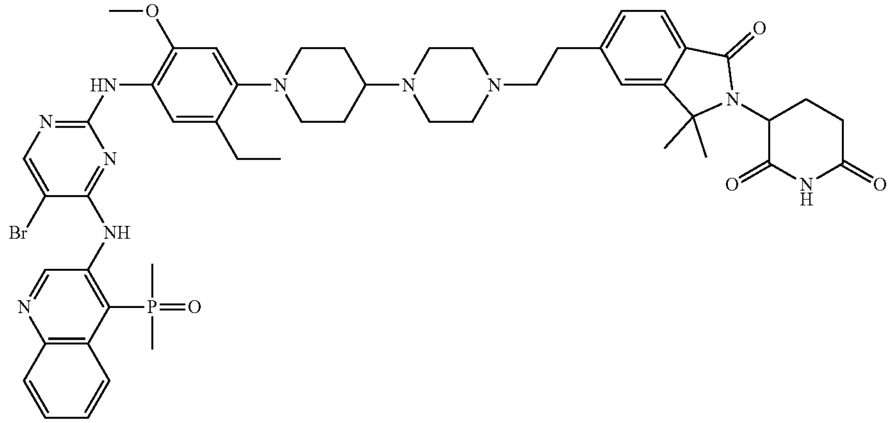
91
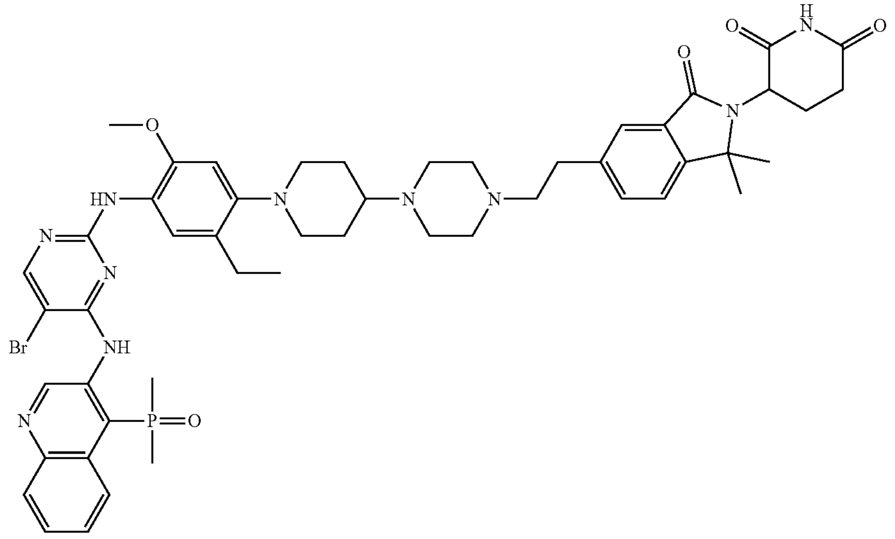

-continued
92
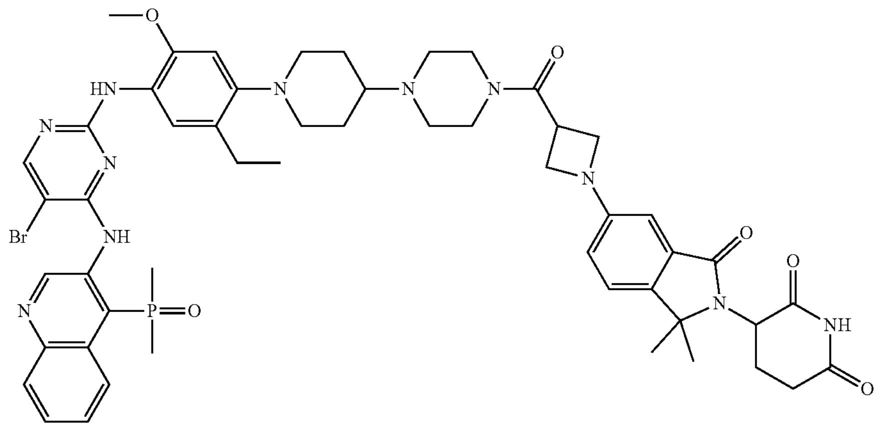
93
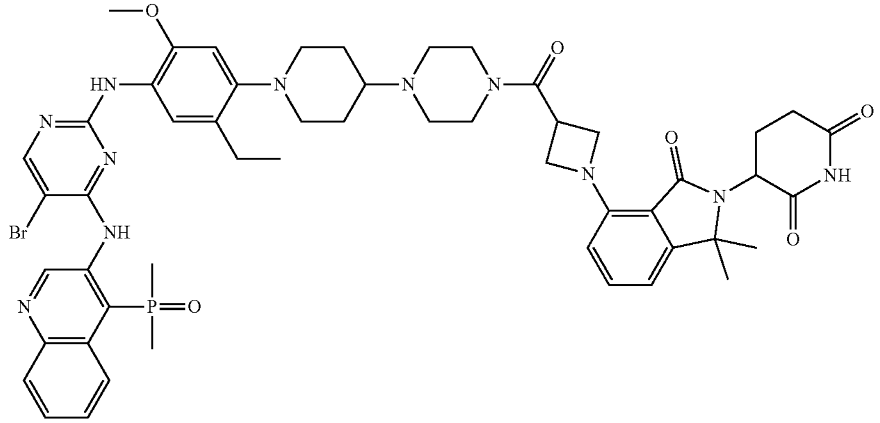
94
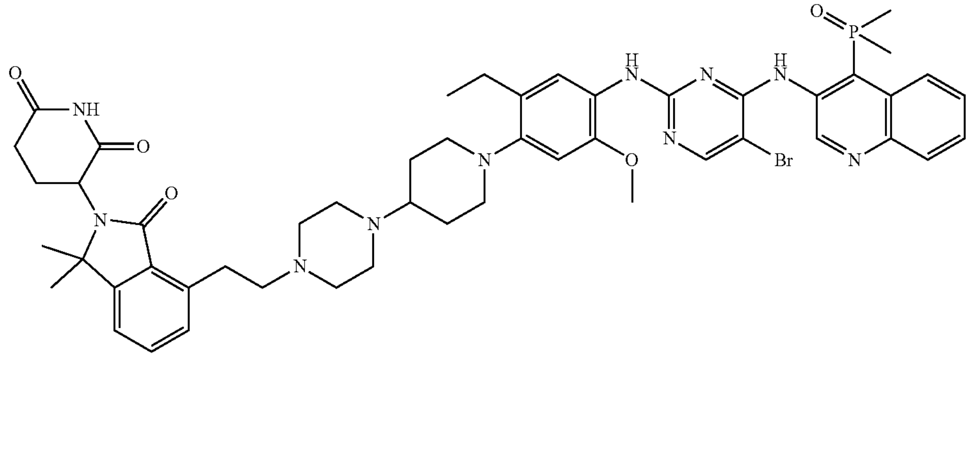

-continued
95
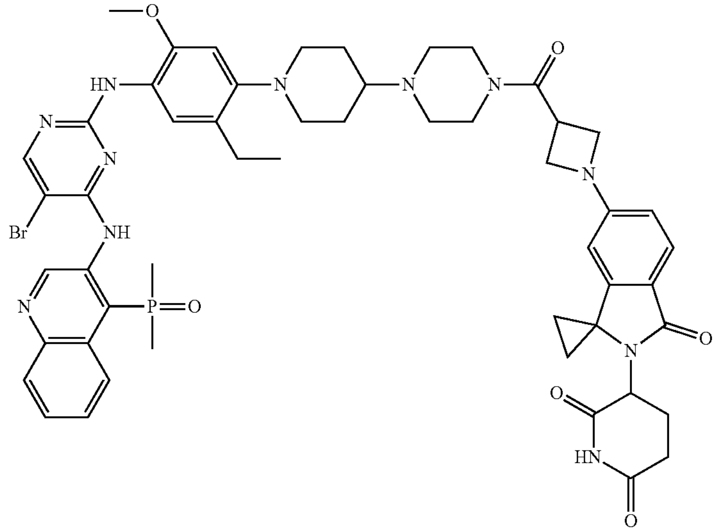
96
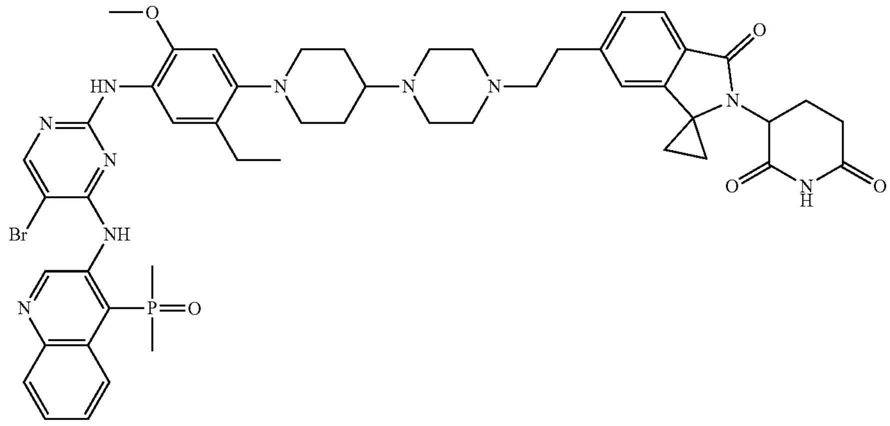
97
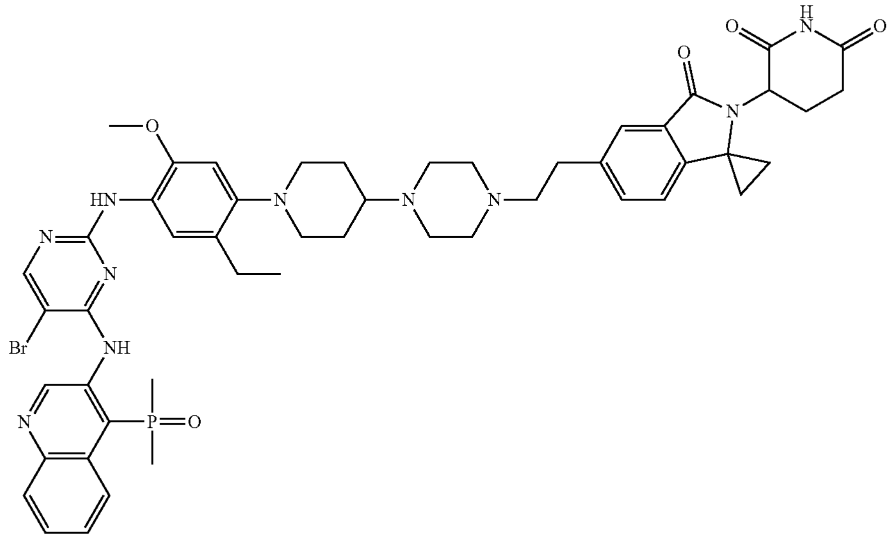

-continued
98
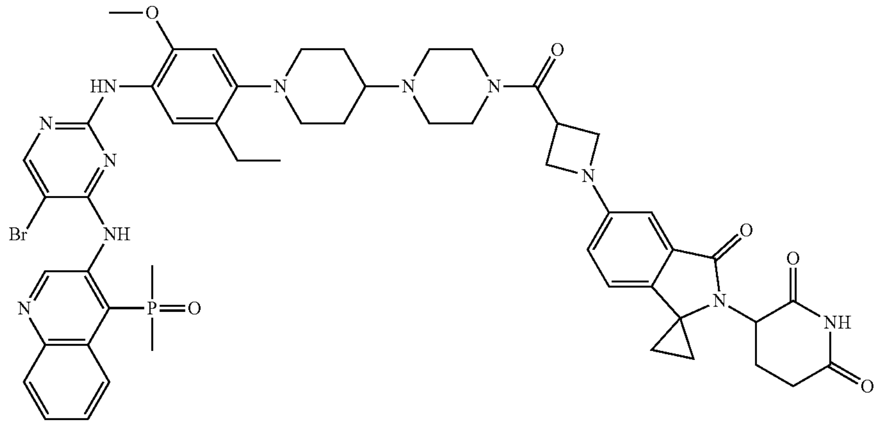
99
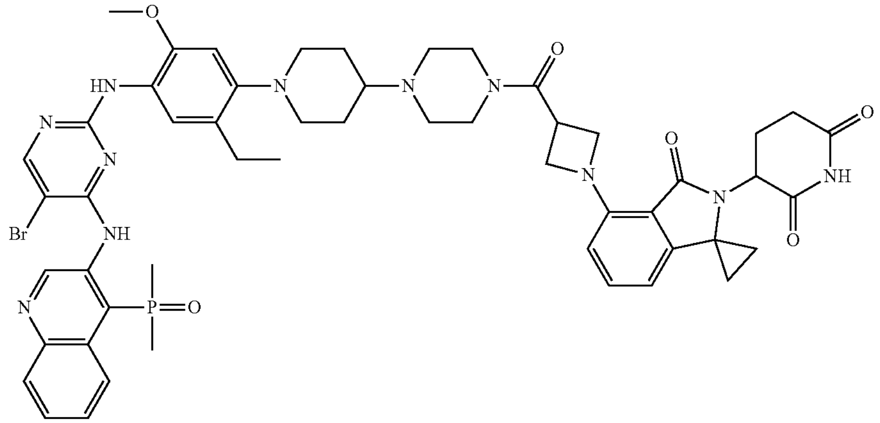
100
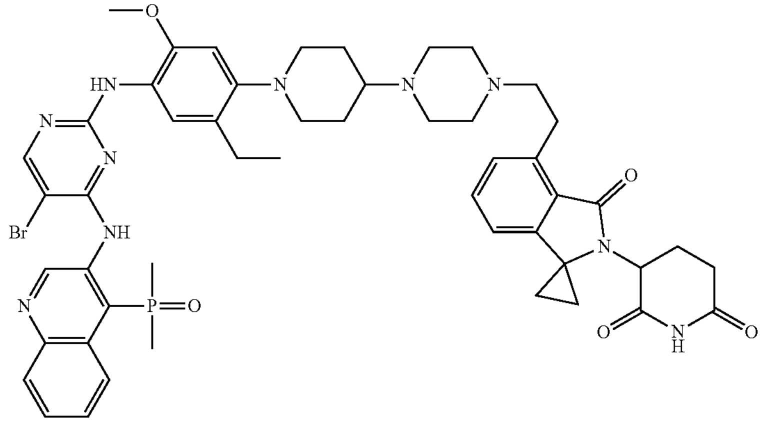

-continued
101
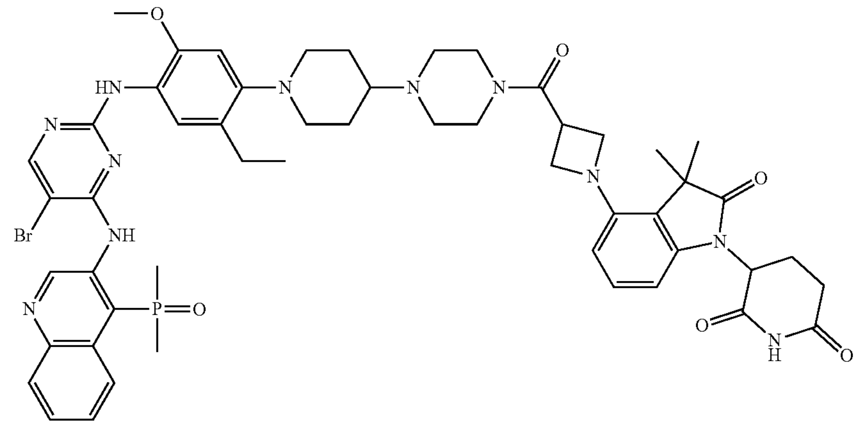
102
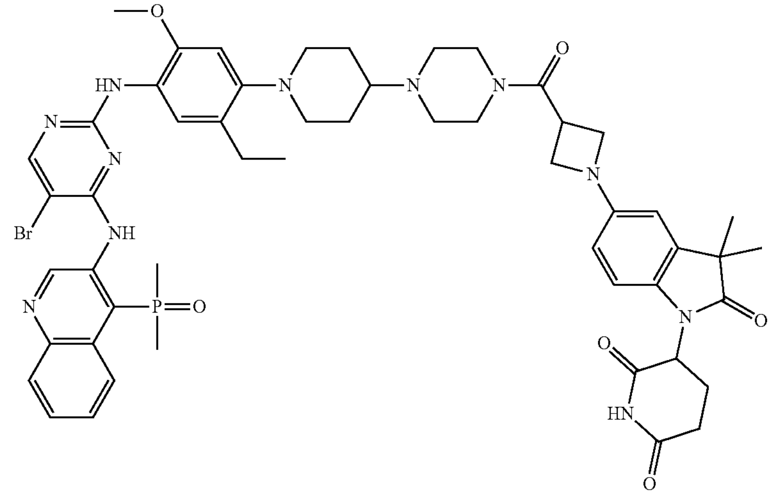
103
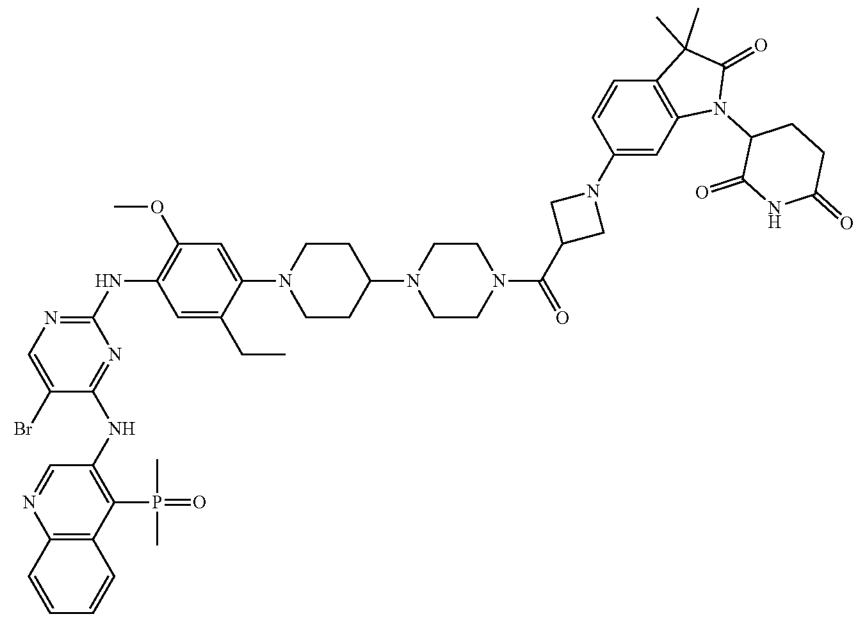

-continued
104
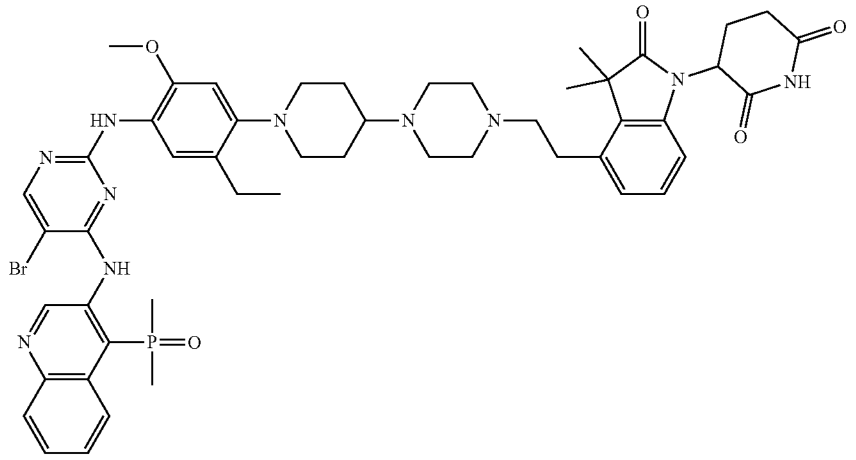
105
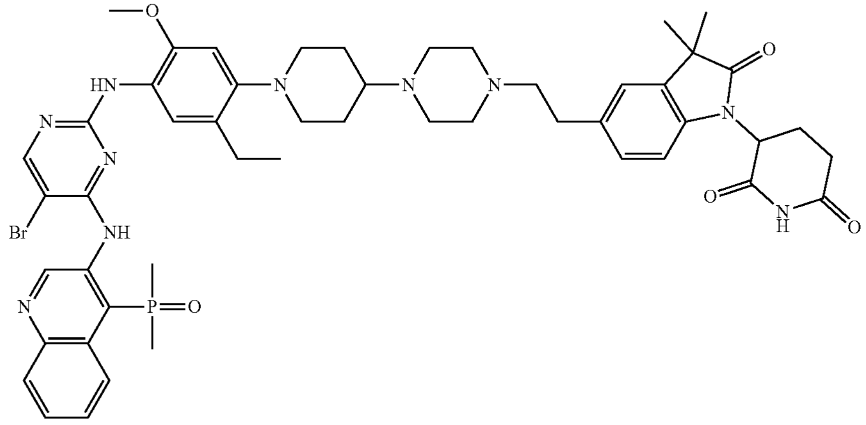
106
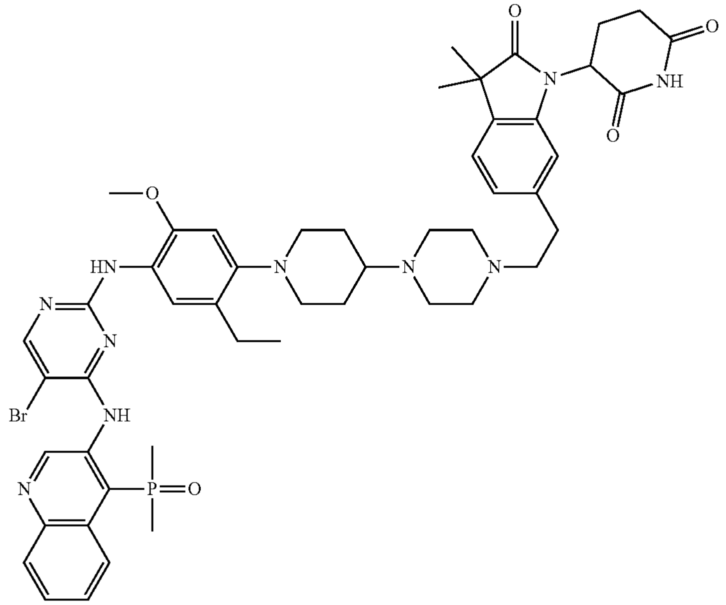

-continued
107
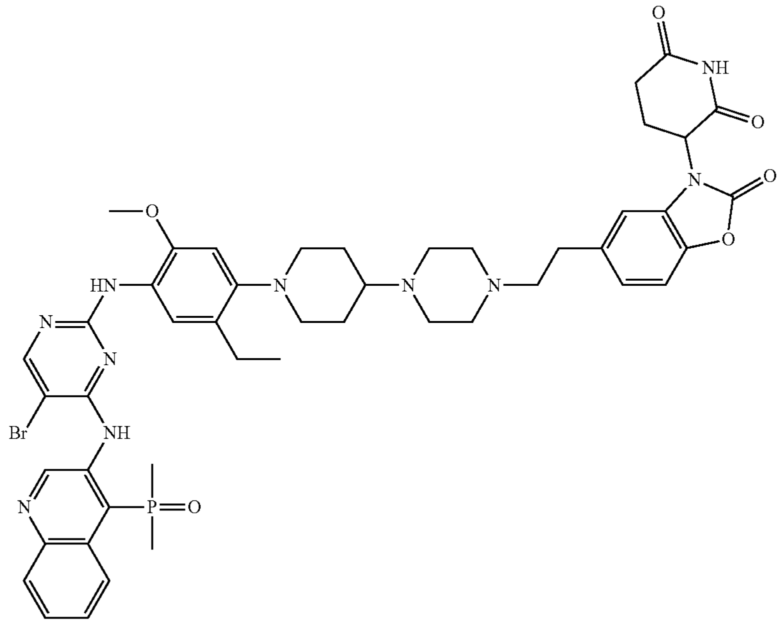
108
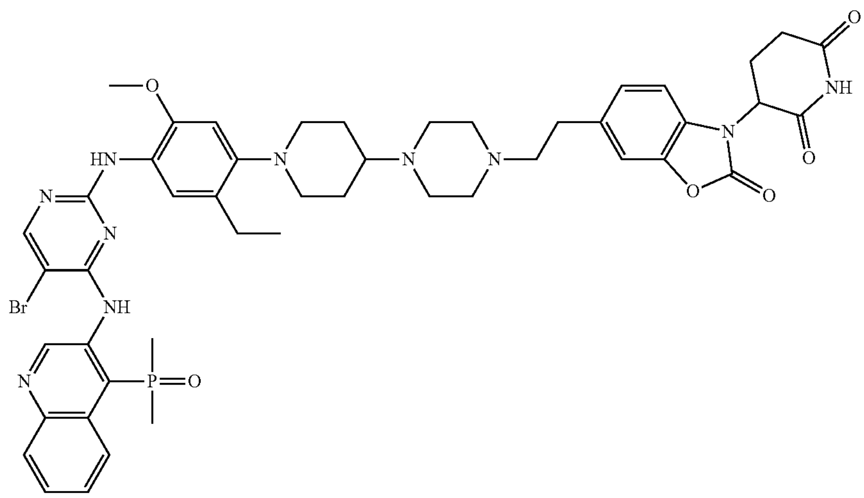

-continued
109
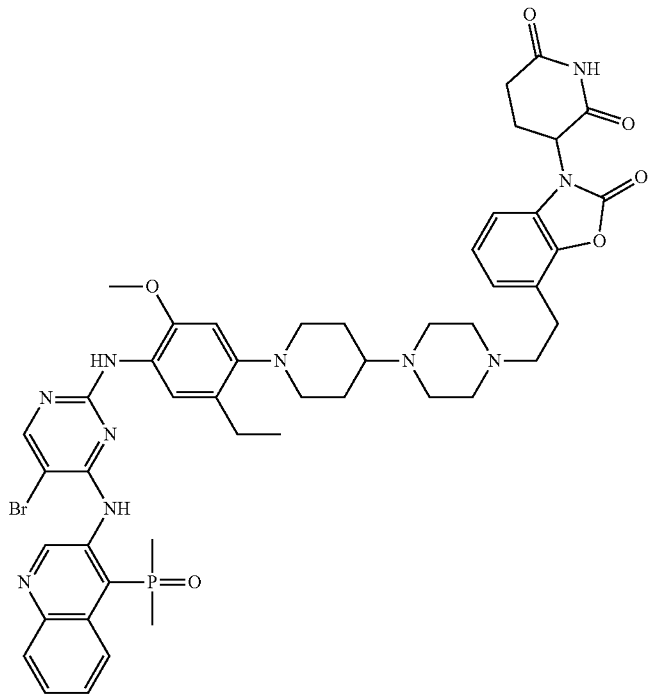
110
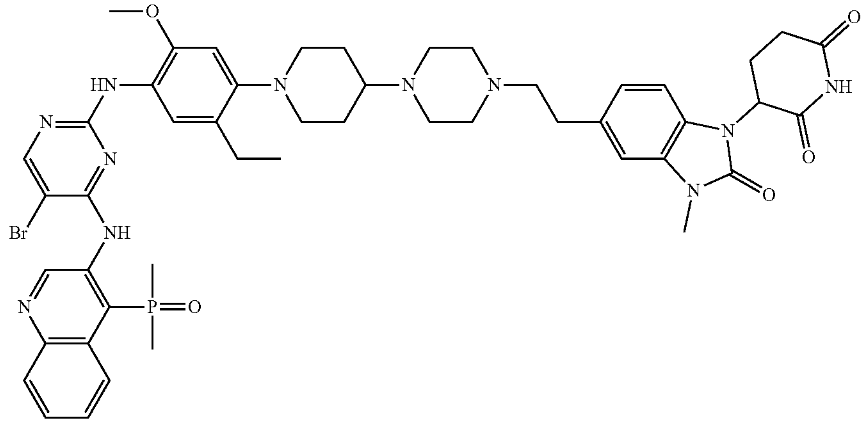
111
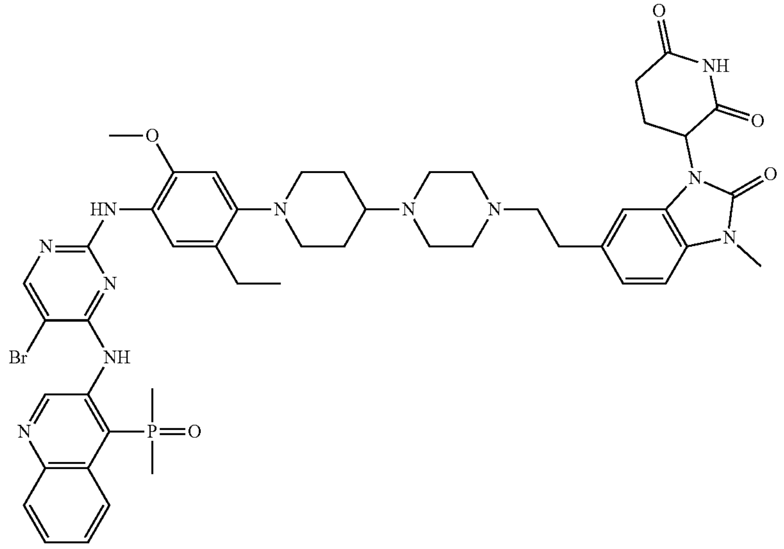

-continued
112
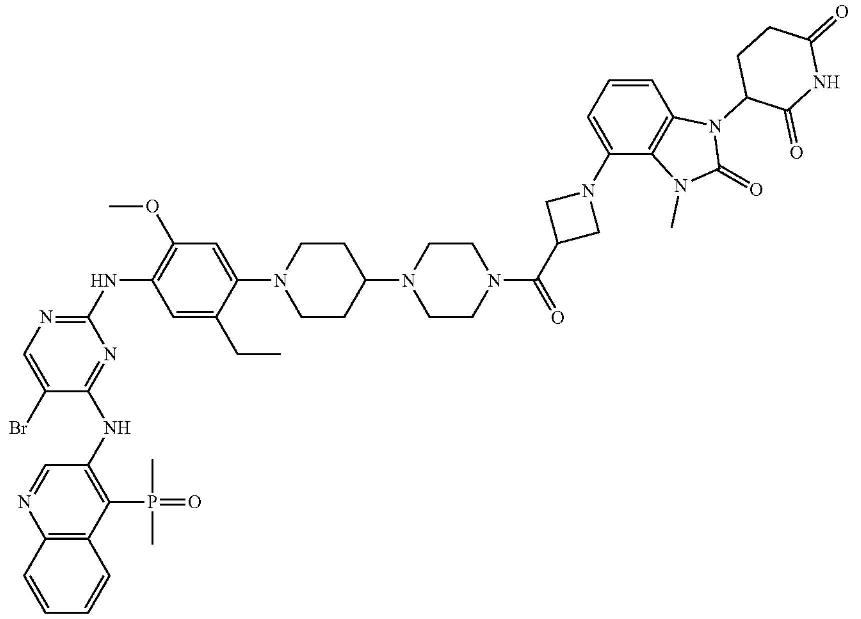
113
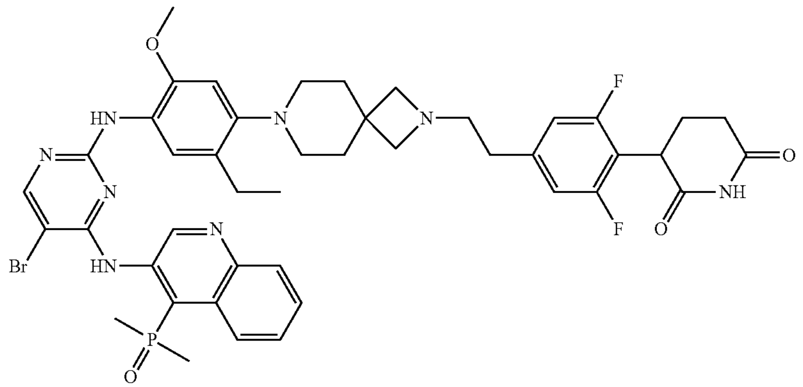
114
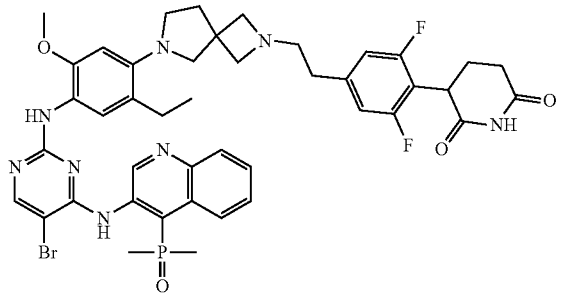
115
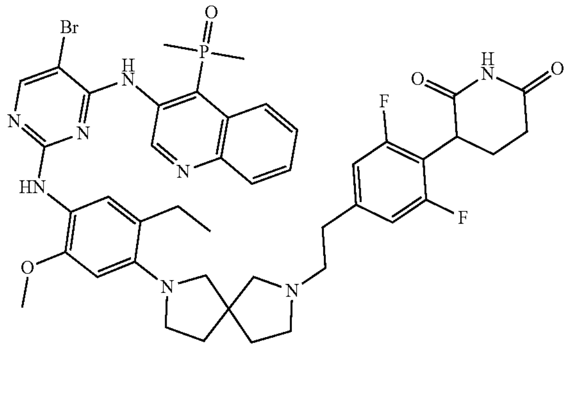

-continued
116
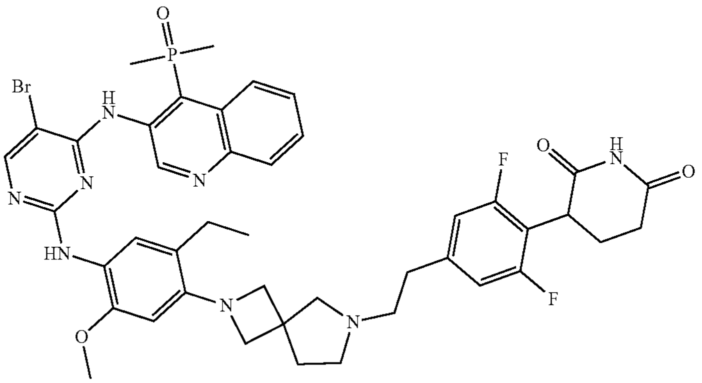
117
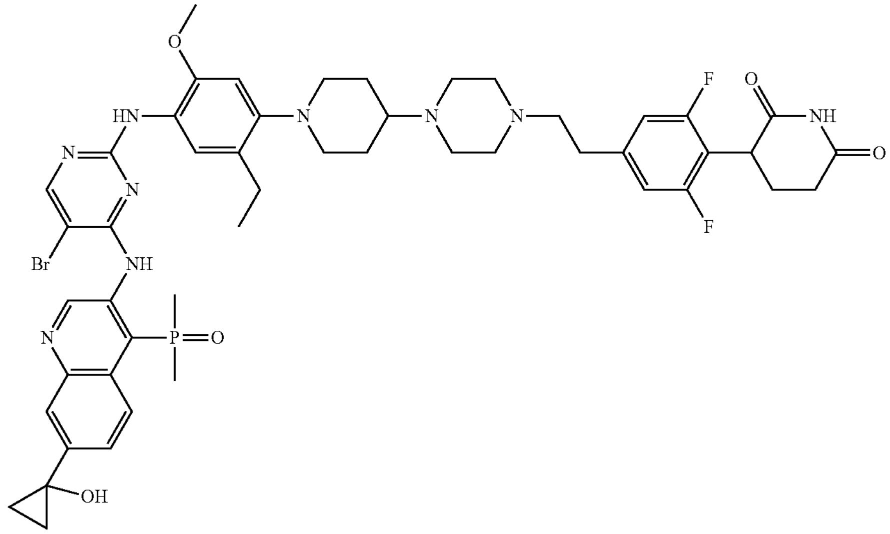
118
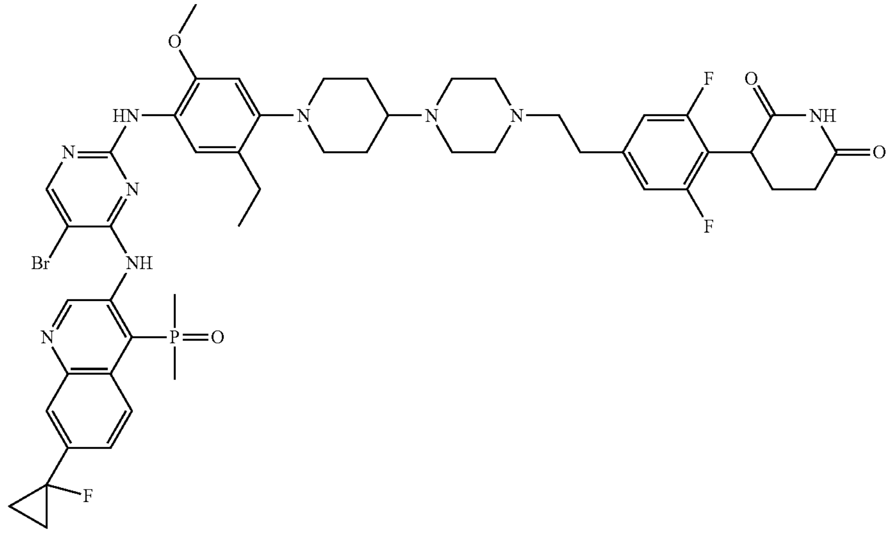

-continued
119
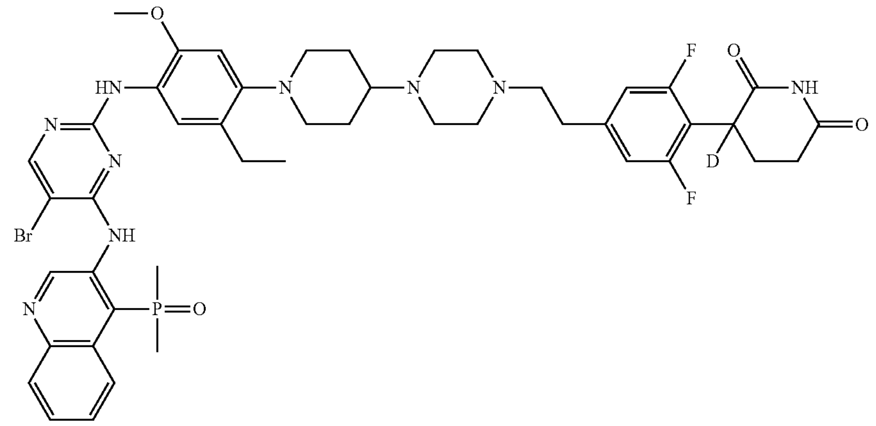
120
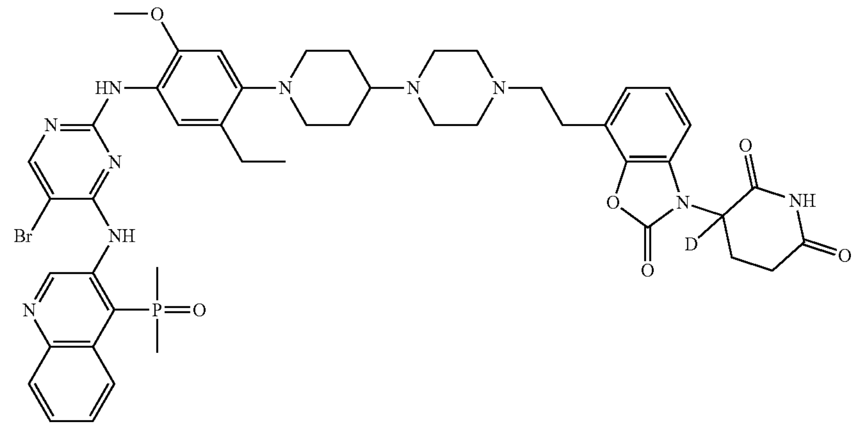
121
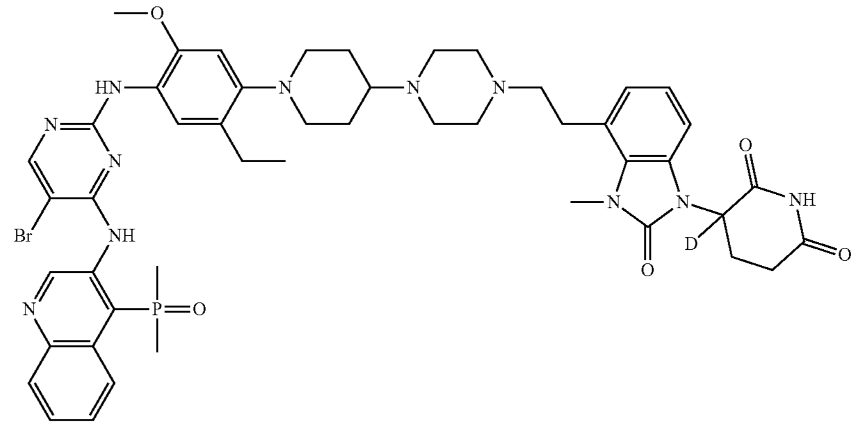

-continued
124
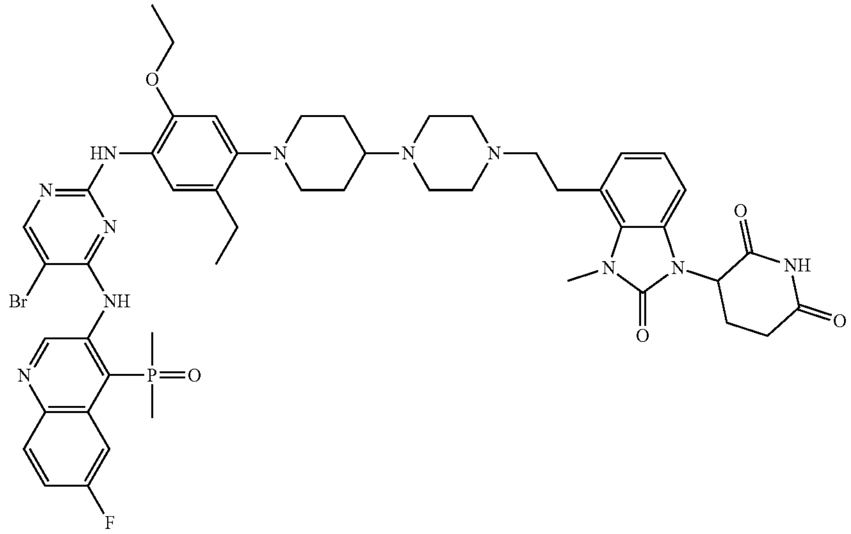
125
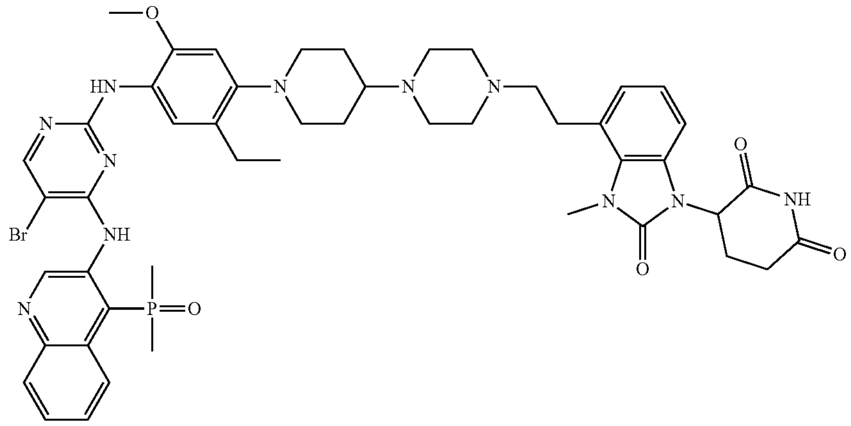
126
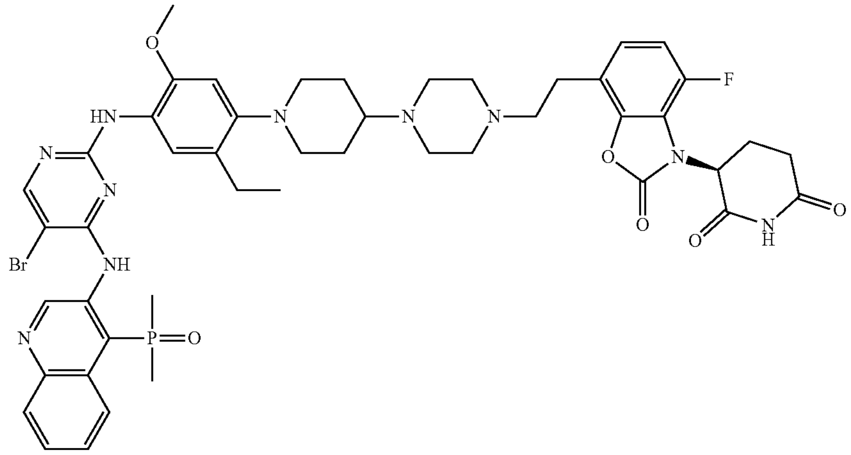

-continued
130
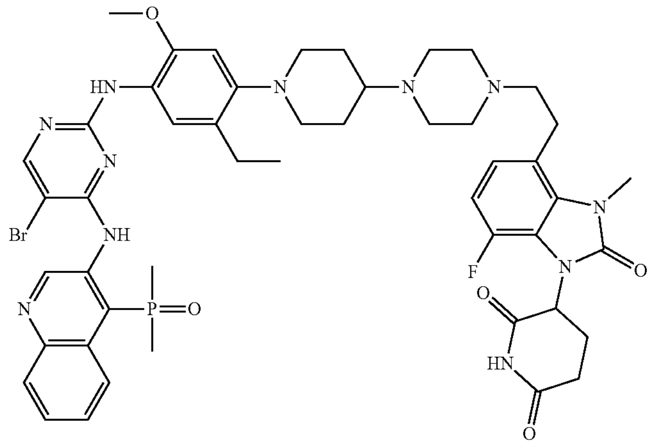
132
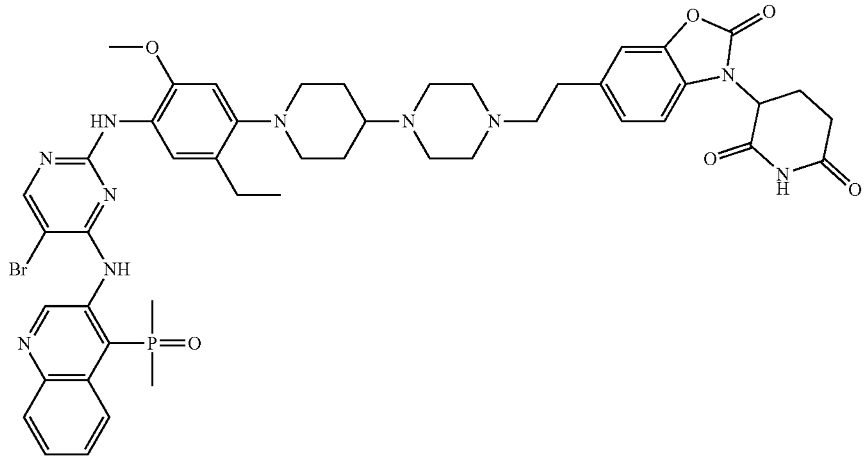
133
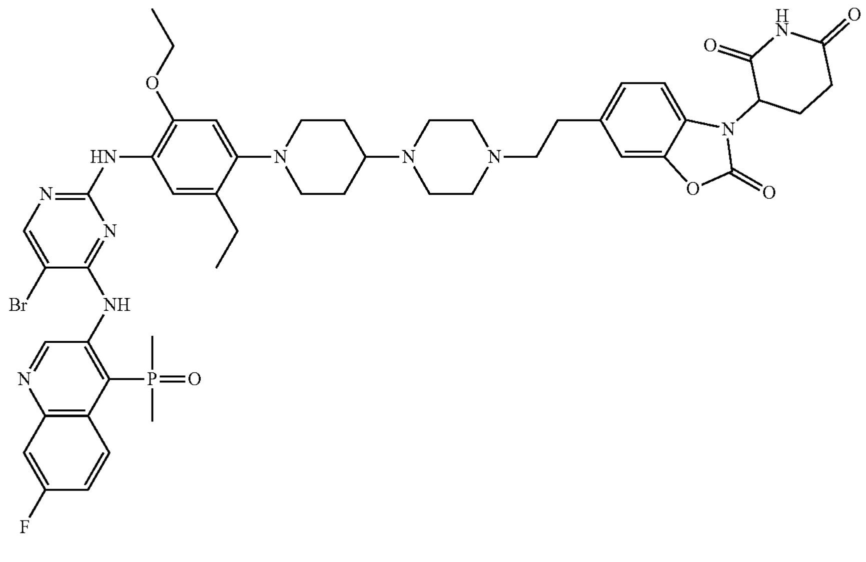

-continued
134
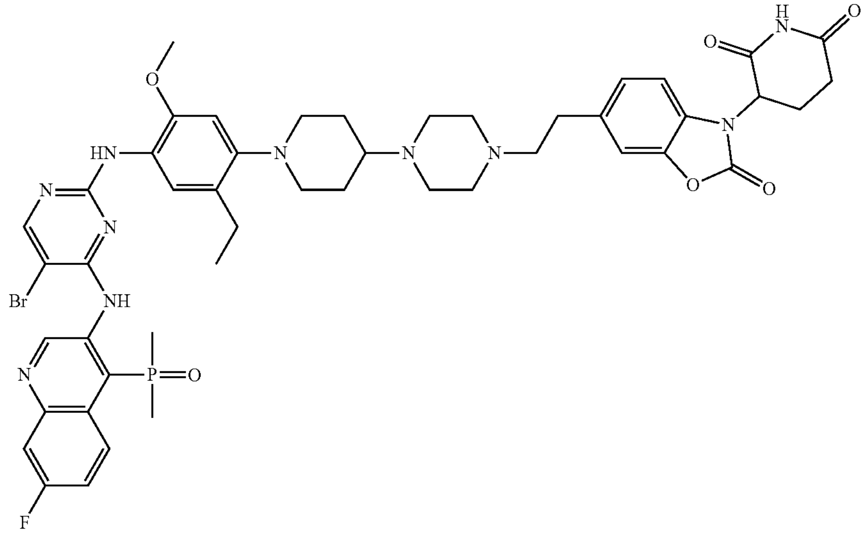
135
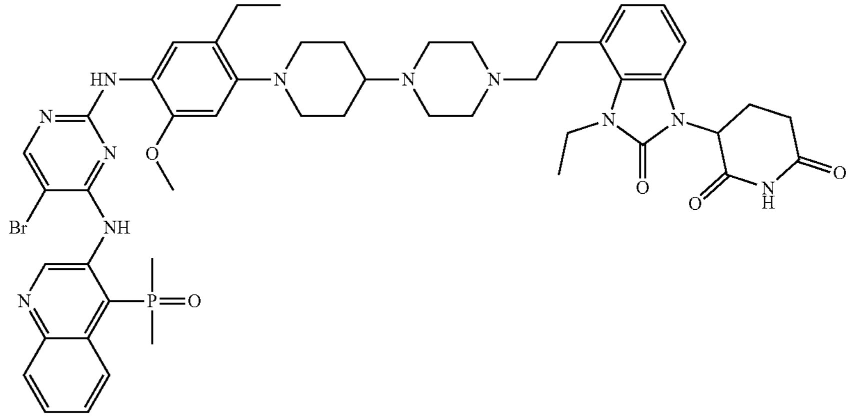
136
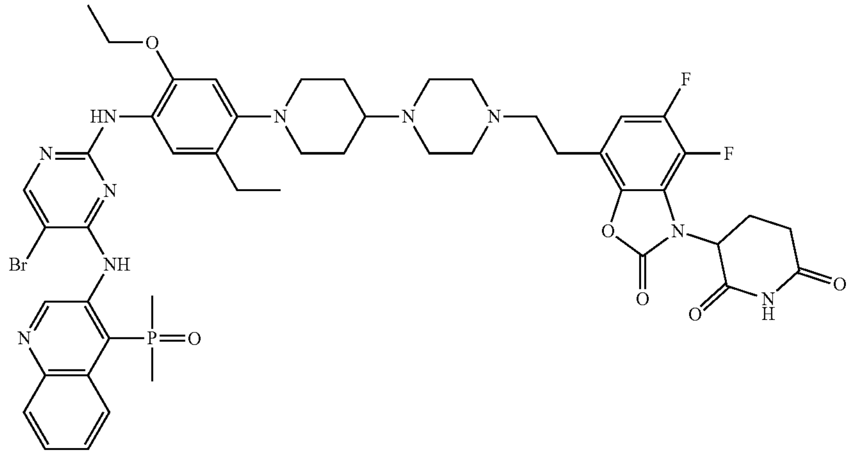

-continued
137
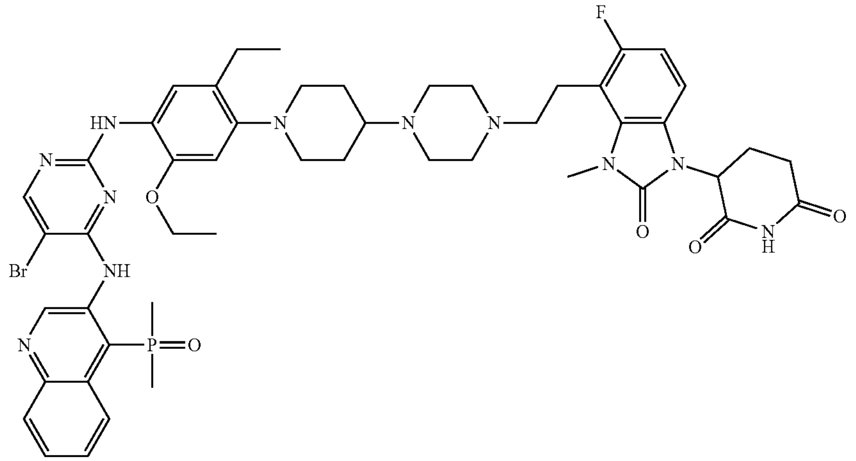
138
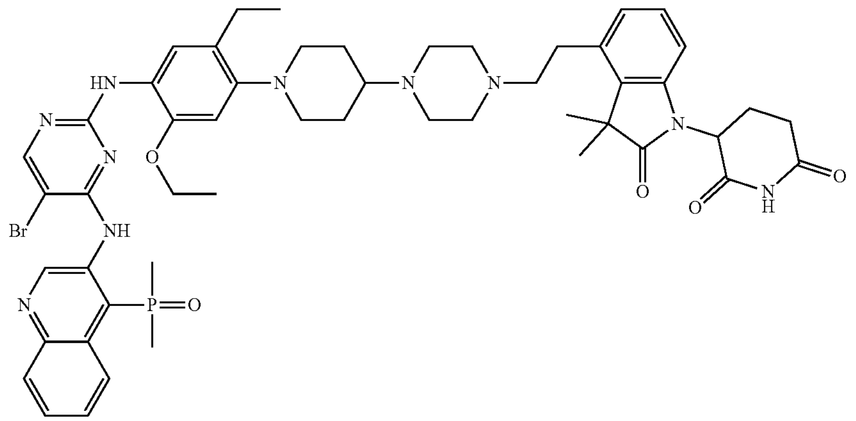
139
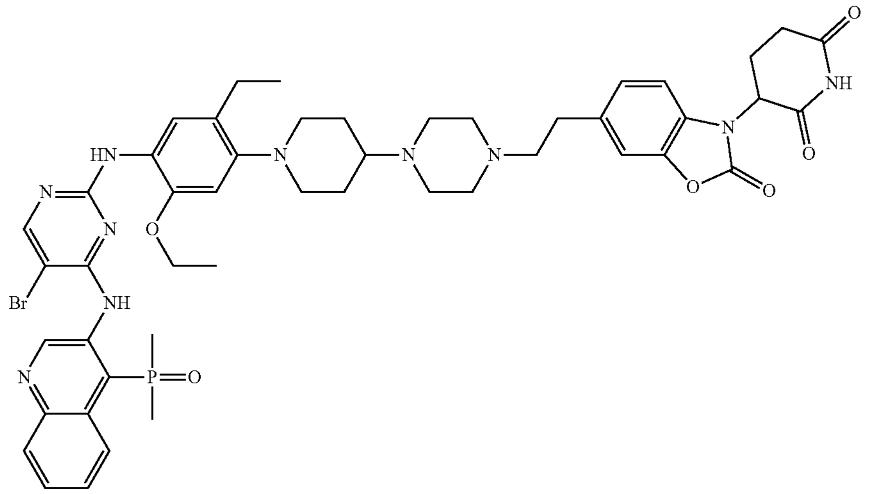

-continued
140
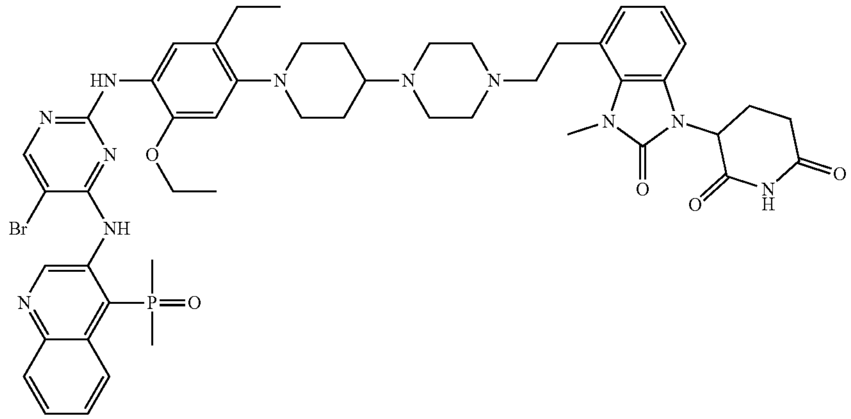
142
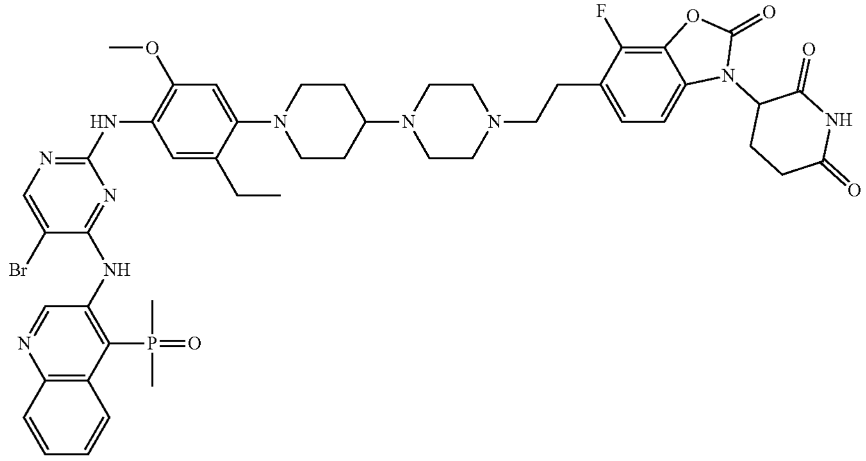
147
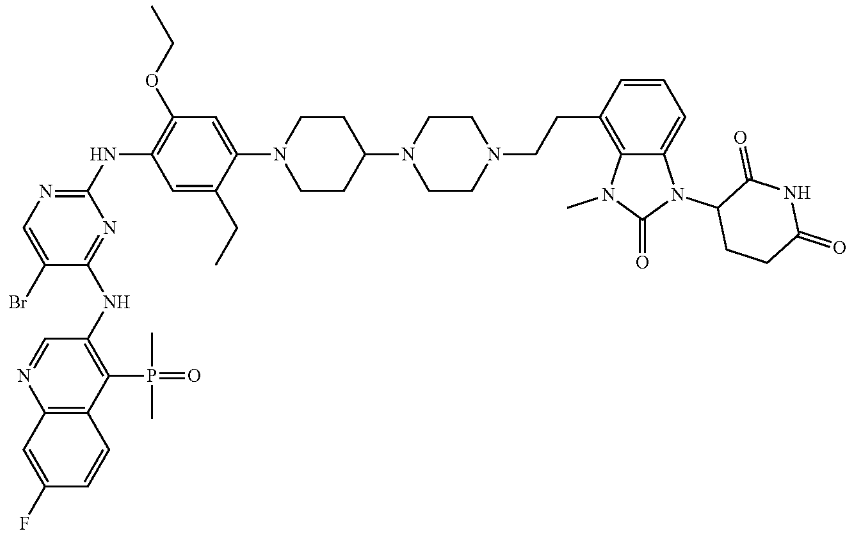

-continued
149
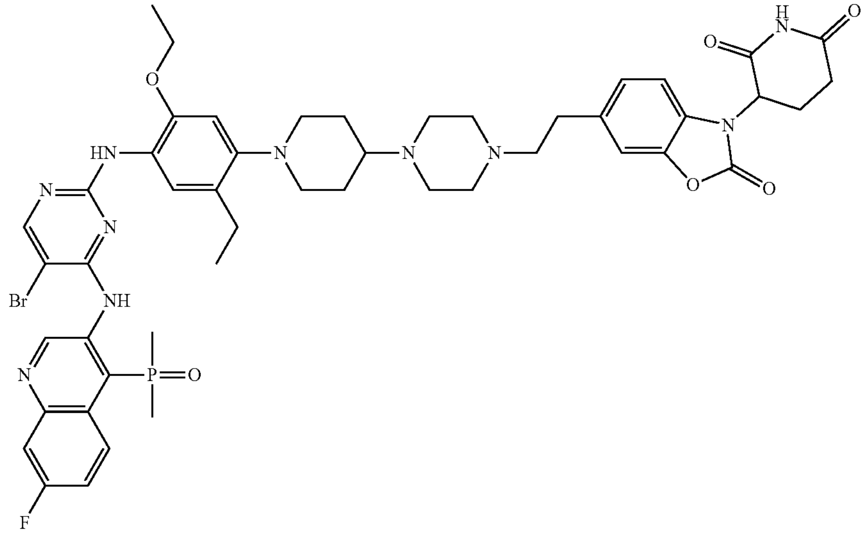
151
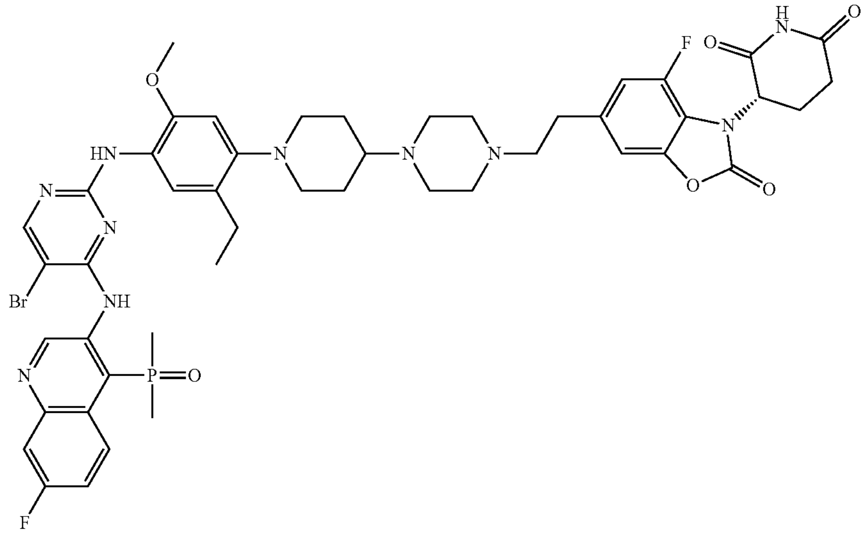
153
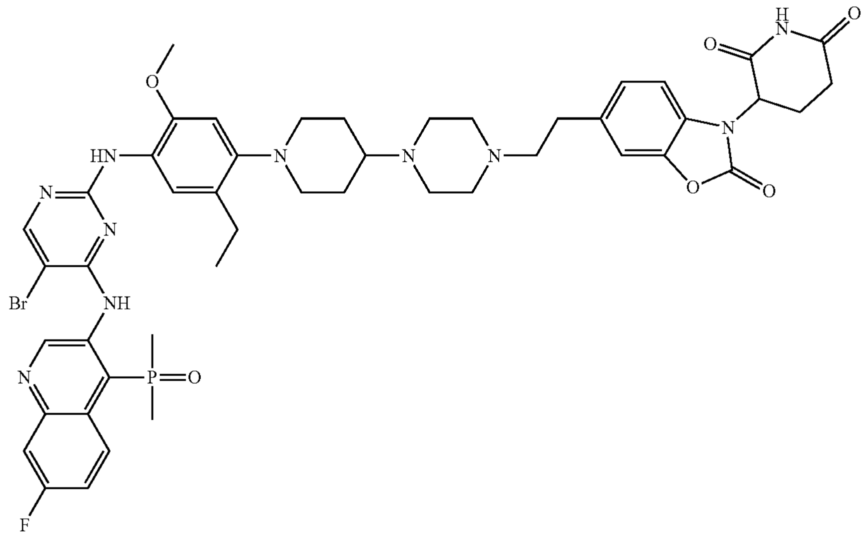

-continued
155
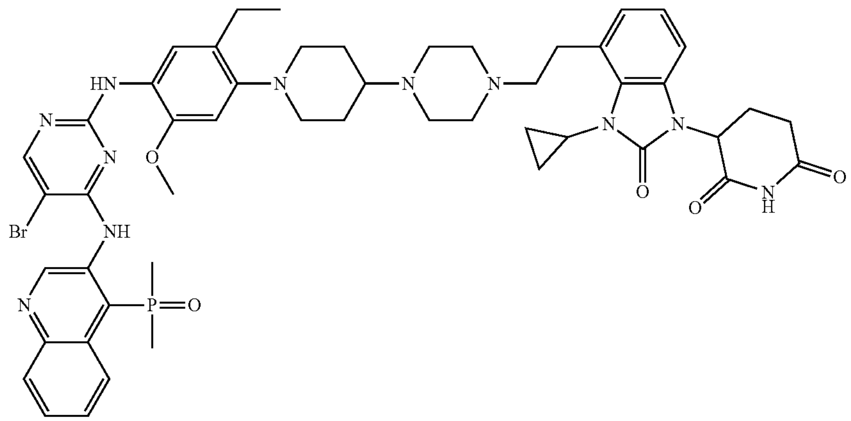
159
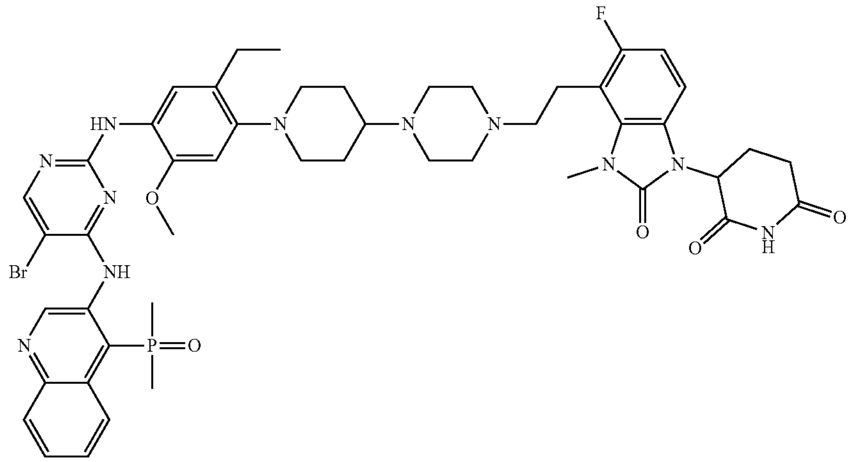
163
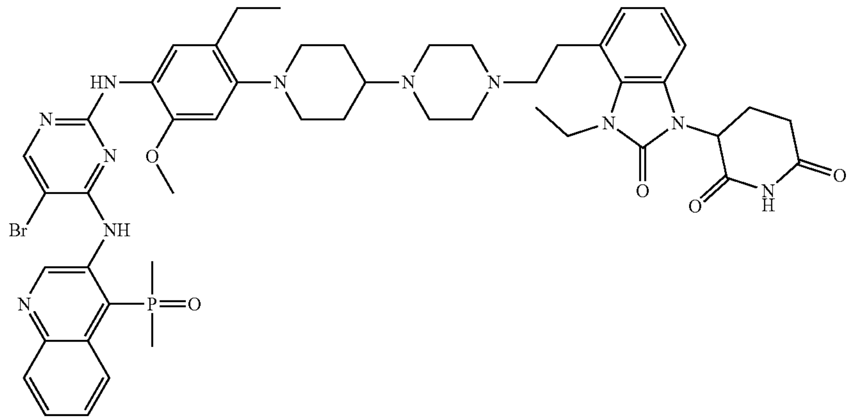

-continued
164
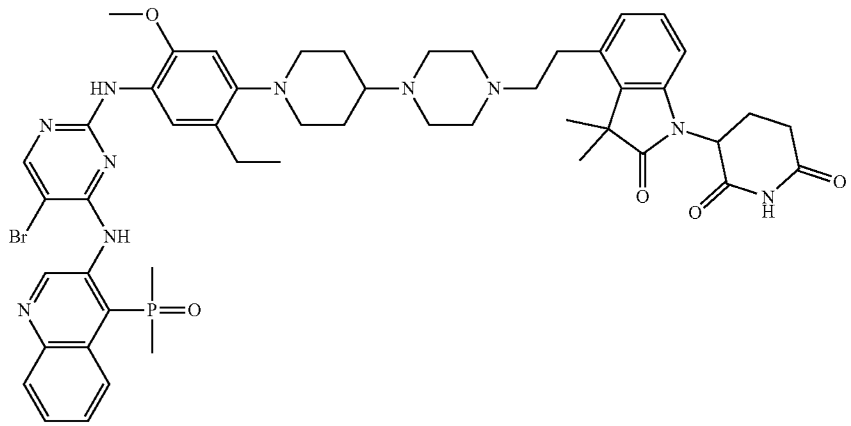
165
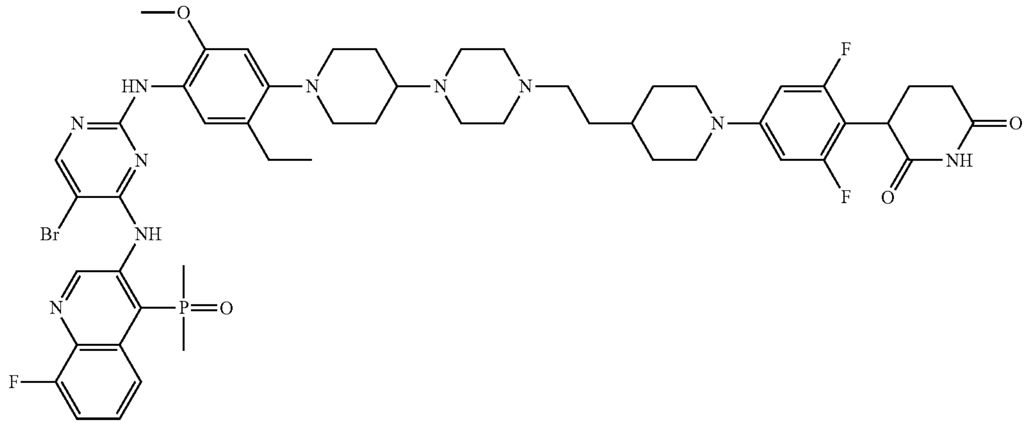
166
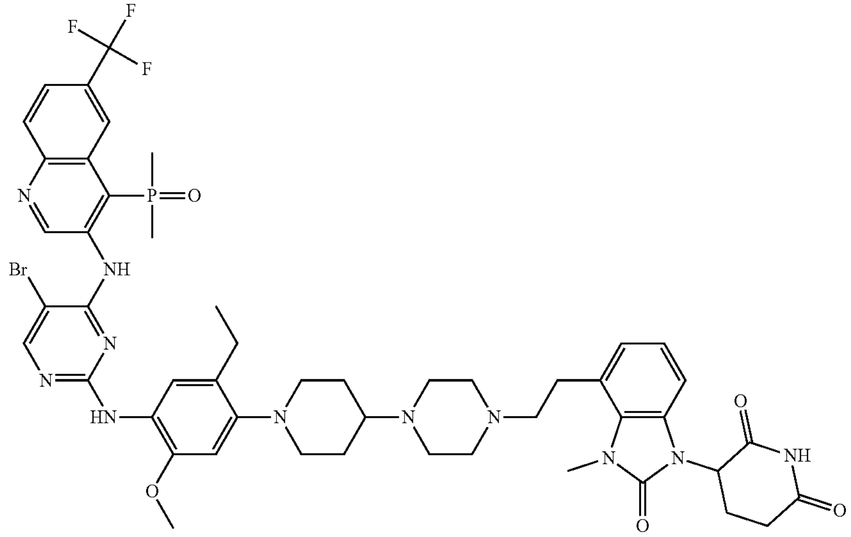

-continued
167
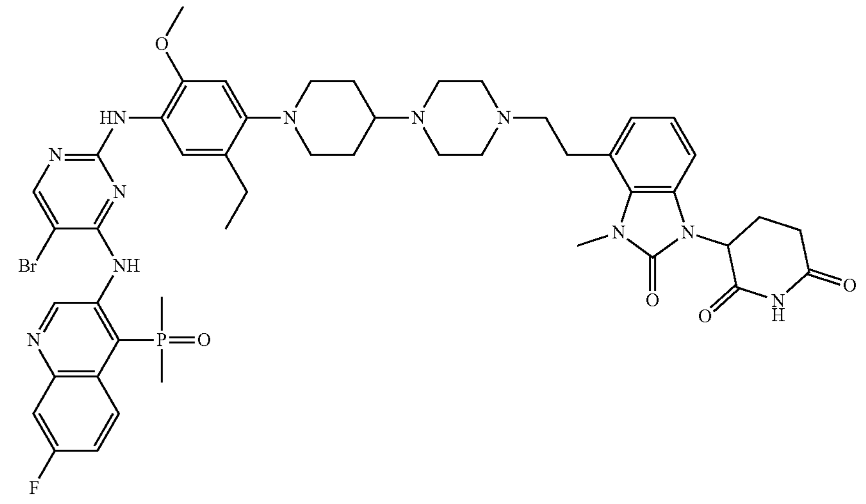
168
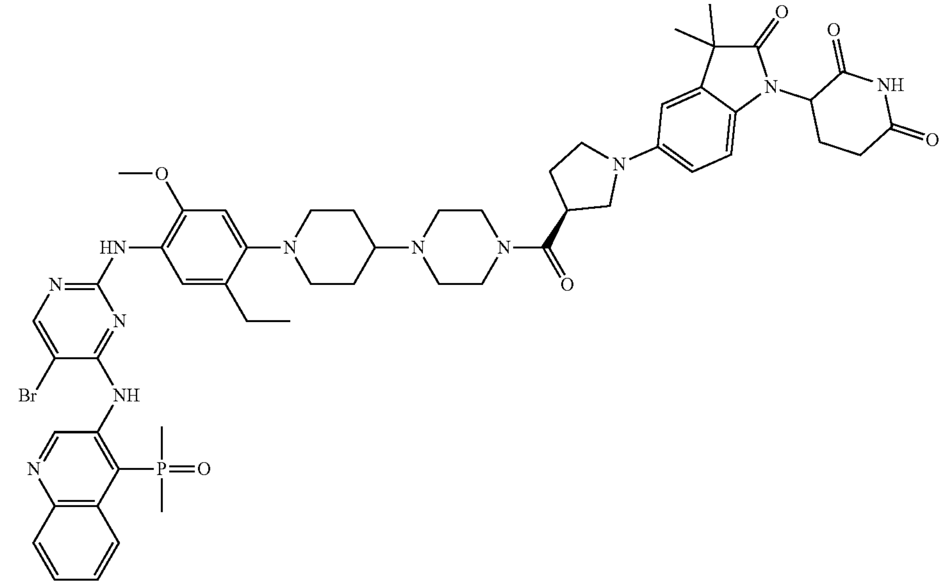

-continued
169
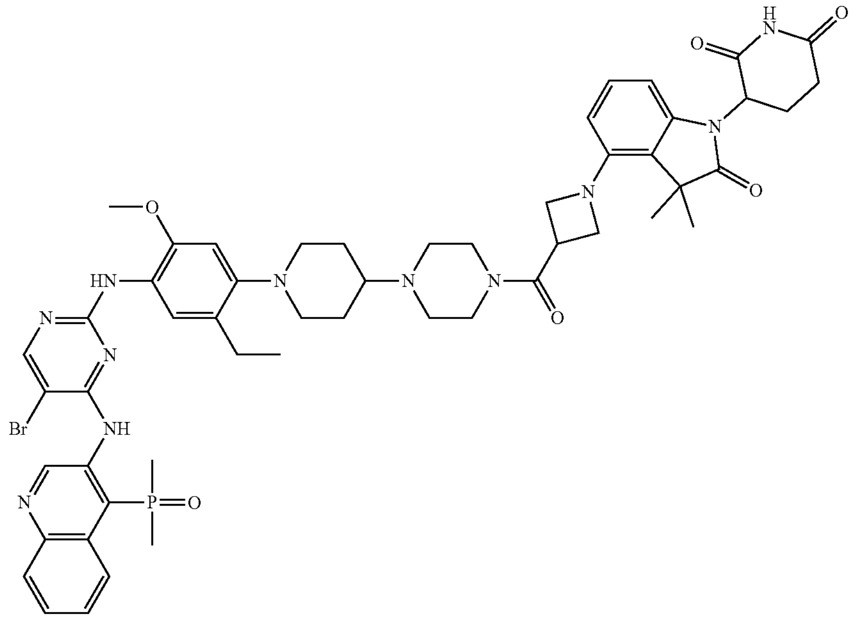
170
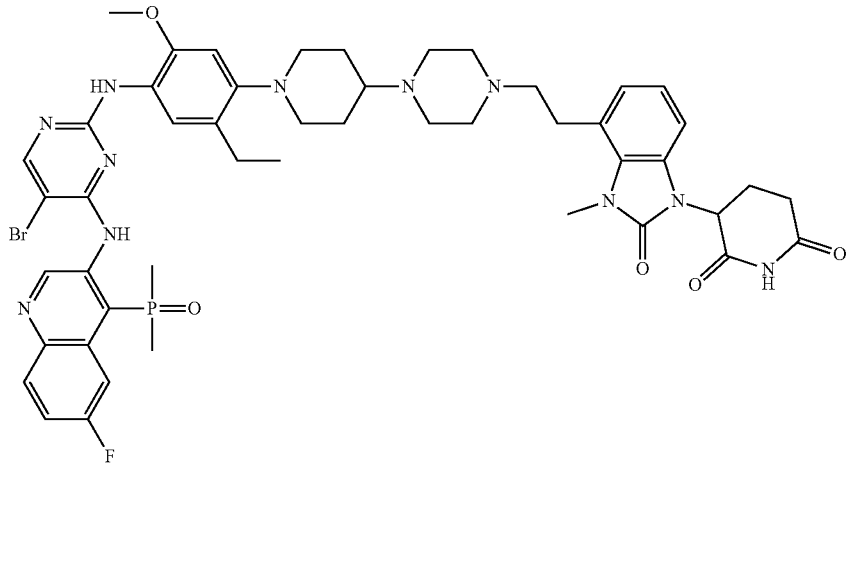

171
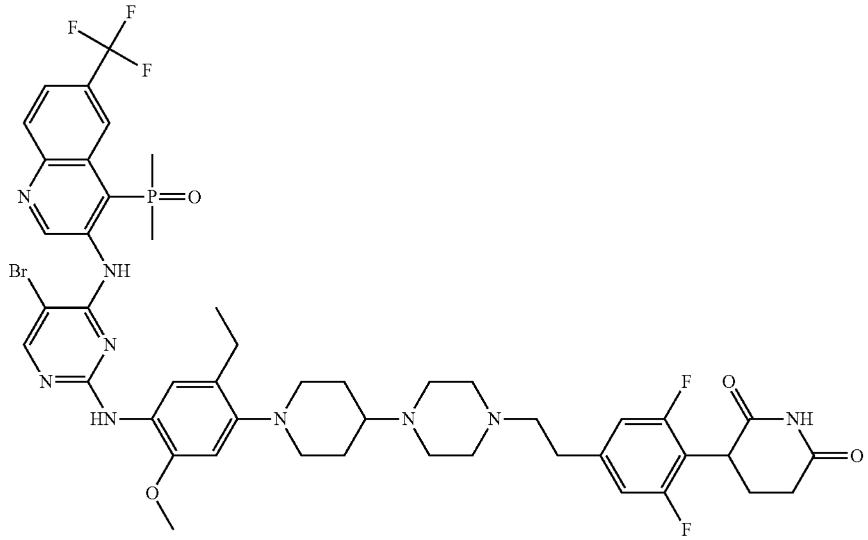
172
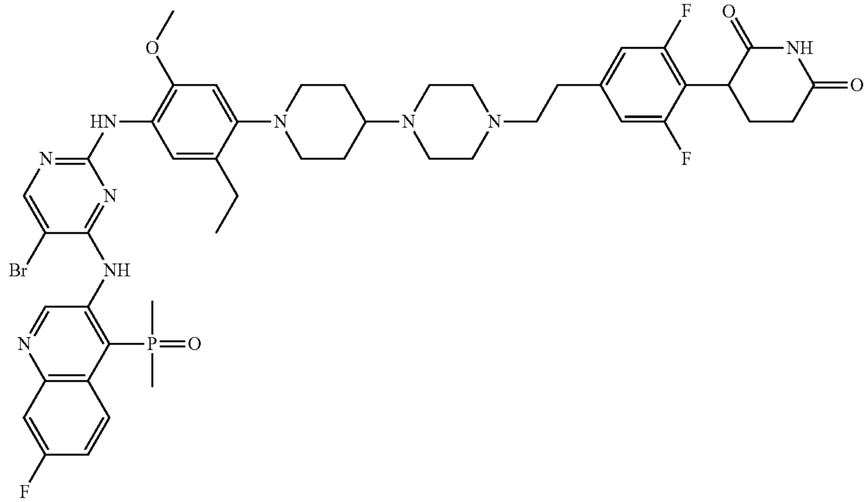
173
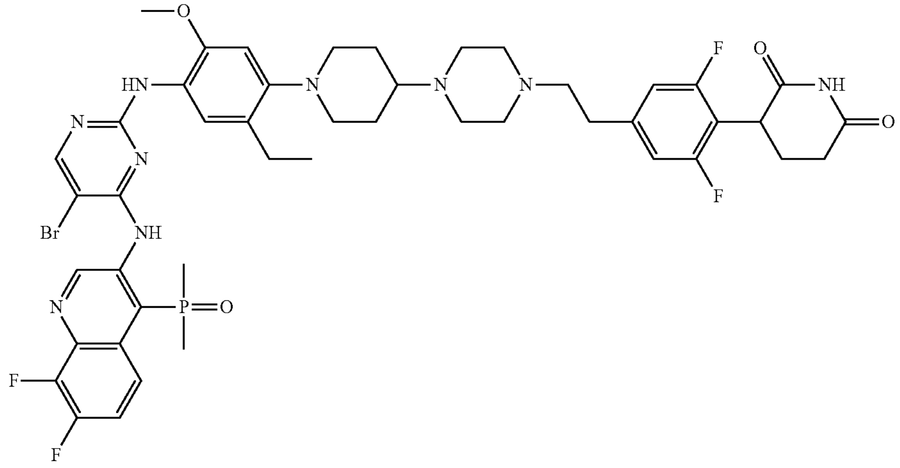

-continued
174
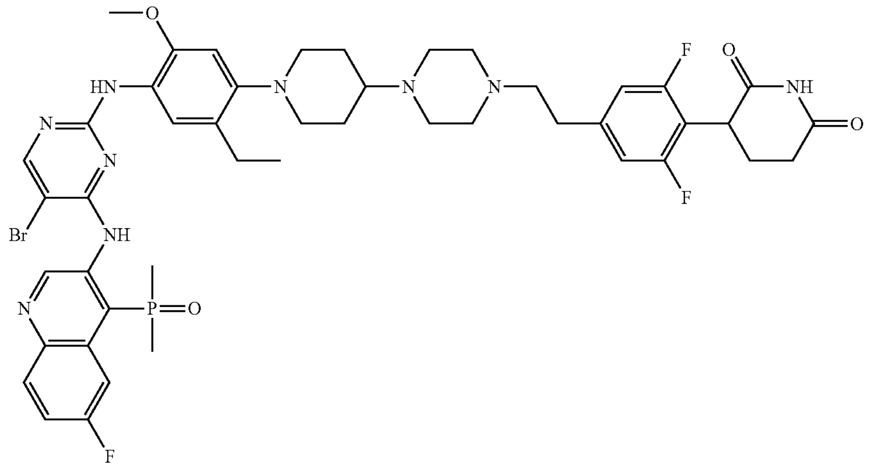
175
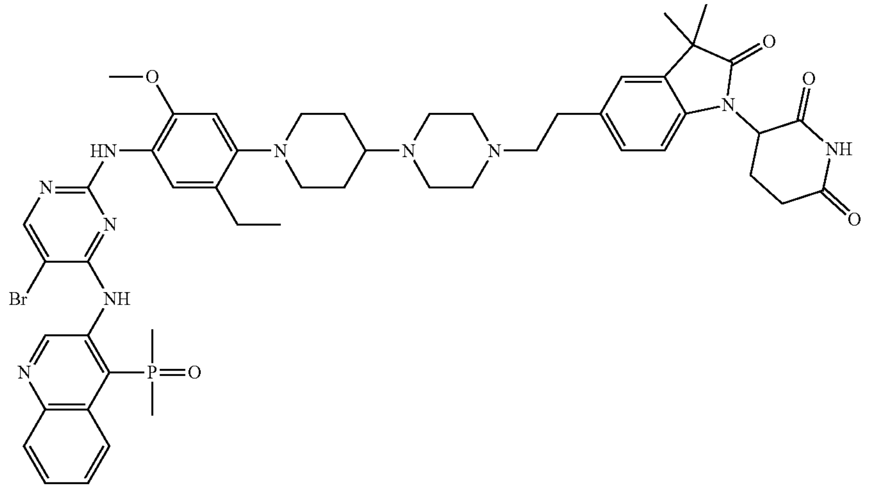
176
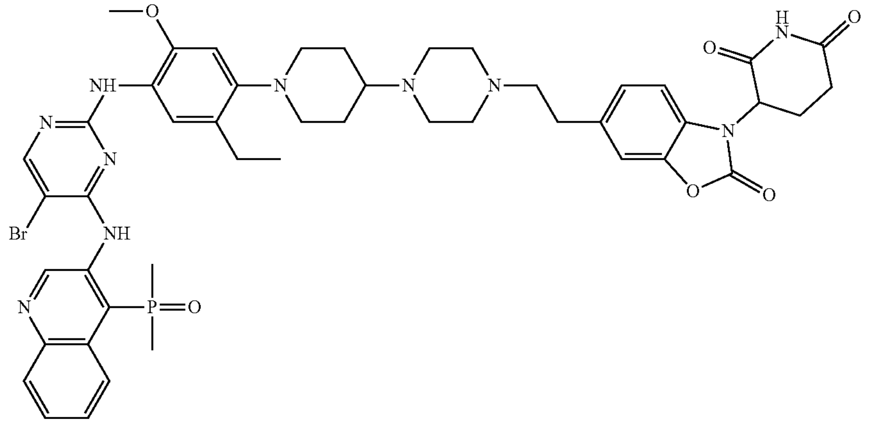

-continued
178
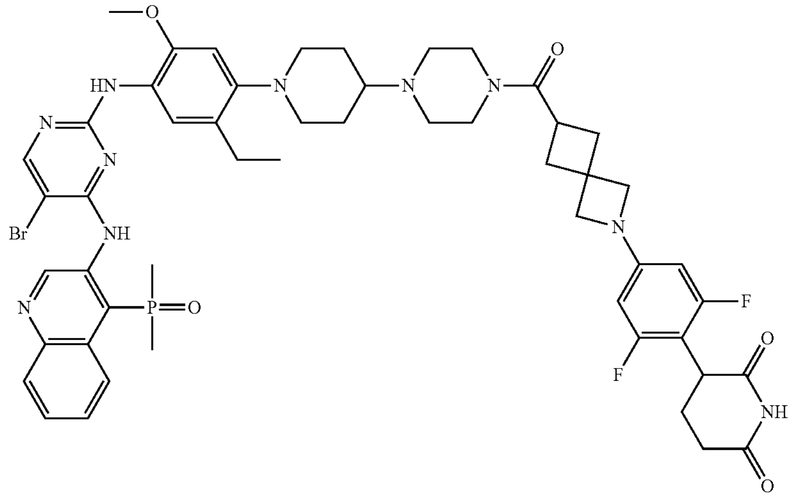
179
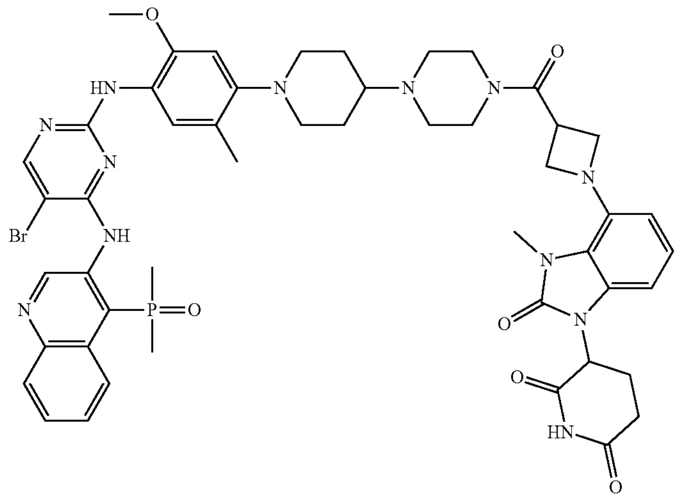
180
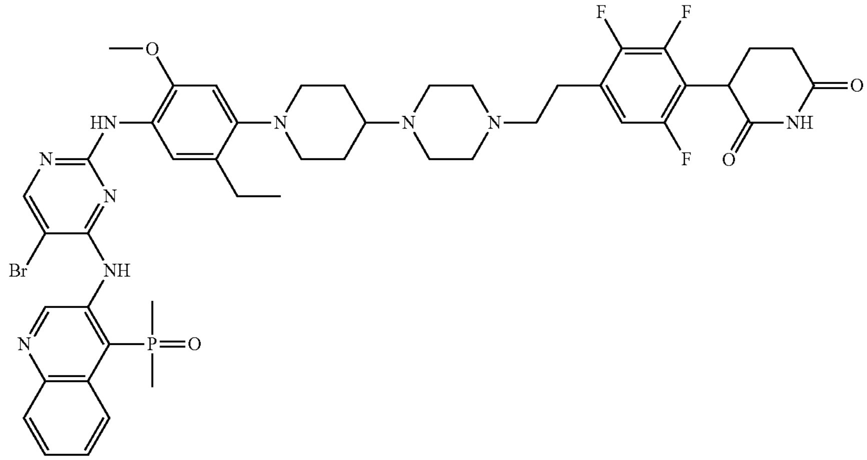

-continued
181
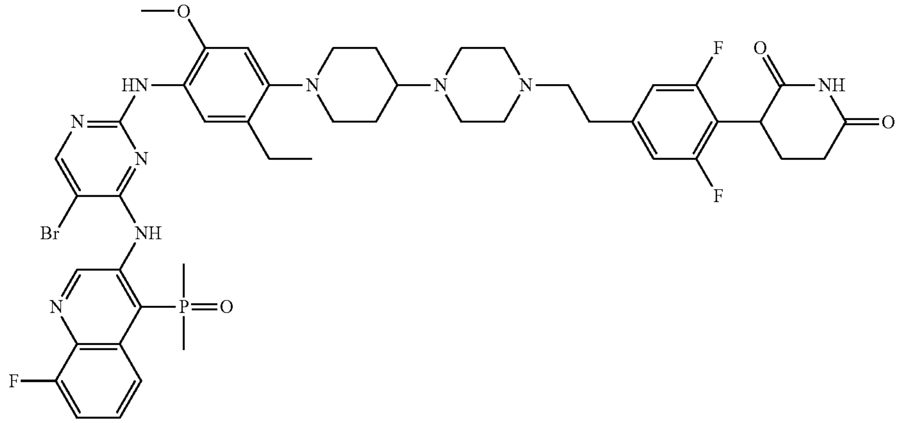
182
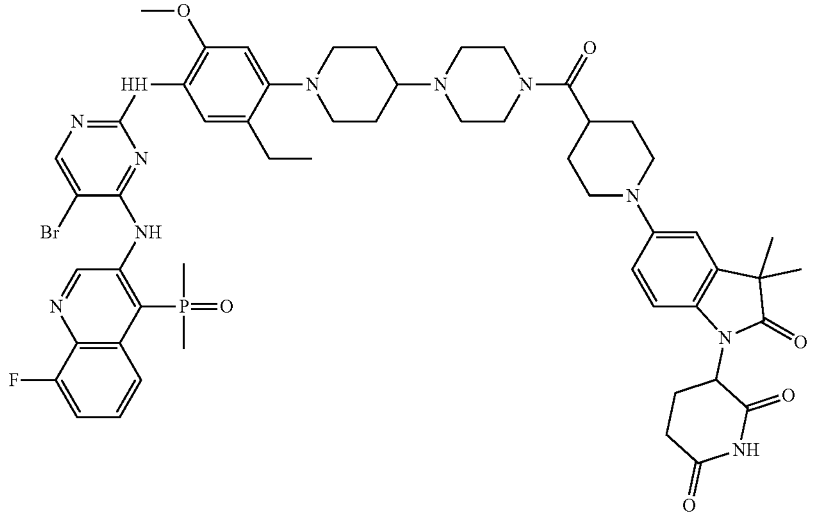
183
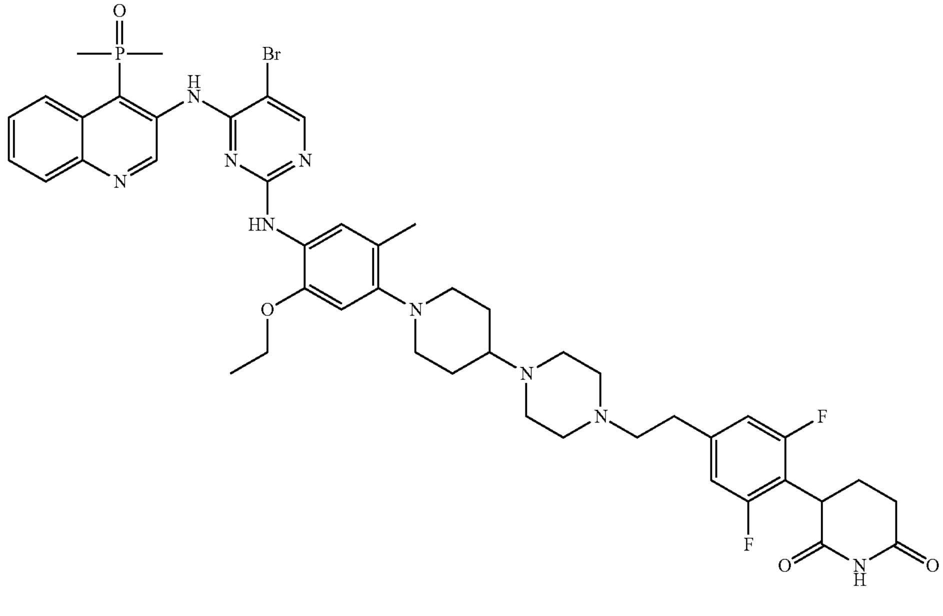

-continued
184
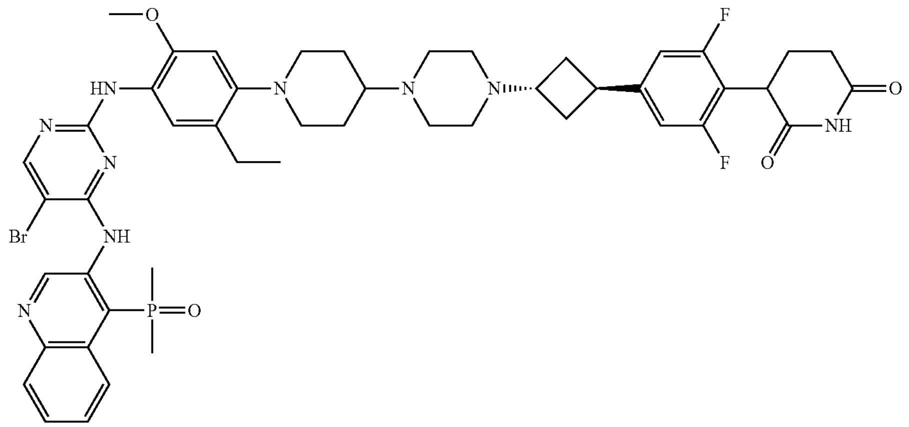
185
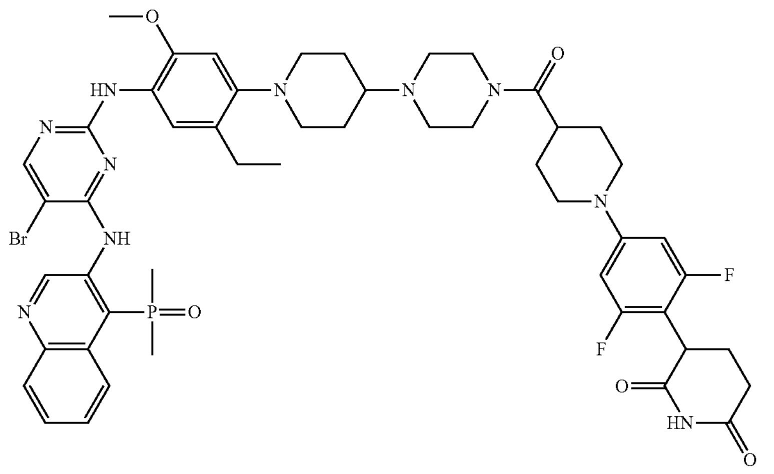
186
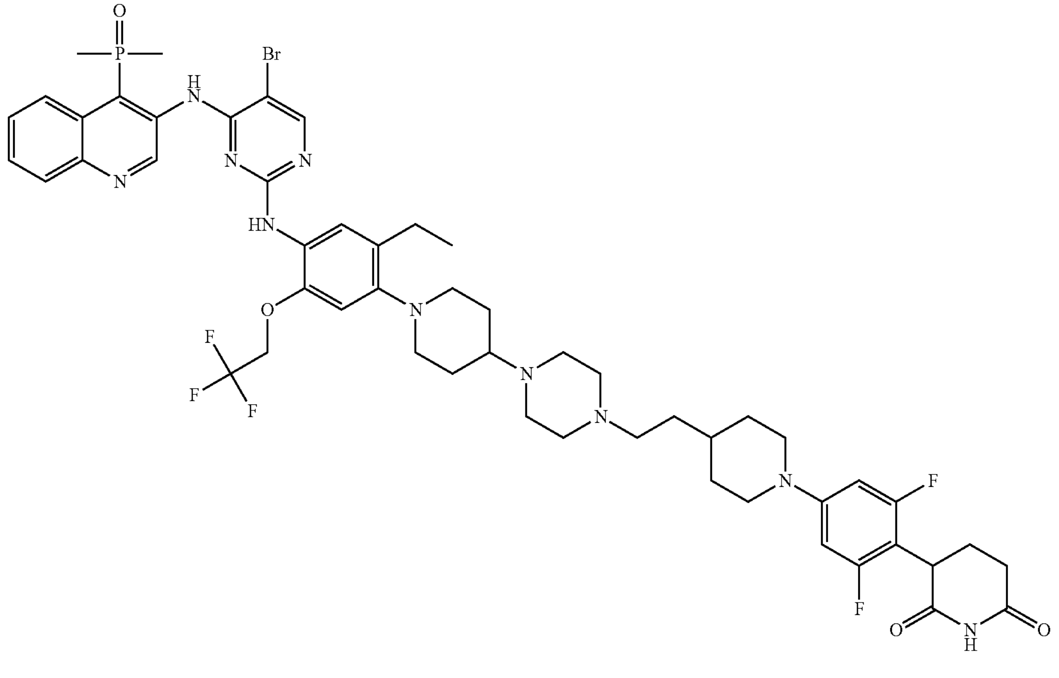

-continued
187
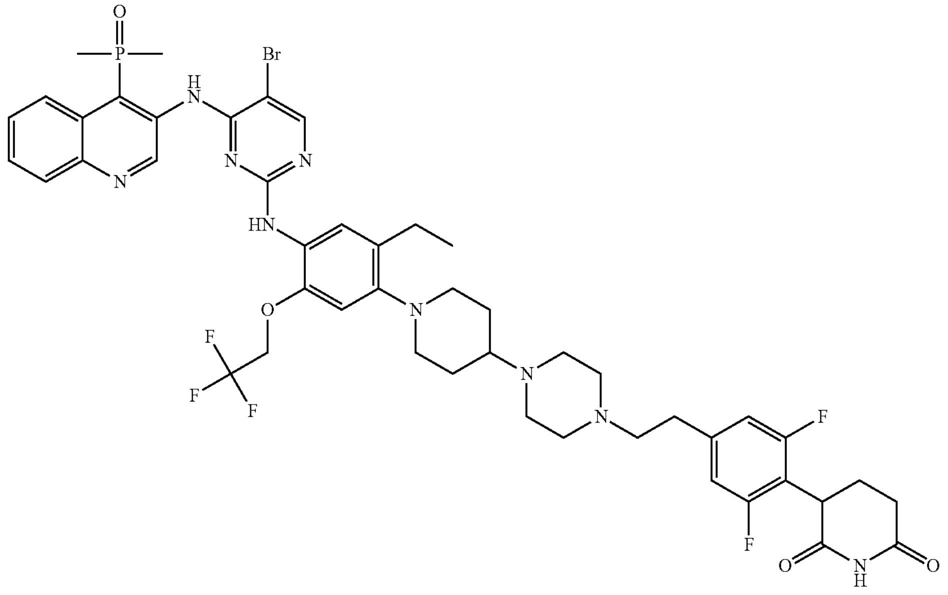
188
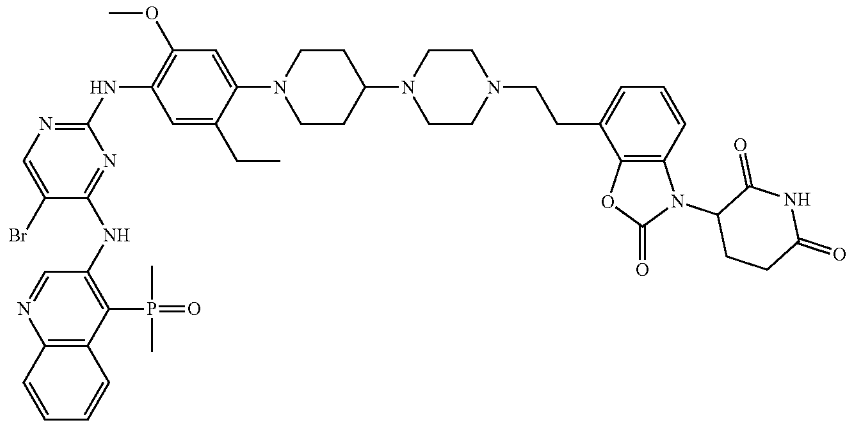
189
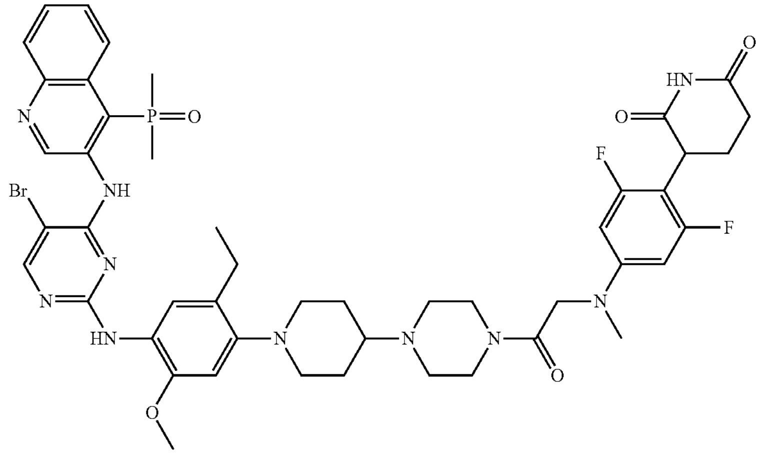

Aspect 40. A pharmaceutical composition comprising a compound of any one of Aspects 1-39 or a pharmaceutically acceptable salt, stereoisomer, tautomer or prodrug thereof, together with a pharmaceutically acceptable excipient.

Aspect 41. A method of decreasing EGFR activity by inhibition and/or degradation, which comprises administering to an individual the compound according to any one of Aspects 1-39, or a pharmaceutically acceptable salt thereof, including the compound of formula (I) or the specific compounds exemplified herein.

Aspect 42. The method of Aspect 41, wherein the disease is selected from cancer, preferred pancreatic cancer, breast cancer, glioblastoma multiforme, head and neck cancer, or non-small cell lung cancer.

Aspect 43. Use of a compound of any one of Aspects 1-39 or a pharmaceutically acceptable salt, stereoisomer, tautomer or prodrug thereof in the preparation of a medicament for treating a disease that can be affected by EGFR modulation.

Aspect 44. The use of Aspect 43, wherein the disease is cancer, preferred pancreatic cancer, breast cancer, glioblastoma multiforme, head and neck cancer, or non-small cell lung cancer.

Aspect 45. A method of treating a disease or disorder in a patient comprising administering to the patient a therapeutically effective amount of the compound any one of Aspects 1-39, or a pharmaceutically acceptable salt thereof as a EGFR kinase inhibitor and/or degrader, wherein the disease or disorder is associated with inhibition of EGFR.

Aspect 46. The method of Aspect 45, wherein the disease is selected from cancer, preferred pancreatic cancer, breast cancer, glioblastoma multiforme, head and neck cancer, or non-small cell lung cancer.

DETAILED DESCRIPTION OF THE INVENTION

The following terms have the indicated meanings throughout the specification:

Unless specifically defined elsewhere in this document, all other technical and scientific terms used herein have the meaning commonly understood by one of ordinary skill in the art to which this invention belongs.

The following terms have the indicated meanings throughout the specification:

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" includes a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "propyl" includes 1-propyl or n-propyl ("n-Pr"), 2-propyl or isopropyl ("i-Pr").

The term "butyl" includes 1-butyl or n-butyl ("n-Bu"), 2-methyl-1-propyl or isobutyl ("i-Bu"), 1-methylpropyl or s-butyl ("s-Bu"), 1,1-dimethylethyl ort-butyl ("t-Bu").

The term "pentyl" includes 1-pentyl, 2-pentyl, 3-pentyl, 2-methyl-2-butyl, 3-methyl-2-butyl, 3-methyl-1-butyl, 2-methyl-1-butyl.

The term "hexyl" includes 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "alkylene" refers to a divalent alkyl group by removing two hydrogen from alkane. Alkylene includes but not limited to methylene, ethylene, propylene, and so on.

The term "cycloalkylene" refers to a divalent alkenyl group by removing two hydrogen from cycloalkylene. Cycloalkylene includes but not limited to, cyclopropyl, cyclobutyl, cyclopentyl, cyclohexyl, cycloheptyl, cyclooctyl, and so on.

The term "halogen" includes fluoro (F), chloro (Cl), bromo (Br) and iodo (I).

The term "alkenyl" includes a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkenylene" refers to a divalent alkenyl group by removing two hydrogen from alkene. Alkenylene includes but not limited to, vinylidene, butenylene, and so on.

The term "alkynyl" includes a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "alkynylene" refers to a divalent alkynyl group by removing two hydrogen from alkyne. Alkenylene includes but not limited to ethynylene and so on.

The term "cycloalkyl" includes a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "spiro cycloalkyl" includes a cyclic structure which contains carbon atoms and is formed by at least two rings sharing one atom.

The term "fused cycloalkyl" includes a bicyclic cycloalkyl group as defined herein which is saturated and is formed by two or more rings sharing two adjacent atoms.

The term "bridged cycloalkyl" includes a cyclic structure which contains carbon atoms and is formed by two rings sharing two atoms which are not adjacent to each other. The term "7 to 10 membered bridged cycloalkyl" includes a cyclic structure which contains 7 to 12 carbon atoms and is formed by two rings sharing two atoms which are not adjacent to each other.

Examples of fused cycloalkyl, fused cycloalkenyl, or fused cycloalkynyl include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2,3-dihydro-1H-indenyl, 1H-indenyl, 1, 2, 3,4-tetralyl, 1,4-dihydronaphthyl, etc. Preferred embodiments are 8 to 9 membered fused rings, which refer to cyclic structures containing 8 to 9 ring atoms within the above examples.

The term "aryl" used alone or in combination with other terms includes a group selected from:

- 5- and 6-membered carbocyclic aromatic rings, e.g., phenyl;
- bicyclic ring systems such as 7 to 12 membered bicyclic ring systems, wherein at least one ring is carbocyclic and aromatic, e.g., naphthyl and indanyl; and,
- tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" includes a bicyclic aryl ring as defined herein. The typical bicyclic fused aryl is naphthalene.

The term "heteroaryl" includes a group selected from:

- 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
- 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and
- 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" includes a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

"Heterocyclyl", "heterocycle" or "heterocyclic" are interchangeable and include a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "at least one substituent" disclosed herein includes, for example, from 1 to 4, such as from 1 to 3, further as 1 or 2, substituents, provided that the theory of valence is met. For example, "at least one substituent F" disclosed herein includes from 1 to 4, such as from 1 to 3, further as 1 or 2, substituents F.

The term "divalent" refers to a linking group capable of forming covalent bonds with two other moieties. For example, "a divalent cycloalkyl group" refers to a cycloalkyl group obtained by removing two hydrogen from the corresponding cycloalkane to form a linking group. the term "divalent aryl group", "divalent heterocyclyl group" or "divalent heteroaryl group" should be understood in a similar manner.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art could select and apply the techniques most likely to achieve the desired separation.

"Diastereomers" refer to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H, et al. "*Chromatographic resolution of enantiomers: Selective review.*" *J Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

Some of the compounds disclosed herein may exist with different points of attachment of hydrogen, referred to as tautomers. For example, compounds including carbonyl $—CH_2C(O)—$ groups (keto forms) may undergo tautomerism to form hydroxyl $—CH{=}C(OH)—$ groups (enol forms). Both keto and enol forms, individually as well as mixtures thereof, are also intended to be included where applicable.

"Prodrug" refers to a derivative of an active agent that requires a transformation within the body to release the active agent. In some embodiments, the transformation is an enzymatic transformation. Prodrugs are frequently, although not necessarily, pharmacologically inactive until converted to the active agent.

"Pharmaceutically acceptable salts" refer to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base. The term also includes salts of the stereoisomers (such as enantiomers and/or diastereomers), tautomers and prodrugs of the compound of the invention.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The term "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer, tautomer or prodrug thereof, and/or at least one pharmaceutically acceptable salt thereof disclosed herein effective to "treat" as defined herein, a disease or disorder in a subject. In the case of combination therapy, the term "therapeutically effective amount" refers to the total amount of the combination objects for the effective treatment of a disease, a disorder or a condition.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "Cn-m" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

EXAMPLES

The examples below are intended to be purely exemplary and should not be considered to be limiting in any way. Efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless indicated otherwise. Unless indicated otherwise, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

$^1$H NMR spectra were recorded on an Agilent instrument operating at 400 MHz. $^1$HNMR spectra were obtained using $CDCl_3$, $CD_2Cl_2$, $CD_3OD$, $D_2O$, $d_6$-DMSO, $d_6$-acetone or $(CD_3)_2CO$ as solvent and tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm; $d_6$-acetone: 2.05; $(CD_3)_3CO$: 2.05) as the reference standard. When peak multiplicities are reported, the following abbreviations are used: s (singlet), d (doublet), t (triplet), q (quartet), qn (quintuplet), sx (sextuplet), m (multiplet), br (broadened), dd (doublet of doublets), dt (doublet of triplets). Coupling constants, when given, are reported in Hertz (Hz).

LCMS-1: LC-MS spectrometer (Agilent 1260 Infinity) Detector: MWD (190-400 nm), Mass detector: 6120 SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.8 mL/min Time (min) A (%) B (%)

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS, LCMS-3: LC-MS spectrometer (Agilent 1260 Infinity II) Detector: MWD (190-400 nm), Mass detector: G6125C SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.8 mL/min Time (min) A (%) B Time (min) A (%) B (%)

| Time (min) | A(%) | B(%) |
|---|---|---|
| 0.00 | 95 | 5 |
| 1.5 | 5 | 95 |
| 2.0 | 5 | 95 |
| 2.1 | 95 | 5 |
| 3.0 | 95 | 5 |

LCMS-2: LC-MS spectrometer (Agilent 1290 Infinity II) Detector: MWD (190-400 nm), Mass detector: G6125C SQ Mobile phase: A: water with 0.1% Formic acid, B: acetonitrile with 0.1% Formic acid Column: Poroshell 120 EC-C18, 4.6×50 mm, 2.7 pm Gradient method: Flow: 1.2 mL/min Time (min) A (%) B (%)

| Time (min) | A(%) | B(%) |
|---|---|---|
| 0.00 | 90 | 10 |
| 1.5 | 5 | 95 |
| 2.0 | 5 | 95 |
| 2.1 | 90 | 10 |
| 3.0 | 90 | 10 |

Preparative HPLC was conducted on a column (150×21.2 mm ID, 5 pm, Gemini NXC 18) at a flow rate of 20 ml/min, injection volume 2 ml, at room temperature and UV Detection at 214 nm and 254 nm.

In the following examples, the abbreviations below are used:

| | |
|---|---|
| $(BPin)_2$ | 4,4,4',4',5,5,5',5'-Octamethyl-2,2'-bi-1,3,2-dioxaborolane |
| $Ac_2O$ | acetic anhydride |
| AcCl | Acetyl chloride |
| Ac | Acetyl |
| ACN or MeCN | Acetonitrile |
| AcOH or HOAc | Acetic acid |
| AcONa or NaOAc | Sodium acetate |
| Aq | Aqueous |
| BINAP | (±)-2,2'-Bis(diphenylphosphino)-1,1'-BINAPhthyl |
| Bn | benzyl |
| BnBr | Benzyl Bromide |
| Boc | t-Butyloxy carbonyl |
| $Boc_2O$ | Di-tert-butyl pyrocarbonate |

-continued

| | |
|---|---|
| C:40691-33-6 | dichlorobis(tri-o-tolylphosphine)palladium(II) |
| Cbz | Benzyloxycarbonyl |
| CDI | N,N'-Carbonyldiimidazole |
| DCM | Dichloromethane |
| Con. or conc. | Concentrated |
| DavePhos | 2'-(Dicyclohexylphosphino)-N,N-dimethyl-2-biphenylamine |
| DBU | 1,8-diazabicyclo[5.4.0]undec-7-ene |
| DCE | dichloroethane |
| DHP | 3,4-Dihydro-2H-pyran |
| DIBAL-H | Diisobutylaluminium hydride |
| DIEA or DIPEA | N,N-diisopropylethylamine |
| DMAP | 4-N,N-dimethylaminopyridine |
| DMP | Dess-Martin periodinane |
| DMF | N,N-Dimethylformamide |
| DMSO | Dimethyl sulfoxide |
| Dppf | 1,1''-bis(diphenylphosphino)ferrocene |
| EA or EtOAc | Ethyl acetate |
| Et | Ethyl |
| EtOH | ethanol |
| FA | Formic acid |
| h or hr | Hour |
| HATU | 2-(7-Azabenzotriazol-1-yl)-N,N,N',N'-tetramethyluronium hexafluorophosphate |
| HBTU | O-(7-Benzotriazole-1-yl)-N,N,N',N'-tetramethyluronium hexafluorophosphate |
| Hex | Hexane |
| HPLC | High Performance Liquid Chromatography |
| hrs | hours |
| IBX | 2-Iodoxybenzoic acid |
| IPA | 2-propanol |
| i-PrOH or iPrOH | Isopropyl alcohol |
| KHMDS | Potassium bis(trimethylsilyl)amide |
| LiHMDS | Lithium bis(trimethylsilyl)amide |
| KOAc or AcOK | Potassium Acetate |
| MeCN or ACN | Acetonitrile |
| MeOH | Methanol |
| Min | Minutes |
| ms or MS | Mass spectrum |
| Ms | Methanesulfonyl |
| MsCl | Methanesulfonyl chloride |
| MsOH | Methanesulfonic acid |
| MTBE | Methyl tert-butyl ether |
| NMP | N-Methyl pyrrolidone |
| NMR | Nuclear Magnetic Resonance |
| o/n | overnight |
| $Pd(dppf)Cl_2$ | [1,1'-Bis(diphenylphosphino)ferrocene]dichloropalladium(II) |
| $Pd_2(dba)_3$ | Tris(dibenzylideneacetone)dipalladium |
| $Pd(dtBPF)Cl_2$ | [1,1'-Bis(di-tert-butylphosphino)ferrocene]dichloropalladium(II) |
| $Pd(PPh_3)_2Cl_2$ | Bis(triphenylphosphine)palladium(II) dichloride |
| PE | Petroleum ether |
| PhMe | Toluene |
| $PPh_3$ | triphenylphosphine |
| PMB | 4-Methoxybenzyl |
| PPA | Polyphosphoric acid |
| pre-HPLC or prep-HPLC | Preparation High Performance Liquid Chromatography |
| Prep-TLC | Preparation Thin Layer Chromatography |
| R.T. or r.t. | Room temperature |
| Rt | Retention time |
| Ruphos-G3 | (2-Dicyclohexylphosphino-2',6'-diisopropoxy-1,1'-biphenyl)[2-(2'-amino-1,1'-biphenyl)]palladium(II) methanesulfonate |
| SEMCl | 2-(Trimethylsilyl)ethoxymethyl chloride |
| SEM | 2-(Trimethylsilyl)ethoxymethyl |
| STAB | Sodium Triacetoxyborohydride;Sodium triacetoborohydride |
| Sat. | saturated |
| TBAF | Tetra-butyl ammonium fluoride |
| TBDPS | tert-Butyldiphenylsilyl |
| TBS | tert-Butyldimethylsilyl |
| TBSCl | tert-Butyldimethylsilyl chloride |
| Ti(OiPr)4 | Titanium tetraisopropanolate |
| t-Bu | tert-butyl |
| t-BuOH | tert-Butanol |
| t-BuONa | Sodium tert-butoxide |
| t-BuOK | Potassium tert-butoxide |
| TEA | Triethylamine |
| $Tf_2O$ | Triflic anhydride |
| TFA | Trifluoroacetic acid |
| THF | Tetrahydrofuran |
| TLC | Thin layer chromatography |

-continued

| | |
|---|---|
| TMSOK | Potassium trimethylsilanolate |
| Ts | para-Toluenesulfonyl |
| TsCl | 4-Toluenesulfonyl chloride |
| TsOH | p-toluenesulfonic acid |
| TsOH,Py | Pyridinium toluene-4-sulphonate |
| Xphos or X-phos | 2-Dicyclohexylphosphino-2',4',6'-triisopropylbiphenyl |
| XantPhos | 4,5-Bis(diphenylphosphino)-9,9-dimethylxanthene |

Example 1: 3-(4-(4-(2-(4-(1-(4-((5-bromo-4-((4-(dimethylphosphoryl)quinolin-3-yl)amino)pyrimidin-2-yl)amino)-2-ethyl-5-methoxyphenyl)piperidin-4-yl)piperazin-1-yl)ethyl)piperidin-1-yl)-2,6-difluorophenyl)piperidine-2,6-dione

Step 1: 4-iodoquinolin-3-amine

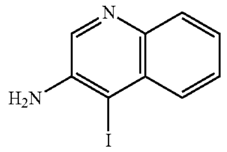 [SMILES: Nc1cnc2ccccc2c1I]

To a solution of quinolin-3-amine (10 g, 69.4 mmol) in AcOH (50 mL) was added iodine chloride (14.62 g, 90.22 mmol) in AcOH (20 mL) dropwise at 5° C. After addition, the reaction mixture was stirred at room temperature for 5 hours. The resulting mixture was diluted with water and extracted with EtOAc (3×500 mL). The combined organic layers were washed with brine (500 mL), dried over anhydrous $Na_2SO_4$. After filtration, the filtrate was concentrated under reduced pressure to afford the product (9.9 g, 52.8%). $[M+H]^+$=271.1.

Step 2: (3-aminoquinolin-4-yl)dimethylphosphine oxide

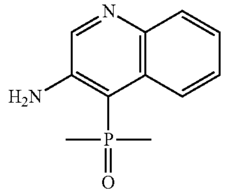

A mixture of 4-iodoquinolin-3-amine (9.0 g, 33.3 mmol), dimethylphosphine oxide (5.2 g, 66.6 mmol), $Pd(OAc)_2$ (746 mg, 3.33 mmol), Xantphos (3.85 g, 6.66 mmol) and $K_3PO_4$ (21.18 g, 99.9 mmol) in dioxane (150 mL) was stirred in a round bottom flask at 100° C. under nitrogen atmosphere for 16 hrs. The reaction mixture was allowed to cool down to room temperature. The resulting mixture was diluted with water (200 mL) and extracted with DCM (3×200 mL). The combined organic layers were washed with brine (1000 mL), dried over anhydrous $Na_2SO_4$. After filtration, the filtrate was concentrated under reduced pressure. The residue was purified by silica gel column chromatography, eluted with DCM/MeOH (10:1) to afford the product (6.5 g, 81.3%), $[M+H]^+$=221.3.

Step 3: (3-((5-bromo-2-chloropyrimidin-4-yl)amino)quinolin-4-yl)dimethylphosphine oxide

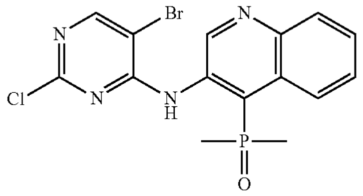 [SMILES: CP(C)(=O)c1c(Nc2nc(Cl)ncc2Br)cnc2ccccc12]

A mixture of (3-aminoquinolin-4-yl)dimethylphosphine oxide (5.5 g, 25.1 mmol), 5-bromo-2,4-dichloropyrimidine (11.4 g, 50.2 mmol) in THF (90 mL) was stirred in a round bottom flask at 0° C. under nitrogen atmosphere, LiHMDS (32.6 mL, 32.6 mmol) was added. The reaction mixture was allowed to warm up to room temperature for 2 hours. The reaction was quenched with water and the mixture was extracted with DCM (3×50 mL), washed triple with saturated brine, dried over anhydrous $Na_2SO_4$. After filtration, the filtrate was concentrated under reduced pressure. The residue was purified by silica gel column chromatography, eluted with DCM/MeOH (10:1) to afford the product (4.7 g, 46.1%). $[M+H]^+$=411.2.

Step 4: (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide

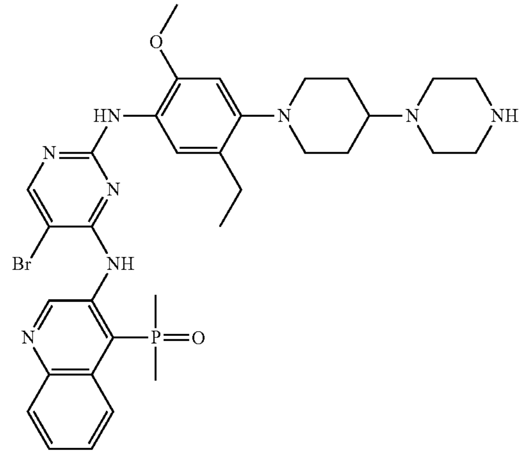 [SMILES: CCc1cc(Nc2ncc(Br)c(Nc3cnc4ccccc4c3P(C)(C)=O)n2)c(OC)cc1N1CCC(N2CCNCC2)CC1]

A mixture of (3-((5-bromo-2-chloropyrimidin-4-yl)amino)quinolin-4-yl)dimethylphosphine oxide (2.2 g, 5.35 mmol), tert-butyl 4-(1-(4-amino-2-ethyl-5-methoxyphenyl)piperidin-4-yl)piperazine-1-carboxylate (2.46 g, 5.89 mmol)

and TsOH (2.76 g, 16.05 nm) in n-BuOH (40 mL) was stirred in a round bottom flask at 100° C. under nitrogen atmosphere for 16 h. The reaction mixture was concentrated under reduced pressure. The residue was dissolved in water and adjusted pH>8. The resulting mixture was extracted with DCM (3×60 mL). The combined organic layers were washed with brine (100 mL), dried over anhydrous $Na_2SO_4$. After filtration, the filtrate was concentrated under reduced pressure. the residue was purified by silica gel column chromatography to afford the product (1.5 g, 40.5%). $[M+H]^+$=693.1.

Step 5: 2,6-bis(benzyloxy)-3-(4,4,5,5-tetramethyl-1,3,2-dioxaborolan-2-yl)pyridine

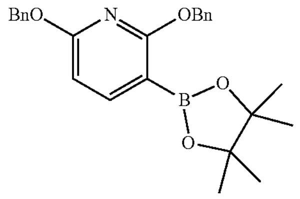 [SMILES: CC1(C)OB(c2ccc(OCc3ccccc3)nc2OCc2ccccc2)OC1(C)C]

A mixture of 2,6-bis(benzyloxy)-3-bromopyridine (15 g, 40.65 mmol) and 4,4,4',4',5,5,5',5'-octamethyl-2,2'-bi(1,3,2-dioxaborolane) (12.6 g, 49.61 mmol), Pd(dppf)$Cl_2$ (3.32 g, 4.07 mmol), KOAc (12 g, 122.45 mmol) in dioxane (200 mL) was stirred overnight at 100° C. under nitrogen atmosphere. The resulting mixture was filtered, the filter cake was washed with MeOH and DCM. The filtrate was concentrated under reduced pressure. The residue was purified by silica gel column chromatography, eluted with PE/EtOAc (8:1) to afford the product (9.00 g, 53%). m/z$[M+H]^+$=418.3.

Step 6: 2,6-bis(benzyloxy)-3-(4-bromo-2,6-difluorophenyl)pyridine

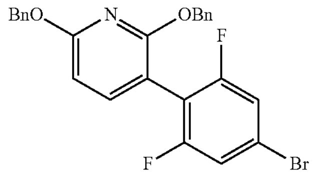 [SMILES: Fc1cc(Br)cc(F)c1-c1ccc(OCc2ccccc2)nc1OCc1ccccc1]

A mixture of 2,6-bis(benzyloxy)-3-(4,4,5,5-tetramethyl-1,3,2-dioxaborolan-2-yl)pyridine (9.00 g, 21.56 mmol) and 5-bromo-1,3-difluoro-2-iodobenzene (6.88 g, 21.57 mmol), $K_2CO_3$ (10.43 g, 75.48 mmol), Pd(dppf)$Cl_2$ (789 mg, 1.078 mmol) in dioxane (90 mL) and $H_2O$ (30 mL) was stirred for 16 h at 100° C. under nitrogen atmosphere. The resulting mixture was extracted with EtOAc (50 mL×3). The combined organic layers were washed with brine, dried over anhydrous $Na_2SO_4$. After filtration, the filtrate was concentrated under reduced pressure. The residue was purified by silica gel column chromatography, eluted with PE/EtOAc (5:1) to afford the product (4 g, 38%). $[M+H]^+$=482.4.

Step 7: ethyl 2-(1-(4-(2,6-bis(benzyloxy)pyridin-3-yl)-3,5-difluorophenyl)piperidin-4-yl)acetate

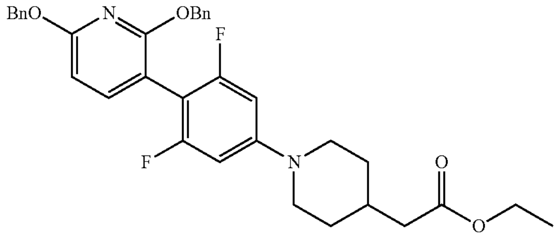 [SMILES: CCOC(=O)CC1CCN(c2cc(F)c(-c3ccc(OCc4ccccc4)nc3OCc3ccccc3)c(F)c2)CC1]

A mixture of 2,6-bis(benzyloxy)-3-(4-bromo-2,6-difluorophenyl)pyridine (4.00 g, 8.29 mmol), ethyl 2-(piperidin-4-yl)acetate (2.13 g, 12.43 mmol), $Cs_2CO_3$ (8.11 g, 24.89 mmol), DavePhos (652.7 mg, 1.659 mmol), $Pd_2(dba)_3$ (759.4 mg, 0.829 mmol) in 2-methyl-THF (50 mL) and $H_2O$ (5 mL) was stirred overnight at 100° C. under nitrogen atmosphere. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with PE/EtOAc (1:1) to afford the product (2 g, 42%). $[M+1]^+$=573.1.

Step 8: 2-(1-(4-(2,6-bis(benzyloxy)pyridin-3-yl)-3,5-difluorophenyl)piperidin-4-yl)ethan-1-ol

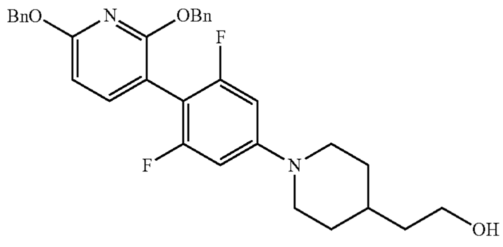 [SMILES: OCCC1CCN(c2cc(F)c(-c3ccc(OCc4ccccc4)nc3OCc3ccccc3)c(F)c2)CC1]

To a stirred mixture of ethyl 2-(1-(4-(2,6-bis(benzyloxy)pyridin-3-yl)-3,5-difluorophenyl)piperidin-4-yl)acetate (2.00 g, 3.49 mmol) in THF (50 mL) was added $LiBH_4$ (1.52 g, 69.77 mmol) in portions at room temperature overnight. The reaction was quenched with water (20 mL) at room temperature. The resulting mixture was extracted with EtOAc (3×50 mL). The combined organic layers were washed with brine, dried over anhydrous $Na_2SO_4$. After filtration, the filtrate was concentrated under reduced pressure to afford the product (1.8 g, 97%) $[M+1]^+$=531.2.

Step 9: 3-(2,6-difluoro-4-(4-(2-hydroxyethyl)piperidin-1-yl)phenyl)piperidine-2,6-dione

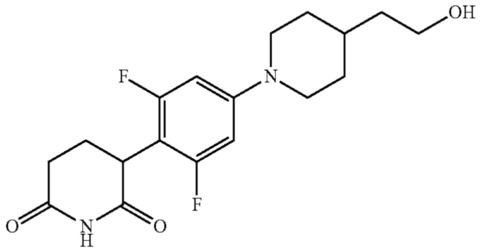 [SMILES: O=C1CCC(c2c(F)cc(N3CCC(CCO)CC3)cc2F)C(=O)N1]

To a stirred mixture of 2-(1-(4-(2,6-bis(benzyloxy)pyridin-3-yl)-3,5-difluorophenyl)piperidin-4-yl)ethan-1-ol (1.80 g, 3.39 mmol) and Pd/C (1 g, 10% wt) in EtOH (20 mL) and DCM (20 mL) were added AcOH (20 mL) at rt and stirred at 40° C. under hydrogen atmosphere overnight. The resulting mixture was filtered, the filter cake was washed with MeOH (20 mL). The filtrate was concentrated under reduced pressure to afford the product (1.2 g, 100%). $[M+1]^+=353.3$.

Step 10: 2-(1-(4-(2,6-dioxopiperidin-3-yl)-3,5-difluorophenyl)piperidin-4-yl)acetaldehyde

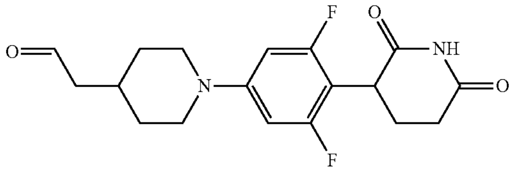 [SMILES: O=CCC1CCN(c2cc(F)c(C3CCC(=O)NC3=O)c(F)c2)CC1]

The titled compound (1.4 g, 92%) was prepared in a manner similar to that in Example 2 step 6 from 3-(2,6-difluoro-4-(4-(2-hydroxyethyl)piperidin-1-yl)phenyl)piperidine-2,6-dione and IBX. $[M+H]^+=351.2$.

Step 11: 3-(4-(4-(2-(4-(1-(4-((5-bromo-4-((4-(dimethylphosphoryl)quinolin-3-yl)amino)pyrimidin-2-yl)amino)-2-ethyl-5-methoxyphenyl)piperidin-4-yl) piperazin-1-yl)ethyl)piperidin-1-yl)-2,6-difluorophenyl)piperidine-2,6-dione

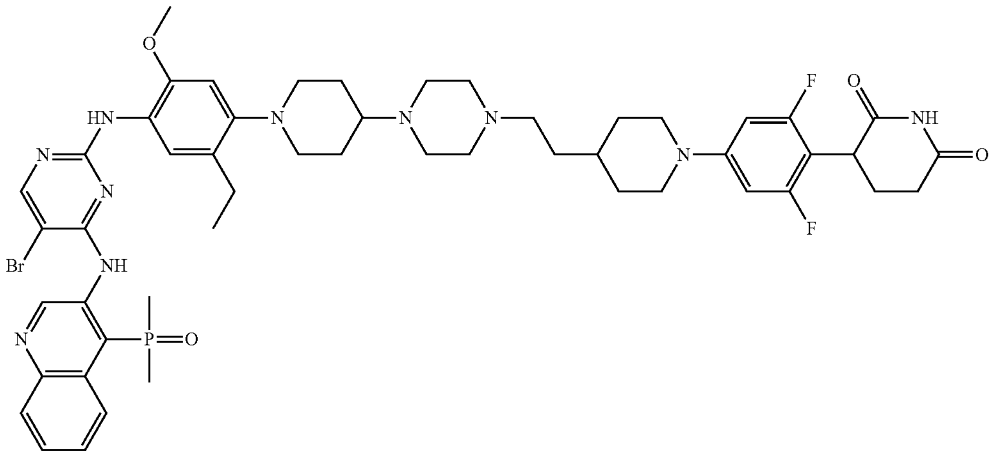 [SMILES: CCc1cc(Nc2ncc(Br)c(Nc3cnc4ccccc4c3P(C)(C)=O)n2)c(OC)cc1N1CCC(N2CCN(CCC3CCN(c4cc(F)c(C5CCC(=O)NC5=O)c(F)c4)CC3)CC2)CC1]

To a solution of (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide (66 mg, 0.1 mmol), and 2-(1-(4-(2,6-dioxopiperidin-3-yl)-3,5-difluorophenyl)piperidin-4-yl)acetaldehyde (42 mg, 0.12 mmol) in DCM (6 mL) and MeOH (1 mL) was added acetic acid (12 mg, 0.2 mmol) at room temperature. After stirring at room temperature for 1 h, $NaBH(OAc)_3$ (64 mg, 0.3 mmol) was added and the resulting mixture was stirred at room temperature for 2 h. The reaction was quenched with water (15 mL) and extracted with DCM (2×30 mL). The combined organic layers were dried over anhydrous $Na_2SO_4$, filtered and evaporated in vacuum to afford the crude residue, which was purified by silica gel column chromatography (DCM:MeOH=100:0~10:1 gradient elution) to give an impure product, which was further purified with pre-HPLC (C-18 column chromatography (0.1% FA in water:acetonitrile=90:10~60:40 gradient elution) to give the desired product (35 mg, 36%). $^1H$ NMR (400 MHz, DMSO) $\delta_H$ 11.68 (s, 1H), 10.86 (s, 1H), 9.45 (s, 1H), 8.25 (s, 1H), 8.18 (d, J=8.3 Hz, 1H), 8.03-7.92 (m, 2H), 7.72 (t, J=7.6 Hz, 1H), 7.64 (t, J=7.8 Hz, 1H), 7.41 (s, 1H), 6.70 (s, 1H), 6.60 (d, J=12.8 Hz, 2H), 4.04 (dd, J=12.7, 5.1 Hz, 1H), 3.77 (s, 5H), 2.92 (d, J=10.2 Hz, 2H), 2.75 (ddd, J=32.2, 21.0, 8.5 Hz, 4H), 2.58 (dd, J=32.2, 20.9 Hz, 5H), 2.41-2.19 (m, 9H), 2.06 (t, J=9.4 Hz, 7H), 1.98-1.90 (m, 1H), 1.81 (d, J=10.7 Hz, 2H), 1.71 (d, J=11.2 Hz, 2H), 1.51 (dd, J=21.9, 10.0 Hz, 3H), 1.41-1.33 (m, 2H), 1.22-1.13 (m, 2H), 0.75 (s, 3H); $[M+H]^+=1027.7$.

Example 2: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazin-1-yl)ethyl)-2-fluorophenyl)piperidine-2,6-dione Step 1: 2-(4-bromo-3-fluorophenyl)ethan-1-ol

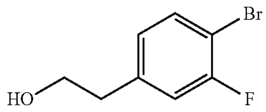 [SMILES: OCCc1ccc(Br)c(F)c1]

To a solution of 2-(4-bromo-3-fluorophenyl)acetic acid (45.0 g, 193 mmol) in THF (270 mL) was added $BH_3THF$ (1 M, 386 mL) at 0° C. Then the mixture was stirred at 20° C. for 2 hrs. Under cooling with ice, MeOH (250 mL) was dropwise added until there was no foaming in the system and the solvent was distilled off under reduced pressure. To the resulting reside, water (50 mL) was added for extraction with EtOAc (3×100 mL). The combined organic phase was washed with brine (40 mL), dried over $Na_2SO_4$, filtered and concentrated in vacuum. 2-(4-bromo-3-fluorophenyl)ethan-1-ol (38.0 g, 89.8%) was obtained. $^1$HNMR (400 MHz, $CDCl_3$-d) δ ppm 7.45 (t, J=7.72 Hz, 1H), 7.00 (dd, J=9.48, 1.76 Hz, 1H), 6.86-6.92 (m, 1H), 3.82 (t, J=6.50 Hz, 2H), 2.80 (t, J=6.50 Hz, 2H), 2.03 (s, 1H); $[M+H]^+$=219.3.

Step 2: (4-bromo-3-fluorophenethoxy)(tert-butyl) dimethylsilane

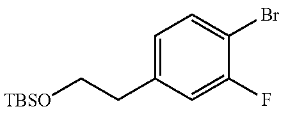 [SMILES: CC(C)(C)[Si](C)(C)OCCc1ccc(Br)c(F)c1]

To a solution of 2-(4-bromo-3-fluorophenyl)ethan-1-ol (38.0 g, 173 mmol) in DCM (210 mL) was added imidazole (17.7 g, 260 mmol) at 20° C. TBSCl (36.6 g, 242 mmol, 29.7 mL) was added to the reaction mixture at 0° C. Then the mixture was stirred at 20° C. for 3 hrs. Then the mixture was adjusted to pH=6 with 5% citric acid (180 mL), and extracted with DCM (150 mL). The organic phase was adjusted to pH=8 with $NaHCO_3$ and then aqueous phase was extracted with DCM (100 mL). The combined organic phase was washed with brine (150 mL), dried over $Na_2SO_4$, filtered and concentrated in vacuum. (4-bromo-3-fluorophenethoxy)(tert-butyl)dimethylsilane (52.0 g, 156 mmol) was obtained. $^1$HNMR (400 MHz, $CDCl_3$-d) δ ppm 7.43 (t, J=7.72 Hz, 1H), 7.00 (dd, J=9.56, 1.87 Hz, 1H), 6.89 (dd, J=8.00, 1.87 Hz, 1H), 3.80 (t, J=6.48 Hz, 2H), 2.78 (t, J=6.48 Hz, 2H), 0.84-0.89 (m, 9H), −0.05-0.01 (m, 6H); $[M+H]^+$=333.2.

Step 3: 2,6-bis(benzyloxy)-3-(4-(2-((tert-butyldimethylsilyl)oxy)ethyl)-2-fluorophenyl)pyridine

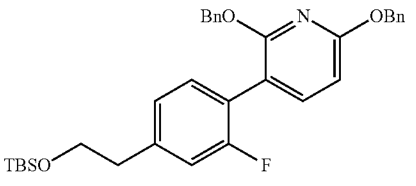 [SMILES: CC(C)(C)[Si](C)(C)OCCc1ccc(-c2ccc(OCc3ccccc3)nc2OCc2ccccc2)c(F)c1]

To a solution of (4-bromo-3-fluorophenethoxy)(tert-butyl)dimethylsilane (52.0 g, 156 mmol) and 2,6-bis(benzyloxy)-3-(4,4,5,5-tetramethyl-1,3,2-dioxaborolan-2-yl) pyridine (65.1 g, 156 mmol) in dioxane (320 mL) was added KOAc (45.9 g, 468 mmol) at 20° C. Pd(dppf)$Cl_2$ (11.4 g, 15.6 mmol) was added to the mixture at 20° C. The suspension was degassed under vacuum and purged with $N_2$ three times. Then the mixture was stirred at 90° C. for 16 hrs. Water (160 mL) was poured into the mixture, extracted with EtOAc (100 mL). The combined organic phase was washed with brine (100 mL), dried over $Na_2SO_4$, filtered and concentrated in vacuum. The residue was purified by column chromatography. 2,6-bis(benzyloxy)-3-(4-(2-((tert-butyldimethylsilyl)oxy)ethyl)-2-fluorophenyl)pyridine (32.0 g, 37.8%) was obtained. $^1$HNMR (400 MHz, $CDCl_3$-d) δ ppm 7.55 (dd, J=8.04, 0.99 Hz, 1H), 7.43-7.47 (m, 2H), 7.33-7.42 (m, 7H), 7.25-7.33 (m, 3H), 6.98-7.05 (m, 2H), 5.40 (d, J=18.4 Hz, 4H), 3.87 (t, J=6.84 Hz, 1H), 3.84-3.89 (m, 1H), 2.86 (t, J=6.84 Hz, 2H), 0.88-0.92 (m, 9H), 0.01-0.03 (m, 6H); $[M+H]^+$=544.2.

Step 4: 3-(4-(2-((tert-butyldimethylsilyl)oxy)ethyl)-2-fluorophenyl)piperidine-2,6-dione

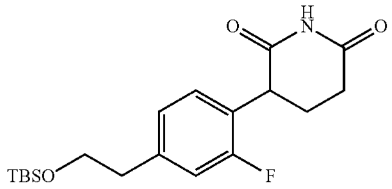 [SMILES: CC(C)(C)[Si](C)(C)OCCc1ccc(C2CCC(=O)NC2=O)c(F)c1]

To a solution of 2,6-bis(benzyloxy)-3-(4-(2-((tert-butyldimethylsilyl)oxy)ethyl)-2-fluorophenyl)pyridine (32.0 g, 58.8 mmol) in THF (50.0 mL) was added Pd/C (0.800 g, 10.0% purity) under Ar at 20° C. The suspension was degassed and purged with $H_2$ for 3 times. The mixture was stirred under $H_2$ (50 Psi) at 50° C. for 16 hrs. The suspension was filtered through a pad of celite and the filter cake was washed with THF (200 mL×3). The combined filtrates were concentrated to dryness to give crude product. The crude product was triturated with petroleum ether (50.0 mL) at 20° C. for 1 hrs. 3-(4-(2-((tert-butyldimethylsilyl)oxy)ethyl)-2-fluorophenyl)piperidine-2,6-dione (12.0 g, 55.7%) was obtained.

$^1$HNMR (400 MHz, $CDCl_3$-d) δ ppm 7.06-7.12 (m, 1H) 7.93 (br s, 1H), 6.96-7.04 (m, 2H), 3.91 (dd, J=11.2, 5.04 Hz, 1H), 3.81 (t, J=6.80 Hz, 2H), 2.82 (t, J=6.80 Hz, 2H), 2.58-2.73 (m, 2H), 2.18-2.34 (m, 2 H), 0.87 (s, 9H), 0.00 (s, 6H); $[M+H]^+$=366.3.

Step 5: 3-(2-fluoro-4-(2-hydroxyethyl)phenyl)piperidine-2,6-dione

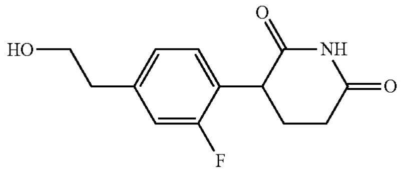 [SMILES: O=C1CCC(c2ccc(CCO)cc2F)C(=O)N1]

To a solution of 3-(4-(2-((tert-butyldimethylsilyl)oxy)ethyl)-2-fluorophenyl)piperidine-2,6-dione (12.0 g, 32.8 mmol) in MeOH (60 mL) was added HCl (12 M, 6 mL) at 20° C. Then the mixture was stirred at 20° C. for 3 hrs. Water (60 mL) was poured into the mixture, extracted with EtOAc (40 mL). The combined organic phase was washed with brine (40 mL), dried over $Na_2SO_4$, filtered and concentrated in vacuum. The combined crude product was purified by re-crystallization from toluene (32.0 mL) at 100° C. 3-(2-fluoro-4-(2-hydroxyethyl)phenyl)piperidine-2,6-dione (6.50 g, 78.8%) was obtained. $^1$HNMR (400 MHz, DMSO-$d_6$) δ ppm 10.8 (s, 1H), 7.19 (t, J=7.84 Hz, 1H), 6.99-7.08 (m, 2H), 4.67 (t, J=5.18 Hz, 1H), 3.99 (dd, J=12.6, 4.74 Hz, 1H), 3.55-3.66 (m, 2H), 2.68-2.75 (m, 3H), 2.18 (qd, J=12.8, 3.86 Hz, 1H), 1.93-2.03 (m, 1H); $[M+H]^+$=252.1.

Step 6: 2-(4-(2,6-dioxopiperidin-3-yl)-3-fluorophenyl)acetaldehyde

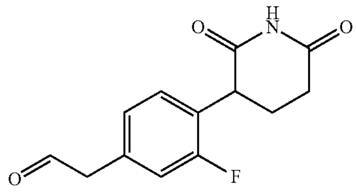 [SMILES: O=CCc1ccc(C2CCC(=O)NC2=O)c(F)c1]

To a solution of 3-(2-fluoro-4-(2-hydroxyethyl)phenyl) piperidine-2,6-dione (200 mg, 0.8 mmol) in DMSO (10 mL) was added IBX (338 mg, 1.2 mmol). The mixture was stirred in a flask at rt overnight. After being determined the reaction to be completed by LCMS, the mixture was extracted with EA (30 mL). The combined organic phase was dried over anhydrous $Na_2SO_4$, and evaporated in vacuum to afford the crude product (100 mg, crude), which was used for next step without further purification. $[M+H]^+$=250.2.

Step 7: 3-(4-(2-(4-(1-(4-((5-bromo-4-((4-(dimethylphosphoryl)quinolin-3-yl)amino)pyrimidin-2-yl) amino)-2-ethyl-5-methoxyphenyl) piperidin-4-yl) piperazin-1-yl)ethyl)fluorophenyl)piperidine-2,6-dione

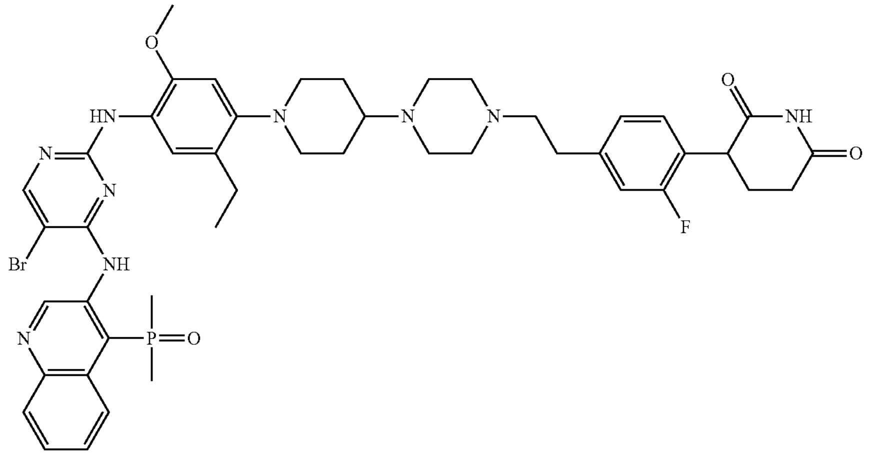 [SMILES: CCc1cc(Nc2ncc(Br)c(Nc3cnc4ccccc4c3P(C)(C)=O)n2)c(OC)cc1N1CCC(N2CCN(CCc3ccc(C4CCC(=O)NC4=O)c(F)c3)CC2)CC1]

The titled compound (1.4 g, 92%) was prepared in a manner similar to that in Example 1 step 11 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and 2-(4-(2,6-dioxopiperidin-3-yl)-3-fluorophenyl)acetaldehyde. $^1H$ NMR (500 MHz, DMSO) $\delta_H$ 11.68 (s, 1H), 10.86 (s, 1H), 9.45 (s, 1H), 8.25 (s, 1H), 8.19 (d, J=8.3 Hz, 1H), 8.05-7.93 (m, 2H), 7.71 (d, J=7.4 Hz, 1H), 7.65 (d, J=8.0 Hz, 1H), 7.41 (s, 1H), 7.20 (t, J=7.9 Hz, 1H), 7.06 (dd, J=20.6, 9.8 Hz, 2H), 6.70 (s, 1H), 4.00 (dd, J=12.5, 4.8 Hz, 1H), 3.77 (s, 3H), 2.93 (d, J=10.9 Hz, 2H), 2.74 (dd, J=15.1, 7.7 Hz, 3H), 2.65-2.51 (m, 10H), 2.48-2.40 (m, 3H), 2.33 (d, J=7.1 Hz, 3H), 2.19 (dt, J=13.0, 9.0 Hz, 1H), 2.05 (d, J=13.5 Hz, 6H), 1.99 (dd, J=9.1, 4.0 Hz, 1H), 1.83 (d, J=11.2 Hz, 2H), 1.53 (d, J=8.8 Hz, 2H), 0.75 (s, 3H); $[M+H]^+$=926.5.

Example 4: 3-(5-((R)-3-((4-(1-(4-((5-bromo-4-((4-(dimethylphosphoryl)quinolin-3-yl)amino)pyrimidin-2-yl)amino)-2-ethyl-5-methoxyphenyl)piperidin-4-yl)piperazin-1-yl)methyl)pyrrolidin-1-yl)-1-oxoisoindolin-2-yl)piperidine-2,6-dione Step 1: methyl (S)-2-cyano-4-(3-(hydroxymethyl) pyrrolidin-1-yl)benzoate

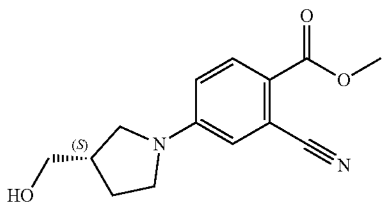

To a stirred mixture of methyl 2-cyano-4-fluorobenzoate (10.0 g, 55.819 mmol) and (S)-pyrrolidin-3-ylmethanol (6.8 g, 66.983 mmol) in DMSO (80 mL) was added DIEA (14.4 g, 111.638 mmol) and stirred overnight at 60° C. The resulting mixture was extracted with EtOAc (500 mL). The combined organic layers were washed with brine (100 mL), dried over anhydrous $Na_2SO_4$. After filtration, the filtrate was concentrated under reduced pressure. methyl (S)-2-cyano-4-(3-(hydroxymethyl)pyrrolidin-1-yl)benzoate (10.0 g, 98.3%) was obtained. $[M+H]^+$=261.2.

Step 2: methyl (S)-2-formyl-4-(3-(hydroxymethyl)pyrrolidin-1-yl)benzoate

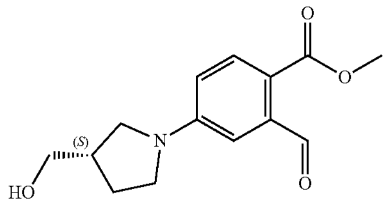

To a stirred mixture of methyl (S)-2-cyano-4-(3-(hydroxymethyl)pyrrolidin-1-yl)benzoate (10.0 g, 38.418 mmol) in AcOH (100 mL) and $H_2O$ (50 mL) was added Raney-Ni (10.0 g, 116.720 mmol) in portions and stirred overnight at 40° C. under hydrogen atmosphere. The resulting mixture was filtered, the filter cake was washed with DCM and MeOH (300 mL). The filtrate was concentrated under reduced pressure. The filtrate was extracted with EtOAc (500 mL). The combined organic layers were washed with brine (500 mL), dried over anhydrous $Na_2SO_4$. After filtration, the filtrate was concentrated under reduced pressure. The residue was purified by silica gel column chromatography, eluted with $CH_2Cl_2$/MeOH (9:1) to afford product (5.0 g, 49.4%). $[M+H]^+$=264.1.

Step 3: 3-(5-((S)-3-(hydroxymethyl)pyrrolidin-1-yl)-1-oxoisoindolin-2-yl)piperidine-2,6-dione

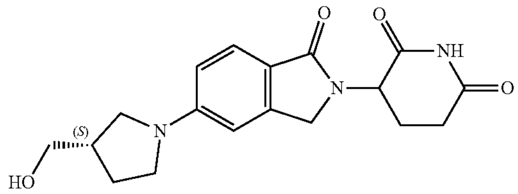

A mixture of 3-aminopiperidine-2,6-dione hydrochloride (4.7 g, 28.485 mmol) and DIEA (4.9 g, 37.980 mmol) in DMF (50 mL) was stirred for 5 h at room temperature. The mixture was acidified to pH<7 with AcOH (5.7 g, 94.950 mmol) followed by the addition of methyl (S)-2-formyl-4-(3-(hydroxymethyl)pyrrolidin-1-yl)benzoate (5.0 g, 18.990 mmol) in DCE (10.00 mL) and DMF (2 mL) at room temperature. The resulting mixture was stirred overnight at room temperature. To the above mixture was added $NaBH_3CN$ (3.6 g, 56.970 mmol) in portions at room temperature. The resulting mixture was stirred for additional 2 h at room temperature. The reaction was quenched with water (50 mL) at room temperature. The resulting mixture was concentrated under reduced pressure. The residue was purified by silica gel column chromatography, eluted with $CH_2Cl_2$/MeOH (5:1) to afford crude product, which was purified by trituration with DCM (40 mL) to afford the product (2.1 g, 33.2%). $[M+H]^+$=344.0.

Step 4: ((3S)-1-(2-(2,6-dioxopiperidin-3-yl)-1-oxoisoindolin-5-yl)pyrrolidin-3-yl)methyl methanesulfonate

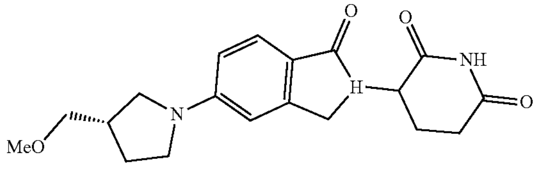

The titled compound (120 mg, 44%) was prepared in a manner similar to that in Example 19 step 4 from 3-(5-((S)-3-(hydroxymethyl)pyrrolidin-1-yl)-1-oxoisoindolin-2-yl)piperidine-2,6-dione and MsCl. $[M+H]^+$=422.2.

Step 5: 3-(5-((R)-3-((4-(1-(4-((5-bromo-4-((4-(dimethylphosphoryl)quinolin-3-yl)amino)pyrimidin-2-yl)amino)-2-ethyl-5-methoxyphenyl)piperidin-4-yl)piperazin-1-yl)methyl)pyrrolidin-1-yl)-1-oxoisoindolin-2-yl)piperidine-2,6-dione

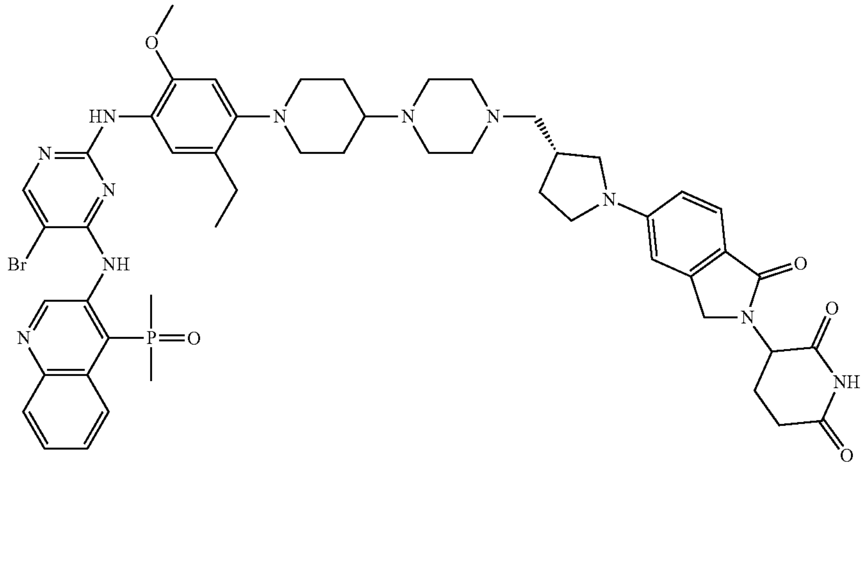 [SMILES: CCc1cc(Nc2ncc(Br)c(Nc3cnc4ccccc4c3P(C)(C)=O)n2)c(OC)cc1N1CCC(N2CCN(C[C@H]3CCN(c4ccc5c(c4)CN(C4CCC(=O)NC4=O)C5=O)C3)CC2)CC1]

The titled compound (12 mg, 25%) was prepared in a manner similar to that in Example 19 step 5 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and ((3S)-1-(2-(2,6-dioxopiperidin-3-yl)-1-oxoisoindolin-5-yl)pyrrolidin-3-yl)methyl methanesulfonate. $^1$H NMR (400 MHz, DMSO) $\delta_H$ 11.68 (s, 1H), 10.93 (s, 1H), 9.44 (s, 1H), 8.25 (s, 1H), 8.19 (d, J=8.3 Hz, 1H), 8.03-7.92 (m, 2H), 7.72 (t, J=7.7 Hz, 1H), 7.64 (t, J=7.4 Hz, 1H), 7.48 (d, J=8.3 Hz, 1H), 7.41 (s, 1H), 6.70 (s, 1H), 6.62 (d, J=9.3 Hz, 2H), 5.03 (dd, J=13.3, 5.4 Hz, 1H), 4.30 (d, J=20.1 Hz, 1H), 4.18 (d, J=16.5 Hz, 1H), 3.78 (s, 3H), 3.42 (d, J=29.0 Hz, 2H), 3.05 (d, J=10.2 Hz, 1H), 2.97-2.85 (m, 4H), 2.64-2.54 (m, 8H), 2.40-2.28 (m, 9H), 2.05 (d, J=13.5 Hz, 8H), 1.95 (s, 1H), 1.83 (s, 2H), 1.74 (s, 1H), 1.53 (d, J=26.3 Hz, 2H), 0.75 (s, 3H); $[M+H]^+$ =1018.7.

Example 7: 3-(4-(2-(4-(1-(4-((5-bromo-4-((4-(dimethylphosphoryl)-1,5-naphthyridin-3-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione Step 1: 4-iodo-1,5-naphthyridin-3-amine

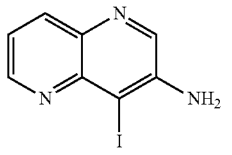 [SMILES: Nc1cnc2cccnc2c1I]

To a solution of 1,5-naphthyridin-3-amine (1.0 g, 6.9 mmol) and $Ag_2SO_4$ (2.4 g, 6.9 mmol) in EtOH (40 mL) was added $I_2$ (1.91 g, 6.9 mmol) at 0° C. Then the mixture was stirred at 30° C. for 2 hrs. The resulting mixture was extracted with DCM (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with DCM/MeOH (15:1) to afford the product (0.4 g, 23%). $[M+H]^+$=271.2.

Step 2: (3-amino-1,5-naphthyridin-4-yl)dimethylphosphine oxide

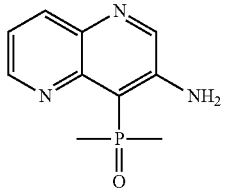

A mixture of 4-iodo-1,5-naphthyridin-3-amine (100 mg, 1.5 mmol), dimethylphosphine oxide (233 mg, 3.0 mmol), $Pd(OAc)_2$ (33 mg, 0.15 mmol) Xanphos (170 mg, 0.3 mmol) and $K_3PO_4$ (950 mg, 4.5 mmol) in dioxane (20 mL) was stirred in a round bottom flask at 100° C. under nitrogen atmosphere for 16 hrs. The reaction mixture was allowed to cool down to room temperature. The resulting mixture was extracted with DCM (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with DCM/MeOH (10:1) to afford the product (300 mg, 90%), $[M+H]^+$=222.0.

Step 3: (3-((5-bromo-2-chloropyrimidin-4-yl)amino)-1,5-naphthyridin-4-yl)dimethylphosphine oxide

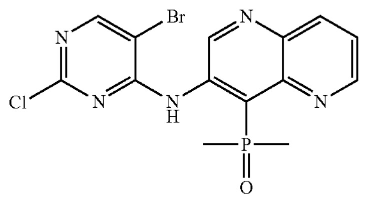 [SMILES: CP(C)(=O)c1c(Nc2nc(Cl)ncc2Br)cnc2cccnc12]

A mixture of (3-amino-1,5-naphthyridin-4-yl)dimethylphosphine oxide (300 mg, 1.35 mmol), 5-bromo-2,4-dichloropyrimidine (610 mg, 2.7 mmol) in DMF (20 mL) was stirred in a round bottom flask at 0° C. under nitrogen atmosphere, NaH (100 mg, 2.7 mmol) was added. The reaction mixture was allowed to warm up to room temperature for 2 hours. The reaction was quenched with water and the mixture was extracted with DCM, washed with saturated brine. dried over anhydrous $Na_2SO_4$. After filtration, the filtrate was concentrated under reduced pressure. The residue was purified by silica gel column chromatography, eluted with DCM/MeOH (10:1) to afford the product (300 mg, 54%). $[M+H]^+$=412.0.

Step 4: (3-((5-bromo-2-((5-ethyl-2-methoxy-4-(4-(piperazin-1-yl)piperidin-1-yl)phenyl)amino)pyrimidin-4-yl)amino)-1,5-naphthyridin-4-yl)dimethylphosphine oxide

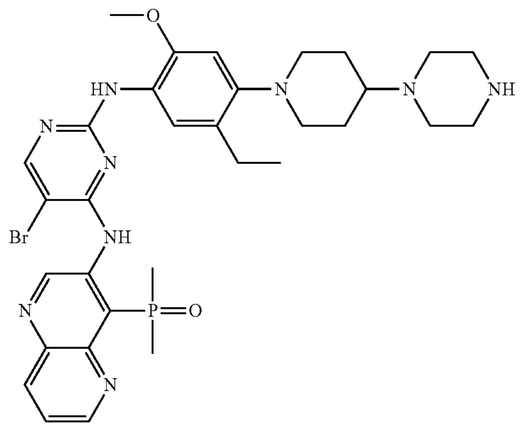 [SMILES: CCc1cc(Nc2ncc(Br)c(Nc3cnc4cccnc4c3P(C)(C)=O)n2)c(OC)cc1N1CCC(N2CCNCC2)CC1]

A mixture of (3-((5-bromo-2-chloropyrimidin-4-yl)amino)-1,5-naphthyridin-4-yl)dimethylphosphine oxide (2 g, 4.8 mmol), tert-butyl 4-(1-(4-amino-2-ethyl-5-methoxyphenyl)piperidin-4-yl)piperazine-1-carboxylate (2.6 g, 6.3 mmol) and MsOH (184 mg, 19.2 nm) in t-BuOH (20 mL) was stirred in a round bottom flask at 90° C. under nitrogen atmosphere for 16 h. The reaction mixture was concentrated under reduced pressure. The residue was purified by HPLC chromatography (C-18 column chromatography (0.1% FA in water:acetonitrile=90:10~60:40 gradient elution) to afford the product (2 g, 60%). [M+H]+=694.0.

Step 5: 3-(4-(2-(4-(1-(4-((5-bromo-4-((4-(dimethylphosphoryl)-1,5-naphthyridin-3-yl)amino)pyrimidin-2-yl)amino)-2-ethyl-5-methoxyphenyl)piperidin-4-yl)piperazin-1-yl)ethyl)-2,6-difluorophenyl) piperidine-2,6-dione

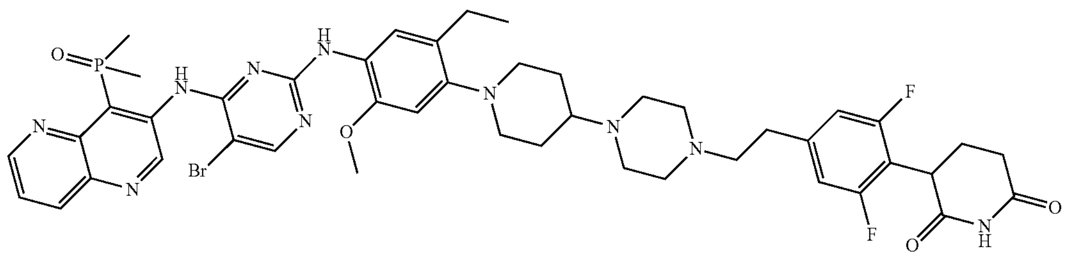 [SMILES: CCc1cc(Nc2ncc(Br)c(Nc3cnc4cccnc4c3P(C)(C)=O)n2)c(OC)cc1N1CCC(N2CCN(CCc3cc(F)c(C4CCC(=O)NC4=O)c(F)c3)CC2)CC1]

A mixture of (3-((5-bromo-2-((5-ethyl-2-methoxy-4-(4-(piperazin-1-yl)piperidin-1-yl)phenyl)amino)pyrimidin-4-yl)amino)-1,5-naphthyridin-4-yl)dimethylphosphine oxide (40 mg, 0.057 mmol) and 2-(4-(2,6-dioxopiperidin-3-yl)-3,5-difluorophenyl)acetaldehyde (the material was synthesized from the similar method of example 2 step 6) (20 mg, 0.069 mmol) and NaOAc (14 mg, 0.17 mmol) in DCM (4 mL) and EtOH (0.5 mL) was stirred in a round bottom flask at room temperature for 2 hour. The mixture was added $NaBH_3CN$ (10 mg, 0.17 mmol) and stirred in a round bottom flask at room temperature 2 h. Then the mixture was evaporated in vacuum to afford the crude product, which was purified with HPLC chromatography (C-18 column chromatography (0.1% FA in water:acetonitrile=90:10~60:40 gradient elution)) to give the product (16 mg, 28%). $^1$H NMR (500 MHz, DMSO) δ 12.25 (s, 1H), 10.95 (s, 1H), 9.83 (s, 1H), 8.93 (dd, J=4.2, 1.6 Hz, 1H), 8.34 (d, J=8.3 Hz, 1H), 8.29 (s, 1H), 8.21 (s, 1H), 7.71 (dd, J=8.4, 4.2 Hz, 1H), 7.43 (s, 1H), 7.03 (d, J=10.0 Hz, 2H), 6.75 (s, 1H), 4.20 (dd, J=12.8, 5.2 Hz, 1H), 3.80 (d, J=16.5 Hz, 3H), 3.00 (d, J=11.5 Hz, 2H), 2.86-2.71 (m, 3H), 2.69-2.61 (m, 3H), 2.55-5.41 (m, 6H), 2.49-2.40 (m, 6H), 2.30-2.20 (m, 1H), 2.11-2.06 (m, 7H), 2.03-1.94 (m, 1H), 1.85 (d, J=10.6 Hz, 2H), 1.61-1.49 (m, 2H), 0.87-0.68 (m, 3H); $[M+H]^+$=945.5.

Example 9: 3-(4-(4-(2-(4-(1-(4-((5-bromo-4-((4-(dimethylphosphoryl)-1,5-naphthyridin-3-yl)amino) pyrimidin-2-yl)amino)-2-ethyl-5-methoxyphenyl) piperidin-4-yl)piperazin-1-yl)ethyl)piperidin-1-yl)-2, 6-difluorophenyl)piperidine-2,6-dione

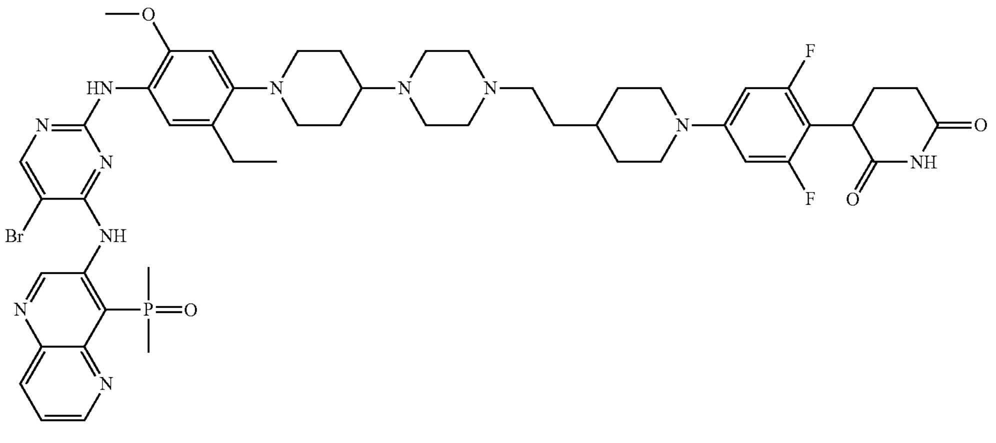 [SMILES: CCc1cc(Nc2ncc(Br)c(Nc3cnc4cccnc4c3P(C)(C)=O)n2)c(OC)cc1N1CCC(N2CCN(CCC3CCN(c4cc(F)c(C5CCC(=O)NC5=O)c(F)c4)CC3)CC2)CC1]

The titled compound was synthesized in the procedures similar to Example 1. $^1H$ NMR (500 MHz, DMSO) δ 12.26 (s, 1H), 10.86 (s, 1H), 9.84 (s, 1H), 8.93 (dd, J=4.2, 1.5 Hz, 1H), 8.36-8.29 (m, 1H), 8.29 (s, 1H), 8.21 (s, 1H), 7.71 (dd, J=8.4, 4.2 Hz, 1H), 7.43 (s, 1H), 6.74 (s, 1H), 6.60 (d, J=12.8 Hz, 2H), 4.04 (dd, J=12.6, 5.1 Hz, 1H), 3.81-3.68 (m, 5H), 3.00 (d, J=11.0 Hz, 2H), 3.01-2.71 (m, 8H), 2.49-2.26 (m, 11H), 2.08 (d, J=14.6 Hz, 7H), 2.01-1.91 (m, 1H), 1.84 (d, J=10.7 Hz, 2H), 1.72 (d, J=11.3 Hz, 2H), 1.60-1.33 (m, 5H), 1.25-1.12 (m, 2H), 0.88 (t, J=5.9 Hz, 3H); $[M+H]^+$=1028.5.

Example 10: 3-(4-(2-(4-(1-(4-((5-bromo-4-((4-(dimethylphosphoryl)-8-methylquinolin-3-yl)amino)pyrimidin-2-yl)amino)-2-ethyl-5-methoxyphenyl)piperidin-4-yl)piperazin-1-yl)ethyl)-2,6-difluorophenyl) piperidine-2,6-dione Step 1: N-(8-methylquinolin-3-yl)-1,1-diphenylmethanimine

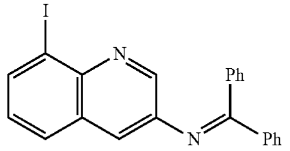 [SMILES: Ic1cccc2cc(N=C(c3ccccc3)c3ccccc3)cnc12]

To a mixture of 3-bromo-8-methylquinoline (2 g, 9.05 mmol), diphenylmethanimine (2.46 g, 13.6 mmol), $Pd_2(dba)_3$ (834 mg, 0.91 mmol), BINAP (1.14 g, 1.82 mmol), $Cs_2CO_3$ (5.9 g, 18.1 mmol) in dioxane (60 mL) was stirred at 100° C. under nitrogen atmosphere for 18 hrs. After cooling to r.t, the reaction mixture was filtered, the filtrate was concentrated in vacuo. The residue was purified by silica gel column (PE:EA=4:1) to afford the product (2.6 g, 89.7%). $[M+H]^+$=323.2.

Step 2: 8-methylquinolin-3-amine

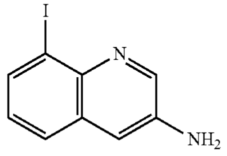 [SMILES: Nc1cnc2c(I)cccc2c1]

To a solution of N-(8-methylquinolin-3-yl)-1,1-diphenylmethanimine (2.6 g, 8.1 mmol) in dioxane (30 mL) was added HCl (6 mL, 2N). The mixture was stirred at 20° C. for 30 min and then sat. aq. $Na_2CO_3$ solution was added until PH=8-9, the resulting mixture was extracted with EtOAc (50 mL×3). The combined organic phase was washed with brine (50 mL), dried over $Na_2SO_4$, filtered and concentrated in vacuum. The residue was purified by silica gel column (PE:EA=1:1) to afford 8-methylquinolin-3-amine (1.3 g, 82%). $[M+H]^+$=159.1.

Step 3: 4-iodo-8-methylquinolin-3-amine

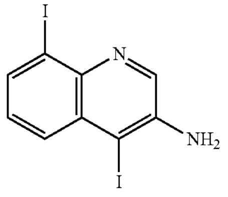 [SMILES: Nc1cnc2c(I)cccc2c1I]

To a solution of 8-methylquinolin-3-amine (1.3 g, 8.23 mmol) in HOAc (10 mL) was added ICl (1.99 g, 12.3 mmol). The mixture was stirred at 20° C. for 3 hrs and then sat. aq. $Na_2CO_3$ solution was added to PH=8-9, the resulting mixture was extracted with EtOAc (70 mL×3). The combined organic phase was washed with brine (60 mL), dried over $Na_2SO_4$, filtered and concentrated in vacuum to afford 4-iodo-8-methylquinolin-3-amine (1.8 g, 77%). $[M+H]^+$=285.2.

Step 4: (3-amino-8-methylquinolin-4-yl)dimethylphosphine oxide

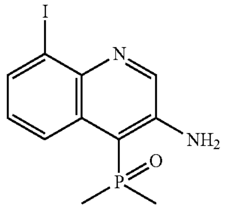 [SMILES: CP(C)(=O)c1c(N)cnc2c(I)cccc12]

To a mixture of 4-iodo-8-methylquinolin-3-amine (1.8 g, 6.32 mmol), dimethylphosphine oxide (720 mg, 9.47 mmol), $Pd(OAc)_2$ (141 mg, 0.63 mmol), Xantphos (731 mg, 1.26 mmol), $K_3PO_4$ (2.68 g, 12.64 mmol) in dioxane (40 mL) was stirred at 100° C. under nitrogen atmosphere for 8 hrs. After cooling to r.t, the reaction mixture was filtered, the filtrate was concentrated in vacuo. The residue was purified by silica gel column (DCM:$CH_3OH$=15:1) to afford (3-amino-8-methylquinolin-4-yl)dimethylphosphine oxide (1.1 g, 74%). $[M+H]^+$=235.2.

Step 5: (3-((5-bromo-2-chloropyrimidin-4-yl)amino)-8-methylquinolin-4-yl)dimethylphosphine oxide

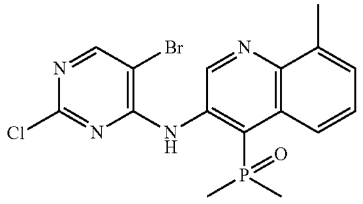 [SMILES: Cc1cccc2c(P(C)(C)=O)c(Nc3nc(Cl)ncc3Br)cnc12]

To a solution of (3-amino-8-methylquinolin-4-yl)dimethylphosphine oxide (1.1 g, 4.68 mmol) in DMF (25 mL) was added NaH (468 mg, 11.7 mmol, 60%) at 0° C. The mixture was stirred at 0° C. for 20 min, then 5-bromo-2,4-dichloropyrimidine (2.12 g, 9.36 mmol) was added, the resulting solution was stirred at rt for 2 hrs. The reaction was quenched by sat. aq. $NH_4Cl$ solution and the resulting mixture was extracted with EtOAc (40 mL×3). The combined organic phase was washed with brine (30 mL), dried over $Na_2SO_4$, filtered and concentrated in vacuum. The residue was purified by silica gel column (DCM: $CH_3OH$=15:1) to afford the product (1.05 g, 52.8%). $[M+H]^+$=425.3.

Step 6: (3-((5-bromo-2-((5-ethyl-2-methoxy-4-(4-(piperazin-1-yl)piperidin-1-yl)phenyl)amino)pyrimidin-4-yl)amino)-8-methylquinolin-4-yl)dimethylphosphine oxide

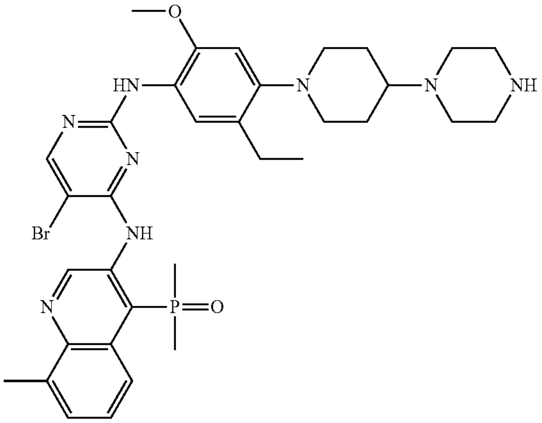 [SMILES: CCc1cc(Nc2ncc(Br)c(Nc3cnc4c(C)cccc4c3P(C)(C)=O)n2)c(OC)cc1N1CCC(N2CCNCC2)CC1]

To a mixture of (3-((5-bromo-2-chloropyrimidin-4-yl) amino)-8-methylquinolin-4-yl)dimethylphosphine oxide (400 mg, 0.94 mmol), tert-butyl 4-(1-(4-amino-2-ethyl-5-methoxyphenyl)piperidin-4-yl)piperazine-1-carboxylate (392 mg, 0.94 mmol), TsOH $H_2O$ (536 mg, 2.82 mmol) in n-BuOH (8 mL) was stirred at 100° C. for 14 hrs. After cooling to r.t, the reaction mixture was concentrated in vacuo. The residue was diluted with DCM, washed with NaOH solution (20 mL, 1N) and brine, dried over $Na_2SO_4$ and then concentrated in vacuo. The residue was purified by silica gel column (DCM:$CH_3OH$=2:1) to afford the product (350 mg, 52.7%). $[M+H]^+$=707.3.

Step 7: 3-(4-(2-(4-(1-(4-((5-bromo-4-((4-(dimethylphosphoryl)-8-methylquinolin-3-yl)amino)pyrimidin-2-yl)amino)-2-ethyl-5-methoxyphenyl)piperidin-4-yl)piperazin-1-yl)ethyl)-2,6-difluorophenyl) piperidine-2,6-dione

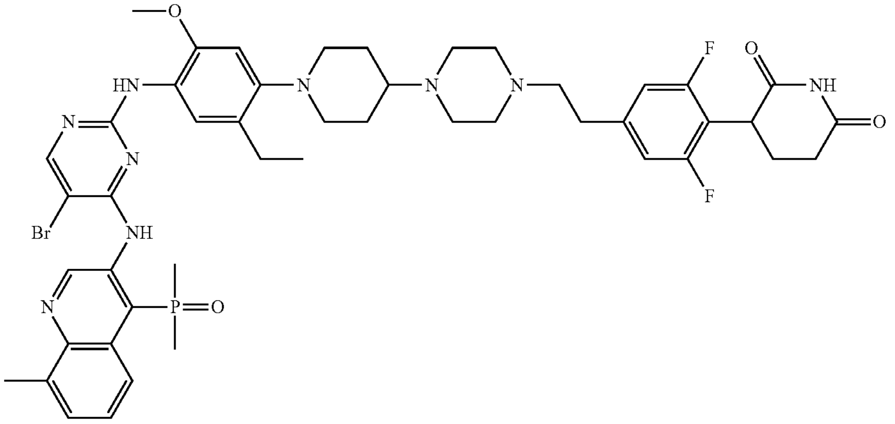 [SMILES: CCc1cc(Nc2ncc(Br)c(Nc3cnc4c(C)cccc4c3P(C)(C)=O)n2)c(OC)cc1N1CCC(N2CCN(CCc3cc(F)c(C4CCC(=O)NC4=O)c(F)c3)CC2)CC1]

The titled compound (4 mg, 12%) was prepared in a manner similar to that in Example 2 step 7 from 2-(4-(2,6-dioxopiperidin-3-yl)-3,5-difluorophenyl)acetaldehyde and (3-((5-bromo-2-((5-ethyl-2-methoxy-4-(4-(piperazin-1-yl) piperidin-1-yl)phenyl)amino)pyrimidin-4-yl)amino)-8-methylquinolin-4-yl)dimethylphosphine oxide. $^1H$ NMR (500 MHz, DMSO) δ 11.76 (s, 1H), 10.95 (s, 1H), 9.51 (s, 1H), 8.25 (s, 1H), 8.07-7.87 (m, 2H), 7.58 (d, J=7.0 Hz, 1H), 7.54-7.47 (m, 1H), 7.39 (s, 1H), 7.03 (d, J=10.0 Hz, 2H), 6.62 (d, J=84.3 Hz, 1H), 4.20 (dd, J=12.7, 5.0 Hz, 1H), 3.80 (s, 3H), 2.92 (d, J=11.0 Hz, 2H), 2.84-2.75 (m, 2H), 2.73 (s, 4H), 2.61 (dd, J=20.2, 9.0 Hz, 3H), 2.53 (d, J=5.8 Hz, 5H), 2.47-2.41 (m, 3H), 2.35 (dd, J=10.1, 4.5 Hz, 3H), 2.27 (t, J=11.1 Hz, 1H), 2.13 (dt, J=13.1, 9.3 Hz, 1H), 2.05 (s, 3H), 2.04-1.93 (m, 5H), 1.82 (d, J=11.1 Hz, 2H), 1.52 (dd, J=20.2, 11.3 Hz, 2H), 0.75 (s, 3H). $[M+H]^+$=958.4.

Example 8: 3-(4-(4-(2-(4-(1-(4-((5-bromo-4-((4-(dimethylphosphoryl)-8-methylquinolin-3-yl)amino)pyrimidin-2-yl)amino)-2-ethyl-5-methoxyphenyl)piperidin-4-yl)piperazin-1-yl)ethyl)piperidin-1-yl)-2,6-difluorophenyl)piperidine-2,6-dione

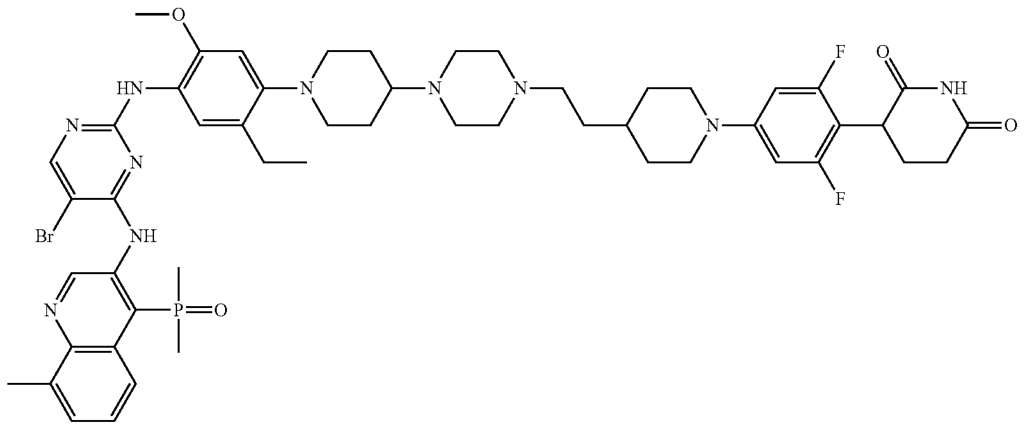 [SMILES: CCc1cc(Nc2ncc(Br)c(Nc3cnc4c(C)cccc4c3P(C)(C)=O)n2)c(OC)cc1N1CCC(N2CCN(CCC3CCN(c4cc(F)c(C5CCC(=O)NC5=O)c(F)c4)CC3)CC2)CC1]

The titled compound was synthesized in the procedures similar to Example 10. $^1$H NMR (500 MHz, DMSO) δ 11.76 (s, 1H), 10.86 (s, 1H), 9.51 (s, 1H), 8.24 (s, 1H), 8.08-7.87 (m, 2H), 7.57 (d, J=7.0 Hz, 1H), 7.56-7.48 (m, 1H), 7.39 (s, 1H), 6.70 (s, 1H), 6.60 (d, J=12.8 Hz, 2H), 4.04 (dd, J=12.5, 5.1 Hz, 1H), 3.80 (s, 3H), 3.73 (d, J=12.4 Hz, 2H), 2.91 (d, J=10.9 Hz, 2H), 2.84-2.75 (m, 1H), 2.74 (d, J=11.6 Hz, 4H), 2.69 (d, J=11.4 Hz, 2H), 2.65-2.55 (m, 3H), 2.54 (s, 2H), 2.44-2.17 (m, 9H), 2.09 (dd, J=12.6, 9.2 Hz, 1H), 2.04 (d, J=13.5 Hz, 7H), 1.96 (dd, J=14.3, 9.0 Hz, 1H), 1.81 (d, J=10.8 Hz, 2H), 1.71 (d, J=11.6 Hz, 2H), 1.51 (dd, J=21.7, 12.3 Hz, 3H), 1.42-1.32 (m, 2H), 1.24-1.06 (m, 2H), 0.74 (s, 3H). $[M+H]^+$=1041.4.

Example 12: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-1H-indazol-1-yl)piperidine-2,6-dione Step 1: 3-(4-bromo-1H-indazol-1-yl)piperidine-2,6-dione

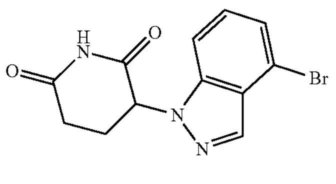 [SMILES: O=C1CCC(n2ncc3c(Br)cccc32)C(=O)N1]

To a solution of 4-bromo-1H-indazole (1.96 g, 10 mmol) in THF (40 mL) was added NaH (60%, 0.48 g, 12 mmol) at 0° C. Then the mixture was stirred at 60° C. for 1 h. To the above solution was added 3-bromopiperidine-2,6-dione (1.97 g, 10 mmol) at 60° C. The resulting mixture was stirred overnight at 60° C. under nitrogen atmosphere. The mixture was cooled to room temperature, quenched with water (20 mL) and extracted with EtOAc (100 mL). The combined organic phase was washed with brine (40 mL), dried over $Na_2SO_4$, filtered and concentrated in vacuum. The residue was purified by column chromatography (DCM:MeOH=10:1) to afford the product (1.2 g, 39%) $[M+H]^+$=308.2.

Step 2: (E)-3-(4-(2-ethoxyvinyl)-1H-indazol-1-yl)piperidine-2,6-dione

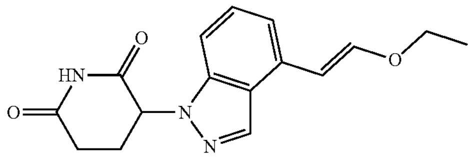 [SMILES: CCO/C=C/c1cccc2c1cnn2C1CCC(=O)NC1=O]

To a solution of 3-(4-bromo-1H-indazol-1-yl)piperidine-2,6-dione (0.616 g, 2 mmol) and (E)-2-(2-ethoxyvinyl)-4,4,5,5-tetramethyl-1,3,2-dioxaborolane (0.475 g, 2.4 mmol) in DMF (16 mL) and $H_2O$ (4 mL) was added CsF (0.608 g, 4 mmol) and Pd(dtBPF)$Cl_2$ (0.163 g, 0.2 mmol) at room temperature. Then the mixture was stirred for 3 hrs at 80° C. under nitrogen atmosphere. The mixture was cooled to room temperature, diluted with water (20 mL) and extracted with EtOAc (100 mL). The combined organic phase was washed with brine (40 mL), dried over $Na_2SO_4$, filtered and concentrated in vacuum. The residue was purified by column chromatography (DCM:MeOH=10:1) to afford the product (366 mg, 61%). $[M+H]^+$=300.3.

Step 3: 2-(1-(2,6-dioxopiperidin-3-yl)-1H-indazol-4-yl)acetaldehyde

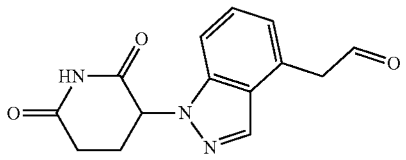 [SMILES: O=CCc1cccc2c1cnn2C1CCC(=O)NC1=O]

A solution of (E)-3-(4-(2-ethoxyvinyl)-1H-indazol-1-yl)piperidine-2,6-dione (60 mg, 0.2 mmol) in HCOOH (3 mL) was stirred for 3 hrs at room temperature. The mixture was concentrated in vacuum to afford the product (70 mg, crude) which was used in next step without further purification. $[M+H]^+$=272.

Step 4: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-1H-indazol-1-yl)piperidine-2,6-dione

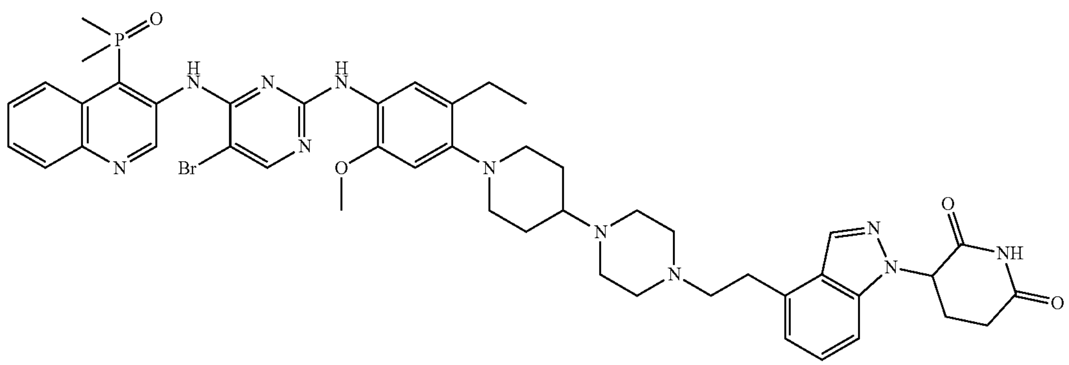 [SMILES: CCc1cc(Nc2ncc(Br)c(Nc3cnc4ccccc4c3P(C)(C)=O)n2)c(OC)cc1N1CCC(N2CCN(CCc3cccc4c3cnn4C3CCC(=O)NC3=O)CC2)CC1]

To a solution of 2-(1-(2,6-dioxopiperidin-3-yl)-1H-indazol-4-yl)acetaldehyde (70 mg crude, 0.2 mmol) in DCM (8 mL) and EtOH (4 mL) was added (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide (69.2 mg, 0.1 mmol) at room temperature. After 3 hrs, $NaBH(OAc)_3$ (42.4 mg, 0.2 mmol) was added to the mixture. The resulting mixture was stirred for 16 h at room temperature. The mixture was diluted with water (10 mL) and extracted with DCM (50 mL). The combined organic phase was washed with brine (20 mL), dried over $Na_2SO_4$, filtered and concentrated in vacuum. The residue was purified by prep. HPLC (C-18 column chromatography (0.1% FA in water:acetonitrile=90:10~60:40 gradient elution) to afford the product (5.44 mg, 5.7%) was obtained. $^1H$ NMR (500 MHz, DMSO-$d_6$) δ ppm 11.68 (s, 1H), 11.10 (s, 1H), 9.45 (s, 1H), 8.27-8.14 (m, 3H), 8.04-7.96 (m, 2H), 7.72 (t, J=5 Hz, 1H), 7.64 (t, J=5 Hz, 1H), 7.48-7.41 (m, 2H), 7.32 (t, J=5 Hz, 1H), 7.01 (d, J=5 Hz, 1H), 6.70 (s, 1H), 5.83 (dd, J=10, 5 Hz, 1H), 3.78 (s, 3H), 3.07 (t, J=5 Hz, 2H), 2.96-2.82 (m, 3H), 2.78-2.69 (m, 2H), 2.66-2.51 (m, 11H), 2.37-2.21 (m, 5H), 2.06 (s, 3H), 2.04 (s, 3H), 1.86-1.80 (m, 2H), 1.58-1.49 (m, 2H), 0.75 (t, J=10 Hz, 3H); $[M+H]^+$=948.2.

Example 14: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-2H-indazol-2-yl)piperidine-2,6-dione Step 1: 3-(4-bromo-2H-indazol-2-yl)piperidine-2,6-dione

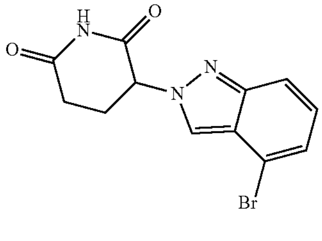 [SMILES: O=C1CCC(n2cc3c(Br)cccc3n2)C(=O)N1]

To a solution of 4-bromo-1H-indazole (1.96 g, 10 mmol) in THF (40 mL) was added NaH (60%, 0.48 g, 12 mmol) at 0° C. Then the mixture was stirred at 60° C. for 1 h. To the above solution was added 3-bromopiperidine-2,6-dione (1.97 g, 10 mmol) at 60° C.

The resulting mixture was stirred overnight at 60° C. under nitrogen atmosphere. The mixture was cooled to room temperature, quenched with water (20 mL) and extracted with EtOAc (100 mL). The combined organic phase was washed with brine (40 mL), dried over $Na_2SO_4$, filtered and concentrated in vacuum. The residue was purified by column chromatography (DCM:MeOH=10:1) to afford the product (0.98 g, 32%). $[M+H]^+$=308.2.

Step 2: (E)-3-(4-(2-ethoxyvinyl)-2H-indazol-2-yl)piperidine-2,6-dione

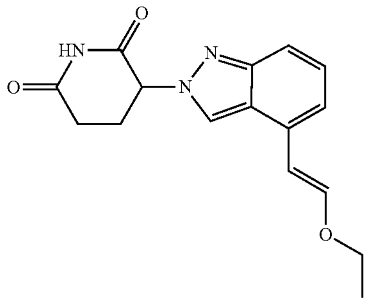 [SMILES: CCO/C=C/c1cccc2nn(C3CCC(=O)NC3=O)cc12]

To a solution of 3-(4-bromo-2H-indazol-2-yl)piperidine-2,6-dione (0.616 g, 2 mmol) and (E)-2-(2-ethoxyvinyl)-4,4,5,5-tetramethyl-1,3,2-dioxaborolane (0.475 g, 2.4 mmol) in DMF (16 mL) and $H_2O$ (4 mL) was added CsF (0.608 g, 4 mmol) and $Pd(dtBPF)Cl_2$ (0.163 g, 0.2 mmol) at room temperature. Then the mixture was stirred for 3 hrs at 80° C. under $N_2$. The mixture was cooled to room temperature, diluted with water (20 mL) and extraction with EtOAc (100 mL). The combined organic phase was washed with brine (40 mL), dried over $Na_2SO_4$, filtered and concentrated in vacuum. The residue was purified by column chromatography (DCM:MeOH=10:1) to afford the product (0.3 g, 50%). $[M+H]^+$=300.2.

Step 3: 2-(2-(2,6-dioxopiperidin-3-yl)-2H-indazol-4-yl)acetaldehyde

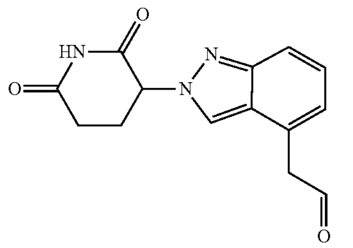 [SMILES: O=CCc1cccc2nn(C3CCC(=O)NC3=O)cc12]

A solution of (E)-3-(4-(2-ethoxyvinyl)-2H-indazol-2-yl) piperidine-2,6-dione (60 mg, 0.2 mmol) in HCOOH (3 mL) was stirred for 3 hrs at room temperature. The mixture was concentrated in vacuum to afford the product (68 mg, crude) which was used in next step without further purification. $[M+H]^+$=272.3.

Step 4: 3-(4-(2-(4-(1-(4-((5-bromo-4-((4-(dimethylphosphoryl)quinolin-3-yl)amino)pyrimidin-2-yl) amino)-2-ethyl-5-methoxyphenyl) piperidin-4-yl) piperazin-1-yl)ethyl)-2H-indazol-2-yl)piperidine-2,6-dione

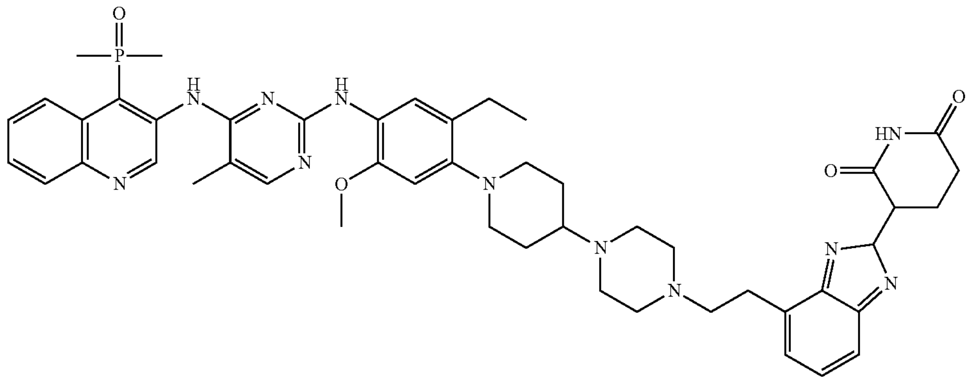 [SMILES: CCc1cc(Nc2ncc(C)c(Nc3cnc4ccccc4c3P(C)(C)=O)n2)c(OC)cc1N1CCC(N2CCN(CCc3cccc4c3=NC(C3CCC(=O)NC3=O)N=4)CC2)CC1]

To a solution of 2-(2-(2,6-dioxopiperidin-3-yl)-2H-indazol-4-yl)acetaldehyde (68 mg, 0.2 mmol) in DCM (8 mL) and EtOH (4 mL) was added (3-((5-bromo-2-((5-ethyl-2-methoxy-4-(4-(piperazin-1-yl)piperidin-1-yl)phenyl)amino) pyrimidin-4-yl)amino)quinolin-4-yl)dimethylphosphine oxide (69.2 mg, 0.1 mmol) at room temperature. After 3 hrs, $NaBH(OAc)_3$ (42.4 mg, 0.2 mmol) was added to the mixture. The resulting mixture was stirred for 16 hrs at room temperature. The mixture was diluted with water (10 mL) and extracted with DCM (50 mL). The combined organic phase was washed with brine (20 mL), dried over $Na_2SO_4$, filtered and concentrated in vacuum. The residue was purified by prep. HPLC (C-18 column chromatography (0.1% FA in water:acetonitrile=90:10~60:40 gradient elution)) to afford the product (8.26 mg, 8.7%). $^1$H NMR (500 MHz, DMSO-$d_6$) δ ppm 11.68 (s, 1H), 11.18 (s, 1H), 9.45 (s, 1H), 8.57 (s, 1H), 8.25 (s, 1H), 8.17 (s, 1H), 8.04-7.95 (m, 2H), 7.72 (t, J=5 Hz, 1H), 7.64 (t, J=5 Hz, 1H), 7.44-7.38 (m, 2H), 7.18-7.14 (m, 1H), 6.88 (d, J=10 Hz, 1H), 6.70 (s, 1H), 5.68 (dd, J=10, 5 Hz, 1H), 3.78 (s, 3H), 3.02-2.70 (m, 8H), 2.69-2.51 (m, 10H), 2.39-2.25 (m, 5H), 2.06 (s, 3H), 2.04 (s, 3H), 1.86-1.80 (m, 2H), 1.58-1.49 (m, 2H), 0.75 (t, J=10 Hz, 3H); $[M+H]^+$=948.3.

Example 15: 3-(5-(4-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazine-1-carbonyl)piperidin-1-yl)-3-methyl-2-oxo-2,3-dihydro-1H-benzo[d]imidazol-1-yl) piperidine-2,6-dione Step 1: 6-bromo-1-methyl-3H-1,3-benzodiazol-2-one

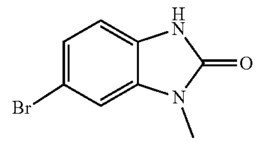

Into a 1000-mL round-bottom flask, were placed 5-bromo-N1-methylbenzene-1,2-diamine (10.0 g, 50.0 mmol), $CH_3CN$ (200 mL), 1,1'-Carbonyldiimidazole (9.4 g, 58.0 mmol). The resulting solution was stirred for 5 h at 70° C. The filtrate was concentrated after filtration. This resulted in 10.0 g (88.6%) of 6-bromo-1-methyl-3H-1,3-benzodiazol-2-one. $^1$H NMR (500 MHz, DMSO-d6) δ ppm 10.98 (s, 1H), 7.31 (t, J=1.5 Hz, 1H), 7.11 (ddd, J=8.2 Hz, 1H), 6.91 (d, J=8.2 Hz, 1H), 3.27 (s, 3H). $[M+H]^+$=227.2.

Step 2: 3-(5-bromo-3-methyl-2-oxo-2,3-dihydro-1H-benzo[d]imidazol-1-yl)-1-(4-methoxybenzyl)piperidine-2,6-dione

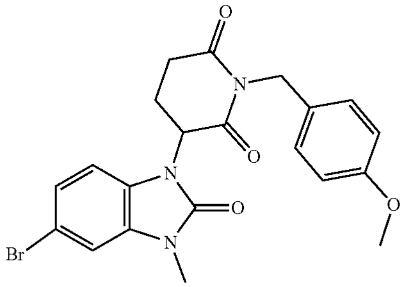 [SMILES: COc1ccc(CN2C(=O)CCC(n3c(=O)n(C)c4cc(Br)ccc43)C2=O)cc1]

Into a 500-mL round-bottom flask purged and maintained with an inert atmosphere of nitrogen, were placed 6-bromo-1-methyl-3H-1,3-benzodiazol-2-one (10.0 g, 44.0 mmol), THF (100 mL), t-BuOK (4.9 g, 44.0 mmol), the resulting solution was stirred for 0.5 h at 0° C. and then was added 3-bromo-1-((4-methoxyphenyl)methyl)piperidine-2,6-dione (13.7 g, 44.0 mmol). The resulting solution was allowed to react, with stirring, for an additional 3 days at rt. The resulting solution was diluted with (200 mL) of EtOAc. The resulting mixture was washed with (3×200 ml) of $H_2O$. The organic phase was dried over anhydrous sodium sulfate and concentrated. The residue was purified by combi-flash (EtOAc/PE=0-50%) to give the product (2.2 g, 11% yield). $^1H$ NMR (500 MHz, DMSO-d6) δ ppm 7.48 (d, J=1.9 Hz, 1H), 7.27-7.14 (m, 3H), 7.02 (d, J=8.4 Hz, 1H), 6.97-6.81 (m, 2H), 4.89-4.71 (m, 2H), 3.74 (s, 3H), 3.36 (s, 3H), 3.15-2.97 (m, 1H), 2.89-2.78 (m, 1H), 2.72 (td, J=13.1 Hz, 1H), 2.13-1.97 (m, 1H). $[M+H]^+$=458.1.

Step 3: tert-butyl 1-(1-(1-(4-methoxybenzyl)-2,6-dioxopiperidin-3-yl)-3-methyl-2-oxo-2,3-dihydro-1H-benzo[d]imidazol-5-yl)piperidine-4-carboxylate

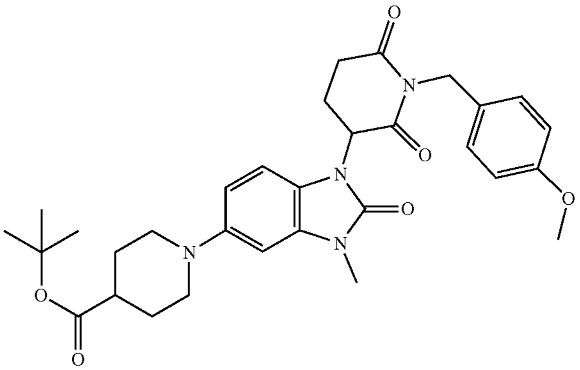 [SMILES: COc1ccc(CN2C(=O)CCC(n3c(=O)n(C)c4cc(N5CCC(C(=O)OC(C)(C)C)CC5)ccc43)C2=O)cc1]

Into a 50-mL vial purged and maintained with an inert atmosphere of nitrogen, were placed 3-(5-bromo-3-methyl-2-oxo-2,3-dihydro-1H-benzo[d]imidazol-1-yl)-1-(4-methoxybenzyl)piperidine-2,6-dione (800.0 mg, 1.7 mmol), dioxane (20 mL), tert-butyl piperidine-4-carboxylate (485.1 mg, 2.6 mmol), $Cs_2CO_3$ (1.1 g, 3.5 mmol), Ruphos-G3 (225.2 mg, 0.3 mmol). The resulting solution was stirred for 15 h at 100° C. The resulting solution was diluted with EtOAc (50 mL). The resulting mixture was washed with water (3×50 mL). The organic phase was dried over anhydrous sodium sulfate and concentrated. The residue was purified by combi-flash (EtOAc/PE=0-25%) to give the product (400 mg, 41% yield). $[M+H]^+$=563.2.

Step 4: 1-(1-(2,6-dioxopiperidin-3-yl)-3-methyl-2-oxo-2,3-dihydro-1H-benzo[d]imidazol-5-yl)piperidine-4-carboxylic acid

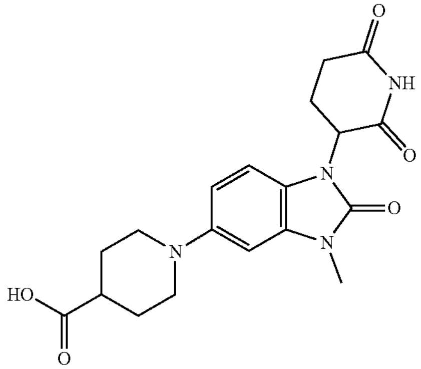 [SMILES: Cn1c(=O)n(C2CCC(=O)NC2=O)c2ccc(N3CCC(C(=O)O)CC3)cc21]

Into a 10-mL vial purged and maintained with an inert atmosphere of nitrogen, were placed tert-butyl 1-(1-(1-(4-methoxybenzyl)-2,6-dioxopiperidin-3-yl)-3-methyl-2-oxo-2,3-dihydro-1H-benzo[d]imidazol-5-yl)piperidine-4-carboxylate (300.0 mg, 0.53 mmol), Toluene (2 mL), $CH_3SO_3H$ (1 mL). The resulting solution was stirred for 2 h at 100° C. The resulting solution was diluted with EtOAc (10 mL). The solids were collected by filtration. The solids were washed with EtOAc (3×20 mL). The solids were dried in vacuum. The product 1-(1-(2,6-dioxopiperidin-3-yl)-3-methyl-2-oxo-2,3-dihydro-1H-benzo[d]imidazol-5-yl)piperidine-4-carboxylic acid (190 mg, 92.22%) was obtained. $[M+H]^+$=387.2.

Step 5: 3-(5-(4-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazine-1-carbonyl)piperidin-1-yl)-3-methyl-2-oxo-2,3-dihydro-1H-benzo[d]imidazol-1-yl)piperidine-2,6-dione

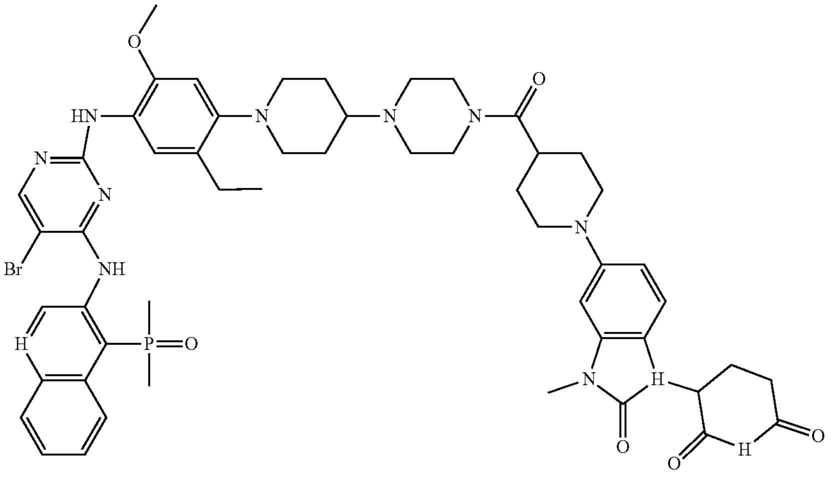

A mixture of (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide (29 mg, 0.075 mmol), HATU (24.2 mg, 0.063 mmol) and DIEA (22.4 mg, 0.17 mmol) in DMF (4 mL) was stirred at rt for 10 min. Then, 1-(1-(2,6-dioxopiperidin-3-yl)-3-methyl-2-oxo-2,3-dihydro-1H-benzo[d]imidazol-5-yl)piperidine-4-carboxylic acid (40 mg, 0.058 mmol) was added to the mixture above. The resulting mixture was stirred at rt for 16 h. The mixture was diluted with water (50 mL), extracted with EA (3×50 mL). The combined organic layers were dried over $Na_2SO_4$, filtered and concentrated under vacuum. The residue was purified by Prep-HPLC with the following conditions: Anal Column: SunFire Prep C18 OBD, 5 μm, 19×150 mm, Column Temp: Room temperature, Mobile Phase A: $H_2O$ (0.1% FA), Mobile Phase B: ACN, Gradient Table: Mobile Phase B (15-28%), Time (min): 0-17 min to afford the product (11.33 mg, 18.5%). $[M+H]^+$=1061.4. $^1$H NMR (500 MHz, DMSO) δH 11.68 (s, 1H), 11.06 (s, 1H), 9.44 (s, 1H), 8.25 (s, 1H), 8.19 (d, J=10.0 Hz, 1H), 8.02-7.97 (m, 2H), 7.75-7.70 (m, 1H), 7.67-7.62 (m, 1H), 7.41 (s, 1H), 6.94 (d, J=5.0 Hz, 1H), 6.84 (s, 1H), 6.70 (s, 1H), 6.66-6.20 (m, 1H), 5.32-5.26 (m, 1H), 3.78 (s, 3H), 3.65-3.59 (m, 2H), 3.57-3.51 (m, 2H), 3.50-3.44 (m, 2H), 2.97-2.86 (m, 3H), 2.78-2.58 (m, 10H), 2.57-2.53 (m, 3H), 2.39-2.30 (m, 4H), 2.06 (s, 3H), 2.04 (s, 3H), 2.01-1.96 (m, 1H), 1.86-1.80 (m, 2H), 1.75-1.69 (m, 4H), 1.60-1.51 (m, 2H), 0.80-0.71 (m, 3H).

Example 16

3-(5-(3-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazine-1-carbonyl)azetidin-1-yl)-1-oxoisoindolin-2-yl)piperidine-2,6-dione Step 1: 1-(3-cyano-4-(methoxycarbonyl)phenyl)azetidine-3-carboxylic acid

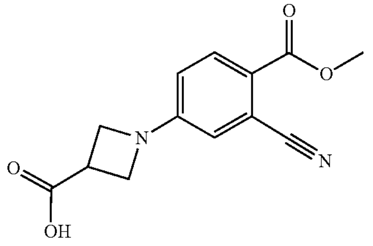 [SMILES: COC(=O)c1ccc(N2CC(C(=O)O)C2)cc1C#N]

To a solution of methyl 2-cyano-4-fluorobenzoate (5.00 g, 27.9 mmol) and azetidine-3-carboxylic acid (4.99 g, 36.3 mmol) in DMSO (35.0 mL). The DIPEA (9.02 g, 69.8 mmol) was added to the reaction mixture. The reaction mixture was warmed to 100° C. for 0.5 hr and then stirred at 100° C. for another 3 hrs. The reaction mixture was diluted with ACN (35.0 mL) and stirred for 15 min, then filtered to get filtrate and adjusted the filtrate pH=8 by sat.aq.$NaHCO_3$ solution (40.0 mL). The mixture was extracted with EtOAc (50.0 mL). Water phase was adjusted pH=3 by 6N HCl (50.0 mL), extracted with EtOAc (50.0 mL×2). The combine organic phase was washed with brine (50.0 mL), dried over anhydrous $Na_2SO_4$, filtered and concentrated in vacuum to obtain product (6.00 g, crude). $[M-H]^-$=259.1.

Step 2: 1-(3-formyl-4-(methoxycarbonyl)phenyl) azetidine-3-carboxylic acid

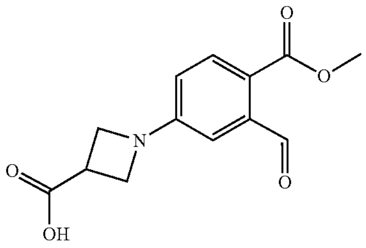 [SMILES: COC(=O)c1ccc(N2CC(C(=O)O)C2)cc1C=O]

To a solution of Raney-Ni (2.00 g, 11.7 mmol) in HCOOH (20.0 mL) at 25° C., 1-(3-cyano-4-(methoxycarbonyl)phenyl)azetidine-3-carboxylic acid in HCOOH (20.0 mL) was added to the reaction mixture at 25° C. Then the mixture was stirred at 25° C. for 15 min. The reaction mixture was diluted with solvent $H_2O$ (20.0 mL) and extracted with EtOAc (40.0 mL×2). The combined organic phase was washed with brine (40.0 mL), dried over anhydrous $Na_2SO_4$, filtered and concentrated in vacuum to obtain product (5.50 g, crude). $[M-H]^-$=262.1.

Step 3: 1-(2-(2,6-dioxopiperidin-3-yl)-1-oxoisoindolin-5-yl)azetidine-3-carboxylic acid

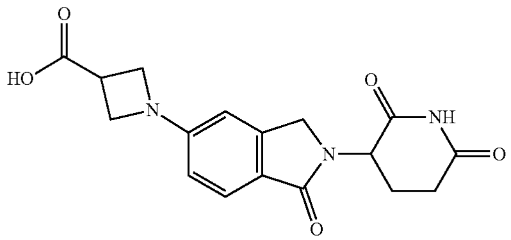 [SMILES: O=C1CCC(N2Cc3cc(N4CC(C(=O)O)C4)ccc3C2=O)C(=O)N1]

To a solution of 1-(3-formyl-4-(methoxycarbonyl)phenyl) azetidine-3-carboxylic acid (5.50 g, 20.9 mmol) and 3-aminopiperidine-2,6-dione hydrochloride (3.44 g, 20.9 mmol) in DMF (35.0 mL) was added DIPEA (8.10 g, 62.7 mmol) at 25° C. The mixture was stirred at 25° C. for 1 hr. Then $CH_3COOH$ (4.39 g, 73.1 mmol) and $NaBH_3CN$ (2.63 g, 41.8 mmol) was added to the reaction mixture at 25° C. The mixture was stirred at 25° C. for 1 hr. The mixture was adjust pH=8 by DIPEA. The mixture was stirred at 25° C. for 1 hr. The mixture was concentrated under reduced pressure to give a residue and purified by prep-HPLC (Phase A: water (0.225% FA), Phase B: ACN; B %: 3%-35%, 20 min) to obtain the product (1.70 g, 4.95 mmol, 23.7% yield). [M+H]+=344.1.

Step 4: 3-(5-(3-(4-(1-(4-((5-bromo-4-((4-(dimethylphosphoryl)quinolin-3-yl)amino)pyrimidin-2-yl) amino)-2-ethyl-5-methoxyphenyl) piperidin-4-yl) piperazine-1-carbonyl)azetidin-1-yl)-1-oxoisoindolin-2-yl)piperidine-2,6-dione

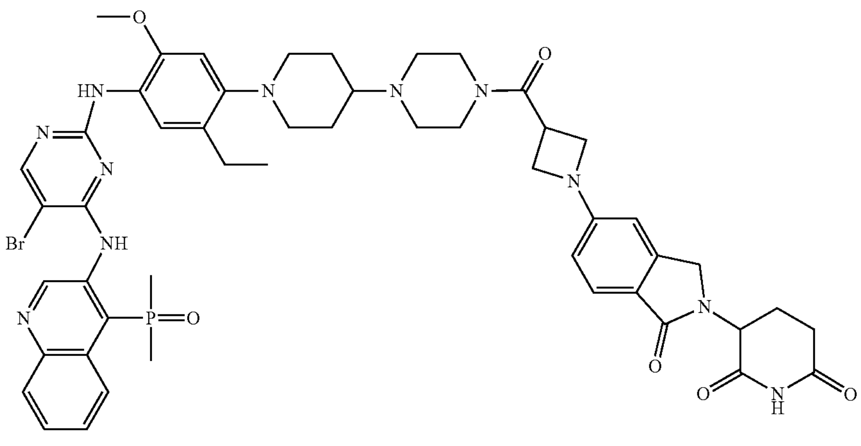 [SMILES: CCc1cc(Nc2ncc(Br)c(Nc3cnc4ccccc4c3P(C)(C)=O)n2)c(OC)cc1N1CCC(N2CCN(C(=O)C3CN(c4ccc5c(c4)CN(C4CCC(=O)NC4=O)C5=O)C3)CC2)CC1]

The titled compound (12 mg, 21%) was prepared in a manner similar to that in Example 15 step 5 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and 1-(2-(2,6-dioxopiperidin-3-yl)-1-oxoisoindolin-5-yl)azetidine-3-carboxylic acid. 1H NMR (400 MHz, DMSO) δ 11.68 (s, 1H), 10.93 (s, 1H), 9.44 (s, 1H), 8.25 (s, 1H), 8.19 (d, J=8.8 Hz, 1H), 8.02-7.97 (m, 2H), 7.72 (t, J=7.4 Hz, 1H), 7.65 (d, J=7.5 Hz, 1H), 7.50 (d, J=8.4 Hz, 1H), 7.41 (s, 1H), 6.70 (s, 1H), 6.57 (s, 1H), 6.52 (d, J=8.3 Hz, 1H), 5.04 (dd, J=13.3, 5.0 Hz, 1H), 4.31 (d, J=17.1 Hz, 1H), 4.19 (d, J=17.1 Hz, 1H), 4.13 (t, J=8.1 Hz, 2H), 4.00 (t, J=6.3 Hz, 2H), 3.89-3.83 (m, 1H), 3.78 (s, 3H), 3.50 (s, 2H), 3.36-3.32 (m, 2H), 3.29 (s, 1H), 2.97-2.93 (m, 2H), 2.89-2.85 (m, 1H), 2.65-2.59 (m, 4H), 2.57-2.51 (m, 3H), 2.38-2.34 (m, 3H), 2.05 (d, J=13.5 Hz, 6H), 1.98-1.93 (m, 1H), 1.82 (d, J=10.4 Hz, 2H), 1.56 (d, J=9.1 Hz, 2H), 0.75 (s, 3H); $[M+H]^+$=1018.6.

Example 17: 3-(5-(4-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazine-1-carbonyl)piperidin-1-yl)-3,3-dimethyl-2-oxoindolin-1-yl)piperidine-2,6-dione Step 1: N-(2,6-bis(benzyloxy)pyridin-3-yl)-1,1-diphenylmethanimine

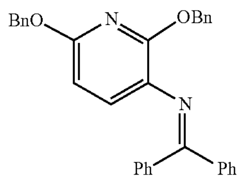 [SMILES: c1ccc(COc2ccc(N=C(c3ccccc3)c3ccccc3)c(OCc3ccccc3)n2)cc1]

To a stirred solution of 2,6-bis(benzyloxy)-3-bromopyridine (30.0 g, 81.0 mmol) and diphenylmethanimine (17.6 g, 97.2 mmol) in dry 1,4-dioxane (400 mL), was added $Cs_2CO_3$ (52.8 g, 162 mmol) at room temperature. BINAP (5.0 g, 8.1 mmol) and $Pd_2(dba)_3$ (7.4 g, 8.1 mmol) were added to the mixture at room temperature. The suspension was degassed under vacuum and purged with $N_2$ three times. Then the mixture was stirred at 100° C. overnight. After cooling to room temperature, the mixture was filtered through a pad of celite, the filtrate was collected and concentrated to afford the residue which was purified by column chromatography (0-5% EA in PE). N-(2,6-bis(benzyloxy)pyridin-3-yl)-1,1-diphenylmethanimine (25.0 g, 65.6%) was obtained. $[M+H]^+$=471.2.

Step 2: 2,6-bis(benzyloxy)pyridin-3-aminium chloride

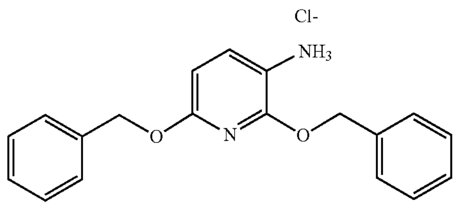 [SMILES: [Cl-] ; Nc1ccc(OCc2ccccc2)nc1OCc1ccccc1]

To a stirred solution of N-(2,6-bis(benzyloxy)pyridin-3-yl)-1,1-diphenylmethanimine (25.0 g, 53.1 mmol) in THF (200 mL), was added 1N HCl (200 mL) at room temperature. The suspension was stirred at room temperature for 16 h, following by rotary evaporation in vacuum to remove the organic solvent. The solid precipitated out during evaporation was collected by filtration, then triturated with PE/EA (200 mL, 10/1) twice, and dried under vacuum to afford product (14.0 g, 76.9%). $[M+H]^+$=307.2.

Step 3: N-(2,6-bis(benzyloxy)pyridin-3-yl)-2-(2,5-dibromophenyl)-2-methylpropanamide

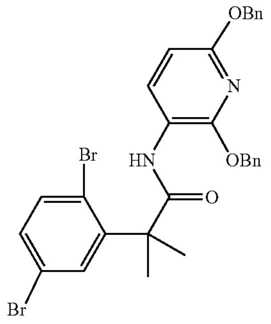 [SMILES: CC(C)(C(=O)Nc1ccc(OCc2ccccc2)nc1OCc1ccccc1)c1cc(Br)ccc1Br]

Into a stirred mixture of 2,6-bis(benzyloxy)pyridin-3-aminium chloride (14.0 g, 40.8 mmol) and 2-(2,5-dibromophenyl)-2-methylpropanoic acid (13.1 g, 40.8 mmol) in dry MeCN (200 mL) under $N_2$ atmosphere, was added 1-methyl-1H-imidazole (16.8 g, 204 mmol) via a syringe. The mixture was stirred at room temperature for 10 minutes, then a solution of N,N,N',N'-Tetramethylchloroformamidinium Hexafluorophosphate (13.8 g, 49.1 mmol) in dry MeCN (50 mL) was added into the mixture via a syringe. The mixture was stirred at 50° C. under $N_2$ atmosphere for 4 hrs. After cooling to room temperature, the reaction was quenched by addition of water (2 mL), then the mixture was concentrated in vacuum by an evaporator to afford the residue which was purified by column chromatography (5% EA in PE) to afford product (15.0 g, 60.2%). $[M+H]^+$=611.2.

Step 4: 1-(2,6-bis(benzyloxy)pyridin-3-yl)-5-bromo-3,3-dimethylindolin-2-one

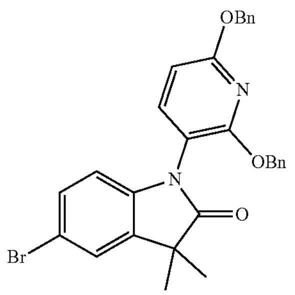 [SMILES: CC1(C)C(=O)N(c2ccc(OCc3ccccc3)nc2OCc2ccccc2)c2ccc(Br)cc21]

To a stirred mixture of N-(2,6-bis(benzyloxy)pyridin-3-yl)-2-(2,5-dibromophenyl)-2-methylpropanamide (10.0 g, 16.4 mmol) and $K_2CO_3$ (11.3 g, 81.9 mmol) in NMP (150 mL), was added CuCl (1.62 g, 16.4 mmol). The suspension was degassed under vacuum and purged with $N_2$ three times.

Pentane-2,4-dione (3.28 g, 32.8 mmol) was added into the mixture via syringe. The suspension was stirred at 85° C. under $N_2$ atmosphere for 2 hrs. After cooling to room temperature, the mixture was poured into EA (500 mL), and washed with brine (200 mL). The organic layer was then dried over anhydrous $Na_2SO_4$ and concentrated in vacuum. The residue was purified by column chromatography (7% EA in PE) to afford product (6.0 g, 69.2%). $[M+H]^+$=529.2.

Step 5: tert-butyl 1-(1-(2,6-bis(benzyloxy)pyridin-3-yl)-3,3-dimethyl-2-oxoindolin-5-yl)piperidine-4-carboxylate

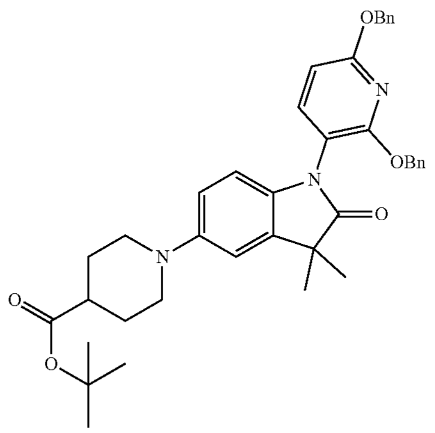 [SMILES: CC(C)(C)OC(=O)C1CCN(c2ccc3c(c2)C(C)(C)C(=O)N3c2ccc(OCc3ccccc3)nc2OCc2ccccc2)CC1]

A mixture of 1-(2,6-bis(benzyloxy)pyridin-3-yl)-5-bromo-3,3-dimethylindolin-2-one (1.0 g, 1.889 mmol) and tert-butyl piperidine-4-carboxylate (419.9 mg, 2.267 mmol), $Cs_2CO_3$ (923.1 g, 2.833 mmol), XPhos (180.1 mg, 0.378 mmol), $Pd_2(dba)_3$ (173.0 mg, 0.189 mmol) in dioxane (20 mL) was stirred overnight at 110° C. under nitrogen atmosphere. The resulting mixture was filtered, the filter cake was washed with EtOAc (150 mL). The filtrate was concentrated under reduced pressure. The residue was purified by Prep-TLC (PE/EtOAc 1:1) to afford product (620.0 mg, 51.7%). $[M+H]^+$=634.1.

Step 6: tert-butyl 1-(1-(2,6-dioxopiperidin-3-yl)-3,3-dimethyl-2-oxoindolin-5-yl)piperidine-4-carboxylate

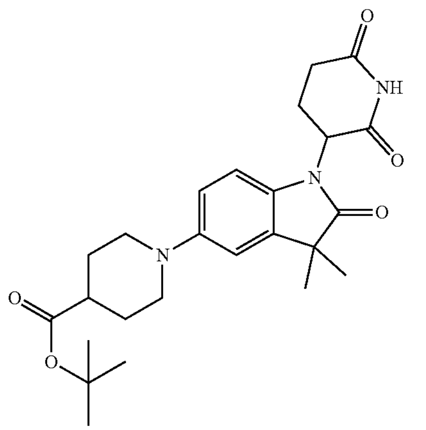 [SMILES: CC(C)(C)OC(=O)C1CCN(c2ccc3c(c2)C(C)(C)C(=O)N3C2CCC(=O)NC2=O)CC1]

To a stirred mixture of tert-butyl 1-(1-(2,6-bis(benzyloxy)pyridin-3-yl)-3,3-dimethyl-2-oxoindolin-5-yl)piperidine-4-carboxylate (620.0 mg, 0.978 mmol) and Pd/C (300.0 mg, 10% wt) in EtOH (10 mL) was added AcOH (50 mL, 872 mmol) dropwise and stirred overnight at 50° C. under hydrogen atmosphere. The resulting mixture was filtered, the filter cake was washed with MeOH (150 mL). The filtrate was concentrated under reduced pressure to afford the product (300.0 mg, 67.3%). $[M+H]^+$=456.2.

Step 7: 1-(1-(2,6-dioxopiperidin-3-yl)-3,3-dimethyl-2-oxoindolin-5-yl)piperidine-4-carboxylic acid

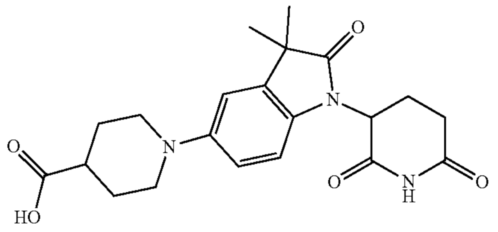 [SMILES: CC1(C)C(=O)N(C2CCC(=O)NC2=O)c2ccc(N3CCC(C(=O)O)CC3)cc21]

A mixture of tert-butyl 1-(1-(2,6-dioxopiperidin-3-yl)-3,3-dimethyl-2-oxoindolin-5-yl)piperidine-4-carboxylate (300.0 mg, 0.659 mmol) in TFA (1.5 mL) and DCM (3 mL) was stirred for 4 h at room temperature. The resulting mixture was concentrated under reduced pressure. The residue was purified by trituration with EtOAc (10 mL). 1-(1-(2,6-dioxopiperidin-3-yl)-3,3-dimethyl-2-oxoindolin-5-yl)piperidine-4-carboxylic acid (158.8 mg, 60.3%) was obtained. $[M+H]^+$=400.2.

Step 8: 3-(5-(4-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazine-1-carbonyl)piperidin-1-yl)-3,3-dimethyl-2-oxoindolin-1-yl)piperidine-2,6-dione

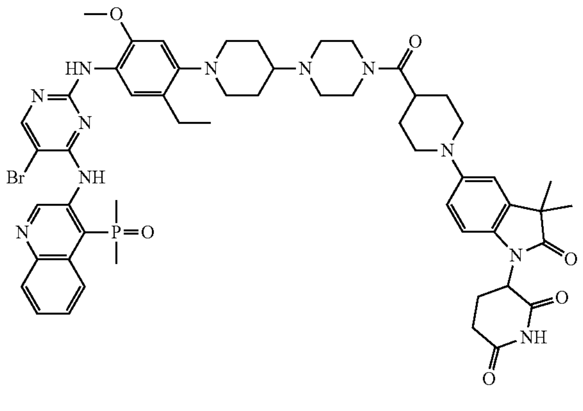 [SMILES: CCc1cc(Nc2ncc(Br)c(Nc3cnc4ccccc4c3P(C)(C)=O)n2)c(OC)cc1N1CCC(N2CCN(C(=O)C3CCN(c4ccc5c(c4)C(C)(C)C(=O)N5C4CCC(=O)NC4=O)CC3)CC2)CC1]

The titled compound (11 mg, 19%) was prepared in a manner similar to that in Example 15 step 5 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and 1-(1-(2,6-dioxopiperidin-3-yl)-3,3-dimethyl-2-oxoindolin-5-yl)piperidine-4-carboxylic acid. 1H NMR (400 MHz, DMSO) δ 11.67 (s, 1H), 11.04 (s, 1H), 9.44 (s, 1H), 8.26-8.21 (m, 2H), 8.00 (d, J=8.2 Hz, 2H), 7.71 (s, 1H), 7.63 (s, 1H), 7.42 (s, 1H), 7.10 (s, 1H), 6.77 (t, J=9.4 Hz, 2H), 6.70 (s, 1H), 5.15 (s, 1H), 3.77 (s, 3H), 3.58 (d, J=11.5 Hz, 2H), 3.53-3.46 (m, 4H), 2.94 (d, J=10.2 Hz, 2H), 2.88-2.83 (m, 1H), 2.74-2.65 (m, 3H), 2.63-2.55 (m, 7H), 2.35 (d, J=12.8 Hz, 3H), 2.04 (d, J=13.4 Hz, 6H), 1.92 (s, 1H), 1.82 (d, J=11.0 Hz, 2H), 1.73-1.68 (m, 4H), 1.55 (d, J=9.8 Hz, 2H), 1.28 (d, J=2.9 Hz, 7H), 0.74 (s, 3H); $[M+H]^+$=1074.4.

Example 18: 3-(4-(((1r,3r)-3-(4-(1-(4-((5-bromo-4-((4-(dimethylphosphoryl)quinolin-3-yl)amino)pyrimidin-2-yl)amino)-2-eth yl-5-methoxyphenyl)piperidin-4-yl)piperazine-1-carbonyl)cyclobutyl)(methyl)amino)-2,6-difluorophenyl)piperidine-2,6-dione Step 1: methyl (1r,3r)-3-((tert-butoxycarbonyl)amino)cyclobutane-1-carboxylate

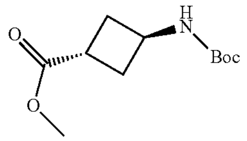 [SMILES: COC(=O)[C@H]1C[C@H](NC(=O)OC(C)(C)C)C1]

To a solution of methyl (1r,3r)-3-aminocyclobutane-1-carboxylate hydrochloride (1.5 g, 9.09 mmol) in dioxane (30 mL) and water (15 mL) was added $Na_2CO_3$ (2.89 g, 27.3 mmol) and $Boc_2O$ (2.97 g, 13.6 mmol). The mixture was stirred at 20° C. for 13 hrs, the resulting mixture was extracted with EtOAc (70 mL×3). The combined organic phase was washed with brine (60 mL), dried over $Na_2SO_4$, filtered and concentrated in vacuum. The residue was purified by silica gel column (PE:EA=1:1). Methyl (1r,3r)-3-((tert-butoxycarbonyl)amino)cyclobutane-1-carboxylate (1.7 g, 81.7%) was obtained. $[M+H]^+$=230.1.

Step 2: methyl (1r,3r)-3-((tert-butoxycarbonyl)(methyl)amino)cyclobutane-1-carboxylate

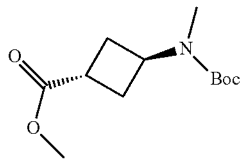 [SMILES: COC(=O)[C@H]1C[C@H](N(C)C(=O)OC(C)(C)C)C1]

To a solution of methyl (1r,3r)-3-((tert-butoxycarbonyl)amino)cyclobutane-1-carboxylate (1.5 g, 6.52 mmol) in DMF (20 mL) was added NaH (522 mg, 13.04 mmol, 60%) at 0° C. The mixture was stirred at 20° C. for 1 hr, then MeI (1.39 g, 9.78 mmol) was added, the reaction was stirred at r.t for 3 hrs and then quenched by sat. $NH_4Cl$ solution (20 mL). The resulting mixture was extracted with EtOAc (40 mL×3). The combined organic phase was washed with brine (30 mL), dried over $Na_2SO_4$, filtered and concentrated in vacuum. The residue was purified by silica gel column (PE:EA=1:1). Methyl (1r,3r)-3-((tert-butoxycarbonyl)(methyl)amino)cyclobutane-1-carboxylate (1.4 g, 88%) was obtained. $[M+H]^+$=244.2.

Step 3: methyl (1r,3r)-3-(methylamino)cyclobutane-1-carboxylate hydrochloride

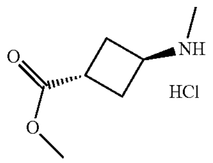

To a mixture of methyl (1r,3r)-3-((tert-butoxycarbonyl)(methyl)amino)cyclobutane-1-carboxylate (1.4 g, 5.76 mmol) and HCl in dioxane (20 mL, 6N) was stirred at 25° C. for 5 hr, then the resulting mixture was concentrated in vacuum. Methyl (1r,3r)-3-(methylamino)cyclobutane-1-carboxylate hydrochloride (700 mg, 84.4%) was obtained. $[M+H]^+$=144.2.

Step 4: methyl (1r,3r)-3-((4-(2,6-bis(benzyloxy)pyridin-3-yl)-3,5-difluorophenyl)(methyl)amino)cyclobutane-1-carboxylate

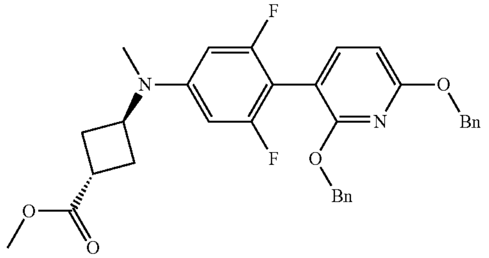 [SMILES: COC(=O)[C@H]1C[C@H](N(C)c2cc(F)c(-c3ccc(OCc4ccccc4)nc3OCc3ccccc3)c(F)c2)C1]

The titled compound (960 mg g, 52%) was prepared in a manner similar to that in Example 23 step 1 from methyl (1r,3r)-3-(methylamino)cyclobutane-1-carboxylate hydrochloride and 2,6-bis(benzyloxy)-3-(4-bromo-2,6-difluorophenyl)pyridine. $[M+H]^+$=545.2.

Step 5: (1r,3r)-3-((4-(2,6-bis(benzyloxy)pyridin-3-yl)-3,5-difluorophenyl)(methyl)amino)cyclobutane-1-carboxylic acid

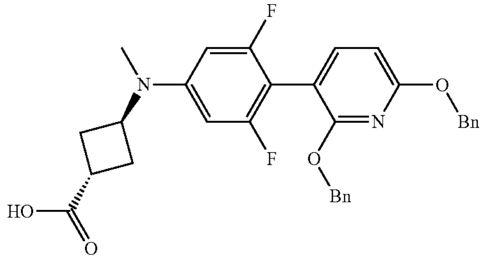 [SMILES: CN(c1cc(F)c(-c2ccc(OCc3ccccc3)nc2OCc2ccccc2)c(F)c1)[C@H]1C[C@H](C(=O)O)C1]

The titled compound (560 mg, 72%) was prepared in a manner similar to that in Example 23 step 2 from methyl (1r,3r)-3-((4-(2,6-bis(benzyloxy)pyridin-3-yl)-3,5-difluorophenyl)(methyl)amino)cyclobutane-1-carboxylate and LiOH. $[M-H]^-$=529.2.

Step 6: (1r,3r)-3-((4-(2,6-dioxopiperidin-3-yl)-3,5-difluorophenyl)(methyl)amino)cyclobutane-1-carboxylic acid

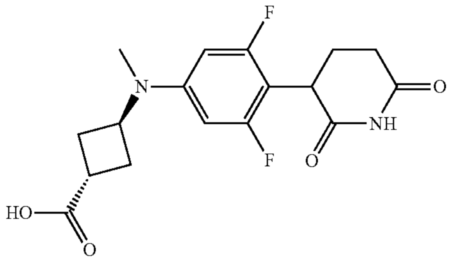 [SMILES: CN(c1cc(F)c(C2CCC(=O)NC2=O)c(F)c1)[C@H]1C[C@H](C(=O)O)C1]

The titled compound (160 mg, 42%) was prepared in a manner similar to that in Example 23 step 3 from (1r,3r)-3-((4-(2,6-bis(benzyloxy)pyridin-3-yl)-3,5-difluorophenyl)(methyl)amino)cyclobutane-1-carboxylic acid and Pd/C. $[M-H]^-$=351.1.

Step 7: 3-(4-(((1r,3r)-3-(4-(1-(4-((5-bromo-4-((4-(dimethylphosphoryl)quinolin-3-yl)amino)pyrimidin-2-yl)amino)-2-ethyl-5-methoxyphenyl)piperidin-4-yl)piperazine-1-carbonyl)cyclobutyl)(methyl)amino)-2,6-difluorophenyl)piperidine-2,6-dione

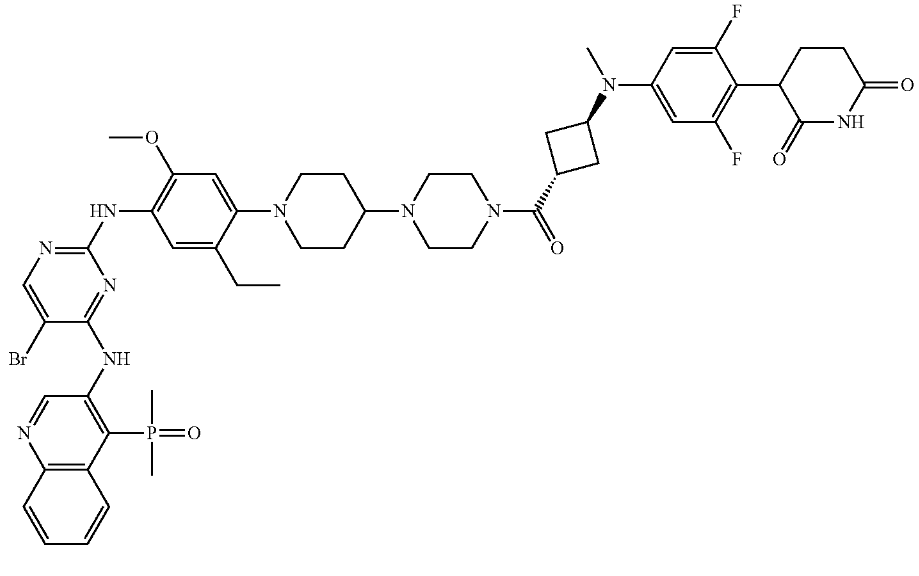 [SMILES: CCc1cc(Nc2ncc(Br)c(Nc3cnc4ccccc4c3P(C)(C)=O)n2)c(OC)cc1N1CCC(N2CCN(C(=O)[C@H]3C[C@H](N(C)c4cc(F)c(C5CCC(=O)NC5=O)c(F)c4)C3)CC2)CC1]

The titled compound (15 mg, 22%) was prepared in a manner similar to that in Example 15 step 5 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and (1r,3r)-3-((4-(2,6-dioxopiperidin-3-yl)-3,5-difluorophenyl)(methyl)amino)cyclobutane-1-carboxylic acid. 1H NMR (400 MHz, DMSO) δ 11.68 (s, 1H), 10.86 (s, 1H), 9.44 (s, 1H), 8.25 (s, 1H), 8.19 (d, J=9.0 Hz, 1H), 8.02-7.96 (m, 2H), 7.72 (t, J=7.3 Hz, 1H), 7.64 (t, J=7.5 Hz, 1H), 7.41 (s, 1H), 6.70 (s, 1H), 6.37 (d, J=12.6 Hz, 2H), 4.10-4.02 (m, 2H), 3.77 (s, 3H), 3.50 (s, 2H), 3.31-3.28 (m, 2H), 3.23-3.20 (m, 1H), 2.93 (d, J=10.8 Hz, 2H), 2.85 (s, 3H), 2.81-2.73 (m, 1H), 2.61 (t, J=11.2 Hz, 2H), 2.51 (s, 2H), 2.49-2.46 (m, 4H), 2.39-2.31 (m, 5H), 2.08-2.05 (m, 8H), 1.97-1.92 (m, 1H), 1.81 (d, J=11.0 Hz, 2H), 1.55 (d, J=8.9 Hz, 2H), 0.75 (s, 3H); $[M+H]^+$=1027.5.

Example 19: 3-(4-(3-((4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazin-1-yl)methyl)azetidin-1-yl)-2,6-difluorophenyl)piperidine-2,6-dione Step 1: methyl 1-(4-(2,6-bis(benzyloxy)pyridin-3-yl)-3,5-difluorophenyl)azetidine-3-carboxylate

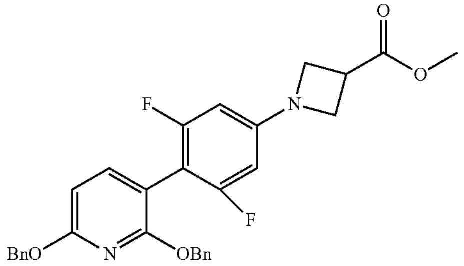 [SMILES: COC(=O)C1CN(c2cc(F)c(-c3ccc(OCc4ccccc4)nc3OCc3ccccc3)c(F)c2)C1]

A mixture of 2,6-bis(benzyloxy)-3-(4-bromo-2,6-difluorophenyl)pyridine (3.00 g, 6.22 mmol), methyl azetidine-3-carboxylate hydrochloride (1.41 g, 9.33 mmol), $Cs_2CO_3$ (6.06 g, 18.66 mmol) and RuPhos Pd G3 (520.7 mg, 0.622 mmol) in toluene (50 mL) was stirred overnight at 100° C. under nitrogen atmosphere. The resulting mixture was extracted with EtOAc. The combined organic layers were washed with brine, dried over anhydrous $Na_2SO_4$. After filtration, the filtrate was concentrated under reduced pressure. The residue was purified by silica gel column chromatography, eluted with PE/EtOAc (2:1) to afford the product (1.7 g, 53%). $[M+1]^+$=517.1.

Step 2: (1-(4-(2,6-bis(benzyloxy)pyridin-3-yl)-3,5-difluorophenyl)azetidin-3-yl)methanol

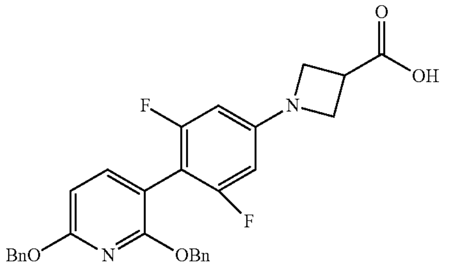 [SMILES: O=C(O)C1CN(c2cc(F)c(-c3ccc(OCc4ccccc4)nc3OCc3ccccc3)c(F)c2)C1]

To a stirred mixture of methyl 1-(4-(2,6-bis(benzyloxy)pyridin-3-yl)-3,5-difluorophenyl)azetidine-3-carboxylate (1.7 g, 3.29 mmol) in THF (20 mL) was added $LiAlH_4$ (1 M in THF, 4.27 mL, 4.27 mmol) dropwise at 0° C. Then the mixture was stirred for 2 hours, the reaction was quenched with water (10 mL) at 0° C. The resulting mixture was extracted with EtOAc (3×50 mL). The combined organic layers were washed with brine, dried over anhydrous $Na_2SO_4$. After filtration, the filtrate was concentrated under reduced pressure to afford the product (1.4 g, 87%) $[M+1]^+$=489.2.

Step 3: 3-(2,6-difluoro-4-(3-(hydroxymethyl)azetidin-1-yl)phenyl)piperidine-2,6-dione

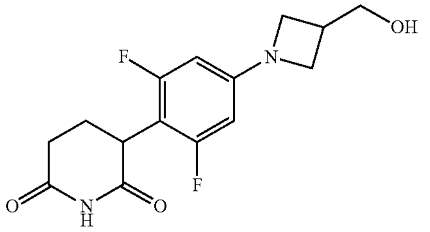 [SMILES: O=C1CCC(c2c(F)cc(N3CC(CO)C3)cc2F)C(=O)N1]

To a solution of (1-(4-(2,6-bis(benzyloxy)pyridin-3-yl)-3,5-difluorophenyl)azetidin-3-yl)methanol (1.40 g, 2.87 mmol) in iPrOH (20 mL) and DCM (20 mL) was added Pd/C (1.0 g, 10% wt) which was stirred at room temperature under hydrogen atmosphere for 48 hours. The resulting mixture was filtered, the filter cake was washed with MeOH (20 mL). The filtrate was concentrated under reduced pressure to afford the product (450 mg, 51%). $[M+1]^+$=311.3.

Step 4: (1-(4-(2,6-dioxopiperidin-3-yl)-3,5-difluorophenyl)azetidin-3-yl)methyl methanesulfonate

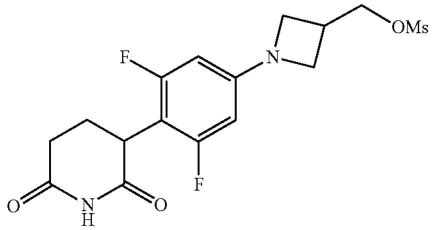 [SMILES: CS(=O)(=O)OCC1CN(c2cc(F)c(C3CCC(=O)NC3=O)c(F)c2)C1]

To a solution of 3-(2,6-difluoro-4-(3-(hydroxymethyl)azetidin-1-yl)phenyl)piperidine-2,6-dione (200 mg, 0.65 mmol) and $Et_3N$ (262 mg, 2.6 mmol) in DCM (5 mL) and THF (5 mL), MsCl (150 mg, 1.30 mmol) was slowly added at 0° C. The mixture was stirred at 25° C. for 2 hours. The mixture was quenched with water (10 mL). The organic phase was separated and concentrated in vacuum. The residue was purified by prep-TLC (DCM:MeOH=20:1) to afford the product (180 mg, 72% yield). $[M+H]^+$=389.1.

Step 5: 3-(4-(3-((4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)methyl)azetidin-1-yl)-2,6-difluorophenyl)piperidine-2,6-dione

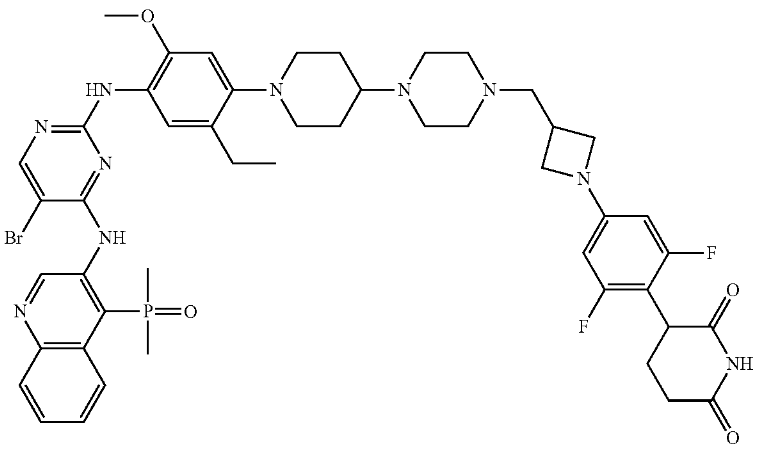 [SMILES: CCc1cc(Nc2ncc(Br)c(Nc3cnc4ccccc4c3P(C)(C)=O)n2)c(OC)cc1N1CCC(N2CCN(CC3CN(c4cc(F)c(C5CCC(=O)NC5=O)c(F)c4)C3)CC2)CC1]

To a solution of (3-((5-bromo-2-((5-ethyl-2-methoxy-4-(4-(piperazin-1-yl)piperidin-1-yl)phenyl)amino)pyrimidin- 4-yl)amino)quinolin-4-yl)dimethylphosphine oxide (50 mg, 0.072 mmol), (1-(4-(2,6-dioxopiperidin-3-yl)-3,5-difluorophenyl)azetidin-3-yl)methyl methanesulfonate (42 mg, 0.108 mmol), KI (36 mg, 0.216 mmol) and DIEA (37 mg, 0.288 mmol) in 5 mL ACN. The mixture was stirred at 80° C. for 16 hours. The mixture was concentrated in vacuum. The residue was dissolved in DCM and filtered. The organic phase was concentrated in vacuum and purified by prep-HPLC with C-18 column chromatography (0.1% FA in water:acetonitrile=90:10~60:40 gradient elution) to afford the product (6.05 mg, 8.5% yield). 1H NMR (400 MHz, DMSO) δ 11.68 (s, 1H), 10.85 (s, 1H), 9.45 (s, 1H), 8.25 (s, 1H), 8.19 (d, J=7.6 Hz, 1H), 8.02-7.97 (m, 2H), 7.71 (t, J=7.7 Hz, 1H), 7.66-7.62 (m, 1H), 7.41 (s, 1H), 6.70 (s, 1H), 6.11 (d, J=11.1 Hz, 2H), 4.02 (d, J=7.8 Hz, 1H), 3.93 (t, J=7.4 Hz, 2H), 3.77 (s, 3H), 3.49-3.45 (m, 2H), 3.29 (s, 2H), 2.99-2.87 (m, 3H), 2.79-2.73 (m, 1H), 2.65-2.57 (m, 3H), 2.54 (d, J=6.8 Hz, 3H), 2.39-2.32 (m, 6H), 2.05 (d, J=13.4 Hz, 8H), 1.97-1.93 (m, 2H), 1.83-1.80 (m, 2H), 1.55-1.50 (m, 2H), 0.75 (s, 3H); $[M+H]^+$=985.5.

Example 20: 3-(4-(3-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazine-1-carbonyl)azetidin-1-yl)-2,6-difluorophenyl)piperidine-2,6-dione

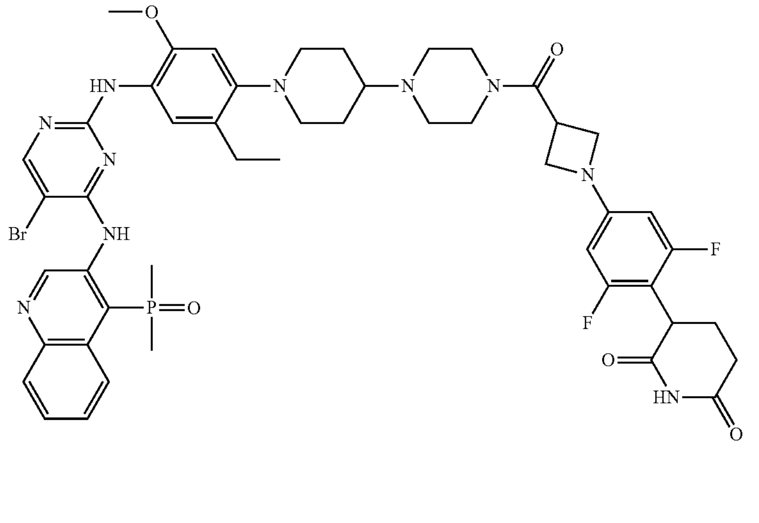 [SMILES: CCc1cc(Nc2ncc(Br)c(Nc3cnc4ccccc4c3P(C)(C)=O)n2)c(OC)cc1N1CCC(N2CCN(C(=O)C3CN(c4cc(F)c(C5CCC(=O)NC5=O)c(F)c4)C3)CC2)CC1]

The titled compound was synthesized in the procedures similar to Example 18. 1H NMR (400 MHz, DMSO) δ 11.68 (s, 1H), 10.86 (s, 1H), 9.43 (s, 1H), 8.26-8.23 (m, 2H), 8.00 (d, J=8.1 Hz, 2H), 7.71 (s, 1H), 7.63 (s, 1H), 7.43 (s, 1H), 6.70 (s, 1H), 6.17 (d, J=11.2 Hz, 2H), 4.06-4.01 (m, 3H), 3.92 (t, J=6.4 Hz, 2H), 3.85-3.81 (m, 1H), 3.77 (s, 3H), 3.49 (s, 2H), 2.93 (d, J=10.2 Hz, 2H), 2.77 (dd, J=21.2, 8.8 Hz, 1H), 2.62 (t, J=11.1 Hz, 2H), 2.53-2.50 (m, 3H), 2.49-2.45 (m, 3H), 2.38-2.31 (m, 3H), 2.04 (d, J=13.4 Hz, 8H), 1.95 (d, J=5.6 Hz, 1H), 1.81 (d, J=11.0 Hz, 2H), 1.58-1.52 (m, 2H), 0.74 (s, 3H); $[M+H]^+$=999.5.

Example 21: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazin-1-yl)ethyl)-3-methyl-2-oxo-2,3-dihydro-1H-benzo[d]imidazol-1-yl)piperidine-2,6-dione Step 1: 7-bromo-1-methyl-1,3-dihydro-2H-benzo[d] imidazol-2-one

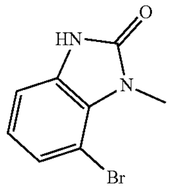

To a solution of 6-bromo-N1-methylbenzene-1,2-diamine (4 g, 19.9 mmol) in $CH_3CN$ (50 mL) was added CDI (6.4 g, 39.8 mmol). The resulting solution was stirred for 6 h at 90° C. under nitrogen atmosphere. The solid was collected by filtration. This was resulted in 7-bromo-1-methyl-1,3-dihydro-2H-benzo[d]imidazol-2-one (4.1 g, 90.7%). $[M+H]^+$=227.0.

Step 2: 3-(4-bromo-3-methyl-2-oxo-2,3-dihydro-1H-benzo[d]imidazol-1-yl)-1-(4-methoxybenzyl)piperidine-2,6-dione

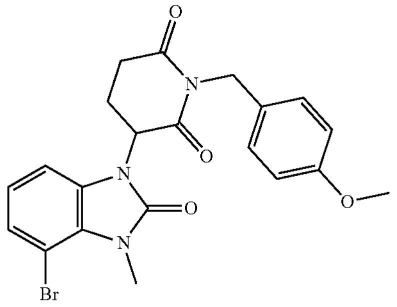 [SMILES: COc1ccc(CN2C(=O)CCC(n3c(=O)n(C)c4c(Br)cccc43)C2=O)cc1]

To a solution of 7-bromo-1-methyl-1,3-dihydro-2H-benzo[d]imidazol-2-one (600 mg, 2.6 mmol) in THF (10 mL) was added t-BuOK (1M in THF, 3.2 mL, 3.1 mmol) dropwise in 10 min at 0° C., the reaction solution was stirred for 30 min at 0° C., then to this was added 1-(4-methoxybenzyl)-2,6-dioxopiperidin-3-yl trifluoromethanesulfonate (This intermediate was prepared according the same manner described in WO 2020113233A1) (1.1 g, 2.9 mmol) in THF (5 mL) dropwise in 10 min. The resulting solution was stirred for 2 h at 0-10° C. The reaction was quenched by the addition of sat.aq. $NH_4Cl$ solution, extracted with EtOAc (10 mL×3), combined the organic layer, and washed with brine, dried over anhydrous $Na_2SO^4$, after filtration, the filtrate was concentrated under reduced pressure. The residue was purified by a silica gel column, eluted with PE/EtOAc (1:1) to afford product (910 mg, 75.2%). $[M+H]^+$= 458.1.

Step 3: 3-(4-bromo-3-methyl-2-oxo-2,3-dihydro-1H-benzo[d]imidazol-1-yl)piperidine-2,6-dione

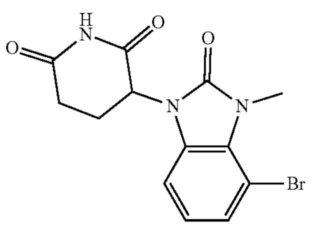 [SMILES: Cn1c(=O)n(C2CCC(=O)NC2=O)c2cccc(Br)c21]

3-(4-bromo-3-methyl-2-oxo-2,3-dihydro-1H-benzo[d]imidazol-1-yl)-1-(4-methoxybenzyl)piperidine-2,6-dione (800 mg, 1.75 mmol) was dissolved in $MeSO_3H$/toluene (2 mL/6 mL). The resulting mixture was stirred for 3 h at 100° C. Solvent was removed and the residue was poured into ice/water. The solid was collected by filtration. 3-(4-bromo-3-methyl-2-oxo-2,3-dihydro-1H-benzo[d]imidazol-1-yl)piperidine-2,6-dione was obtained (510 mg, 86.4%). $[M+H]^+$= 338.1.

Step 4: (E)-3-(4-(2-ethoxyvinyl)-3-methyl-2-oxo-2,3-dihydro-1H-benzo[d]imidazol-1-yl)piperidine-2,6-dione

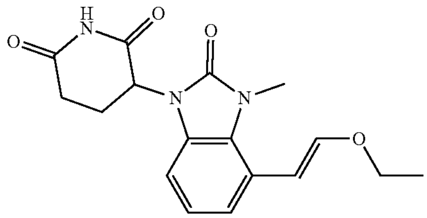 [SMILES: CCO/C=C/c1cccc2c1n(C)c(=O)n2C1CCC(=O)NC1=O]

To a stirred solution of 3-(4-bromo-3-methyl-2-oxo-2,3-dihydro-1H-benzo[d]imidazol-1-yl)piperidine-2,6-dione (250 mg, 0.74 mmol) and (E)-2-(2-ethoxyvinyl)-4,4,5,5-tetramethyl-1,3,2-dioxaborolane (176 mg, 0.89 mmol) in DMF/$H_2O$ (8 mL/2 mL) were added Pd(dtbpf)$Cl_2$ (48 mg, 0.074 mmol) and CsF (225 mg, 1.48 mmol). The resulting mixture was stirred for 2 h at 80° C. under nitrogen atmosphere. The reaction solution was diluted with water, extracted with EtOAc (10 mL×3). The organic layer was washed with water and brine, dried over anhydrous $Na_2SO_4$ which was evaporated to dryness. The residue was purified by a silica gel column, eluted with PE/EtOAc=1:1 to afford the product. (180 mg, 73.8%). $[M+H]^+$=330.2.

Step 5:2-(1-(2,6-dioxopiperidin-3-yl)-3-methyl-2-oxo-2,3-dihydro-1H-benzo[d]imidazol-4-yl)acetaldehyde

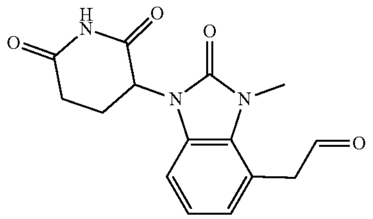 [SMILES: Cn1c(=O)n(C2CCC(=O)NC2=O)c2cccc(CC=O)c21]

(E)-3-(4-(2-ethoxyvinyl)-3-methyl-2-oxo-2,3-dihydro-1H-benzo[d]imidazol-1-yl)piperidine-2,6-dione (180 mg, 0.55 mmol) was dissolved in HCOOH (2 mL). The resulting solution was stirred for 2 h at room temperature. The reaction solution was evaporated to dryness to afford product (125 mg, 75.3%) which was used directly in the next step. m/z $[M+H]^+$=302.1.

Step 6: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazin-1-yl)ethyl)-3-methyl-2-oxo-2,3-dihydro-1H-benzo[d]imidazol-1-yl)piperidine-2,6-dione

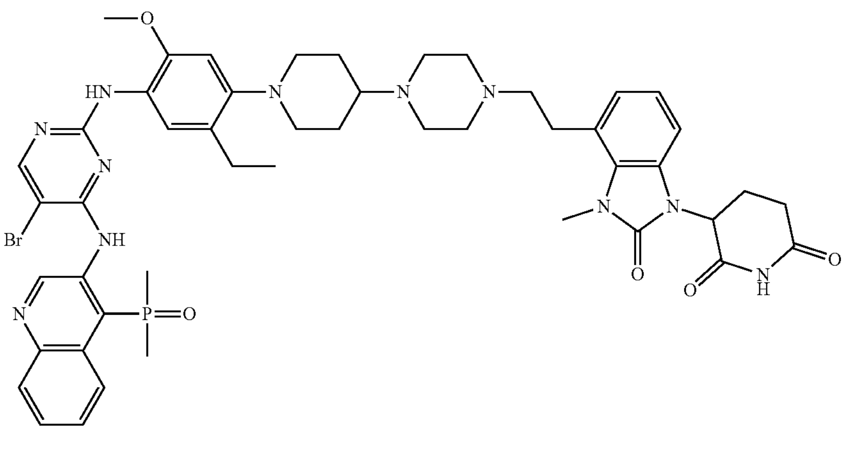 [SMILES: CCc1cc(Nc2ncc(Br)c(Nc3cnc4ccccc4c3P(C)(C)=O)n2)c(OC)cc1N1CCC(N2CCN(CCc3cccc4c3n(C)c(=O)n4C3CCC(=O)NC3=O)CC2)CC1]

The titled compound (12 mg, 19%) was prepared in a manner similar to that in Example 1 step 11 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and 2-(1-(2,6-dioxopiperidin-3-yl)-3-methyl-2-oxo-2,3-dihydro-1H-benzo[d]imidazol-4-yl)acetaldehyde. $^1$H NMR (500 MHz, DMSO-$d_6$) $\delta_H$ 11.61 (s, 1H), 11.03 (s, 1H), 9.38 (s, 1H), 8.05-8.24 (m, 2H), 7.84-7.99 (m, 2H), 7.65 (t, J=7.6 Hz, 1H), 7.57 (t, J=7.6 Hz, 1H), 7.35 (s, 1H), 6.87-6.95 (m, 2H), 6.84 (dd, J=6.2, 2.5 Hz, 1H), 6.64 (s, 1H), 5.30 (dd, J=12.7, 5.3 Hz, 1H), 3.71 (s, 3H), 3.52 (s, 4H), 2.92-3.05 (m, 3H), 2.75-2.91 (m, 4H), 2.60-2.70 (m, 1H), 2.45-2.59 (m, 10H), 2.16-2.32 (m, 3H), 1.88-2.04 (m, 7H), 1.76 (d, J=10.7 Hz, 2H), 1.46 (dd, J=20.3, 11.1 Hz, 2H), 0.68 (s, 3H). $[M+H]^+$=979.7

Example 23: 3-(4-((6-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazine-1-carbonyl)spiro[3.3]heptan-2-yl)amino)-2,6-difluorophenyl)piperidine-2,6-dione Step 1: Methyl 6-((4-(2,6-bis(benzyloxy)pyridin-3-yl)-3,5-difluorophenyl)amino)spiro[3.3]heptane-2-carboxylate

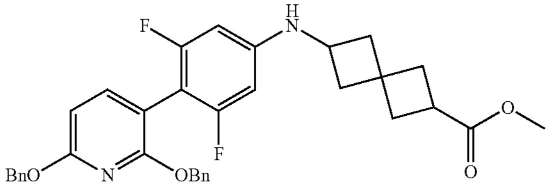 [SMILES: COC(=O)C1CC2(CC(Nc3cc(F)c(-c4ccc(OCc5ccccc5)nc4OCc4ccccc4)c(F)c3)C2)C1]

To a mixture of 2,6-bis(benzyloxy)-3-(4-bromo-2,6-difluorophenyl)pyridine (1 g, 2.08 mmol), HCl salt of methyl 6-aminospiro[3.3]heptane-2-carboxylate (640 mg, 3.12 mmol), Ruphos Pd G3 (176 mg, 0.21 mmol), $Cs_2CO_3$ (2.37 g, 7.28 mmol) in toluene (20 mL) was stirred at 100° C. under nitrogen atmosphere for 16 hrs. After cooling to rt, the reaction mixture was filtered, the filtrate was concentrated in vacuo. The residue was purified by silica gel column (PE: EA=1:1) to afford the product (530 mg, 45%). $[M+H]^+$=571.2.

Step 2: 6-((4-(2,6-bis(benzyloxy)pyridin-3-yl)-3,5-difluorophenyl)amino)spiro[3.3]heptane-2-carboxylic acid

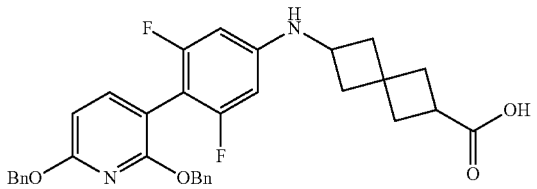 [SMILES: O=C(O)C1CC2(CC(Nc3cc(F)c(-c4ccc(OCc5ccccc5)nc4OCc4ccccc4)c(F)c3)C2)C1]

To a mixture of methyl 6-((4-(2,6-bis(benzyloxy)pyridin-3-yl)-3,5-difluorophenyl)amino)spiro[3.3]heptane-2-carboxylate (530 mg, 0.93 mmol) in THF (20 mL) and $H_2O$ (10 mL) was added LiOH (111 mg, 4.64 mmol). The reaction solution was stirred at 25° C. for 4 hrs. HCl (2 N) was added to the mixture until PH=5-6. The resulting mixture was extracted with EA (25 mL×3), washed with brine and dried over $Na_2SO_4$, concentrated in vacuo to afford the product (490 mg, 94.6%). $[M+H]^+$=557.1.

Step 3: 6-((4-(2,6-dioxopiperidin-3-yl)-3,5-difluorophenyl)amino)spiro[3.3]heptane-2-carboxylic acid

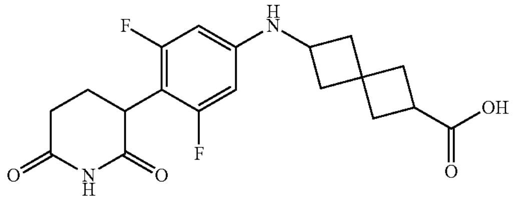 [SMILES: O=C1CCC(c2c(F)cc(NC3CC4(C3)CC(C(=O)O)C4)cc2F)C(=O)N1]

To a solution of 6-((4-(2,6-bis(benzyloxy)pyridin-3-yl)-3,5-difluorophenyl)amino)spiro[3.3]heptane-2-carboxylic acid (490 mg, 0.81 mmol) in MeOH (3 mL) and DCM (10 mL) was added Pd/C (200 mg, 10%). The reaction mixture was stirred at rt under $H_2$ balloon for 16 h. The catalyst was filtered off, the filtrate was concentrated in vacuum to afford the product (260 mg, 85%). $[M+H]^+$=379.1.

Step 4: 3-(4-((6-(4-(1-(4-((5-bromo-4-((4-(dimethylphosphoryl)quinolin-3-yl)amino)pyrimidin-2-yl) amino)-2-ethyl-5-methoxyphenyl) piperidin-4-yl) piperazine-1-carbonyl)spiro[3.3]heptan-2-yl)amino)-2,6-difluorophenyl)piperidine-2,6-dione

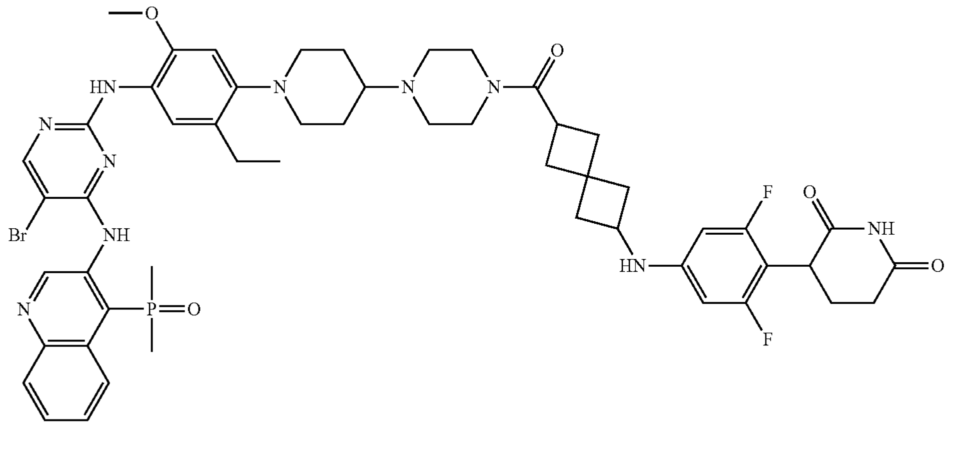 [SMILES: CCc1cc(Nc2ncc(Br)c(Nc3cnc4ccccc4c3P(C)(C)=O)n2)c(OC)cc1N1CCC(N2CCN(C(=O)C3CC4(CC(Nc5cc(F)c(C6CCC(=O)NC6=O)c(F)c5)C4)C3)CC2)CC1]

The titled compound (11 mg, 24%) was prepared in a manner similar to that in Example 15 Step 5 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and 6-((4-(2,6-dioxopiperidin-3-yl)-3,5-difluorophenyl)amino)spiro[3.3]heptane-2-carboxylic acid. $^1$H NMR (500 MHz, DMSO) δ 11.68 (s, 1H), 10.88 (d, J=59.5 Hz, 1H), 9.44 (s, 1H), 8.25 (s, 1H), 8.23-8.14 (m, 1H), 8.04-7.89 (m, 2H), 7.72 (t, J=7.5 Hz, 1H), 7.64 (t, J=7.6 Hz, 1H), 7.41 (s, 1H), 6.66 (d, J=37.1 Hz, 1H), 6.45 (d, J=6.2 Hz, 1H), 6.12 (d, J=11.8 Hz, 2H), 3.96 (dt, J=24.5, 12.3 Hz, 1H), 3.77 (s, 3H), 3.71-3.58 (m, 1H), 3.43 (d, J=4.7 Hz, 2H), 3.22 (dt, J=17.1, 8.6 Hz, 2H), 2.93 (d, J=10.5 Hz, 2H), 2.84-2.69 (m, 1H), 2.68-2.53 (m, 4H), 2.47 (s, 5H), 2.40-2.28 (m, 4H), 2.26-2.14 (m, 3H), 2.07 (d, J=12.7 Hz, 4H), 2.03 (s, 4H), 1.96-1.91 (m, 1H), 1.89-1.68 (m, 4H), 1.53 (dd, J=20.5, 11.6 Hz, 2H), 0.75 (s, 3H). $[M+H]^+$=1053.4.

Example 24: 3-(5'-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazin-1-yl)ethyl)-2'-oxospiro[cyclopropane-1,3'-indolin]-1'-yl)piperidine-2,6-dione Step1: 1-(tert-butyl) 3-methyl 2-(5-bromo-2-nitrophenyl)malonate

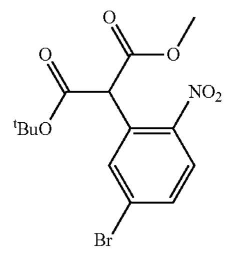 [SMILES: COC(=O)C(C(=O)OC(C)(C)C)c1cc(Br)ccc1[N+](=O)[O-]]

A mixture of 1-tert-butyl 3-methyl propanedioate (66.5 g, 381.823 mmol), $Cs_2CO_3$ (311 g, 954.558 mmol) and 4-bromo-2-fluoro-1-nitrobenzene (70 g, 318.186 mmol) in DMF (700 mL) was stirred for 16 h at 70° C. under nitrogen atmosphere. The resulting mixture was filtered, the filter cake was washed with EtOAc (3×2 L). The solution was acidified to pH=6 with HCl (aq., 1 M) and diluted with water (5 L). The resulting solution was extracted with EtOAc (3×800 mL). The combined organic layers were washed with brine (500 mL), dried over anhydrous $Na_2SO_4$. After filtration, the filtrate was concentrated under reduced pressure. The residue was purified by silica gel column chromatography, eluted with EtOAc in PE (0%-2%) to afford the product (100 g, 84%). $[M+H]^+$=374.1.

Step 2: methyl 2-(5-bromo-2-nitrophenyl)acetate

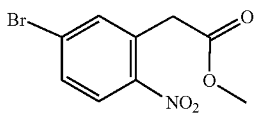

A solution of 1-(tert-butyl) 3-methyl 2-(5-bromo-2-nitrophenyl)malonate (80 g, 213.797 mmol) and p-toluenesulfonic acid·$H_2O$ (20.33 g, 106.898 mmol) in toluene (800 mL) was stirred for 2 h at 110° C. The resulting mixture was concentrated under reduced pressure. The resulting mixture was added water (200 mL) and extracted with EtOAc (3×1500 mL). The combined organic layers were washed with brine (2×500 mL), dried over anhydrous $Na_2SO_4$. After filtration, the filtrate was concentrated under reduced pressure. The residue was purified by silica gel column chromatography, eluted with EtOAc in PE (0%-2%) to afford the product (45.8 g, 69.5%). $[M+H]^+$=273.9.

Step 3: methyl 2-(5-bromo-2-nitrophenyl)acrylate

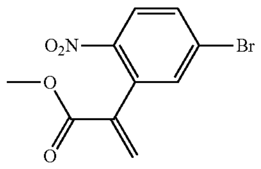 [SMILES: C=C(C(=O)OC)c1cc(Br)ccc1[N+](=O)[O-]]

To a stirred solution of N,N,N-triethylanilinium iodide (13.36 g, 43.784 mmol) and methyl 2-(5-bromo-2-nitrophenyl)acetate (10 g, 36.487 mmol) in toluene (200 mL) were added paraformaldehyde (7.12 g, 237.166 mmol) and $K_2CO_3$ (10.09 g, 72.974 mmol) at room temperature. The resulting mixture was heated to 80° C. over 40 min. The resulting mixture was stirred for 1 h at 80° C. The resulting mixture was concentrated under reduced pressure. The residue was purified by silica gel column chromatography, eluted with EtOAc in petroleum ether (0%-15%) to afford the product (8.7 g, 83.35%). $[M+H]^+$=287.1.0.

Step 4: methyl 1-(5-bromo-2-nitrophenyl)cyclopropane-1-carboxylate

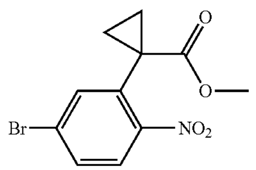 [SMILES: COC(=O)C1(c2cc(Br)ccc2[N+](=O)[O-])CC1]

A mixture of t-BuOK (3.77 g, 33.557 mmol) and trimethylsulfoxonium iodide (7.38 g, 33.557 mmol) in THF (160 mL) was stirred for 0.5 h at 0° C. under nitrogen atmosphere. To the above mixture was added methyl 2-(5-bromo-2-nitrophenyl)acrylate (8 g, 27.964 mmol) in THF (20 mL) dropwise at 0° C. The resulting mixture was stirred for 2 h at room temperature. The reaction was quenched with sat. $NH_4Cl$ (aq.) (20 mL) at 0° C. and diluted with water (1 L). The resulting mixture was extracted with EtOAc (3×200 mL). The combined organic layers were washed with brine (2×100 mL), dried over anhydrous $Na_2SO_4$. After filtration, the filtrate was concentrated under reduced pressure. The residue was purified by silica gel column chromatography, eluted with EtOAc in petroleum ether (0%-15%) to afford the product (6.6 g, 78.64%). $[M+H]^+$=301.1

Step 5: 5'-bromospiro[cyclopropane-1,3'-indolin]-2'-one

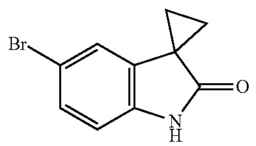 [SMILES: O=C1Nc2ccc(Br)cc2C12CC2]

To a stirred solution of methyl 1-(5-bromo-2-nitrophenyl) cyclopropane-1-carboxylate (6.6 g, 21.992 mmol) in AcOH (66 mL) was added Fe (12.28 g, 219.921 mmol) in portions at room temperature under air atmosphere. The resulting mixture was stirred for 2 h at room temperature under air atmosphere. The resulting mixture was concentrated under reduced pressure. The residue was purified by silica gel column chromatography, eluted with EtOAc in petroleum ether (20%-90%) to afford the product (5 g, 95.49%). $[M+H]^+$=237.9.

Step 6: 3-(5'-bromo-2'-oxospiro[cyclopropane-1,3'-indolin]-1'-yl)-1-(4-methoxybenzyl)piperidine-2,6-dione

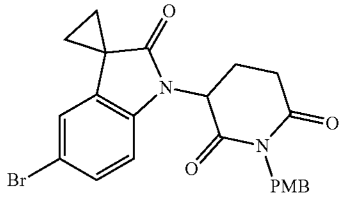

To a stirred mixture of 5'-bromospiro[cyclopropane-1,3'-indolin]-2'-one (5 g, 21.0 mmol) in THF (40 mL) was added t-BuOK (2.83 g, 25.201 mmol) in portions at 0° C. under nitrogen atmosphere. The resulting mixture was stirred for 1 h at room temperature under nitrogen atmosphere. To the above mixture was added 1-[(4-methoxyphenyl)methyl]-2,6-dioxopiperidin-3-yl trifluoromethanesulfonate (9.61 g, 25.201 mmol) in THF (20 mL) at 0° C. The resulting mixture was stirred for 2 h at room temperature. The reaction was quenched with sat. $NH_4Cl$ (aq.) (100 mL) at 0° C. The resulting mixture was extracted with EtOAc (3×300 mL). The combined organic layers were washed with brine (2×200 mL), dried over anhydrous $Na_2SO_4$. After filtration, the filtrate was concentrated under reduced pressure. The residue was purified by silica gel column chromatography, eluted with EtOAc in petroleum ether (10%-50%) to afford the product (7 g, 71.02%). $[M+H]^+$=470.3.

Step 7: 3-(5'-bromo-2'-oxospiro[cyclopropane-1,3'-indolin]-1'-yl)piperidine-2,6-dione

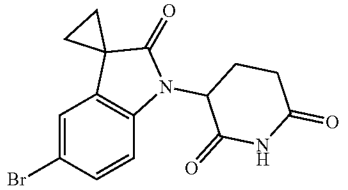 [SMILES: O=C1CCC(N2C(=O)C3(CC3)c3cc(Br)ccc32)C(=O)N1]

A solution of 3-(5'-bromo-2'-oxospiro[cyclopropane-1,3'-indolin]-1'-yl)-1-(4-methoxybenzyl)piperidine-2,6-dione (2 g, 4.261 mmol) and $(NH_4)_2Ce(NO_3)_6$ (9.38 g, 17.045 mmol) in MeCN (50 mL) and $H_2O$ (10 mL) was stirred for 4 h at room temperature. The reaction was quenched by the addition of sat. $NaHSO_3$ (aq.) (10 mL) at room temperature. The resulting mixture was diluted with water (80 mL). The resulting mixture was extracted with EtOAc (3×100 mL). The combined organic layers were washed with brine (2×50 mL), dried over anhydrous $Na_2SO_4$. After filtration, the filtrate was concentrated under reduced pressure. The residue was purified by silica gel column chromatography, eluted with EtOAc in petroleum ether (10%-60%) to afford the product (950 mg, 63.84%). $[M+H]^+$=349.0.

Step 8: 3-(5'-bromo-2'-oxospiro[cyclopropane-1,3'-indolin]-1'-yl)-1-((2-(trimethylsilyl)ethoxy)methyl) piperidine-2,6-dione

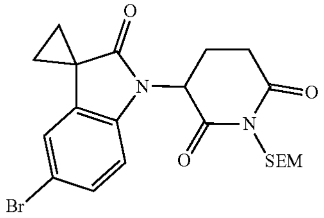 [SMILES: C[Si](C)(C)CCOCN1C(=O)CCC(N2C(=O)C3(CC3)c3cc(Br)ccc32)C1=O]

To a stirred mixture of 3-(5'-bromo-2'-oxospiro[cyclopropane-1,3'-indolin]-1'-yl)piperidine-2,6-dione (950 mg, 2.721 mmol) and DIEA (8.99 mL, 54.420 mmol) in DMF (45 mL) was added SEM-Cl (1.93 mL, 10.884 mmol) dropwise at 0° C. under nitrogen atmosphere. The resulting mixture was stirred for 3 h at room temperature. The reaction was quenched with water (300 mL) at room temperature. The resulting mixture was extracted with EtOAc (2×200 mL). The combined organic layers were washed with brine (3×80 mL), dried over anhydrous $Na_2SO_4$. After filtration, the filtrate was concentrated under reduced pressure. The residue was purified by silica gel column chromatography, eluted with EtOAc in petroleum ether (0-20%) to afford the product (848 mg, 65.01%). $[M+H]^+$=479.1.

Step 9: 3-(5'-allyl-2'-oxospiro[cyclopropane-1,3'-indolin]-1'-yl)-1-((2-(trimethylsilyl)ethoxy)methyl) piperidine-2,6-dione

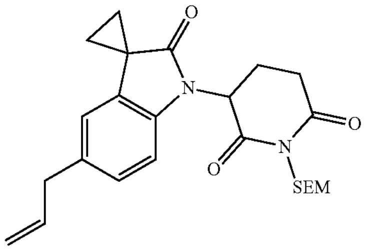 [SMILES: C=CCc1ccc2c(c1)C1(CC1)C(=O)N2C1CCC(=O)N(COCC[Si](C)(C)C)C1=O]

To a stirred solution of 3-(5'-bromo-2'-oxospiro[cyclopropane-1,3'-indolin]-1'-yl)-1-((2-(trimethylsilyl)ethoxy) methyl)piperidine-2,6-dione (850 mg, 1.773 mmol) and tributyl(prop-2-en-1-yl)stannane (0.88 g, 2.659 mmol) in DMF (16 mL) was added $Pd(PPh_3)_2Cl_2$ (0.19 mL, 0.266 mmol) at room temperature under nitrogen atmosphere. The resulting mixture was stirred for 2 h at 105° C. under nitrogen atmosphere. The resulting mixture was diluted with water (50 mL). The resulting mixture was extracted with EtOAc (3×100 mL). The combined organic layers were washed with brine (3×50 mL), dried over anhydrous $Na_2SO_4$. After filtration, the filtrate was concentrated under reduced pressure. The residue was purified by silica gel column chromatography, eluted with 1-40% EtOAc in PE to afford crude product (450 mg). The crude product was purified by reverse flash chromatography with the following conditions: column, C18; mobile phase, MeCN in water (0.1% FA), 50% to 90% gradient in 10 min; detector, UV 254 nm. to afford the product (350 mg, 44.81%). [M+Na]+ =463.4.

Step 10: 2-(1'-(2,6-dioxo-1-((2-(trimethylsilyl) ethoxy)methyl)piperidin-3-yl)-2'-oxospiro[cyclopropane-1,3'-indolin]-5'-yl) acetaldehyde

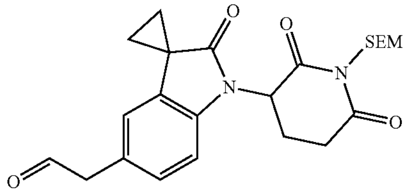 [SMILES: C[Si](C)(C)CCOCN1C(=O)CCC(N2C(=O)C3(CC3)c3cc(CC=O)ccc32)C1=O]

A mixture of 3-(5'-allyl-2'-oxospiro[cyclopropane-1,3'-indolin]-1'-yl)-1-((2-(trimethylsilyl)ethoxy)methyl)piperidine-2,6-dione (220 mg, 0.5 mmol), $K_2OsO_4$ (1.84 mg, 0.005 mmol), $NaIO_4$ (428 mg, 2 mmol) in dioxane (8 mL) and $H_2O$ (2 mL) was stirred at rt for 1 h. The mixture was diluted with water (50 mL), extracted with DCM (3×50 mL). The combined organic layers were dried over $Na_2SO_4$, filtered and concentrated under vacuum. The residue was purified by silica gel column chromatography, eluted with EA/PE (2:1) to afford product (120 mg, 54.3%). $[M+H]^+$ =443.2.

Step 11: 3-(5'-(2-(4-(1-(4-((5-bromo-4-((4-(dimethylphosphoryl)quinolin-3-yl)amino)pyrimidin-2-yl) amino)-2-ethyl-5-methoxyphenyl) piperidin-4-yl) piperazin-1-yl)ethyl)-2'-oxospiro[cyclopropane-1,3'-indolin]-1'-yl)-1-((2-(trimethylsilyl) ethoxy)methyl) piperidine-2,6-dione

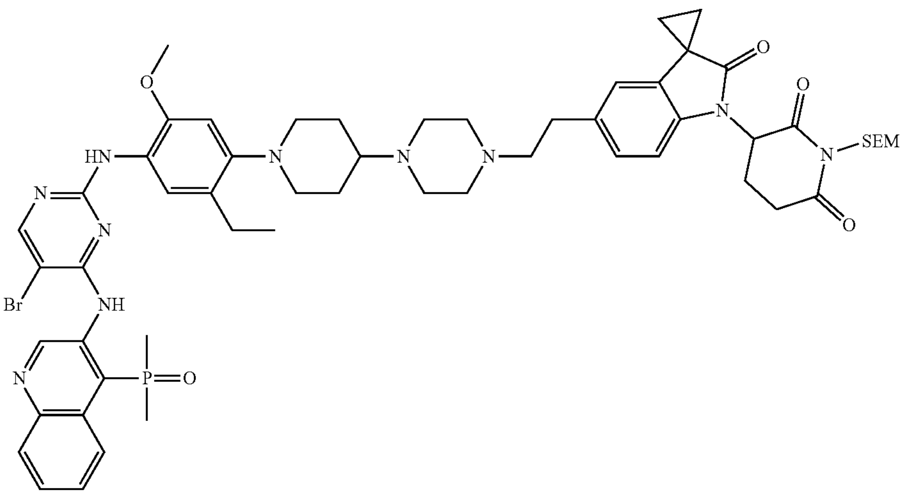 [SMILES: CCc1cc(Nc2ncc(Br)c(Nc3cnc4ccccc4c3P(C)(C)=O)n2)c(OC)cc1N1CCC(N2CCN(CCc3ccc4c(c3)C3(CC3)C(=O)N4C3CCC(=O)N(COCC[Si](C)(C)C)C3=O)CC2)CC1]

A mixture of (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide (62 mg, 0.09 mmol), 2-(1'-(2,6-dioxo-1-((2-(trimethylsilyl)ethoxy)methyl)piperidin-3-yl)-2'-oxospiro[cyclopropane-1,3'-indolin]-5'-yl)acetaldehyde (60 mg, 0.13 mmol) and AcOH (0.2 mL) in MeOH (5 mL) and DCM (5 mL) was stirred at rt for 16 h. Then, STAB (38.2 mg, 0.18 mmol) was added to the mixture above. The mixture was stirred at rt for 5 h. The mixture was diluted with water (50 mL), extracted with DCM (3x50 mL). The combined organic layers were dried over $Na_2SO_4$, filtered and concentrated under vacuum. The residue was purified by silica gel column chromatography, eluted with MeOH/DCM (1:9) to afford product (36 mg, 35.8%). $[M+H]^+$=1119.4.

Step 12: 3-(5'-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazin-1-yl)ethyl)-2'-oxospiro[cyclopropane-1,3'-indolin]-1'-yl)piperidine-2,6-dione

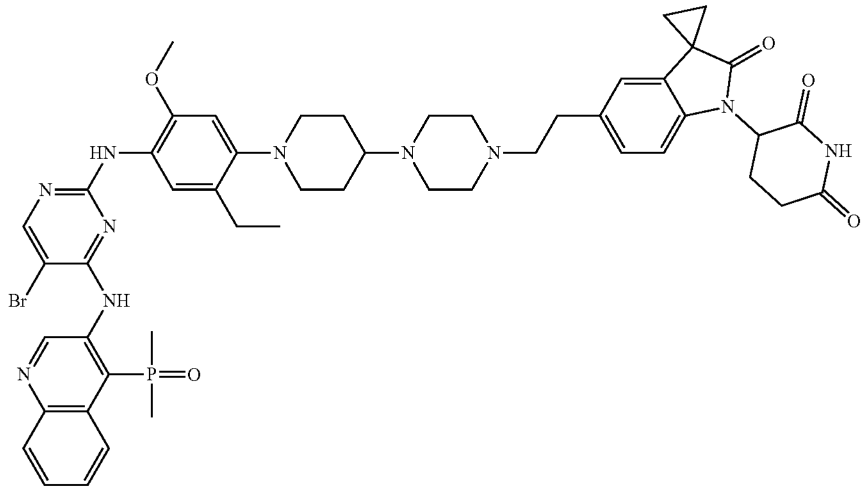 [SMILES: CCc1cc(Nc2ncc(Br)c(Nc3cnc4ccccc4c3P(C)(C)=O)n2)c(OC)cc1N1CCC(N2CCN(CCc3ccc4c(c3)C3(CC3)C(=O)N4C3CCC(=O)NC3=O)CC2)CC1]

A mixture of 3-(5'-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-2'-oxospiro[cyclopropane-1,3'-indolin]-1'-yl)-1-((2-(trimethyl silyl)ethoxy)methyl)piperidine-2,6-dione (35 mg, 0.03 mmol) in DCM (1 mL) was added TFA (5 mL) which was stirred at rt for 16 h. The mixture was concentrated under vacuum. The residue was dissolved in THF (5 mL) and added $NH_3 \cdot H_2O$ (0.5 mL). The mixture was stirred at rt for 5 min. The mixture was diluted with water (50 mL), extracted with DCM (3x50 mL). The combined organic layers were dried over $Na_2SO_4$, filtered and concentrated under vacuum. The residue was purified by Prep-HPLC with the following conditions: Anal Column: SunFire Prep C18 OBD, 5 μm, 19x150 mm, Column Temp: Room temperature, Mobile Phase A: $H_2O$ (0.1% FA), Mobile Phase B: ACN, Gradient Table: Mobile Phase B (15-35%), Time (min): 0-17 min to afford the product (6.56 mg, 20.6%). $[M+H]^+$=989.4. $^1H$ NMR (500 MHz, DMSO) $\delta_H$ 11.68 (s, 1H), 11.07 (s, 1H), 9.44 (s, 1H), 8.25 (s, 1H), 8.21-8.14 (m, 1H), 8.02-7.96 (m, 2H), 7.75-7.69 (m, 1H), 7.67-7.62 (m, 1H), 7.43-7.39 (m, 1H), 7.07-7.04 (m, 1H), 6.93-6.88 (m, 2H), 6.71-6.69 (m, 1H), 5.36-5.27 (m, 1H), 3.77 (s, 3H), 2.97-2.83 (m, 4H), 2.75-2.54 (m, 14H), 2.39-2.25 (m, 4H), 2.06 (s, 3H), 2.04 (s, 3H), 1.99-1.92 (m, 1H), 1.87-1.78 (m, 2H), 1.66-1.60 (m, 2H), 1.57-1.49 (m, 4H), 0.81-0.69 (m, 3H).

Example 25: 3-(5-(3-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazine-1-carbonyl)azetidin-1-yl)-1H-indazol-1-yl)piperidine-2,6-dione Step 1: Tert-butyl 1-(1-(1-(4-methoxybenzyl)-2,6-dioxopiperidin-3-yl)-1H-indazol-5-yl)azetidine-3-carboxylate

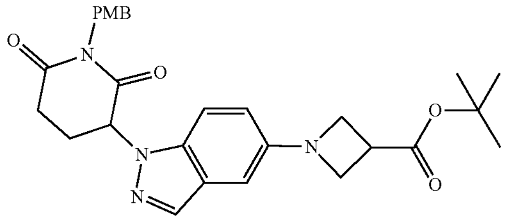

To a mixture of 3-(5-bromo-1H-indazol-1-yl)-1-(4-methoxybenzyl)piperidine-2,6-dione (1 g, 2.34 mmol), HCl salt of tert-butyl azetidine-3-carboxylate (677 mg, 3.51 mmol), Ruphos Pd G3 (198 mg, 0.23 mmol), $Cs_2CO_3$ (3.05 g, 9.36 mmol) in toluene (25 mL) was stirred at 100° C. for 15 hrs. After cooling to r.t, the solid was filtered off, the filtrate was concentrated in vacuo. The residue was purified by silica gel column (PE:EA=1:1) to afford the product (580 mg, 49%). $[M+H]^+$=505.2.

Step 2: 1-(1-(2,6-dioxopiperidin-3-yl)-1H-indazol-5-yl)azetidine-3-carboxylic acid

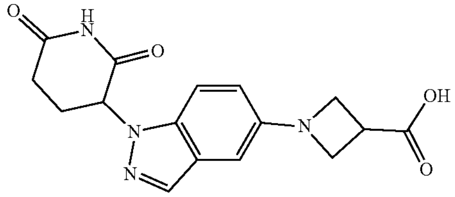 [SMILES: O=C1CCC(n2ncc3cc(N4CC(C(=O)O)C4)ccc32)C(=O)N1]

To a solution of tert-butyl 1-(1-(1-(4-methoxybenzyl)-2,6-dioxopiperidin-3-yl)-1H-indazol-5-yl)azetidine-3-carboxylate (580 mg, 1.15 mmol) in toluene (6 mL) and MsOH (2 mL) was stirred at 80° C. for 16 hrs. After cooling to r.t, the reaction mixture was concentrated in vacuum. The residue was purified by reversed phase column ($CH_3CN$: $H_2O$ (0.1% FA)=20:80) to afford the product (140 mg, 37%). $[M-H]^-$=327.1.

Step 3: 3-(5-(3-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazine-1-carbonyl)azetidin-1-yl)-1H-indazol-1-yl)piperidine-2,6-dione

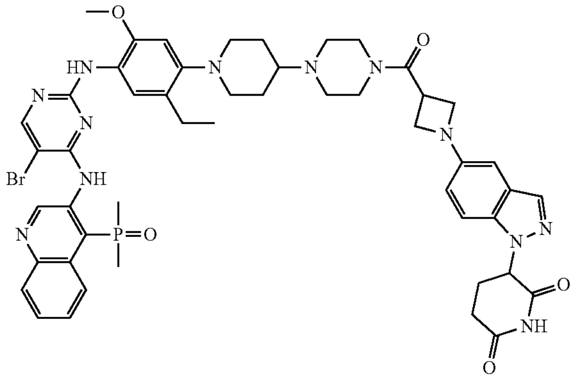 [SMILES: CCc1cc(Nc2ncc(Br)c(Nc3cnc4ccccc4c3P(C)(C)=O)n2)c(OC)cc1N1CCC(N2CCN(C(=O)C3CN(c4ccc5c(cnn5C5CCC(=O)NC5=O)c4)C3)CC2)CC1]

The titled compound (14 mg, 32%) was prepared in a manner similar to that in Example 15 step 5 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and 1-(1-(2,6-dioxopiperidin-3-yl)-1H-indazol-5-yl)azetidine-3-carboxylic acid. $^1H$ NMR (500 MHz, DMSO) δ 11.61 (s, 1H), 10.99 (s, 1H), 9.38 (s, 1H), 8.19 (s, 1H), 8.11 (t, J=11.0 Hz, 1H), 7.98-7.87 (m, 2H), 7.83 (s, 1H), 7.66 (t, J=7.8 Hz, 1H), 7.58 (t, J=7.2 Hz, 1H), 7.42 (d, J=9.0 Hz, 1H), 7.35 (s, 1H), 6.69 (dd, J=9.0, 2.1 Hz, 1H), 6.64 (s, 1H), 6.60 (d, J=1.8 Hz, 1H), 5.69-5.66 (m, 1H), 3.97 (t, J=7.3 Hz, 2H), 3.85-3.80 (m, 2H), 3.78-3.74 (m, 1H), 3.71 (s, 3H), 3.42 (s, 2H), 3.28 (s, 3H), 2.87 (d, J=10.7 Hz, 2H), 2.82-2.75 (m, 1H), 2.69-2.60 (m, 2H), 2.58-2.54 (m, 2H), 2.47 (s, 2H), 2.34-2.21 (m, 4H), 2.20-2.09 (m, 1H), 1.96 (t, J=19.2 Hz, 6H), 1.75 (d, J=11.0 Hz, 2H), 1.55-1.39 (m, 2H), 0.69 (s, 3H). $[M+H]^+$=1003.3.

Example 26: 3-(5-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazin-1-yl)ethyl)-1H-indazol-1-yl)piperidine-2,6-dione Step 1: 3-(5-bromo-1H-indazol-1-yl)-1-(4-methoxybenzyl)piperidine-2,6-dione and 3-(5-bromo-2H-indazol-2-yl)-1-(4-methoxybenzyl)piperidine-2,6-dione compound 1

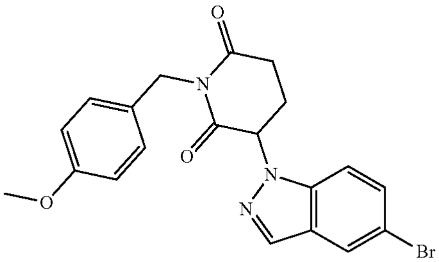

-continued compound 2

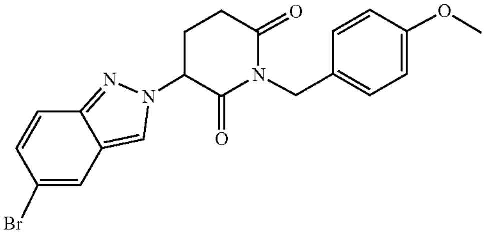

To a solution of 5-bromo-1H-indazole (2.0 g, 10.2 mmol) and 1-(4-methoxybenzyl)-2,6-dioxopiperidin-3-yl trifluoromethanesulfonate (This intermediate was prepared according to the same manner described in WO2020113233A1) (5.8 g, 15.3 mmol) in THF (50 mL) was added t-BuOK (15 mL, 15.3 mmol) at 0° C. Then the mixture was stirred at 30° C. for 2 hrs. The reaction was quenched with water and the mixture was extracted with DCM (3×300 mL). The combined organic layers were washed with brine (300 mL), dried over anhydrous $Na_2SO_4$. After filtration, the filtrate was concentrated under reduced pressure. The residue was purified by silica gel column chromatography, eluted with DCM/MeOH (15:1) to afford the title compound 1 (1.2 g, 28%). $[M+H]^+$=428.2 and title compound 2 (1.3 g, 30%) $[M+H]^+$=428.1

Step 2:
3-(5-bromo-1H-indazol-1-yl)piperidine-2,6-dione

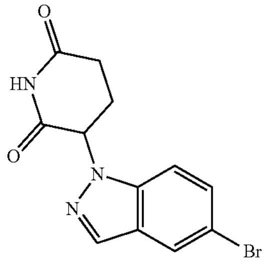 [SMILES: O=C1CCC(n2ncc3cc(Br)ccc32)C(=O)N1]

A mixture of 3-(5-bromo-1H-indazol-1-yl)-1-(4-methoxybenzyl)piperidine-2,6-dione (1.2 g, 2.8 mmol) in toluene (10 mL) and MsOH (5 mL) was stirred in a round bottom flask at 100° C. under nitrogen atmosphere for 3 hours. The reaction mixture was concentrated under reduced pressure. The residue was purified by purified by silica gel column chromatography, eluted with DCM/MeOH (15:1) to afford the product (480 mg, 56%), [M+H]+=308.2.

Step 3: (E)-3-(5-(2-ethoxyvinyl)-1H-indazol-1-yl) piperidine-2,6-dione

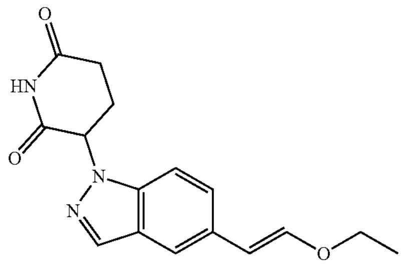 [SMILES: CCO/C=C/c1ccc2c(cnn2C2CCC(=O)NC2=O)c1]

A mixture of 3-(5-bromo-1H-indazol-1-yl)piperidine-2,6-dione (70 mg, 0.23 mmol), (E)-2-(2-ethoxyvinyl)-4,4,5,5-tetramethyl-1,3,2-dioxaborolane (91 mg, 0.46 mmol), $Pd(dppf)Cl_2$ (15 mg, 0.023 mmol) and CsF (100 mg, 0.69 mmol) in DMF (5 mL) was stirred in a round bottom flask at 90° C. under nitrogen atmosphere for 2 hrs. The reaction mixture was allowed to cool down to room temperature. The resulting mixture was extracted with DCM (3×100 mL). The combined organic layers were washed with brine (100 mL), dried over anhydrous $Na_2SO_4$. After filtration, the filtrate was concentrated under reduced pressure. The residue was purified by silica gel column chromatography, eluted with DCM/MeOH (15:1) to afford the product (50 mg, 72%), [M+H]+=300.0.

Step 4: 2-(1-(2,6-dioxopiperidin-3-yl)-1H-indazol-5-yl)acetaldehyde

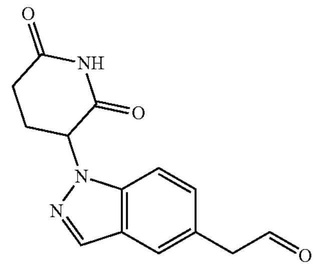 [SMILES: O=CCc1ccc2c(cnn2C2CCC(=O)NC2=O)c1]

A mixture of (E)-3-(5-(2-ethoxyvinyl)-1H-indazol-1-yl) piperidine-2,6-dione (51 mg, 0.17 mmol) in HCOOH (2 mL) was stirred in a round bottom flask at 25° C. under nitrogen atmosphere for 30 min. The reaction mixture was concentrated under reduced pressure to afford crude product which was directly used for the next step. [M+H]+=272.2.

Step 5: 3-(5-(2-(4-(1-(4-((5-bromo-4-((4-(dimethylphosphoryl)quinolin-3-yl)amino)pyrimidin-2-yl) amino)-2-ethyl-5-methoxyphenyl) piperidin-4-yl) piperazin-1-yl)ethyl)-1H-indazol-1-yl)piperidine-2,6-dione

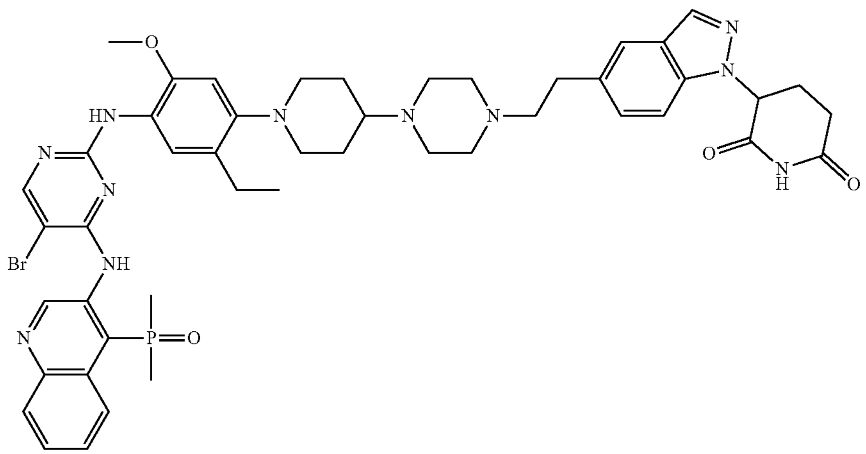 [SMILES: CCc1cc(Nc2ncc(Br)c(Nc3cnc4ccccc4c3P(C)(C)=O)n2)c(OC)cc1N1CCC(N2CCN(CCc3ccc4c(cnn4C4CCC(=O)NC4=O)c3)CC2)CC1]

The titled compound (7 mg, 12%) was prepared in a manner similar to that in Example 1 step 11 from (3-((5-bromo-2-((5-ethyl-2-methoxy-4-(4-(piperazin-1-yl)piperidin-1-yl)phenyl)amino)pyrimidin-4-yl)amino)quinolin-4-yl)dimethylphosphine oxide and 2-(1-(2,6-dioxopiperidin-3-yl)-1H-indazol-5-yl)acetaldehyde. $^1H$ NMR (500 MHz, DMSO) δ 11.68 (s, 1H), 11.09 (s, 1H), 9.44 (s, 1H), 8.29-8.13 (m, 2H), 8.00 (dd, J=21.3, 13.0 Hz, 3H), 7.72 (t, J=7.4 Hz, 1H), 7.64 (t, J=7.7 Hz, 1H), 7.59 (s, 1H), 7.53 (d, J=8.7 Hz, 1H), 7.42 (s, 1H), 7.30 (d, J=8.7 Hz, 1H), 6.70 (s, 1H), 5.81 (dd, J=11.4, 4.1 Hz, 1H), 3.77 (s, 3H), 2.98-2.66 (m, 8H), 2.65-2.50 (m, 10H), 2.37-2.19 (m, 5H), 2.05 (d, J=13.4 Hz, 6H), 1.82 (d, J=10.7 Hz, 2H), 1.59-1.44 (m, 2H), 0.75 (s, 3H); $[M+H]^+$=948.3.

Example 30: 3-(4'-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl) piperazin-1-yl)ethyl)-2'-oxospiro[cyclopropane-1,3'-indolin]-1'-yl)piperidine-2,6-dione

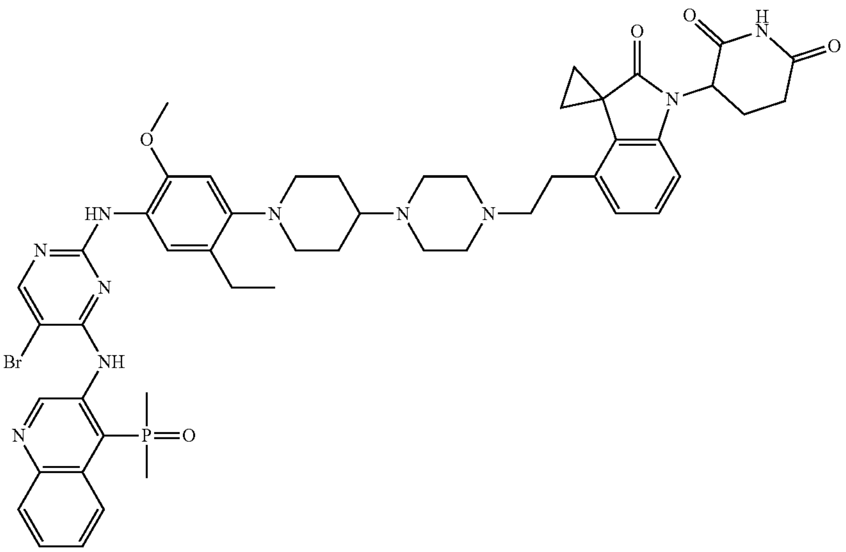 [SMILES: CCc1cc(Nc2ncc(Br)c(Nc3cnc4ccccc4c3P(C)(C)=O)n2)c(OC)cc1N1CCC(N2CCN(CCc3cccc4c3C3(CC3)C(=O)N4C3CCC(=O)NC3=O)CC2)CC1]

The titled compound was synthesized in the procedures similar to Example 24. $[M+H]^+$=989.4. $^1$H NMR (500 MHz, DMSO) $\delta_H$ 11.68 (s, 1H), 11.08 (s, 1H), 9.45 (s, 1H), 8.26 (s, 1H), 8.19 (d, J=10.0 Hz, 1H), 8.03-7.97 (m, 2H), 7.72 (t, J=10.0 Hz, 1H), 7.64 (t, J=10.0 Hz, 1H), 7.42 (s, 1H), 7.19-7.13 (m, 1H), 6.91-6.85 (m, 2H), 6.71 (s, 1H), 5.37-5.27 (m, 1H), 3.78 (s, 3H), 2.98-2.90 (m, 2H), 2.89-2.82 (m, 1H), 2.66-2.60 (m, 7H), 2.57-2.54 (m, 6H), 2.39-2.30 (m, 6H), 2.07 (s, 3H), 2.04 (s, 3H), 1.99-1.93 (m, 3H), 1.89-1.79 (m, 2H), 1.58-1.44 (m, 4H), 0.80-0.71 (m, 3H).

Example 32: 3-(4-((((1r,3r)-3-((4-(1-(4-((5-bromo-4-((4-(dimethylphosphoryl)quinolin-3-yl)amino)pyrimidin-2-yl)amino)-2-ethyl-5-methoxyphenyl)piperidin-4-yl)piperazin-1-yl)methyl)cyclobutyl)(methyl)amino)-2,6-difluorophenyl)piperidine-2,6-dione

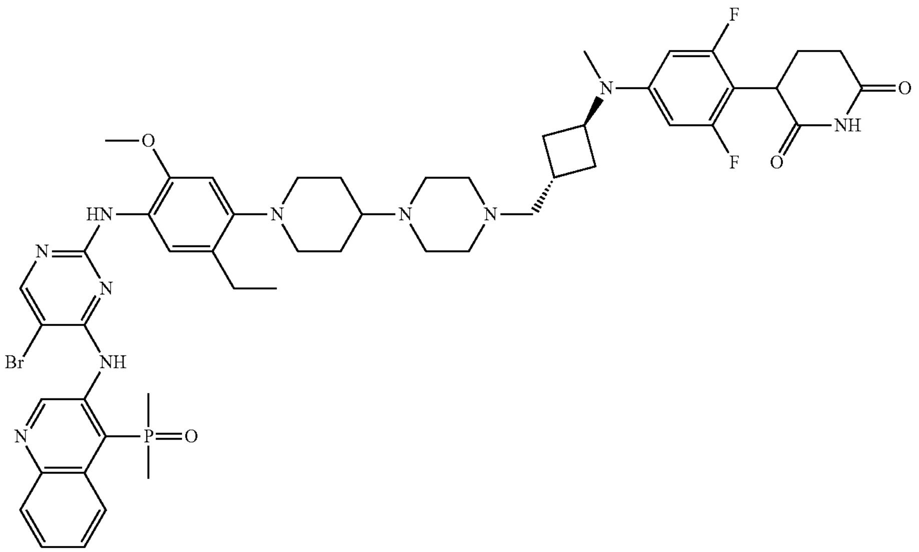 [SMILES: CCc1cc(Nc2ncc(Br)c(Nc3cnc4ccccc4c3P(C)(C)=O)n2)c(OC)cc1N1CCC(N2CCN(C[C@H]3C[C@H](N(C)c4cc(F)c(C5CCC(=O)NC5=O)c(F)c4)C3)CC2)CC1]

The titled compound was synthesized in the procedures similar to Example 1. 1H NMR (400 MHz, DMSO) δ 11.68 (s, 1H), 10.85 (s, 1H), 9.44 (s, 1H), 8.25 (s, 1H), 8.20-8.17 (m, 1H), 8.02-7.97 (m, 2H), 7.72 (t, J=7.7 Hz, 1H), 7.64 (t, J=7.5 Hz, 1H), 7.41 (s, 1H), 6.70 (s, 1H), 6.42 (s, 1H), 6.40 (s, 1H), 4.28-4.22 (m, 1H), 4.03 (dd, J=12.5, 5.1 Hz, 1H), 3.77 (s, 3H), 2.92 (d, J=10.9 Hz, 2H), 2.83 (s, 3H), 2.76 (dd, J=17.0, 5.3 Hz, 1H), 2.61 (t, J=11.3 Hz, 3H), 2.58-2.51 (m, 4H), 2.48 (d, J=7.8 Hz, 3H), 2.40 (s, 2H), 2.35-2.31 (m, 3H), 2.27 (s, 1H), 2.23-2.18 (m, 2H), 2.09-2.04 (m, 9H), 2.02-2.00 (m, 1H), 1.97-1.93 (m, 1H), 1.82 (d, J=10.5 Hz, 2H), 1.55-1.48 (m, 2H), 0.75 (s, 3H); $[M+H]^+$=1013.4.

Example 33: 3-(4-(2-(4-(1-(4-((5-bromo-4-((4-(dimethylphosphoryl)quinolin-3-yl)amino)pyrimidin-2-yl)amino)-3-methoxyphenyl) piperidin-4-yl)piperazin-1-yl)ethyl)-2,6-difluorophenyl)piperidine-2,6-dione

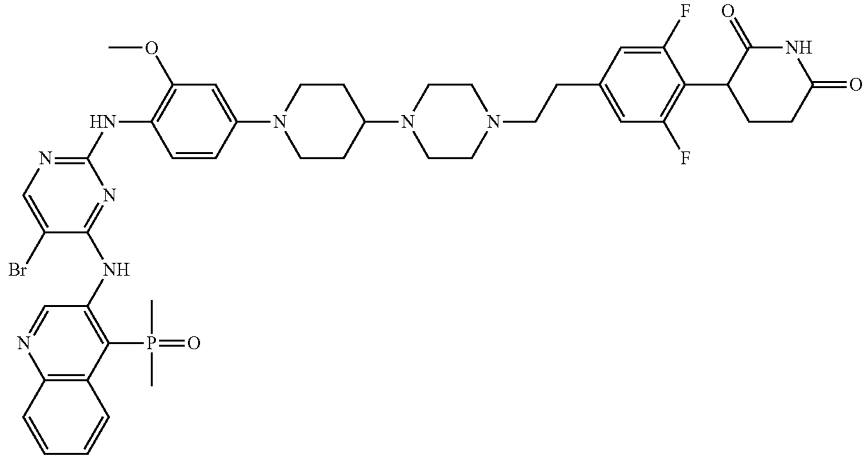 [SMILES: COc1cc(N2CCC(N3CCN(CCc4cc(F)c(C5CCC(=O)NC5=O)c(F)c4)CC3)CC2)ccc1Nc1ncc(Br)c(Nc2cnc3ccccc3c2P(C)(C)=O)n1]

The titled compound was synthesized in the procedures similar to Example 1. 1H NMR (400 MHz, DMSO) δ 11.74 (s, 1H), 10.95 (s, 1H), 9.50 (s, 1H), 8.20 (s, 1H), 8.15 (d, J=8.4 Hz, 1H), 8.03 (d, J=8.2 Hz, 1H), 8.00 (s, 1H), 7.71 (t, J=7.6 Hz, 1H), 7.63 (t, J=7.6 Hz, 1H), 7.30 (d, J=7.6 Hz, 1H), 7.02 (d, J=10.1 Hz, 2H), 6.55 (d, J=1.9 Hz, 1H), 6.22 (s, 1H), 4.20 (dd, J=12.7, 5.1 Hz, 1H), 3.77 (s, 3H), 3.62 (d, J=11.7 Hz, 2H), 2.86-2.79 (m, 1H), 2.76 (dd, J=15.4, 8.1 Hz, 3H), 2.60 (t, J=11.4 Hz, 3H), 2.56-2.51 (m, 3H), 2.46-2.36 (m, 5H), 2.31-2.26 (m, 1H), 2.12 (dd, J=13.4, 4.1 Hz, 1H), 2.05 (d, J=13.5 Hz, 7H), 2.02-1.97 (m, 1H), 1.82 (d, J=11.2 Hz, 2H), 1.51-1.44 (m, 2H); $[M+H]^+$=916.4.

Example 34: 3-(4-(2-(4-(1-(4-((5-bromo-4-((4-(dimethylphosphoryl)quinolin-3-yl)amino)pyrimidin-2-yl)amino)-5-methoxy-2-methylphenyl)piperidin-4-yl)piperazin-1-yl)ethyl)-2,6-difluorophenyl) piperidine-2,6-dione

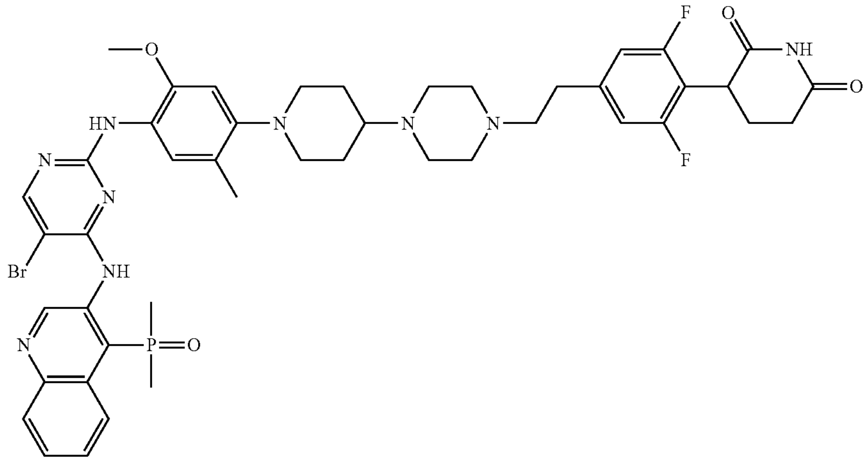 [SMILES: COc1cc(N2CCC(N3CCN(CCc4cc(F)c(C5CCC(=O)NC5=O)c(F)c4)CC3)CC2)c(C)cc1Nc1ncc(Br)c(Nc2cnc3ccccc3c2P(C)(C)=O)n1]

The titled compound was synthesized in the procedures similar to Example 1. 1H NMR (400 MHz, DMSO) δ 11.75 (s, 1H), 10.95 (s, 1H), 9.49 (d, J=3.7 Hz, 1H), 8.24 (s, 1H), 8.18 (d, J=8.3 Hz, 1H), 8.01 (d, J=8.3 Hz, 1H), 7.96 (s, 1H), 7.72 (t, J=7.6 Hz, 1H), 7.64 (t, J=7.8 Hz, 1H), 7.37 (s, 1H), 7.04 (s, 1H), 7.02 (s, 1H), 6.64 (s, 1H), 4.20 (dd, J=12.6, 5.1 Hz, 1H), 3.77 (s, 3H), 3.01 (d, J=11.3 Hz, 2H), 2.86-2.81 (m, 1H), 2.76 (dd, J=14.6, 6.9 Hz, 3H), 2.59-2.53 (m, 8H), 2.48-2.43 (m, 3H), 2.31-2.27 (m, 1H), 2.13 (dd, J=13.0, 3.9 Hz, 1H), 2.05 (d, J=13.5 Hz, 7H), 2.02-1.97 (m, 1H), 1.94 (s, 3H), 1.83 (d, J=11.3 Hz, 2H), 1.57-1.52 (m, 2H); [M+H]*=930.4.

Example 35: 3-(4-(2-(4-(1-(4-((5-bromo-4-((4-(dimethylphosphoryl)quinolin-3-yl)amino)pyrimidin-2-yl)amino)-5-ethoxy-2-ethylphenyl) piperidin-4-yl) piperazin-1-yl)ethyl)-2,6-difluorophenyl)piperidine-2,6-dione Step 1: 4-ethyl-3-fluorophenol

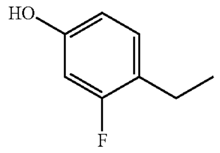

To a solution of 1-(2-fluoro-4-hydroxyphenyl)ethan-1-one (5.0 g, 32 mmol) in $H_2O$ (17 mL) was added Zn powder (6.5 g, 100 mmol) and HCl (conc., 17 mL). The reaction mixture was stirred at 115° C. for 18 hours. After cooling to room temperature, the mixture was extracted with MTBE (2×30 mL). The organic phase was combined and washed with brine (2×60 mL). The organic phase was concentrated to afford the crude product, which was used in next step without further purification.

Step 2: 4-ethoxy-1-ethyl-2-fluorobenzene

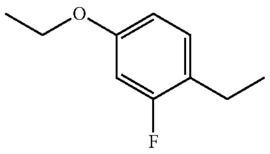

To a solution of 4-ethyl-3-fluorophenol (1.4 g, 10 mmol) in DMF (50 mL) was added $K_2CO_3$ (2.1 g, 15 mmol), EtI (2.0 g, 13 mmol). The reaction mixture was stirred at 20-30° C. for 18 hours. After quenching the reaction with $H_2O$ (50 mL), the reaction mixture was extracted with PE/EA (1:1, 30 mL). The organic phase was combined and washed with brine (2×50 mL). Organic phase was concentrated and purified by silica gel column chromatography with PE (100%) to give product (1.2 g, 71.4%). $^1H$ NMR (500 MHz, CDCl3) δ 7.06 (t, J=9.0 Hz, 1H), 6.62-6.55 (m, 2H), 3.98 (q, J=7.0 Hz, 2H), 2.59 (q, J=7.5 Hz, 2H), 1.39 (t, J=7.0 Hz, 3H), 1.19 (t, J=7.5 Hz, 3H).

Step 3: 1-ethoxy-4-ethyl-5-fluoro-2-nitrobenzene

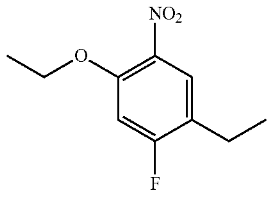

To a solution of 4-ethoxy-1-ethyl-2-fluorobenzene (1.4 g, 8.3 mmol) in $Ac_2O$ (15 mL) was added $HNO_3$ (conc., 4 mL) dropwise. After stirring for 30 min at 0° C., the reaction was quenching with $H_2O$ (30 mL) and $Na_2CO_3$ solution (20 mL). The mixture was extracted with EA (2×30 mL). Organic phase was combined and washed with brine (2×50 ml), which was concentrated to afford the crude residue. The crude residue was purified by pre-flash with pure PE to give the product (1.2 g, 67.8%). $[M+H]^+$=214.2.

Step 4: tert-butyl 4-(1-(5-ethoxy-2-ethyl-4-nitrophenyl)piperidin-4-yl)piperazine-1-carboxylate

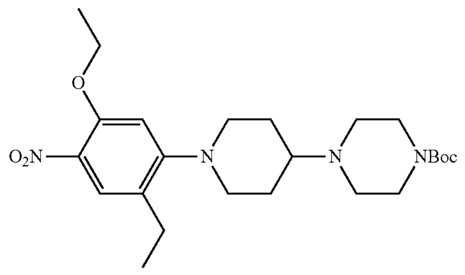 [SMILES: CCOc1cc(N2CCC(N3CCN(C(=O)OC(C)(C)C)CC3)CC2)c(CC)cc1[N+](=O)[O-]]

A solution of 1-ethoxy-4-ethyl-5-fluoro-2-nitrobenzene (0.7 g, 3.3 mmol), tert-butyl 4-(piperidin-4-yl)piperazine-1-carboxylate (0.97 g, 3.6 mmol) and $K_2CO_3$ (0.9 g, 6.6 mmol) in DMF was stirred at 120° C. for 18 hs. The reaction was quenched with $H_2O$ (50 mL) and extracted with EA (2×50 mL). The organic was combined and washed with brine (2×100 mL). After concentration, the crude product (0.9 g) was purified by silica gel column chromatography (DCM/MeOH=100:1 to 10:1) to afford the product (915 mg, 60%). $^1H$ NMR (500 MHz, $CDCl_3$) δ7.81 (s, 1H), 6.58 (s, 1H), 4.17-4.11 (m, 3H), 3.48 (br, 4H), 3.26 (d, J=12 Hz, 2H), 2.69 (t, J=12 Hz, 2H), 2.62-2.57 (m, 6H), 2.43 (br, 1H), 1.94 (br, 2H), 1.73 (br, 2H), 1.50-1.43 (m, 12H), 1.32-1.15 (t, J=7.5 Hz, 3H).

Step 5: tert-butyl 4-(1-(4-amino-5-ethoxy-2-ethylphenyl)piperidin-4-yl)piperazine-1-carboxylate

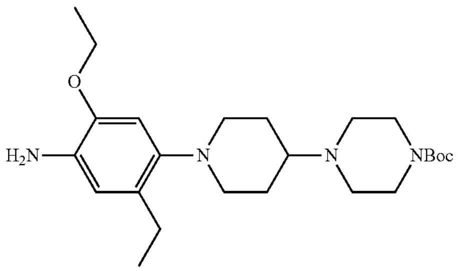

A solution of tert-butyl 4-(1-(5-ethoxy-2-ethyl-4-nitrophenyl)piperidin-4-yl)piperazine-1-carboxylate (0.9 g, 1.9 mmol) and Pd/C (0.09 g) in THF (30 mL) was stirred at room temperature for 18 hours under $H_2$ atmosphere. After filtering off solid, the filtrate was concentrated to afford the crud product (0.50 g, 61%) for next step without further purification. $[M+H]^+=433.5$.

Step 6: (3-((5-bromo-2-((2-ethoxy-5-ethyl-4-(4-(piperazin-1-yl)piperidin-1-yl)phenyl)amino)pyrimidin-4-yl)amino)quinolin-4-yl)dimethylphosphine oxide

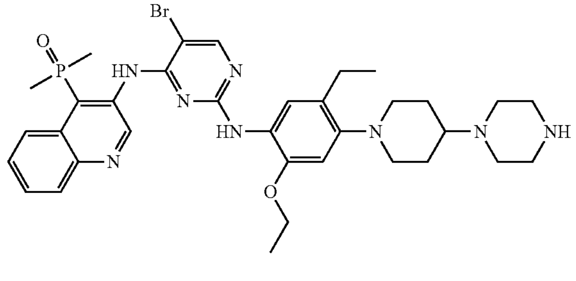 [SMILES: CCOc1cc(N2CCC(N3CCNCC3)CC2)c(CC)cc1Nc1ncc(Br)c(Nc2cnc3ccccc3c2P(C)(C)=O)n1]

A solution of tert-butyl 4-(1-(4-amino-5-ethoxy-2-ethylphenyl)piperidin-4-yl)piperazine-1-carboxylate (120 mg, 0.3 mmol), TsOH (268 mg, 1.6 mmol) and (3-((5-bromo-2-chloropyrimidin-4-yl)amino)quinolin-4-yl)dimethylphosphine oxide (169 mg, 0.39 mmol) in n-BuOH was stirred at 105° C. for 18 hours. The solvent was evaporated to afford the residue and was washed with sat. aq. $Na_2CO_3$ solution (30 mL) and the mixture was extracted with DCM (2×20 mL). Organic phase was concentrated and purified by pre-TLC with DCM/MeOH (5:1) to afford the product (115 mg, 54%). $[M+H]^+=707.4$.

Step 7: 3-(4-(2-(4-(1-(4-((5-bromo-4-((4-(dimethylphosphoryl)quinolin-3-yl)amino)pyrimidin-2-yl)amino)-5-ethoxy-2-ethylphenyl) piperidin-4-yl)piperazin-1-yl)ethyl)-2,6-difluorophenyl)piperidine-2,6-dione

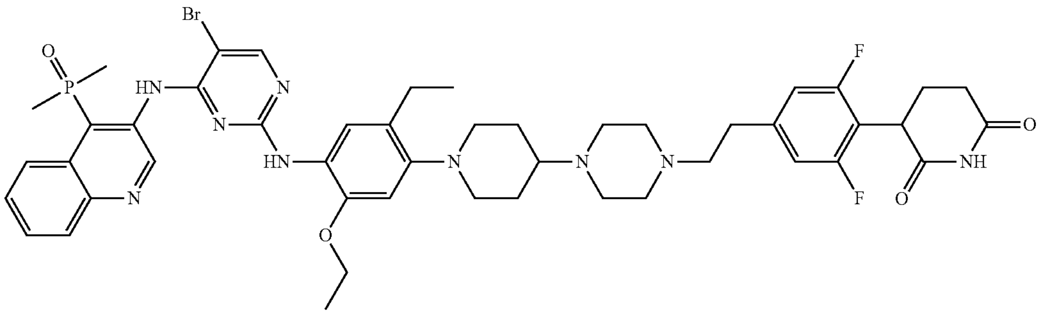 [SMILES: CCOc1cc(N2CCC(N3CCN(CCc4cc(F)c(C5CCC(=O)NC5=O)c(F)c4)CC3)CC2)c(CC)cc1Nc1ncc(Br)c(Nc2cnc3ccccc3c2P(C)(C)=O)n1]

To a solution of (3-((5-bromo-2-((2-ethoxy-5-ethyl-4-(4-(piperazin-1-yl)piperidin-1-yl)phenyl)amino)pyrimidin-4-yl)amino)quinolin-4-yl)dimethylphosphine oxide (40 mg, 0.06 mmol), 2-(4-(2,6-dioxopiperidin-3-yl)-3,5-difluorophenyl)acetaldehyde (15 mg, 0.06 mmol) in DCM/EtOH (5:1, 30 mL) was added NaOAc (50 mg, 0.6 mmol). After stirring for 30 min, $NaBH(OAc)_3$ (100 mg, 0.5 mmol) was added. The mixture was stirred for another 18 hs. The solvent was evaporated to afford the crude residue which was purified by pre-HPLC (0.1% FA in water:acetonitrile=90:10~60:40 gradient elution) to afford the product (6.8 mg, 12%). $^1H$ NMR (500 MHz, d-DMSO) δ 11.64 (s, 1H), 10.95 (s, 1H), 9.43 (d, J=4.0 Hz, 1H), 8.27 (s, 1H), 8.22 (d, J=8.5 Hz, 1H), 8.01 (d, J=8.5 Hz, 1H), 7.90 (s, 1H), 7.73 (t, J=7.5 Hz, 1H), 7.65 (t, J=7.5 Hz, 1H), 7.45 (s, 1H), 7.04 (d, J=10.0 Hz, 2H), 6.68 (s, 1H), 4.20 (dd, J=12.5, 5.5 Hz, 1H), 4.03 (q, J=7.0 Hz, 2H), 3.04-2.53 (m, 17H), 2.28 (d, J=7.0 Hz, 3H), 2.18-1.95 (m, 9H), 1.89 (br, 2H), 1.56 (br, 2H), 1.29 (t, J=7.0 Hz, 3H), 0.68 (s, 3H). $[M+H]^+=958.5$.

Example 36: 3-(4-(4-(2-(4-(1-(4-((5-bromo-4-((4-(dimethylphosphoryl)quinolin-3-yl)amino)pyrimidin-2-yl)amino)-5-ethoxy-2-ethylphenyl)piperidin-4-yl)piperazin-1-yl)ethyl)piperidin-1-yl)-2,6-difluorophenyl)piperidine-2,6-dione

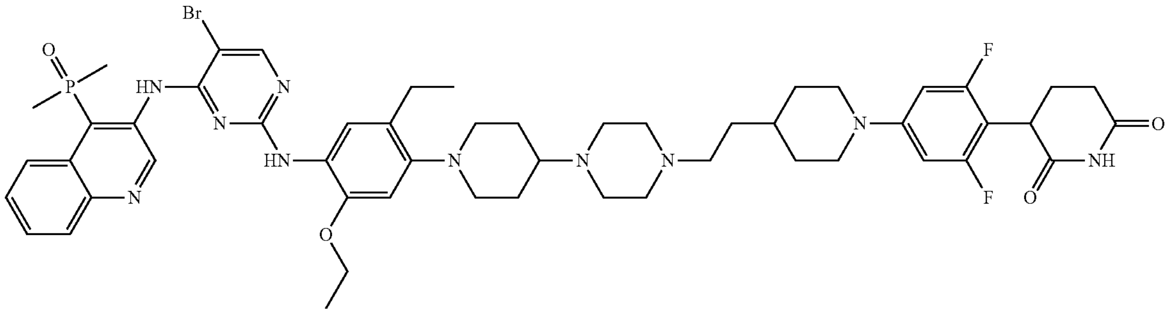 [SMILES: CCOc1cc(N2CCC(N3CCN(CCC4CCN(c5cc(F)c(C6CCC(=O)NC6=O)c(F)c5)CC4)CC3)CC2)c(CC)cc1Nc1ncc(Br)c(Nc2cnc3ccccc3c2P(C)(C)=O)n1]

The titled compound was synthesized in the procedures similar to Example 35. $^1$H NMR (500 MHz, d-DMSO) δ 11.64 (s, 1H), 10.86 (s, 1H), 9.43 (s, 1H), 8.29-8.15 (m, 2H), 8.00 (d, J=7.5 Hz, 1H), 7.89 (s, 1H), 7.72 (s, 1H), 7.64 (s, 1H), 7.44 (s, 1H), 6.69-6.44 (m, 3H), 4.12-3.91 (m, 4H), 3.73 (d, J=12.5 Hz, 2H), 2.98-2.53 (m, 10H), 2.40-2.15 (m, 8H), 2.15-1.86 (m, 10H), 1.85-1.64 (m, 4H), 1.56-1.07 (m, 10H), 0.67 (s, 3H). $[M+H]^+$=1041.7

Example 37: 3-(4-(2-(4-(1-(4-((5-bromo-2-((4-(dimethylphosphoryl)-1,8-naphthyridin-3-yl)amino)pyrimidin-4-yl)amino)-2-ethyl-5-methoxyphenyl)piperidin-4-yl)piperazin-1-yl)ethyl)-2,6-difluorophenyl)piperidine-2,6-dione Step 1: 4-iodo-1,8-naphthyridin-3-amine

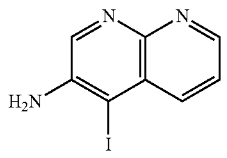 [SMILES: Nc1cnc2ncccc2c1I]

The titled compound (440 mg, 46%) was prepared in a manner similar to that in Example 1 step 1 from 1,8-naphthyridin-3-amine and iodine chloride. [M+H]+=272.0.

Step 2: (3-amino-1,8-naphthyridin-4-yl)dimethylphosphine oxide

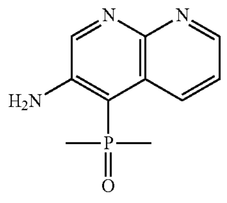

The titled compound (340 mg, 46%) was prepared in a manner similar to that in Example 1 step 2 from 4-iodo-1,8-naphthyridin-3-amine and dimethylphosphine oxide. [M+H]+=222.1

Step 3: (3-((5-bromo-2-chloropyrimidin-4-yl)amino)-1,8-naphthyridin-4-yl)dimethylphosphine oxide

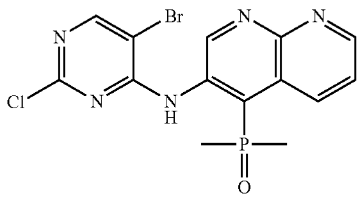 [SMILES: CP(C)(=O)c1c(Nc2nc(Cl)ncc2Br)cnc2ncccc12]

The titled compound (330 mg, 68%) was prepared in a manner similar to that in Example 1 step 3 from (3-amino-1,8-naphthyridin-4-yl)dimethylphosphine oxide and 5-bromo-2,4-dichloropyrimidine. $[M+H]^+$=412.0.

Step 4: (3-((5-bromo-2-((5-ethyl-2-methoxy-4-(4-(piperazin-1-yl)piperidin-1-yl)phenyl)amino)pyrimidin-4-yl)amino)-1,8-naphthyridin-4-yl)dimethylphosphine oxide

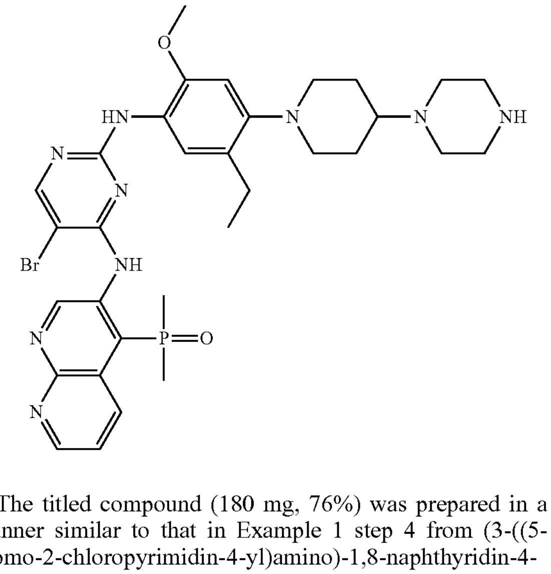

The titled compound (180 mg, 76%) was prepared in a manner similar to that in Example 1 step 4 from (3-((5-bromo-2-chloropyrimidin-4-yl)amino)-1,8-naphthyridin-4-yl)dimethylphosphine oxide and tert-butyl 4-(1-(4-amino-2-ethyl-5-methoxyphenyl)piperidin-4-yl)piperazine-1-carboxylate. $[M+H]^+$=694.1.

Step 5: 3-(4-(2-(4-(1-(4-((5-bromo-2-((4-(dimethylphosphoryl)-1,8-naphthyridin-3-yl)amino)pyrimidin-4-yl)amino)-2-ethyl-5-methoxyphenyl)piperidin-4-yl)piperazin-1-yl)ethyl)-2,6-difluorophenyl) piperidine-2,6-dione

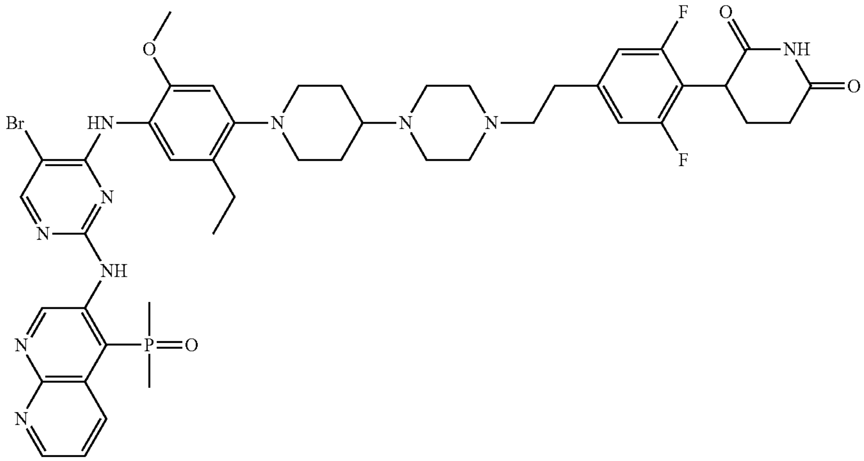 [SMILES: CCc1cc(Nc2nc(Nc3cnc4ncccc4c3P(C)(C)=O)ncc2Br)c(OC)cc1N1CCC(N2CCN(CCc3cc(F)c(C4CCC(=O)NC4=O)c(F)c3)CC2)CC1]

The titled compound (10.2 mg, 28%) was prepared in a manner similar to that in Example 2 step 7 from (3-((5-bromo-2-((5-ethyl-2-methoxy-4-(4-(piperazin-1-yl)piperidin-1-yl)phenyl)amino)pyrimidin-4-yl)amino)-1,8-naphthyridin-4-yl) dimethylphosphine oxide and 2-(4-(2,6-dioxopiperidin-3-yl)-3,5-difluorophenyl)acetaldehyde. 1H NMR (500 MHz, DMSO) δ 11.47 (s, 1H), 10.94 (s, 1H), 9.59 (s, 1H), 9.00 (s, 1H), 8.79 (s, 1H), 8.26 (s, 1H), 7.98 (s, 1H), 7.63 (s, 1H), 7.40 (s, 1H), 7.03 (d, J=10.0 Hz, 2H), 6.68 (s, 1H), 4.20 (dd, J=12.6, 5.2 Hz, 1H), 3.77 (m, 4H), 2.92 (d, J=10.5 Hz, 2H), 2.83-2.74 (m, 3H), 2.62-2.52 (m, 7H), 2.48-2.42 (m, 4H), 2.27 (s, 3H), 2.17-1.99 (m, 9H), 1.81 (d, J=10.7 Hz, 2H), 1.57-1.47 (m, 2H), 0.67 (m, 3H). $[M+H]^+$ =945.5.

Example 38: 3-(4-(2-(4-(1-(4-((5-bromo-4-((4-(dimethylphosphoryl)-1,7-naphthyridin-3-yl)amino)pyrimidin-2-yl)amino)-2-ethyl-5-methoxyphenyl)piperidin-4-yl)piperazin-1-yl)ethyl)-2,6-difluorophenyl) piperidine-2,6-dione

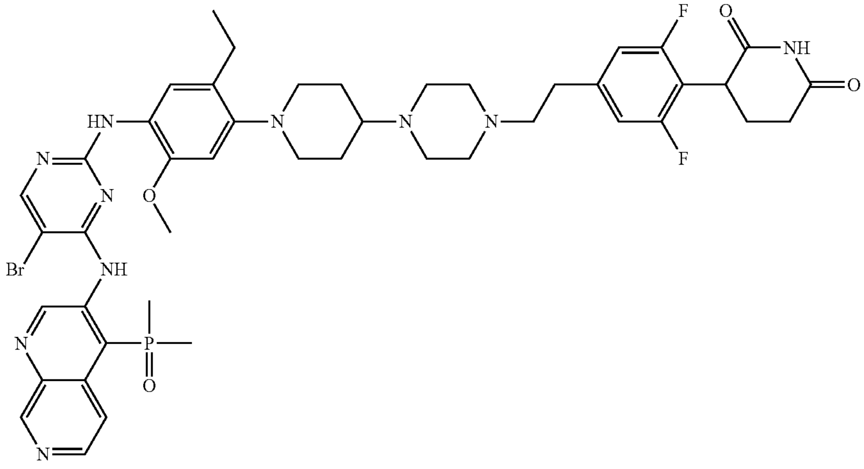 [SMILES: CCc1cc(Nc2ncc(Br)c(Nc3cnc4cnccc4c3P(C)(C)=O)n2)c(OC)cc1N1CCC(N2CCN(CCc3cc(F)c(C4CCC(=O)NC4=O)c(F)c3)CC2)CC1]

Step 1: 4-iodo-1,7-naphthyridin-3-amine

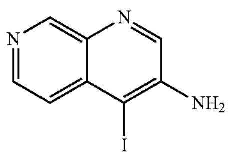 [SMILES: Nc1cnc2cnccc2c1I]

The titled compound (1.8 g, 97%) was prepared in a manner similar to that in Example 1 step 1 from 1,7-naphthyridin-3-amine and iodine monochloride. $[M+H]^+$= 271.9.

Step 2: (3-amino-1,7-naphthyridin-4-yl)dimethylphosphine oxide

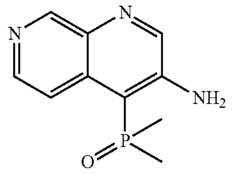

The titled compound (1.4 g, 95%) was prepared in a manner similar to that in Example 1 step 2 from 4-iodo-1,7-naphthyridin-3-amine and dimethylphosphine oxide. $[M+H]^+$=222.1.

Step 3: (3-((5-bromo-2-chloropyrimidin-4-yl)amino)-1,7-naphthyridin-4-yl)dimethylphosphine oxide

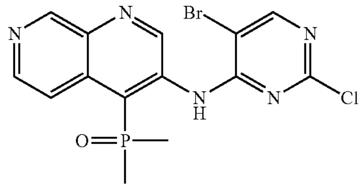 [SMILES: CP(C)(=O)c1c(Nc2nc(Cl)ncc2Br)cnc2cnccc12]

The titled compound (60 mg, 16%) was prepared in a manner similar to that in Example 1 step 3 from (3-amino-1,7-naphthyridin-4-yl)dimethylphosphine oxide and 5-bromo-2,4-dichloropyrimidine. $[M+H]^+$=411.9.

Step 4: (3-((5-bromo-2-((5-ethyl-2-methoxy-4-(4-(piperazin-1-yl)piperidin-1-yl)phenyl)amino)pyrimidin-4-yl)amino)-1,7-naphthyridin-4-yl)dimethylphosphine oxide

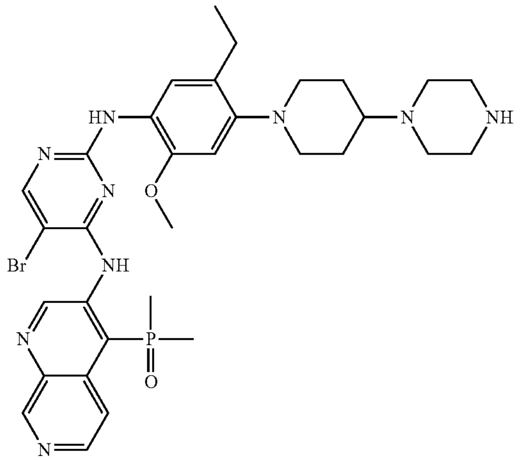 [SMILES: CCc1cc(Nc2ncc(Br)c(Nc3cnc4cnccc4c3P(C)(C)=O)n2)c(OC)cc1N1CCC(N2CCNCC2)CC1]

The titled compound (60 mg, 71%) was prepared in a manner similar to that in Example 1 step 4 from (3-((5-bromo-2-chloropyrimidin-4-yl)amino)-1,7-naphthyridin-4-yl)dimethylphosphine oxide and tert-butyl 4-(1-(4-amino-2-ethyl-5-methoxyphenyl)piperidin-4-yl)piperazine-1-carboxylate. $[M+H]^+$=694.2.

Step 5: 3-(4-(2-(4-(1-(4-((5-bromo-4-((4-(dimethylphosphoryl)-1,7-naphthyridin-3-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

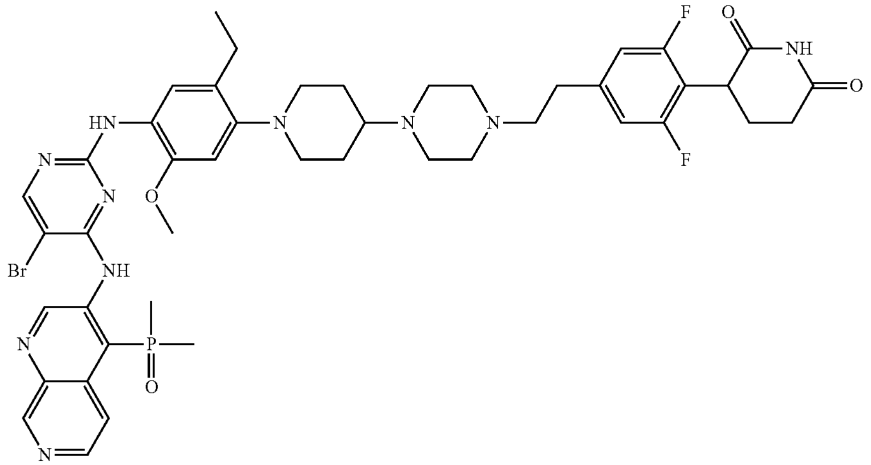 [SMILES: CCc1cc(Nc2ncc(Br)c(Nc3cnc4cnccc4c3P(C)(C)=O)n2)c(OC)cc1N1CCC(N2CCN(CCc3cc(F)c(C4CCC(=O)NC4=O)c(F)c3)CC2)CC1]

To a solution of (3-((5-bromo-2-((5-ethyl-2-methoxy-4-(4-(piperazin-1-yl)piperidin-1-yl)phenyl)amino)pyrimidin-4-yl)amino)-1,7-naphthyridin-4-yl)dimethylphosphine oxide (30 mg, 0.04 mmol) in DCM (5 mL) was added 2-(4-(2,6-dioxopiperidin-3-yl)-3,5-difluorophenyl)acetaldehyde (11 mg, 0.04 mmol) at 20° C. The mixture was stirred at 20° C. for 1 hr and STAB (18 mg, 0.08 mmol) was added. Then the mixture was stirred at 20° C. for 12 hrs. Water (10 mL) was poured into the mixture. Then the mixture was extracted with DCM (50 mL). The organic phase was washed with brine (50 mL), dried over $Na_2SO_4$, filtered and concentrated in vacuum. The residue was purified by prep-HPLC with C-18 column chromatography (0.1% FA in water:acetonitrile=90:10~60:40 gradient elution) to afford the product (2.3 mg, 5.5%). $^1H$ NMR (500 MHz, DMSO) δ 12.16 (s, 1H), 10.96 (s, 1H), 9.68 (s, 1H), 9.25 (s, 1H), 8.56 (d, J=6.0 Hz, 1H), 8.29 (d, J=28.2 Hz, 2H), 7.97 (d, J=5.8 Hz, 1H), 7.39 (s, 1H), 7.09 (d, J=10.0 Hz, 2H), 6.74 (s, 1H), 4.22 (dd, J=12.7, 4.9 Hz, 1H), 3.79 (s, 3H), 3.51-3.29 (m, 4H), 3.05 (d, J=9.2 Hz, 4H), 2.93-2.75 (m, 5H), 2.72-2.55 (m, 5H), 2.43-2.36 (m, 3H), 2.23-1.94 (m, 10H), 1.75 (s, 2H), 0.83 (s, 3H). $[M+H]^+$=945.6.

Example 124: 3-(4-(2-(4-(1-(4-((5-bromo-4-((4-(dimethylphosphoryl)-6-fluoroquinolin-3-yl)amino)pyrimidin-2-yl)amino)-5-ethoxy-2-ethylphenyl)piperidin-4-yl)piperazin-1-yl)ethyl)-3-methyl-2-oxo-2,3-dihydro-1H-benzol[d]imidazol-1-yl) piperidine-2,6-dione

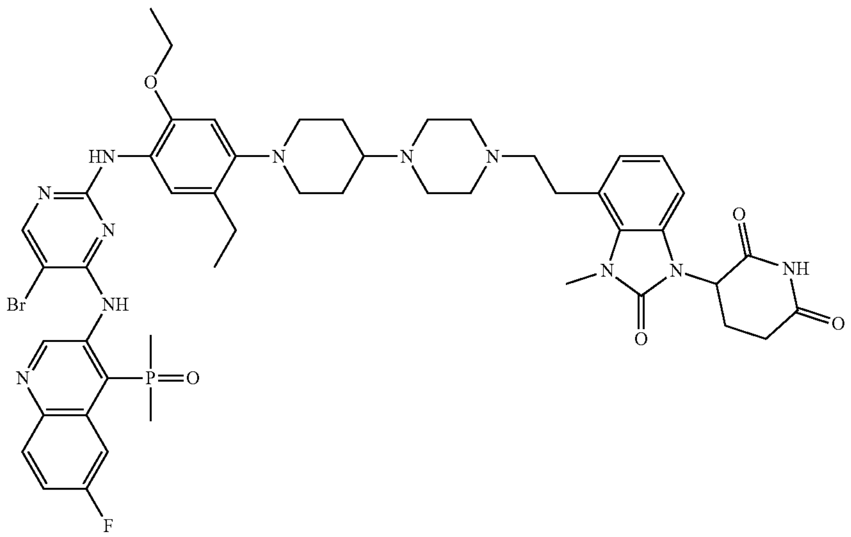 [SMILES: CCOc1cc(N2CCC(N3CCN(CCc4cccc5c4n(C)c(=O)n5C4CCC(=O)NC4=O)CC3)CC2)c(CC)cc1Nc1ncc(Br)c(Nc2cnc3ccc(F)cc3c2P(C)(C)=O)n1]

The title compound was prepared in a procedure similar to that in Example 1. $[M+H]^+$=1010.4.

Example 125: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-3-methyl-2-oxo-2,3-dihydro-1H-benzo[d]imidazol-1-yl)piperidine-2,6-dione

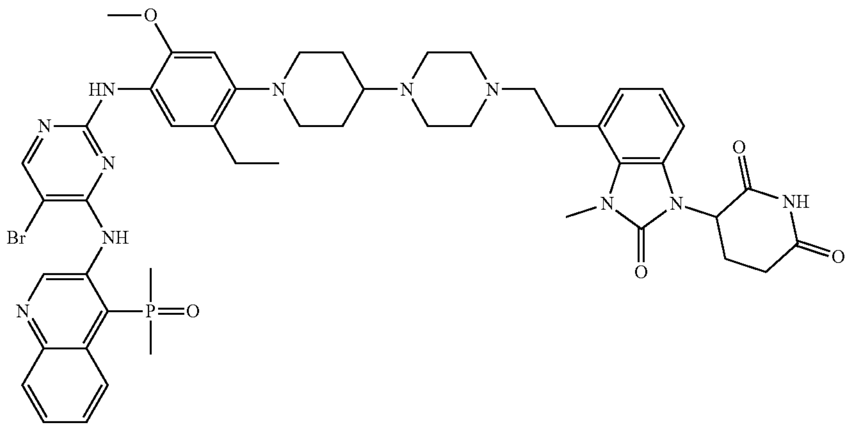 [SMILES: CCc1cc(Nc2ncc(Br)c(Nc3cnc4ccccc4c3P(C)(C)=O)n2)c(OC)cc1N1CCC(N2CCN(CCc3cccc4c3n(C)c(=O)n4C3CCC(=O)NC3=O)CC2)CC1]

The title compound was prepared in a procedure similar to that in Example 1. $[M+H]^+$=978.7.

Example 126: (S)-3-(7-(2-(4-(1-(4-((5-bromo-4-((4-(dimethylphosphoryl)quinolin-3-yl)amino)pyrimidin-2-yl)amino)-2-ethyl-5-methoxyphenyl)piperidin-4-yl)piperazin-1-yl)ethyl)-4-fluoro-2-oxobenzo[d]oxazol-3(2H)-yl)piperidine-2,6-dione

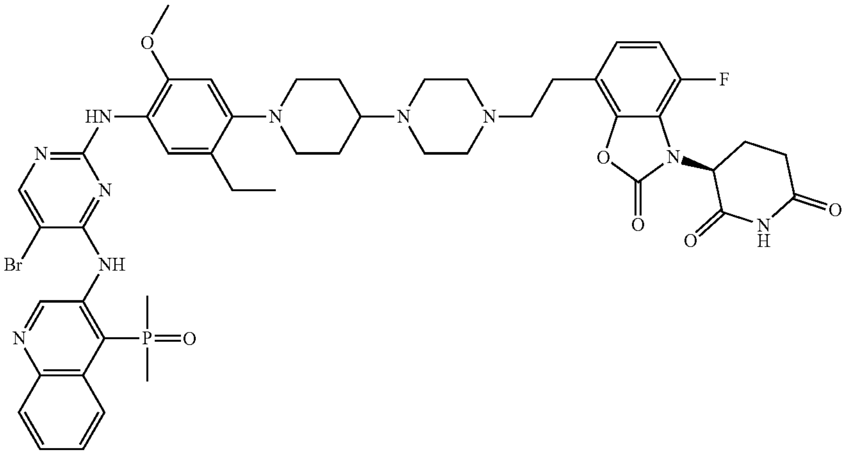 [SMILES: CCc1cc(Nc2ncc(Br)c(Nc3cnc4ccccc4c3P(C)(C)=O)n2)c(OC)cc1N1CCC(N2CCN(CCc3ccc(F)c4c3oc(=O)n4[C@H]3CCC(=O)NC3=O)CC2)CC1]

The title compound was prepared in a procedure similar to that in Example 1. $[M+H]^+$=983.7.

Example 130: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-7-fluoro-3-methyl-2-oxo-2,3-dihydro-1H-benzo[d]imidazol-1-yl) piperidine-2,6-dione

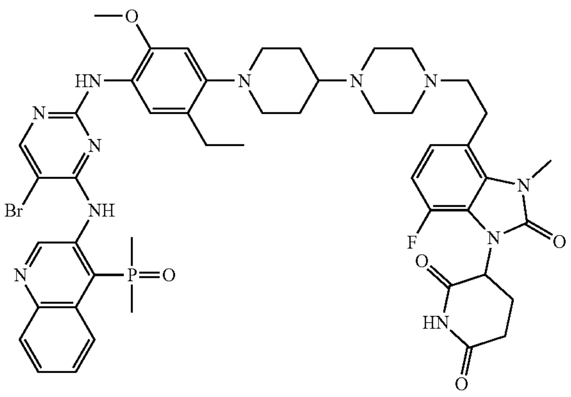 [SMILES: CCc1cc(Nc2ncc(Br)c(Nc3cnc4ccccc4c3P(C)(C)=O)n2)c(OC)cc1N1CCC(N2CCN(CCc3ccc(F)c4c3n(C)c(=O)n4C3CCC(=O)NC3=O)CC2)CC1]

The title compound was prepared in a procedure similar to that in Example 1. $[M+H]^+$=996.7.

Example 132: 3-(6-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-2-oxobenzo[d]oxazol-3(2H)-yl)piperidine-2,6-dione

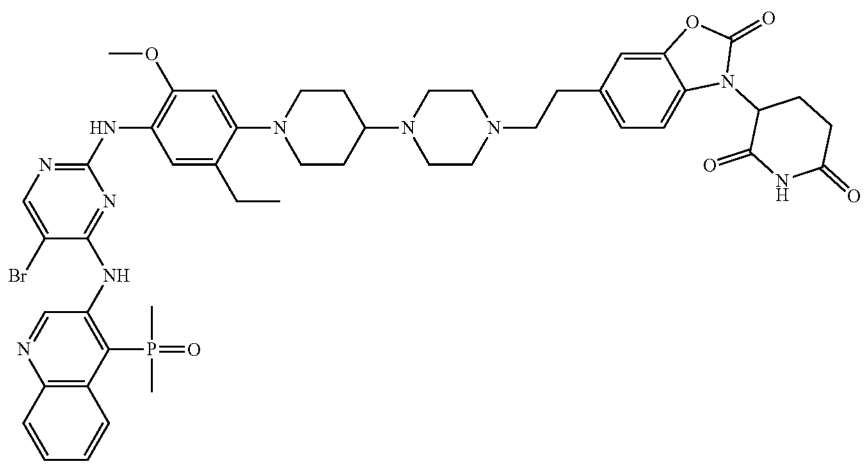 [SMILES: CCc1cc(Nc2ncc(Br)c(Nc3cnc4ccccc4c3P(C)(C)=O)n2)c(OC)cc1N1CCC(N2CCN(CCc3ccc4c(c3)oc(=O)n4C3CCC(=O)NC3=O)CC2)CC1]

The title compound was prepared in a procedure similar to that in Example 1. $[M+H]^+$=965.3.

Example 133: 3-(6-(2-(4-(1-(4-((5-bromo-4-((4-(dimethylphosphoryl)-7-fluoroquinolin-3-yl)amino) pyrimidin-2-yl)amino)-5-ethoxy-2-ethylphenyl)piperidin-4-yl)piperazin-1-yl)ethyl)-2-oxobenzo[d] oxazol-3(2H)-yl)piperidine-2,6-dione

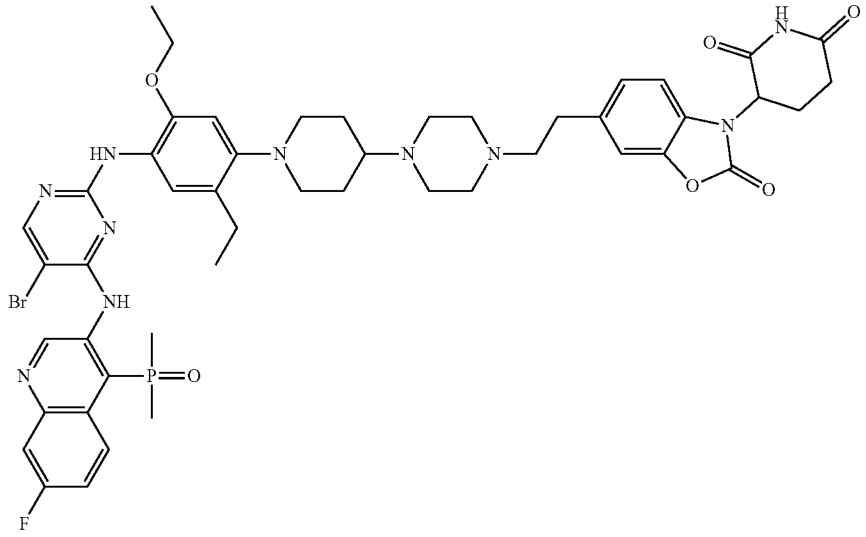 [SMILES: CCOc1cc(N2CCC(N3CCN(CCc4ccc5c(c4)oc(=O)n5C4CCC(=O)NC4=O)CC3)CC2)c(CC)cc1Nc1ncc(Br)c(Nc2cnc3cc(F)ccc3c2P(C)(C)=O)n1]

The title compound was prepared in a procedure similar to that in Example 1. $[M+H]^+$=997.7.

Example 134: 3-(6-(2-(4-(1-(4-((5-bromo-4-((4-(dimethylphosphoryl)-7-fluoroquinolin-3-yl)amino) pyrimidin-2-yl)amino)-2-ethyl-5-methoxyphenyl) piperidin-4-yl)piperazin-1-yl)ethyl)-2-oxobenzo[d] oxazol-3(2H)-yl)piperidine-2,6-dione

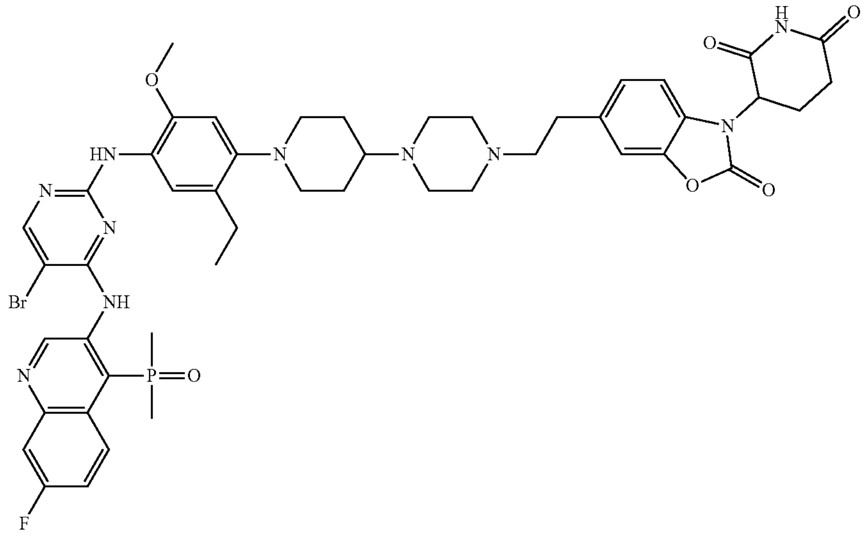 [SMILES: CCc1cc(Nc2ncc(Br)c(Nc3cnc4cc(F)ccc4c3P(C)(C)=O)n2)c(OC)cc1N1CCC(N2CCN(CCc3ccc4c(c3)oc(=O)n4C3CCC(=O)NC3=O)CC2)CC1]

The title compound was prepared in a procedure similar to that in Example 1. $[M+H]^+$=983.6.

Example 135: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-3-ethyl-2-oxo-2,3-dihydro-1H-benzo[d]imidazol-1-yl)piperidine-2,6-dione

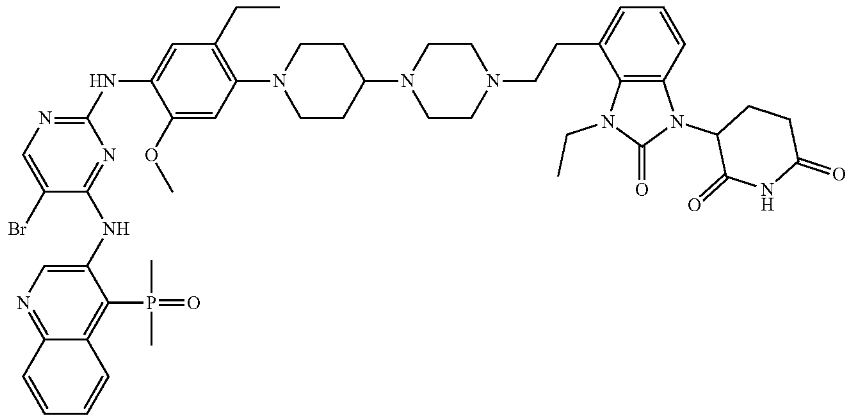

The title compound was prepared in a procedure similar to that in Example 1. $[M+H]^+$=992.1.

Example 136: 3-(7-(2-(4-(1-(4-((5-bromo-4-((4-(dimethylphosphoryl)quinolin-3-yl)amino)pyrimidin-2-yl)amino)-5-ethoxy-2-ethylphenyl) piperidin-4-yl)piperazin-1-yl)ethyl)-4,5-difluoro-2-oxobenzo[d]oxazol-3(2H)-yl)piperidine-2,6-dione

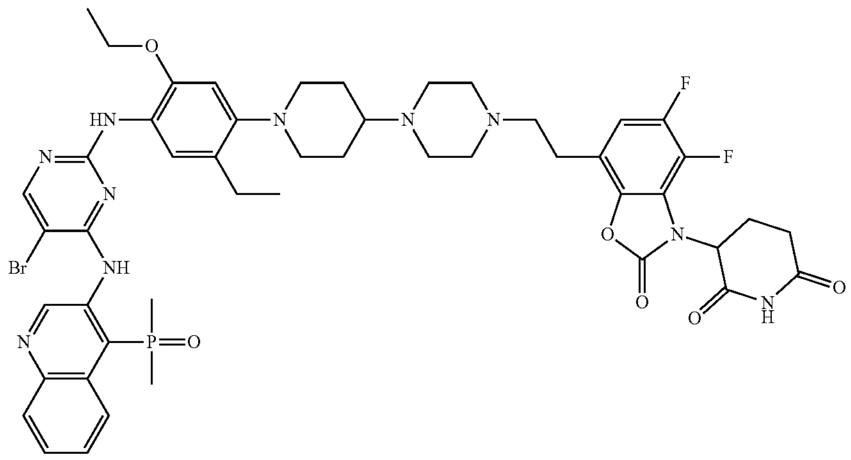 [SMILES: CCOc1cc(N2CCC(N3CCN(CCc4cc(F)c(F)c5c4oc(=O)n5C4CCC(=O)NC4=O)CC3)CC2)c(CC)cc1Nc1ncc(Br)c(Nc2cnc3ccccc3c2P(C)(C)=O)n1]

The title compound was prepared in a procedure similar to that in Example 1. $[M+H]^+=1015.6$.

Example 137: 3-(4-(2-(4-(1-(4-((5-bromo-4-((4-(dimethylphosphoryl)quinolin-3-yl)amino)pyrimidin-2-yl)amino)-5-ethoxy-2-ethylphenyl) piperidin-4-yl)piperazin-1-yl)ethyl)-5-fluoro-3-methyl-2-oxo-2,3-dihydro-1H-benzo[d]imidazol-1-yl) piperidine-2,6-dione

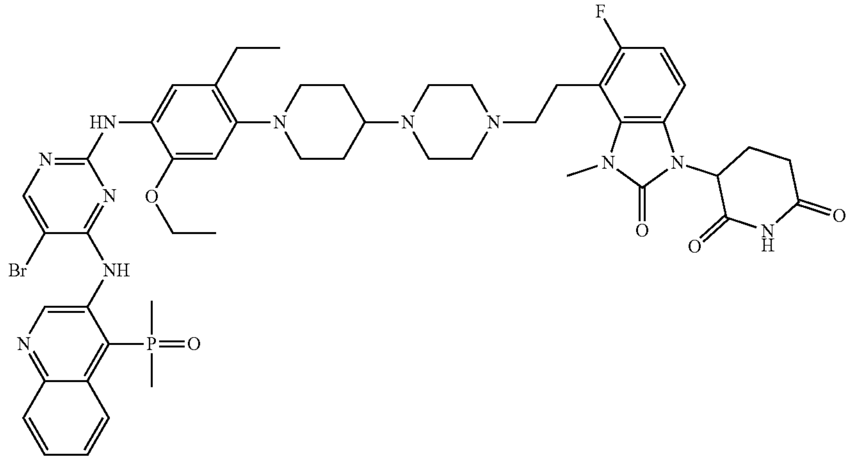 [SMILES: CCOc1cc(N2CCC(N3CCN(CCc4c(F)ccc5c4n(C)c(=O)n5C4CCC(=O)NC4=O)CC3)CC2)c(CC)cc1Nc1ncc(Br)c(Nc2cnc3ccccc3c2P(C)(C)=O)n1]

The title compound was prepared in a procedure similar to that in Example 1. $[M+H]^+=1010.2$.

Example 138: 3-(4-(2-(4-(1-(4-((5-bromo-4-((4-(dimethylphosphoryl)quinolin-3-yl)amino)pyrimidin-2-yl)amino)-5-ethoxy-2-ethylphenyl) piperidin-4-yl)piperazin-1-yl)ethyl)-3,3-dimethyl-2-oxoindolin-1-yl)piperidine-2,6-dione

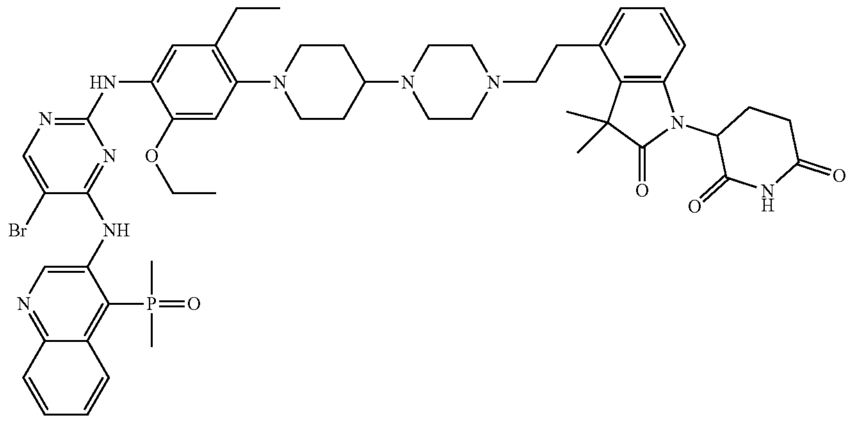 [SMILES: CCOc1cc(N2CCC(N3CCN(CCc4cccc5c4C(C)(C)C(=O)N5C4CCC(=O)NC4=O)CC3)CC2)c(CC)cc1Nc1ncc(Br)c(Nc2cnc3ccccc3c2P(C)(C)=O)n1]

The title compound was prepared in a procedure similar to that in Example 1. $[M+H]^+$=1005.2.

Example 139: 3-(6-(2-(4-(1-(4-((5-bromo-4-((4-(dimethylphosphoryl)quinolin-3-yl)amino)pyrimidin-2-yl)amino)-5-ethoxy-2-ethylphenyl) piperidin-4-yl)piperazin-1-yl)ethyl)-2-oxobenzo[d]oxazol-3(2H)-yl)piperidine-2,6-dione

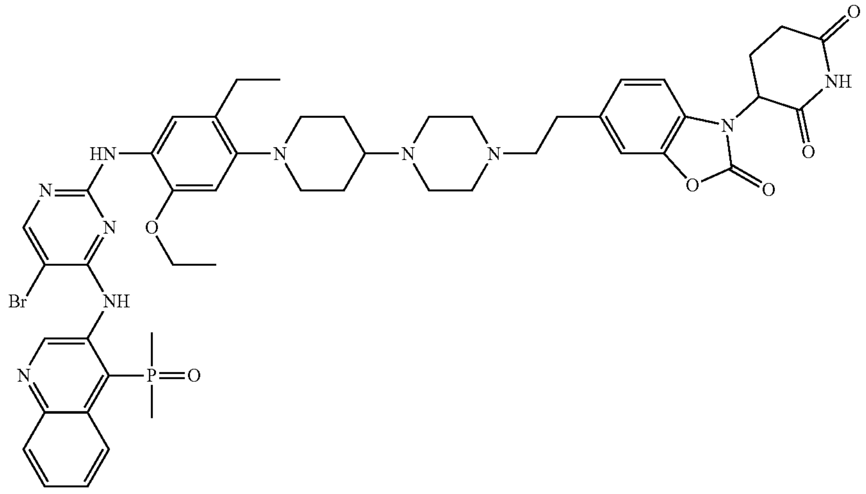 [SMILES: CCOc1cc(N2CCC(N3CCN(CCc4ccc5c(c4)oc(=O)n5C4CCC(=O)NC4=O)CC3)CC2)c(CC)cc1Nc1ncc(Br)c(Nc2cnc3ccccc3c2P(C)(C)=O)n1]

The title compound was prepared in a procedure similar to that in Example 1. $[M+H]^+$=979.1.

Example 140: 3-(4-(2-(4-(1-(4-((5-bromo-4-((4-(dimethylphosphoryl)quinolin-3-yl)amino)pyrimidin-2-yl)amino)-5-ethoxy-2-ethylphenyl) piperidin-4-yl)piperazin-1-yl)ethyl)-3-methyl-2-oxo-2,3-dihydro-1H-benzo[d]imidazol-1-yl)piperidine-2,6-dione

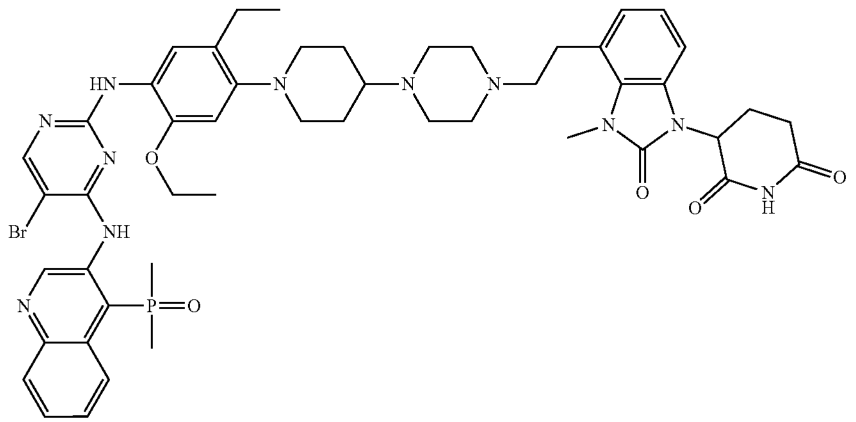 [SMILES: CCOc1cc(N2CCC(N3CCN(CCc4cccc5c4n(C)c(=O)n5C4CCC(=O)NC4=O)CC3)CC2)c(CC)cc1Nc1ncc(Br)c(Nc2cnc3ccccc3c2P(C)(C)=O)n1]

The title compound was prepared in a procedure similar to that in Example 1. $[M+H]^+$=992.3.

Example 142: 3-(6-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-7-fluoro-2-oxobenzo[d]oxazol-3(2H)-yl)piperidine-2,6-dione

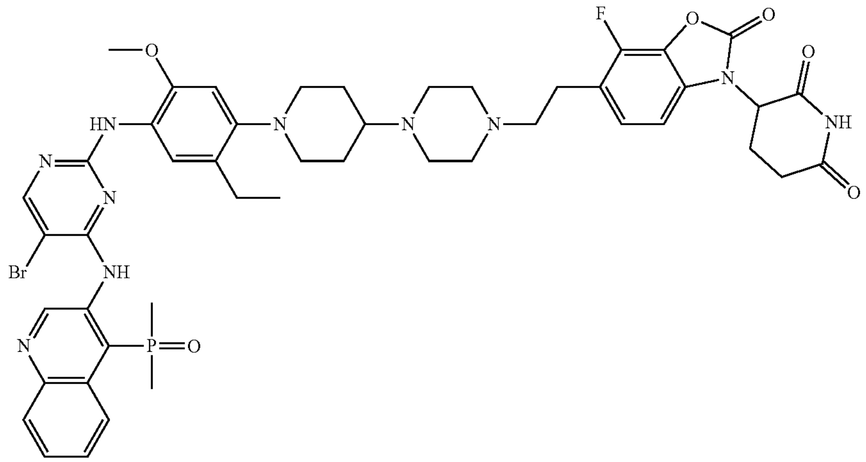 [SMILES: CCc1cc(Nc2ncc(Br)c(Nc3cnc4ccccc4c3P(C)(C)=O)n2)c(OC)cc1N1CCC(N2CCN(CCc3ccc4c(oc(=O)n4C4CCC(=O)NC4=O)c3F)CC2)CC1]

The title compound was prepared in a procedure similar to that in Example 1. $[M+H]^+$=983.7.

Example 147: 3-(4-(2-(4-(1-(4-((5-bromo-4-((4-(dimethylphosphoryl)-7-fluoroquinolin-3-yl)amino)pyrimidin-2-yl)amino)-5-ethoxy-2-ethylphenyl)piperidin-4-yl)piperazin-1-yl)ethyl)-3-methyl-2-oxo-2,3-dihydro-1H-benzol[d]imidazol-1-yl) piperidine-2,6-dione

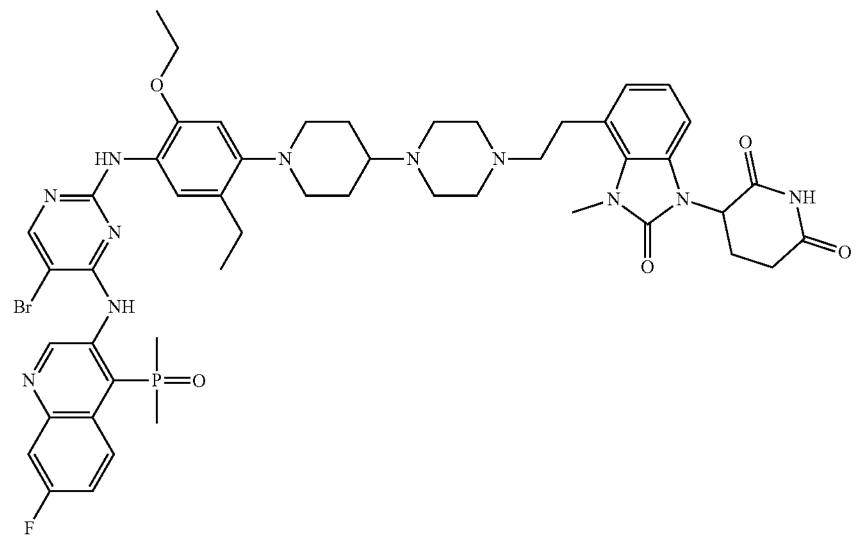 [SMILES: CCOc1cc(N2CCC(N3CCN(CCc4cccc5c4n(C)c(=O)n5C4CCC(=O)NC4=O)CC3)CC2)c(CC)cc1Nc1ncc(Br)c(Nc2cnc3cc(F)ccc3c2P(C)(C)=O)n1]

The title compound was prepared in a procedure similar to that in Example 1. $[M+H]^+=1010.7$.

Example 149: 3-(6-(2-(4-(1-(4-((5-bromo-4-((4-(dimethylphosphoryl)-7-fluoroquinolin-3-yl)amino)pyrimidin-2-yl)amino)-5-ethoxy-2-ethylphenyl)piperidin-4-yl)piperazin-1-yl)ethyl)-2-oxobenzo[d]oxazol-3(2H)-yl)piperidine-2,6-dione

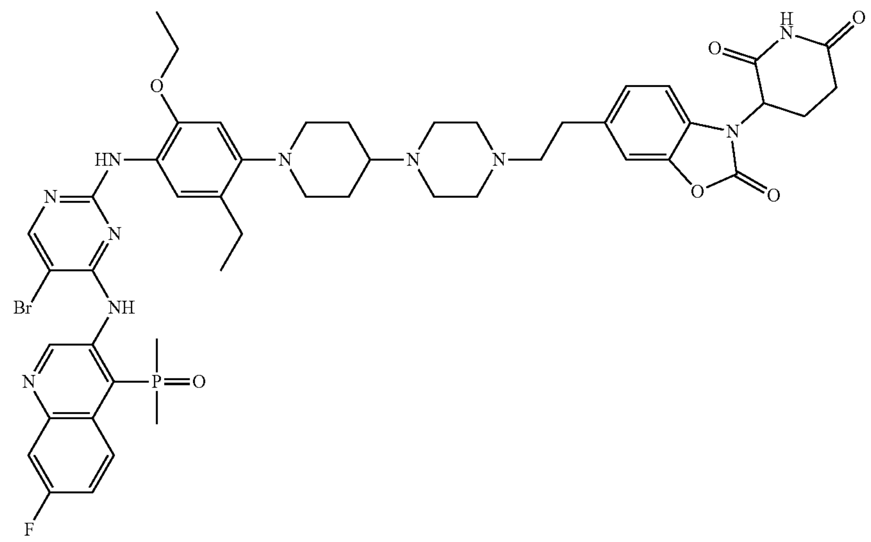

The title compound was prepared in a procedure similar to that in Example 1. $[M+H]^+=997.7$.

Example 151: (S)-3-(6-(2-(4-(1-(4-((5-bromo-4-((4-(dimethylphosphoryl)-7-fluoroquinolin-3-yl)amino)pyrimidin-2-yl)amino)-2-ethyl-5-methoxyphenyl)piperidin-4-yl)piperazin-1-yl)ethyl)-4-fluoro-2-oxobenzo[d]oxazol-3(2H)-yl)piperidine-2,6-dione

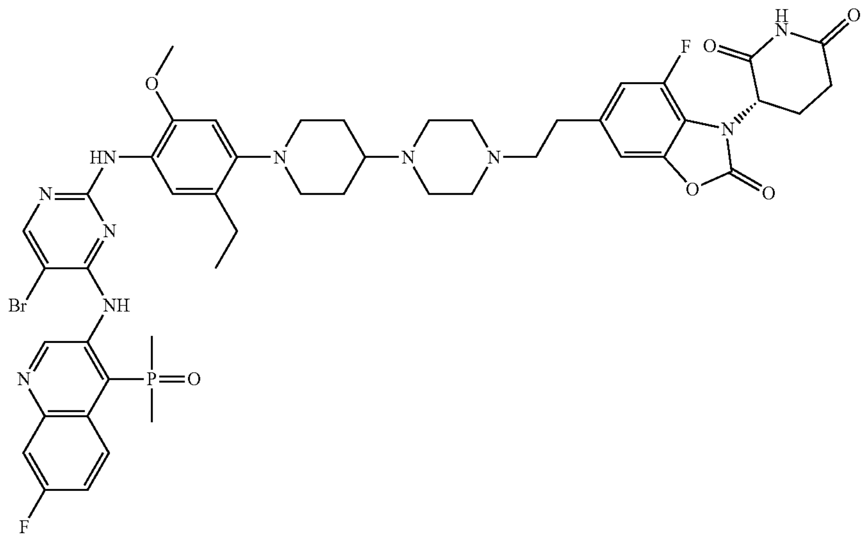

The title compound was prepared in a procedure similar to that in Example 1. $[M+H]^+=1001.7$.

Example 153: 3-(6-(2-(4-(1-(4-((5-bromo-4-((4-(dimethylphosphoryl)-7-fluoroquinolin-3-yl)amino)pyrimidin-2-yl)amino)-2-ethyl-5-methoxyphenyl)piperidin-4-yl)piperazin-1-yl)ethyl)-2-oxobenzo[d]oxazol-3(2H)-yl)piperidine-2,6-dione

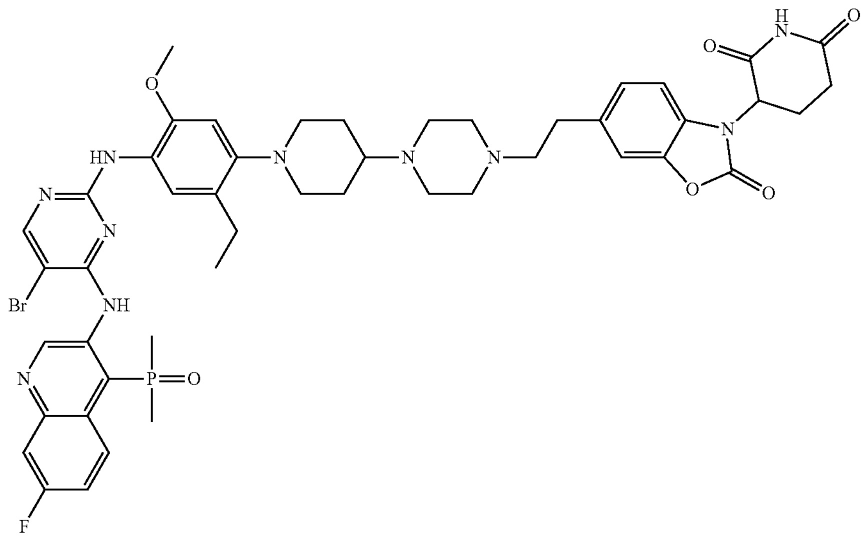 [SMILES: CCc1cc(Nc2ncc(Br)c(Nc3cnc4cc(F)ccc4c3P(C)(C)=O)n2)c(OC)cc1N1CCC(N2CCN(CCc3ccc4c(c3)oc(=O)n4C3CCC(=O)NC3=O)CC2)CC1]

The title compound was prepared in a procedure similar to that in Example 1. $[M+H]^+=983.4$.

Example 155: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-3-cyclopropyl-2-oxo-2,3-dihydro-1H-benzo[d]imidazol-1-yl)piperidine-2,6-dione

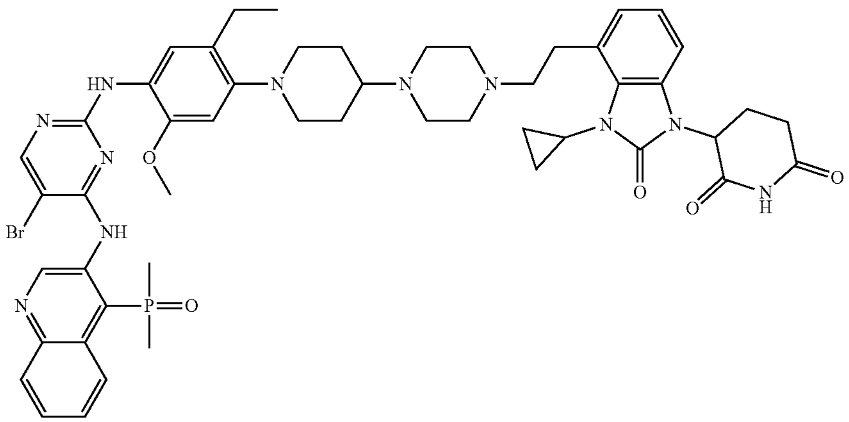 [SMILES: CCc1cc(Nc2ncc(Br)c(Nc3cnc4ccccc4c3P(C)(C)=O)n2)c(OC)cc1N1CCC(N2CCN(CCc3cccc4c3n(C3CC3)c(=O)n4C3CCC(=O)NC3=O)CC2)CC1]

The title compound was prepared in a procedure similar to that in Example 1. $[M+H]^+$=1004.2.

Example 159: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-5-fluoro-3-methyl-2-oxo-2,3-dihydro-1H-benzo[d]imidazol-1-yl) piperidine-2,6-dione

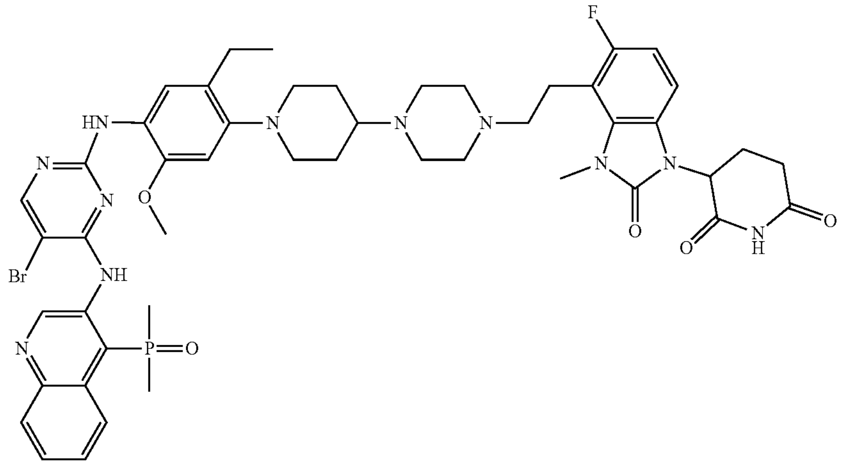 [SMILES: CCc1cc(Nc2ncc(Br)c(Nc3cnc4ccccc4c3P(C)(C)=O)n2)c(OC)cc1N1CCC(N2CCN(CCc3c(F)ccc4c3n(C)c(=O)n4C3CCC(=O)NC3=O)CC2)CC1]

The title compound was prepared in a procedure similar to that in Example 1. $[M+H]^+$=996.1.

Example 163: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-3-ethyl-2-oxo-2,3-dihydro-1H-benzo[d]imidazol-1-yl)piperidine-2,6-dione

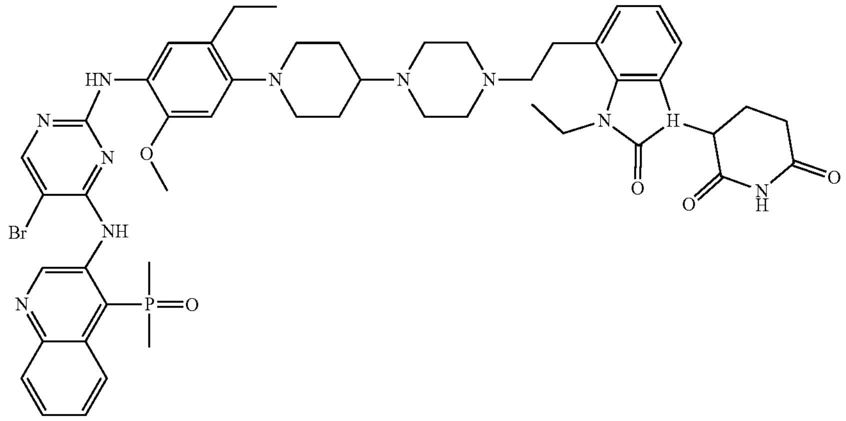

The title compound was prepared in a procedure similar to that in Example 1. $[M+H]^+$=992.1.

Example 164: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-3,3-dimethyl-2-oxoindolin-1-yl)piperidine-2,6-dione

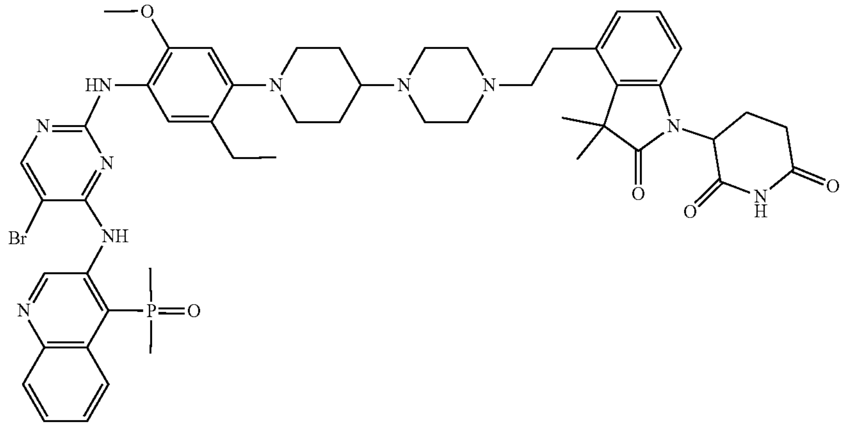 [SMILES: CCc1cc(Nc2ncc(Br)c(Nc3cnc4ccccc4c3P(C)(C)=O)n2)c(OC)cc1N1CCC(N2CCN(CCc3cccc4c3C(C)(C)C(=O)N4C3CCC(=O)NC3=O)CC2)CC1]

The title compound was prepared in a procedure similar to that in Example 1. $[M+H]^+$=991.7.

Example 165: 3-(4-(4-(2-(4-(1-(4-((5-bromo-4-((4-(dimethylphosphoryl)-8-fluoroquinolin-3-yl)amino)pyrimidin-2-yl)amino)-2-ethyl-5-methoxyphenyl)piperidin-4-yl)piperazin-1-yl)ethyl)piperidin-1-yl)-2,6-difluorophenyl)piperidine-2,6-dione

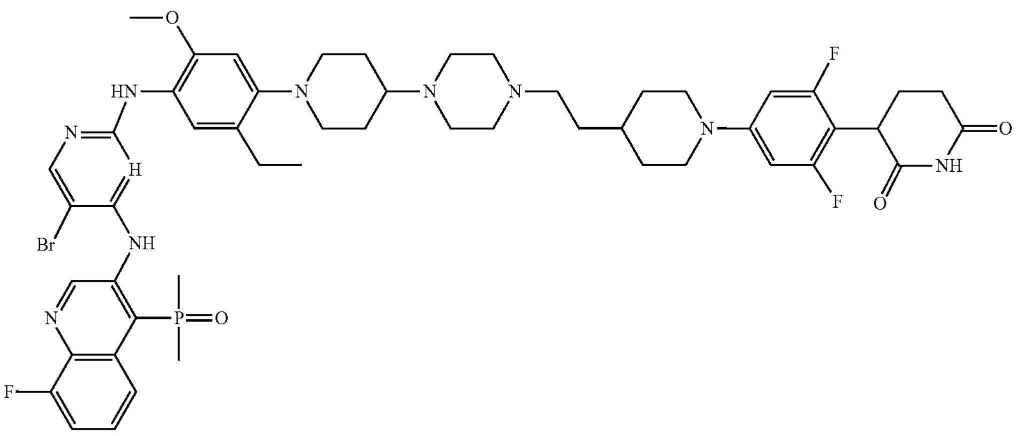

The title compound was prepared in a procedure similar to that in Example 1. $[M+H]^+=1045.7$.

Example 166: 3-(4-(2-(4-(1-(4-((5-bromo-4-((4-(dimethylphosphoryl)-6-(trifluoromethyl)quinolin-3-yl)amino)pyrimidin-2-yl)amino)-2-ethyl-5-methoxyphenyl)piperidin-4-yl)piperazin-1-yl)ethyl)-3-methyl-2-oxo-2,3-dihydro-1H-benzo[d]imidazol-1-yl)piperidine-2,6-dione

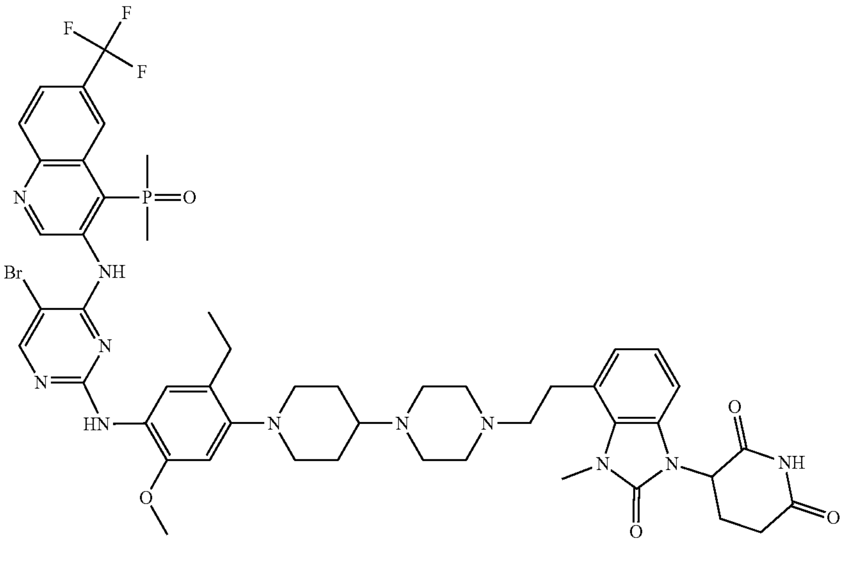 [SMILES: CCc1cc(Nc2ncc(Br)c(Nc3cnc4ccc(C(F)(F)F)cc4c3P(C)(C)=O)n2)c(OC)cc1N1CCC(N2CCN(CCc3cccc4c3n(C)c(=O)n4C3CCC(=O)NC3=O)CC2)CC1]

The title compound was prepared in a procedure similar to that in Example 1. $[M+H]^+=1046.1$.

Example 167: 3-(4-(2-(4-(1-(4-((5-bromo-4-((4-(dimethylphosphoryl)-7-fluoroquinolin-3-yl)amino)pyrimidin-2-yl)amino)-2-ethyl-5-methoxyphenyl)piperidin-4-yl)piperazin-1-yl)ethyl)-3-methyl-2-oxo-2,3-dihydro-1H-benzo[d]imidazol-1-yl)piperidine-2,6-dione

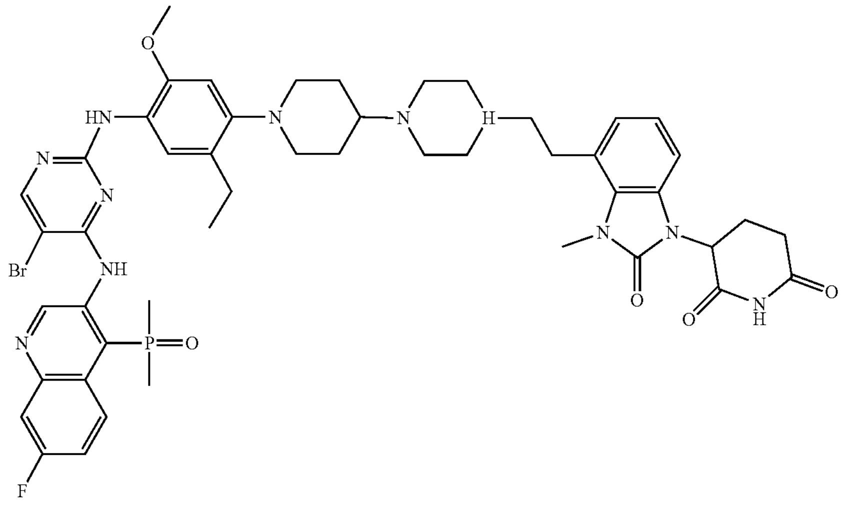

The title compound was prepared in a procedure similar to that in Example 1. $[M+H]^+$=996.6.

Example 168: 3-(5-((S)-3-(4-(1-(4-((5-bromo-4-((4-(dimethylphosphoryl)quinolin-3-yl)amino)pyrimidin-2-yl)amino)-2-ethyl-5-methoxyphenyl)piperidin-4-yl)piperazine-1-carbonyl)pyrrolidin-1-yl)-3,3-dimethyl-2-oxoindolin-1-yl)piperidine-2,6-dione

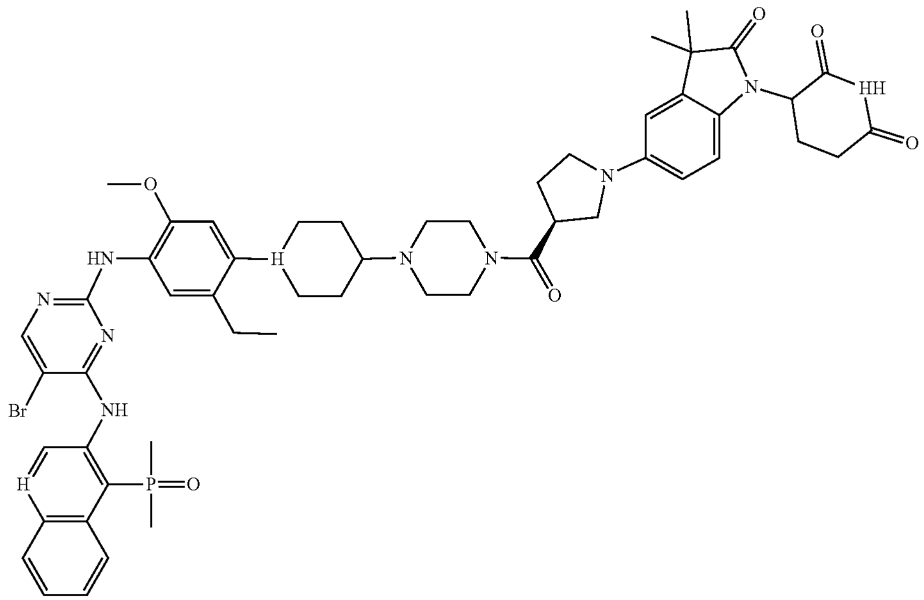

The title compound was prepared in a procedure similar to that in Example 23. $[M+H]^+$=1060.7.

Example 169: 3-(4-(3-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazine-1-carbonyl)azetidin-1-yl)-3,3-dimethyl-2-oxoindolin-1-yl)piperidine-2,6-dione

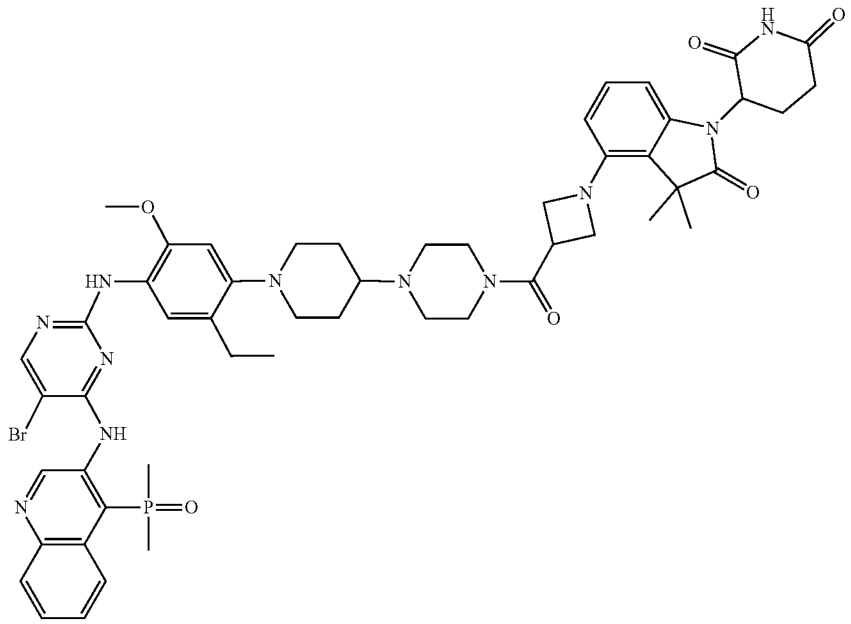 [SMILES: CCc1cc(Nc2ncc(Br)c(Nc3cnc4ccccc4c3P(C)(C)=O)n2)c(OC)cc1N1CCC(N2CCN(C(=O)C3CN(c4cccc5c4C(C)(C)C(=O)N5C4CCC(=O)NC4=O)C3)CC2)CC1]

The title compound was prepared in a procedure similar to that in Example 23. $[M+H]^+=1046.7$.

Example 170: 3-(4-(2-(4-(1-(4-((5-bromo-4-((4-(dimethylphosphoryl)-6-fluoroquinolin-3-yl)amino) pyrimidin-2-yl)amino)-2-ethyl-5-methoxyphenyl) piperidin-4-yl)piperazin-1-yl)ethyl)-3-methyl-2-oxo-2,3-dihydro-1H-benzo[d]imidazol-1-yl)piperidine-2,6-dione

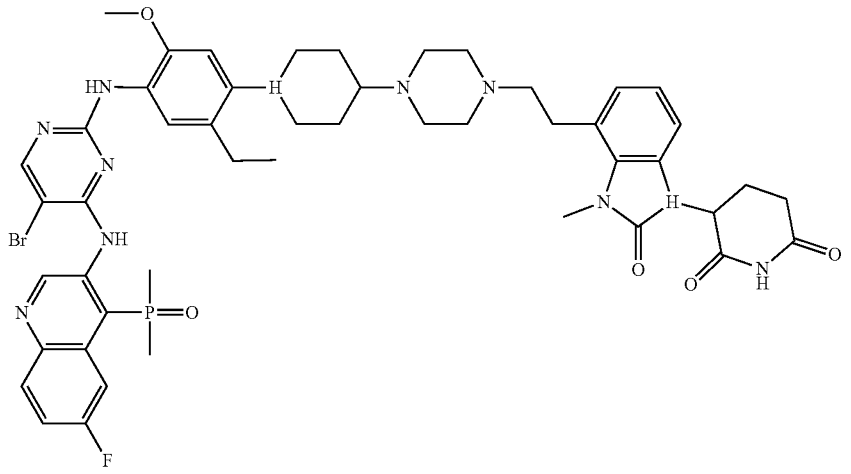

The title compound was prepared in a procedure similar to that in Example 1. $[M+H]^+=996.5$.

Example 171: 3-(4-(2-(4-(1-(4-((5-bromo-4-((4-(dimethylphosphoryl)-6-(trifluoromethyl)quinolin-3-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

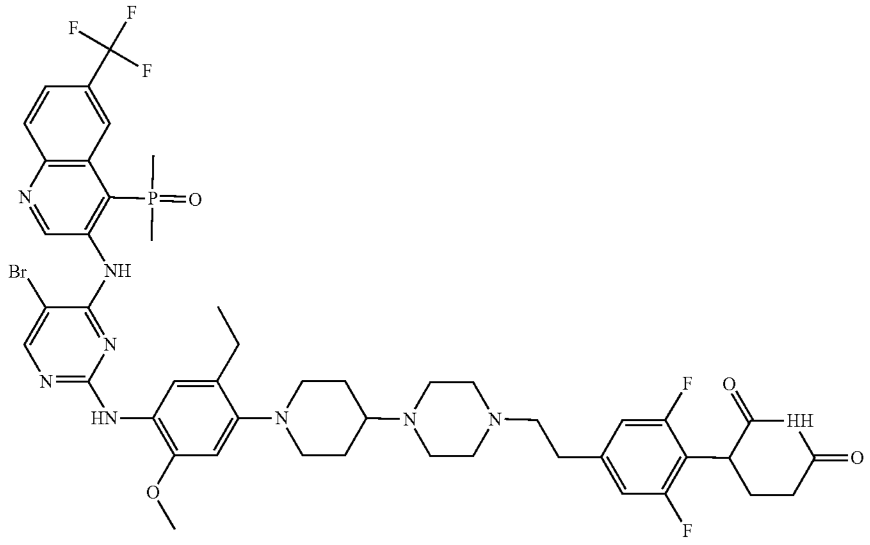

The title compound was prepared in a procedure similar to that in Example 1. $[M+H]^+$=1012.3.

Example 172: 3-(4-(2-(4-(1-(4-((5-bromo-4-((4-(dimethylphosphoryl)-7-fluoroquinolin-3-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

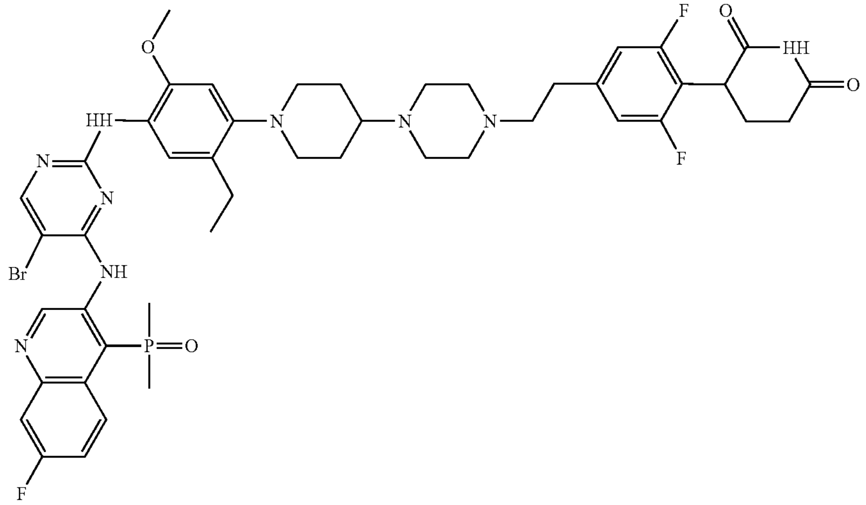

The title compound was prepared in a procedure similar to that in Example 1. $[M+H]^+$=962.6.

Example 173: 3-(4-(2-(4-(1-(4-((5-bromo-4-((4-(dimethylphosphoryl)-7,8-difluoroquinolin-3-yl)amino)pyrimidin-2-yl)amino)-2-ethyl-5-methoxy-phenyl)piperidin-4-yl)piperazin-1-yl)ethyl)-2,6-difluorophenyl)piperidine-2,6-dione

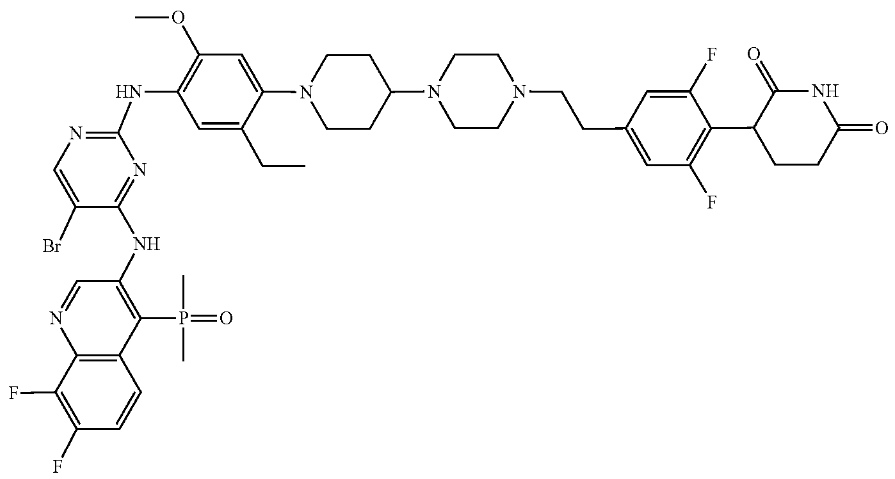 [SMILES: CCc1cc(Nc2ncc(Br)c(Nc3cnc4c(F)c(F)ccc4c3P(C)(C)=O)n2)c(OC)cc1N1CCC(N2CCN(CCc3cc(F)c(C4CCC(=O)NC4=O)c(F)c3)CC2)CC1]

The title compound was prepared in a procedure similar to that in Example 1. $[M+H]^+$=980.4.

Example 174: 3-(4-(2-(4-(1-(4-((5-bromo-4-((4-(dimethylphosphoryl)-6-fluoroquinolin-3-yl)amino)pyrimidin-2-yl)amino)-2-ethyl-5-methoxyphenyl)piperidin-4-yl)piperazin-1-yl)ethyl)-2,6-difluorophenyl)piperidine-2,6-dione

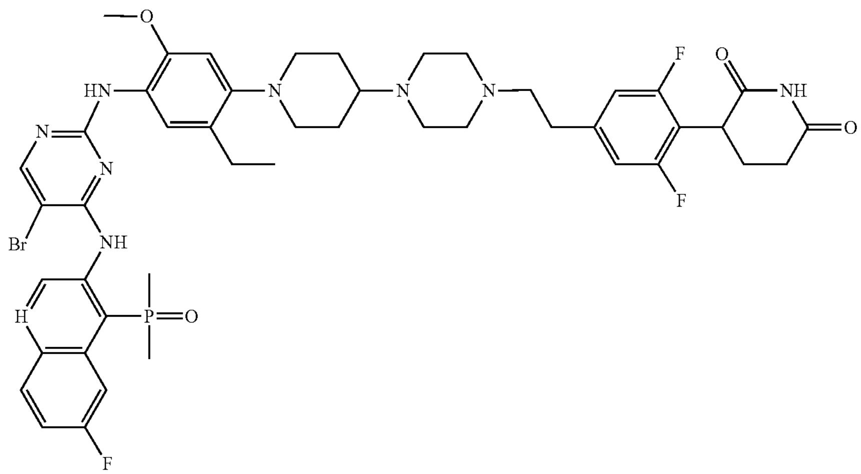

The title compound was prepared in a procedure similar to that in Example 1. $[M+H]^+$=962.5.

Example 175: 3-(5-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-3,3-dimethyl-2-oxoindolin-1-yl)piperidine-2,6-dione

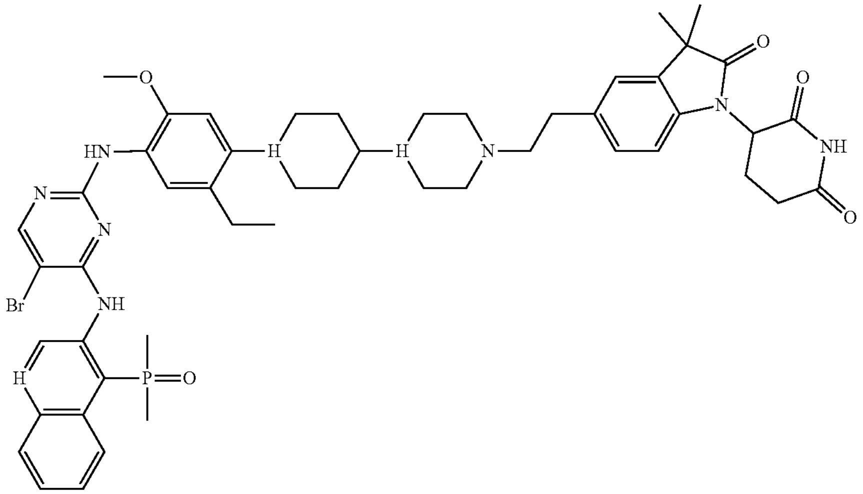

The title compound was prepared in a procedure similar to that in Example 1. $[M+H]^+$=991.7.

Example 176: 3-(6-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-2-oxobenzo[d]oxazol-3(2H)-yl)piperidine-2,6-dione

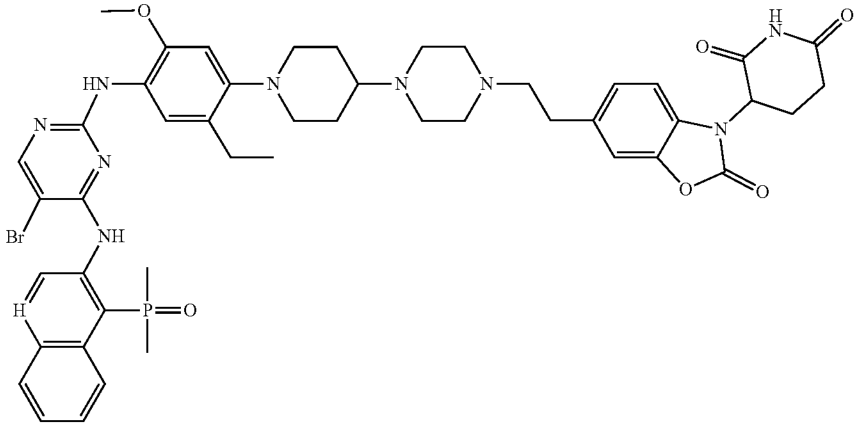

The title compound was prepared in a procedure similar to that in Example 1. $[M+H]^+$=965.6.

Example 178: 3-(4-(6-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazine-1-carbonyl)-2-azaspiro[3.3]heptan-2-yl)-2,6-difluorophenyl)piperidine-2,6-dione

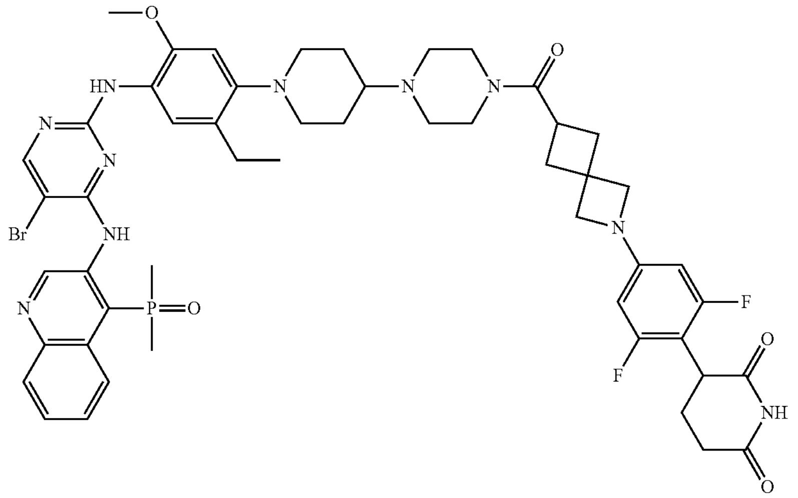 [SMILES: CCc1cc(Nc2ncc(Br)c(Nc3cnc4ccccc4c3P(C)(C)=O)n2)c(OC)cc1N1CCC(N2CCN(C(=O)C3CC4(C3)CN(c3cc(F)c(C5CCC(=O)NC5=O)c(F)c3)C4)CC2)CC1]

The title compound was prepared in a procedure similar to that in Example 23. $[M+H]^+$=1039.6.

Example 179: 3-(4-(3-(4-(1-(4-((5-bromo-4-((4-(dimethylphosphoryl)quinolin-3-yl)amino)pyrimidin-2-yl)amino)-5-methoxy-2-methylphenyl)piperidin-4-yl)piperazine-1-carbonyl)azetidin-1-yl)-3-methyl-2-oxo-2,3-dihydro-1H-benzo[d]imidazol-1-yl)piperidine-2,6-dione

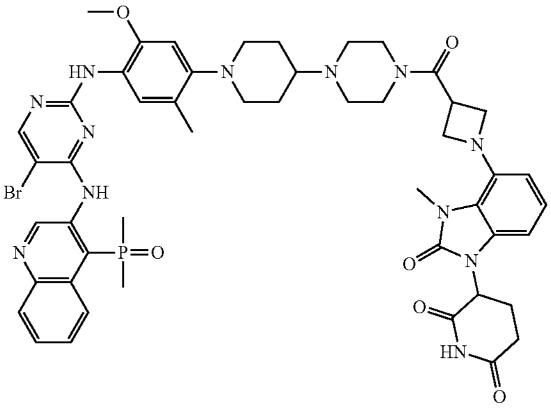 [SMILES: COc1cc(N2CCC(N3CCN(C(=O)C4CN(c5cccc6c5n(C)c(=O)n6C5CCC(=O)NC5=O)C4)CC3)CC2)c(C)cc1Nc1ncc(Br)c(Nc2cnc3ccccc3c2P(C)(C)=O)n1]

The title compound was prepared in a procedure similar to that in Example 23. $[M+H]^+$=1019.6.

Example 180: 3-(4-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-2,3,6-trifluorophenyl) piperidine-2,6-dione

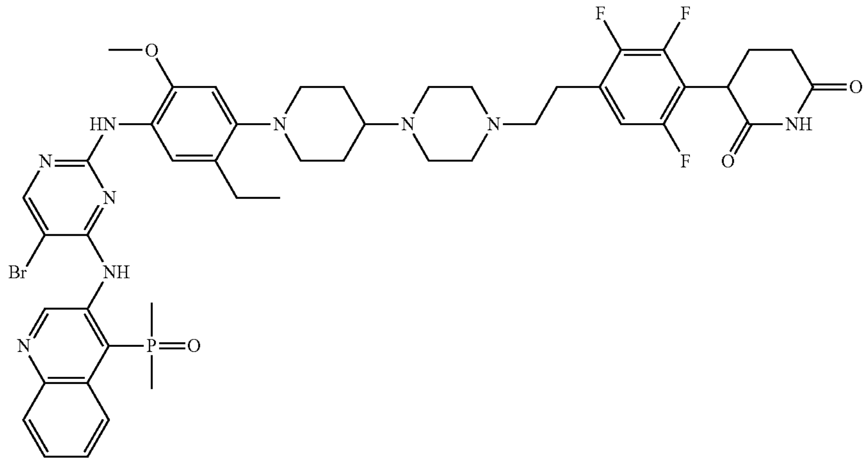 [SMILES: CCc1cc(Nc2ncc(Br)c(Nc3cnc4ccccc4c3P(C)(C)=O)n2)c(OC)cc1N1CCC(N2CCN(CCc3cc(F)c(C4CCC(=O)NC4=O)c(F)c3F)CC2)CC1]

The title compound was prepared in a procedure similar to that in Example 1. $[M+H]^+$=962.4.

Example 181: 3-(4-(2-(4-(1-(4-((5-bromo-4-((4-(dimethylphosphoryl)-8-fluoroquinolin-3-yl)amino) pyrimidin-2-yl)amino)-2-ethyl-5-methoxyphenyl) piperidin-4-yl)piperazin-1-yl)ethyl)-2,6-difluorophenyl)piperidine-2,6-dione

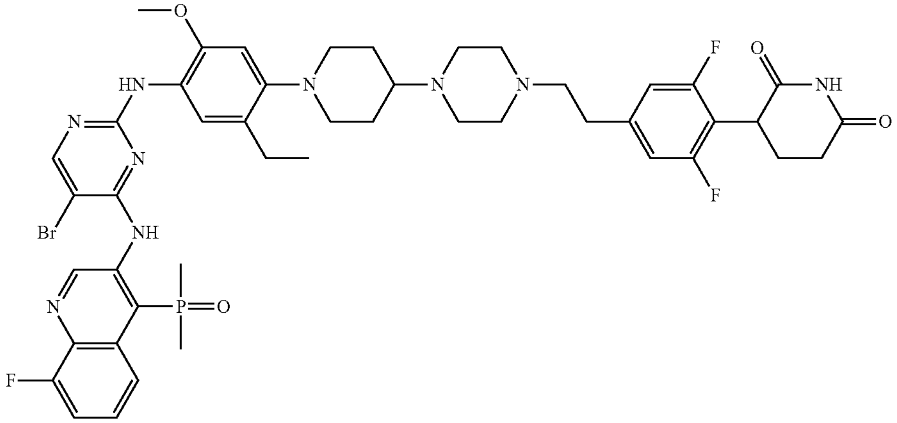 [SMILES: CCc1cc(Nc2ncc(Br)c(Nc3cnc4c(F)cccc4c3P(C)(C)=O)n2)c(OC)cc1N1CCC(N2CCN(CCc3cc(F)c(C4CCC(=O)NC4=O)c(F)c3)CC2)CC1]

The title compound was prepared in a procedure similar to that in Example 1. $[M+H]^+$=962.3.

Example 182: 3-(5-(4-(4-(1-(4-((5-bromo-4-((4-(dimethylphosphoryl)-8-fluoroquinolin-3-yl)amino)pyrimidin-2-yl)amino)-2-ethyl-5-methoxyphenyl)piperidin-4-yl)piperazine-1-carbonyl)piperidin-1-yl)-3,3-dimethyl-2-oxoindolin-1-yl)piperidine-2,6-dione

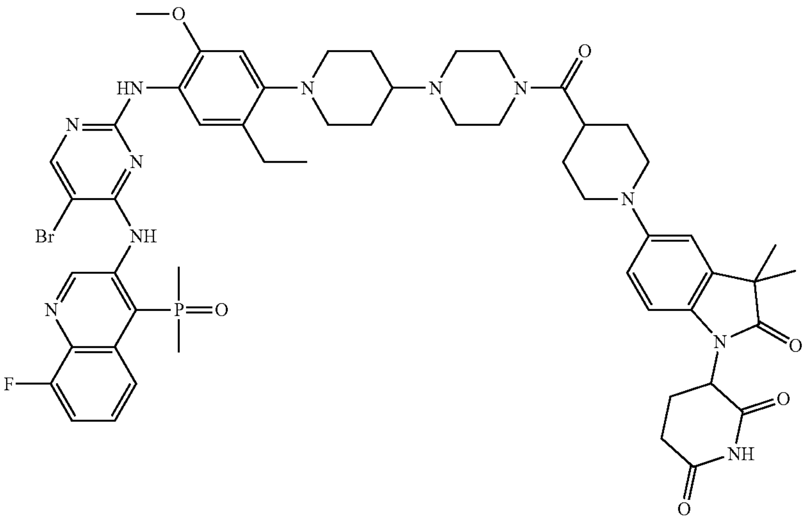 [SMILES: CCc1cc(Nc2ncc(Br)c(Nc3cnc4c(F)cccc4c3P(C)(C)=O)n2)c(OC)cc1N1CCC(N2CCN(C(=O)C3CCN(c4ccc5c(c4)C(C)(C)C(=O)N5C4CCC(=O)NC4=O)CC3)CC2)CC1]

The title compound was prepared in a procedure similar to that in Example 23. [M+H]$^+$=1092.4.

Example 183: 3-(4-(2-(4-(1-(4-((5-bromo-4-((4-(dimethylphosphoryl)quinolin-3-yl)amino)pyrimidin-2-yl)amino)-5-ethoxy-2-methylphenyl)piperidin-4-yl)piperazin-1-yl)ethyl)-2,6-difluorophenyl)piperidine-2,6-dione

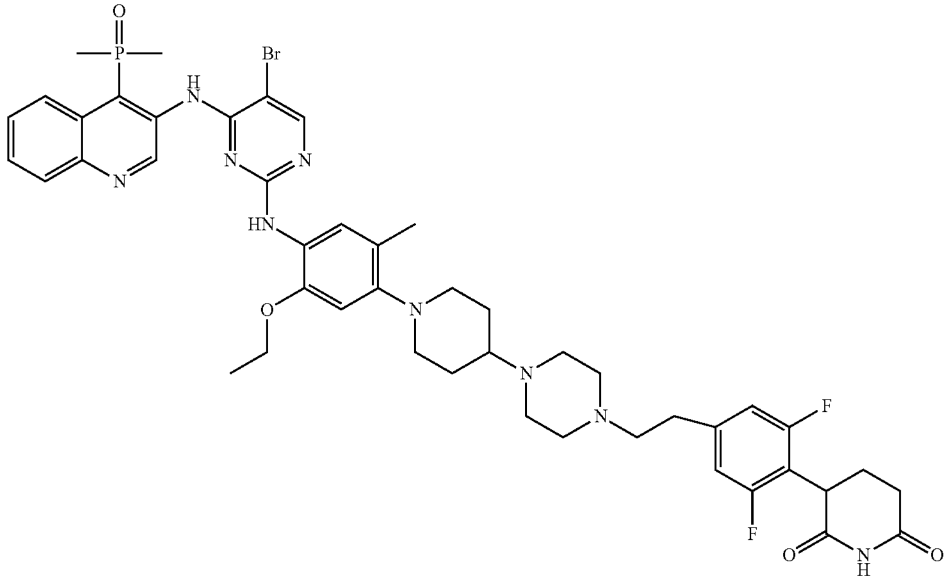 [SMILES: CCOc1cc(N2CCC(N3CCN(CCc4cc(F)c(C5CCC(=O)NC5=O)c(F)c4)CC3)CC2)c(C)cc1Nc1ncc(Br)c(Nc2cnc3ccccc3c2P(C)(C)=O)n1]

The title compound was prepared in a procedure similar to that in Example 1. [M+H]$^+$=944.6.

Example 184: 3-(4-((1r,3r)-3-(4-(1-(4-((5-bromo-4-((4-(dimethylphosphoryl)quinolin-3-yl)amino)pyrimidin-2-yl)amino)-2-eth yl-5-methoxyphenyl)piperidin-4-yl)piperazin-1-yl)cyclobutyl)-2,6-difluorophenyl)piperidine-2,6-dione

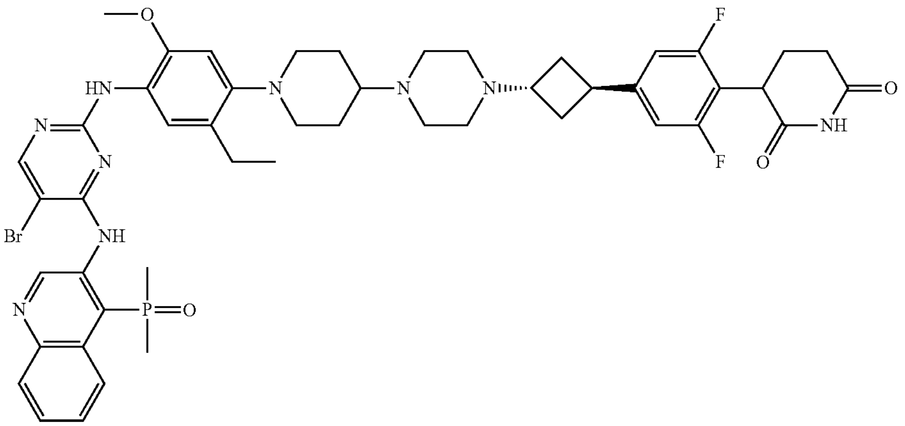 [SMILES: CCc1cc(Nc2ncc(Br)c(Nc3cnc4ccccc4c3P(C)(C)=O)n2)c(OC)cc1N1CCC(N2CCN([C@H]3C[C@H](c4cc(F)c(C5CCC(=O)NC5=O)c(F)c4)C3)CC2)CC1]

The title compound was prepared in a procedure similar to that in Example 1. $[M+H]^+$=970.6.

Example 185: 3-(4-(4-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazine-1-carbonyl)piperidin-1-yl)-2,6-difluorophenyl)piperidine-2,6-dione

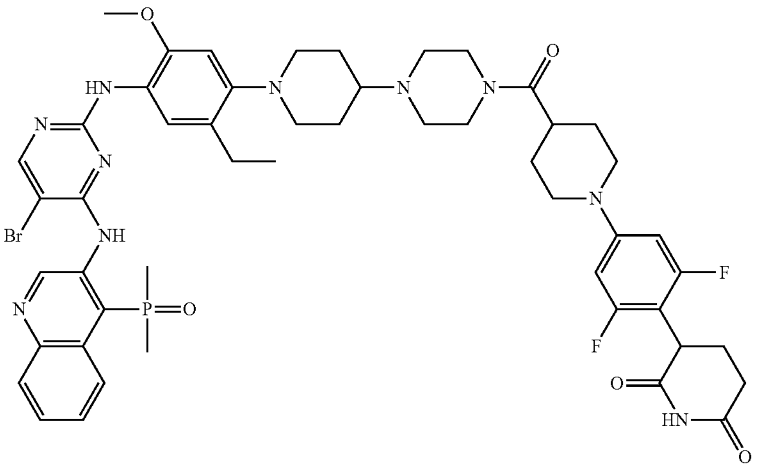 [SMILES: CCc1cc(Nc2ncc(Br)c(Nc3cnc4ccccc4c3P(C)(C)=O)n2)c(OC)cc1N1CCC(N2CCN(C(=O)C3CCN(c4cc(F)c(C5CCC(=O)NC5=O)c(F)c4)CC3)CC2)CC1]

The title compound was prepared in a procedure similar to that in Example 23. $[M+H]^+$=1027.7.

Example 186: 3-(4-(4-(2-(4-(1-(4-((5-bromo-4-((4-(dimethylphosphoryl)quinolin-3-yl)amino)pyrimidin-2-yl)amino)-2-ethyl-5-(2,2,2-trifluoroethoxy)phenyl)piperidin-4-yl)piperazin-1-yl)ethyl)piperidin-1-yl)-2,6-difluorophenyl)piperidine-2,6-dione

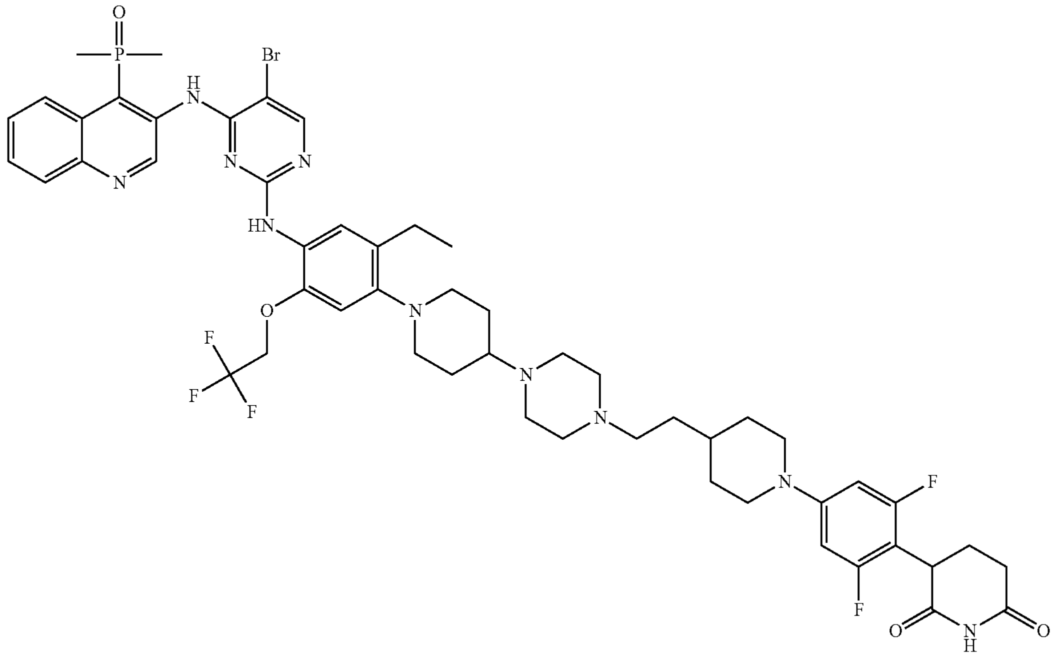 [SMILES: CCc1cc(Nc2ncc(Br)c(Nc3cnc4ccccc4c3P(C)(C)=O)n2)c(OCC(F)(F)F)cc1N1CCC(N2CCN(CCC3CCN(c4cc(F)c(C5CCC(=O)NC5=O)c(F)c4)CC3)CC2)CC1]

The title compound was prepared in a procedure similar to that in Example 1. $[M+H]^+$=1095.2.

Example 187: 3-(4-(2-(4-(1-(4-((5-bromo-4-((4-(dimethylphosphoryl)quinolin-3-yl)amino)pyrimidin-2-yl)amino)-2-ethyl-5-(2,2,2-trifluoroethoxy)phenyl)piperidin-4-yl)piperazin-1-yl)ethyl)-2,6-difluorophenyl)piperidine-2,6-dione

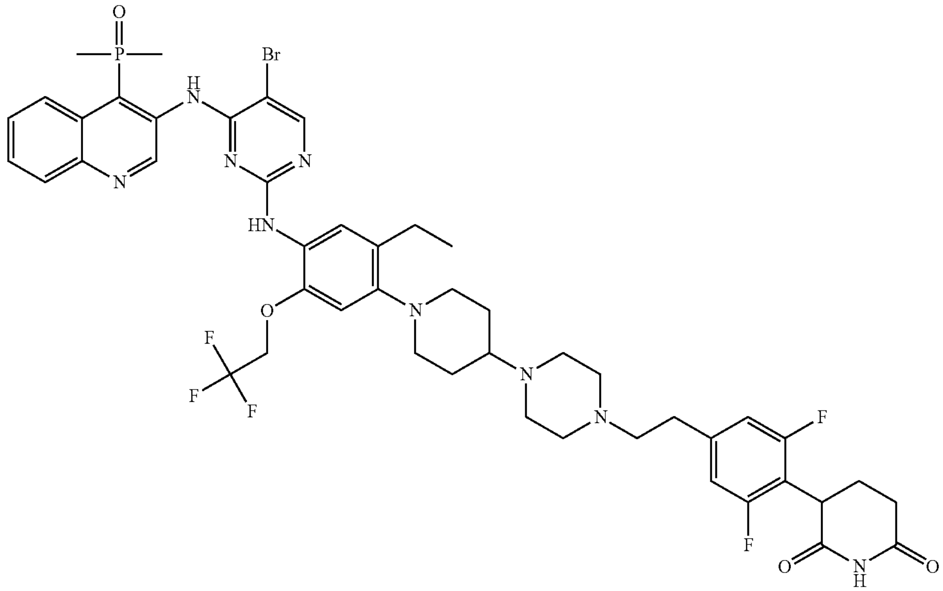 [SMILES: CCc1cc(Nc2ncc(Br)c(Nc3cnc4ccccc4c3P(C)(C)=O)n2)c(OCC(F)(F)F)cc1N1CCC(N2CCN(CCc3cc(F)c(C4CCC(=O)NC4=O)c(F)c3)CC2)CC1]

The title compound was prepared in a procedure similar to that in Example 1. $[M+H]^+$=1012.2.

Example 188: 3-(7-(2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)ethyl)-2-oxobenzo[d]oxazol-3(2H)-yl)piperidine-2,6-dione

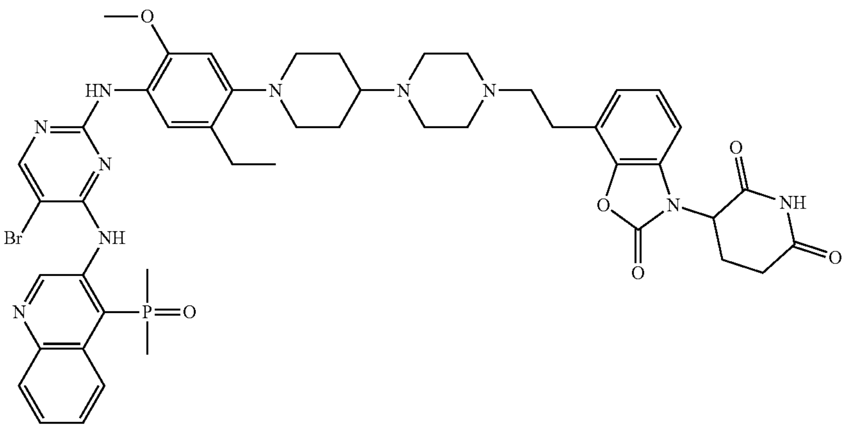 [SMILES: CCc1cc(Nc2ncc(Br)c(Nc3cnc4ccccc4c3P(C)(C)=O)n2)c(OC)cc1N1CCC(N2CCN(CCc3cccc4c3oc(=O)n4C3CCC(=O)NC3=O)CC2)CC1]

The title compound was prepared in a procedure similar to that in Example 1. $[M+H]^+$=965.5.

Example 189: 3-(4-((2-(4-(1-(4-((5-bromo-4-((4-(dimethylphosphoryl)quinolin-3-yl)amino)pyrimidin-2-yl)amino)-2-ethyl-5-methoxyphenyl) piperidin-4-yl)piperazin-1-yl)-2-oxoethyl)(methyl)amino)-2,6-difluorophenyl)piperidine-2,6-dione

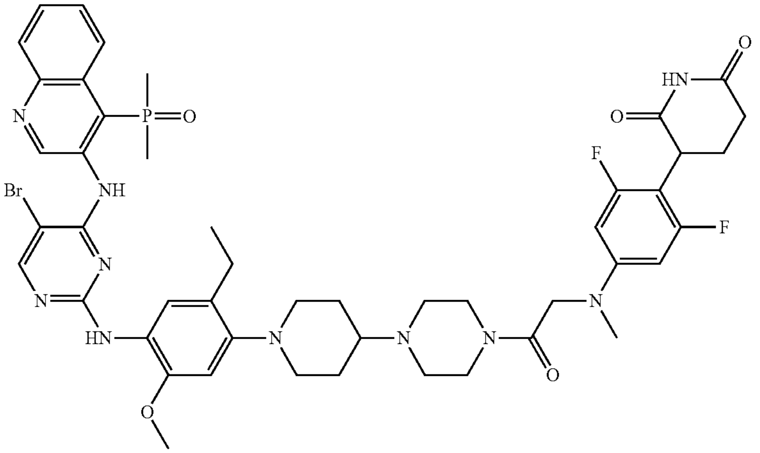 [SMILES: CCc1cc(Nc2ncc(Br)c(Nc3cnc4ccccc4c3P(C)(C)=O)n2)c(OC)cc1N1CCC(N2CCN(C(=O)CN(C)c3cc(F)c(C4CCC(=O)NC4=O)c(F)c3)CC2)CC1]

The title compound was prepared in a procedure similar to that in Example 23. $[M+H]^+$=987.5.

Cell Degradation of Example 1-28

Cell Treatment

BaF3-LTC (L858R/T790M/C797S) and BaF3-DTC (Del19/T790M/C797S) cells are seeded at 100000 cells/well in cell culture medium [RPMI1640 (Gibco, phenol red free, Cat #1 1835-030), 10% heat-inactive FBS, 1% PS (Gibco, Cat #10378)] in Corning 96 well plate (Cat #3799).

BaF3-LTC (L858R/T790M/C797S) and BaF3-DTC (Del19/T790M/C797S) cells are treated with compounds diluted in 0.2% DMSO cell culture medium and incubate for 16 h, 37° C., 5% $CO_2$. The final concentration of compounds in all assay is start with 10 uM, 4-fold dilution, total 8 doses were included.

HTRF Assay

After 16 h treatment, add HTRF lysis buffer to each well; seal the plate and incubate 1 hour at room temperature on a plate shaker; Once the cells are lysed, 16 μL of cell lysate are transferred to a PE 384-well HTRF detection plate; 4 μL of pre-mixed HTRF antibodies are added to each well; Cover the plate with a plate sealer, spin 1000 rpm for 1 min, Incubate overnight at room temperature; Read on BMG PheraStar with HTRF protocol (337 nm-665 nm-620 nm). The inhibition (degradation) percentage of the compound was calculated by the following equation:

Inhibition percentage of Compound=100−100×(Signal−low control)/(High control−low control), wherein signal=each test compound group.

Low control=only lysis buffer without cells, indicating that EGFR is completely degraded;

High control=Cell group with added DMSO and without compound, indicating microplate readings without EGFR degradation;

Dmax is the maximum percentage of inhibition (degradation).

The $IC_{50}$ ($DC_{50}$) value of a compound can be obtained by fitting the following equation $$Y=\text{Bottom}+(\text{TOP}-\text{Bottom})/(1+((C_{50}/X)\hat{}\text{hillslope}))$$

Wherein, X and Y are known values, and $IC_{50}$, Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 000±20%; Top represents the maximum value of the curve obtained by data fitting, which is generally 100%±20%. The experimental data were fitted by calculating and analyzing with Dotmatics data analysis software. When Dmax<50%, $DC_{50}$ will be automatically assigned as larger than 10000 μM.

TABLE 1

Degradation (BaF3) result for Example 1 to Example 28

| | DTC | | LTC | |
|---|---|---|---|---|
| Example | $DC_{50}$(nM) | Dmax (%) | $DC_{50}$(nM) | Dmax (%) |
| 1 | 10.43 | 96.55 | 24.96 | 90.66 |
| 2 | 18.49 | 86.75 | 146.4 | 85.03 |
| 4 | 3.94 | 91.36 | 7.75 | 90.47 |
| 7 | 15.52 | 93.86 | 45.26 | 82.68 |
| 8 | 11.77 | 96.88 | 30.16 | 89.62 |
| 9 | 12.65 | 96.14 | 29.32 | 87.96 |
| 10 | 24.79 | 88.58 | 218.9 | 88.39 |
| 12 | 14.45 | 91.82 | 68.83 | 89.09 |
| 14 | 185.6 | 81.73 | 546.1 | 84.57 |
| 15 | 1.23 | 94.57 | 3.23 | 86.4 |
| 16 | 2.14 | 96.98 | 5.05 | 89.67 |
| 17 | 1.94 | 96.58 | 3.86 | 92.5 |
| 18 | 3.95 | 97.59 | 14.57 | 90.69 |
| 19 | 4.24 | 97.44 | 8.02 | 89.37 |
| 20 | 4.65 | 96.7 | 19.52 | 89.53 |
| 21 | 1.11 | 94.17 | 5.02 | 93.31 |
| 23 | 2.22 | 94.5 | 11.07 | 88.64 |
| 24 | 2.88 | 84.3 | 27.54 | 89.6 |
| 25 | 1.8 | 88.68 | 6.77 | 85.01 |
| 27 | 3.08 | 83.05 | 19.31 | 87.55 |
| 28 | 5.4 | 90.9 | 8.95 | 81.86 |

Cell Degradation of Example 124-189

Cell Treatment

On day 1, H1975-clone #28 (Del19/T790M/C797S) and H1975-clone #25 (L858R/T790M/C797S) cells are seeded at 5000 cells/well correspondingly in cell culture medium [RPMI1640 (Gibco, Cat #72400-047), 10% heat-inactive FBS, 1% PS (Gibco, Cat #10378)] in Corning 96 well plate (Cat #3599). H1975-#28 and H1975-#25 cells are treated with compounds diluted in 0.2% DMSO cell culture medium on day 2, incubate for 16 h, 37° C., 5% CO2. the final concentration of compounds in all assay is start with 10 uM, 5-fold dilution, total 8 doses were included.

HTRF Assay

After 16 h treatment, add HTRF lysis buffer to each well; seal the plate and incubate 1 hour at room temperature on a plate shaker; Once the cells are lysed, 16 μL of cell lysate are transferred to a PE 384-well HTRF detection plate; 4 μL of pre-mixed HTRF antibodies are added to each well; Cover the plate with a plate sealer, spin 1000 rpm for 1 min, Incubate overnight at room temperature; Read on BMG PheraStar with HTRF protocol (337 nm-665 nm-620 nm).

The inhibition (degradation) percentage of the compound was calculated by the following equation:

Inhibition percentage of Compound=100−100×(Signal−low control)/(High control−low control), wherein signal=each test compound group.

Low control=only lysis buffer without cells, indicating that EGFR is completely degraded;

High control=Cell group with added DMSO and without compound, indicating microplate readings without EGFR degradation;

Dmax is the maximum percentage of inhibition (degradation).

The $IC_{50}$ ($DC_{50}$) value of a compound can be obtained by fitting the following equation $$Y=\text{Bottom}+(\text{TOP}-\text{Bottom})/(1+((IC_{50}/X)\hat{}\text{hillslope}))$$

Wherein, X and Y are known values, and $IC_{50}$, Hillslope, Top and Bottom are the parameters obtained by fitting with software. Y is the inhibition percentage (calculated from the equation), X is the concentration of the compound; $IC_{50}$ is the concentration of the compound when the 50% inhibition is reached. The smaller the $IC_{50}$ value is, the stronger the inhibitory ability of the compound is. Vice versa, the higher the $IC_{50}$ value is, the weaker the ability the inhibitory ability of the compound is; Hillslope represents the slope of the fitted curve, generally around 1*; Bottom represents the minimum value of the curve obtained by data fitting, which is generally 0%±20%; Top represents the maximum value of the curve obtained by data fitting, which is generally 100%±20%. The experimental data were fitted by calculating and analyzing with Dotmatics data analysis software. When Dmax<50%, $DC_{50}$ will be automatically assigned as larger than 10000 μM.

TABLE 2

| Degradation (H1975) result for Example 122 to Example 189 | | | | |
|---|---|---|---|---|
| | H1975-clone#28 DTC | | H1975-clone#25 LTC | |
| Example | $DC_{50}$(nM) | Dmax (%) | $DC_{50}$(nM) | Dmax (%) |
| 124 | 1.4 | 73 | 3.4 | 77 |
| 126 | 1.3 | 84 | | |
| 130 | 1.0 | 86 | | |
| 132 | 1.0 | 80 | | |
| 133 | 3.0 | 71 | | |
| 134 | 0.8 | 79 | | |
| 135 | 0.9 | 83 | | |
| 136 | 0.6 | 81 | | |
| 137 | 2.1 | 86 | | |
| 138 | 3.0 | 83 | | |
| 139 | 1.5 | 75 | | |
| 140 | 4.4 | 84 | | |
| 142 | 0.9 | 81 | | |
| 147 | 0.4 | 84 | 15.3 | 77 |
| 149 | 1.3 | 73 | | |
| 151 | 1.1 | 79 | | |
| 153 | 0.8 | 77 | | |
| 155 | 0.7 | 85 | | |
| 159 | 1.4 | 85 | | |
| 163 | 1.1 | 86 | | |
| 164 | 2.1 | 81 | | |
| 165 | 4.2 | 84 | | |
| 166 | 2.8 | 80 | 4.2 | 81 |
| 167 | 0.8 | 74 | | |
| 168 | 2.0 | 47 | | |
| 169 | 4.6 | 65 | | |
| 170 | 2.1 | 82 | | |
| 171 | 4.3 | 79 | | |
| 172 | 1.4 | 81 | | |
| 173 | 2.7 | 82 | | |
| 174 | 1.8 | 80 | | |
| 175 | 5.5 | 47 | | |
| 176 | 1.6 | 73 | | |
| 178 | 2.6 | 67 | | |
| 179 | 2.6 | 54 | | |
| 180 | 2.0 | 83 | | |
| 181 | 4.2 | 82 | | |
| 182 | 0.8 | 56 | | |
| 183 | 4.6 | 73 | | |
| 184 | 1.5 | 81 | | |
| 185 | 1.2 | 71 | | |
| 186 | 8.0 | 72 | | |
| 187 | 3.3 | 69 | | |
| 188 | 0.8 | 84 | | |
| 189 | 2.4 | 77 | | |

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

What is claimed is:

1. A compound of Formula (X):

(X)

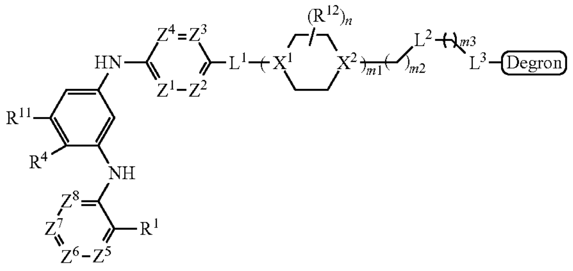

or a N-oxide thereof, or a pharmaceutically acceptable salt thereof, or a stereoisomer thereof, or a deuterated analog thereof, wherein:

$R^1$ is selected from —$P(O)R^{1a}R^{1b}$, —$SO_2R^{1a}$, —$SO_2$—$NR^{1a}R^{1b}$ and —$N(R^{1a})$—$SO_2R^{1b}$, wherein $R^{1a}$ and $R^{1b}$ are each independently selected from hydrogen, —$C_{1-8}$ alkyl and $C_3$-$C_8$cycloalkyl, said —$C_{1-8}$alkyl or $C_3$-$C_8$cycloalkyl is optionally substituted with at least one halogen;

$Z^5$ is selected from —$CR^2$ and N;

$Z^6$ is selected from —$CR^3$ and N;

$Z^7$ is selected from —$CR^9$ and N;

$Z^8$ is selected from —$CR^{10}$ and N;

at least one of $Z^5$, $Z^6$, $Z^7$ and $Z^8$ is N;

$R^2$ and $R^3$ are each independently selected from hydrogen, halogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl, —CN, —$OR^{2a}$, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$, and —$NR^{2a}SO_2R^{2b}$, wherein each of —$C_{1-8}$alkyl, —$C_{2-8}$alkenyl, —$C_{2-8}$ alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{2d}$; or $R^2$ and $R^3$ together with the carbon atoms to which they are attached, form a 5-6 membered saturated or partially or completely unsaturated ring, said ring comprising 0-3 heteroatoms independently selected from nitrogen, oxygen and sulfur; said ring is optionally substituted with at least one substituent $R^{2e}$;

$R^{2e}$, at each occurrence, is independently hydrogen, halogen, —$C_{1-8}$alkyl, —$C_{2-8}$alkenyl, —$C_{2-8}$alkynyl, —$C_{1-8}$alkoxy, —$C_3$-$C_8$cycloalkyl, oxo, 3- to 8-membered heterocyclyl, $C_6$-$C_{12}$aryl, 5- to 12-membered heteroaryl, —CN, —$SO_2R^{2a}$, —$SO_2NR^{2a}R^{2b}$, —$COR^{2a}$, —$CO_2R^{2a}$, —$CONR^{2a}R^{2b}$, —$NR^{2a}R^{2b}$, —$NR^{2a}COR^{2b}$, —$NR^{2a}CO_2R^{2b}$ or —$NR^{2a}SO_2R^{2b}$, wherein each of —$C_{1-8}$alkyl, —$C_{2-8}$alkenyl, —$C_{2-8}$ alkynyl, —$C_{1-8}$alkoxy, $C_3$-$C_8$cycloalkyl, 3- to 8-membered heterocyclyl, $C_6$-$C_{12}$aryl or 5- to 12-membered heteroaryl is optionally substituted with at least one substituent $R^{2d}$;

$R^{2a}$ and $R^{2b}$ are each independently selected from hydrogen, —$C_{1-8}$alkyl, —$C_{2-8}$alkenyl, —$C_{2-8}$alkynyl, $C_{1-8}$alkoxy-$C_{1-8}$alkyl-, $C_3$-$C_8$cycloalkyl, 3- to 8-membered heterocyclyl, $C_6$-$C_{12}$aryl and 5- to 12-membered heteroaryl;

$R^{2d}$, at each occurrence, is independently halogen, —OH, —$C_{1-8}$alkyl, —$C_{1-8}$alkoxy, $C_{1-8}$alkoxy-$C_{1-8}$alkyl-, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl;

$R^4$ is selected from hydrogen, halogen, —$C_{1-8}$alkyl, —$C_{2-8}$ alkenyl, —$C_{2-8}$alkynyl, —$C_{1-8}$alkoxy, —$C_3$-$C_8$cycloalkyl, 3- to 8-membered heterocyclyl, —$C_6$-$C_{12}$aryl, 5- to 12-membered heteroaryl, —CN, —$SO_2R^{4a}$, —$SO_2NR^{4a}R^{4b}$, —$COR^{4a}$, —$CO_2R^{4a}$, —$CONR^{4a}R^{4b}$, —$NR^{4a}R^{4b}$, —$NR^{4a}COR^{4b}$, —$NR^{4a}CO_2R^{4b}$, and —$NR^{4a}SO_2R^{4b}$, wherein each of —$C_{1-8}$alkyl, —$C_{2-8}$alkenyl, —$C_{2-8}$alkynyl, —$C_{1-8}$ alkoxy, —$C_3$-$C_8$cycloalkyl, 3- to 8-membered heterocyclyl, —$C_6$-$C_{12}$aryl or 5- to 12-membered heteroaryl is optionally substituted with halogen, —$C_{1-8}$alkoxy, —$C_{1-8}$alkyl, —$C_{2-8}$alkenyl, —$C_{2-8}$alkynyl, —$C_3$-$C_8$cycloalkyl, 3- to 8-membered heterocyclyl, $C_6$-$C_{12}$aryl, 5- to 12-membered heteroaryl, oxo, —CN, —$OR^{4c}$, —$SO_2R^{4c}$, —$SO_2NR^{4c}R^{4d}$, —$CO^{R4c}$, —$CO_2R^{4c}$, —$CONR^{4c}OR^{4d}$, —$NR^{4c}R^{4d}$, —$NR^{4c}COR^{4d}$, —$NR^{4c}CO_2R^{4d}$, or —$NR^{4c}SO_2R^{4d}$;

$R^{4a}$, $R^{4b}$, $R^{4c}$ and $R^{4d}$ are each independently hydrogen, —$C_{1-8}$alkyl, —$C_{2-8}$alkenyl, —$C_{2-8}$alkynyl, $C_3$-$C_8$cycloalkyl, 3- to 8-membered heterocyclyl, —$C_6$-$C_{12}$aryl, or 5- to 12-membered heteroaryl;

$R^9$, $R^{10}$, $R^{11}$ and $R^{12}$ are each independently selected from hydrogen, halogen, —$C_{1-8}$alkyl, —$C_{2-8}$alkenyl, —$C_{2-8}$ alkynyl, —$NR^{9a}R^{9b}$, —$OR^{9a}$, oxo, —$C_3$-$C_8$cycloalkyl, 3- to 8-membered heterocyclyl, —$C_6$-$C_{12}$aryl, 5- to 12-membered heteroaryl, and —CN, wherein each of —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl is optionally substituted with at least one substituent $R^{9c}$; or two $R^{12}$ together with the carbon atoms to which they are attached, form a 3- to 12-membered ring, said ring comprising 0-3 heteroatoms independently selected from nitrogen, oxygen and sulfur; said ring is optionally substituted with at least one substituent $R^{9c}$;

$R^{9a}$ and $R^{9b}$ are each independently selected from hydrogen, —$C_{1-8}$alkyl, —$C_{2-8}$alkenyl, —$C_{2-8}$alkynyl, —$C_3$-$C_8$cycloalkyl, 3- to 8-membered heterocyclyl, —$C_6$-$C_{12}$aryl and 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{9d}$; or $R^{9c}$ and $R^{9d}$ are each independently halogen, hydroxy, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl, —CN or $NR^{9aa}R^{9bb}$, wherein each of said —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl is optionally substituted with at least one hydrogen, halogen, hydroxy, —$C_1$-8alkyl, —$C_{1-8}$alkoxy, —CN, —$NH_2$ or oxo, and $R^{9aa}$ and $R^{9bb}$ are each independently hydrogen or $C_{1-8}$alkyl;

$Z^1$, $Z^2$, $Z^3$ and $Z^4$ are each independently selected from —$CR^z$ and N;

$R^Z$, at each occurrence, is independently selected from hydrogen, halogen, —$C_{1-8}$alkyl, —$C_{2-8}$alkenyl, —$C_{2-8}$ alkynyl, —$NR^{Za}R^{Zb}$, —$OR^{Za}$, —$SR^{Za}$, $C_3$-$C_8$cycloalkyl, 3- to 8-membered heterocyclyl, $C_6$-$C_{12}$aryl, 5- to 12-membered heteroaryl, and CN, wherein each of —$C_{1-8}$alkyl, —$C_{2-8}$alkenyl, —$C_{2-8}$ alkynyl, $C_3$-$C_8$cycloalkyl, 3- to 8-membered heterocyclyl, $C_6$-$C_{12}$aryl, or 5- to 12-membered heteroaryl is optionally substituted with at least one $R^{Zc}$;

$R^{Za}$ and $R^{Zb}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, and 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl, or 5- to 12-membered heteroaryl is optionally substituted with at least one substituent $R^{Zd}$;

$R^{Zc}$ and $R^{Zd}$ are each independently halogen, hydroxy, —$C_{1-8}$alkyl, —$C_{2-8}$alkenyl, —$C_{2-8}$alkynyl, —$C_{1-8}$ alkoxy, $C_{1-8}$alkoxy-$C_{1-8}$alkyl-, —$C_{2-8}$alkenyl, —$C_{2-8}$ alkynyl, $C_3$-$C_8$cycloalkyl, 3- to 8-membered heterocyclyl, $C_6$-$C_{12}$aryl, or 5- to 12-membered heteroaryl;

$L^1$ is selected from a single bond, —O—, —$SO_2$—, —C(O)—, —$NR^{L1a}$—, —$C_3$-$C_8$cycloalkylene-, $*^{L1}$—O—$C_{1-8}$alkylene-$**^{L1}$, $*^{L1}$-$C_{1-8}$alkylene-O—$**^{L1}$, $*^{L1}$—$SO_2$—$C_{1-8}$alkylene-$**^{L1}$, $*^{L1}$-$C_{1-8}$alkylene-$SO_2$—$**^{L1}$, $*^{L1}$-CO—$C_{1-8}$alkylene-$**^{L1}$, $*^{L1}$-$C_{1-8}$alkylene-CO—$**^{L1}$, $*^{L1}$-$NR^{L1a}$—$C_{1-8}$alkylene-$**^{L1}$, $*^{L1}$-$C_{1-8}$alkylene-$NR^{L1a}$—$**^{L1}$, $*^{L1}$-$NR^{L1a}$C(O)—$**^{L1}$, $*^{L1}$-C(O)$NR^{L1a}$—$**^{L1}$, —$C_{1-8}$alkylene-, —$C_{2-8}$alkenylene-, —$C_{2-8}$alkynylene-, —[O$(CR^{L1a}R^{L1b})_{m4}]_{m5}$—,

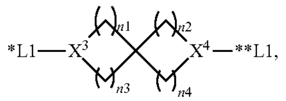

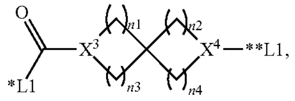

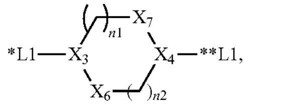

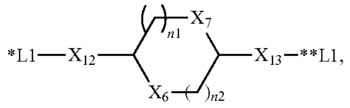

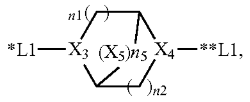

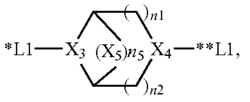

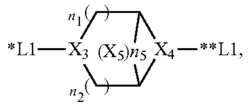

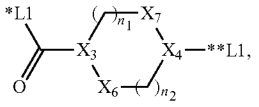

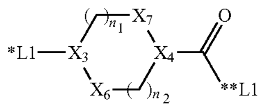 and

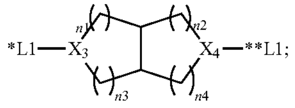

wherein each of said —$C_3$-$C_8$cycloalkylene-, $*^{L1}$—O—$C_{1-8}$alkylene-$**^{L1}$, $*^{L1}$-$C_{1-8}$alkylene-O—$**^{L1}$, $*^{L1}$—$SO_2$—$C_{1-8}$alkylene-$**^{L1}$, $*^{L1}$-$C_{1-8}$alkylene-$SO_2$—$**^{L1}$, $*^{L1}$-CO—$C_{1-8}$alkylene-$**^{L1}$, $*^{L1}$-$C_{1-8}$alkylene-CO—$**^{L1}$, $*^{L1}$-$NR^{L1a}$—$C_{1-8}$alkylene-$**^{L1}$, $*^{L1}$-$C_{1-8}$alkylene-$NR^{L1a}$—$**^{L1}$, —$C_{1-8}$alkylene-, —$C_{2-8}$alkenylene-, —$C_{2-8}$alkynylene-,

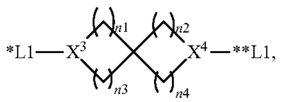
,
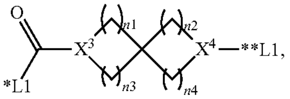
,
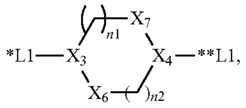
,
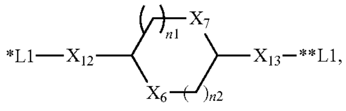
,
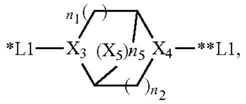
,
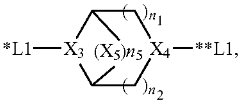
,
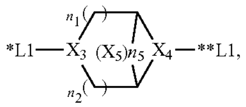
,
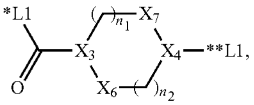
,
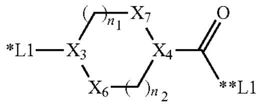
or
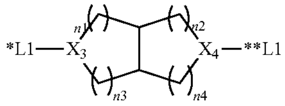

is optionally substituted with at least one $R^{L1c}$; wherein $*^{L1}$ refers to the position attached to

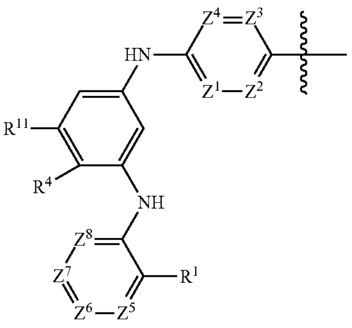

moiety, and $**^{L1}$ refers to the position attached to

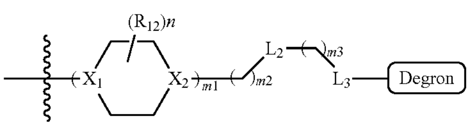

moiety;

$R^{L1a}$ and $R^{L1b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl and 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L1d}$;

each of said $R^{L1c}$ and $R^{L1d}$ are independently halogen, hydroxy, —$C_{1-8}$alkyl, —$C_{1-8}$alkoxy, $C_{1-8}$alkoxy-$C_{1-8}$ alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

$L^2$ is selected from a single bond, —O—, —$SO_2$—, —CO—, —$NR^{L2a}$—, —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O)—$**^{L2}$, $*^{L2}$—C(O)$NR^{L2a}$—$**^{L2}$, —$C_{1-8}$alkylene-, —$C_{2-8}$alkenylene-, —$C_{2-8}$alkynylene-, —$[O(CR^{L2a}R^{L2b})_{m4}]_{m5}$—,

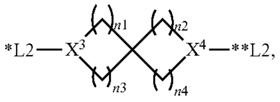
,
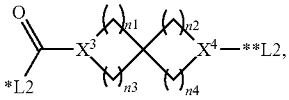
,
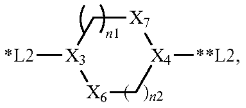
,
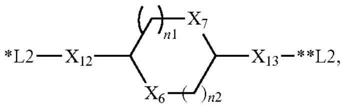
,
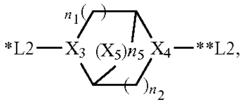
,
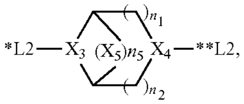
,
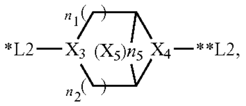
,
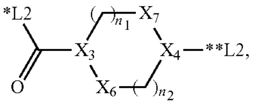
,
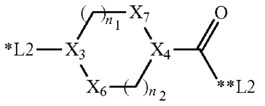
and
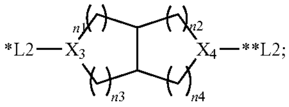
;

wherein each of said —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$^{L2}$, $L^2$-$C_{1-8}$alkylene-CO—$^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, —$C_{1-8}$alkylene-, —$C_{2-8}$alkenylene-, —$C_{2-8}$alkynylene-,

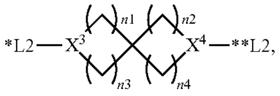
,

-continued

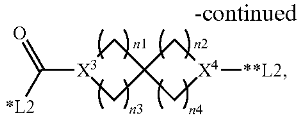

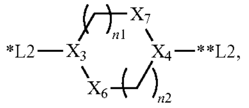

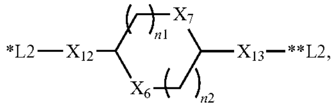

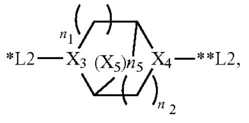 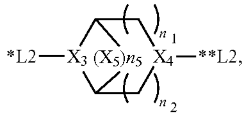

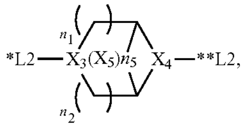 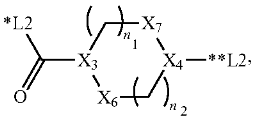

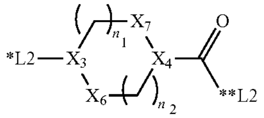 or

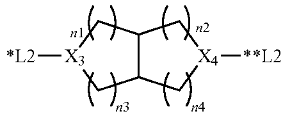

is optionally substituted with at least one substituent $R^{L2c}$;

wherein *12 refers to the position attached to

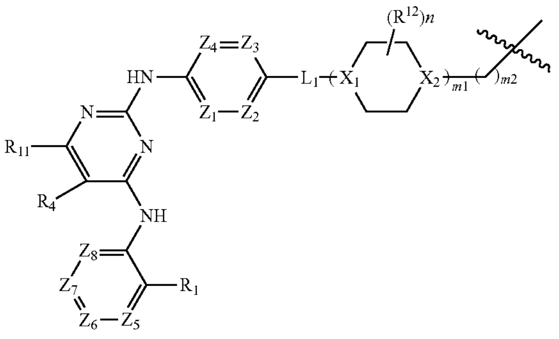

moiety, and $**^{L2}$ refers to the position attached to the

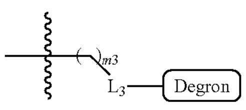

moiety;

$R^{L2a}$ and $R^{L2b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl and 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L2d}$;

each of said $R^{L2c}$ and $R^{L2d}$ are independently halogen, hydroxy, —$C_{1-8}$alkyl, —$C_{1-8}$alkoxy, $C_{1-8}$alkoxy-$C_{1-8}$ alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

$L^3$ is selected from a single bond, —O—, —$SO_2$—, —CO—, —$NR^{L3a}$—, —$C_3$-$C_8$cycloalkylene-$*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-, $SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}$—$NR^{L3a}$C(O)—$**^{L3}$, $*^{L3}$—C(O)$NR^{L3a}$—$**^{L3}$, —$C_{1-8}$alkylene-, —$C_{2-8}$alkenylene-, —$C_{2-8}$alkynylene-, —$[O(CR^{L3a}R^{L3b})_{m4}]_{m5}$—,

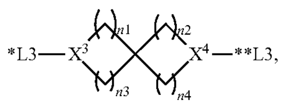

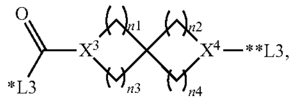

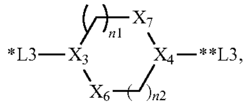

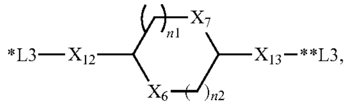

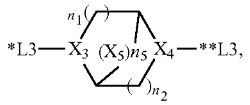 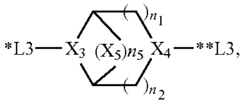

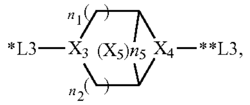 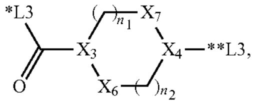

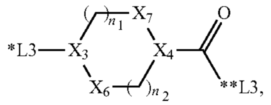 and

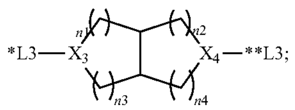

wherein each of said —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$—$C_{1-8}$alkylene-, —$C_{2-8}$alkenylene-, —$C_{2-8}$alkynylene-,

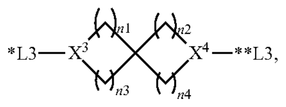

-continued

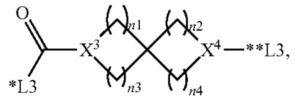

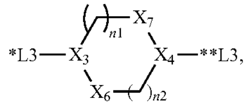

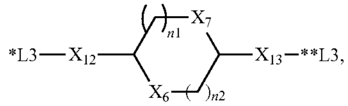

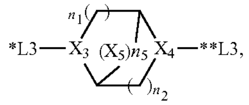 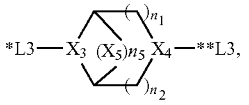

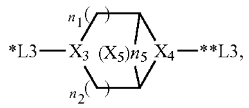 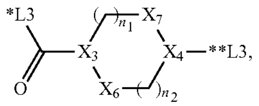

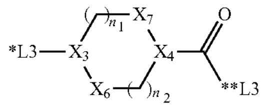 or

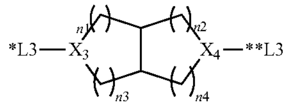

is optionally substituted with at least one substituent $R^{L3c}$, wherein $*^{L3}$ refers to the position attached to

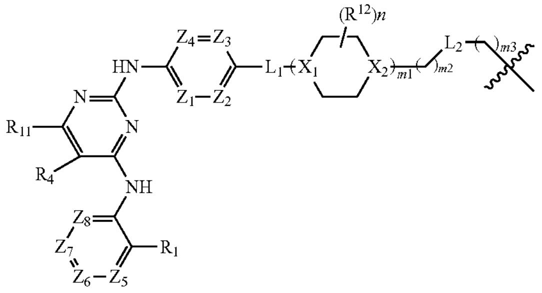

moiety, and $**^{L3}$ refers to the position attached to the

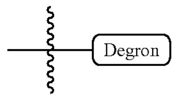

moiety;

$R^{L3a}$ and $R^{L3b}$ are each independently selected from hydrogen, —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl and 5- to 12-membered heteroaryl, wherein each of said —$C_{1-8}$alkyl, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl is optionally substituted with at least one substituent $R^{L3d}$, each of said $R^{L3c}$ and $R^{L3d}$ are independently halogen, hydroxy, —$C_{1-8}$alkyl, —$C_{1-8}$alkoxy, $C_{1-8}$alkoxy-$C_{1-8}$ alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl, 5- to 12-membered heteroaryl or oxo;

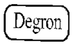 is selected from

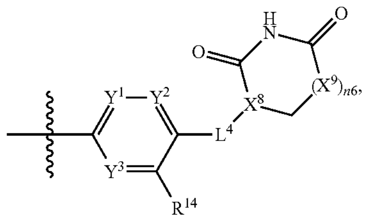

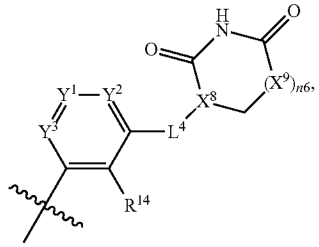

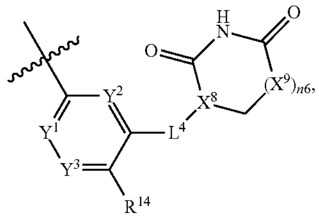

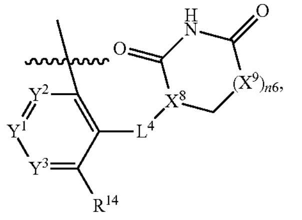

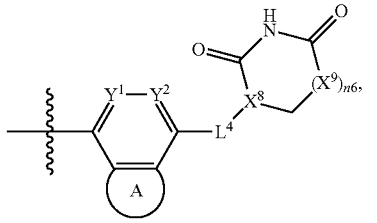

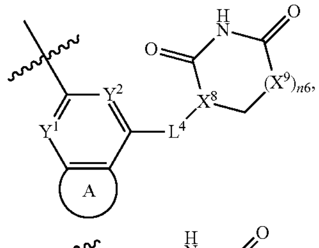

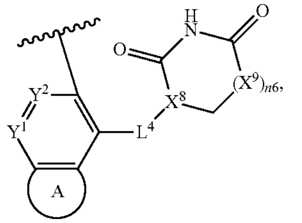

-continued
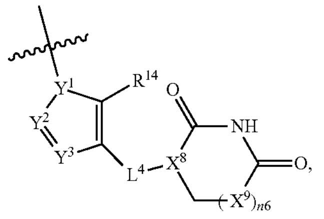
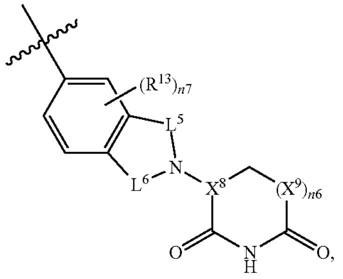
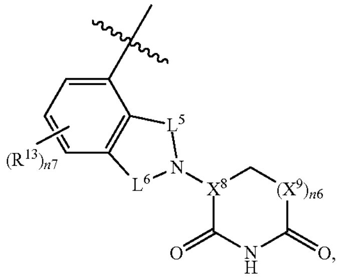
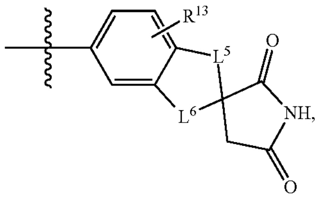
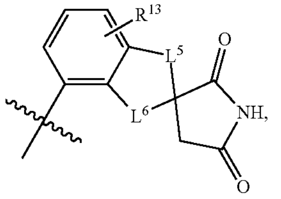
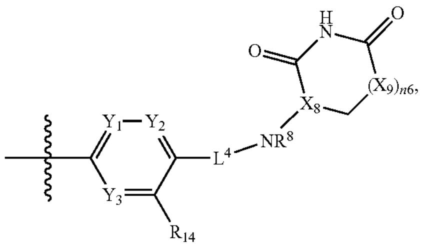
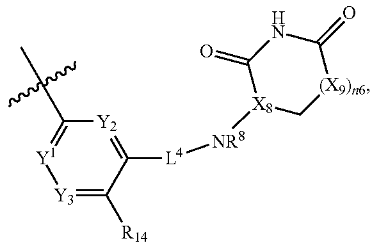
-continued
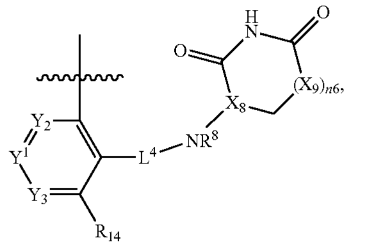
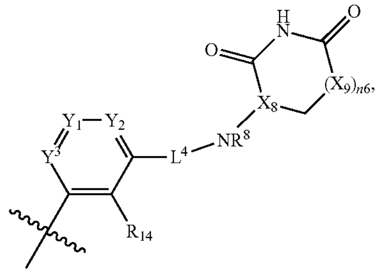
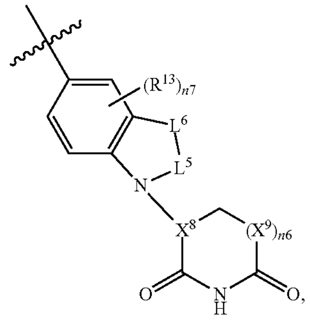
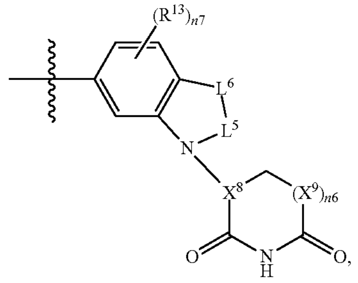
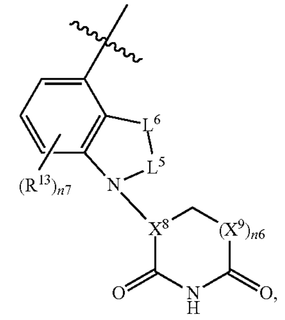
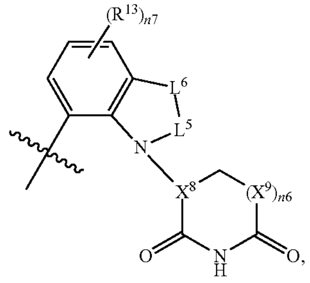

-continued

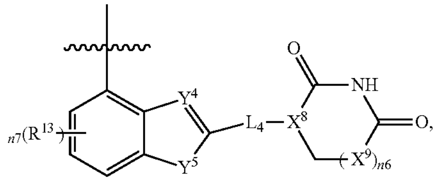

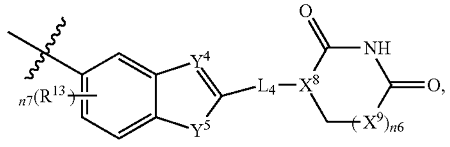

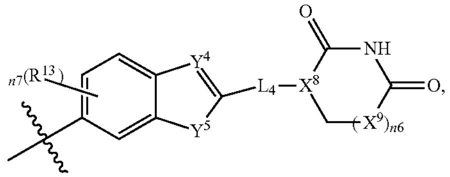

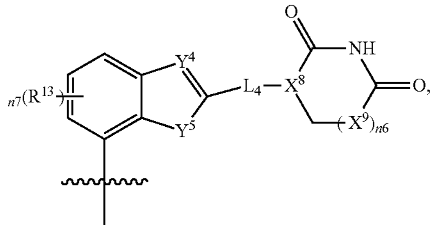

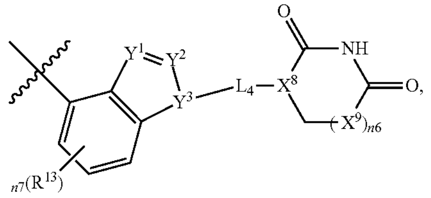

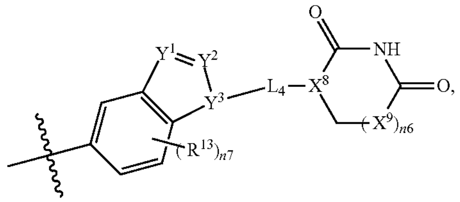

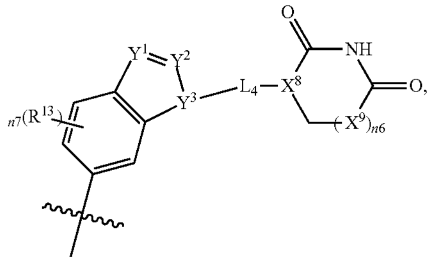

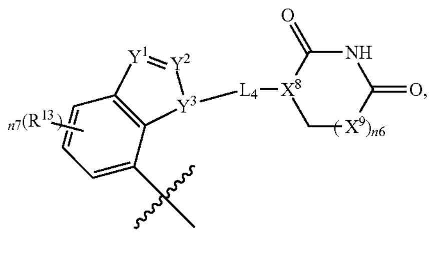

-continued

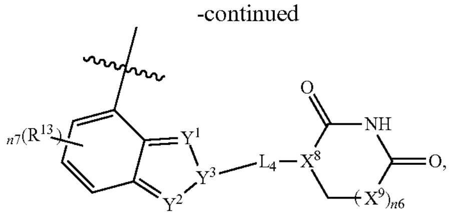

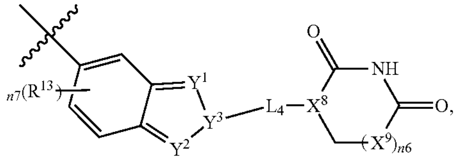

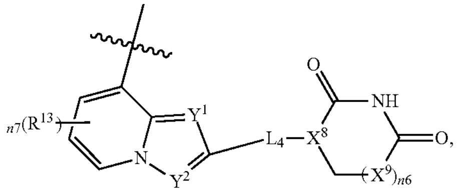

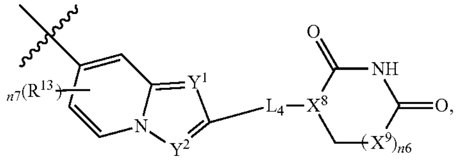

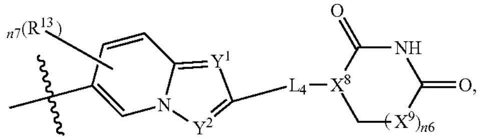

and

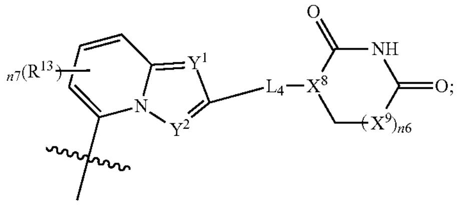

Ring A is selected from 3-12 membered cycloalkyl, 3-12 membered heterocyclyl, aryl, and heteroaryl;

$R^{13}$ and $R^{14}$ are independently selected from hydrogen, halogen, CN, —$C_{1-8}$alkyl, —$C_{2-8}$alkenyl, —$C_{2-8}$alkynyl, —$C_{1-8}$alkoxy, $C_3$-$C_8$cycloalkyl, 3- to 8-membered heterocyclyl, $C_6$-$C_{12}$aryl and 5- to 12-membered heteroaryl; said each —$C_{1-8}$alkyl, —$C_{2-8}$alkenyl, —$C_{2-8}$ alkynyl, —$C_{1-8}$alkoxy, $C_3$-$C_8$cycloalkyl, 3- to 8-membered heterocyclyl, $C_6$-$C_{12}$aryl or 5- to 12-membered heteroaryl is optionally substituted with at least one substituent halogen, —$C_{1-8}$alkyl, $C_{1-8}$alkoxy-$C_{1-8}$alkyl-, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

$X^1$, $X^2$, $X^3$, $X^4$ and $X^8$ are each independently selected from —$CR^a$ and N;

$X^5$, $X^6$, $X^7$ and $X^9$ are each independently selected from —$NR^a$—, —O—, —S— and —$CR^aR^b$—;

$X^{12}$ and $X^{13}$ are each independently selected from —$NR^a$— and —O—;

$L^4$, $L^5$ and $L^6$ are each independently selected from a single bond, —O—, —$NR^a$—, —$(CR^aR^b)_{n8}$—, —$O(CR^aR^b)_{n8}$—, —$NR^a(CR^aR^b)_{n8}$— and —C(O)—;

$Y^1$, $Y^2$, $Y^3$ and $Y^4$ are each independently selected from $CR^a$ and N;

$Y^5$ is selected from $NR^a$, O and S;

$R^a$ and $R^b$ are each independently selected from hydrogen (H, D or T), halogen, CN, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl and 5- to 12-membered heteroaryl, wherein each of said —$C_{1-8}$ alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl is optionally substituted with at least one substituent halogen, hydroxy, halogen, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl or 5- to 12-membered heteroaryl; or $R^a$ and $R^b$ together with the carbon atoms to which they are attached, form a 3- to 12-membered ring, said ring comprising 0-3 heteroatoms independently selected from nitrogen, oxygen and sulfur; said ring is optionally substituted with at least one substituent halogen, hydroxy, —$C_{1-8}$alkyl, —$C_{2-8}$alkenyl, —$C_{2-8}$alkynyl, —$C_{1-8}$alkoxy, —$C_{2-8}$alkenyl, —$C_{2-8}$alkynyl, $C_3$-$C_8$cycloalkyl, 3- to 8-membered heterocyclyl, $C_6$-$C_{12}$aryl or 5- to 12-membered heteroaryl;

$m_1$ is 0 or 1;

$m_2$ and $m_3$ are each independently 0, 1, 2, 3, 4, 5, 6, 7 or 8;

$m_4$ and $m_5$ are each independently 0, 1, 2 or 3;

n, $n_1$, $n_2$, $n_3$, $n_4$ and $n_5$ are each independently 0, 1, 2 or 3; and $n_6$ is 0, 1, 2, 3 or 4

$n_7$ is 0, 1, 2 or 3;

$n_8$ is 0, 1, 2, 3, 4, 5, 6, 7 or 8.

2. The compound of claim 1, wherein $R^1$ is —P(O)$R^{1a}R^{1b}$, wherein $R^{1a}$ and $R^{1b}$ are each independently selected from —$CH_3$, —$CH_2CH_3$, —$CH_2CH_2CH_3$, -iso-$C_3H_7$, —$CH_2CH_2CH_2CH_3$, -iso-$C_4H_9$, -sec-$C_4H_9$, -tert-$C_4H_9$, cyclopropyl, cyclobutyl and cyclopentyl.

3. The compound of claim 1, wherein $R^1$ is —P(O)$(CH_3)_2$.

4. The compound of claim 1, wherein $Z^7$ is N.

5. The compound of claim 1, wherein $R^2$ and $R^3$ are each independently selected from hydrogen, halogen, methyl, ethyl, propyl, butyl, pentyl, hexyl, heptyl and octyl.

6. The compound of claim 1, wherein when $Z^5$ is —$CR^2$ and $Z^6$ is —$CR^3$, wherein $R^2$ and $R^3$ together with the carbon atoms to which they are attached, form a 5 or 6 membered unsaturated ring, said ring comprising 0, 1 or 2 heteroatoms independently selected from nitrogen, oxygen, and sulfur; said ring is optionally substituted with at least one substituent $R^{2e}$;

$R^{2e}$, at each occurrence, is independently hydrogen, —F, —Cl, —Br, —I, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl or oxo, wherein each of methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl or cyclooctyl is optionally substituted with at least one substituent $R^{2d}$, and $R^{2d}$, at each occurrence, is independently —F, —Cl, —Br, —I, —OH, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl or phenyl.

7. The compound of claim 1, wherein the

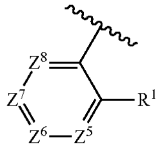

moiety is

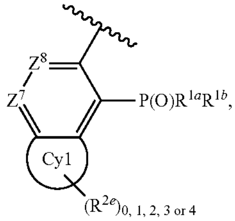

wherein Cyl is a 5-6 membered aromatic ring, said ring comprising 0-3 heteroatoms independently selected from nitrogen, oxygen and sulfur.

8. The compound of claim 1, wherein $R^{2e}$ at each occurrence, is independently hydrogen, —F, —Cl, —Br, —I, methyl, ethyl, propyl, butyl, pentyl, cyclopropyl, cyclobutyl, or cyclopentyl, wherein each of methyl, ethyl, propyl, butyl, pentyl, cyclopropyl, cyclobutyl, or cyclopentyl is optionally substituted with at least one $R^{2d}$, and $R^{2d}$, at each occurrence, is independently —F, —Cl, —Br, —I, or —OH.

9. The compound of claim 1, wherein $R^{2e}$ at each occurrence, is independently hydrogen, —F, —Cl, —Br, —I, —$CH_3$, —$CH_2CH_3$, —$CH_2CH_2CH_3$, —$CH(CH_3)_2$, —$CH_2CH_2CH_2CH_3$, —$CH(CH_3)$ $CH_2CH_3$, —$CH_2CH(CH_3)_2$, —$C(CH_3)_3$, —$CF_3$,

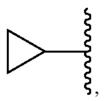,
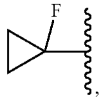,
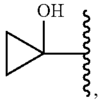,
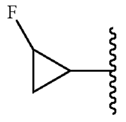
or
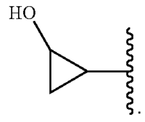.

10. The compound of claim 1, wherein the

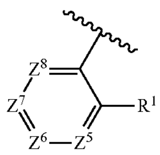

moiety is
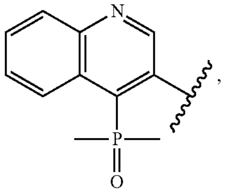
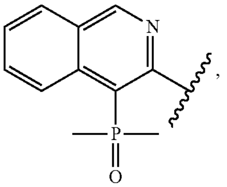
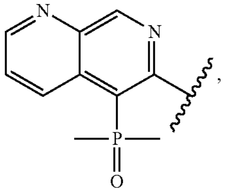
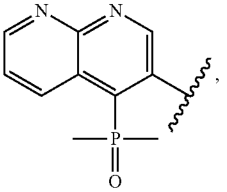
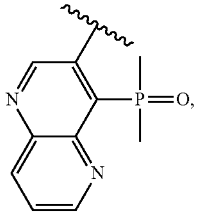
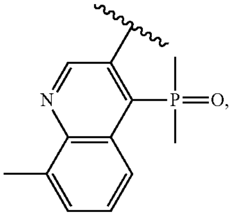
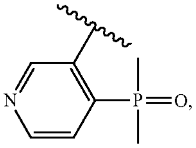
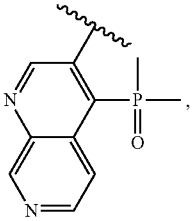
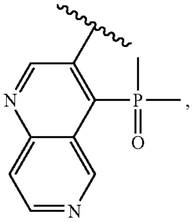
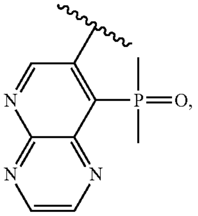
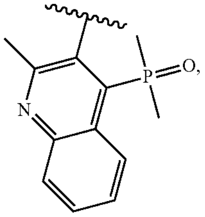
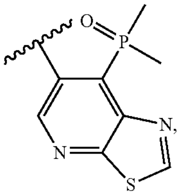
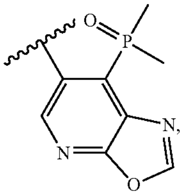
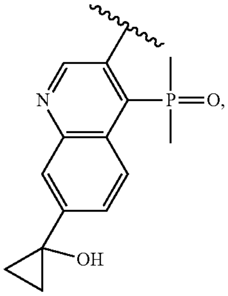
-continued
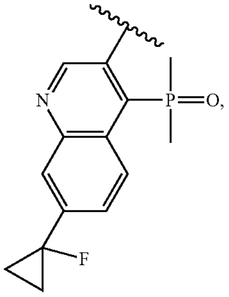
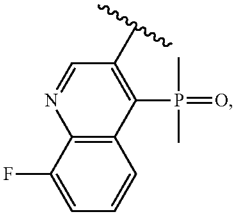
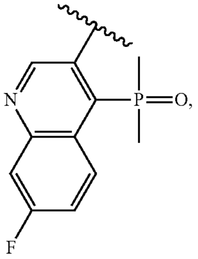
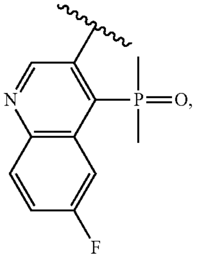
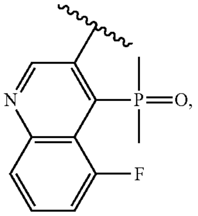
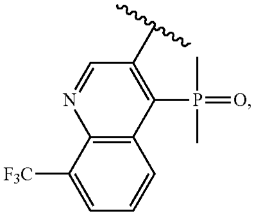
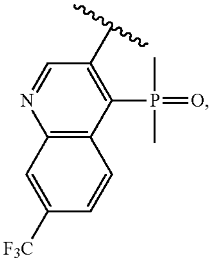
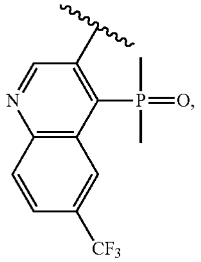
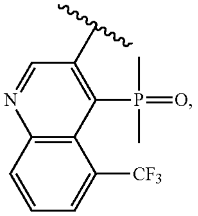
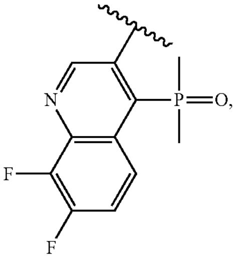
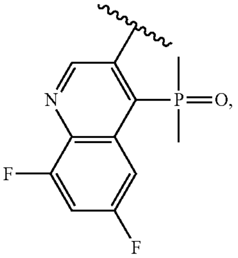
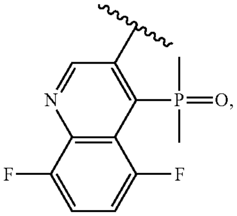

-continued

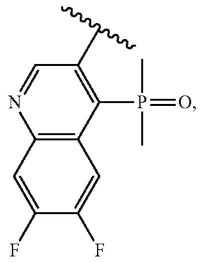

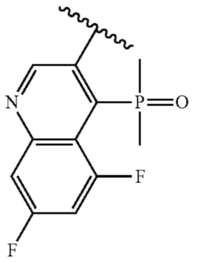

or

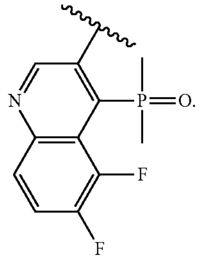

11. The compound of claim 1, wherein $R^9$, $R^{10}$, $R^{11}$ and $R^{12}$ are each independently selected from hydrogen, —F, —Cl, —Br, —I, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl, $—NH_2$ and oxo, wherein each of methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, or cyclooctyl is optionally substituted with at least one substituent $R^{9c}$; or two $R^{12}$ together with the carbon atoms to which they are attached, form a 3, 4, 5, 6, 7 or 8-membered ring, said ring comprising 0, 1, 2 or 3 heteroatoms independently selected from nitrogen, oxygen and sulfur; said ring is optionally substituted with at least one substituent $R^{9c}$, wherein $R^{9c}$ is independently —F, —Cl, —Br, —I, hydroxy, methyl, ethyl, propyl, butyl, pentyl, hexyl, heptyl, octyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl, $—C_{2-8}$ alkenyl, $—C_{2-8}$alkynyl, 3- to 8-membered heterocyclyl, phenyl, 5- to 12-membered heteroaryl, $NH_2$, or $—NHCH_3$.

12. The compound of claim 1, wherein $R^9$, $R^{10}$, $R^{11}$ and $R^{12}$ are each independently selected from hydrogen, F, Cl, Br, $—NH_2$, $—CH_3$, $—C_2H_5$, $—C_3H_7$, $—CH_2F$, $—CHF_2$, $—CF_3$, $—C_4H_9$, $—C_5H_{11}$, $—OCH_3$, $—OC_2H_5$, $—OC_3H_7$, $—OC_4H_9$, $—OCH_{11}$, —CN, cyclopropyl and oxo; or two $R^{12}$ together with the carbon atoms to which they are attached, form a 3, 4, 5, 6, 7 or 8-membered ring, said ring comprising 0, 1, 2 or 3 heteroatoms independently selected from nitrogen, oxygen and sulfur; said ring is optionally substituted with at least one substituent-H, —F, —Cl, —Br, —I, methyl, ethyl, propyl, butyl, $—NH_2$, $—NHCH_3$, —OH, $—OCH_3$, $—OC_2H_5$, cyclopropyl, cyclobutyl, cyclopentyl, or cyclohexyl.

13. The compound of claim 1, wherein $R^4$ is selected from —H, —F, —Cl, —Br, —I, $—CH_3$, $—C_2H_5$, $—C_3H_7$, $—C_4H_9$, cyclopropyl, and cyclobutyl, wherein each of $—CH_3$, $—C_2H_5$, $—C_3H_7$, $—C_4H_9$, cyclopropyl, or cyclobutyl is optionally substituted with —F, —Cl, —Br, or —I.

14. The compound of claim 1, wherein $L^1$ is selected from a single bond, —O—, $—SO_2—$, —C(O)—, $—NR^{L1a}—$, $—C_3$-$C_8$cycloalkylene-, $*^{L1}—O—C_{1-8}$alkylene-$**^{L1}$, $*^{L1}$-$C_{1-8}$alkylene-O—$**^{L1}$, $*^{L1}—SO_2—C_{1-8}$alkylene-$**^{L1}$, $*^{L1}$-$C_{1-8}$alkylene-$SO_2—**^{L1}$, $*^{L1}$-CO—$C_{1-8}$alkylene-$**^{L1}$, $*^{L1}$-$C_{1-8}$alkylene-CO—$**^{L1}$, $*^{L1}$-$NR^{L1a}—C_{1-8}$alkylene-$**^{L1}$, $*^{L1}$-$C_{1-8}$alkylene-$NR^{L1a}—**^{L1}$, $*^{L1}$, $NR^{L1a}$C(O)—$**^{L1}$, $*^{L1}$-C(O)$NR^{L1a}**^{L1}$, $—C_{1-8}$alkylene-, $—C_{2-8}$ alkenylene-, $—C_{2-8}$alkynylene-, $—[O(CR^{L1a}R^{L1b})_{m4}]m_5—$,

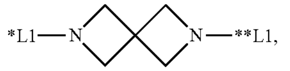

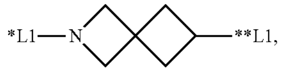

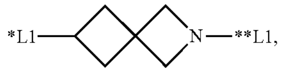

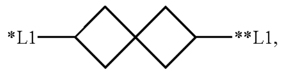

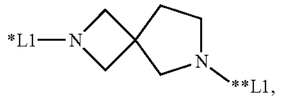

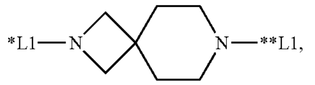

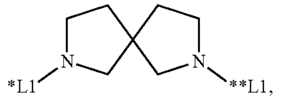

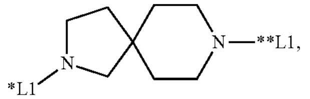

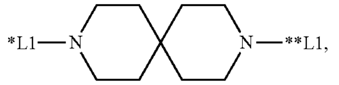

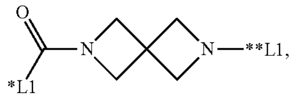

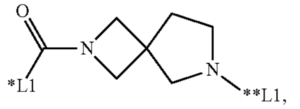

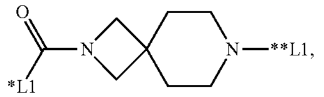

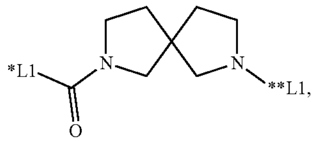

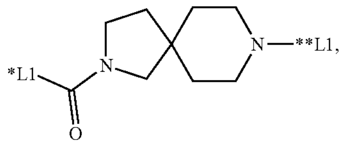

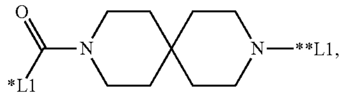

-continued
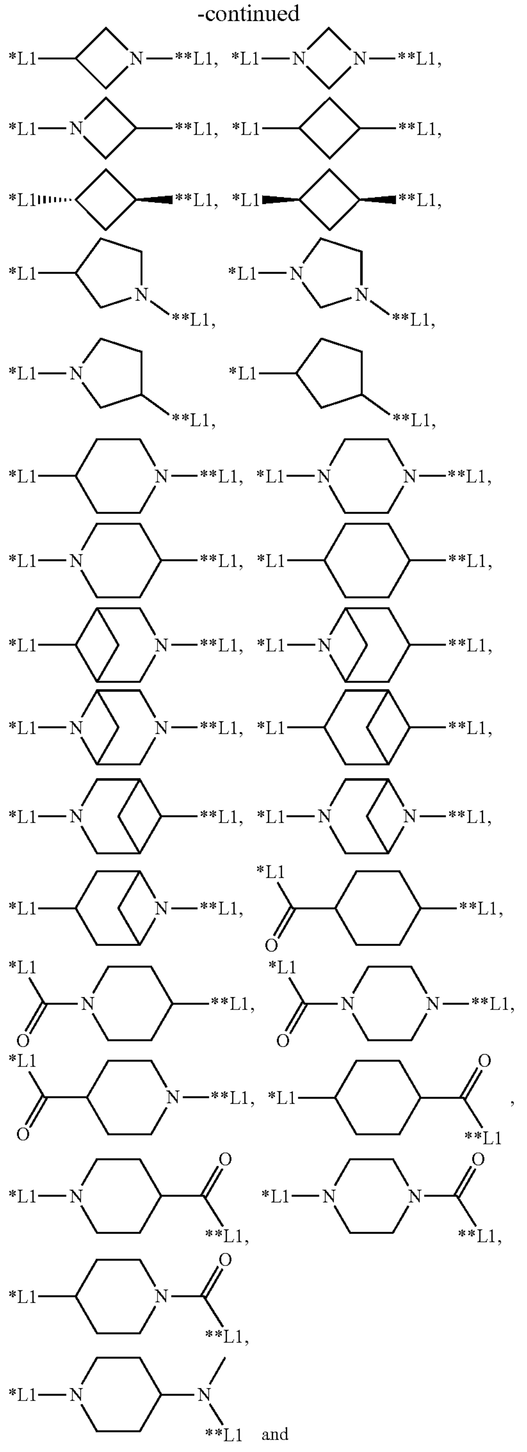
and
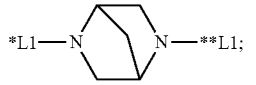
wherein each of said —$C_3$-$C_8$cycloalkylene-, $*^{L1}$—O—$C_{1-8}$alkylene-$**^{L1}$, $*^{L1}$-C salkylene-O—$**^{L1}$, $*^{L1}$—$SO_2$—$C_{1-8}$alkylene-$**^{L1}$, $*^{L1}$-$C_{1-8}$alkylene-$SO_2$—$**^{L1}$, $*^{L1}$-CO—$C_{1-8}$alkylene-$**^{L1}$, $*^{L1}$-$C_{1-8}$alkylene-CO—$**^{L1}$, $*^{L1}$-$NR^{L1a}$—$C_{1-8}$alkylene-$**^{L1}$, $*^{L1}$-$C_{1-8}$alkylene-$NR^{L1a}$—$**^{L1}$, —$C_{1-8}$alkylene-, —$C_{2-8}$alkenylene-,
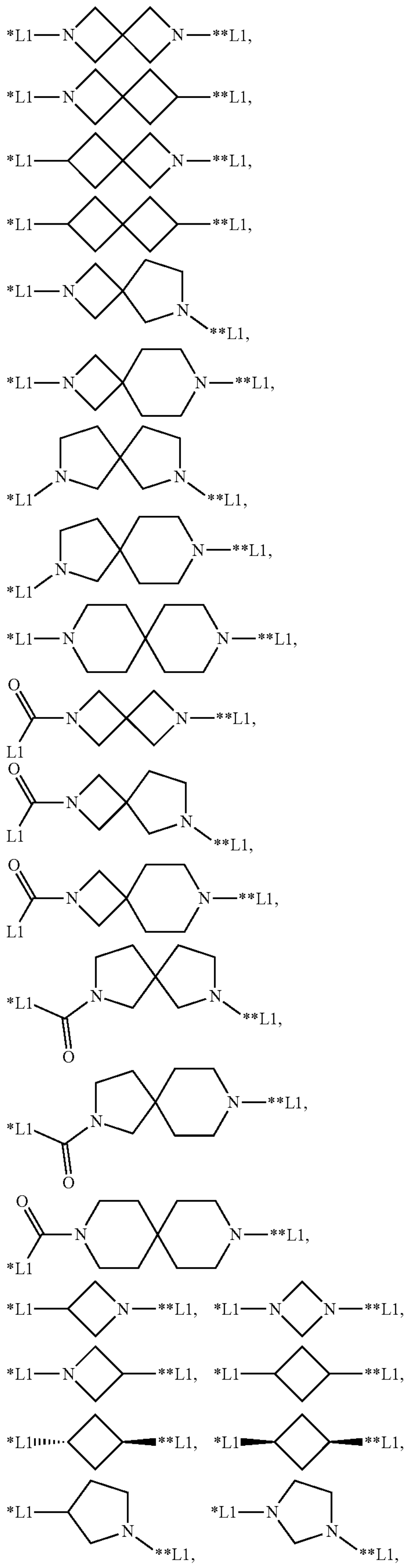

-continued

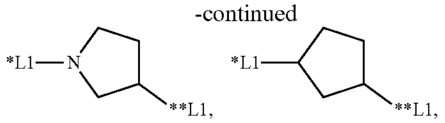
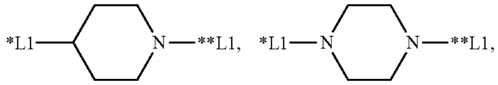
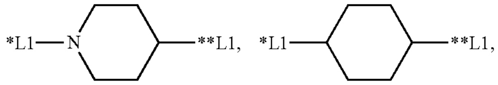
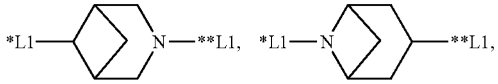
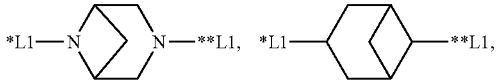
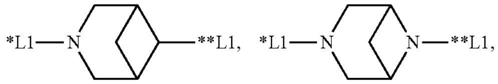
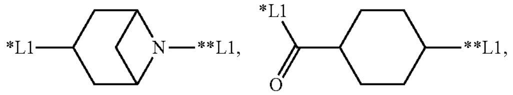
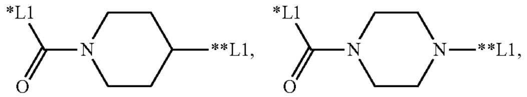
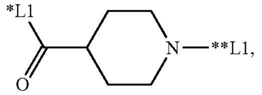
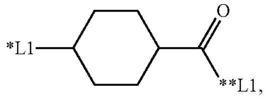
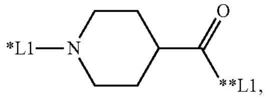
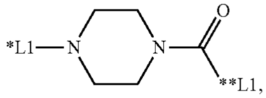
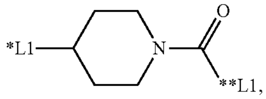
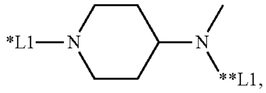

or

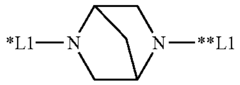

is optionally substituted with at least one $R^{L1c}$, $R^{L1a}$ and $R^{L1b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl and pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L1d}$, and each of said $R^{L1c}$ and $R^{L1d}$ are independently —F, —Cl, —Br, —I, —OH, methyl, ethyl, propyl, butyl, pentyl, hexyl, heptyl, octyl, vinyl, ethynyl, methoxy, ethoxy, propoxy, butoxy, pentoxy, hexoxy, heptoxy, octoxy, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo.

15. The compound of claim 1, wherein $L^1$ is selected from a single bond, $—CH_2—$, $—C_2H_4—$, $—C_3H_6—$, —CO—, —O—, $—N(CH_3)—$, —NH—,

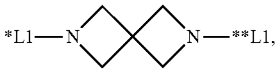
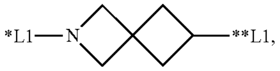
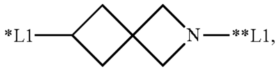
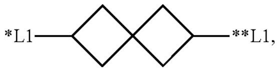
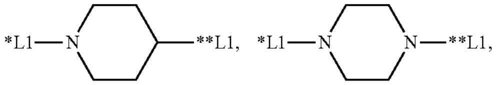
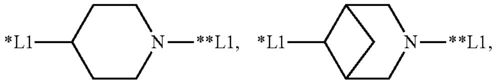
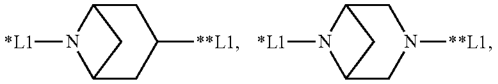
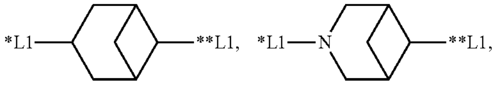
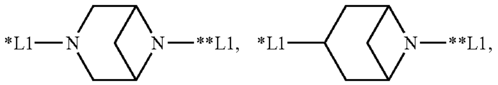
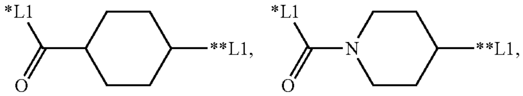
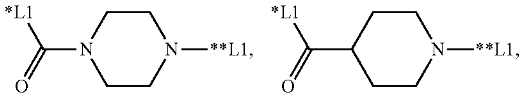
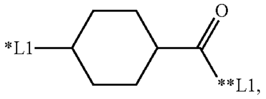
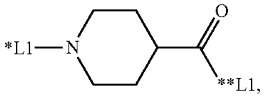

-continued
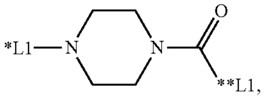
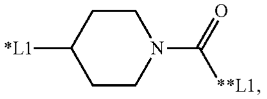
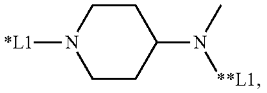
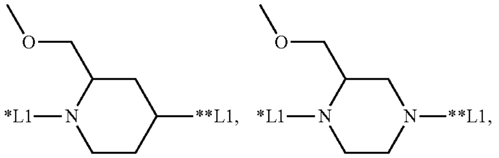
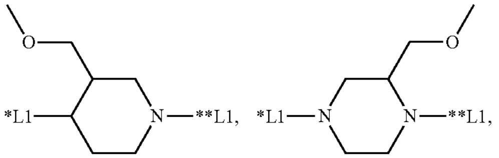
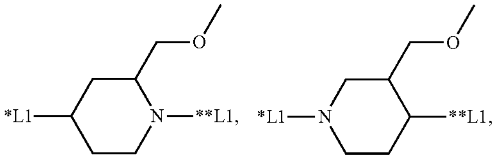
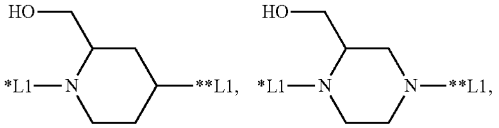
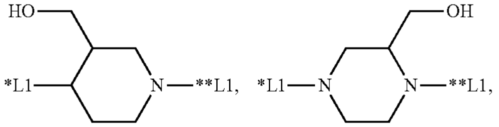
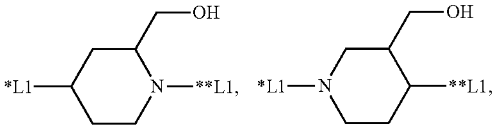
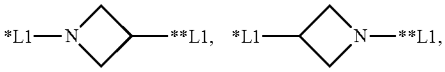
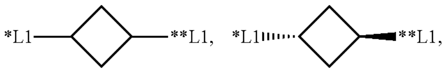
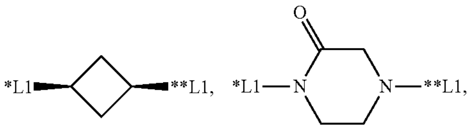
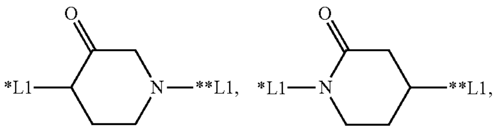
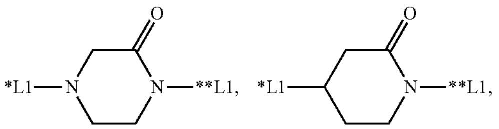
-continued
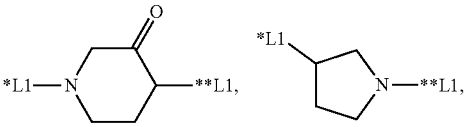
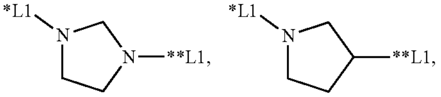
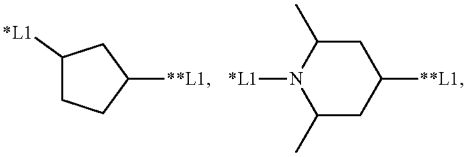
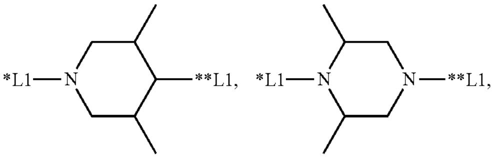
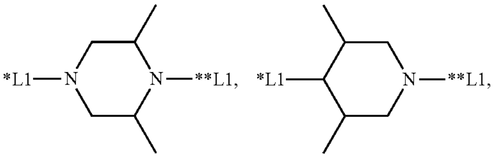
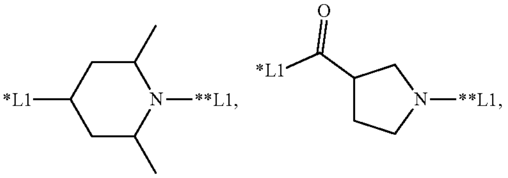
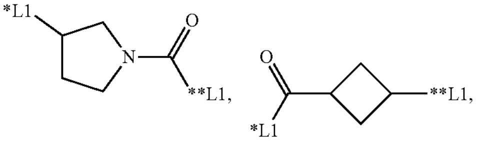
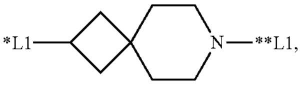
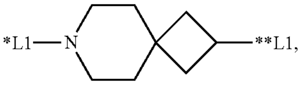
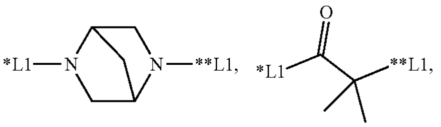
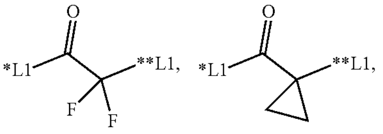
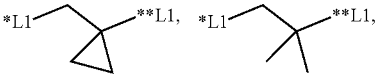
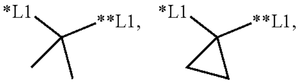
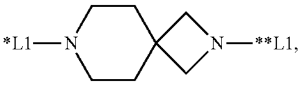

-continued

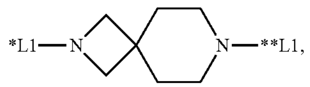

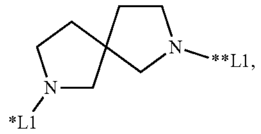

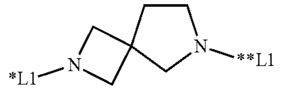

and

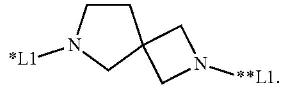

16. The compound of claim 1, wherein $X^1$ and $X^2$ are each independently selected from —$CR^a$ and N;

$R^a$ is selected from hydrogen, —F, —Cl, —Br, —I, CN, methyl, ethyl, methoxy, ethoxy, and cyclopropyl, wherein each of said methyl, ethyl, methoxy, ethoxy, or cyclopropyl is optionally substituted with at least one substituent-F, —Cl, —Br, —I, hydroxy, methyl, ethyl;

$m_1$ is 1 or 0; and $R^{12}$ is hydrogen, oxo, methoxymethyl, hydroxymethyl, —CN or —$CH_3$.

17. The compound of claim 1, wherein the

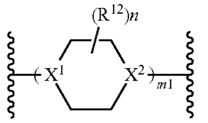

moiety is

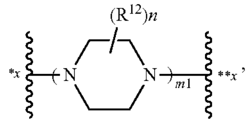

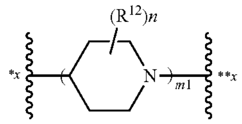

or

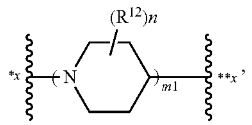

wherein $*^X$ refers to the position attached to

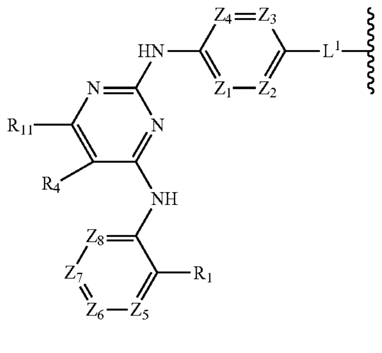

moiety, and $**^X$ refers to the position attached to the

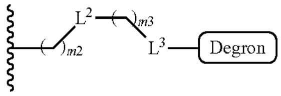

moiety.

18. The compound of claim 1, wherein $m_1$ is 0.

19. The compound of claim 1, wherein the

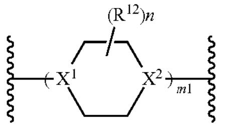

moiety is

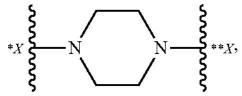

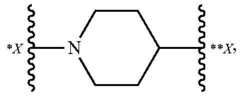

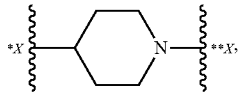

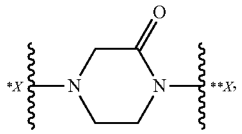

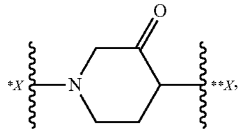

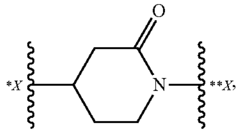

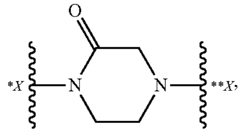

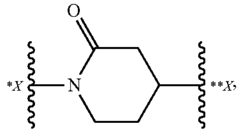

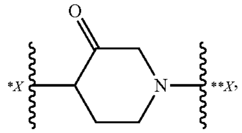

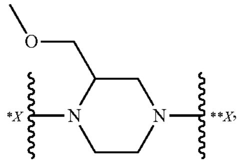

-continued

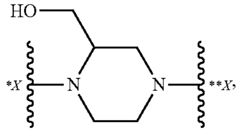

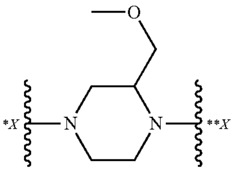

or

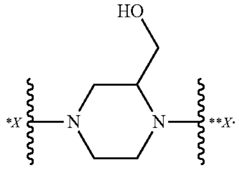

20. The compound of claim 1, wherein $m_2$ is selected from 0, 1, 2, 3, 4 and 5.

21. The compound of claim 1, wherein $L^2$ is selected from a single bond, —O—, —$SO_2$—, —CO—, —$NR^{L2a}$—, —$C_3$-$C_8$cycloalkylene-, $*^{L2}$—O—$C_{1-8}$alkylene-$**^{L2}$, $*^{L2}$—$C_{1-8}$alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$ alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$, $*^{L2}$—$NR^{L2a}$C(O)—$^{L2}$, $L^2$-C(O)$NR^{L2a}$—$^{L2}$, —$C_{1-8}$alkylene-, —$C_{2-8}$alkenylene-, —$C_{2-8}$ alkynylene-, —[O($CR^{L2a}R^{L2b}$)$_{m4}$]$m_5$—,

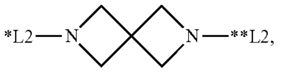

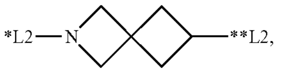

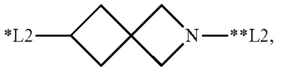

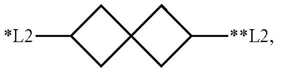

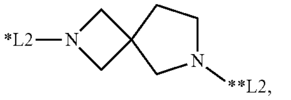

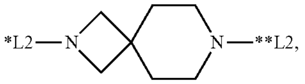

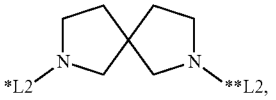

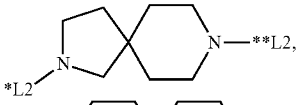

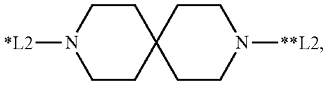

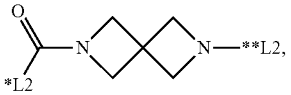

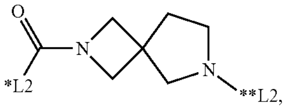

-continued

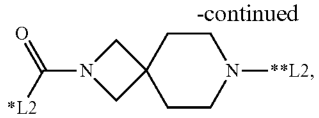

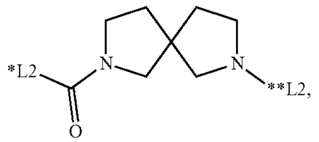

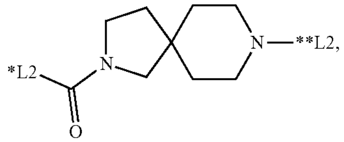

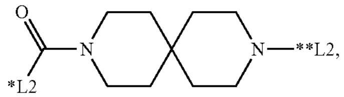

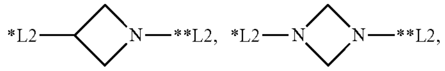

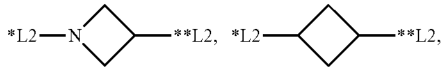

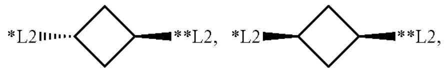

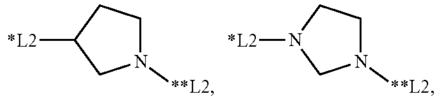

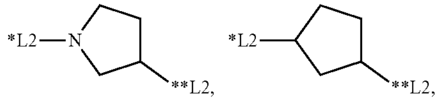

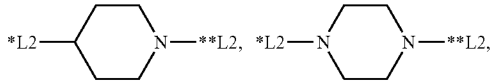

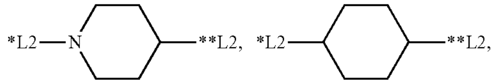

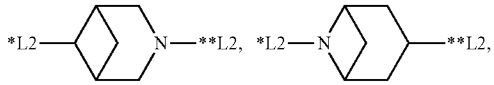

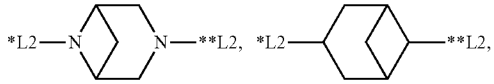

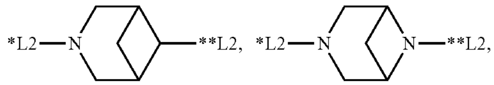

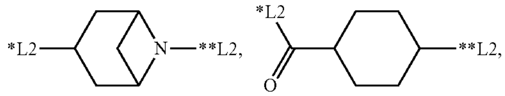

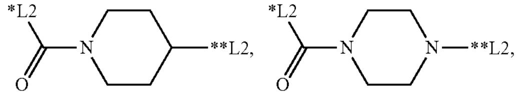

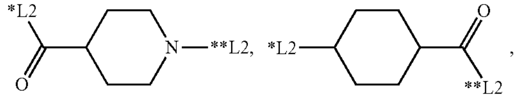

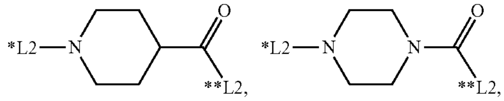

-continued
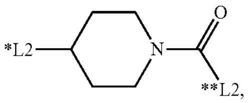
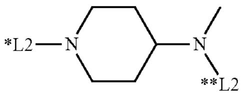
and
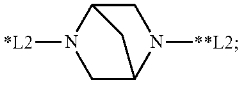
wherein each of said —$C_3$-$C_8$cycloalkylene-, $*^{L2}$—O—$C_{1-8}$alkylene-$**^{L2}$, $*^{L2}$—C 8alkylene-O—$**^{L2}$, $*^{L2}$—$SO_2$—$C_{1-8}$alkylene-$**^{L2}$, $*^{L2}$—$C_{1-8}$alkylene-$SO_2$—$**^{L2}$, $*^{L2}$—CO—$C_{1-8}$alkylene-$**^{L2}$, $*^{L2}$—$C_{1-8}$alkylene-CO—$**^{L2}$, $*^{L2}$—$NR^{L2a}$—$C_{1-8}$alkylene-$**^{L2}$, $*^{L2}$—$C_{1-8}$alkylene-$NR^{L2a}$—$**^{L2}$—$C_{1-8}$alkylene-, —$C_{2-8}$alkenylene-, —$C_{2-8}$alkynylene-,
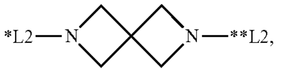
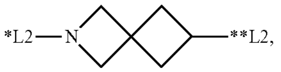
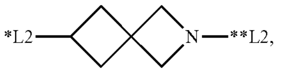
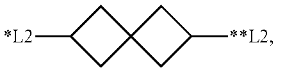
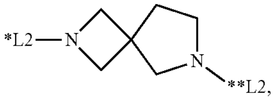
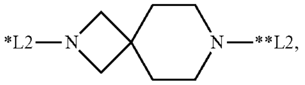
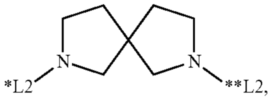
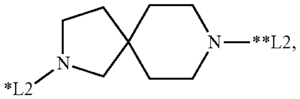
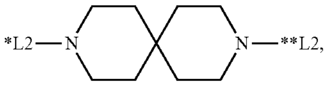
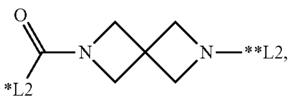
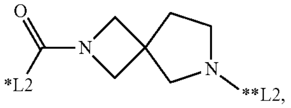
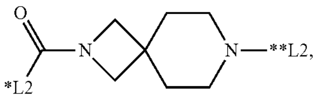
-continued
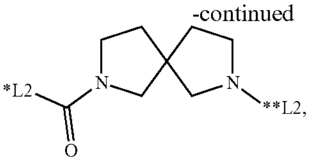
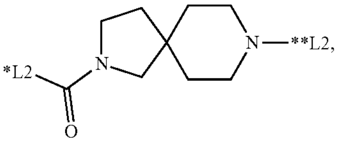
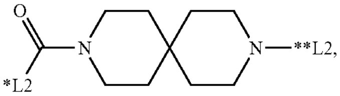
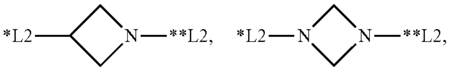
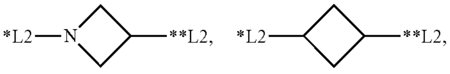
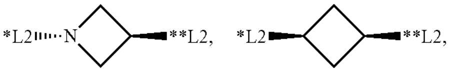
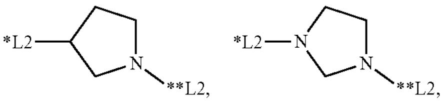
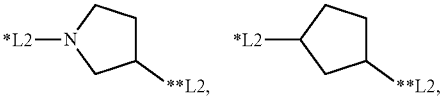
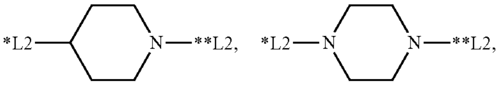
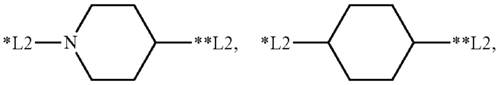
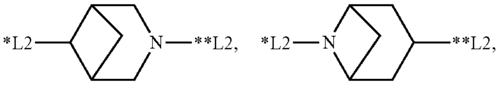
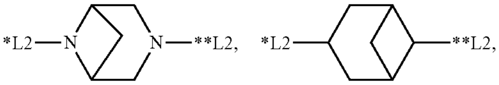
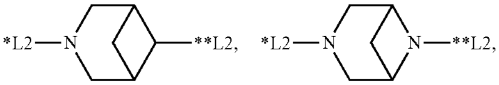
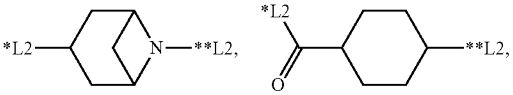
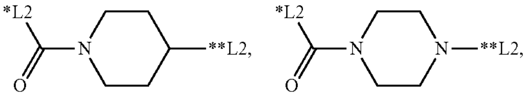
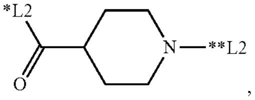
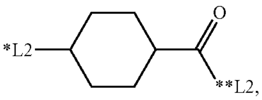
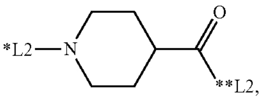

-continued

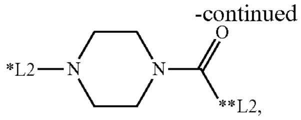

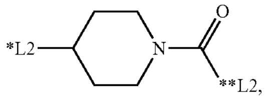

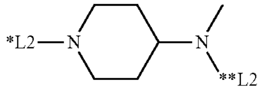

or

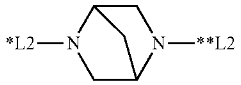

is optionally substituted with at least one substituent $R^{L2c}$, $R^{L2a}$ and $R^{L2b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl and pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L2d}$, and each of said $R^{L2c}$ and $R^{12d}$ are independently —F, —Cl, —Br, —I, —OH, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo.

22. The compound of claim 1, wherein $L^2$ is selected from a single bond, —$CH_2$—, —$C_2H_4$—, —$C_3H_6$—, —CO—, —O—, —$N(CH_3)$—, —NH—,

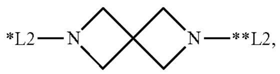

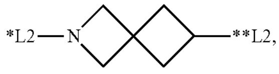

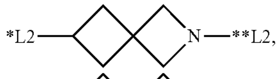

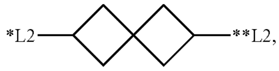

-continued

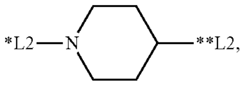
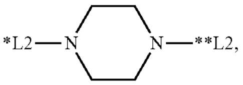

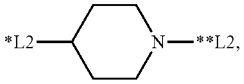
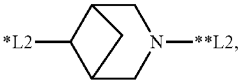

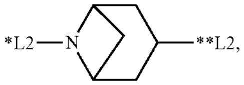
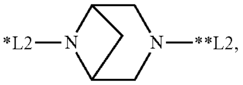

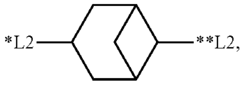
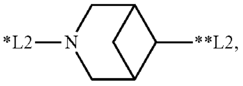

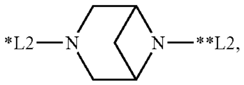
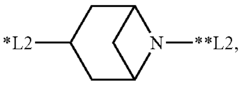

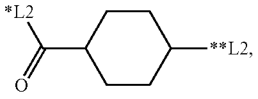
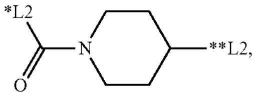

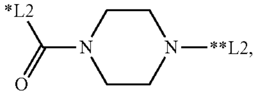
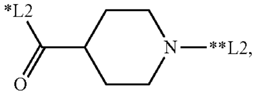

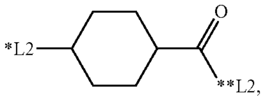

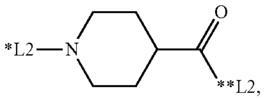

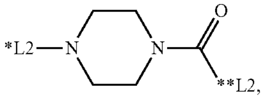

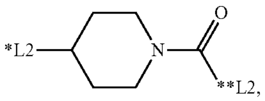

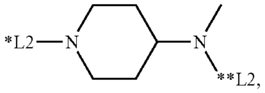

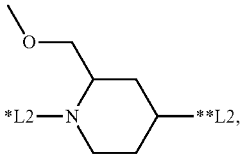
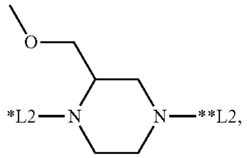

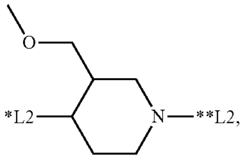
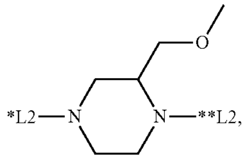

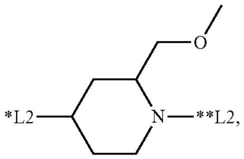
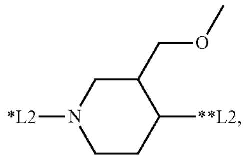

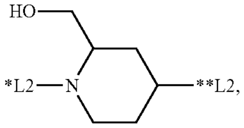
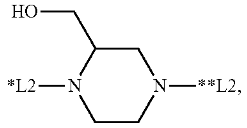

-continued

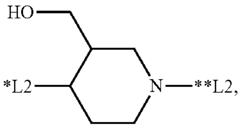 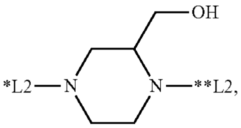

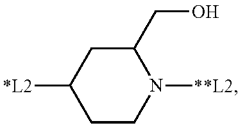 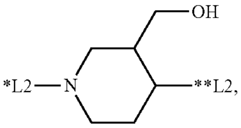

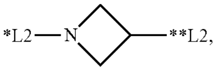 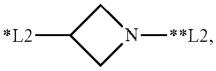

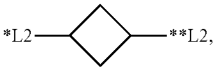 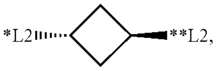

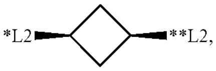 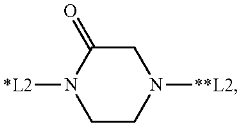

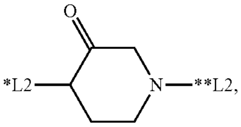 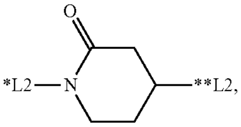

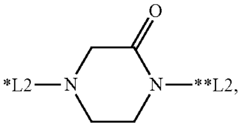 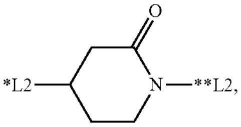

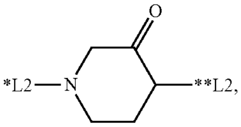 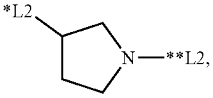

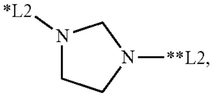 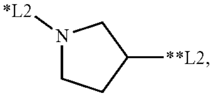

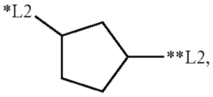 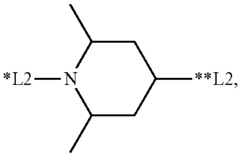

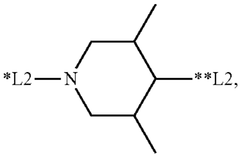 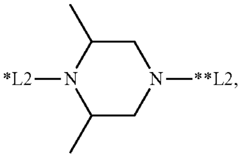

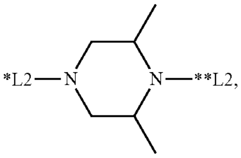 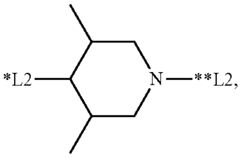

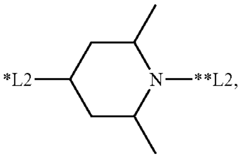 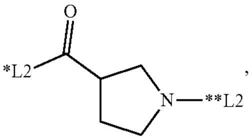 ,

-continued

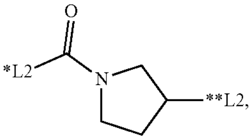

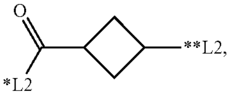

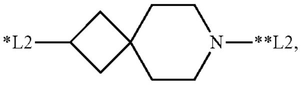

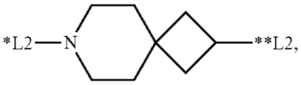

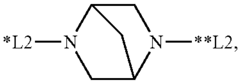

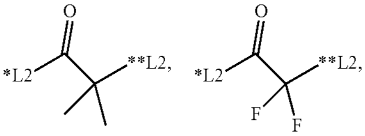

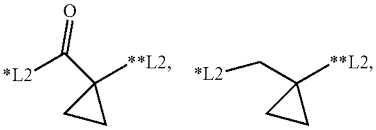

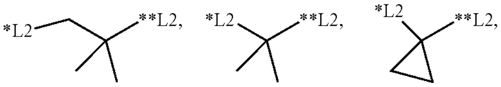

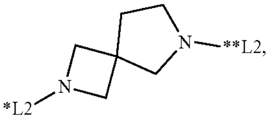

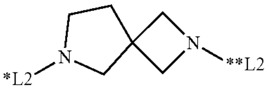 and

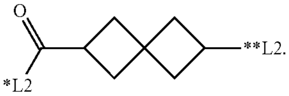

23. The compound of claim 1, wherein $m_3$ is 0, 1, 2, 3, 4, 5 or 6.

24. The compound of claim 1, wherein $L^3$ is selected from a single bond, —O—, —$SO_2$—, —CO—, —$NR^{L3a}$—, —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, $*^{L3}$—$NR^{L3a}$C(O)—$**^{L3}$, $*^{L3}$—C(O)$NR^{L3a}$—$**^{L3}$, —$C_{1-8}$alkylene-, —$C_{2-8}$alkenylene-, —$C_{2-8}$alkynylene-, —$[O(CR^{L3a}R^{L3b})_{m4}]m_5$—,

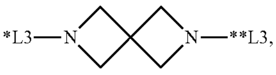

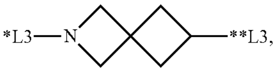

-continued
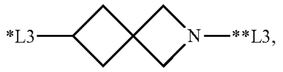
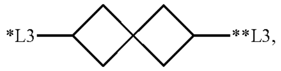
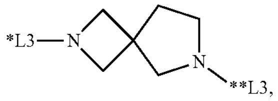
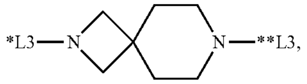
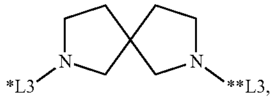
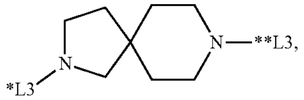
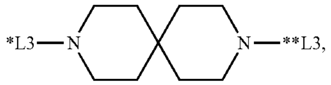
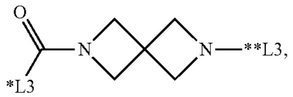
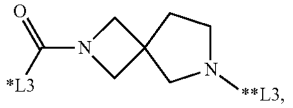
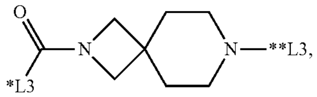
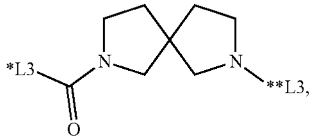
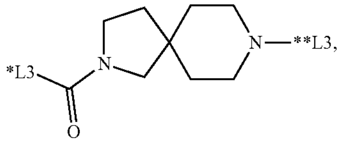
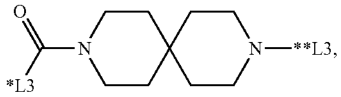
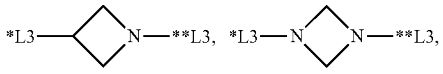
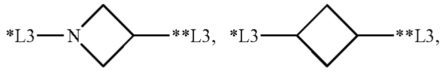
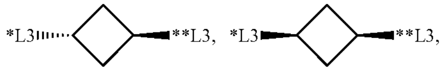
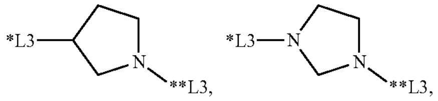
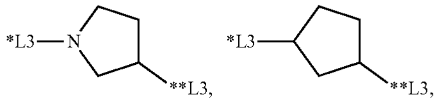
-continued
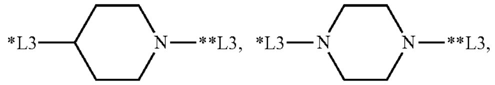
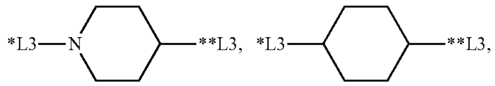
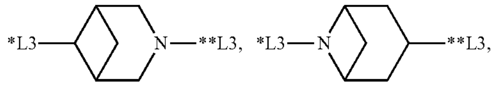
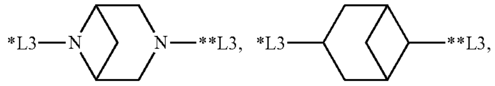
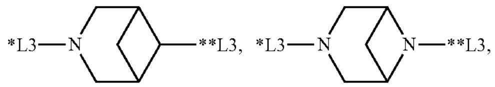
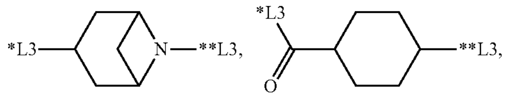
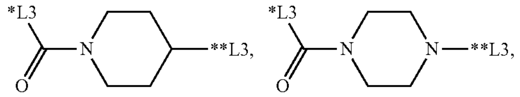
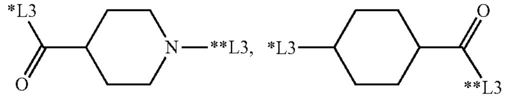
,
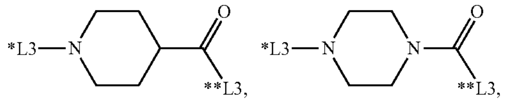
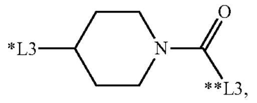
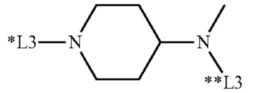
and
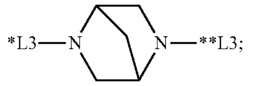
wherein each of said —$C_3$-$C_8$cycloalkylene-, $*^{L3}$—O—$C_{1-8}$alkylene-$**^{L3}$, $*^{L3}$—$C_{1-8}$alkylene-O—$**^{L3}$, $*^{L3}$—$SO_2$—$C_{1-8}$alkylene-$**^{L3}$, $*^{L3}$—$C_{1-8}$alkylene-$SO_2$—$**^{L3}$, $*^{L3}$—CO—$C_{1-8}$alkylene-$**^{L3}$, $*^{L3}$—$C_{1-8}$alkylene-CO—$**^{L3}$, $*^{L3}$—$NR^{L3a}$—$C_{1-8}$alkylene-$**^{L3}$, $*^{L3}$—$C_{1-8}$alkylene-$NR^{L3a}$—$**^{L3}$, —$C_{1-8}$alkylene-, —$C_{2-8}$alkenylene-, —$C_{2-8}$alkynylene-,
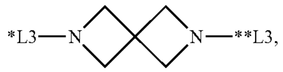
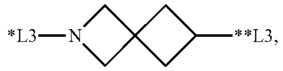
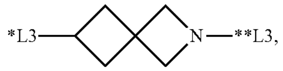
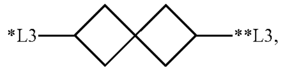

-continued

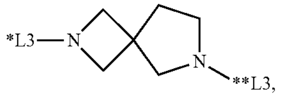

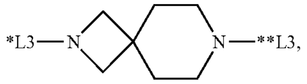

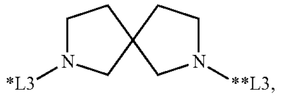

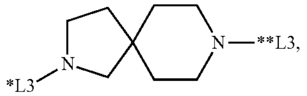

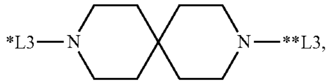

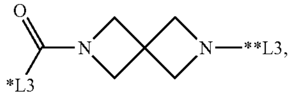

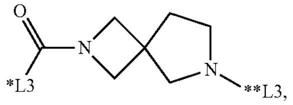

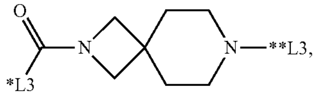

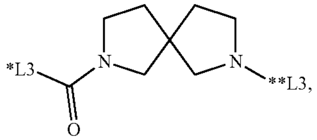

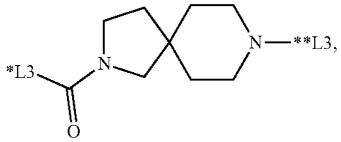

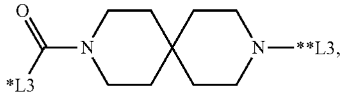

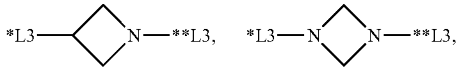

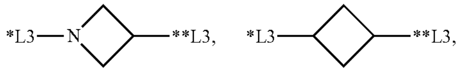

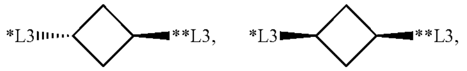

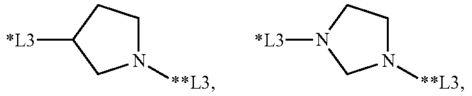

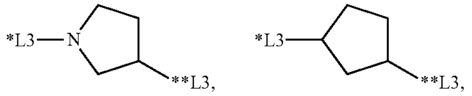

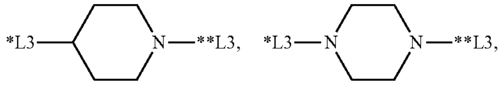

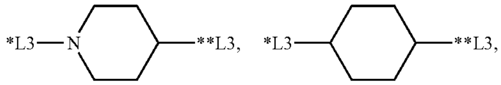

-continued

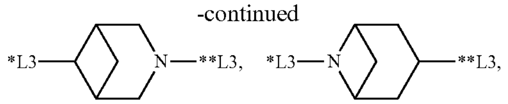

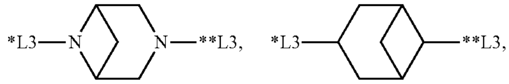

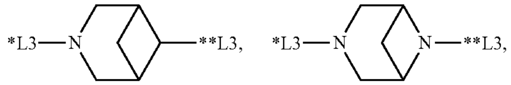

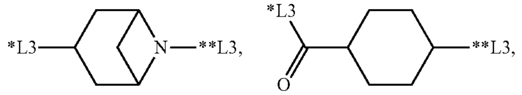

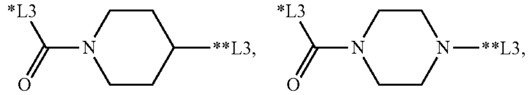

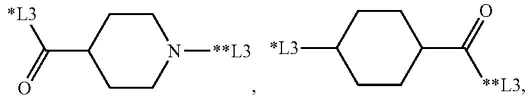

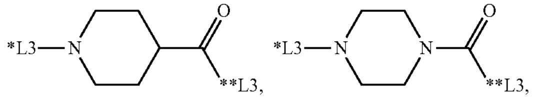

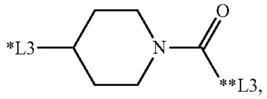

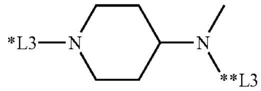

or

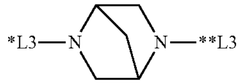

is optionally substituted with at least one substituent $R^{L3c}$, $R^{L3a}$ and $R^{L3b}$ are each independently selected from hydrogen, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl and pyrazinyl, wherein each of said methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl or pyrazinyl is optionally substituted with at least one substituent $R^{L3d}$, and each of said $R^{L3c}$ and $R^{L3d}$ are independently —F, —Cl, —Br, —I, —OH, methyl, ethyl, propyl, butyl, pentyl, hexyl, heptyl, octyl, vinyl, ethynyl, cyclopropyl, cyclobutyl, cyclopentyl, cyclohexyl, cycloheptyl, cyclooctyl, oxazolidinyl, imidazolidinyl, thiazolidinyl, pyrazolidinyl, morpholinyl, piperidinyl, piperazinyl, oxazinyl, imidazolyl, thiazolyl, oxazolyl, pyridyl, pyrimidinyl, pyrazinyl, pyridazinyl, phenyl, pyrrolyl, imidazolyl, pyrazolyl, thiazolyl, oxazolyl, triazolyl, thiophenyl, furanyl, pyridyl, pyrimidinyl, pyrazinyl or oxo.

25. The compound of claim 1, wherein $L^3$ is selected from single bond, $-CH_2-$, $-C_2H_4-$, $-C_3H_6-$, $-CO-$, $-O-$, $-N(CH_3)-$, $-NH-$,

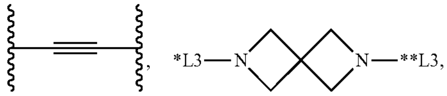

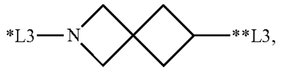

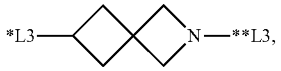

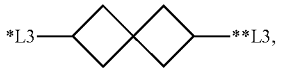

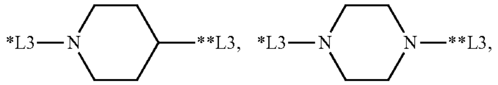

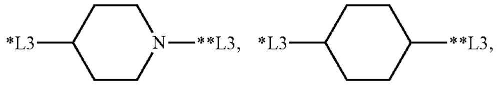

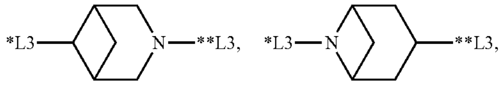

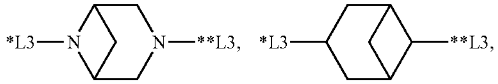

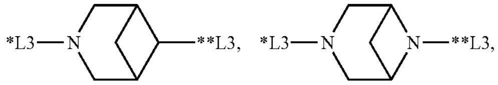

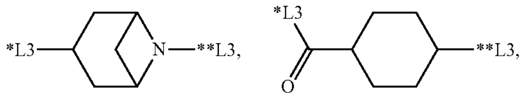

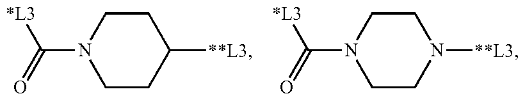

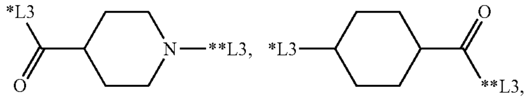

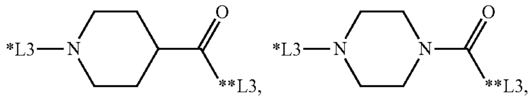

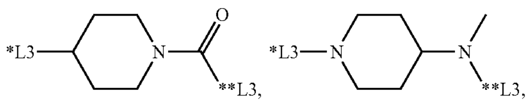

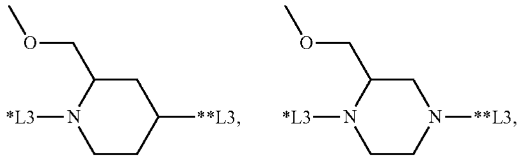

-continued

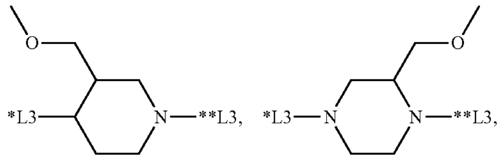

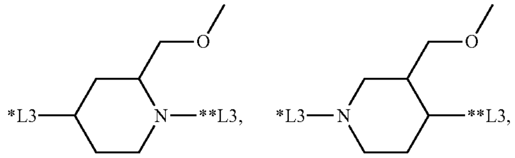

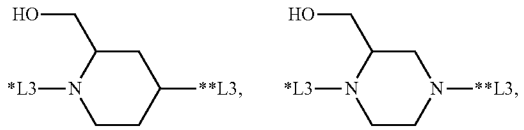

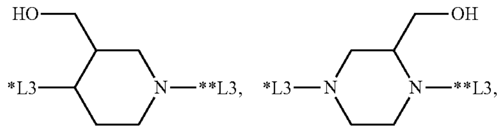

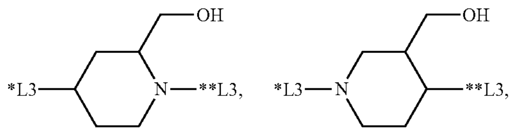

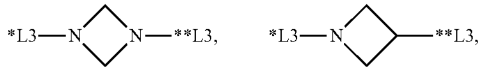

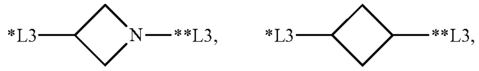

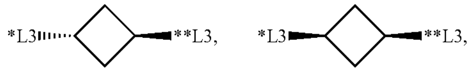

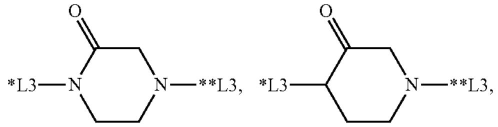

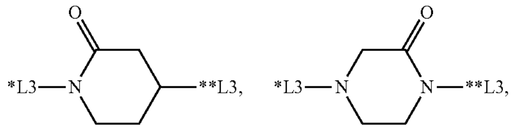

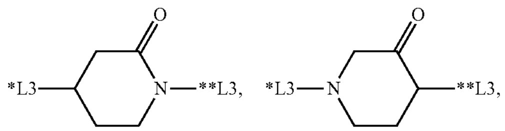

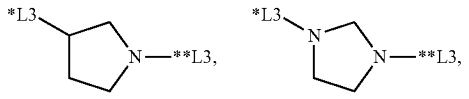

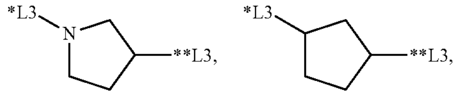

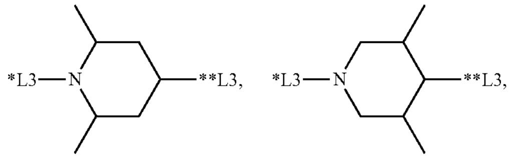

-continued
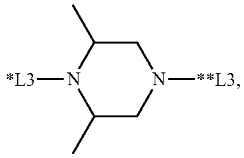
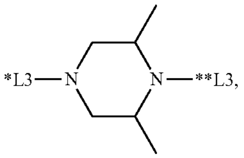
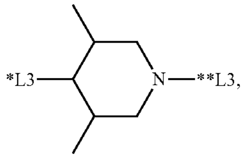
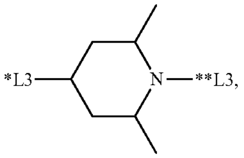
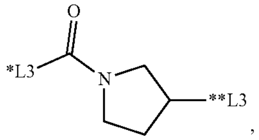
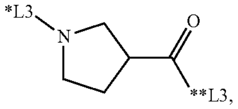
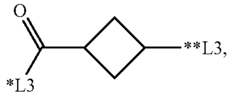
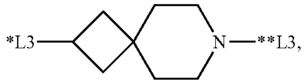
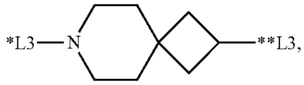
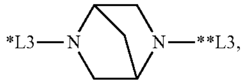
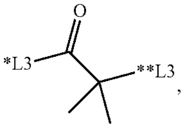
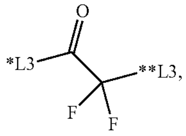
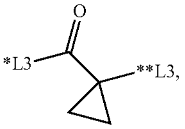
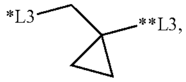
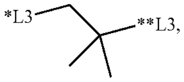
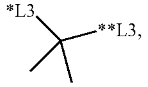
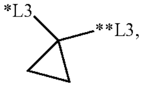
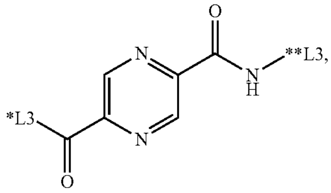
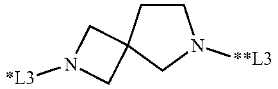
and
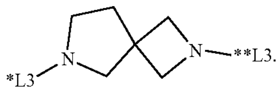
26. The compound of claim 1, wherein
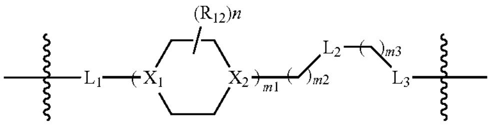
is selected from $—CH_2CH_2—$,
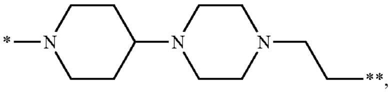
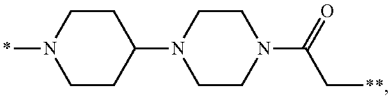
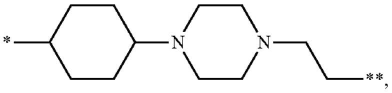
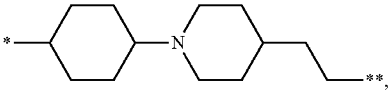
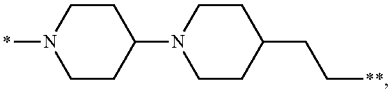
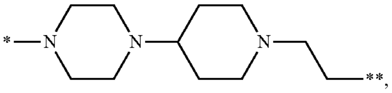
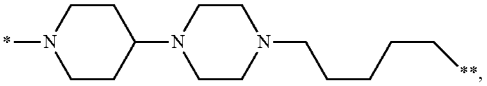
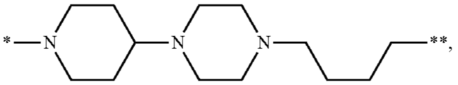
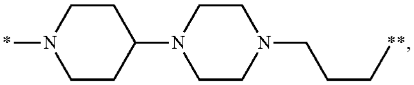
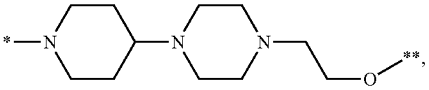
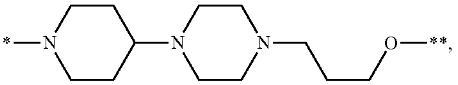
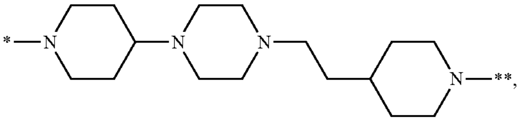
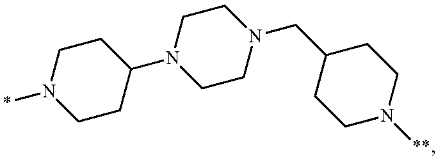
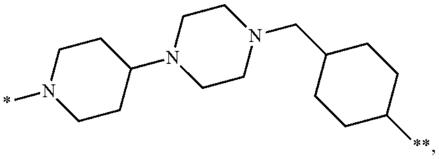

-continued
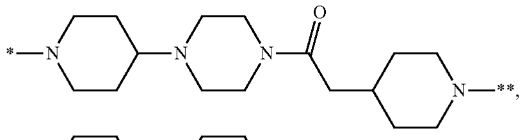
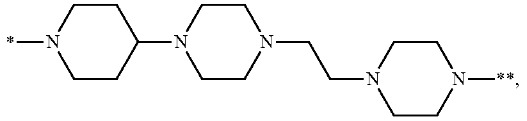
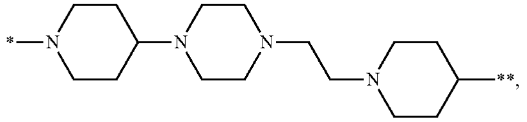
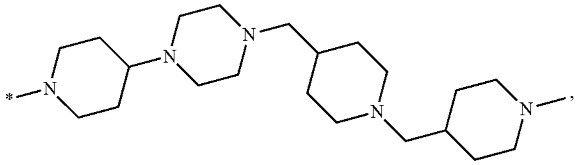
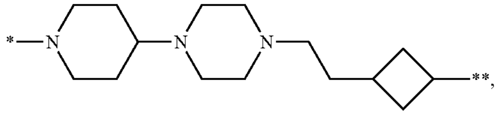
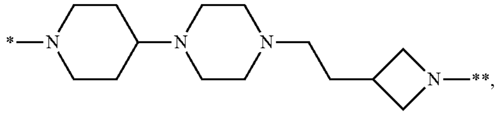
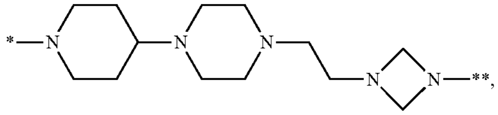
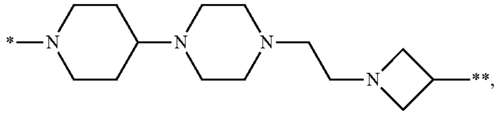
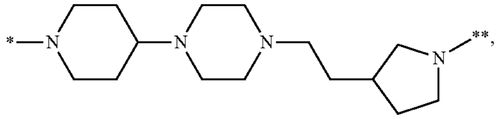
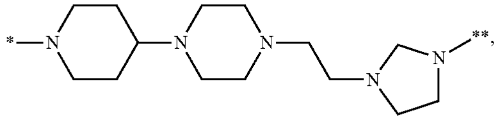
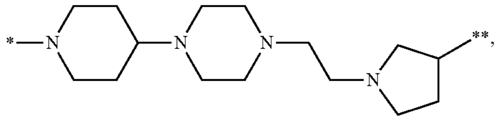
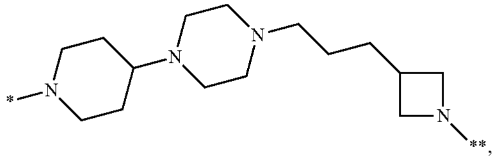
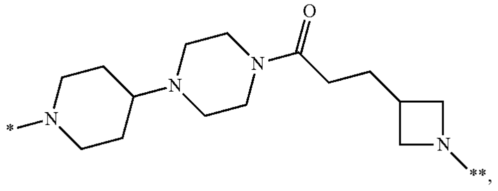
-continued
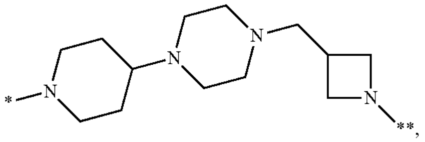
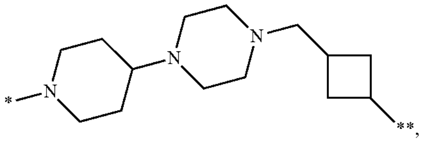
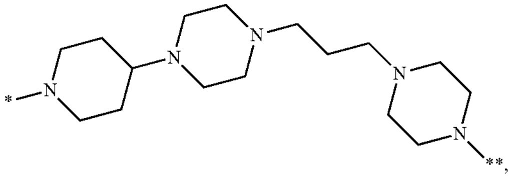
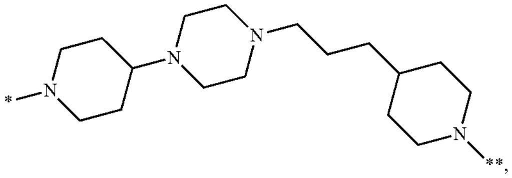
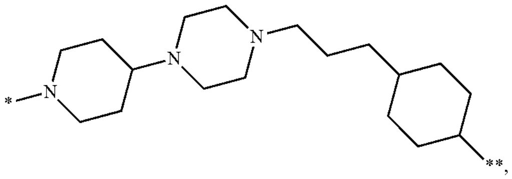
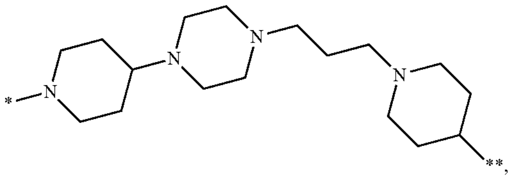
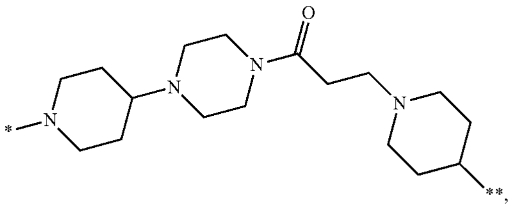
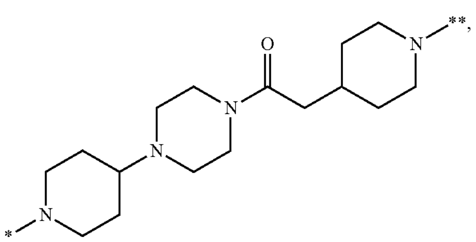
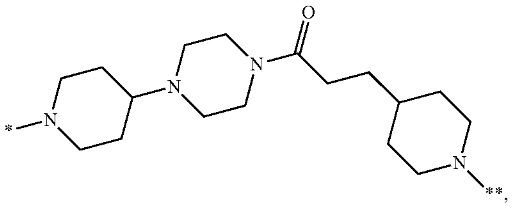

-continued
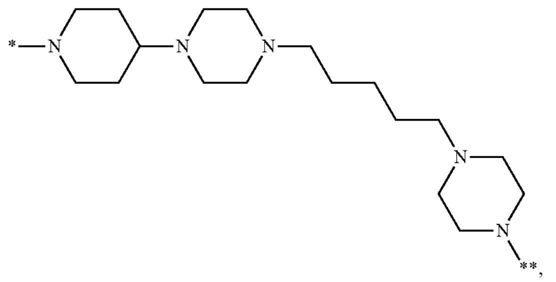
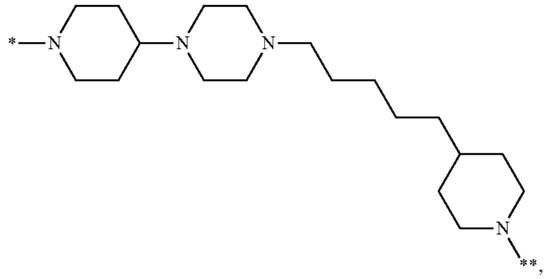
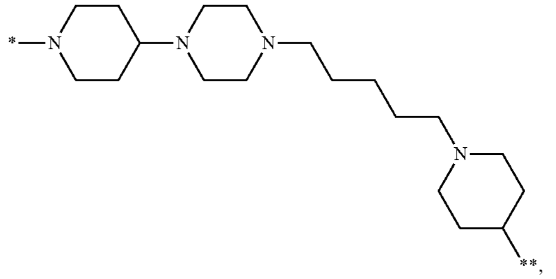
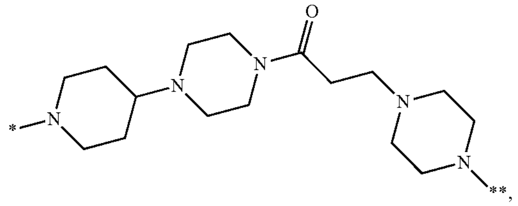
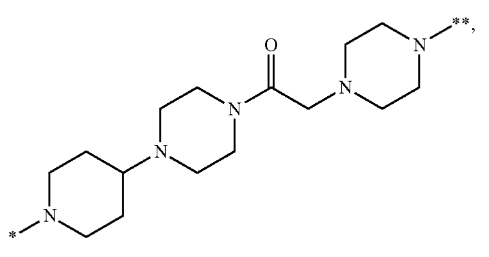
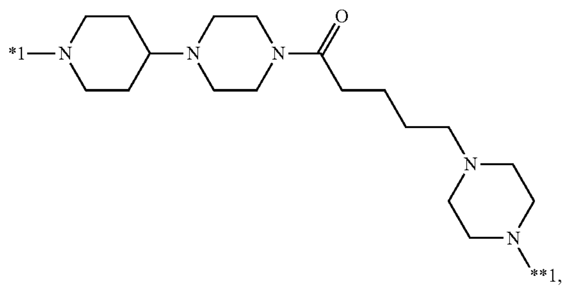
-continued
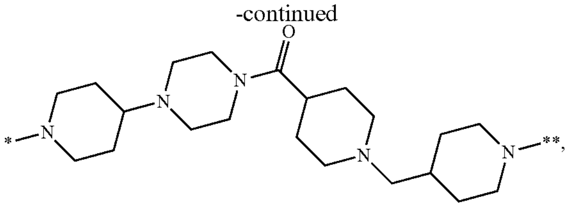
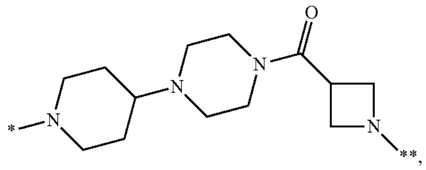
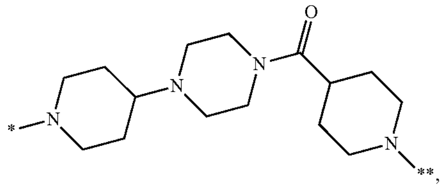
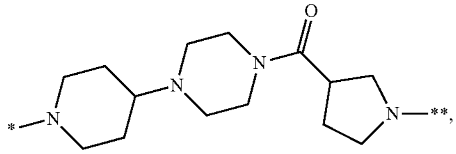
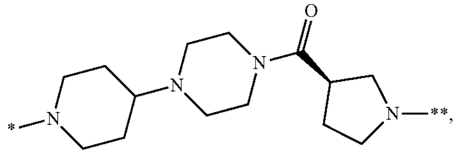
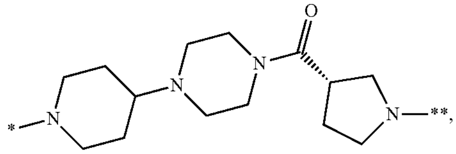
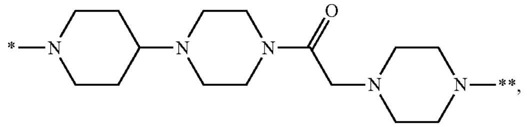
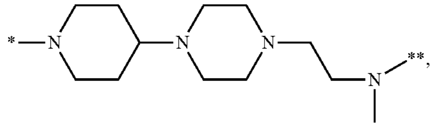
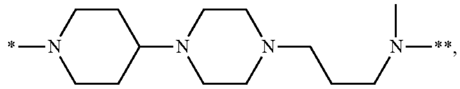
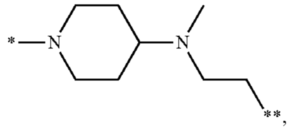
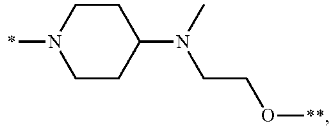
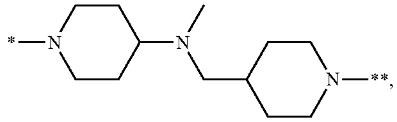

-continued
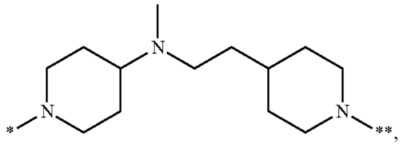
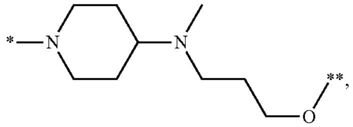
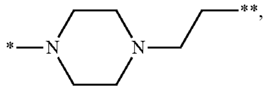
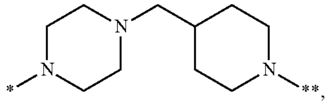
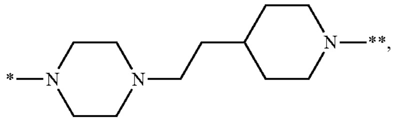
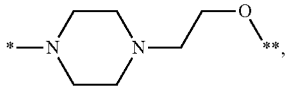
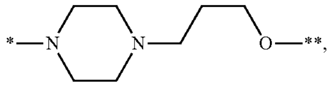
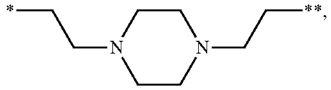
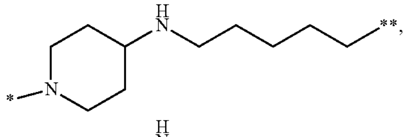
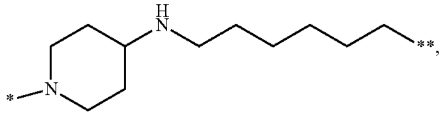
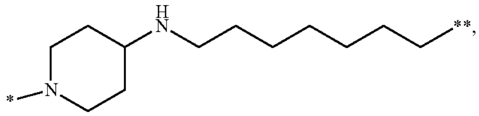
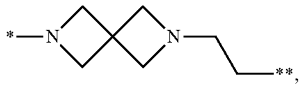
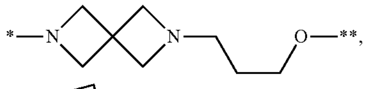
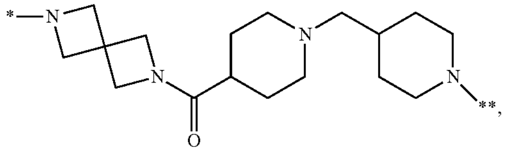
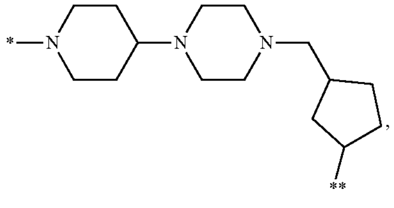
-continued
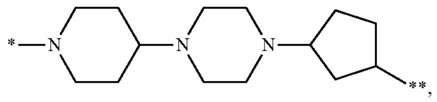
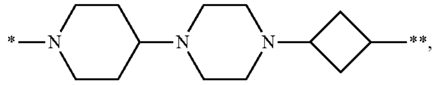
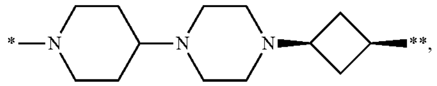
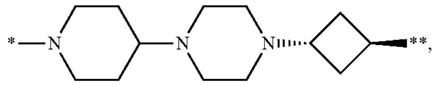
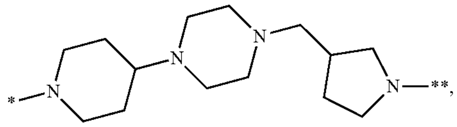
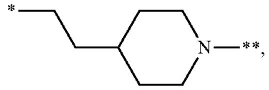
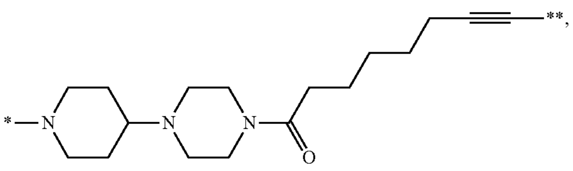
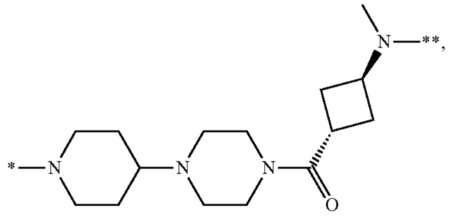
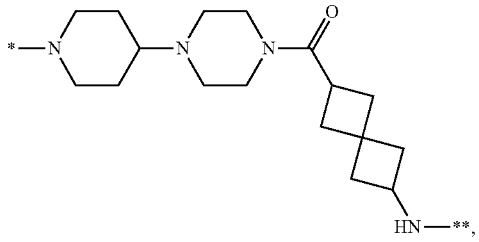
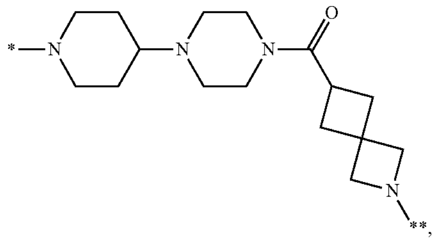
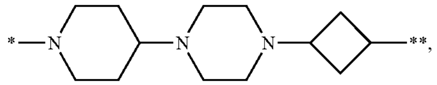
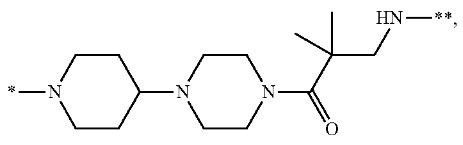

-continued
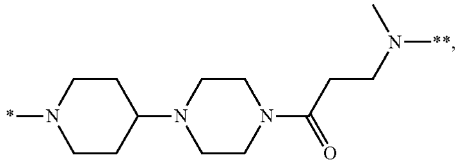
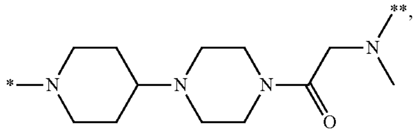
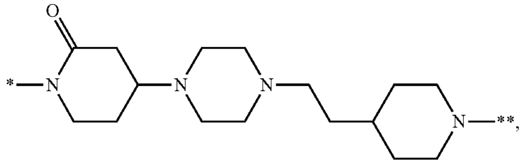
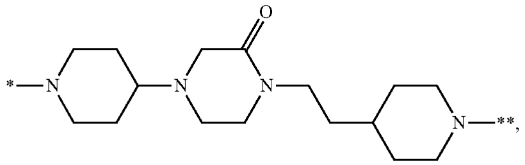
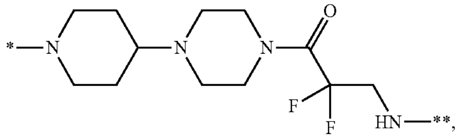
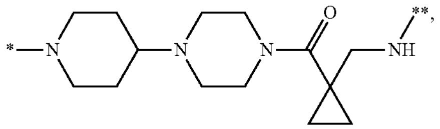
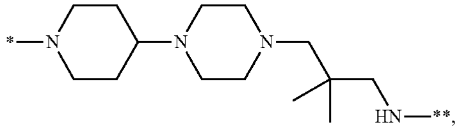
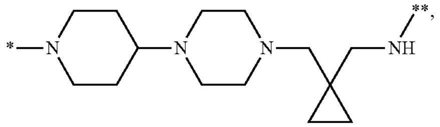
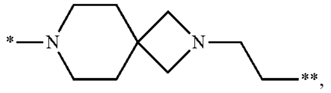
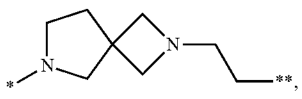
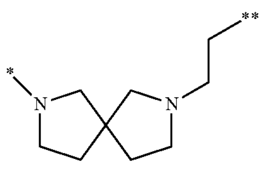
or
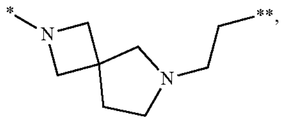
wherein * refers to the position, attached to
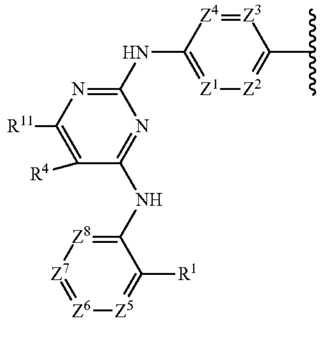
moiety, and ** refers to the position attached to the
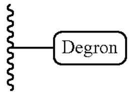
moiety.
27. The compound of claim 1, wherein 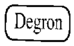 is selected from
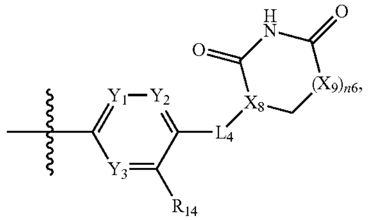
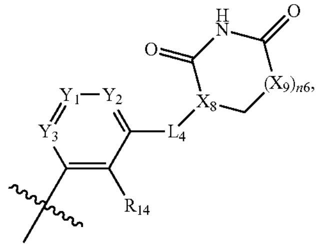
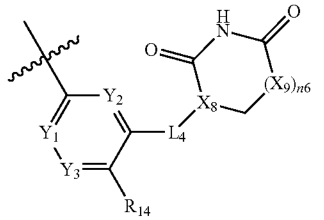
or
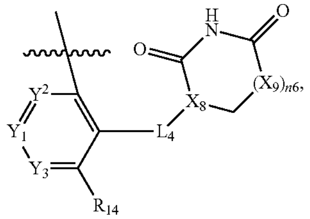

-continued
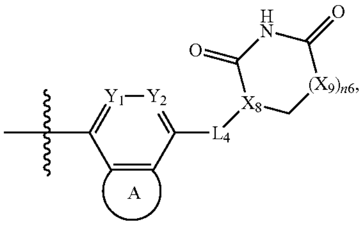
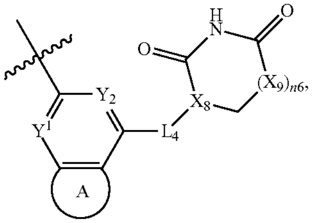
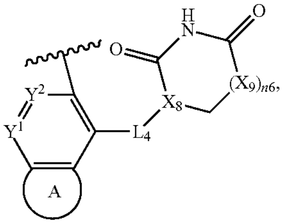
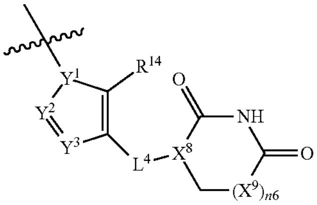
or
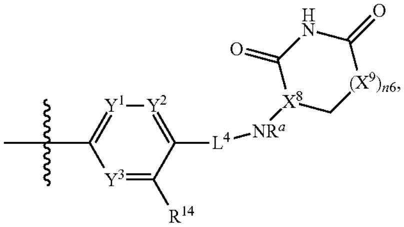
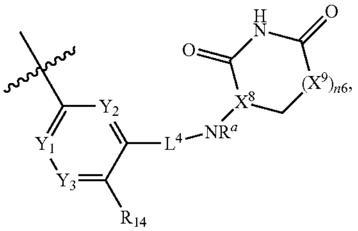
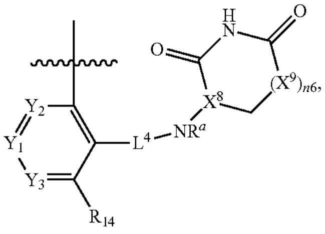
-continued
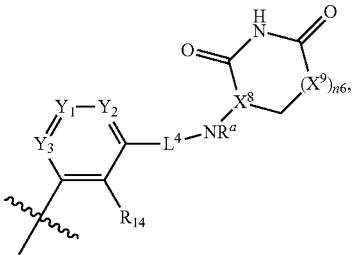
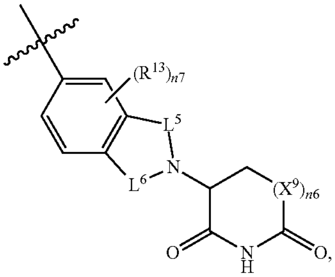
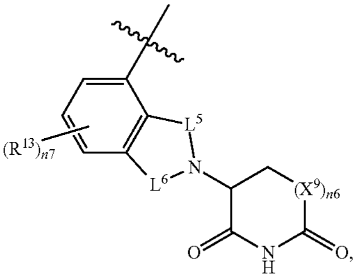
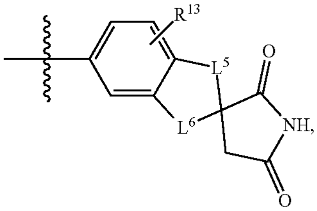
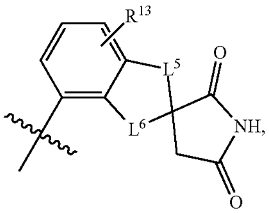
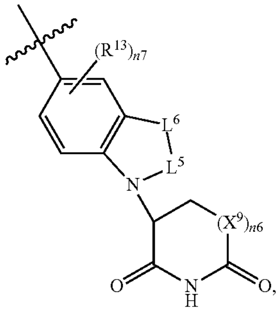

-continued
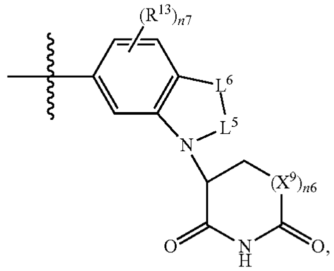
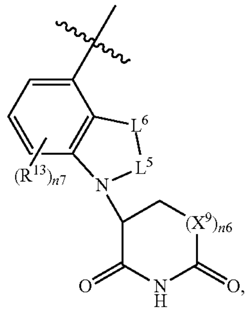
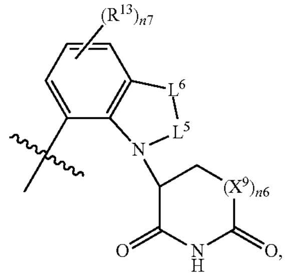
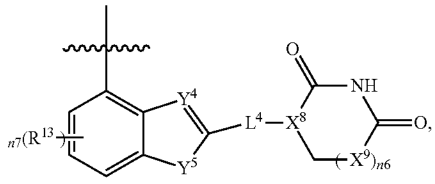
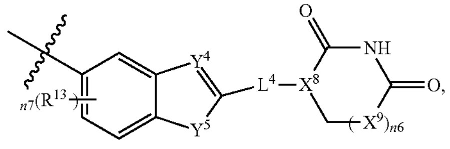
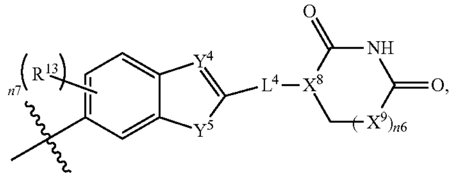
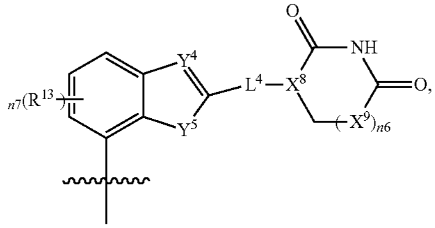
-continued
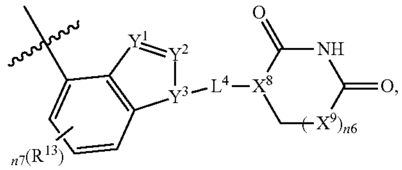
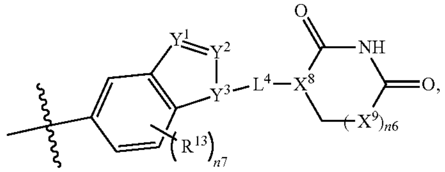
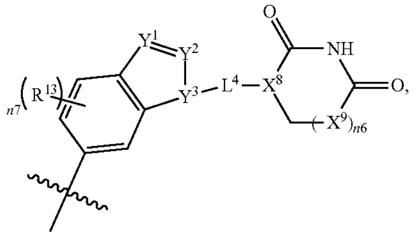
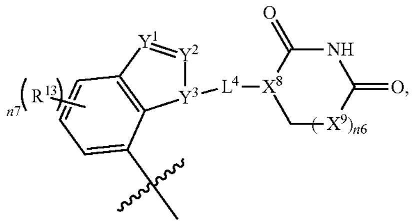
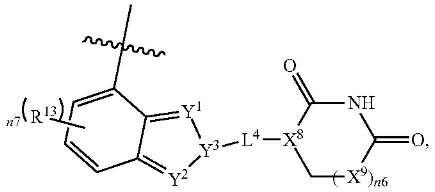
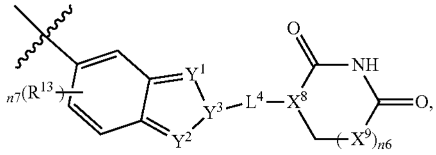
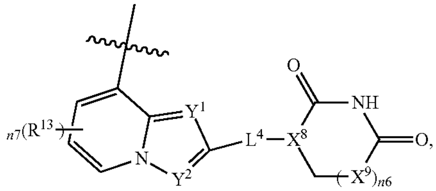
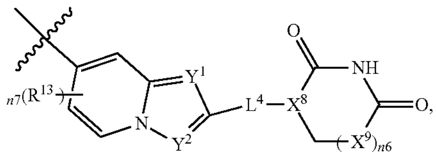
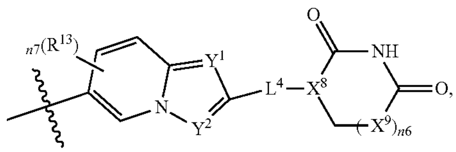 and -continued

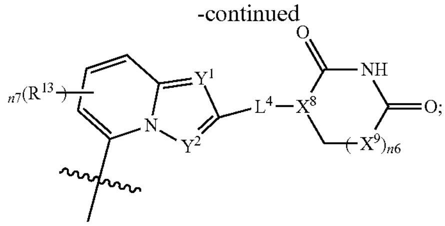

Ring A is selected from 5- to 7-membered cycloalkyl, 5- to 7-membered heterocyclyl, aryl, and heteroaryl;

$R^{14}$ is independently selected from hydrogen, halogen, —$C_{1-8}$alkyl, —$C_{1-8}$alkoxy, and CN; said each —$C_{1-8}$ alkyl or —$C_{1-8}$alkoxy is optionally substituted with one or more halogen or —$C_{1-8}$alkyl;

$X^8$ is independently selected from CH, CD, $C(CH_3)$, $C(C_2H_5)$, $C(C_3H_7)$, C(CN), C(F), and N;

$L^4$ is independently selected from a single bond,

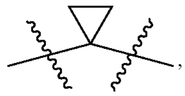 [SMILES: *C1(*)CC1]

—O—, —NH—, —$CH_2$—, —CHF—, and —$CF_2$—;

$Y^1$, $Y^2$, and $Y^3$ are each independently selected from $CR^a$ and N;

$X^9$ is $CH_2$;

$R^a$ is each independently selected from hydrogen, halogen, —$C_{1-8}$alkyl, and —$C_{1-8}$alkoxy, wherein each of said —$C_{1-8}$alkyl or —$C_{1-8}$alkoxy is optionally substituted with at least one or more halogen, hydroxy, halogen, —$C_{1-8}$alkyl, or —$C_{1-8}$alkoxy;

$L^5$ is —CO— or —$CH_2$—;

$L^6$ is

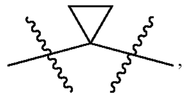 [SMILES: *C1(*)CC1]

—O—, —NH—, —NMe-, —$N(CH_2CH_3)$—, —$CH_2$—, —CHF—, —$CF_2$—, —$C(CH_3)_2$— or —CO—;

each $R^{13}$ is independently selected from hydrogen, —F, —Cl, —Br, —I, CN, —$C_{1-8}$alkyl, and —$C_{1-8}$alkoxy;

$n_6$ is independently 0 or 1;

$n_7$ is 0, 1, or 2;

each $R^{13}$ is independently selected from hydrogen, —F, —Cl, —Br, —I, —CN, —$C_{1-8}$alkyl, and —$C_{1-8}$alkoxy;

$Y^1$, $Y^2$, $Y^3$ and $Y^4$ are each independently selected from CH, $C(CH_3)$, $C(CH_2CH_3)$, C(F), and N; and $Y^5$ is selected from NH, $N(CH_3)$, O and S.

28. The compound of claim 1, wherein Degron is selected from

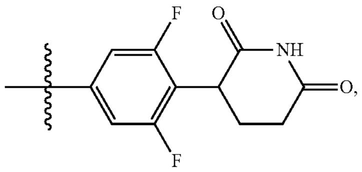

-continued

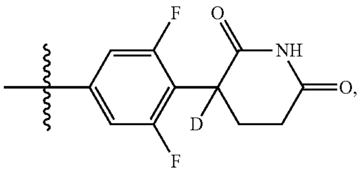

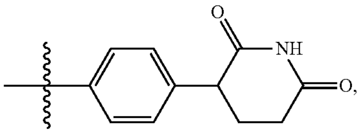

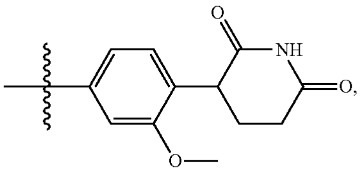

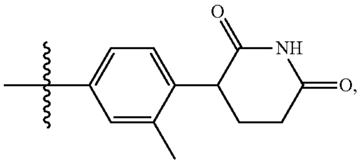

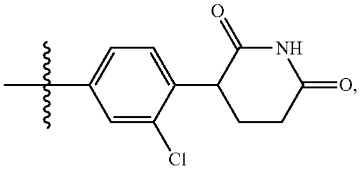

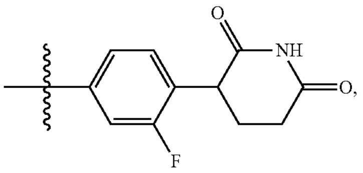

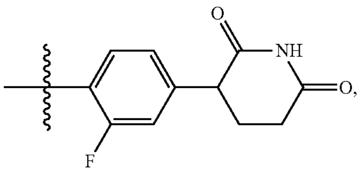

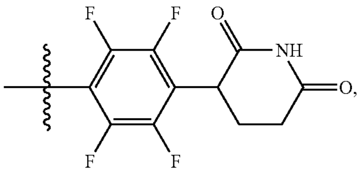

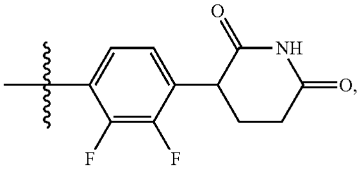

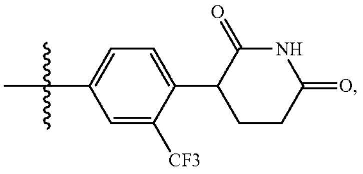

-continued
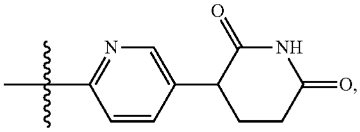
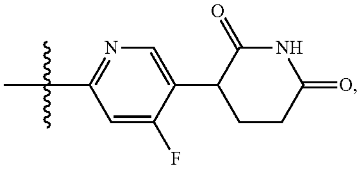
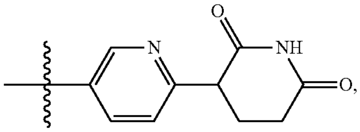
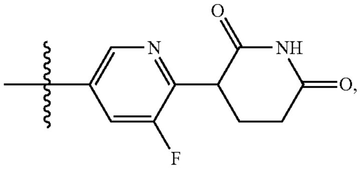
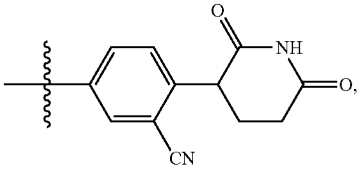
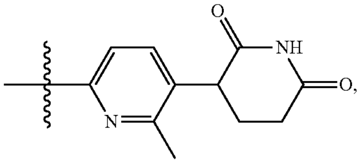
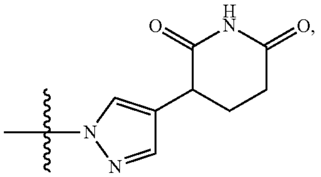
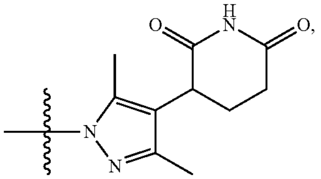
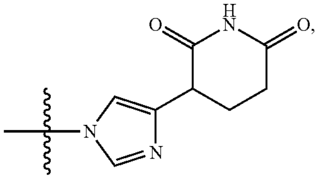
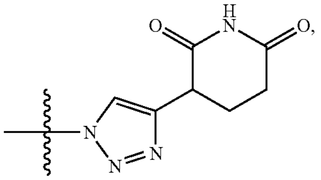
-continued
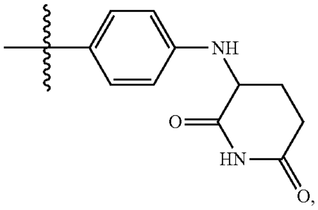
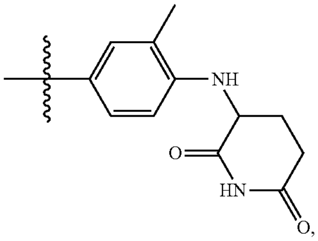
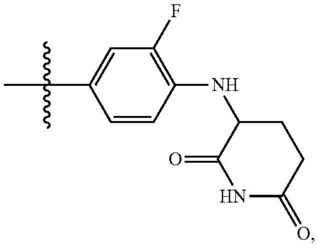
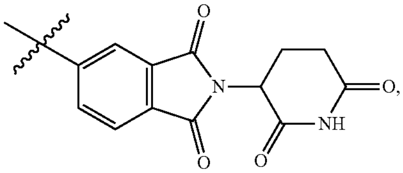
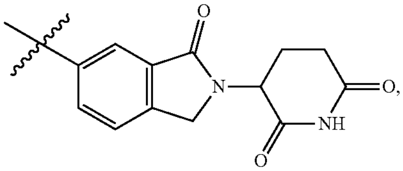
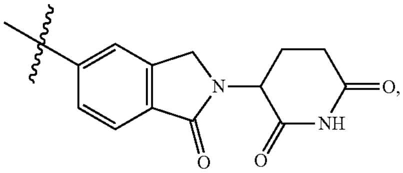
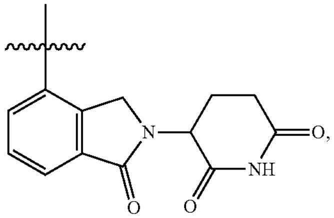
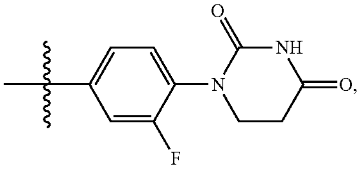

-continued
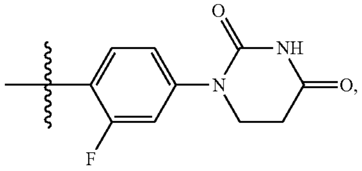
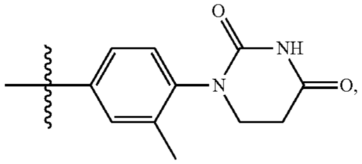
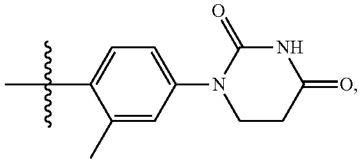
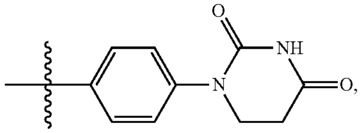
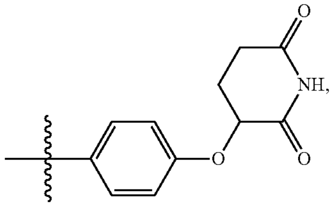
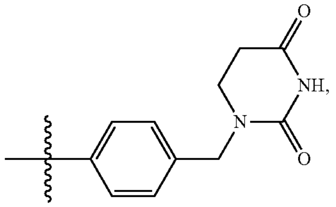
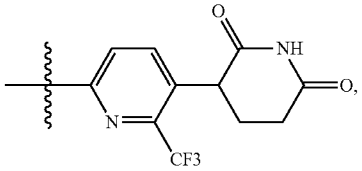
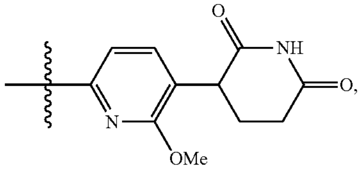
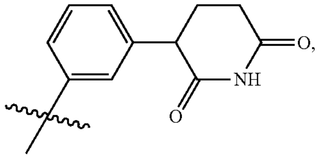
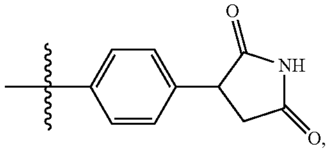
-continued
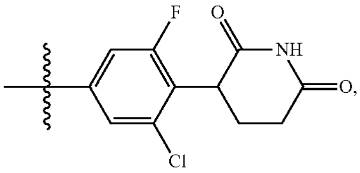
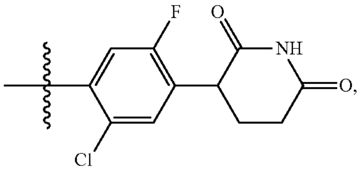
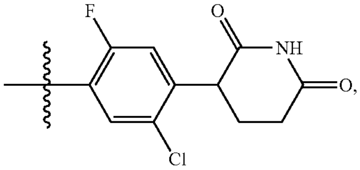
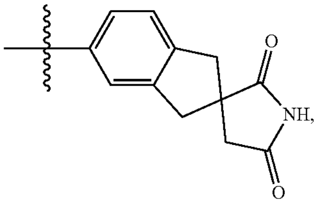
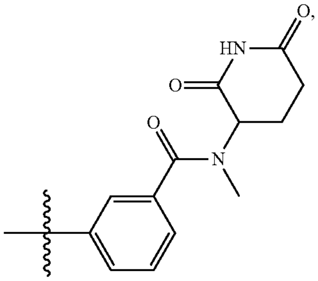
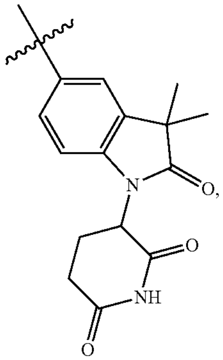
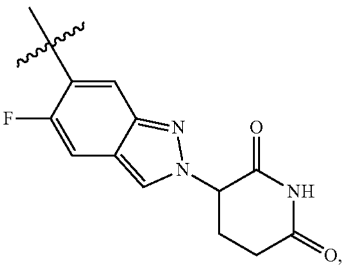

-continued
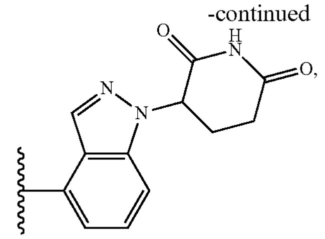
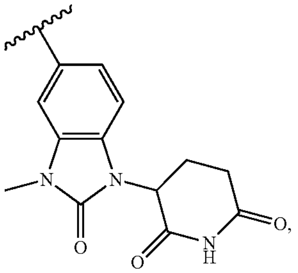
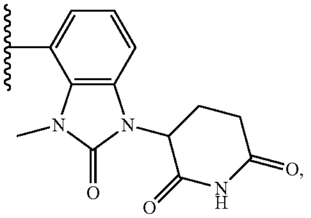
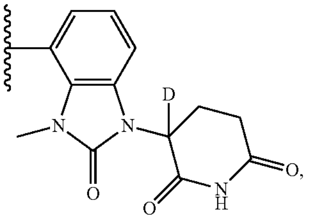
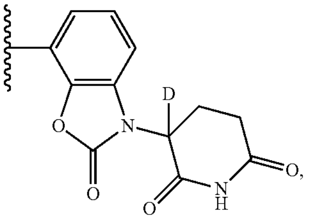
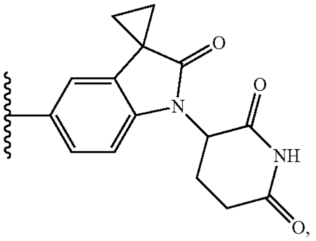
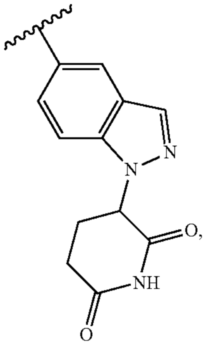
-continued
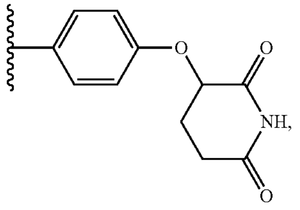
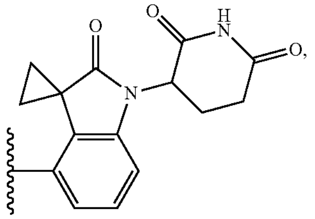
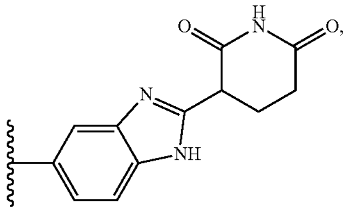
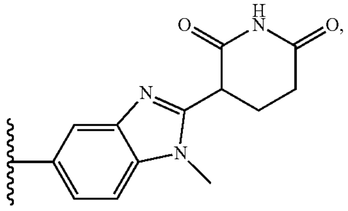
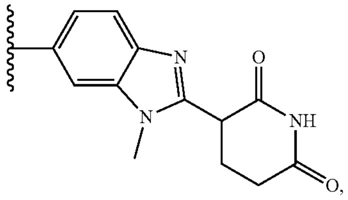
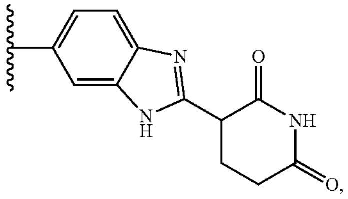
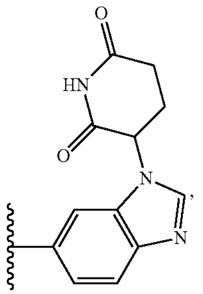

-continued
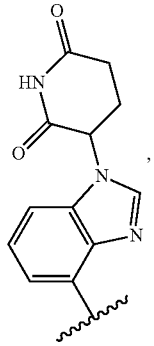
,
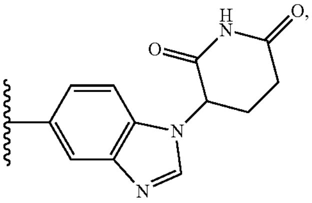
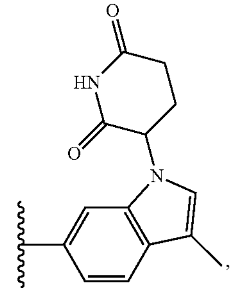
,
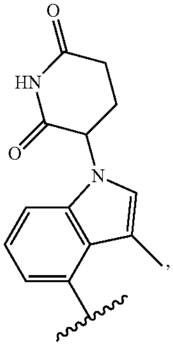
,
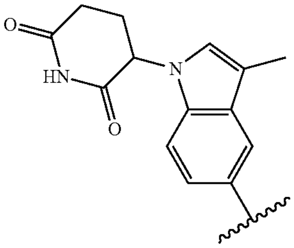
,
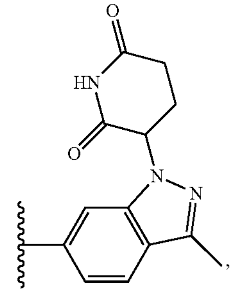
,
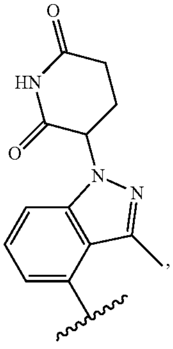
,
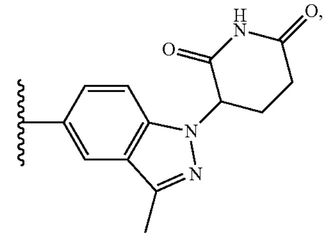
-continued
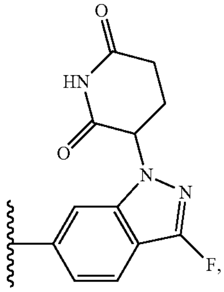
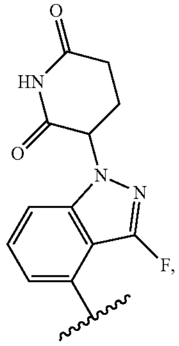
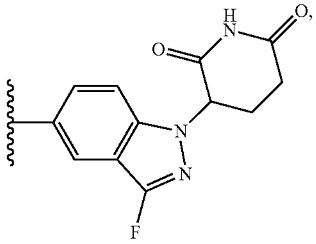
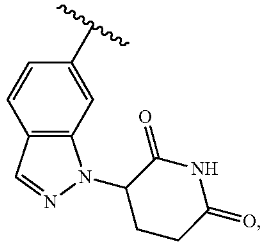
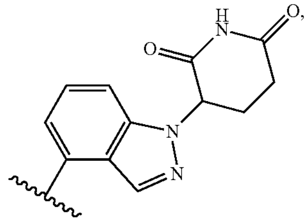
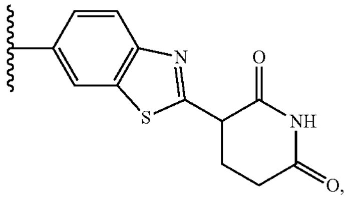
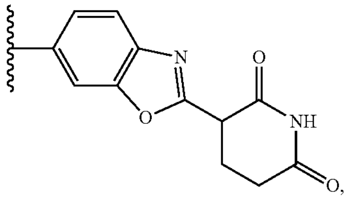
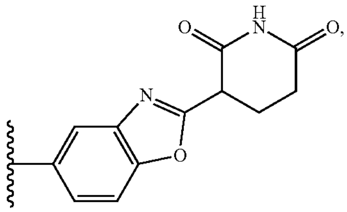

-continued
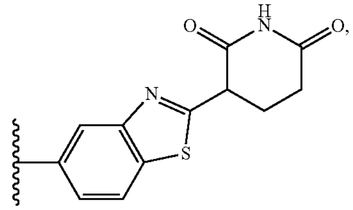
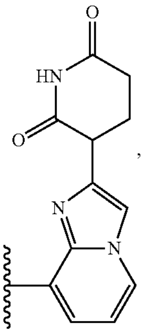
,
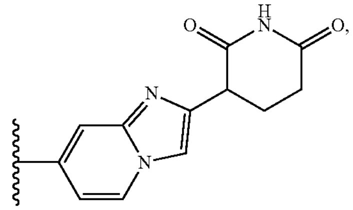
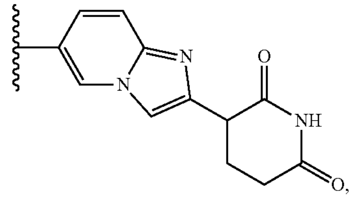
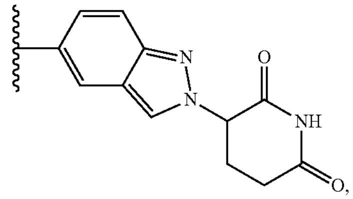
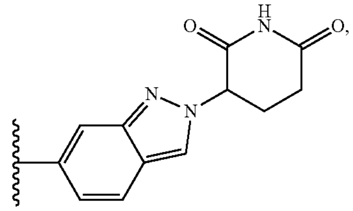
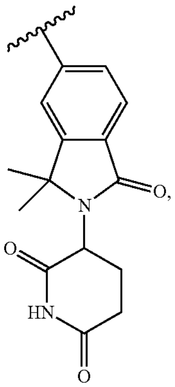
-continued
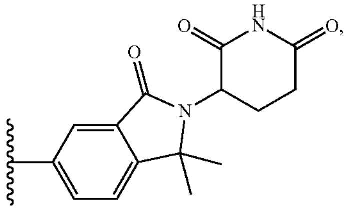
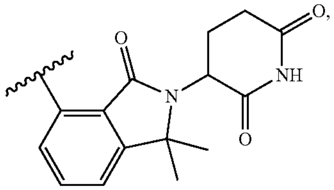
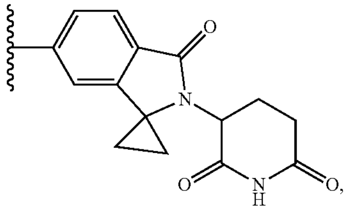
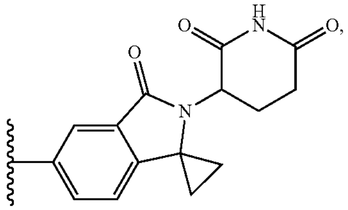
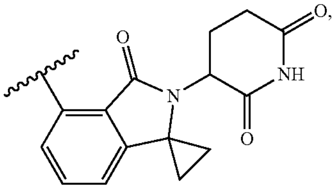
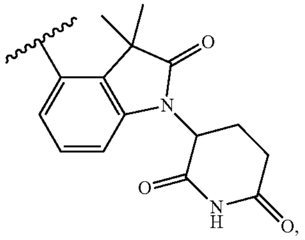
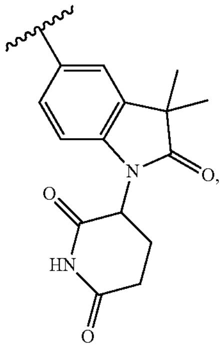

-continued
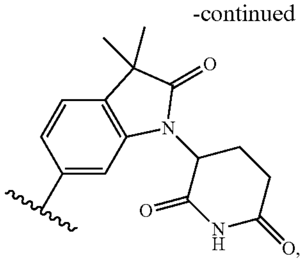,
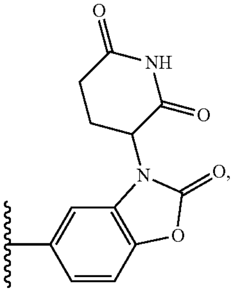,
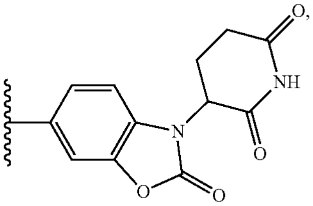,
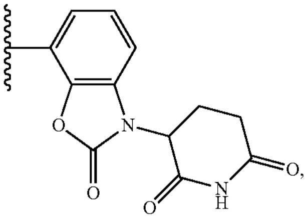,
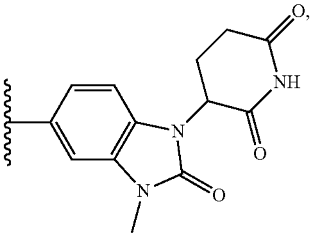,
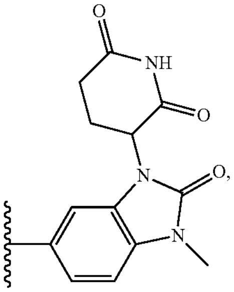,
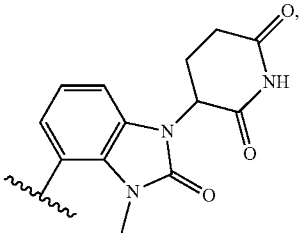,
-continued
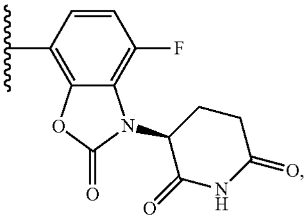, 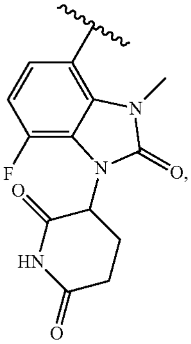,
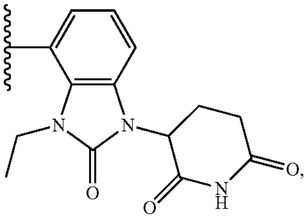,
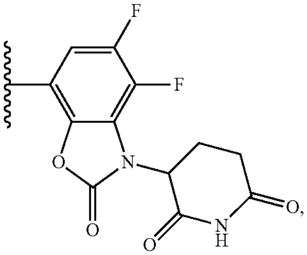,
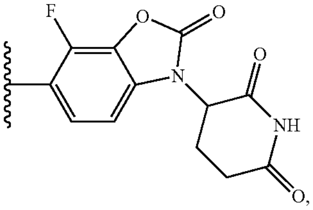,
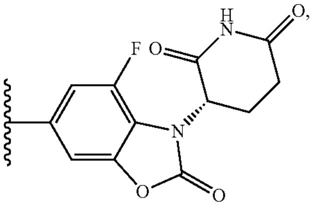,
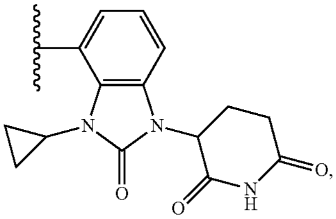,
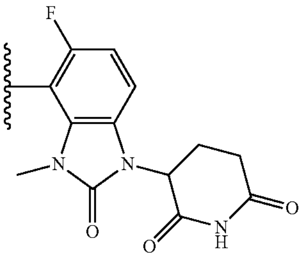 and -continued

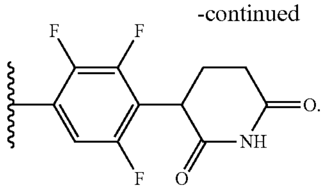

29. The compound of claim 1, wherein $Z^1$, $Z^2$, $Z^3$ and $Z^4$ are each independently —$CR^2$;

$R^Z$, at each occurrence, is independently selected from hydrogen, —F, —Cl, —Br, —I, methyl, ethyl, propyl, butyl, —$OR^{Za}$, cyclopropyl, and cyclobutyl, wherein each of methyl, ethyl, propyl, butyl, pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl is optionally substituted with at least one $R^{Ze}$, $R^{Za}$ is independently selected from hydrogen, methyl, ethyl, propyl, butyl, pentyl, hexyl, heptyl, octyl, —$C_{2-8}$ alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl and 5- to 12-membered heteroaryl, wherein each of said hydrogen, methyl, ethyl, propyl, butyl, pentyl, hexyl, heptyl, octyl, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl or 5- to 12-membered heteroaryl is optionally substituted with at least one substituent $R^{Zd}$, and $R^{Zc}$ and $R^{Zd}$ are each independently —F, —Cl, —Br, —I, hydroxy, methyl, ethyl, propyl, butyl, pentyl, hexyl, heptyl, octyl, —$C_{1-8}$alkoxy, —$C_{2-8}$alkenyl, —$C_{2-8}$ alkynyl, cyclopropyl, cyclobutyl, cyclopentyl, cyclohexyl, cycloheptyl, cyclooctyl, 3- to 8-membered heterocyclyl, phenyl, or 5- to 12-membered heteroaryl.

30. The compound of claim 1, wherein Rz is independently selected from H, —$CH_3$, —$C_2H_5$, F, —$CH_2F$, —$CHF_2$, —$CF_3$, —$OCH_3$, —$OC_2H_5$, —$C_3H_7$, —$OCH_2F$, —$OCHF_2$, —$OCH_2CF_3$, —$OCF_3$, —$SCF_3$, —$CF_3$ and —$CH(OH)CH_3$.

31. A compound selected from

1

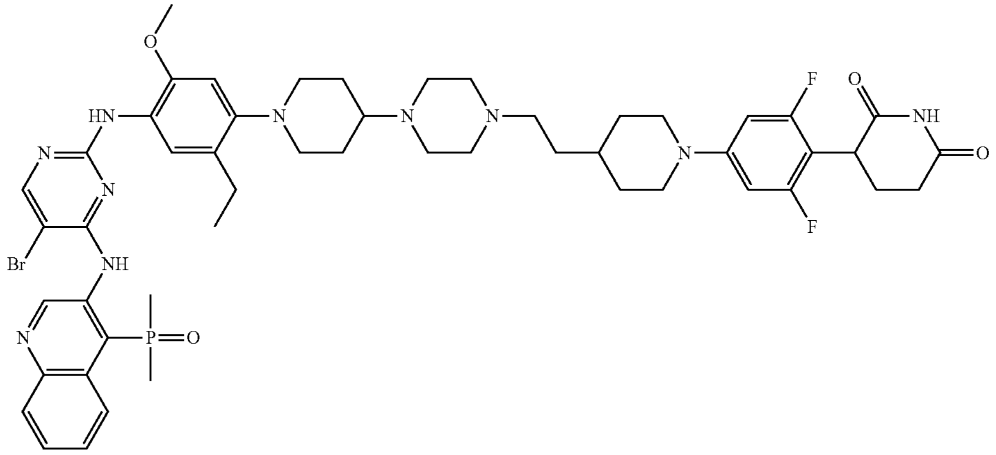

2

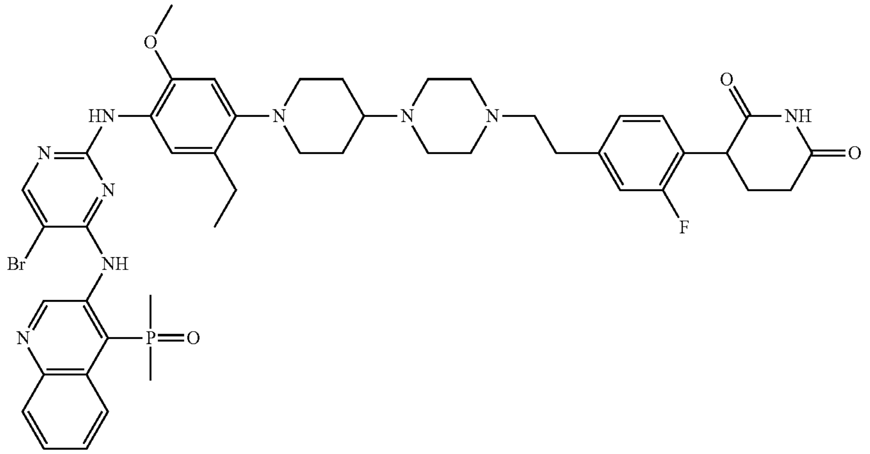

-continued
3
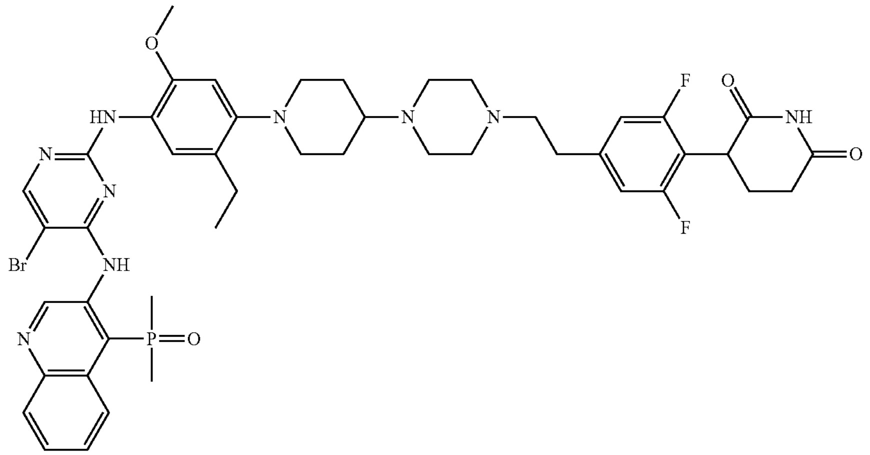
4
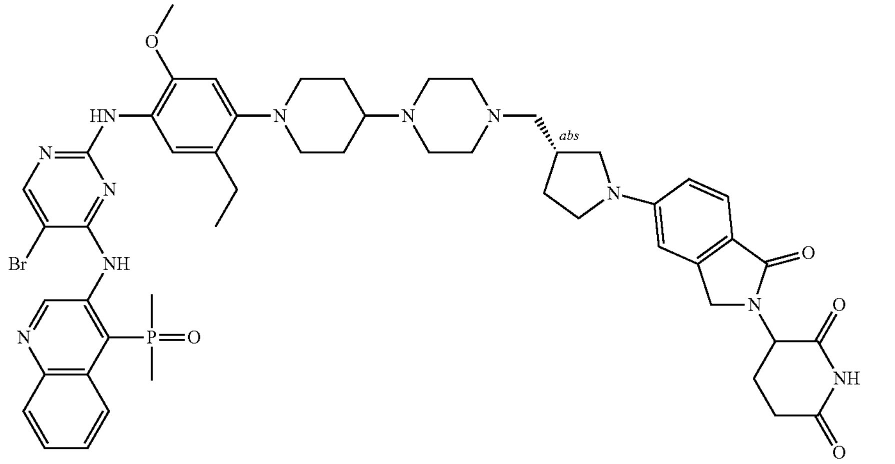
7
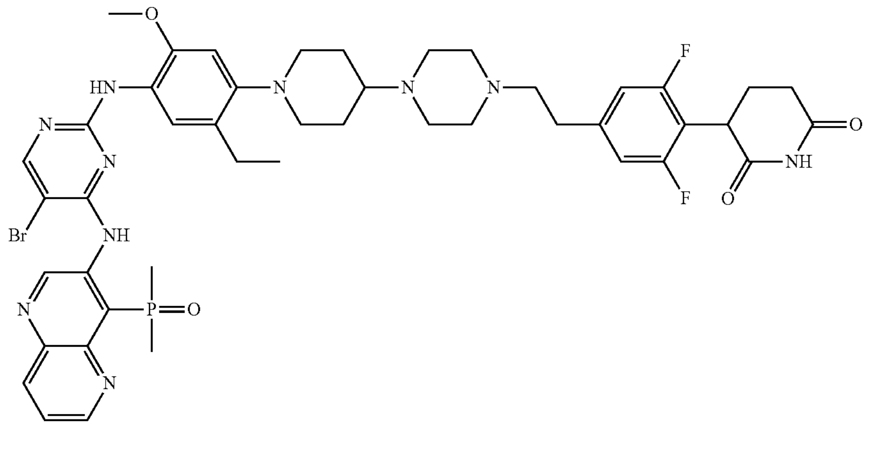

-continued
8
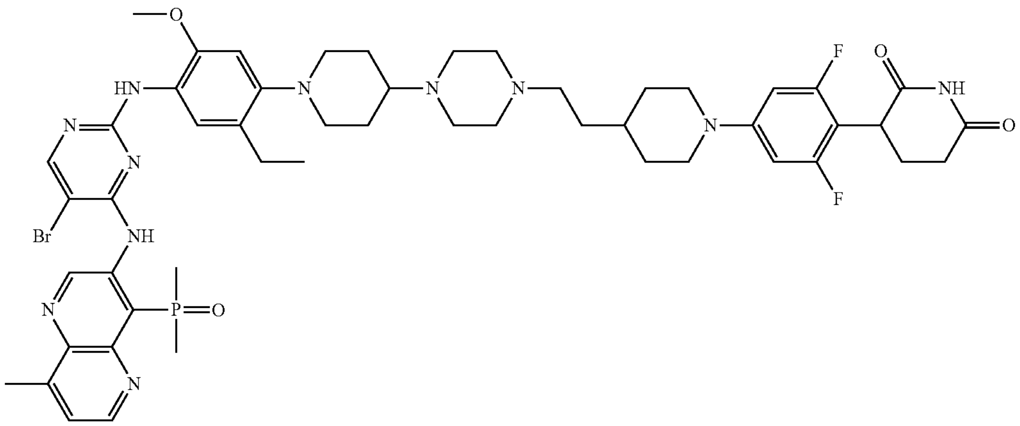
9
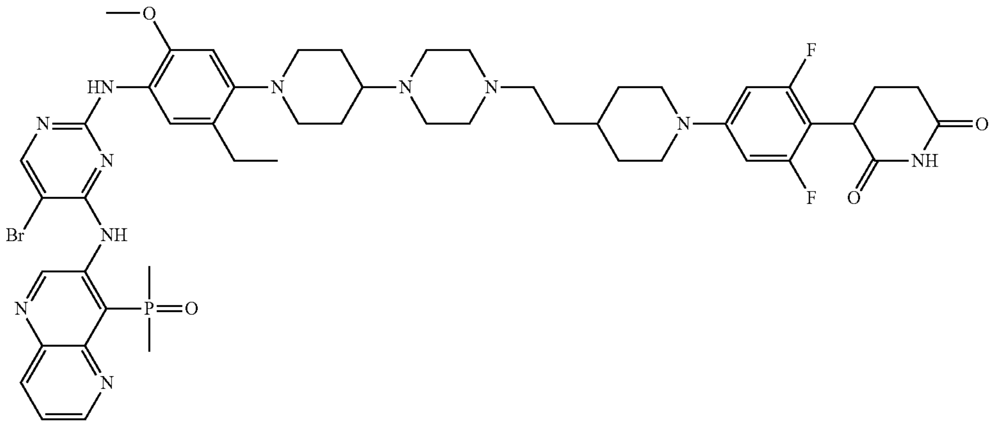
10
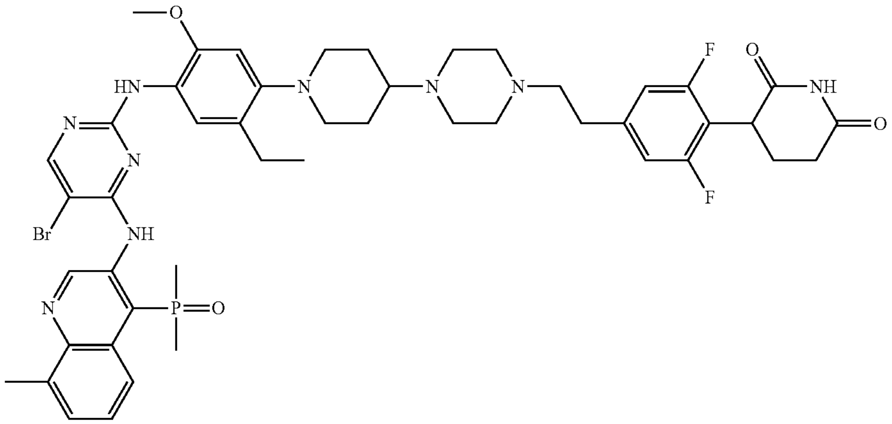

-continued
11
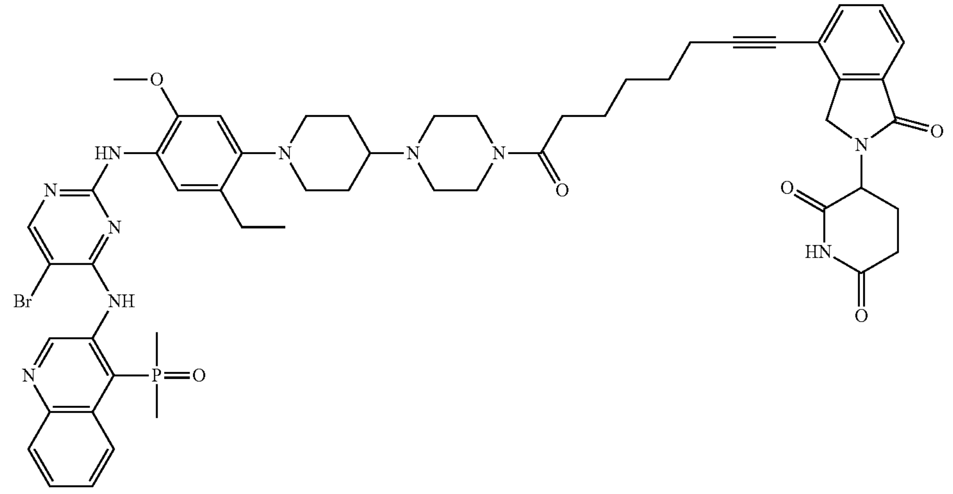
12
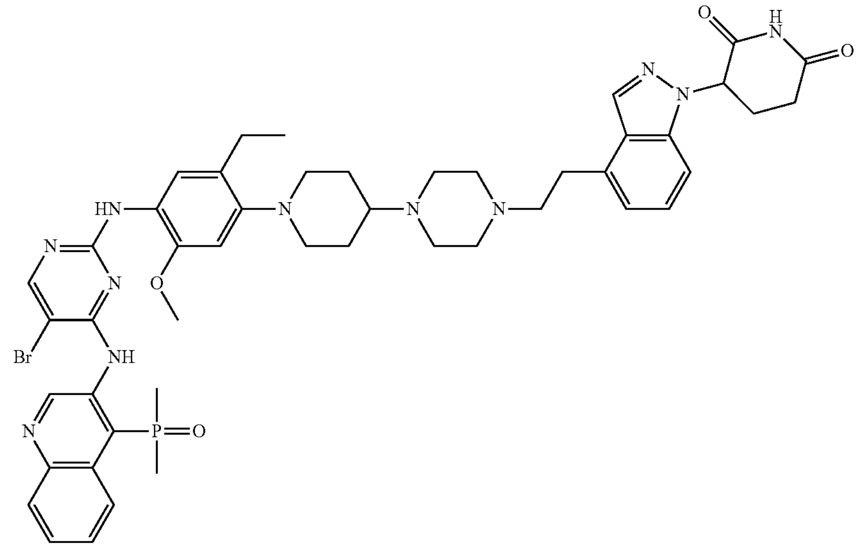
13
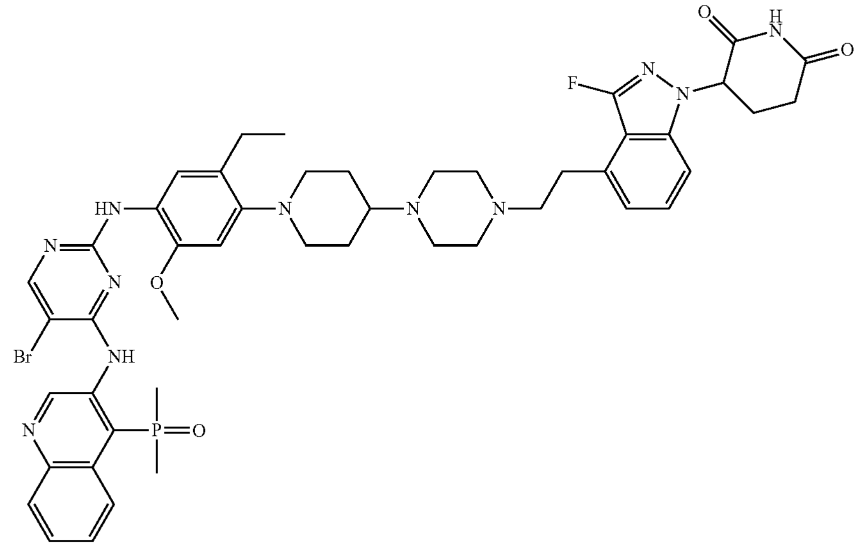

-continued
14
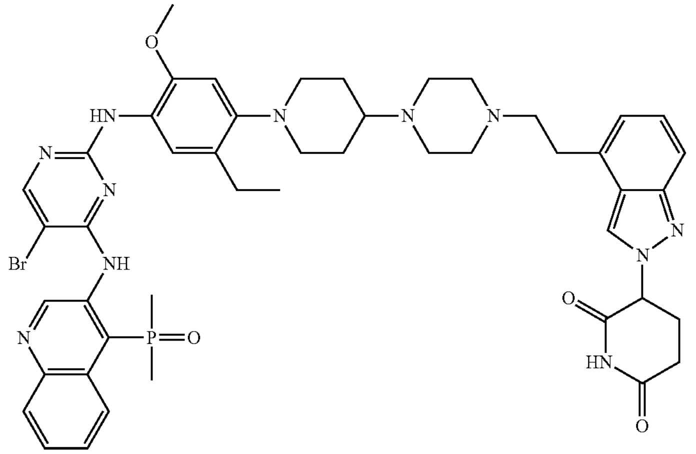
15
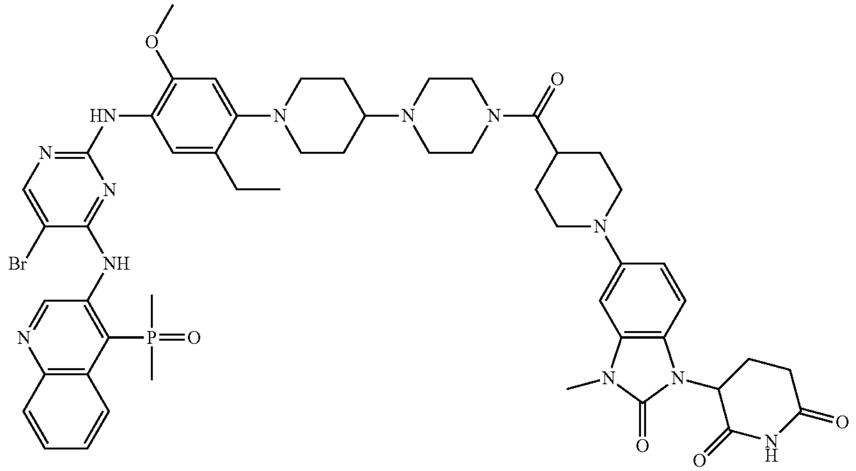
16
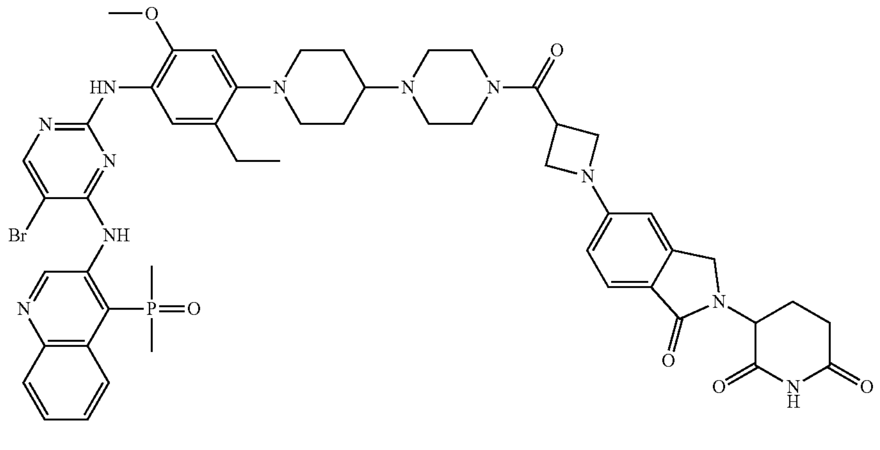

-continued
17
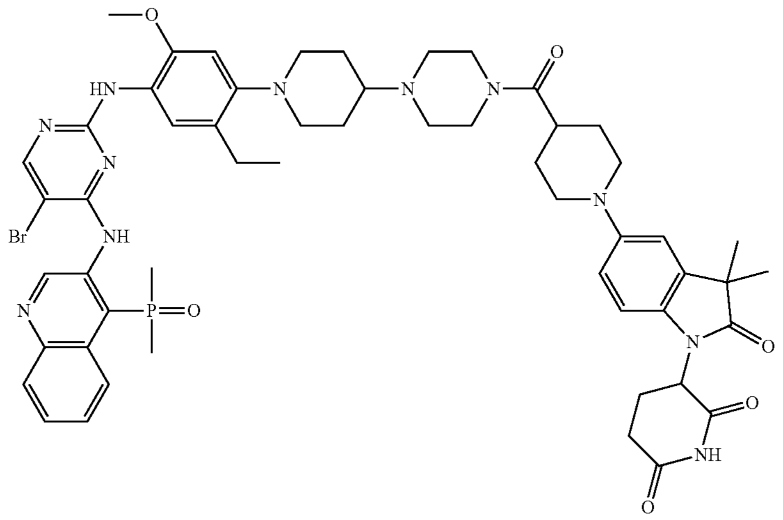
18
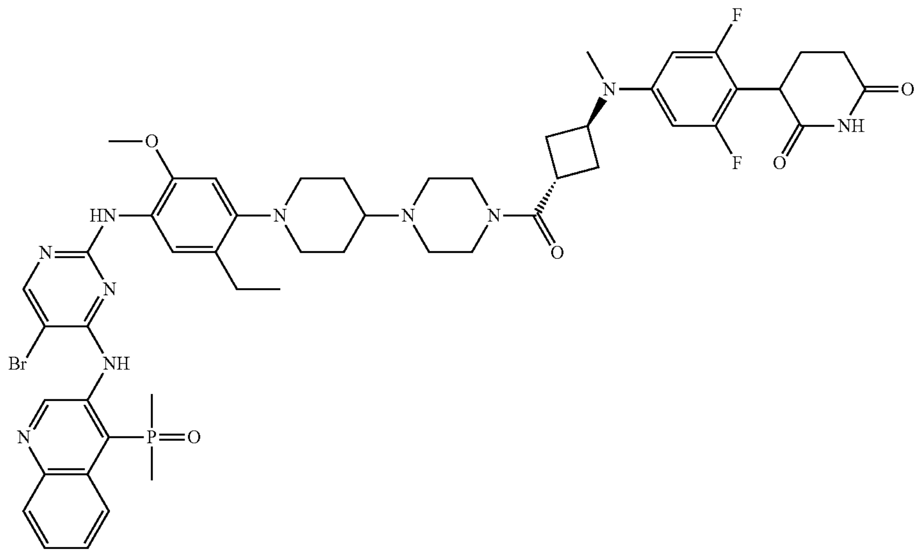
19
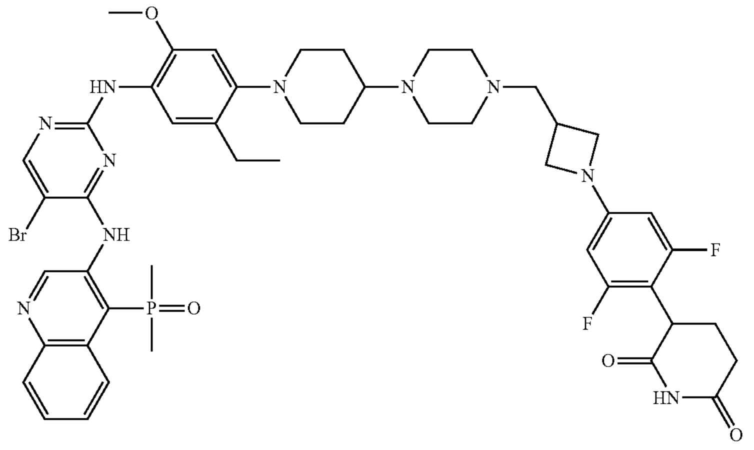

-continued
20
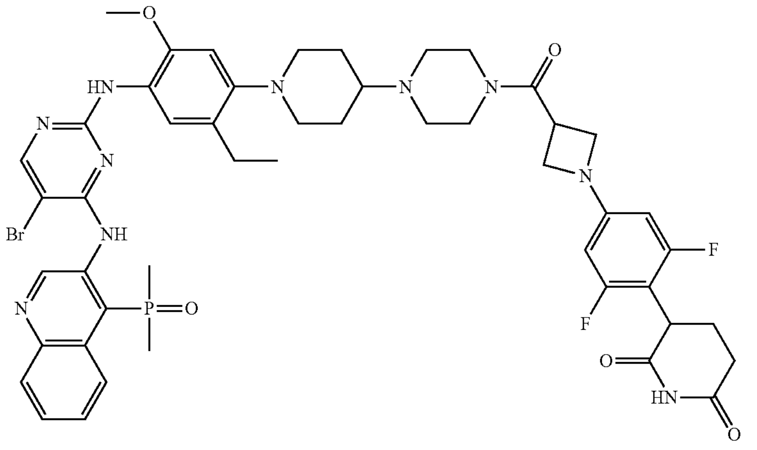
21
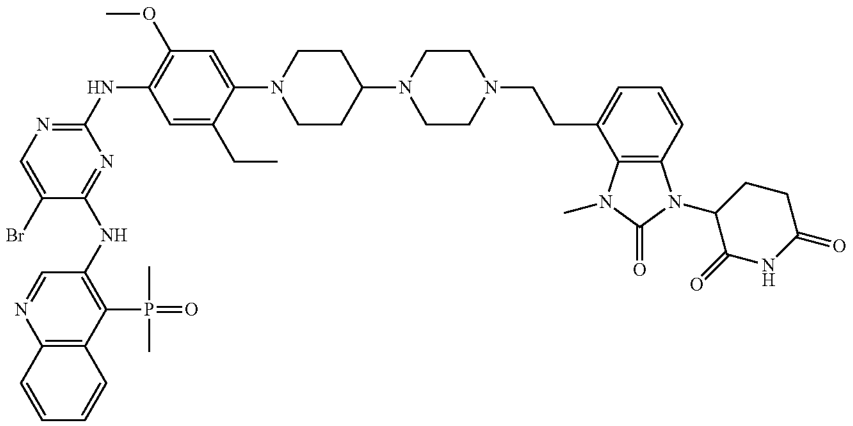
22
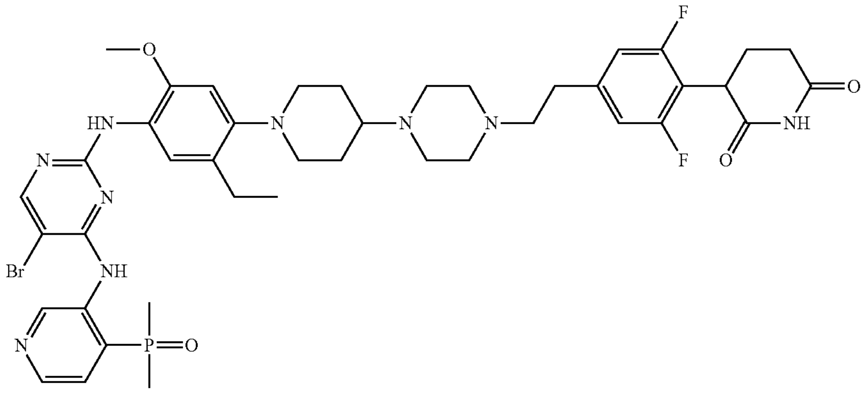

-continued
23
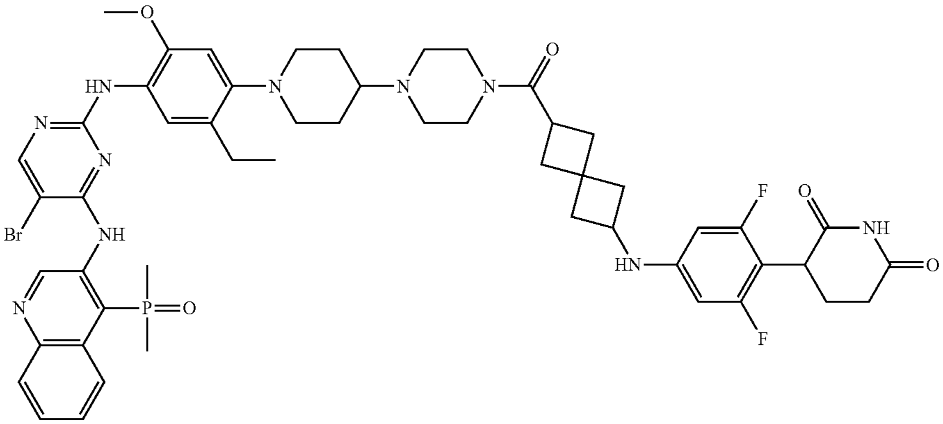
24
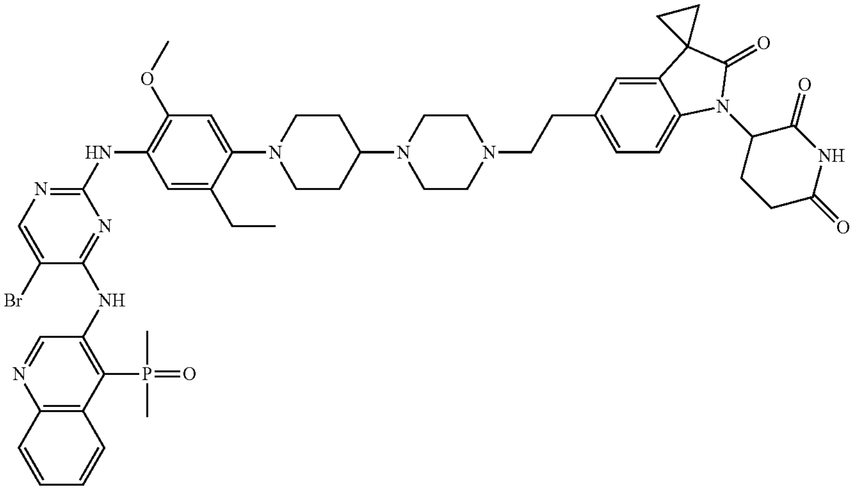
25
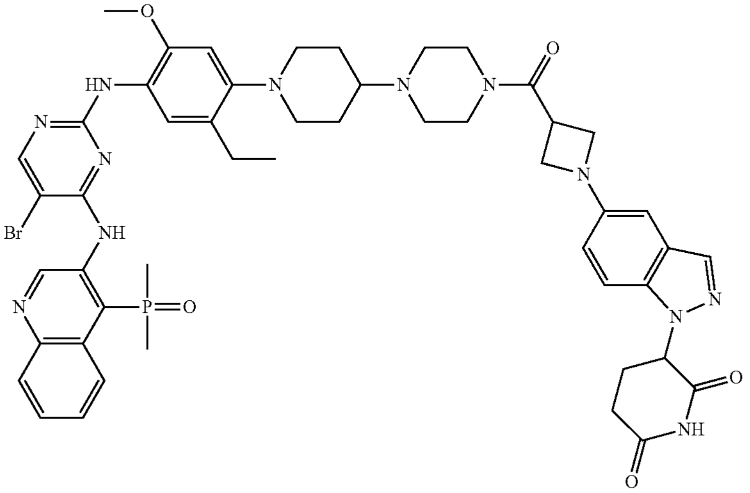

-continued
26
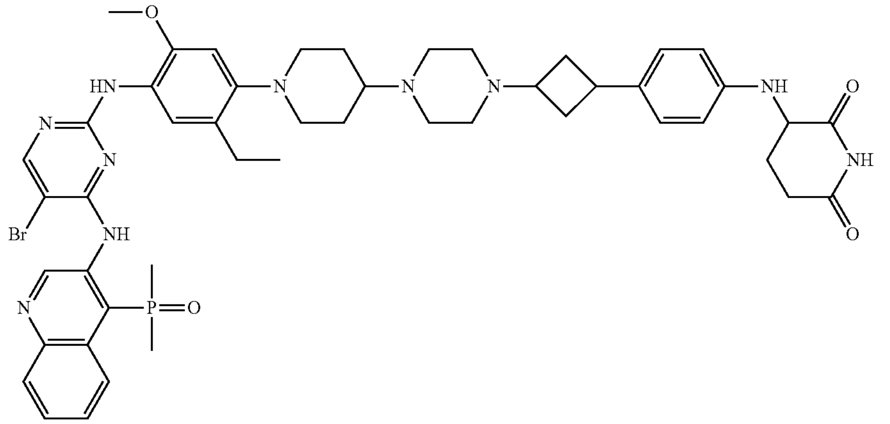
27
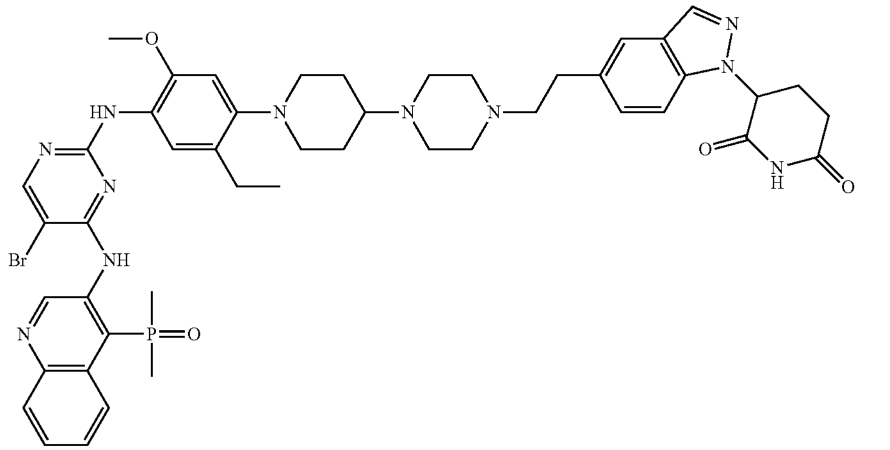
28
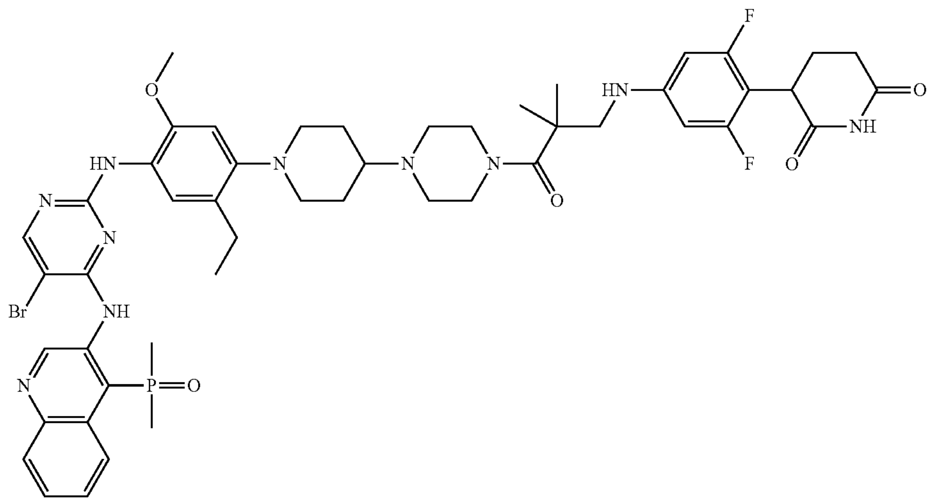

-continued
29
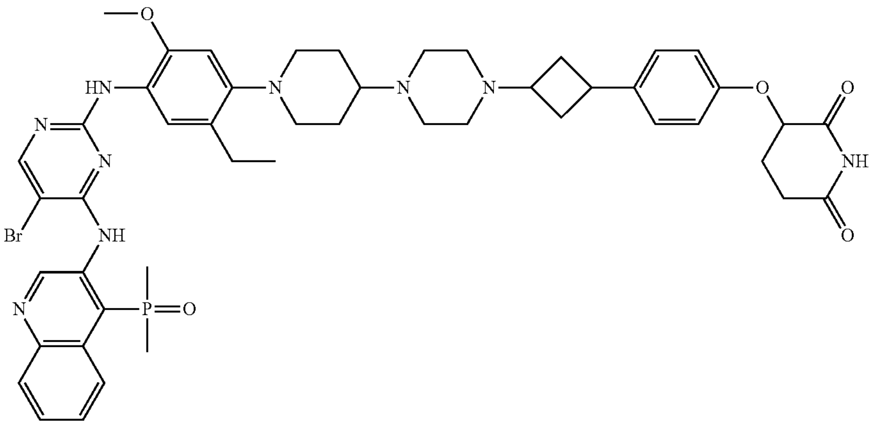
30
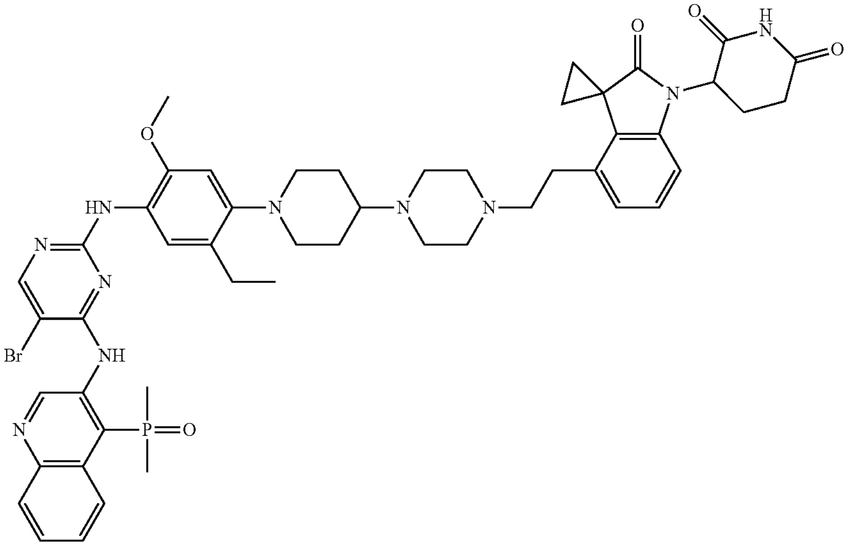
31
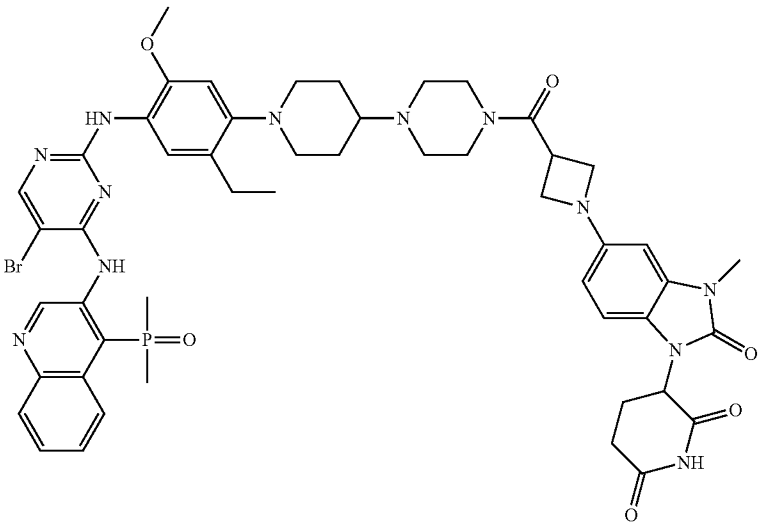

-continued
32
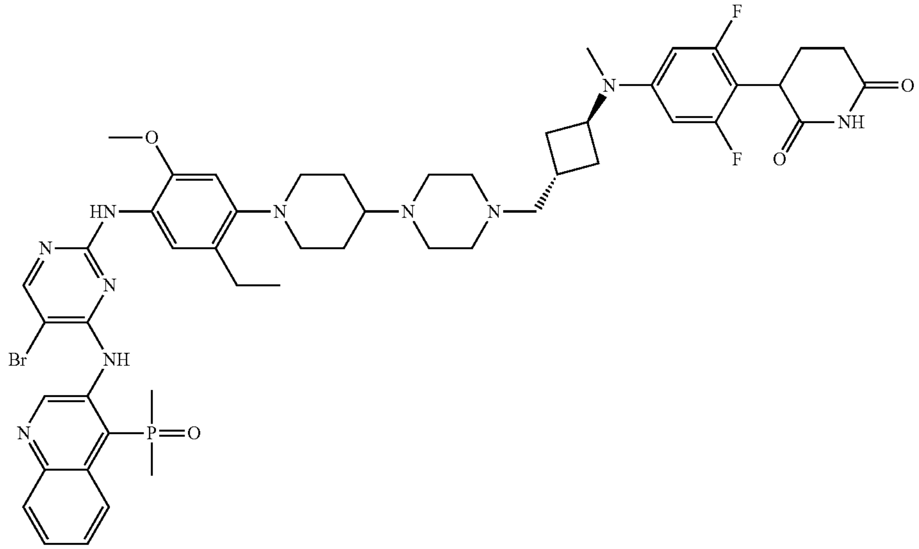
33
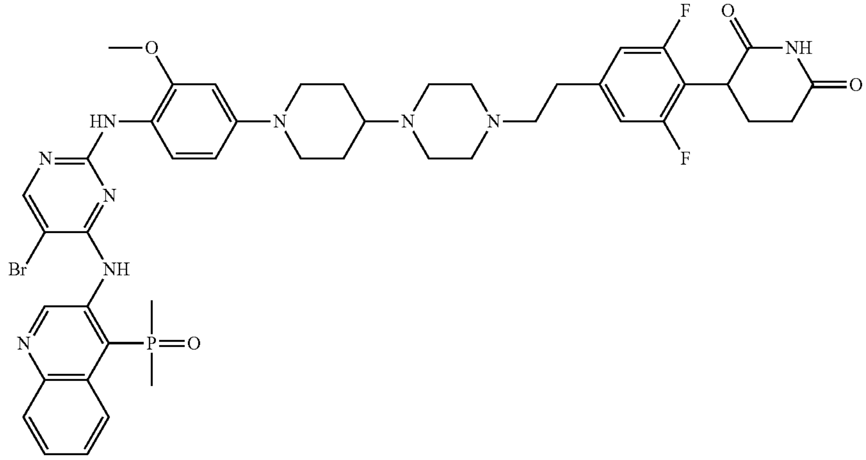
34
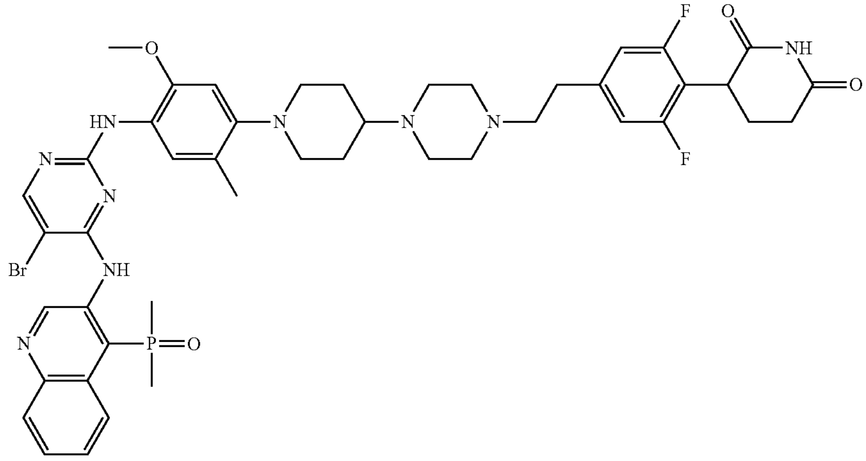

-continued
35
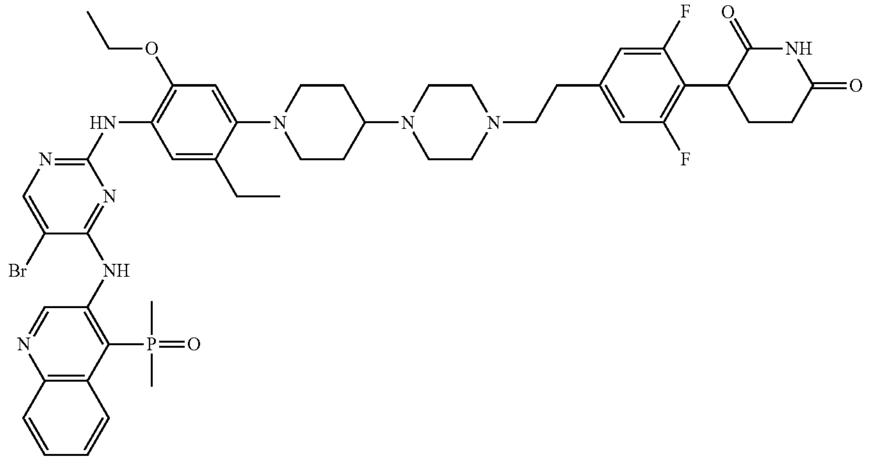
36
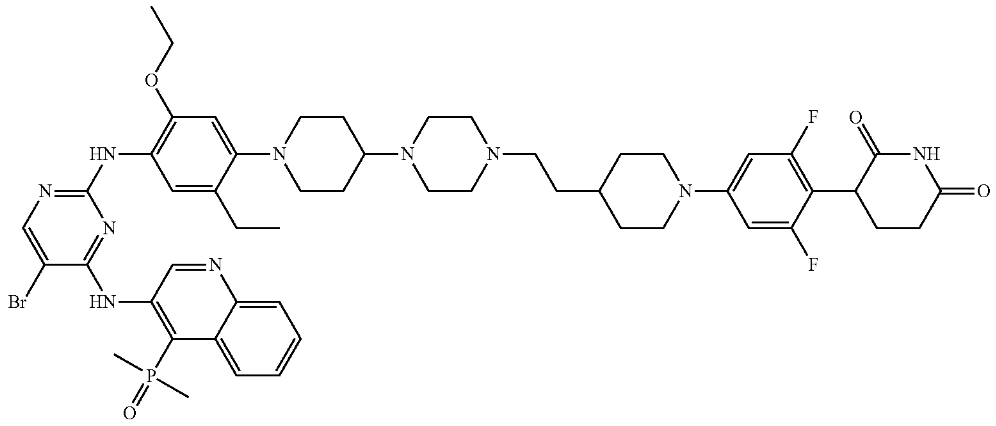
37
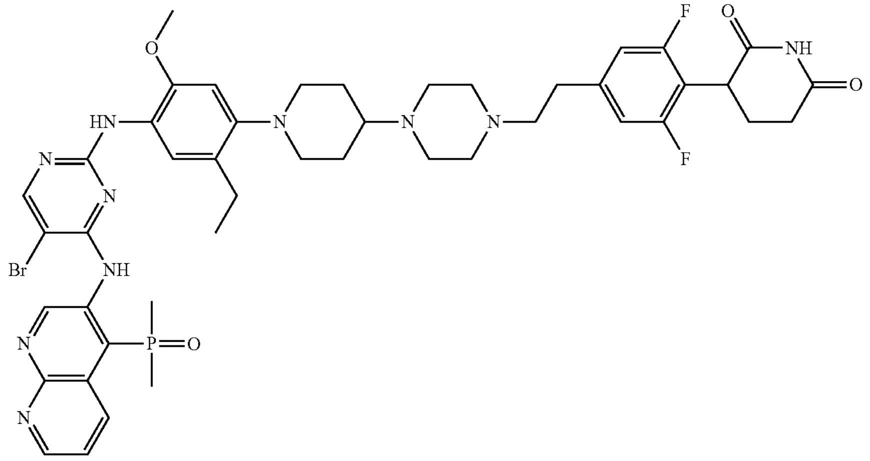

-continued
38
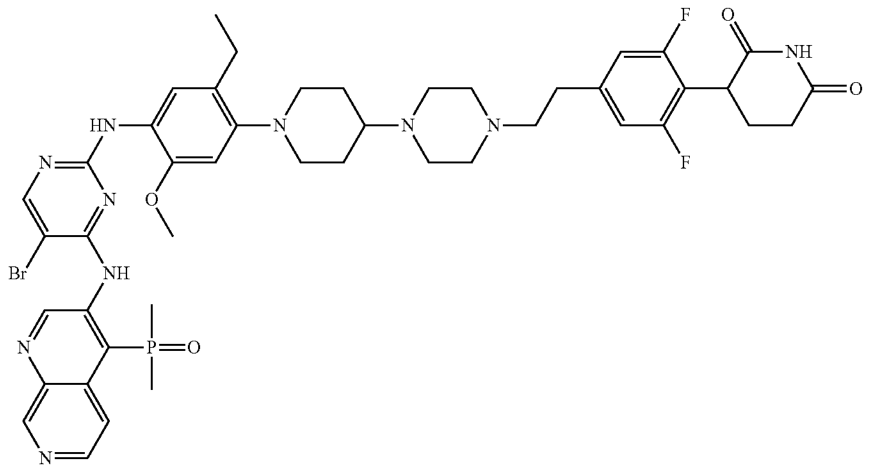
39
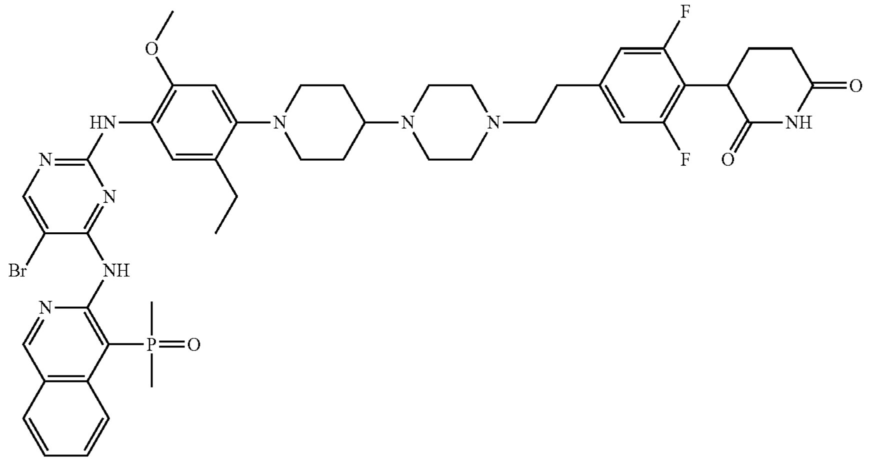
40
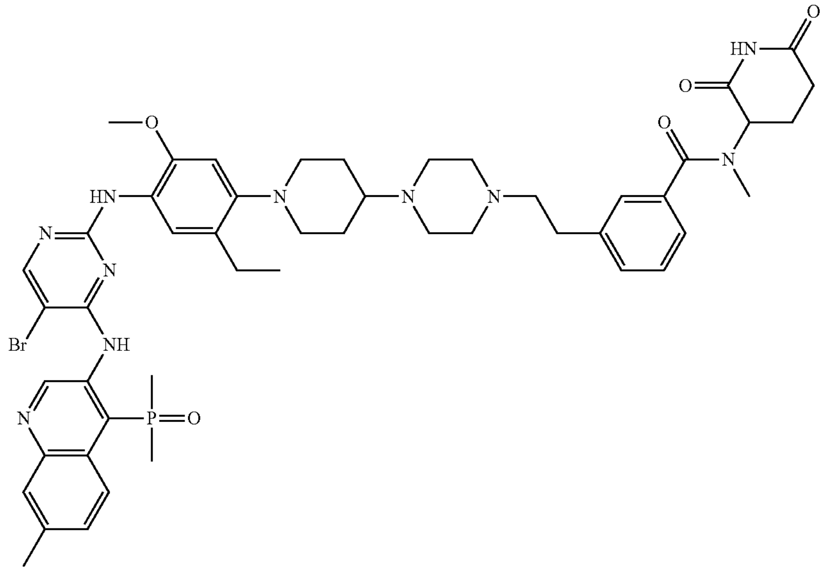

-continued
41
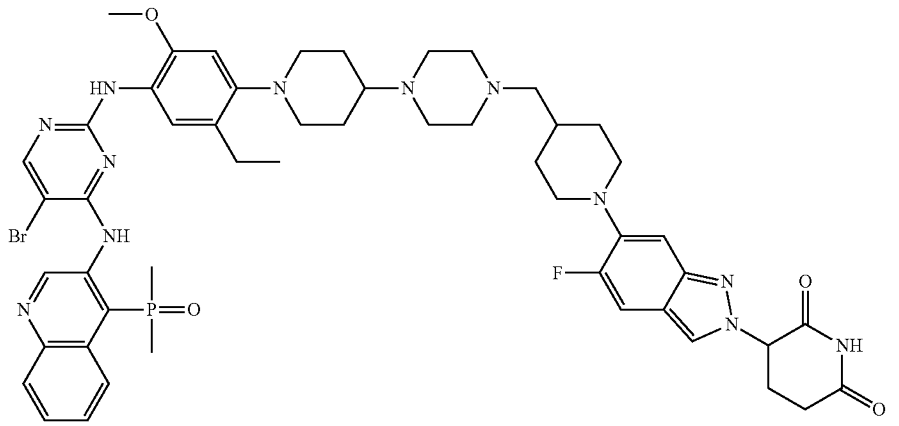
42
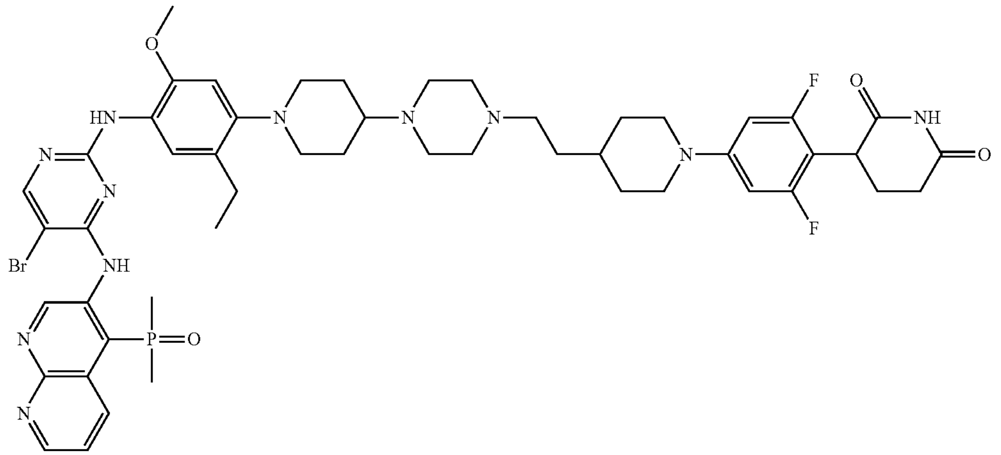
43
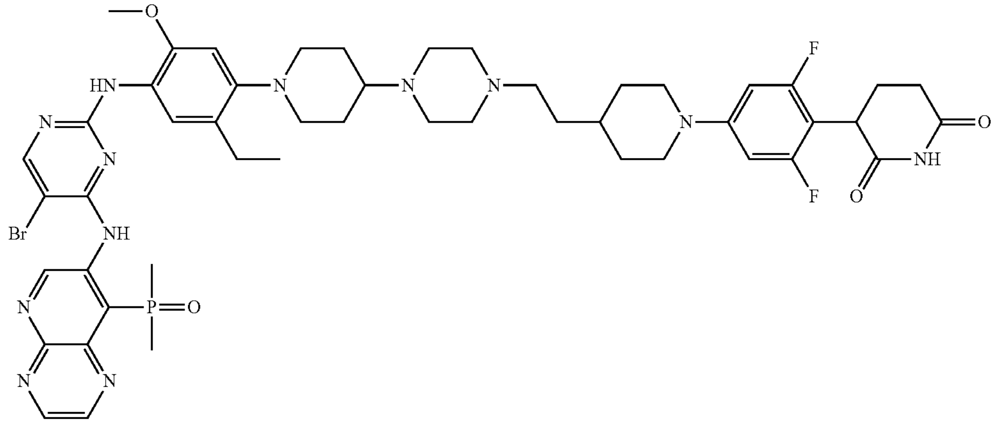

-continued
44
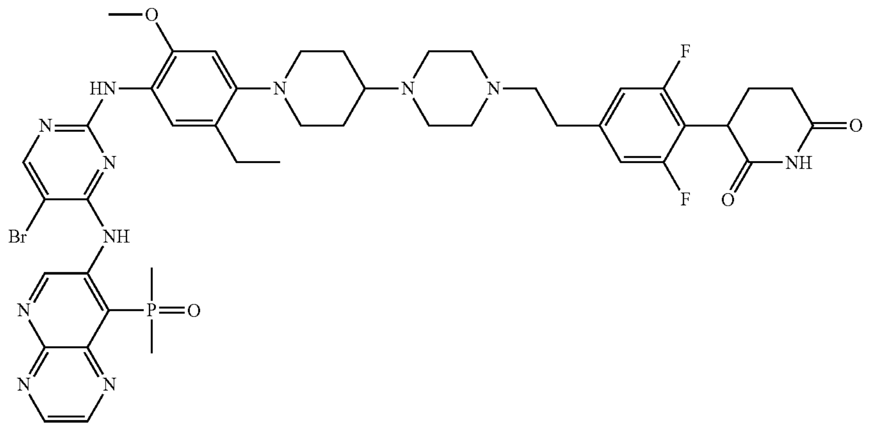
45
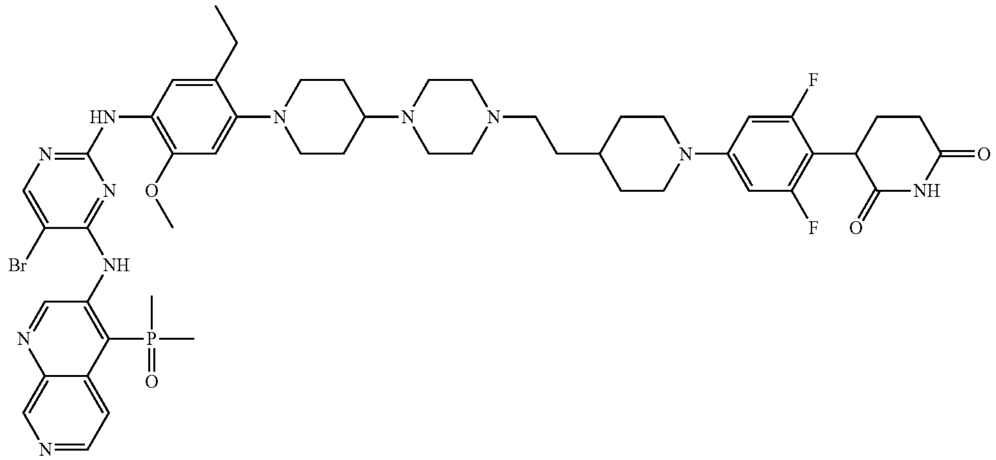
46
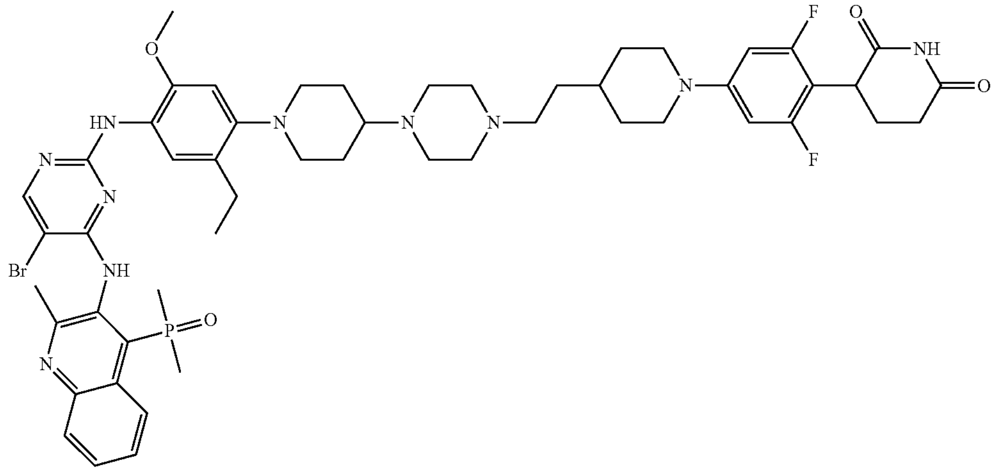

-continued
47
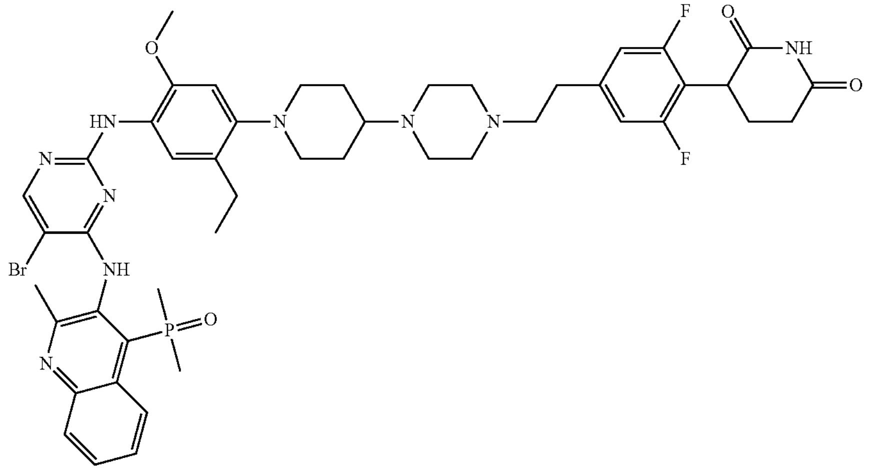
48
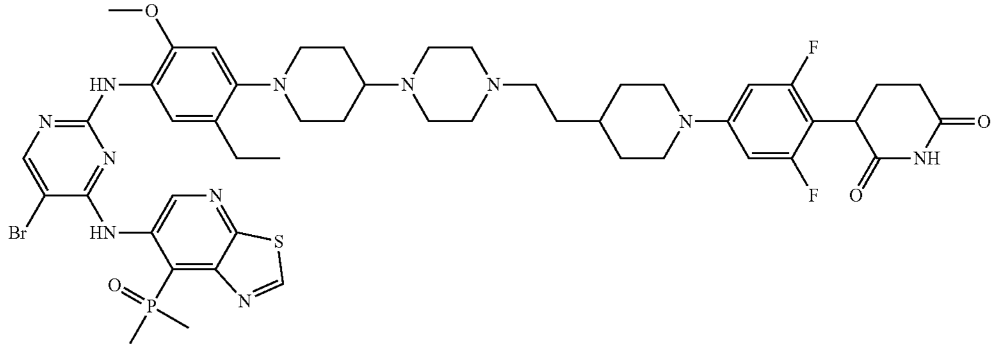
49
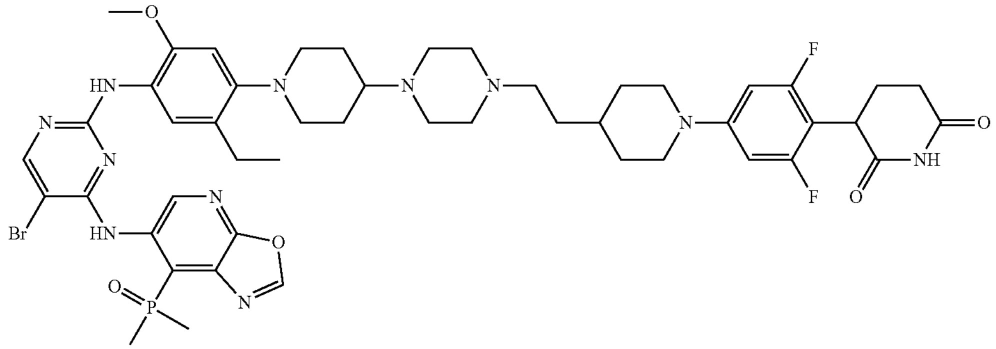
50
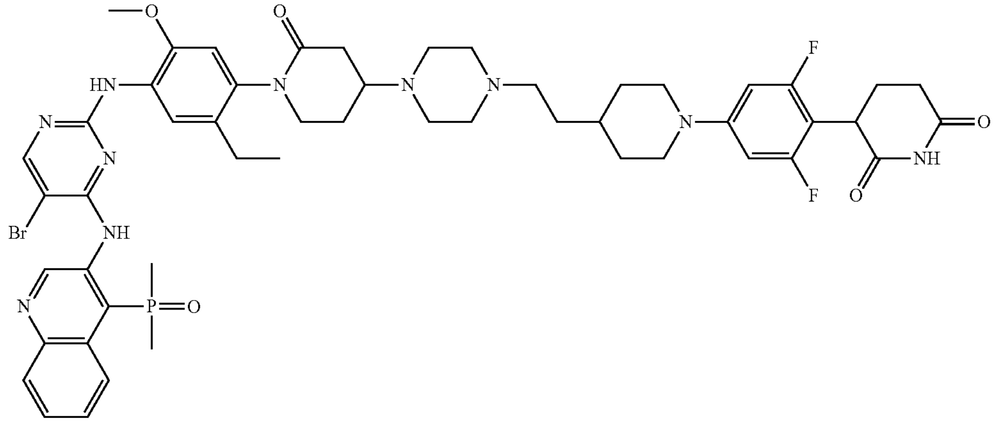

-continued
51
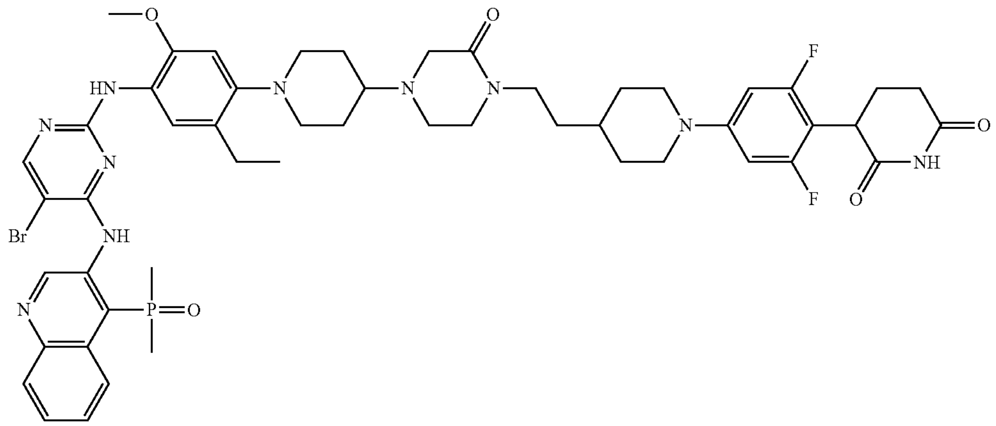
52
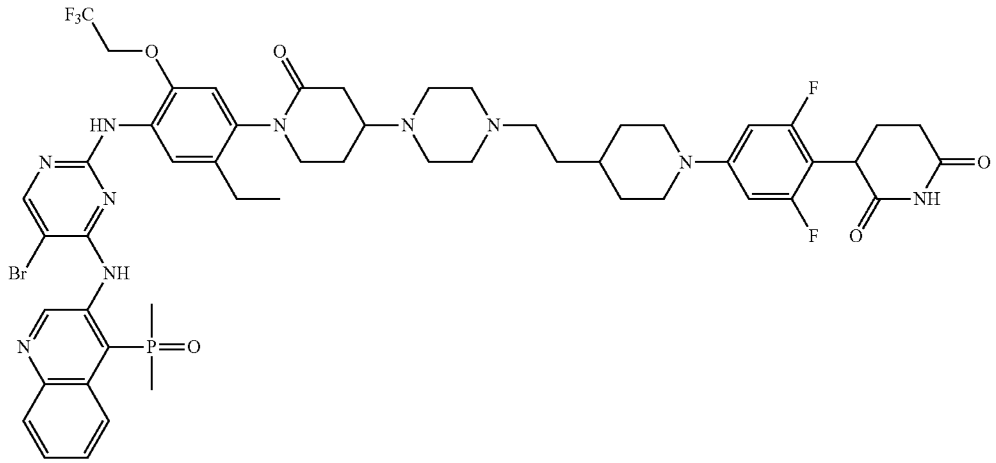
53
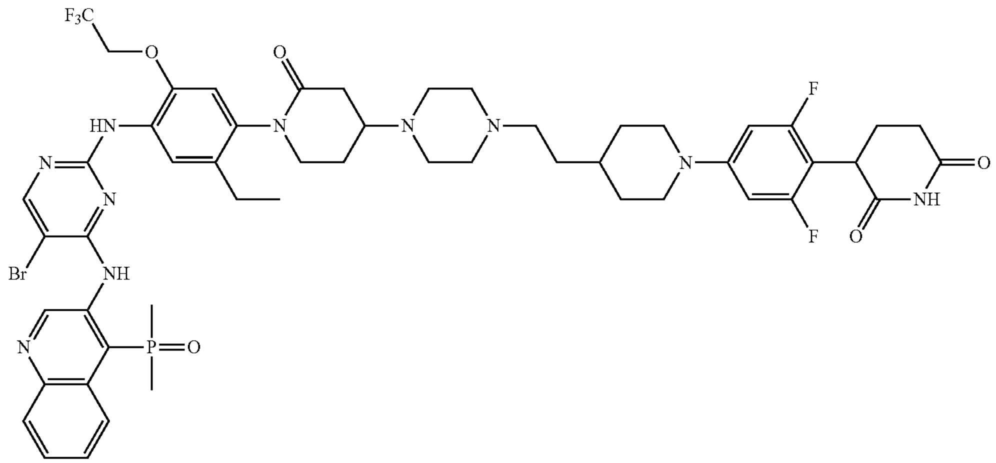

-continued
54
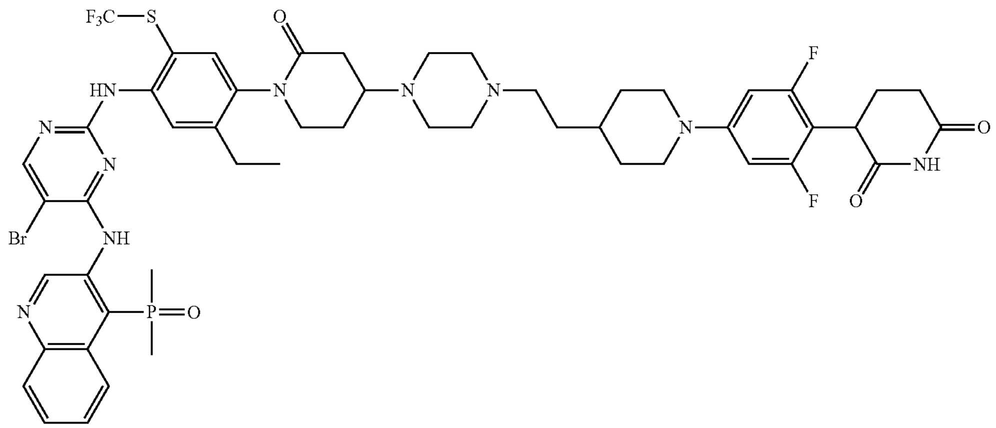
55
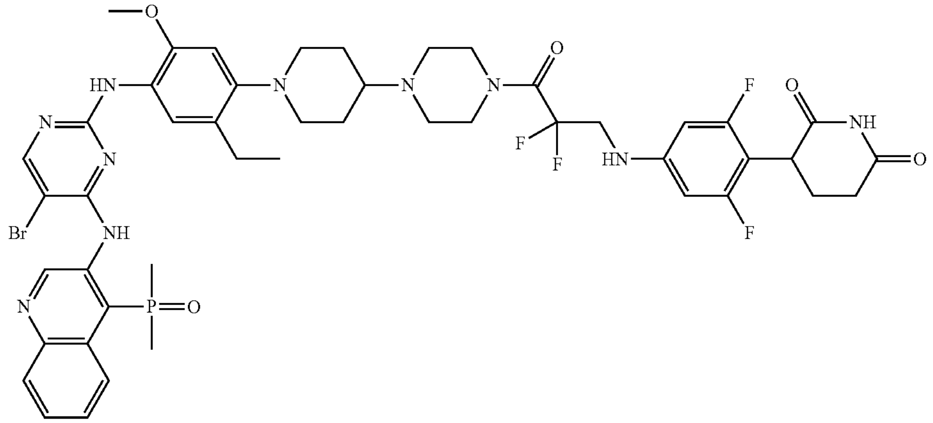
56
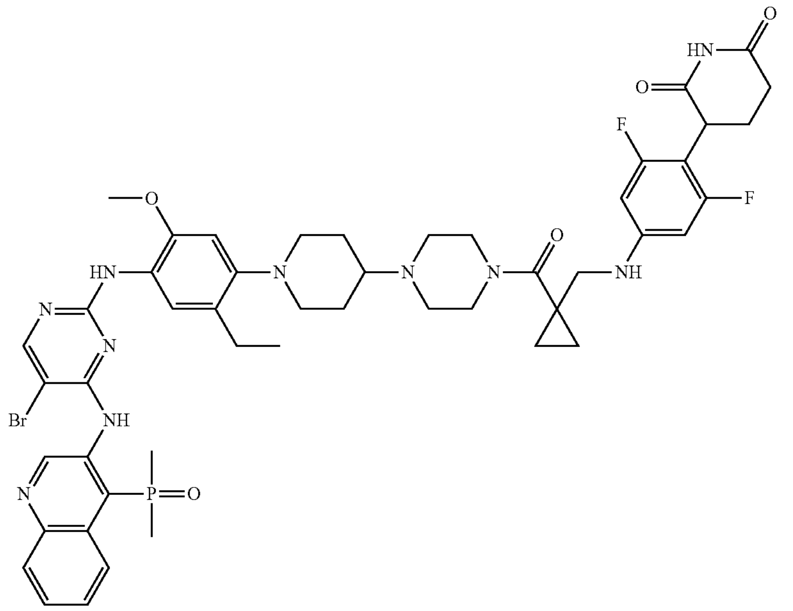

-continued
57
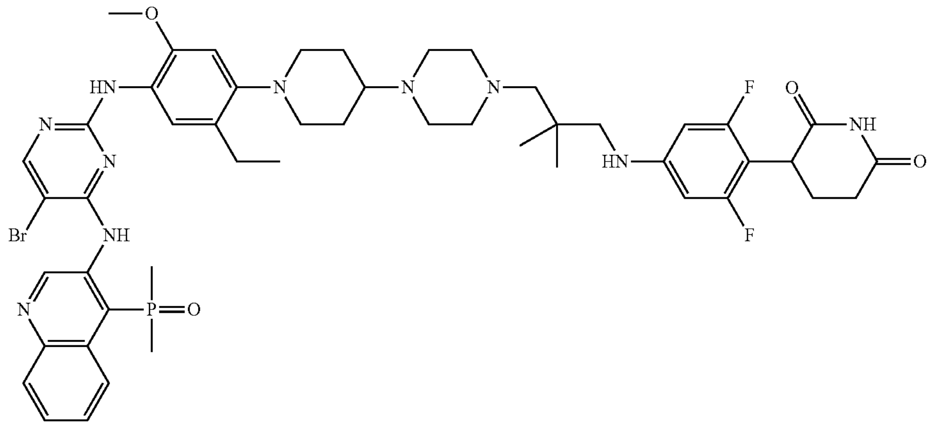
58
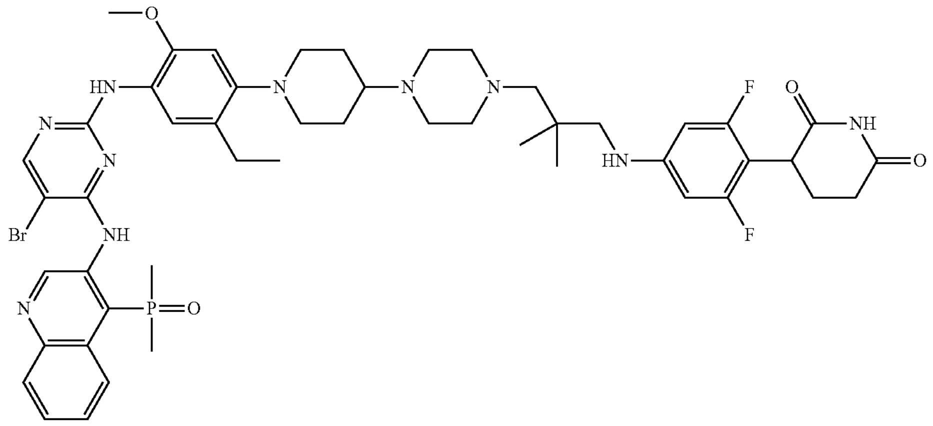
59
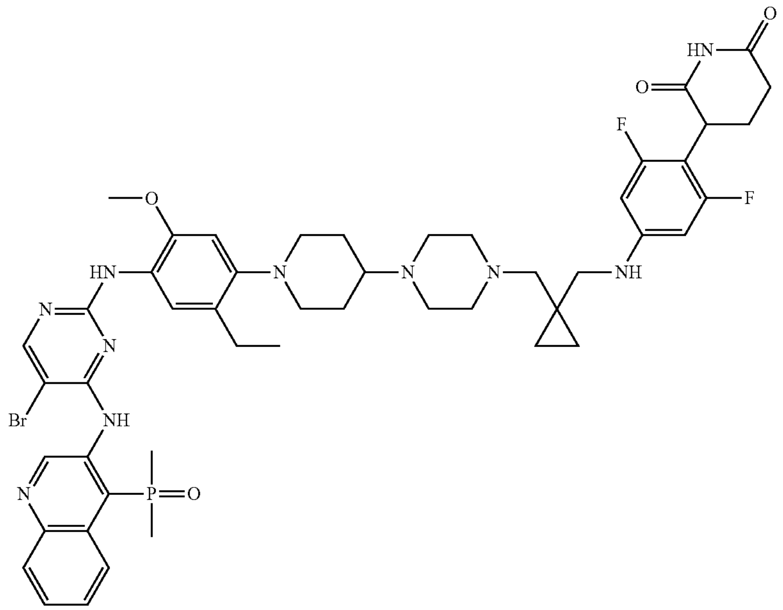

-continued
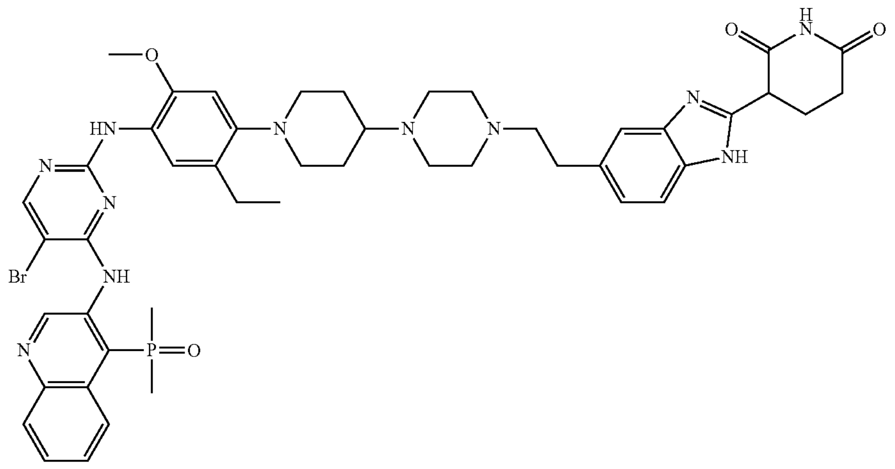
60
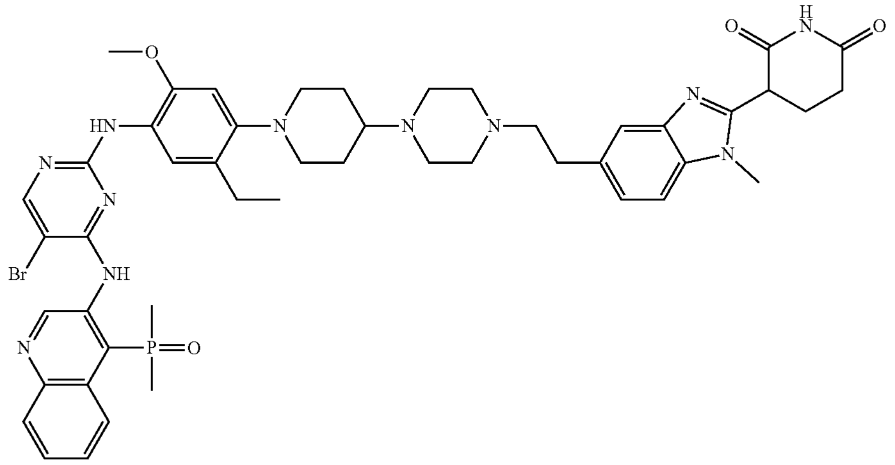
61
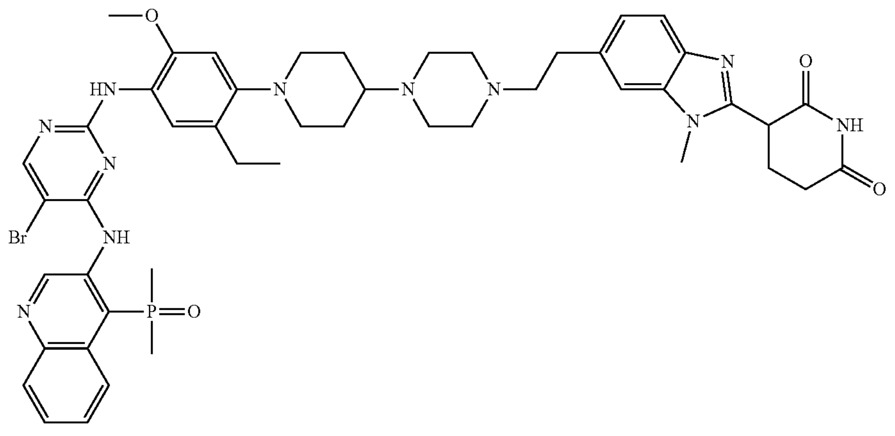
62

-continued
63
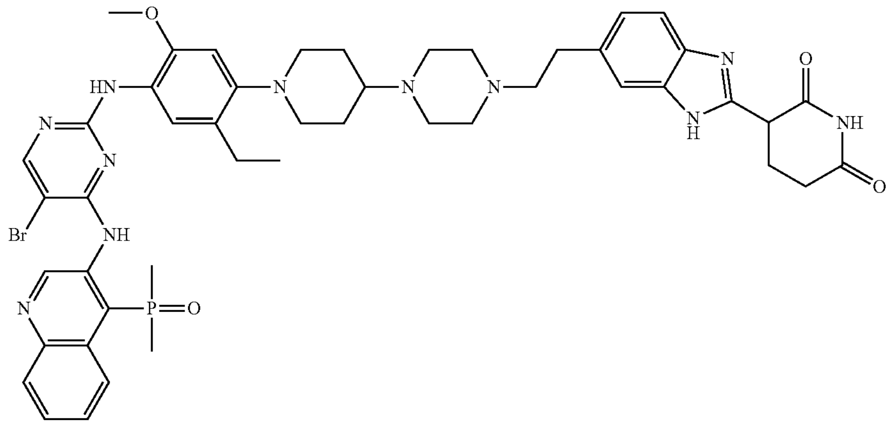
64
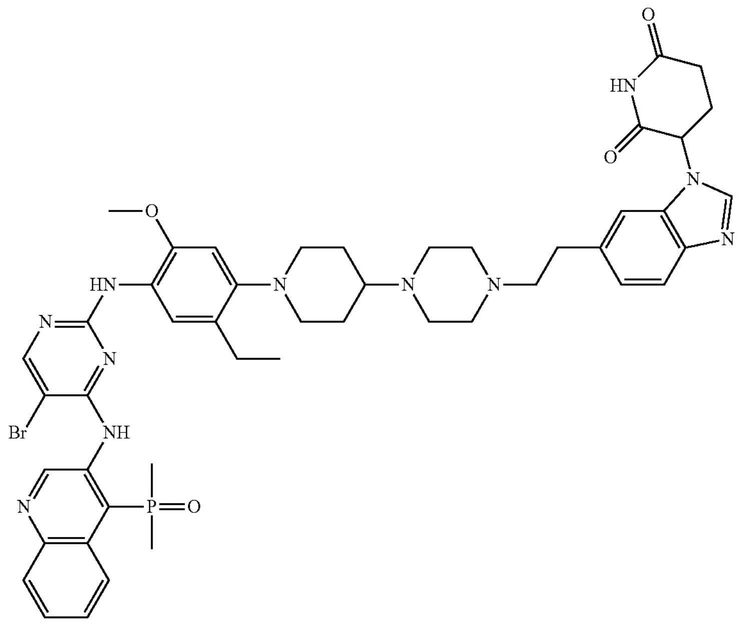

-continued
65
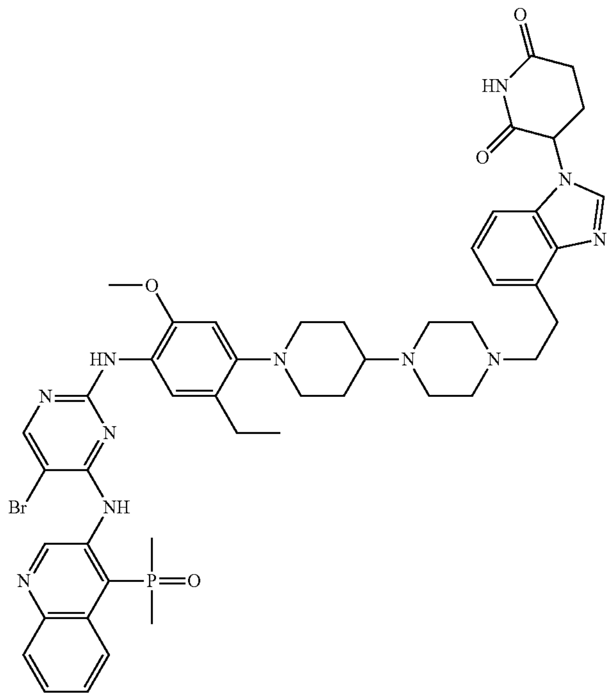
66
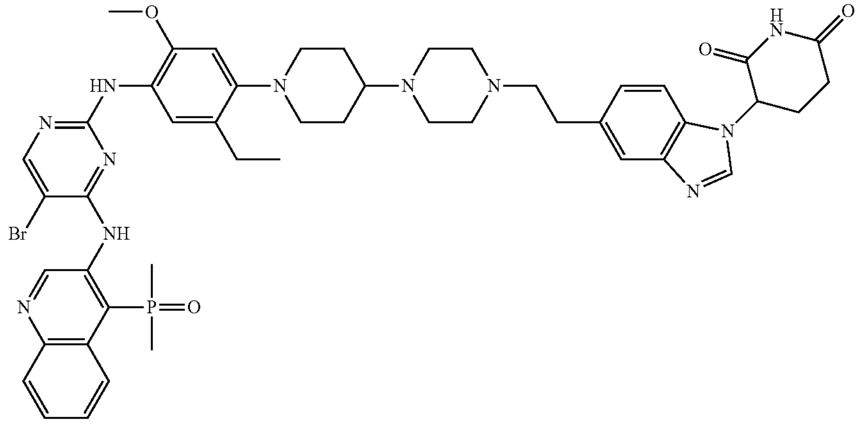

-continued
67
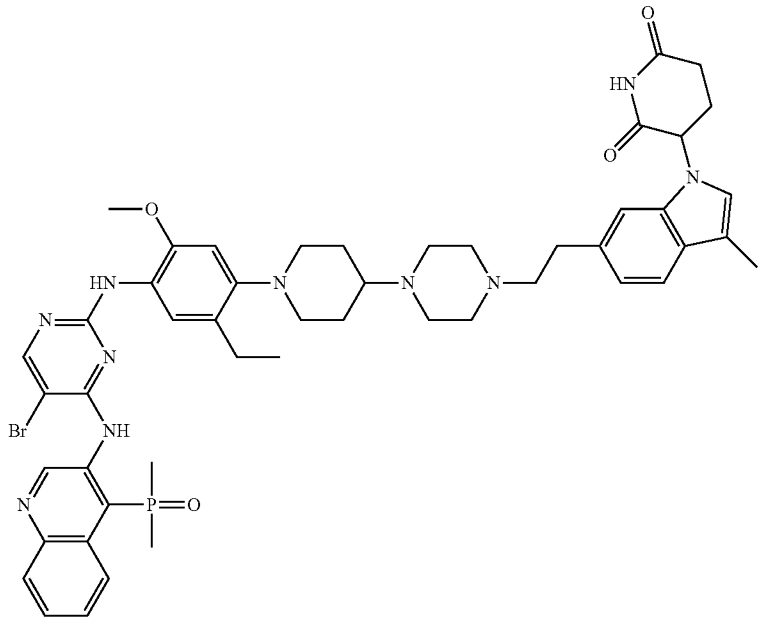
68
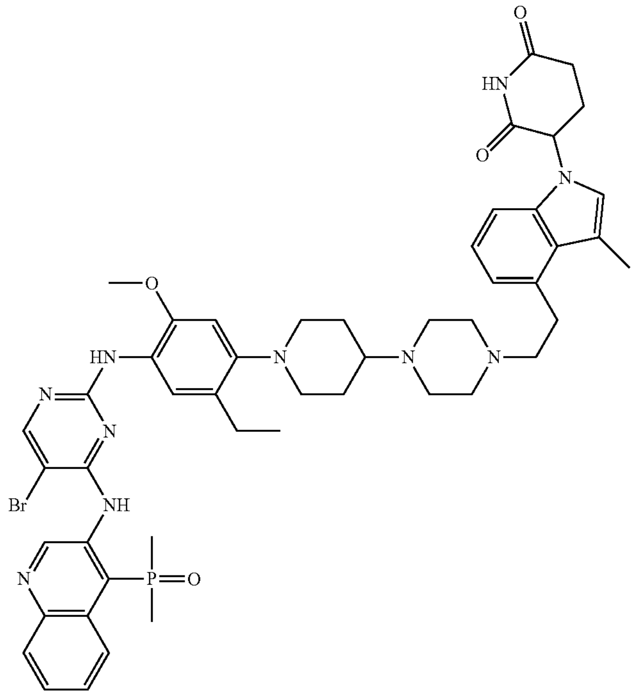

-continued
69
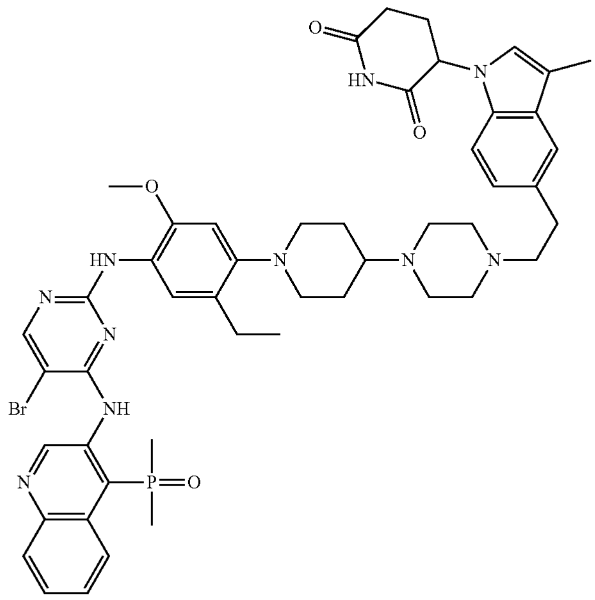
70
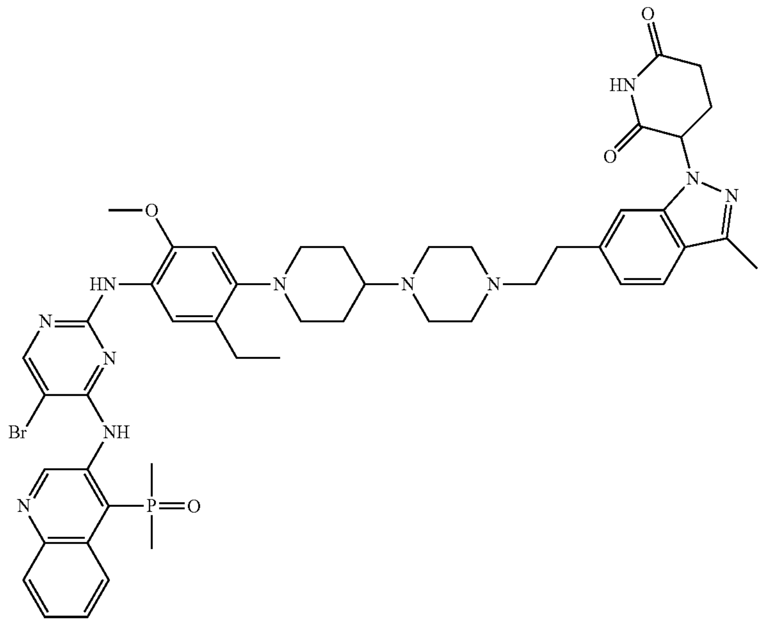

-continued
71
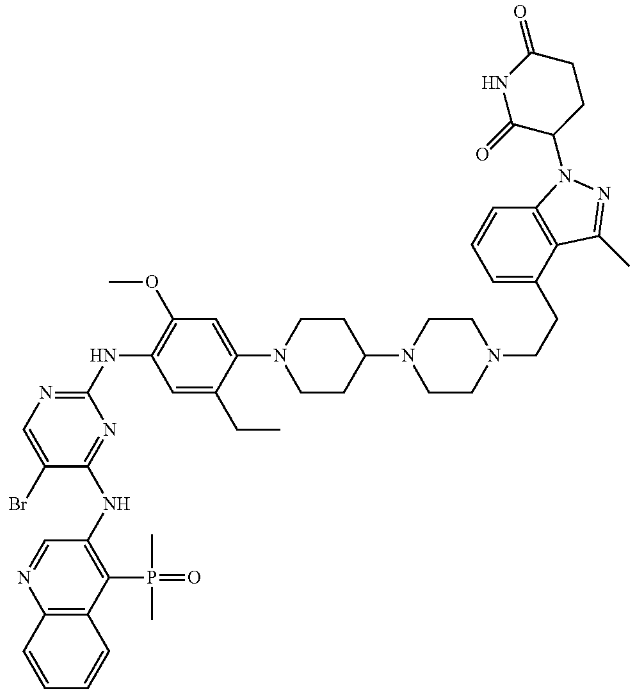
72
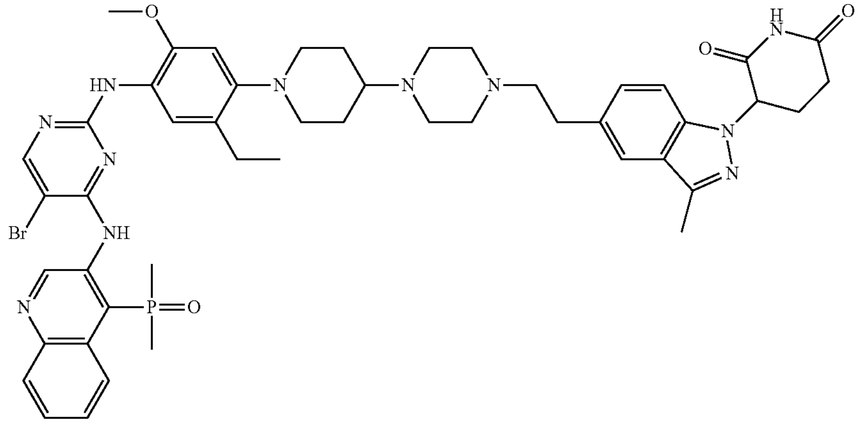

-continued
73
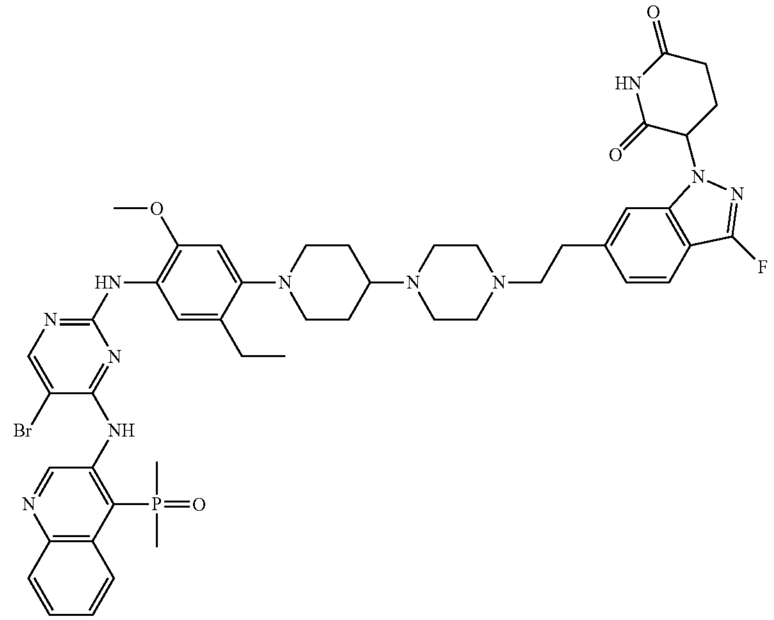
74
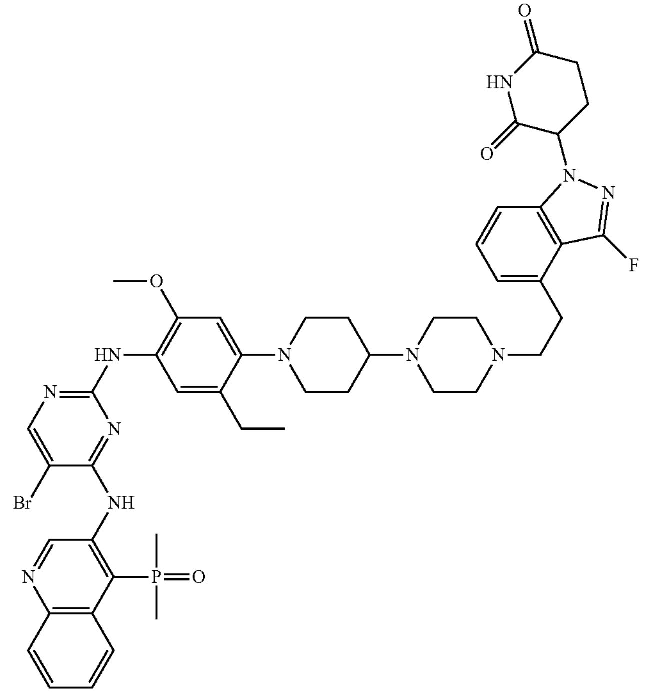

-continued
75
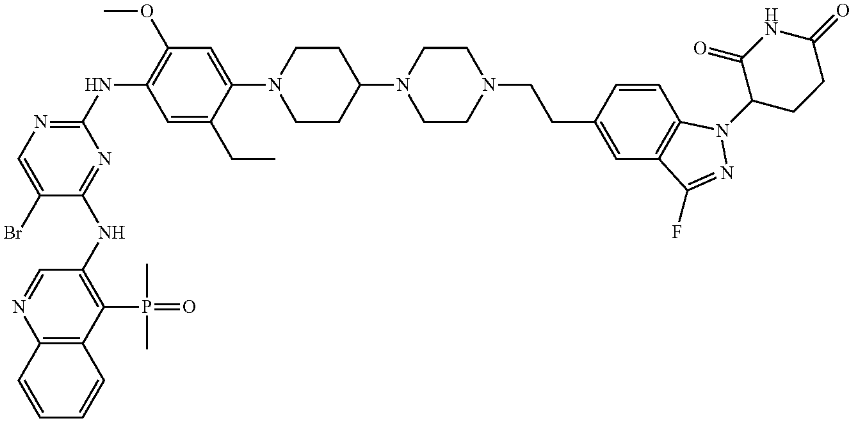
76
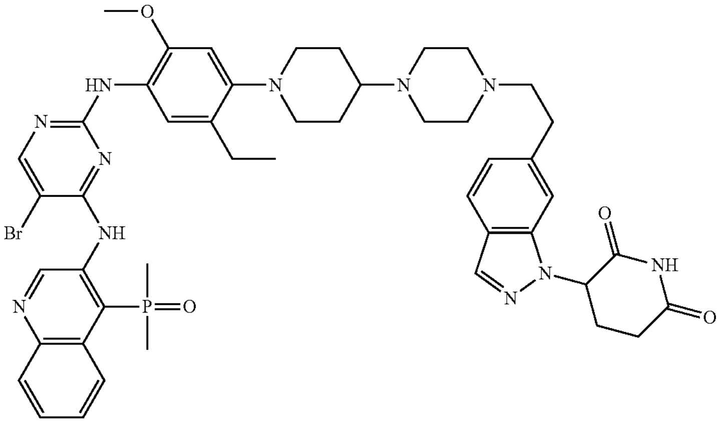
77
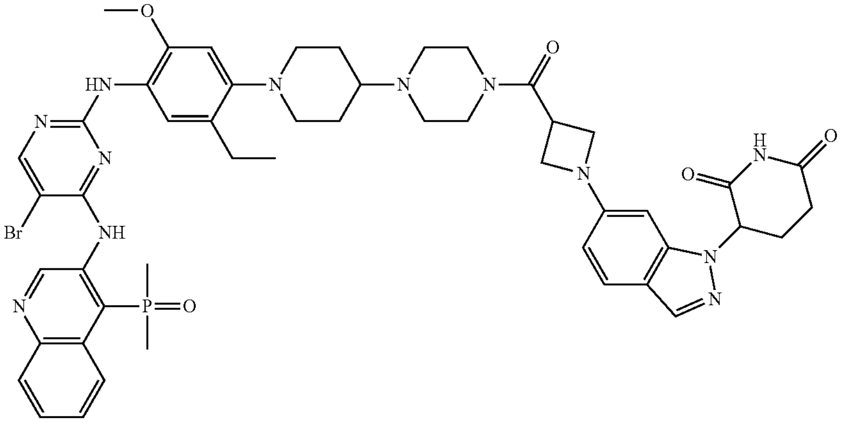

-continued
78
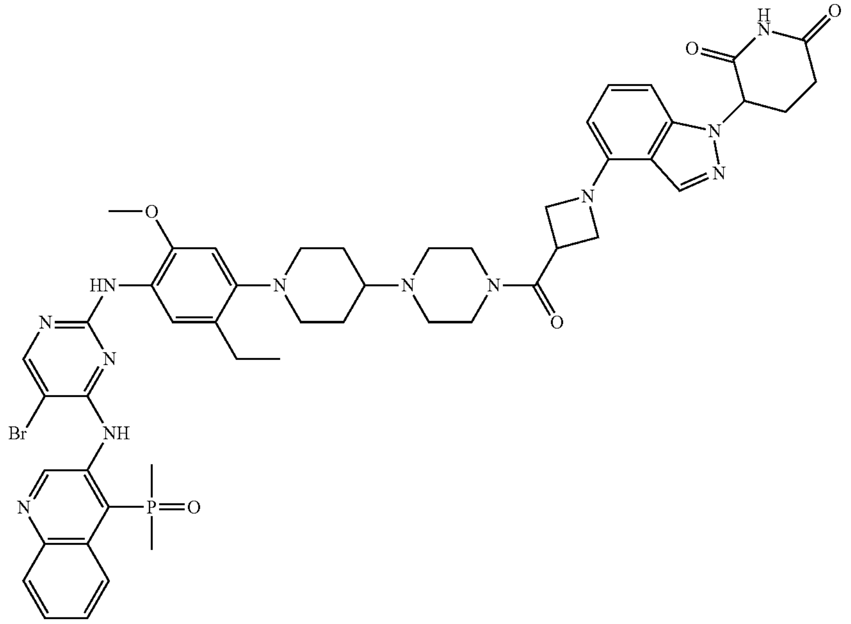
79
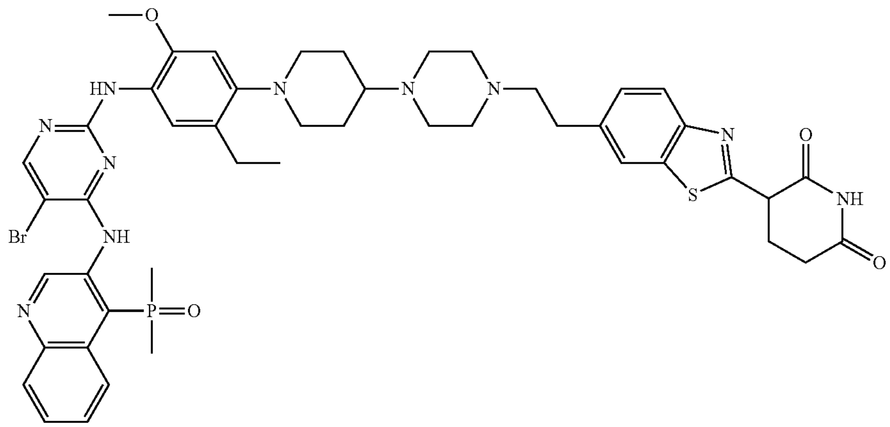
80
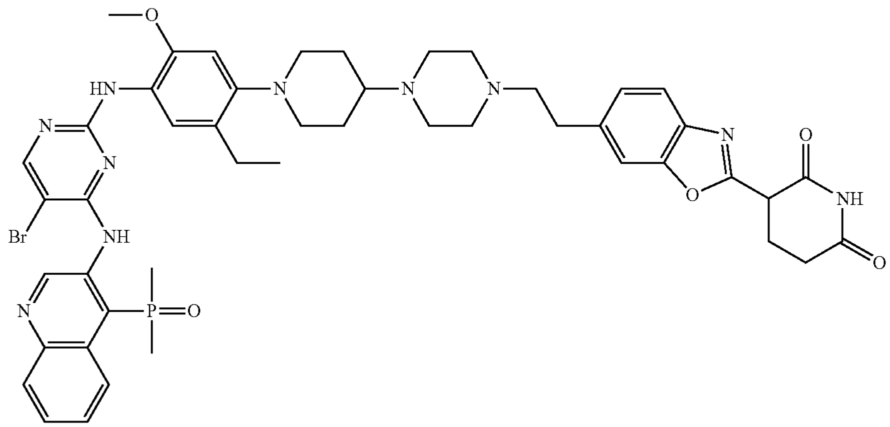

-continued
81
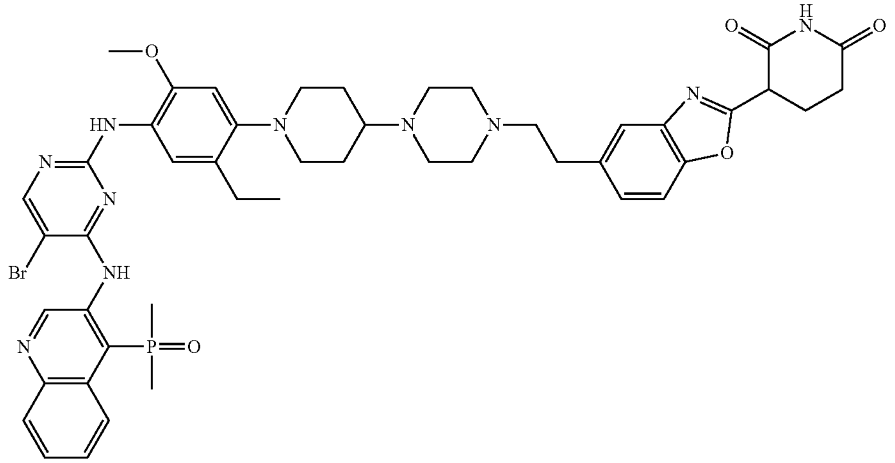
82
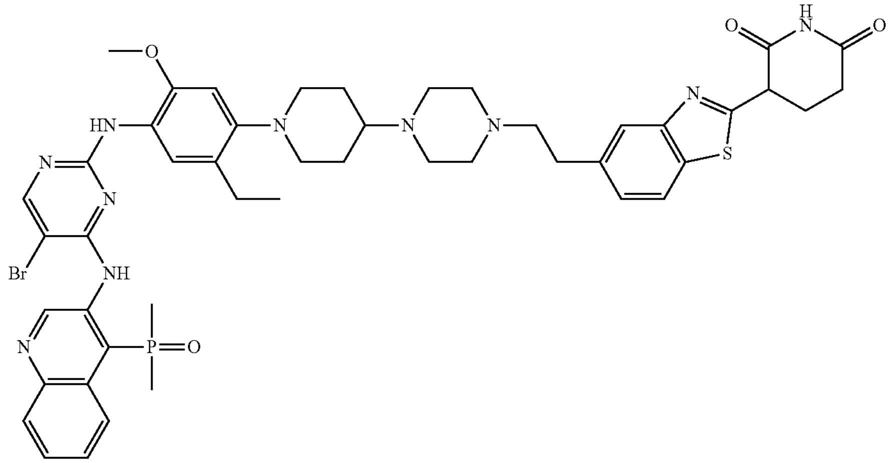
83
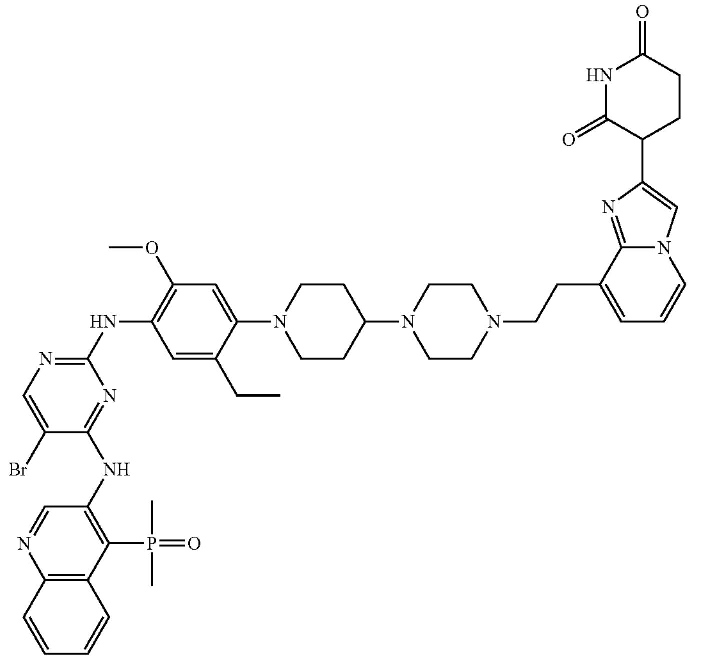

-continued
84
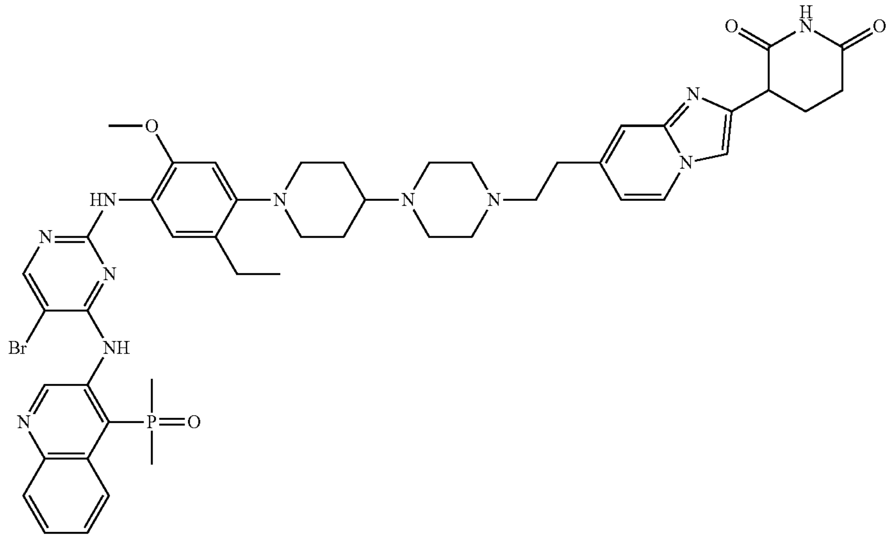
85
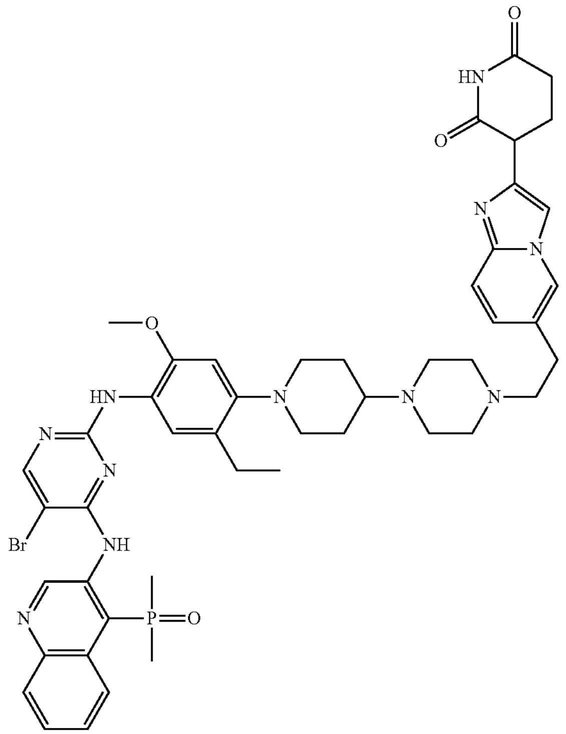

-continued
86
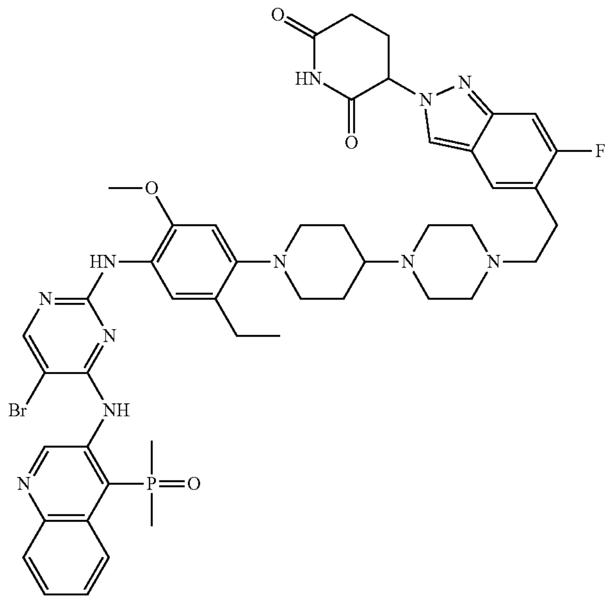
87
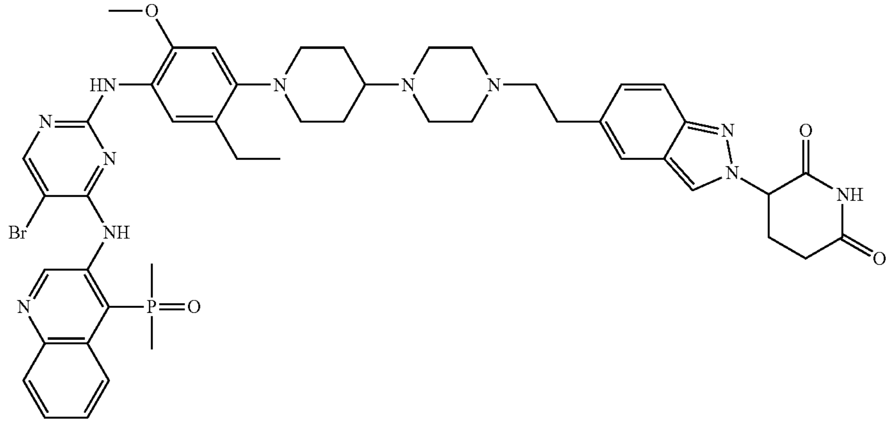
88
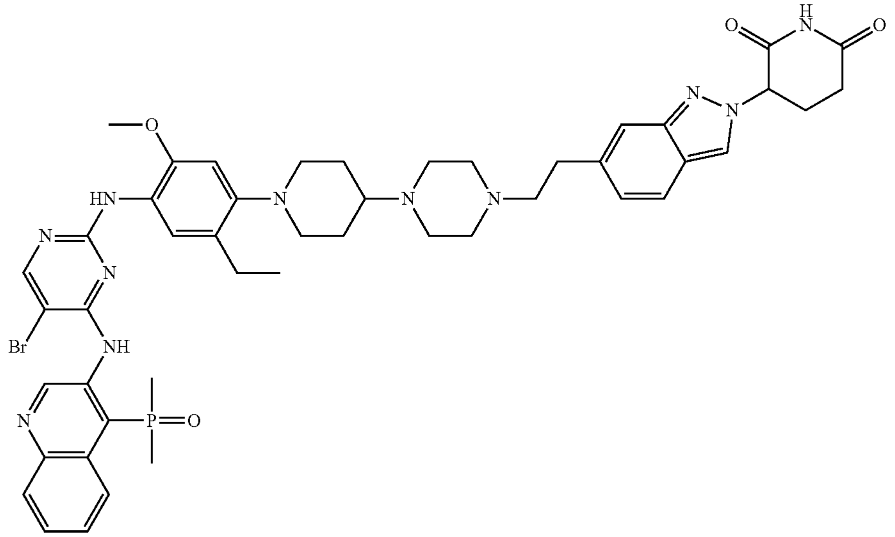

-continued
89
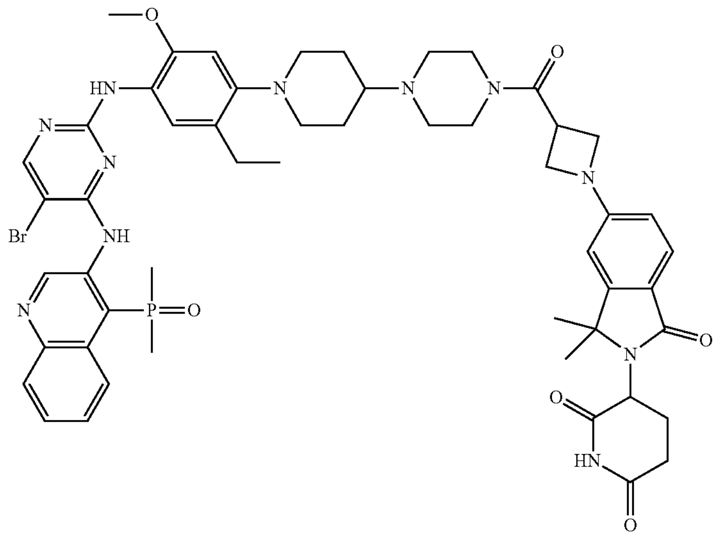
90
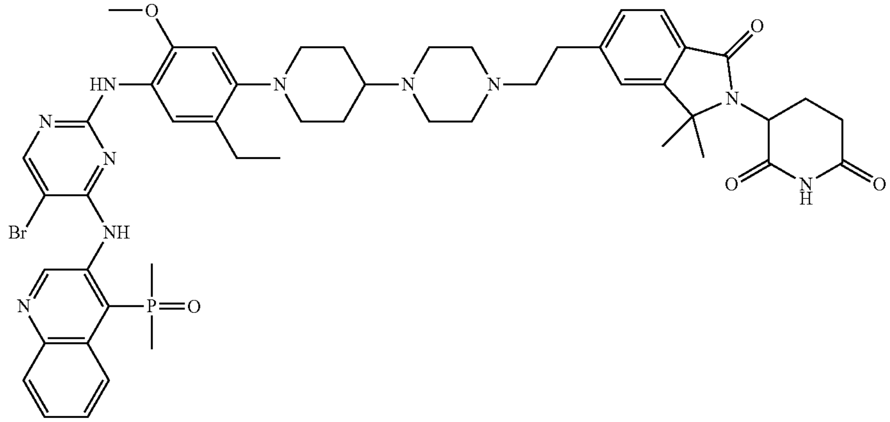
91
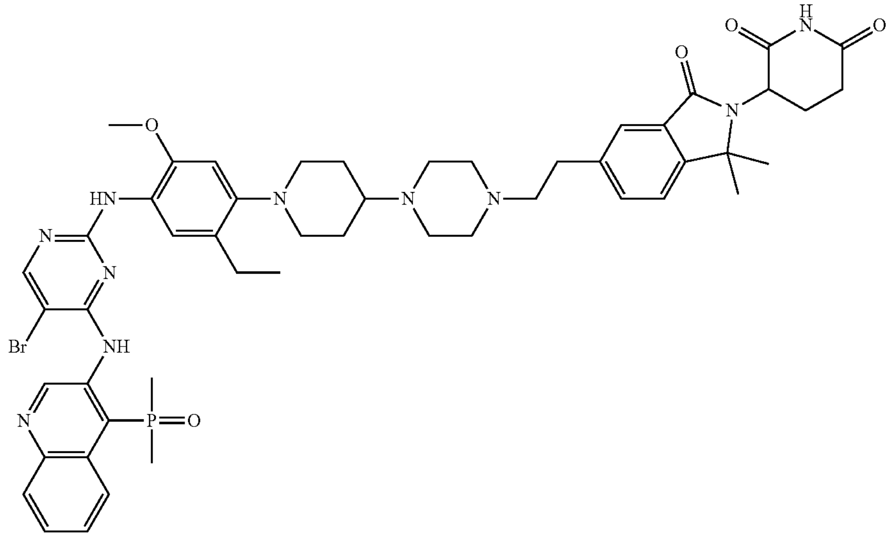

-continued
92
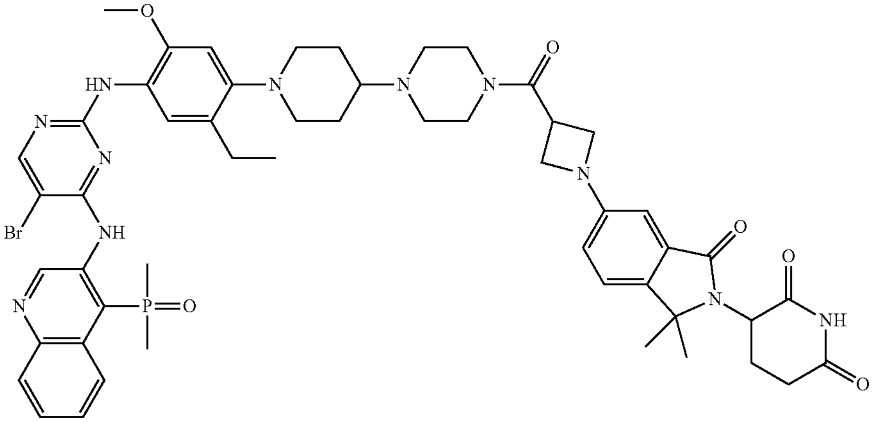
93
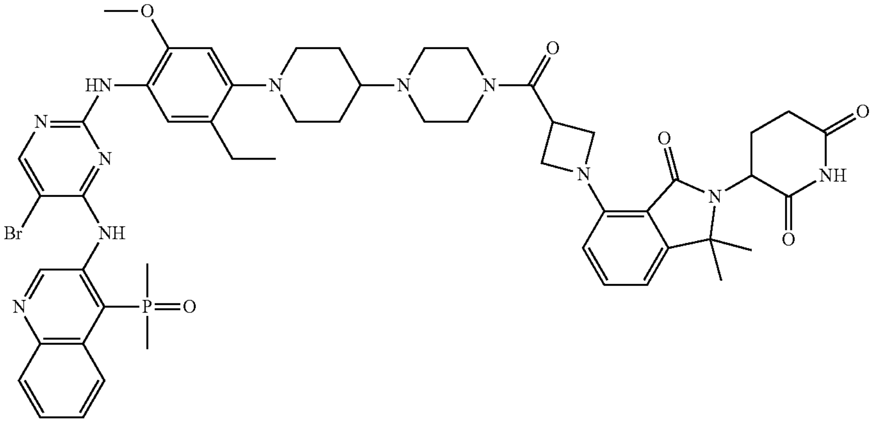
94
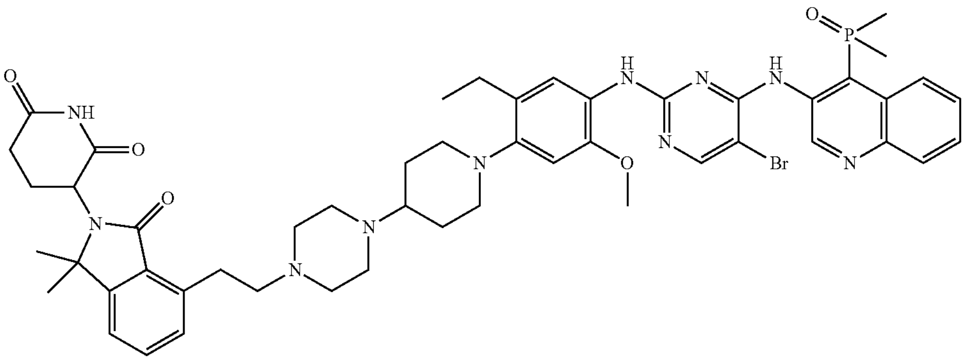

-continued
95
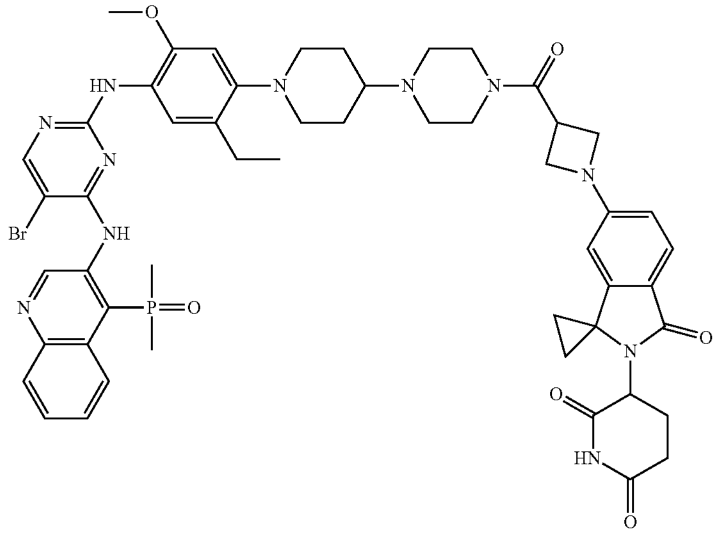
96
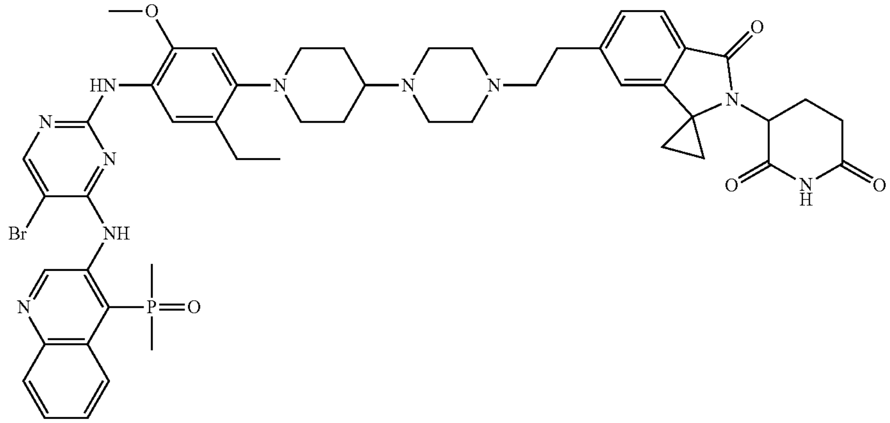
97
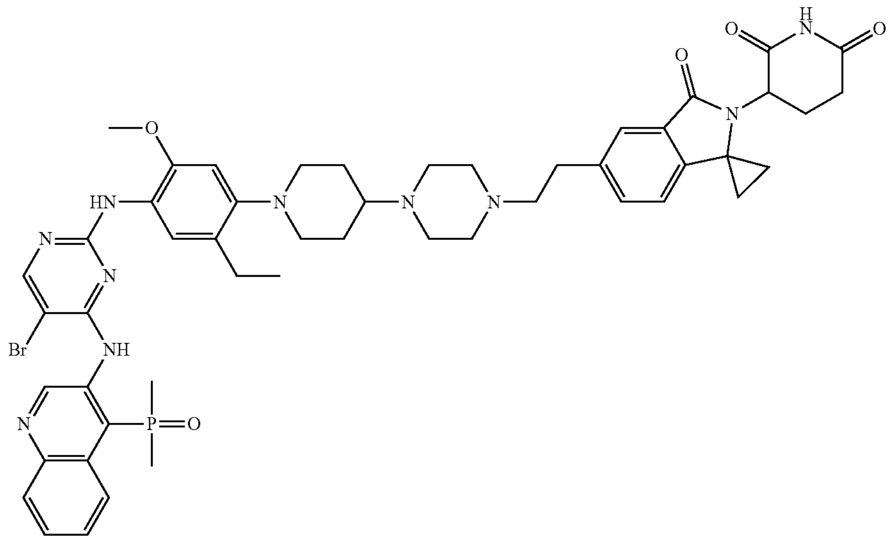

-continued
98
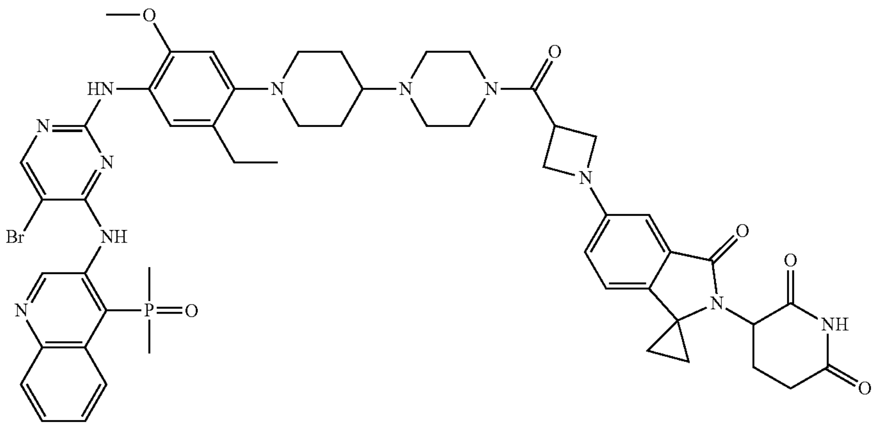
99
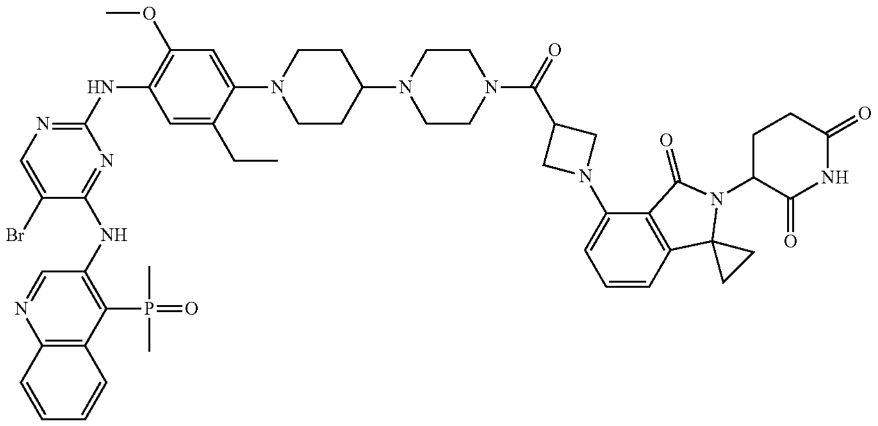
100
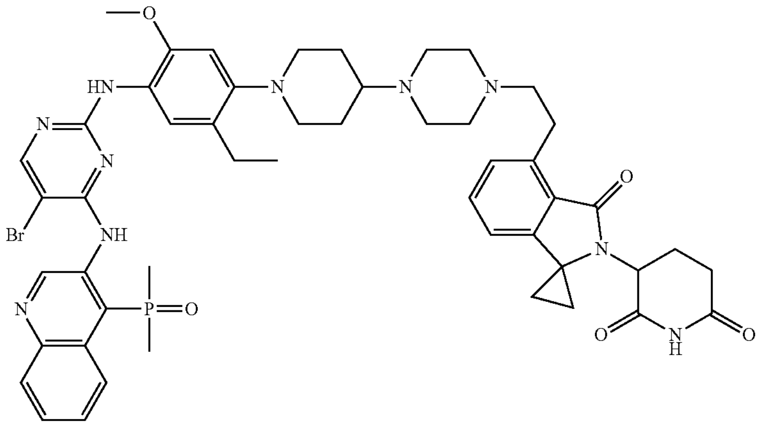

-continued
101
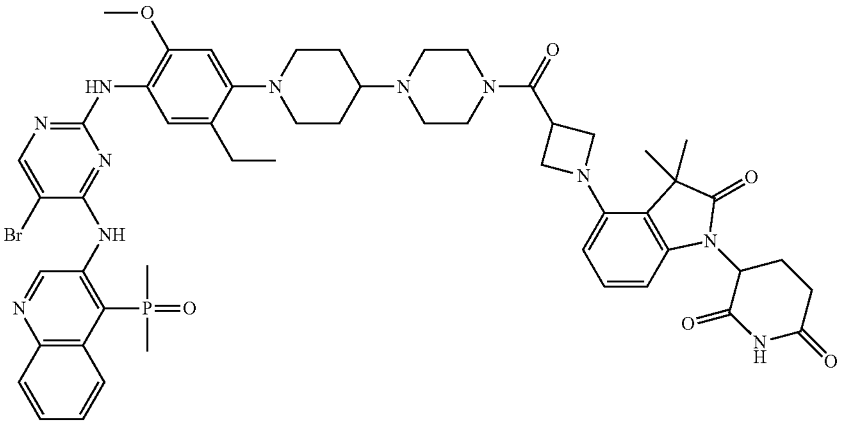
102
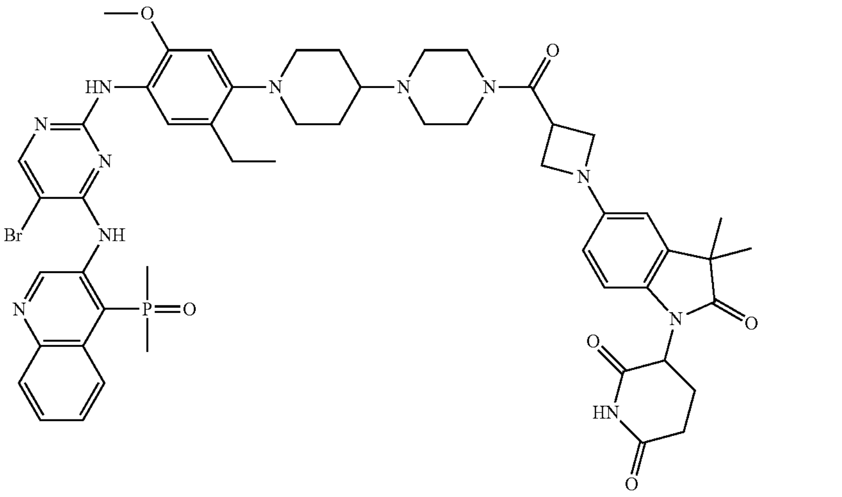
103
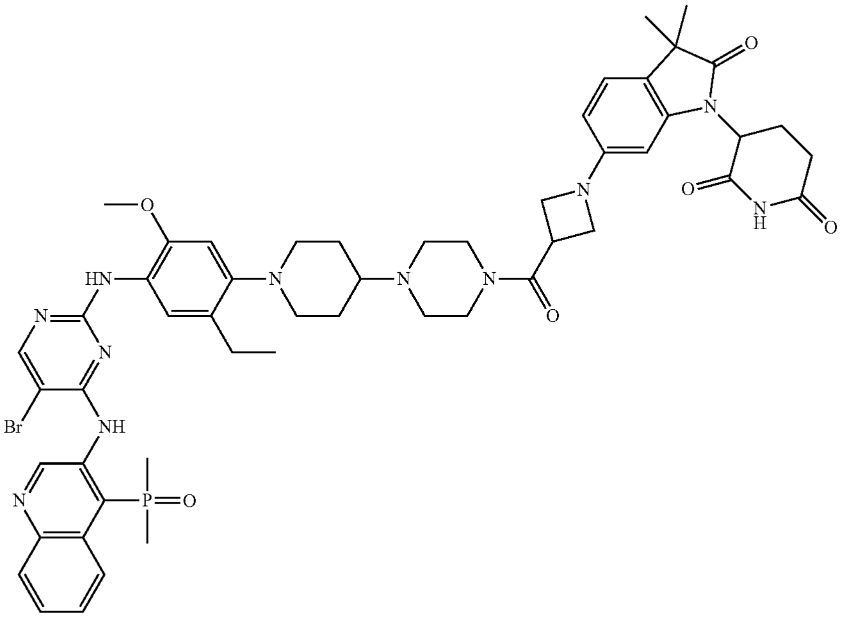

-continued
104
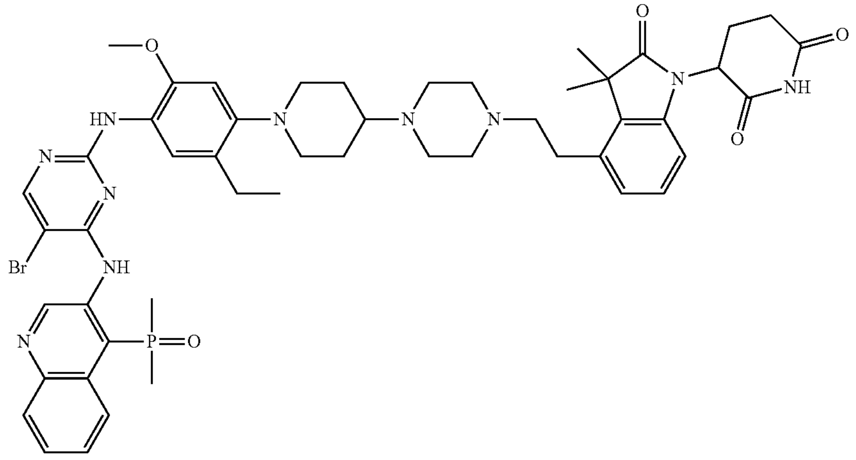
105
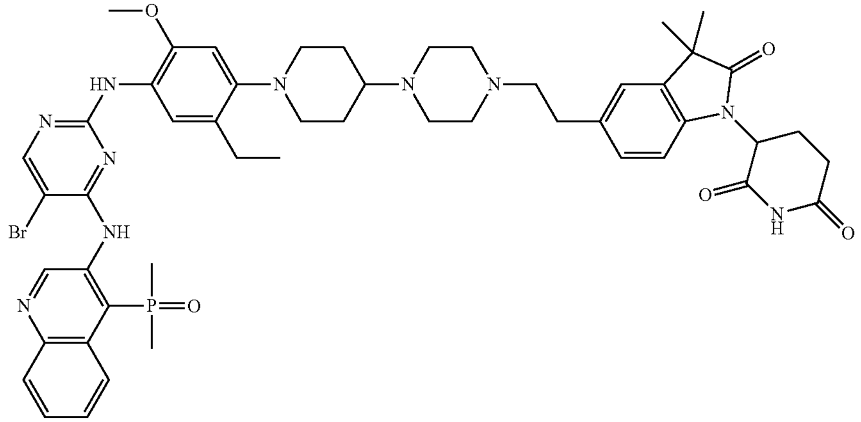
106
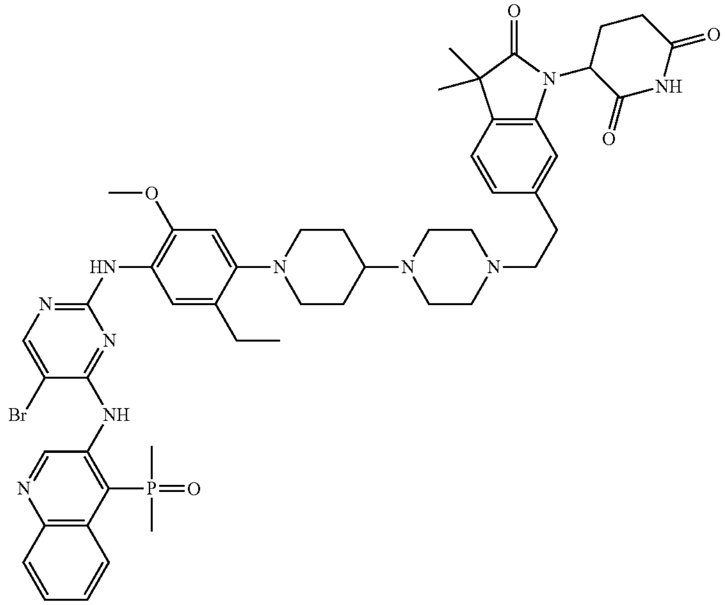

-continued
107
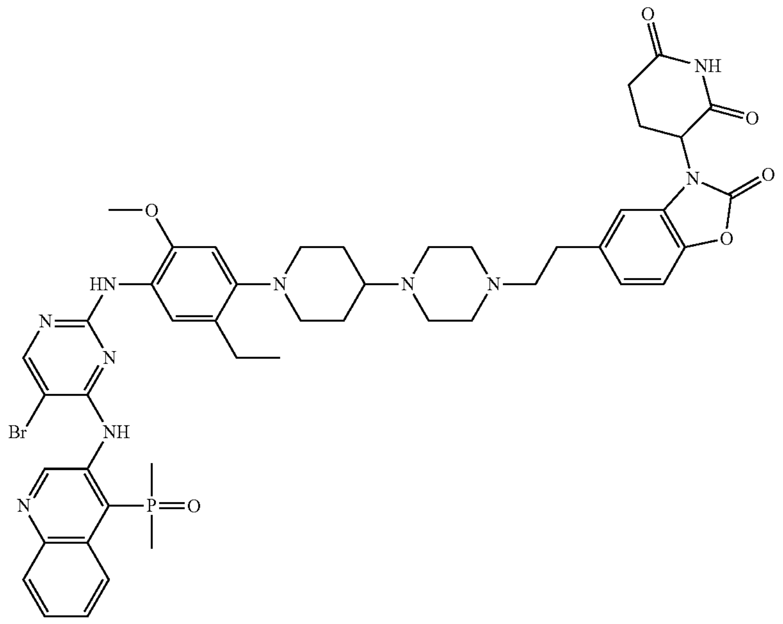
108
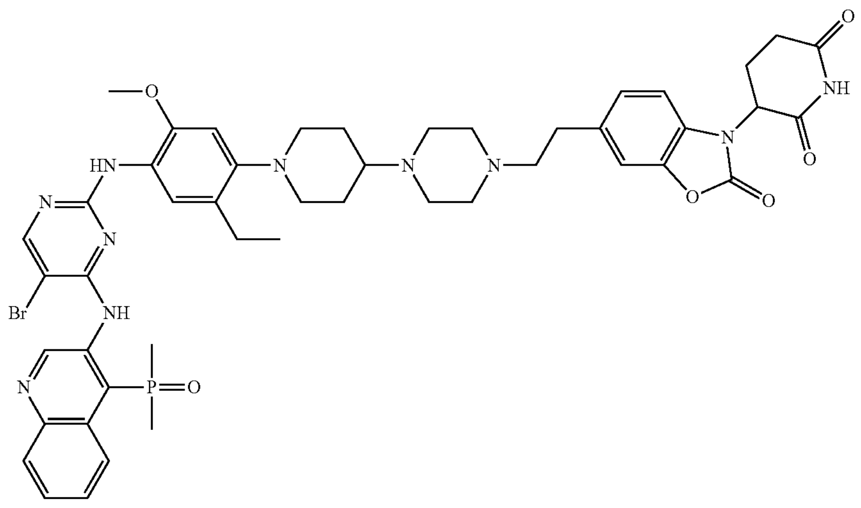

-continued
109
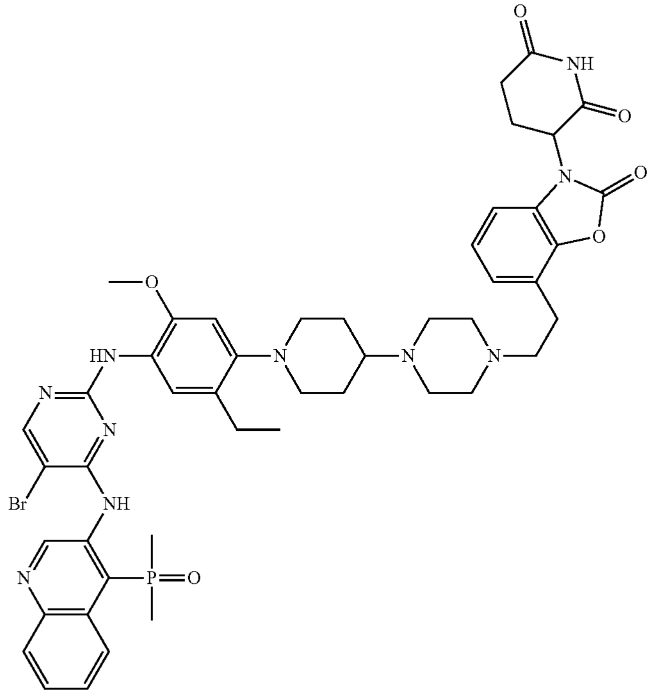
110
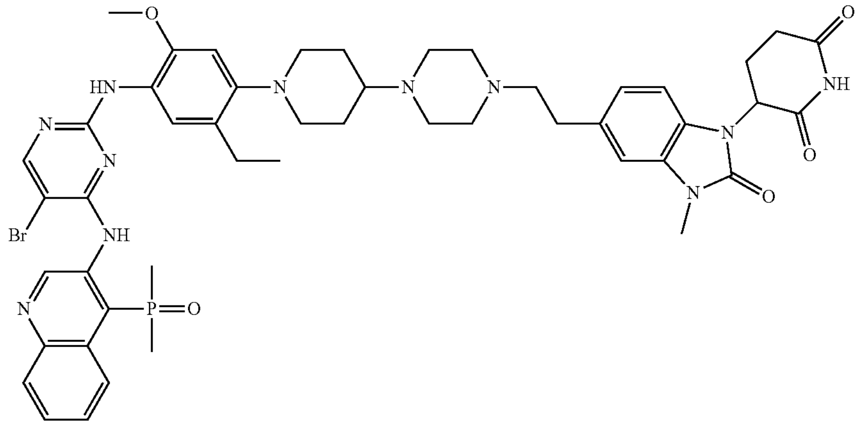
111
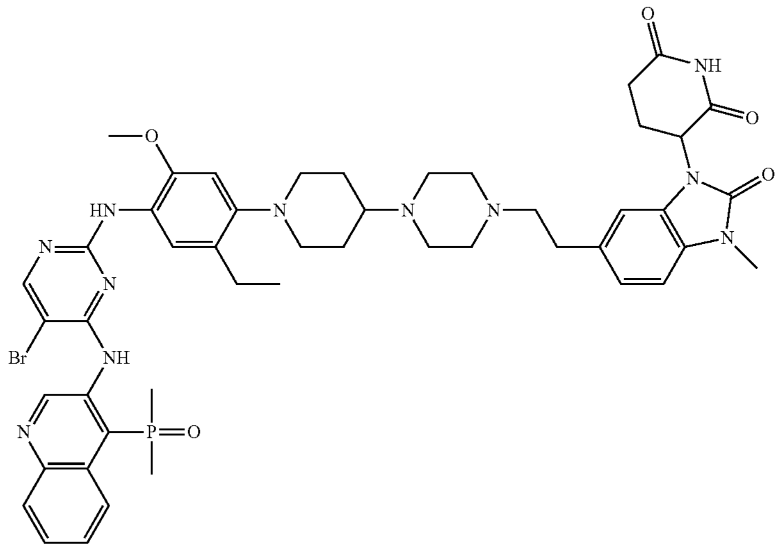

-continued
112
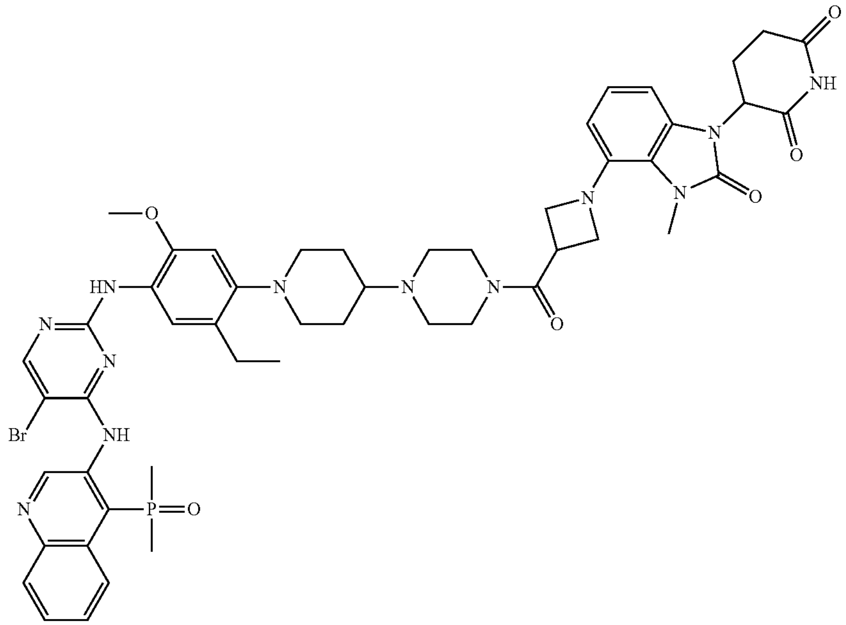
113
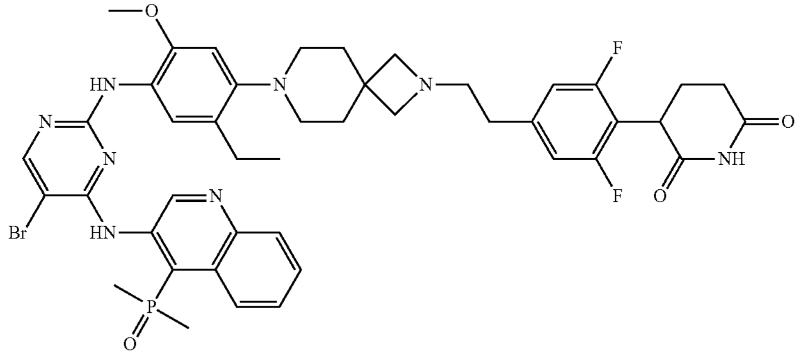
114
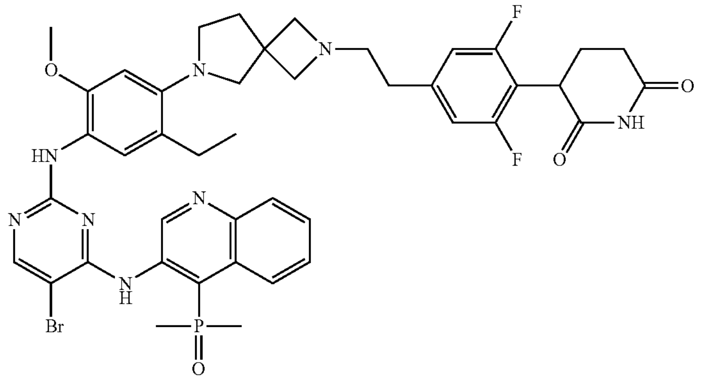

-continued
115
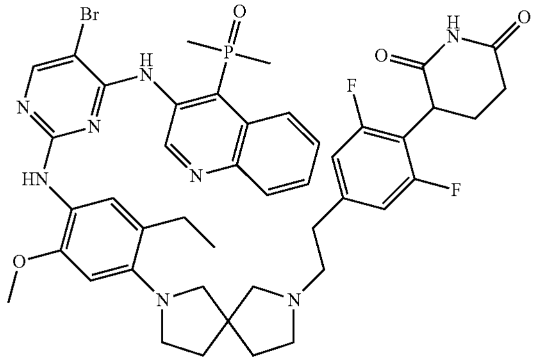
116
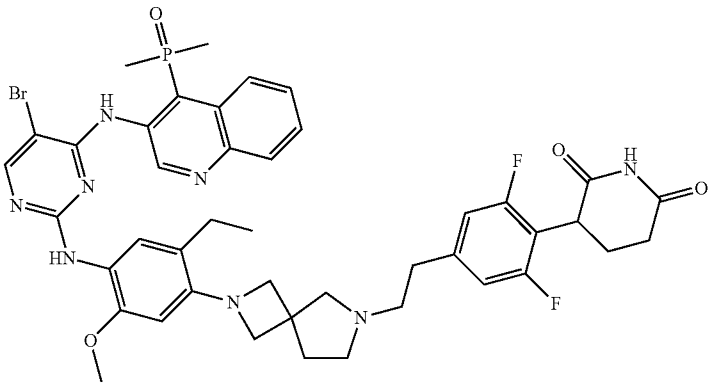
117
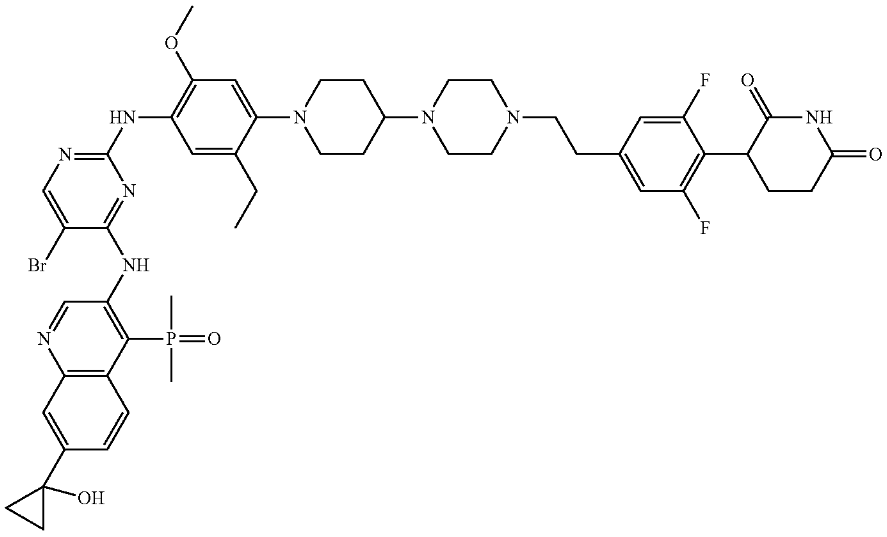

-continued
118
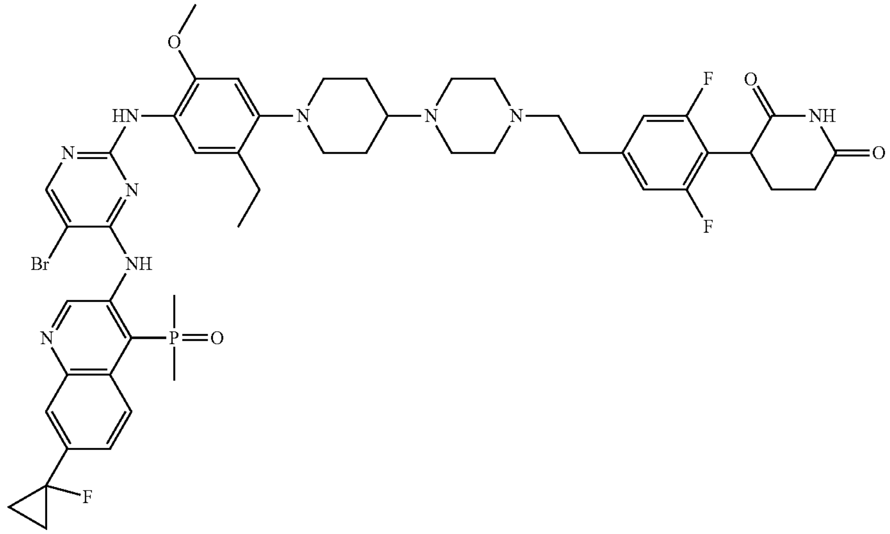
119
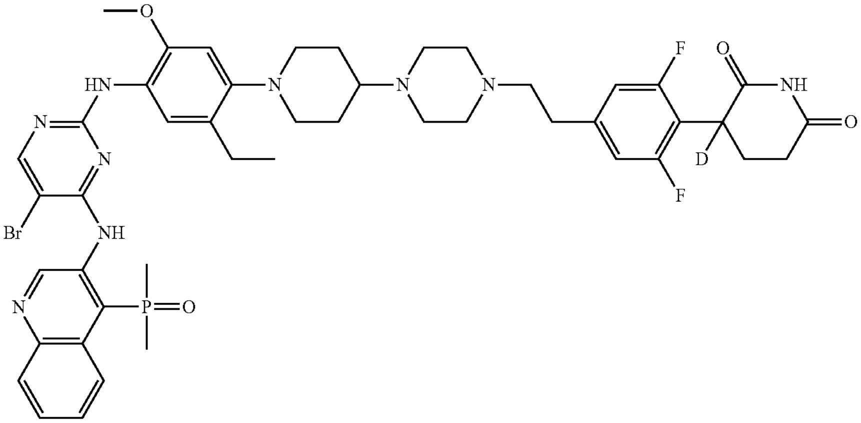
120
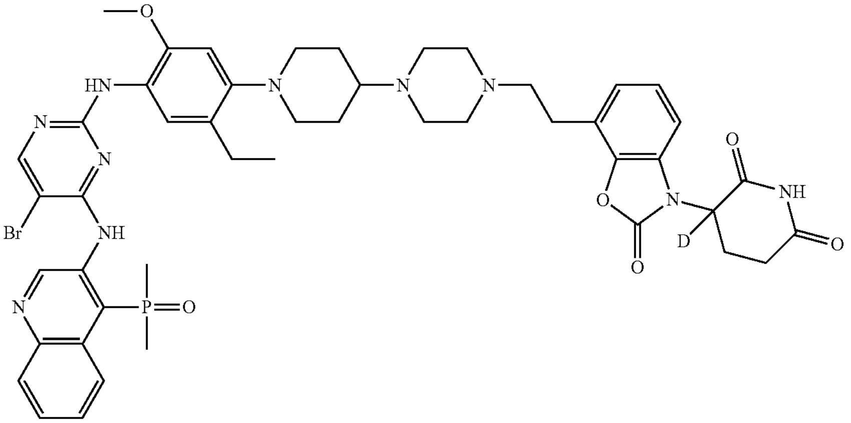

-continued
121
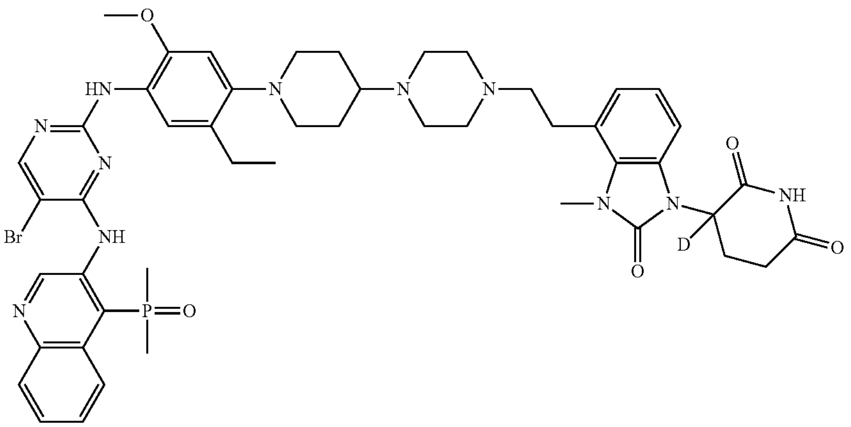
124
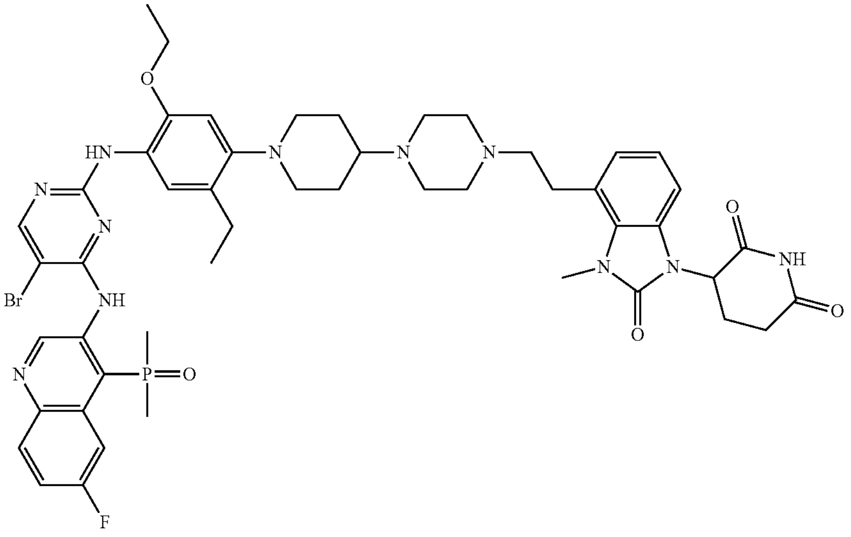
125
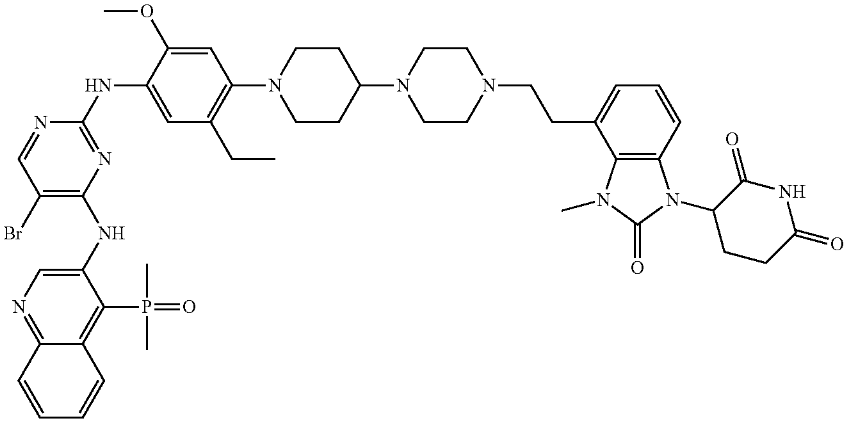

-continued
126
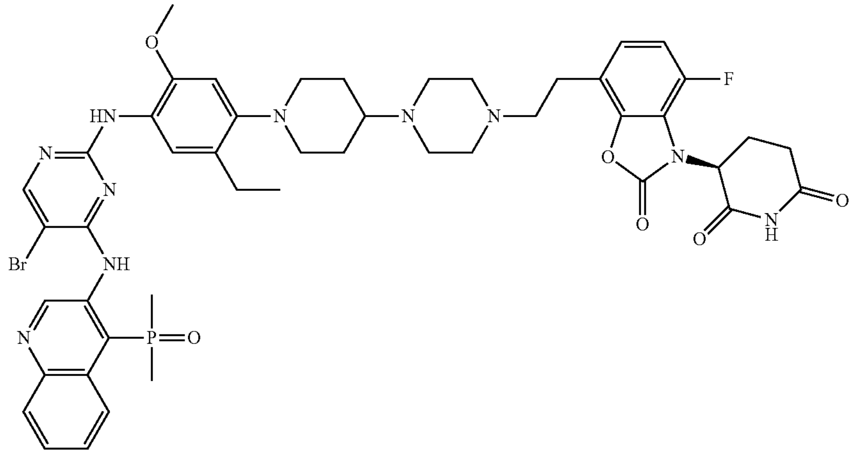
130
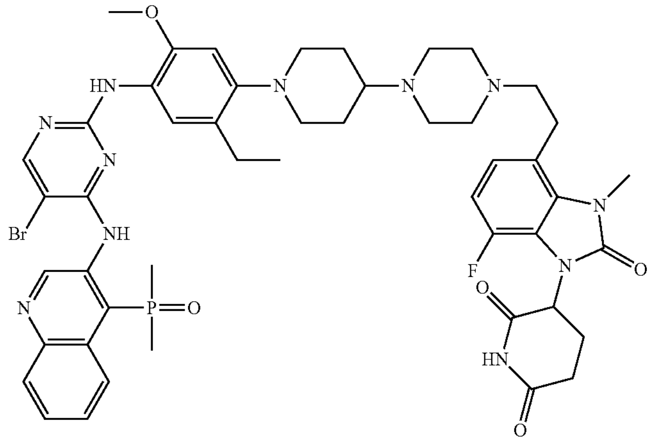
132
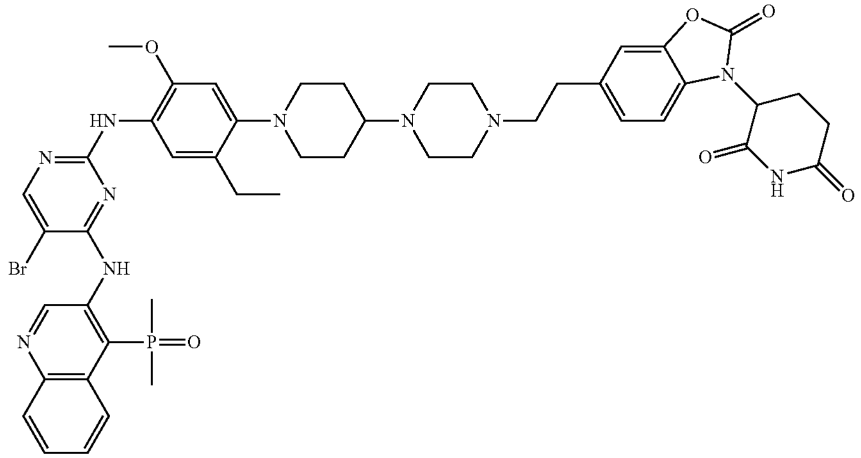

-continued
133
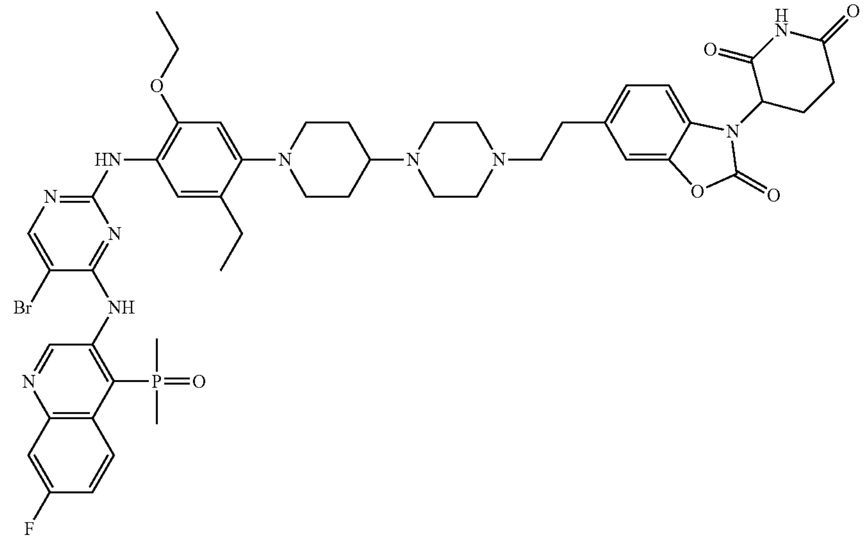
134
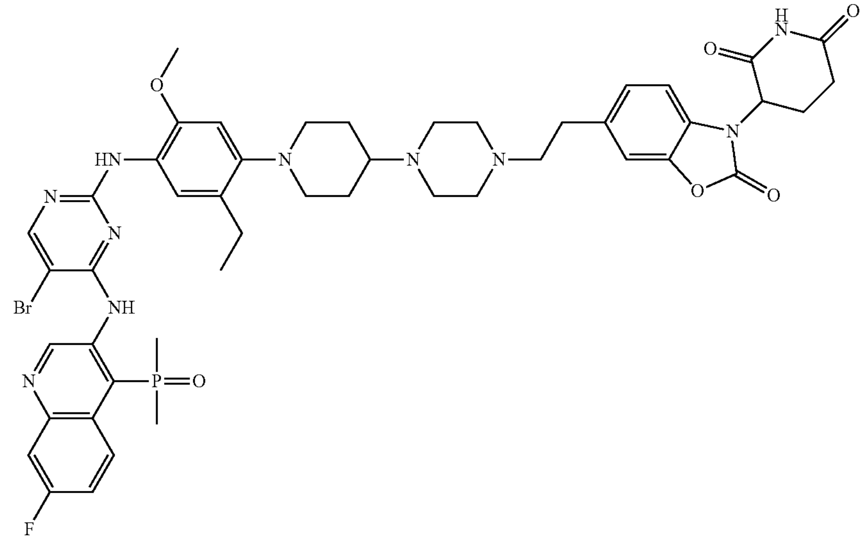
135
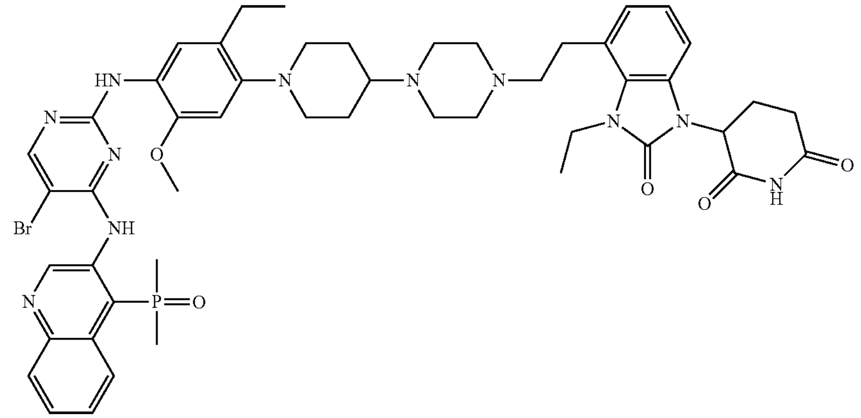

-continued
136
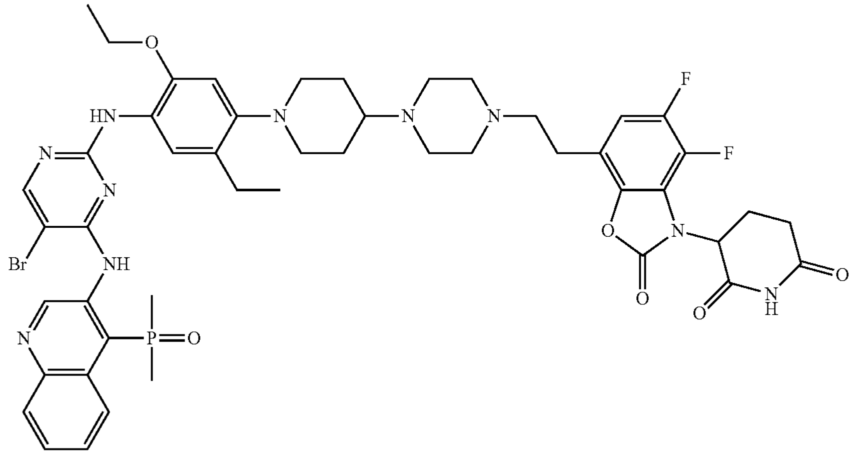
137
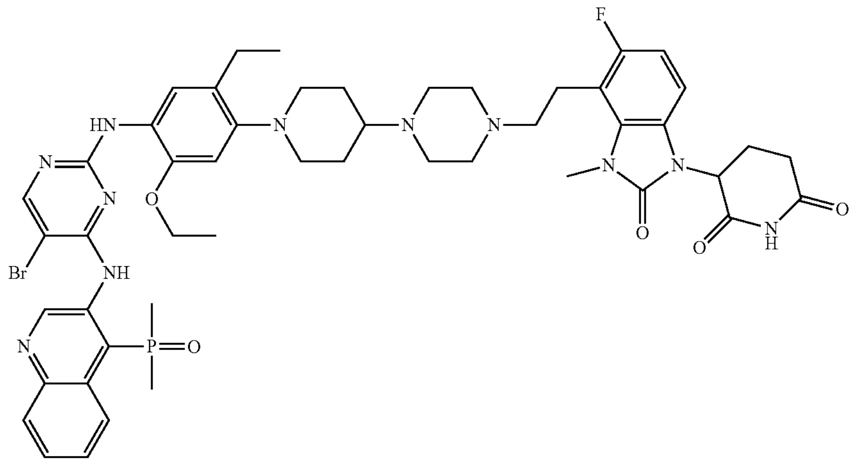
138
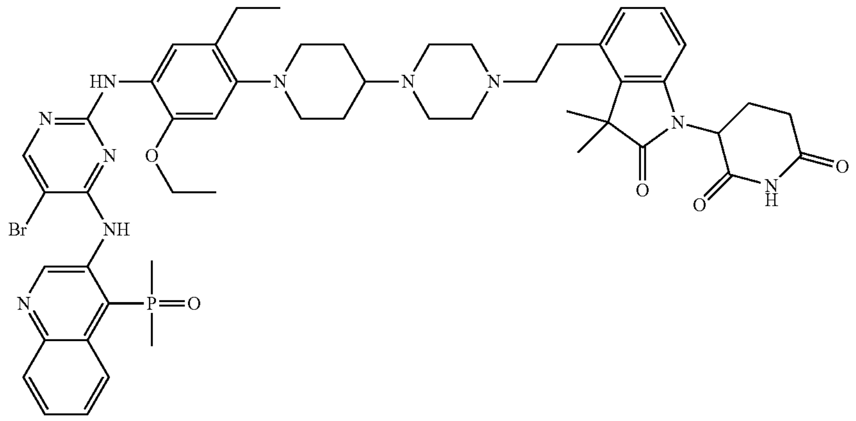

-continued
139
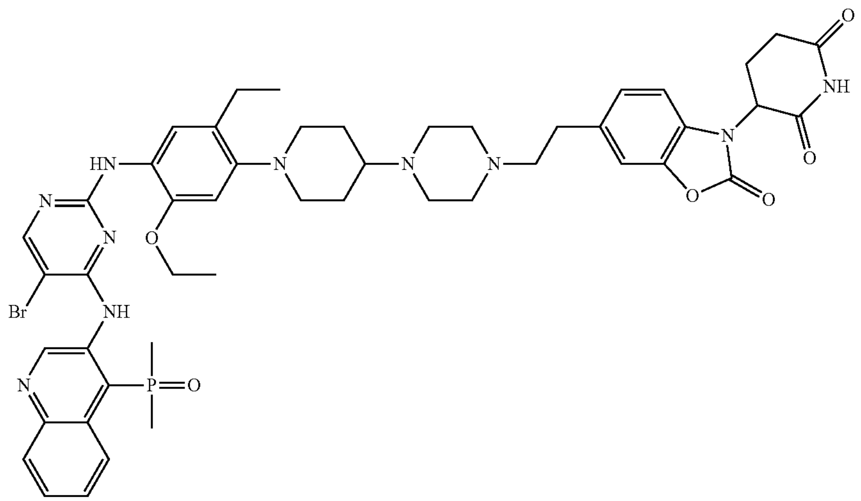
140
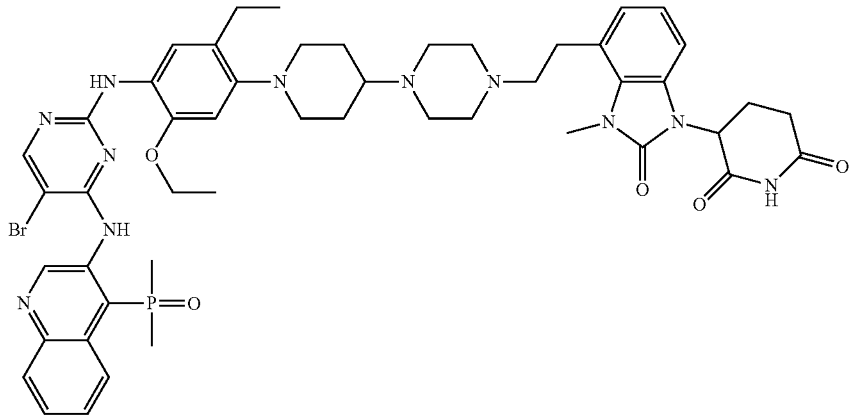
142
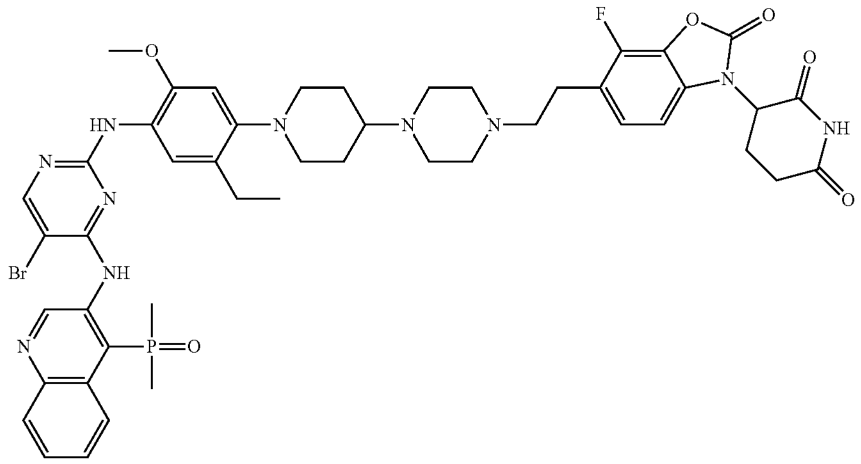

-continued
147
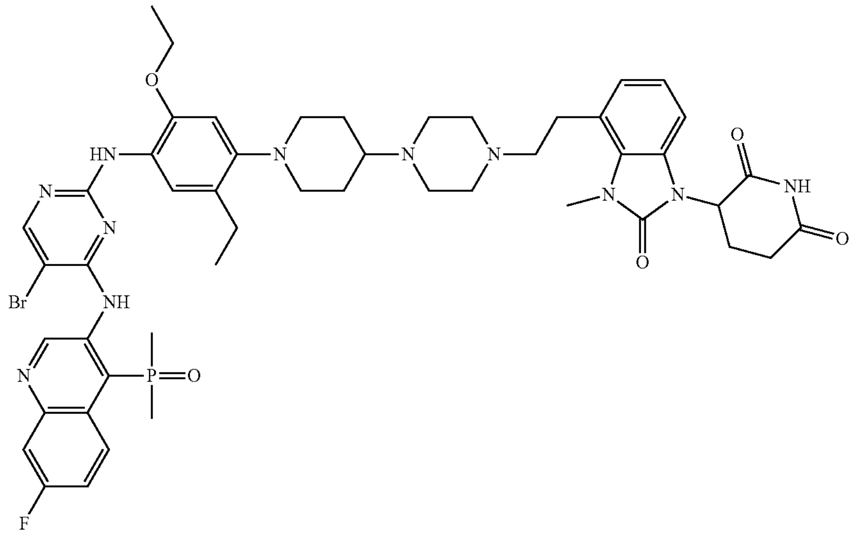
149
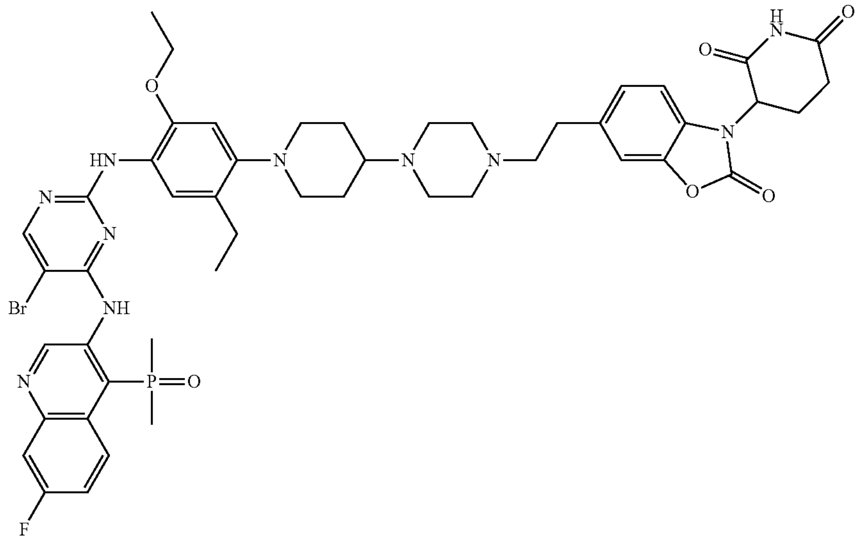
151
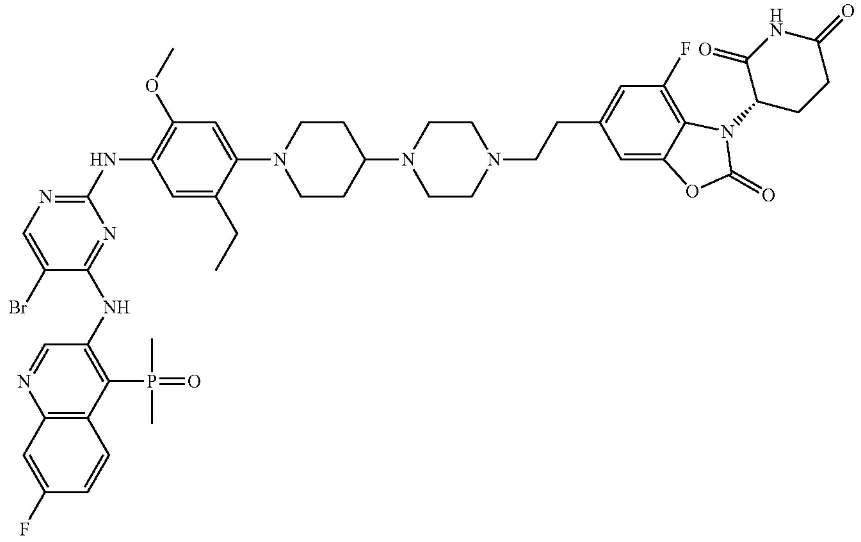

-continued
153
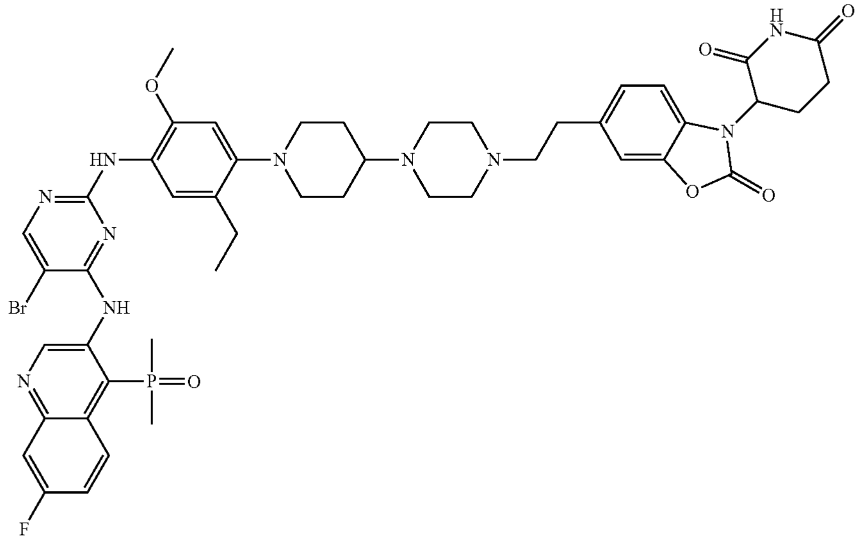
155
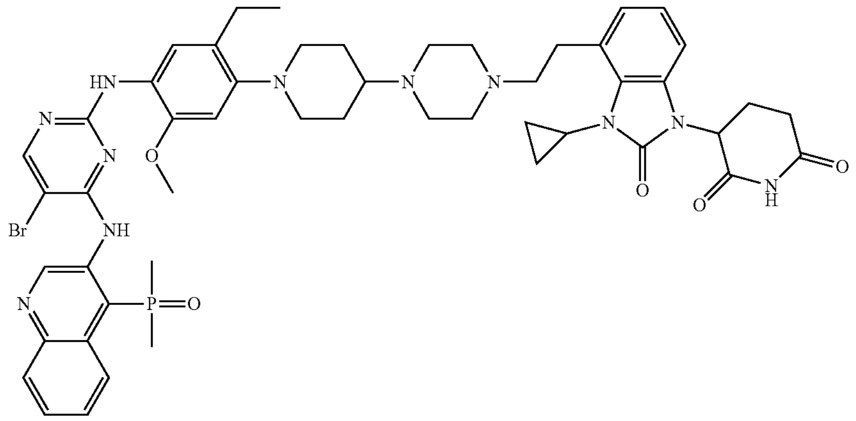
159
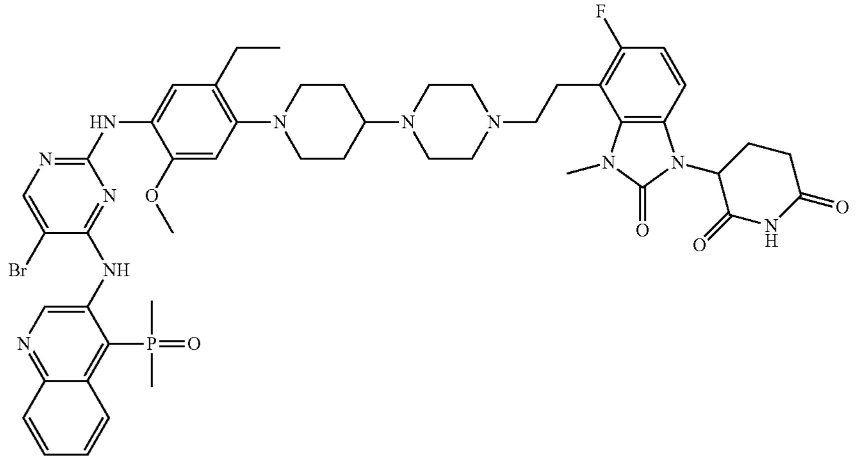

-continued
163
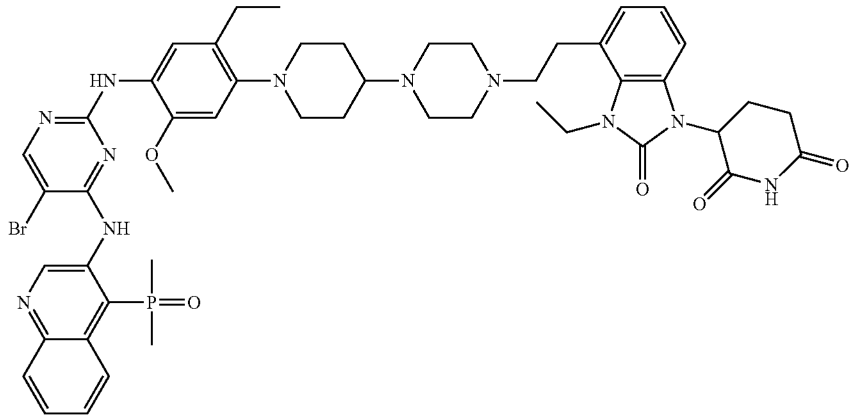
164
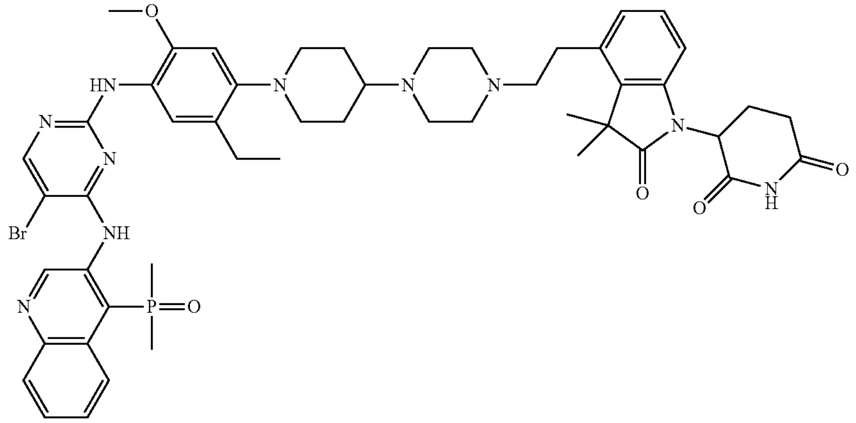
165
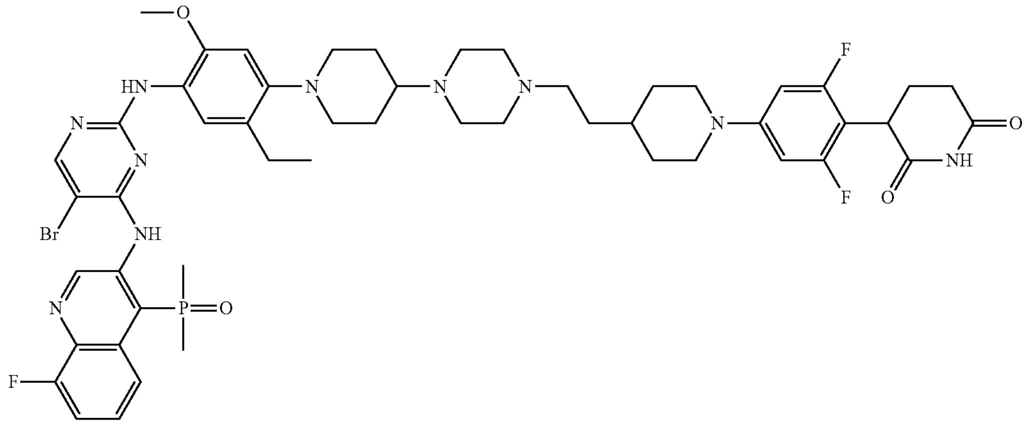

-continued
166
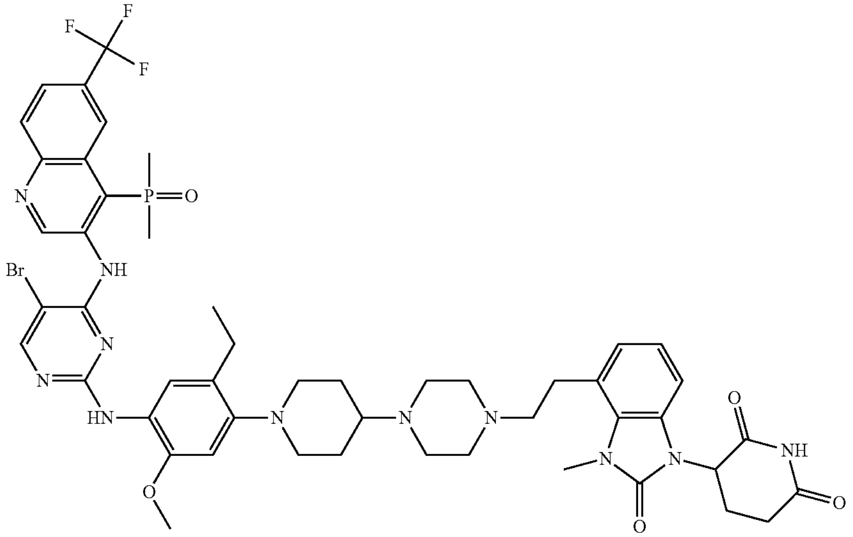
167
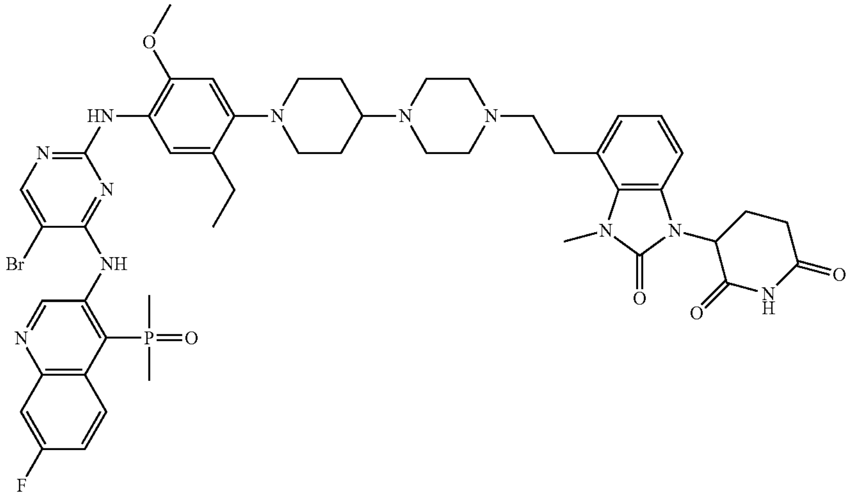
168
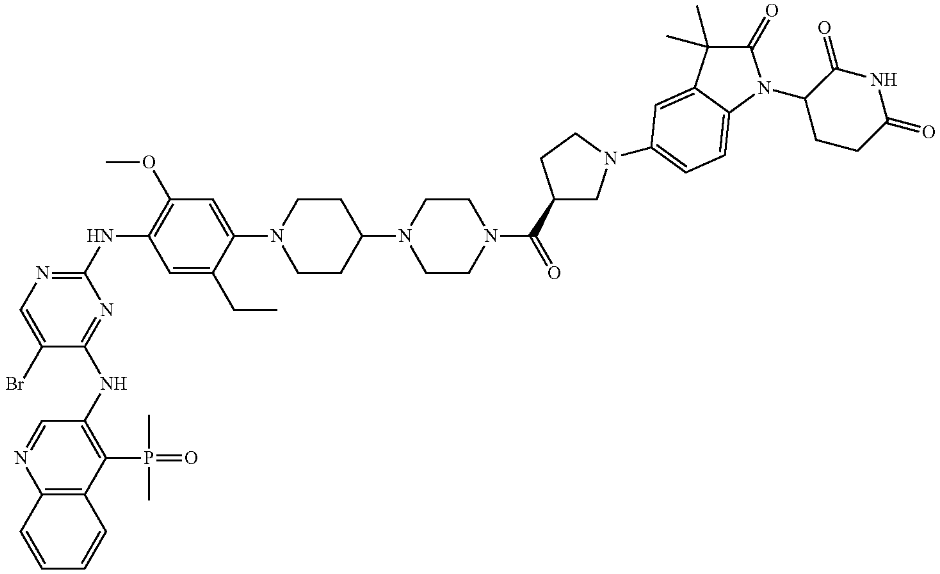

-continued
169
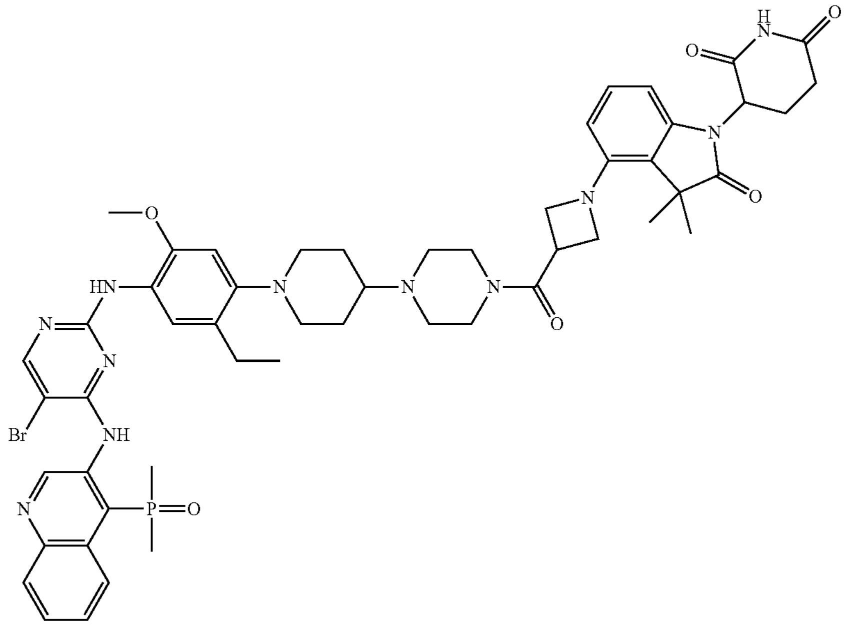
170
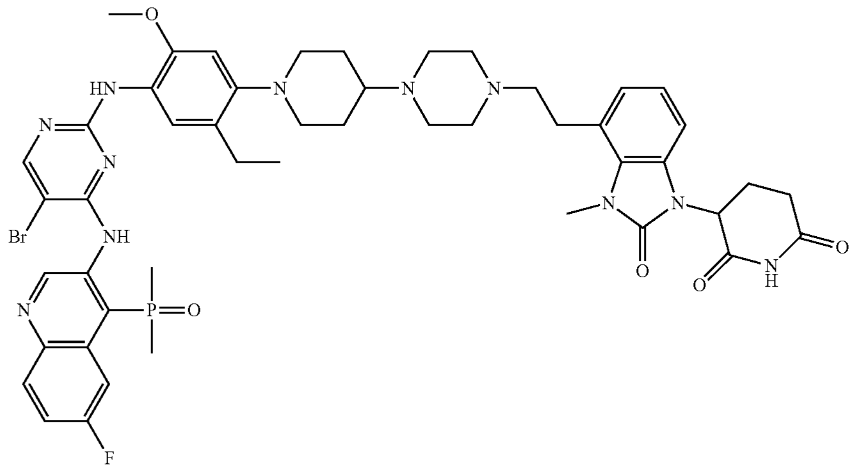
171
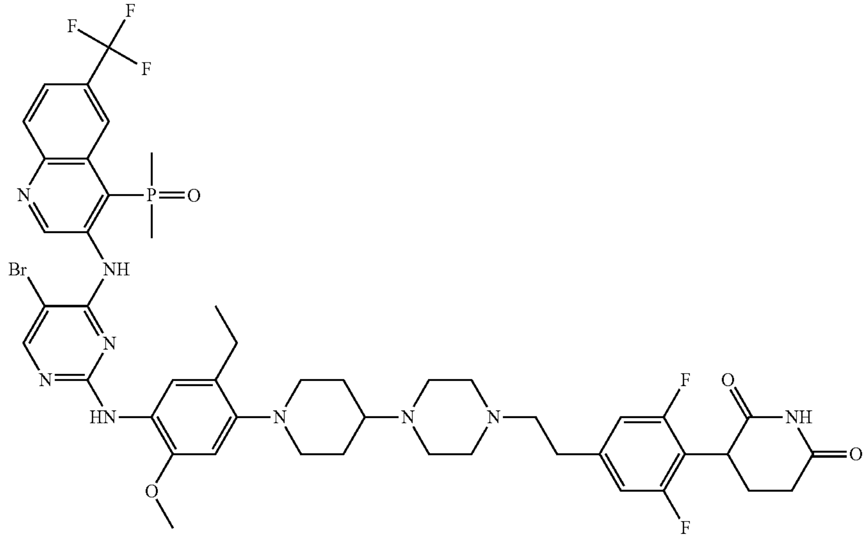

-continued
172
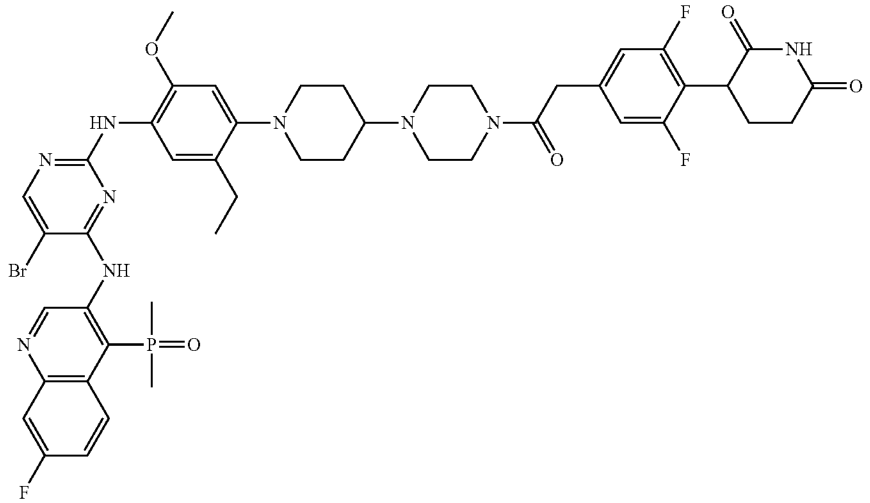
173
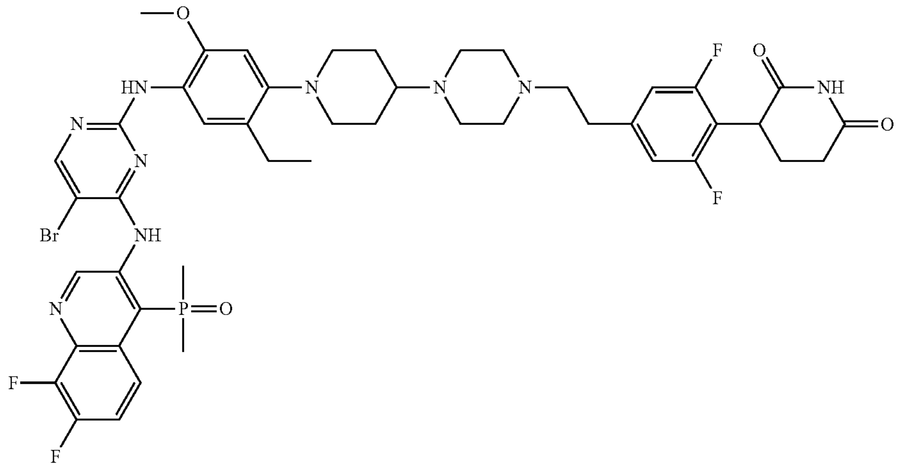
174
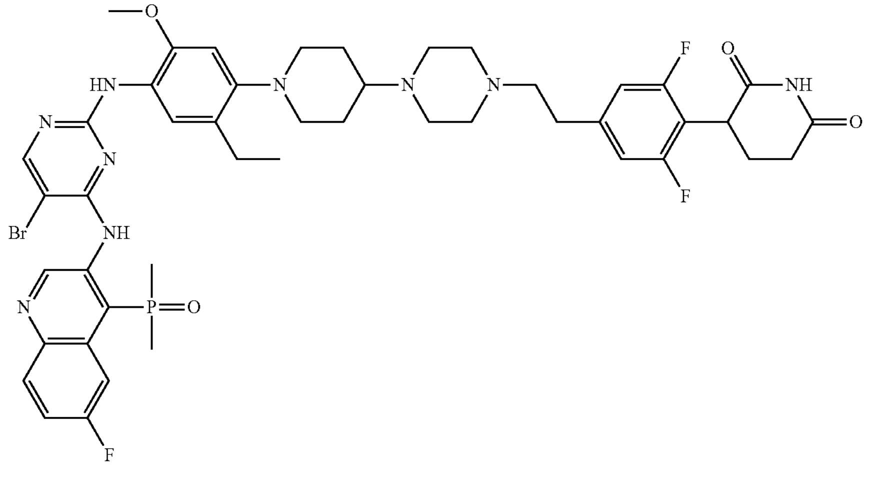

-continued
175
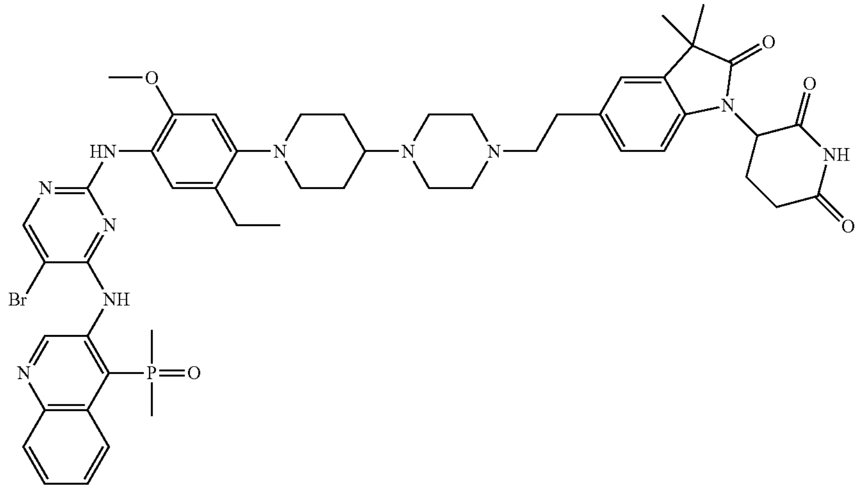
176
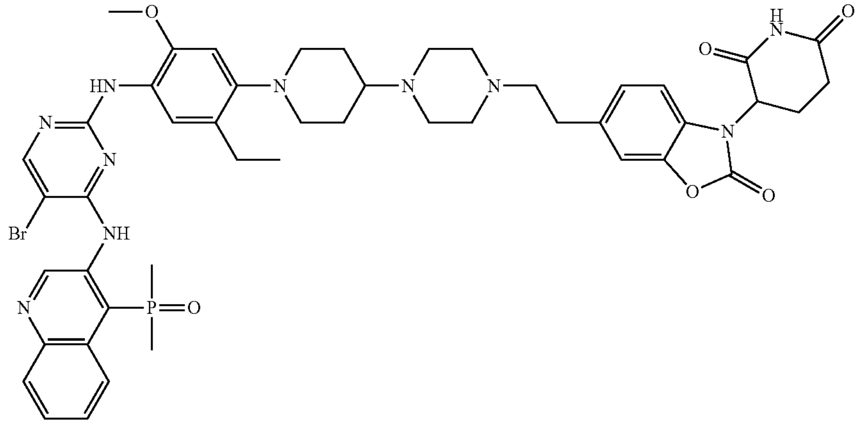
178
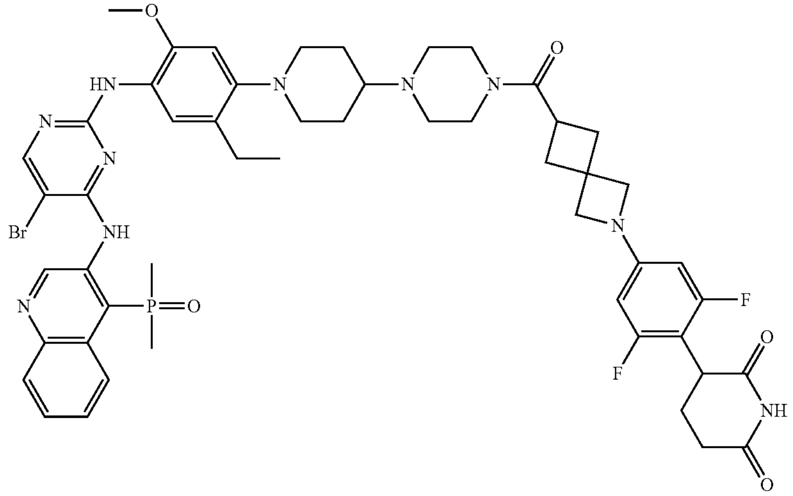

-continued
179
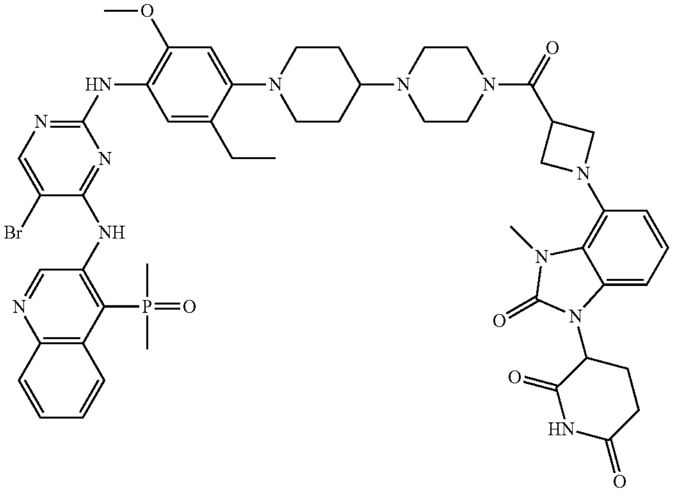
180
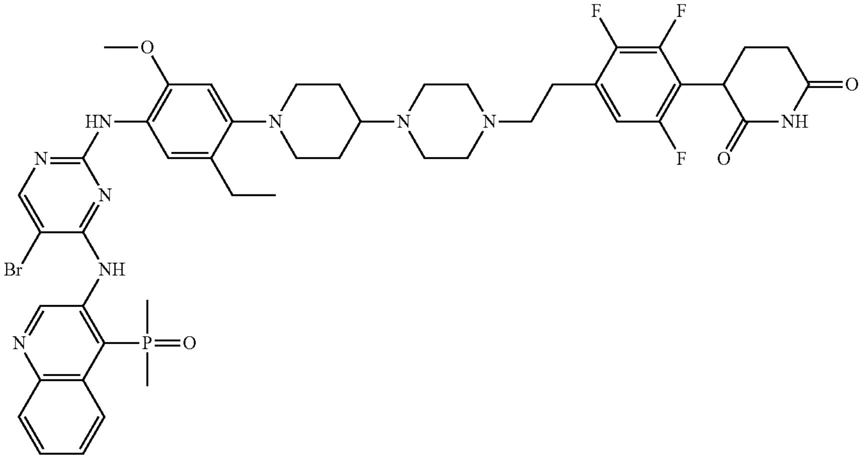
181
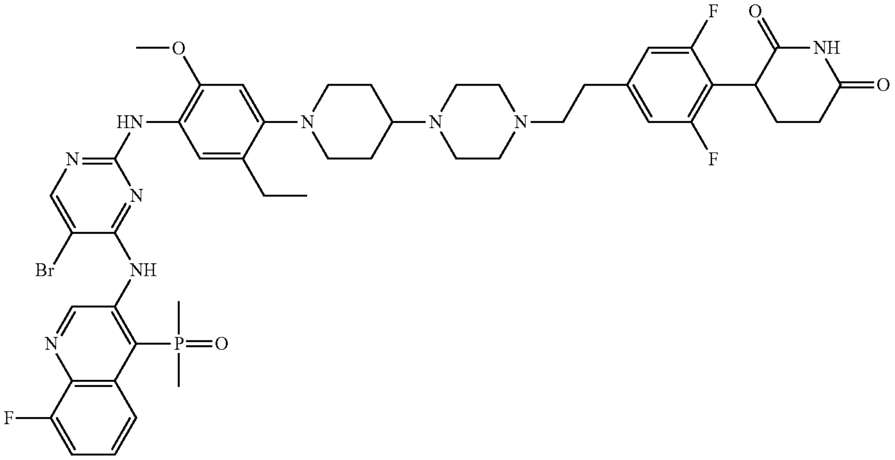

-continued
182
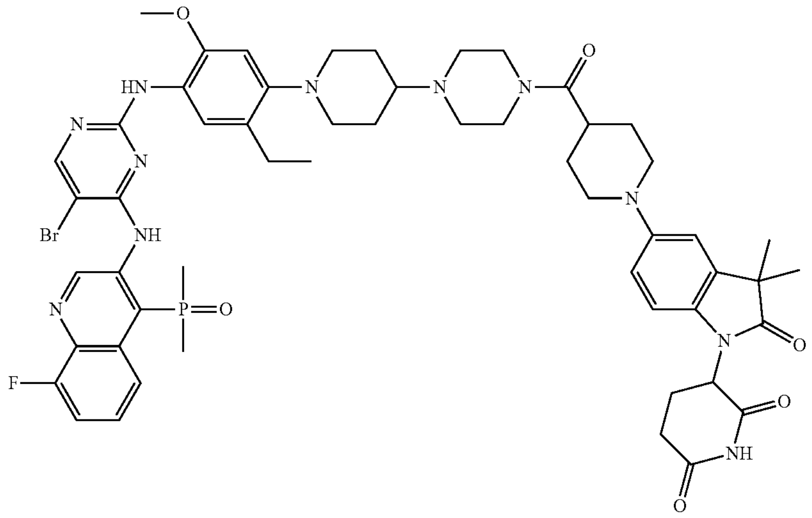
183
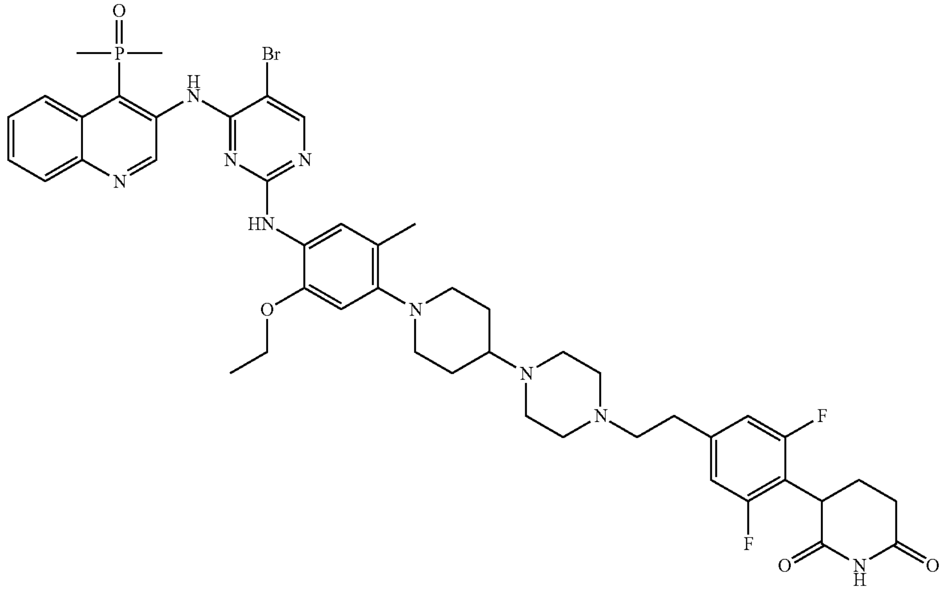
184
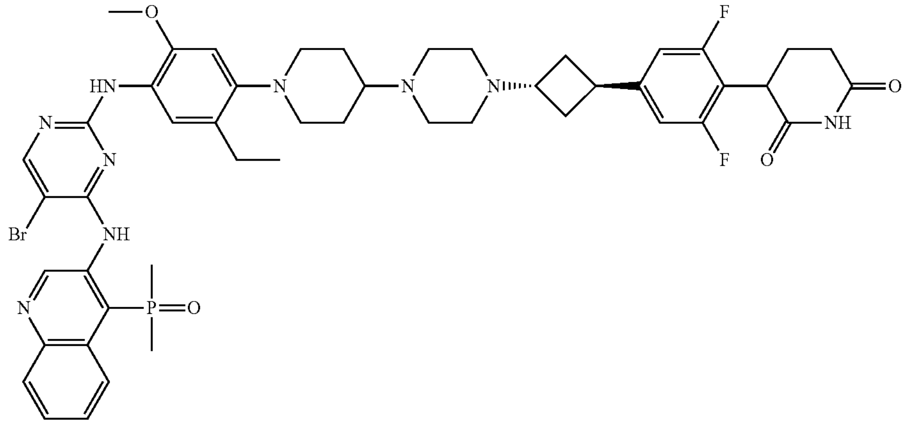

-continued
185
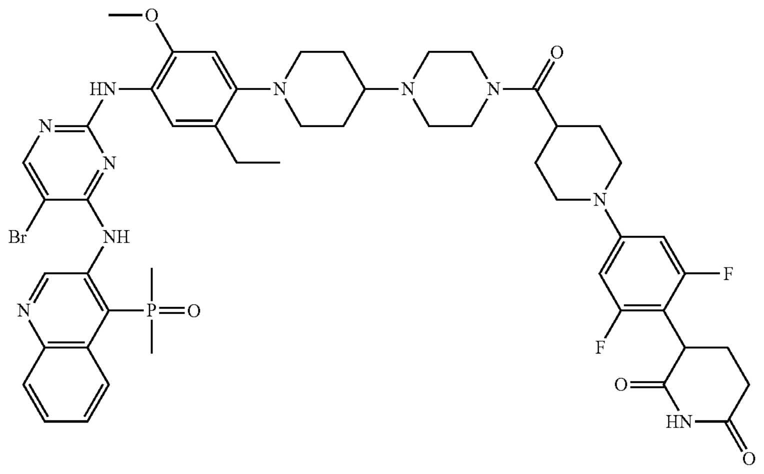
186
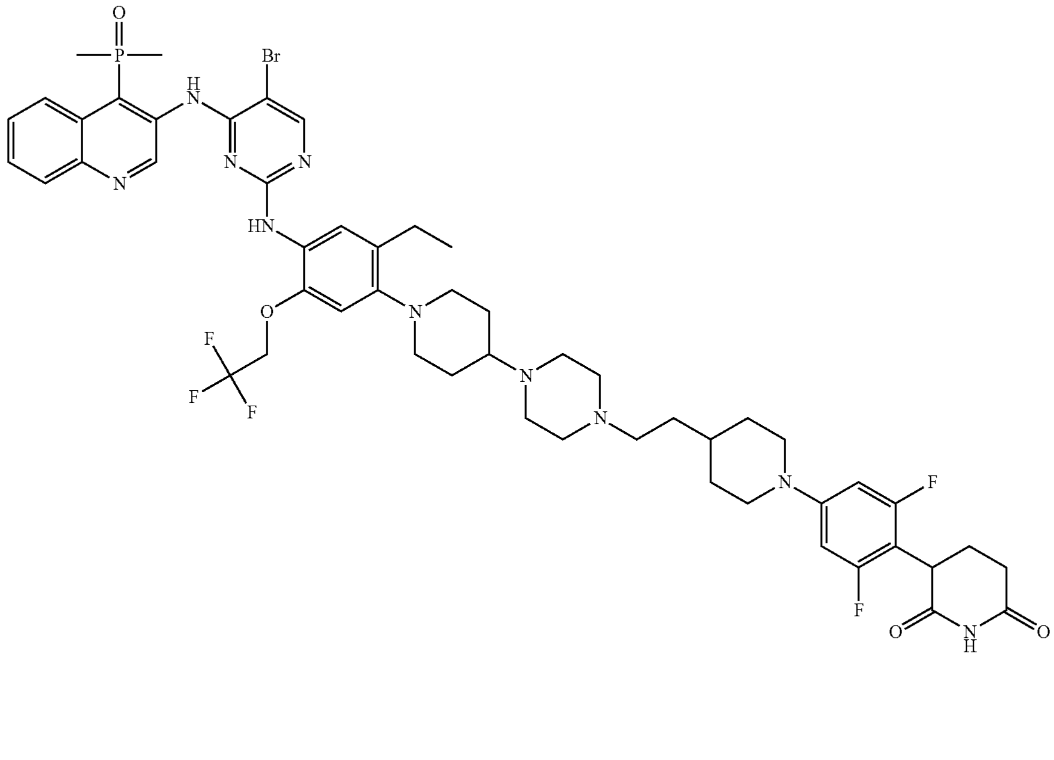

-continued
187
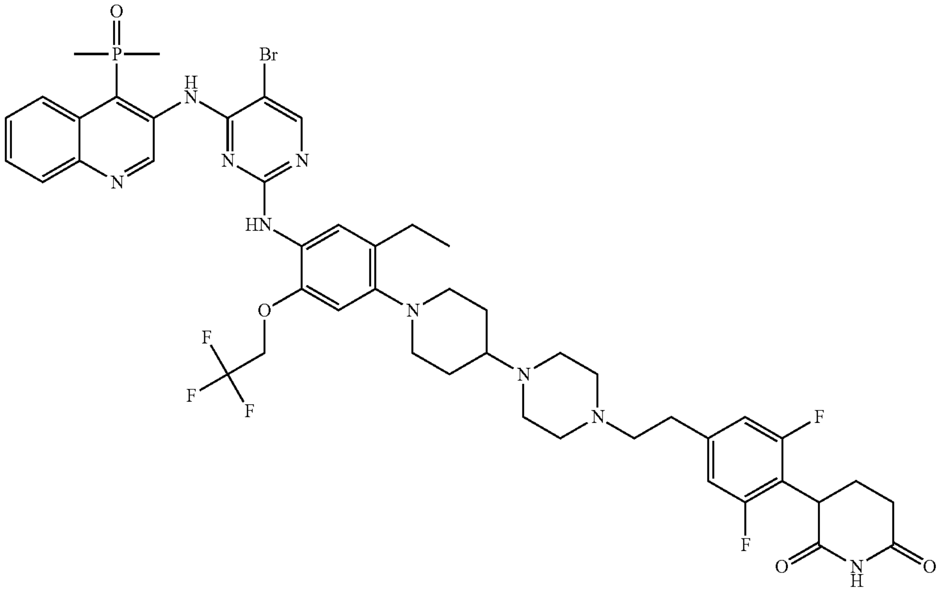
188
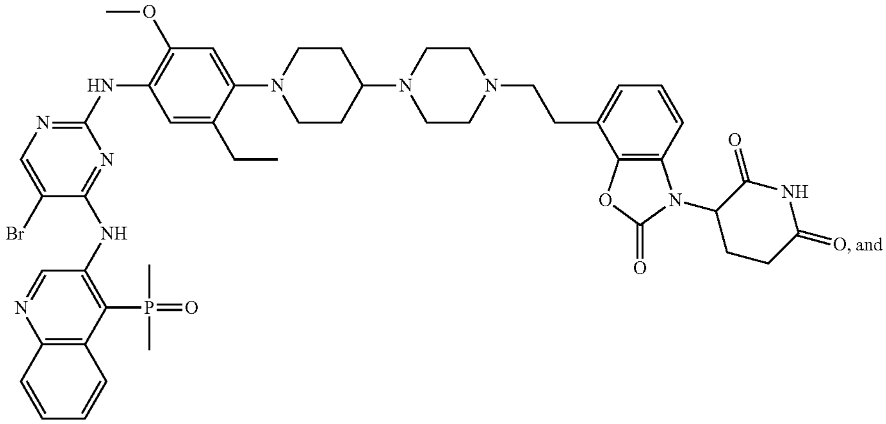
, and
189
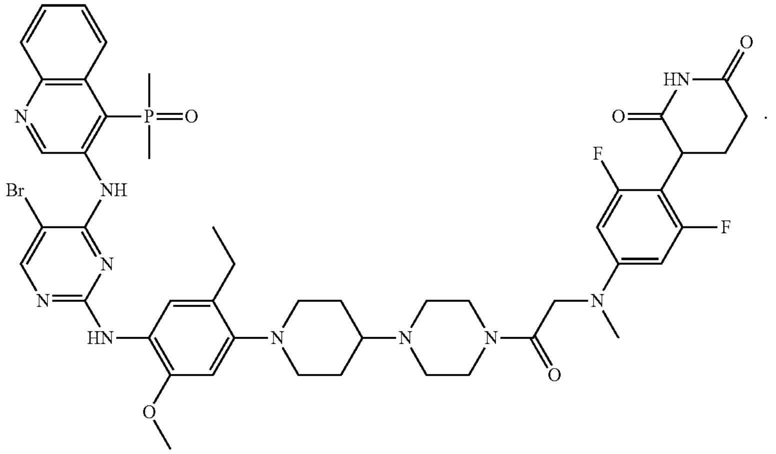
.

32. A method of decreasing EGFR activity by inhibition and/or degradation, which comprises administering to an individual a compound according to claim 1, or a pharmaceutically acceptable salt thereof.

33. A method of treating a disease or disorder in a patient comprising administering to the patient a therapeutically effective amount of a compound claim 1, or a pharmaceutically acceptable salt thereof as a EGFR kinase inhibitor and/or degrader, wherein the disease or disorder is associated with inhibition of EGFR.

34. The method of claim 33, wherein the disease is selected from pancreatic cancer, breast cancer, glioblastoma multiforme, head and neck cancer, and non-small cell lung cancer.

35. The compound of claim 1, wherein the

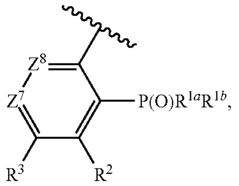

moiety is

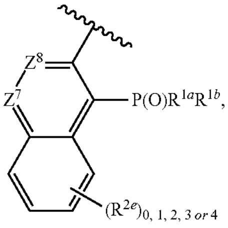

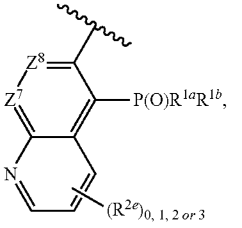

-continued

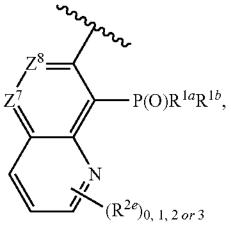

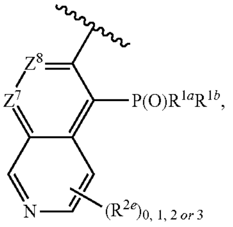

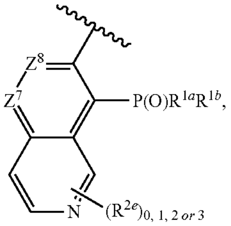

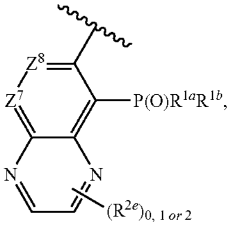

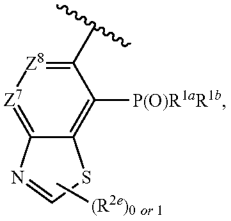

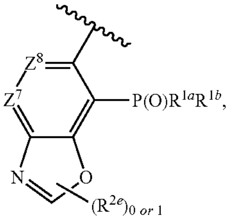

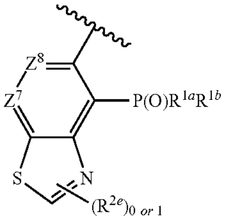

or

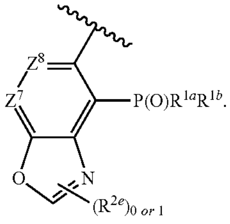

* * * * *